(12) United States Patent
Picataggio et al.

(10) Patent No.: US 8,114,641 B2
(45) Date of Patent: Feb. 14, 2012

(54) METHYLBUTANOL AS AN ADVANCED BIOFUEL

(75) Inventors: Stephen Picataggio, Solana Beach, CA (US); Robert C. Brown, San Diego, CA (US); Jessica R. Kristof, San Diego, CA (US); Gena Roy, San Diego, CA (US); Prachee Prakash, La Jolla, CA (US); Stuart A. Underwood, La Jolla, CA (US); Kevin Watts, Minneapolis, MN (US); Kevin V. Martin, Solana Beach, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 313 days.

(21) Appl. No.: 12/332,305

(22) Filed: Dec. 10, 2008

(65) Prior Publication Data

US 2009/0288337 A1    Nov. 26, 2009

Related U.S. Application Data

(60) Provisional application No. 61/012,749, filed on Dec. 10, 2007.

(51) Int. Cl.
| | | |
|---|---|---|
| *C12P 7/00* | (2006.01) | |
| *C12P 7/16* | (2006.01) | |
| *C12P 5/02* | (2006.01) | |
| *C12P 21/06* | (2006.01) | |
| *C12N 9/02* | (2006.01) | |
| *C12N 9/00* | (2006.01) | |
| *C12N 1/16* | (2006.01) | |
| *C10L 1/18* | (2006.01) | |
| *C07H 21/04* | (2006.01) | |

(52) U.S. Cl. ........ 435/132; 435/160; 435/167; 435/189; 435/183; 435/69.1; 435/254.21; 536/23.2; 44/447

(58) Field of Classification Search .................. None
See application file for complete search history.

(56) References Cited

U.S. PATENT DOCUMENTS

| | | | |
|---|---|---|---|
| 4,260,845 A * | 4/1981 | Shioyama | 585/640 |
| 4,589,996 A * | 5/1986 | Inoue et al. | 252/299.65 |
| 6,218,583 B1 | 4/2001 | Patrini et al. | |
| 6,455,284 B1 | 9/2002 | Gokarn et al. | |
| 2007/0092956 A1 | 4/2007 | Rajgarhia et al. | |
| 2007/0092957 A1 | 4/2007 | Donaldson et al. | |
| 2007/0117183 A1 | 5/2007 | Pompejus et al. | |
| 2007/0259411 A1 | 11/2007 | Bramucci et al. | |
| 2008/0015396 A1 | 1/2008 | D'Amore et al. | |
| 2008/0081746 A1 | 4/2008 | Woodruff et al. | |
| 2008/0132471 A1 | 6/2008 | Hibi et al. | |
| 2008/0132733 A1 | 6/2008 | Manzer et al. | |
| 2008/0132734 A1 | 6/2008 | Manzer et al. | |
| 2008/0261230 A1 | 10/2008 | Liao et al. | |
| 2009/0081746 A1 * | 3/2009 | Liao et al. | 435/160 |
| 2009/0111154 A1 | 4/2009 | Liao et al. | |

FOREIGN PATENT DOCUMENTS

| | | | |
|---|---|---|---|
| WO | WO2007136133 | | 11/2007 |
| WO | WO-2008/098227 | * | 8/2008 |
| WO | WO2009006429 | | 1/2009 |

OTHER PUBLICATIONS

Whisstock et al. Quaterly Reviews of Biophysics, 2003, "Prediction of protein function from protein sequence and structure", 36(3): 307-340.*

Witkowski et al. Conversion of a beta-ketoacyl synthase to a malonyl decarboxylase by replacement of the active-site cysteine with glutamine, Biochemistry. Sep. 7, 1999;38(36)11643-50.*

Risso et al., "Elucidation of an Alternate Isoleucine Biosynthesis Pathway in *Geobacter sulfurreducens*", *J. Bacteriology* 190(7):2266-2274, 2008.

Atsumi and Liao (2008) "Directed Evolution of *Methanococcus jannaschii* Citramalate Synthase for Biosynthesis of 1-Propanol and 1-Butanol by *Escherichia coli*" Appl and Environ Microbiol 74: 7802-7808.

Atsumi et al. (2008) "Nonfermentative pathways for synthesis of branched-chain higher alcohols as biofuels" Nature 451: 86-89.

Cann et al. (2008) "Production of 2-methyl-1-butanol in engineered *Escherichia coli*" Appl Microbiol Biotech. 81: 89-98.

Dickinson et al. (2003) "The catabolism of amino acids to long chain and complex alcohols in *Saccharomyces cerevisiae*" J Biol Chem 78: 8028-8034.

Drevland et al. (2007) "Enzymology and Evolution of the Pyruvate Pathway to 2-Oxobutyrate in *Methanocaldococcus jannaschii*" J Bacteriol 189: 4391-4400.

Howell et al. (1999) "(*R*)-Citramalate Synthase in Methanogenic Archea" J Bacteriol 181: 331-333.

Koon et al. (2004) "Crystal Structure of LeuA from *Mycobacterium tuberculosis*, a key enzyme in leucine biosynthesis" PNAS 101: 8295-8300.

Ma et al. (2008) "Molecular Basis of the Substrate Specificity and the Catalytic Mechanism of Citramalate Synthase from *Leptospira interrogans*" Biochemical Journal published online as manuscript 415: 45-56.

Xu et al. (2004) "Isoleucine Buiosynthesis in *Leptospira interrogans* Serotype lai Strain 56601 Proceeds via a Threonine-Independent Pathway" J Bacteriol 186: 5400-5409.

Yep et al. (2006) "Determinants of substrate specificity in KdcA, a thiamin diphosphate-dependent decarboxylase" Bioorganic Chemistry 34: 325-336.

(Continued)

*Primary Examiner* — Anand Desai
*Assistant Examiner* — Iqbal H Chowdhury
(74) *Attorney, Agent, or Firm* — DLA Piper LLP (US)

(57) ABSTRACT

This invention describes genes, metabolic pathways, microbial strains and methods to produce methyl butanol and other compounds of interest from renewable feedstocks.

16 Claims, 76 Drawing Sheets

OTHER PUBLICATIONS

Chemistry World (online) Better bugs for brewing butanol (Jan. 2, 2008).
2,3-dihydroxy-3-methylbutanoate (retrieved from internet Jan. 29, 2010).
Synthetic Genomics, Inc., PCT/US08/086296, Written Opinion, Jun. 2009.
Synthetic Genomics, Inc. PCT/US09/67589, Written Opinion, Mar. 2010.
Deanda et al. (1996) *Appl and Environ Microbiol* 62: 4465-4470.
Dien et al. (2003) *Appl Microbiol Biotechnol* 63: 258-266.
Larroy et al. (2002) *Eur. J. Biochem.* 269: 5738-5745.
Leskovac et al. (2002) *FEMS Yeast Res* 2: 481-494.
Kutter et al. (2006) *FEBS* 273: 4199-4209.
Kohl et al. (1998) *Eur. J. Biochem.* 257: 538-546.
Sakurai et al. (2004) *FEMS Yeast Res* 4: 649-654.
Scotcher et al. (2003) *J Ind Microbiol Biotechnol* (2003) 30: 414-420.
Woods (1995) *Trends in Biotechnology* 13: 259-264.
Cirino et al. (2006) *Biotechnol and Bioengineering* 95: 1168-1176.
Gross et al. (2006) *Chemistry and Biology* 13: 1253-1264.
Kawaguchi et al. (2006) *Appl and Environ Microbiol* 72: 3418-3428
Gorgens et al. (2005).
Mutka et al. (2006) *FEMS Yeast Res* 6: 40-47.
Wada et al. (2007) *Appl Microbiol Biotechnol* 76: 819-825.
Romero et al. (2007) *Appl Microbiol Biotechnol* 73: 5190-5198.
Wierckx et al. (2005) *Appl Microbiol Biotechnol* 71: 8221-8227.
Zhang et al. (2007) Appl Microbiol Biotechnol 77: 355-366 (*Escherichia*).
Zhou et al. (2001) *Appl and Environ Microbiol* 67: 6-14.
Gorgens et al., FEMS Yeast Research 5: 677-683.
Nyyssola et al., J. Biotechnology 118 (2005) 55-66.
Teng et al. (2007) *Appl Microbiol Biotechnol* 74: 1074-1083.

\* cited by examiner

FIGURE 23
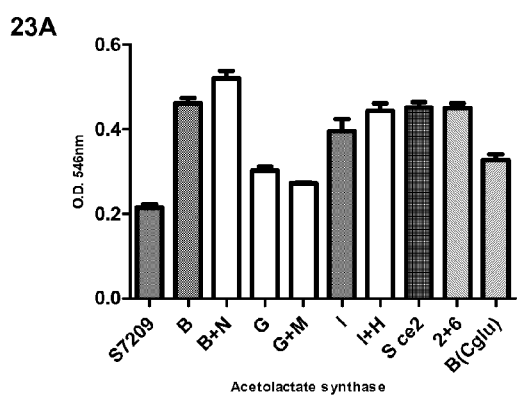
23A
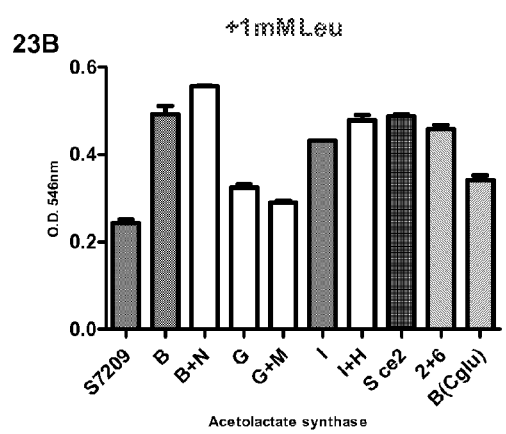
23B
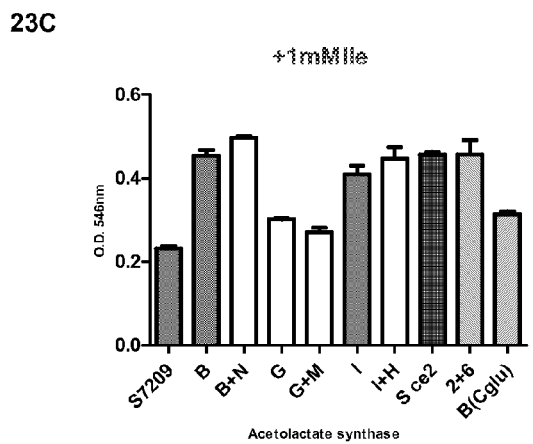
23C
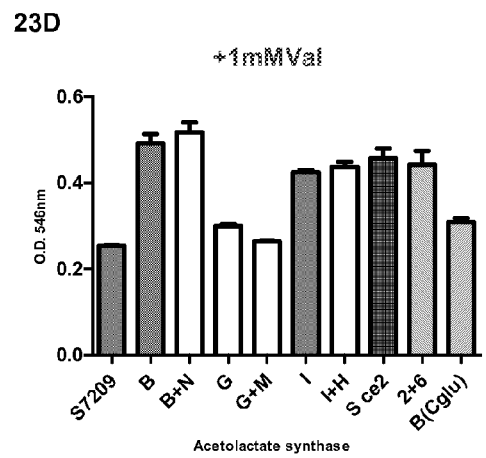
23D

FIGURE 28
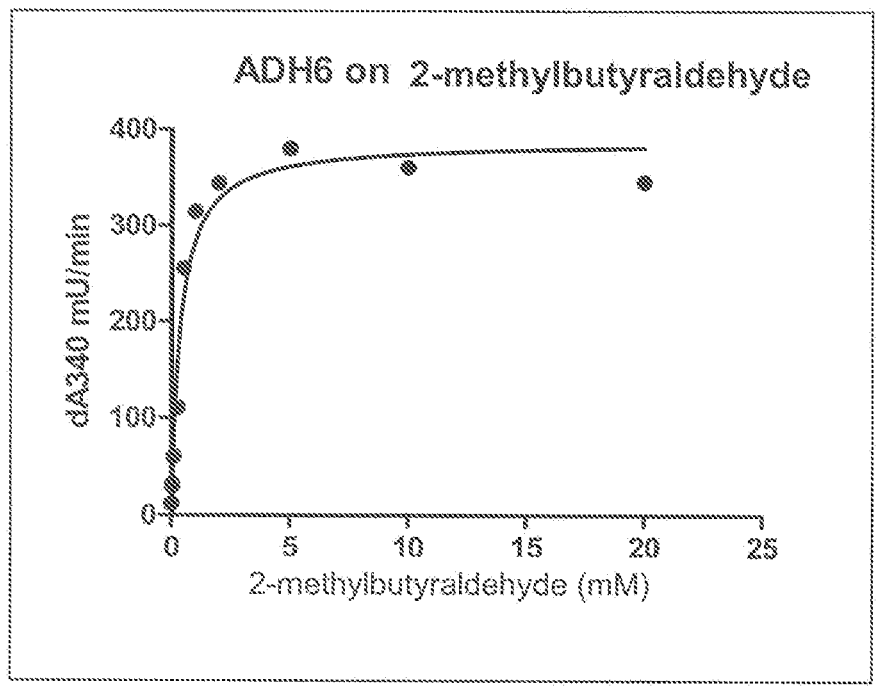
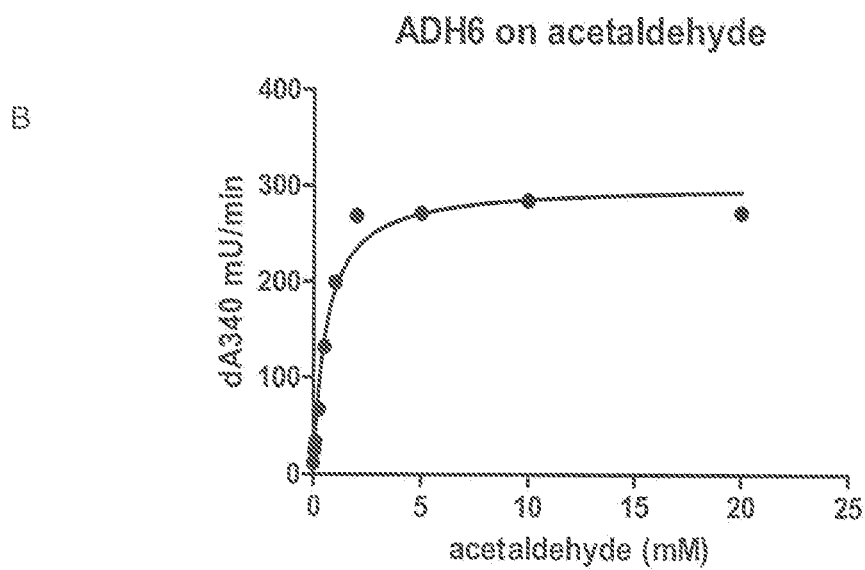

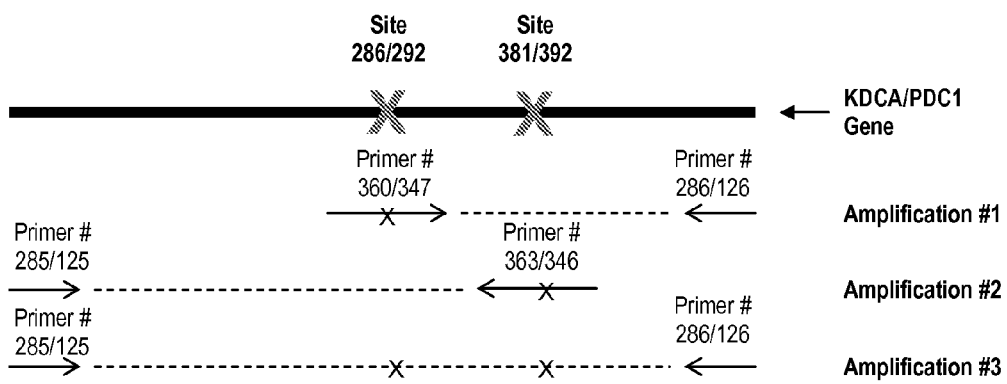

| Primer # | Primer | SEQ ID NO |
|---|---|---|
| 285 | 5'-CTAGAACTAGTGGATCCCCCATGTATACTGTGGGGGATTATTTGTTGGAT-3' | SEQ ID NO:100 |
| 286 | 5'-ATATCGAATTCCTGCAGCCCTTATTTGTTTTGCTCAGCAAATAGTTTCCC-3' | SEQ ID NO:101 |
| 363 | 5'-TCAGAAAAATTGTAGAGGCACCAAAKNNTGAGGTCCCTTGCTCTGCAACTATA-3' | SEQ ID NO:102 |
| 360 | 5'-atgttgggcgtcaagctgacggatNNKtctacgggggctttcactcac-3' | SEQ ID NO:103 |
| 125 | 5'-ctagaactagtggatccaccatgtctgaaattactttgggtaaatatttg-3' | SEQ ID NO:104 |
| 126 | 5'-atatcgaattcctgcagcccttaaatcgcttattgcttag-3' | SEQ ID NO:105 |
| 346 | 5'-GAAAGTGGTTTGGTTGATACCGAANNNGGAGGTACCGGTTTCAGCAATGA-3' | SEQ ID NO:106 |
| 347 | 5'-ctgtcggtgctttgttgtctgatNNNaacaccggttctttctcttactct-3' | SEQ ID NO:107 |

Pdc1p (*S.cerevisiae*)

FIGURE 36

Exchange Site #1

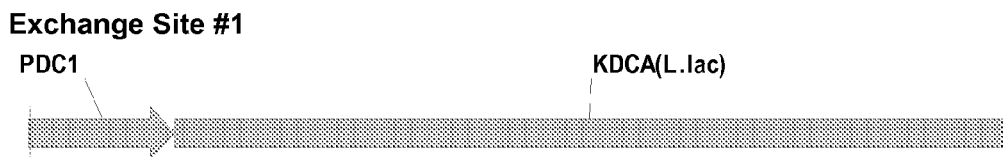

S.cer-L.lac PDC1-KDCA ES1
1650 bp

SEQ ID NO:110 atgtctgaaattactttgggtaaatatttgttcgaaagattaaagcaagtcaacgttaacaccgttttcggtttgccag
gtgacttcaacttgtccttgttggacaagatctacgaagttgaaggtatgagatgggctggtaacgccaacgaatt
gaacgctgcttacgccgctgatggttacgctcgtatcaagggtatgtcttgtatcatcaccaccttcggtgtcggtga
attgtctgctattaacggactggccggtagttatgctgaaaatttgccagtagttgaaatagtcggaagcccaactt
ctaaagtgcaaaacgatggcaaattcgtgcatcatactctggcagatggtgatttaagcacttcatgaaaatgca
tgaacccgtaacggctgccagaactcttttaacagccgagaatgcgacatatgaaattgatcgtgtactttctcag
cttttaaaggagagaaaacctgtttacataaacttacctgtcgatgttgctgctgccaaagcagagaagccagcc
ctgtctcttgaaaaagaaagctccaccaccaacactaccgaacaagtgatattatctaaaattgaggaatcactt
aaaaacgctcagaaaccagtagtcatagcgggtcatgaagtcataagtttcggtcttgaaaagactgtaacaca
atttgtcagcgaaacaaaattgcctatcactactttgaactttggcaaaagtgcggtcgacgagtcgttgccatcat
ttttgggtatctacaatggcaaactatcagaaatctcattgaaaaatttcgtagaaagtgcggatttcattctgatgtt
gggcgtcaagctgacggattcttctacgggggctttcactcaccatttggatgaaaacaaaatgatttcattgaac
atcgatgaagggatcatctttaataaggtagtggaagatttcgattttagagccgtggtttcctccttatcagagttaa
aaggtattgagtacgaagggcagtatattgataagcagtacgaggaatttattccttcttctgctccactttctcaag
atcgtttatggcaagcagtcgagtccctgacacaaagcaacgagactatagttgcagagcaagggacctcattc
tttggtgcctctacaattttctgaaatccaacagcagatttataggacaaccccctttggggctctattggatatacttt
cccgcagcccttggttcacaaatcgcagataaggagtcaagacatctgttattcataggtgatggtagtctacaat
taacagttcaagaattaggcctatcaataagggagaagttaaacccaatctgtttcataattaacaatgacggcta
cactgttgaaagggagatccacggaccaacacaatcatacaatgatattcccatgtggaactatagcaaattac
cggagactttcggcgcaaccgaggatagagtagtttcgaagatcgttaggactgagaatgaatttgttagcgttat
gaaggaagcccaggctgatgtcaatagaatgtattggattgaattagttttggaaaaggaagatgcacctaaatt
actaaaaagatggggaaactatttgctgagcaaaacaaataa

*Highlighted regions is the PDC1 DNA, non-highlighted is KDCA DNA

FIGURE 37

Exchange Site #2

S.cer-L.lac PDC1-KDCA ES2
1701 bp

SEQ ID NO:111 atgtctgaaattactttggglaaatatttgttcgaaagattaaagcaagtcaacgttaacaccgttttcggtttgccag
gtgacttcaacttgtccttgttggacaagatctacgaagttgaaggtatgagatgggctggtaacgccaacgaatt
gaacgctgcttacgccgctgatggttacgctcgtatcaagggtatgtcttgtatcatcaccaccttcggtgtcggtga
attgtctgctttgaacggtattgccggttcttacgctgaacacgtcggtgttttgcacgttgttggtgtcccatccatctct
gctcaagctaagcaattgttgttgcaccacaccttgggtaacggtgacttcactgttttccacagaatgtctgccaa
catttctgaaaccactgctatgatcactgacattgctaccgccccagctgaaattgacagatgtatcagaaccact
tacgtcacccaaagaccagtctacttaggtttgccagctaacttggtcgacttgaacgtcccagctaagttgttgca
aactccaattgacatgtctttgaagccaaacgatgctgaatccgaaaaggaagtcattgacaccatcttggctttg
gtcaaggatgctaagaacccagttatcttggctgatgcttgttgttccagacacgacgtcaaggctgaaactaag
aagttgattgacttgactcaattcccagctttcgtcaccccaatgggtaagggttccattgacgaacaacacccaa
gatacggtggtgtttacgtcggtaccttgtccaagccagaagttaaggaagccgttgaatctgctgacttgattttgt
ctgtcggtgctttgttgtctgatttcaacaccggttctttctcttactcttacaagaccaagaacattgtcgaattccact
ccgaccacatgaagatcagaaacgccactttcccaggtgtccaaatgaaattcgttttgcaaaagttgttgacca
ctattgctgacgccgctaagggttacaagccagttgctgtcgggcagtatattgataagcagtacgaggaatttatt
ccttcttctgctccactttctcaagatcgtttatggcaagcagtcgagtccctgacacaaagcaacgagactatagt
tgcagagcaagggacctcattctttggtgcctctacaatttttctgaaatccaacagcagatttataggacaacccc
tttggggctctattggatatacttttcccgcagcccttggttcacaaatcgcagataaggagtcaagacatctgttatt
cataggtgatggtagtctacaattaacagttcaagaattaggcctatcaataagggagaagttaaacccaatctg
tttcataattaacaatgacggctacactgttgaaagggagatccacggaccaacacaatcatacaatgatattcc
catgtggaactatagcaaattaccggagactttcggcgcaaccgaggatagagtagtttcgaagatcgttagga
ctgagaatgaatttgttagcgttatgaaggaagcccaggctgatgtcaatagaatgtattggattgaattagttttgg
aaaaggaagatgcacctaaattactaaaaaagatggggaaactatttgctgagcaaaacaaacatcaccatc
accatcactaa

*Highlighted regions is the PDC1 DNA, non-highlighted is KDCA DNA

FIGURE 38

Exchange Site #3

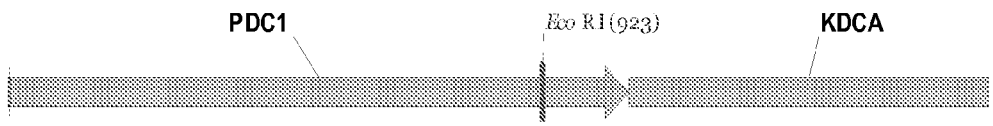

S.cer-L.lac PDC1-KDCA ES3
1695 bp

SEQ ID NO:112 atgtctgaaattactttgggtaaatatttgttcgaaagattaaagcaagtcaacgttaacaccgttttcggtttgccag
gtgacttcaacttgtccttgttggacaagatctacgaagttgaaggtatgagatgggctggtaacgccaacgaatt
gaacgctgcttacgccgctgatggttacgctcgtatcaagggtatgtcttgtatcatcaccaccttcggtgtcggtga
attgtctgctttgaacggtattgccggttcttacgctgaacacgtcggtgttttgcacgttgttggtgtcccatccatctct
gctcaagctaagcaattgttgttgcaccacaccttgggtaacggtgacttcactgttttccacagaatgtctgccaa
catttctgaaaccactgctatgatcactgacattgctaccgccccagctgaaattgacagatgtatcagaaccact
tacgtcacccaaagaccagtctacttaggtttgccagctaacttggtcgacttgaacgtcccagctaagttgttgca
aactccaattgacatgtctttgaagccaaacgatgctgaatccgaaaaggaagtcattgacaccatcttggctttg
gtcaaggatgctaagaacccagttatcttggctgatgcttgttgttccagacacgacgtcaaggctgaaactaag
aagttgattgacttgactcaattcccagctttcgtcaccccaatgggtaagggttccattgacgaacaacacccaa
gatacggtggtgtttacgtcggtaccttgtccaagccagaagttaaggaagccgttgaatctgctgacttgattttgt
ctgtcggtgctttgttgtctgatttcaacaccggttctttctcttactcttacaagaccaagaacattgtcgaattccact
ccgaccacatgaagatcagaaacgccactttcccaggtgtccaaatgaaattcgttttgcaaaagttgttgacca
ctattgctgacgccgctaagggttacaagccagttgctgtcccagctagaactccagctaacgcttttattccttcttc
tgctccactttctcaagatcgtttatggcaagcagtcgagtccctgacacaaagcaacgagactatagttgcaga
gcaagggacctcattctttggtgcctctacaattttttctgaaatccaacagcagatttataggacaaccccctttgggg
ctctattggatatacttttcccgcagcccttggttcacaaatcgcagataaggagtcaagacatctgttattcataggt
gatggtagtctacaattaacagttcaagaattaggcctatcaataagggagaagttaaacccaatctgtttcataa
ttaacaatgacggctacactgttgaaagggagatccacggaccaacacaatcatacaatgatattcccatgtgg
aactatagcaaattaccggagactttcggcgcaaccgaggatagagtagtttcgaagatcgttaggactgagaa
tgaatttgttagcgttatgaaggaagcccaggctgatgtcaatagaatgtattggattgaattagttttggaaaagg
aagatgcacctaaattactaaaaaagatggggaaactatttgctgagcaaaacaaacatcaccatcaccatca
ctaa

*Highlighted regions is the PDC1 DNA, non-highlighted is KdcA DNA

FIGURE 39

Fusion proteins between *Lactococcus lactis* KDCA and *Pichia stipitis* PDC 3-6 for increasing the affinity for branched keto acids

KDCA-PDC 3/6 fusion 1

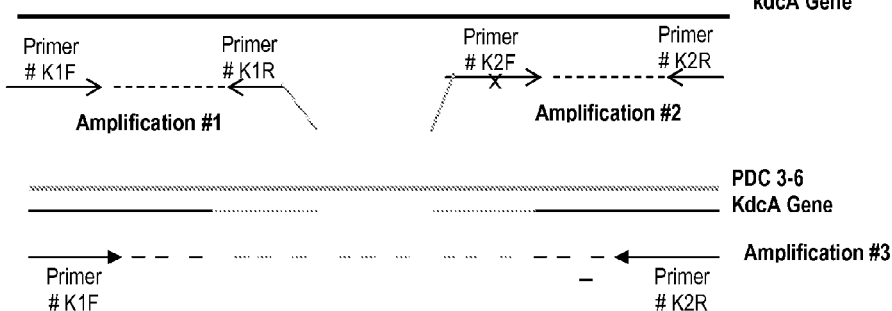

KDCA-PDC 3/6 fusion 2

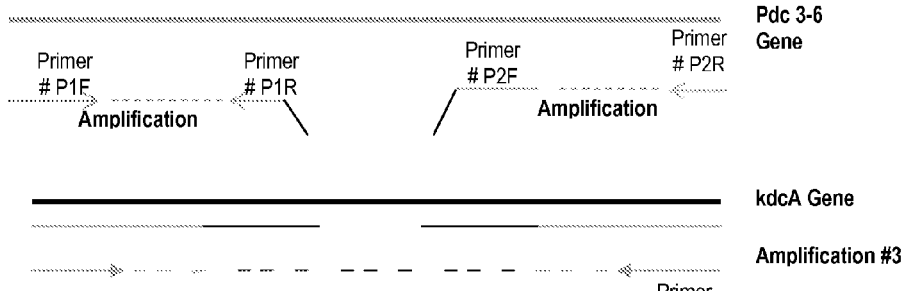

| Primer # | Sequence | SEQ ID NO |
|---|---|---|
| K1F | 5'-CTAGAACTAGTGGATCCCCCATGTATACAGTAGGAGATTACCTGTTAGAC | 113 |
| K1R | 5'-TTACTCTTGTACAATCTGAACAAAATAGCGTCAACAACGTCTTCTAATACTTCGACGCCAGAAGTGGTCAATTGGATTTCTTCTAAAGATAATGCAGGCTTCTCTGCTTT | 114 |
| K2F | 5'- ATGAGAATTTGCAGCCTGGTGATCTTTTGGTAATGGACACCATGTCATTCTGCTTTGCTTTACCTGACATAATGCTTCCAGAATTTATTCCATCAAGTGCTCCCTTATCA | 115 |
| K2R | 5'-ATATCGAATTCCTGCAGCCCCTATTTATTTTGCTCAGCAAATAATTTACC | 116 |
| P1F | 5'-CTAGAACTAGTGGATCCCCCATGACCCCTGTGCAAGAAACAATACGCCTT | 117 |
| P1R | 5'-GGTTTTTGGGCATTTTTCAAACTTTCTTCAATCTTACTCAAAATCACTTGTTCAGTTGTATTTGTTGTAGAGCTTTCTTTAGAAGTGGTCAATTGGATTTCAAGAGGTAA | 118 |
| P2F | 5'-ATTTTAGAGCAGTGGTTTCTTCTTTATCAGAATTAAAAGGAATAGAATATGAAGGACAATATATTGATAAGCAATATGAATACTATGGATCCATTGGCTATGCATTGCCA | 119 |
| P2R | 5'-ATATCGAATTCCTGCAGCCCCTATTTCTTGCAAAACATTTCGCTAAATCT | 120 |

FIGURE 40

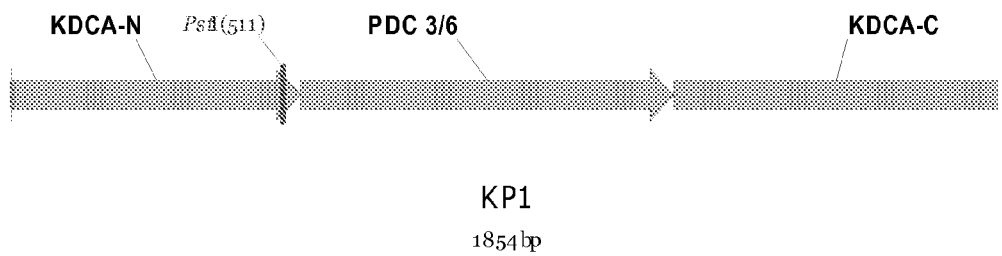

KP1
1854 bp

SEQ ID NO: 121 tatcacaagaccgtctatggcaggcagttgaaagtttgactcaaagcaatgaaacaatcgttgctgaacaaggaa
cctcattttttggagcttcaacaatttcttaaaatcaaatagtcgttttattggacaacctttatggggttctattggatat
acttttccagcggctttaggaagccaaattgcggataaagagagcagacacctttttatttattggtgatggttcactt
caacttaccgtacaagaattaggactatcaatcagagaaaaactcaatccaatttgttttatcataaataatgatggtt
atacagttgaaagagaaatccacggacctactcaaagttataacgacattccaatgtggaattactcgaaattacc
agaaacatttggagcaacagaagatcgtgtagtatcaaaaattgttagaacagagaatgaatttgtgtctgtcatga
agaagcccaagcagatgtcaatagaatgtattggatagaactagttttggaaaaagaagatgcgccaaaattac
tgaaaaaaatgggtaaattatttgctgagcaaaataaatagatgtatacagtaggagattacctgttagaccgatta
cacgagttgggaattgaagaaattttggagttcctggtgactataacttacaattttagatcaaattatttcacgcga
agatatgaaatggattggaaatgctaatgaattaaatgcttcttatatggctgatggttatgctcgtactaaaaaagct
gccgcatttctcaccacatttggagtcggcgaattgagtgcgatcaatggactggcaggaagttatgccgaaaatt
taccagtagtagaaattgttggttcaccaacttcaaaagtacaaaatgacggaaaatttgtccatcatacactagca
gatggtgattttaaacacttttatgaagatgcatgaacctgttacagcagcgcggactttactgacagcagaaaatg
ccacatatgaaattgaccgagtactttctcaattactaaaagaaagaaaaccagtctatattaacttaccagtcgatg
ttgctgcagcaaaagcagagaagcctgcattatctttagaagaaatccaattgaccacttctggcgtcgaagtatta
gaagacgttgttgacgctatttttgttcagattgtacaagagtaagaacccatcgttgttgtcggattgcttgactacca
gattcaatcttcaagacaagttaatacacttgttgctaaattaccttccaacttcgtcaagttgttttcgacaaacatg
gctagaaacatagatgagtcgctcagcaactttgtaggtctttactttggcattggttcttcaagcaaggaagtgtcc
agacaattggagagaaacaccgatttcttgatcaatttgggatactttaatgctgaaactacgactgctggttattcc
aatgacttctccaatatcgaggagtatattgaaatcaaccctgattacatcaaggtcaatgaacacatcattaacatt
aaaaatcctgagtctggaaagaggttgttctctatgggccagttgttggatgcattactctttaaattagacctcaac
aagattgagaacataaacaacaataatattagctacaagttcttcccaccaactttatatgagcaagacaacaatac
cgattacattccacaaacaaaactagtggactatttgaatgagaatttgcagcctggtgatcttttggtaatggacac
catgtcattctgctttgctttacctgacataatgcttccagaatttattccatcaagtgctccct

FIGURE 41

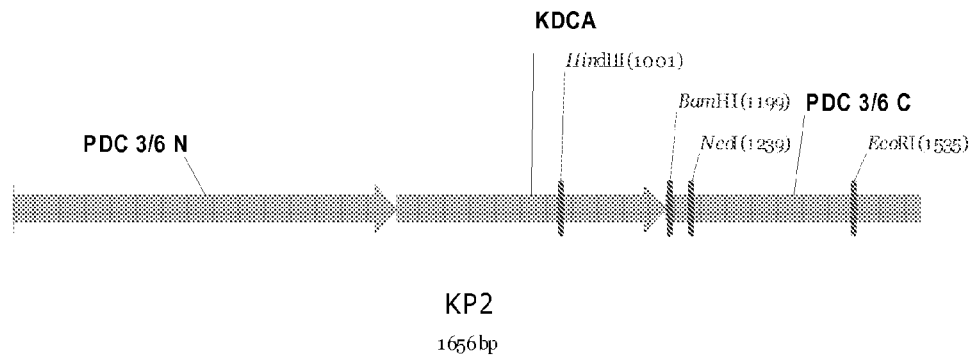

SEQ ID NO: 122 atgacccctgtgcaagaaacaatacgccttccaggcacttcttctcctacggttcctgaaaacgtcactttgg
gcgagtatctcttcctcagaatctctcaggctaatccaaagttgaggtccatctttggtattcctggcgacttca
atgtcgatttgttggaacacttgtactctccagttgtcgctggaagagacataaagtttattggcttatgtaacga
attgaatggtgcctacactgctgatggatactccagggccattggaggtttgagcactttatttctacattcggt
gttggtgaattgtcggccattaacggaatcgctggatcgtttgctgagttttctcctgtgcttcacattgtaggca
ccacctccttaccacaacgtgaccatgccattaacggcagcgacgttagaaaccaccaccacttaattcaaa
acaagaatcctttgtgtcagccaaatcatgatgtctacaagaagatgattgaacctatctcagttattcaggaat
ctttagacagtgatttgcaaaggaacatggaaaagattgatagagttttggttaagattctccaggaatctaga
cctggatacctctttatcccttgtgatattaccaacttaatagtcccaagctatagattatatgaaaccccattac
ctcttgaaatccaattgaccacttctaaagaaagctctacaacaaatacaactgaacaagtgattttgagtaag
attgaagaaagtttgaaaaatgcccaaaaaccagtagtgattgcaggacacgaagtaattagttttggtttaga
aaaaacggtaactcagtttgtttcagaaacaaaactaccgattacgacactaaattttggtaaaagtgctgttg
atgaatctttgccctcattttaggaatatataacgggaaactttcagaaatcagtcttaaaaattttgtggagtcc
gcagactttatcctaatgcttggagtgaagcttacggactcctcaacaggtgcattcacacatcatttagatga
aaataaaatgatttcactaaacatagatgaaggaataattttcaataaagtggtagaagattttgattttagagca
gtggtttcttctttatcagaattaaaaggaatagaatatgaaggacaatatattgataagcaatatgaatactatg
gatccattggctatgcattgccatccactttcggtgctaccatggcagtcaatgaccttggtagtgatagaaga
atcatcttaattgaaggtgatggggcagcccagatgactatccaggaattgtcttcgttcctcaaatacaagga
attttttgccaaacatgcctaagatcttcttgatcaataacgatggttacactgtcgagagaatgattaagggacc
aaccagatcatacaatgacatcaatggtgaatggagttggacacaattgcttggtgtgtttggagataaagag
caaaagtaccactctactgccttgttgcgcaatgtcaacgaattcaacaagtattttgaatttcaaaggcagac
tgacaattctaagttggagttcattgagttgatagccggcaaatacgattgtcctcttagatttagcgaaatgtttt
gcaagaaatag FIGURE 45
Isothermal Stitching of Hybrid Truncation Cassettes D,E,F,G
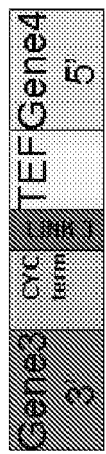
FRAG D
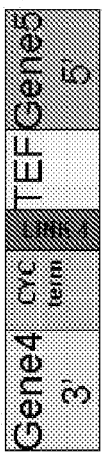
FRAG E
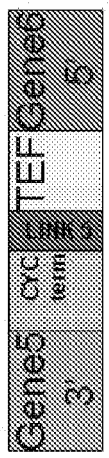
FRAG F
FRAG G
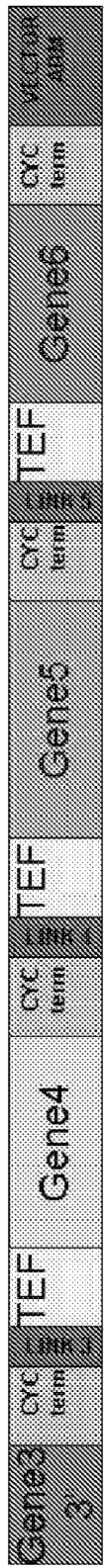
Isothermal product=frag DEFG FIGURE 58
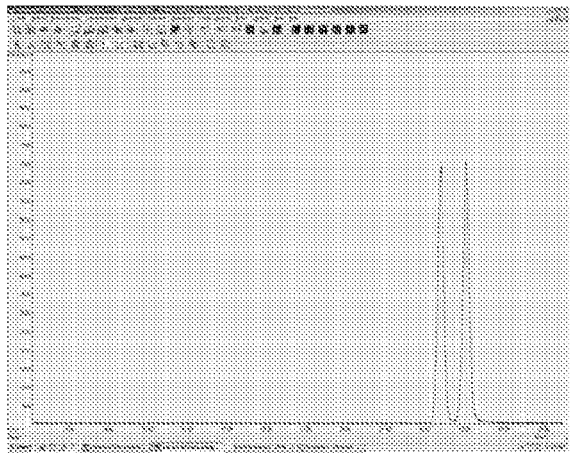
A.
±)-2-methylbutanol
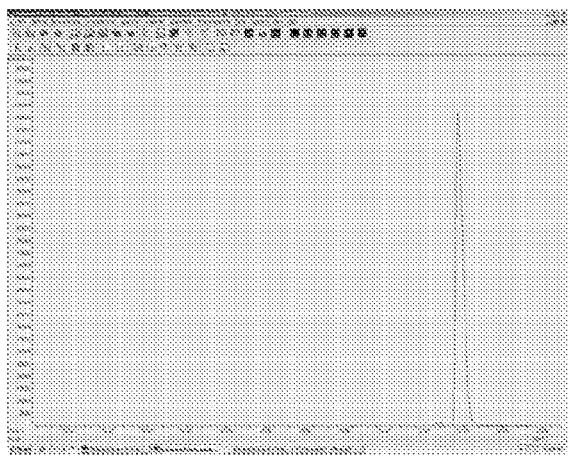
B.
(S)-2-methylbutanol
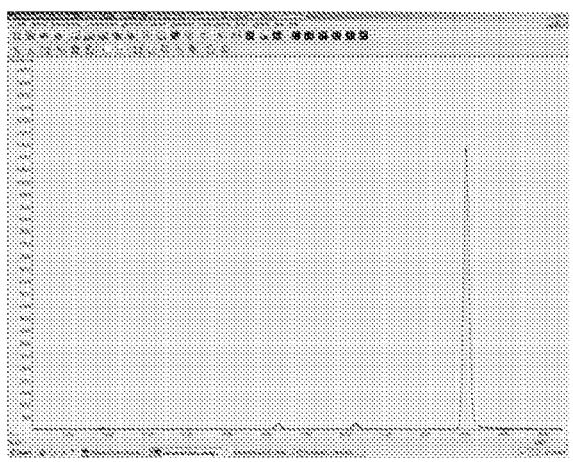
C.
$CH_2Cl_2$ extraction of broth YAC6insert
13812 bp YAC9-insert with hom3fbr on CUP promoter
20810 bp YAC7insert
16463 bp YAC7-insert with hom3fbr on CUP promoter
16079 bp YAC5insert
11315 bp YAC5-insert with ilv1fbr on CUP promoter YAC5truncated insert
10952 bp YAC5truncated insert with ilv1fbr on CUP promoter
10868 bp YAC14insert with hom3fbr, ilv1fbr on CUP promoter
32081bp YAC14insert with ILV truncations
31886 bp YAC14insert with ILV truncations, hom3fbr, ilv1fbr on CUP promoter
31718 bp FIGURE 74
A.
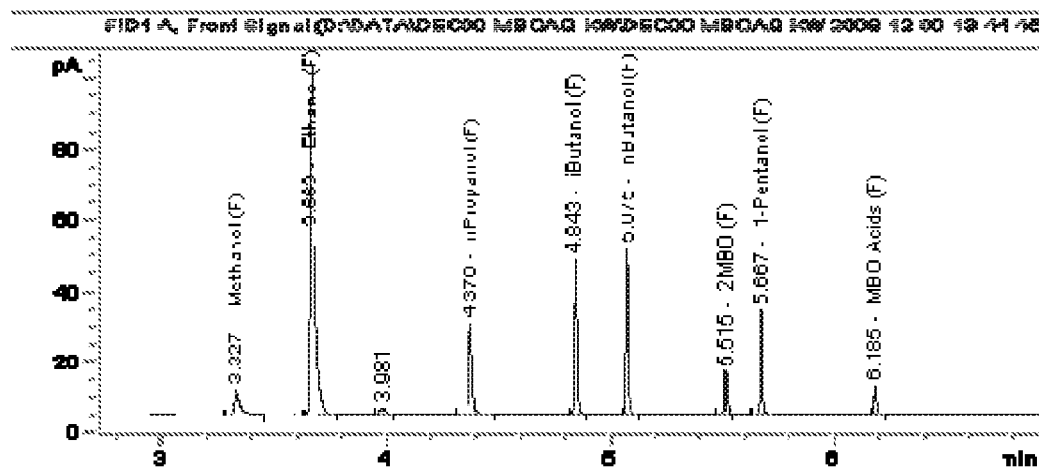
B.
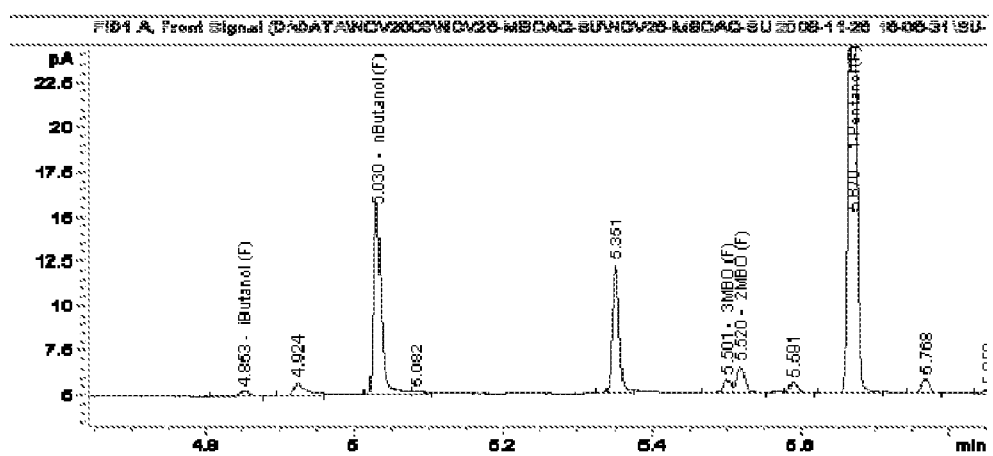
C.
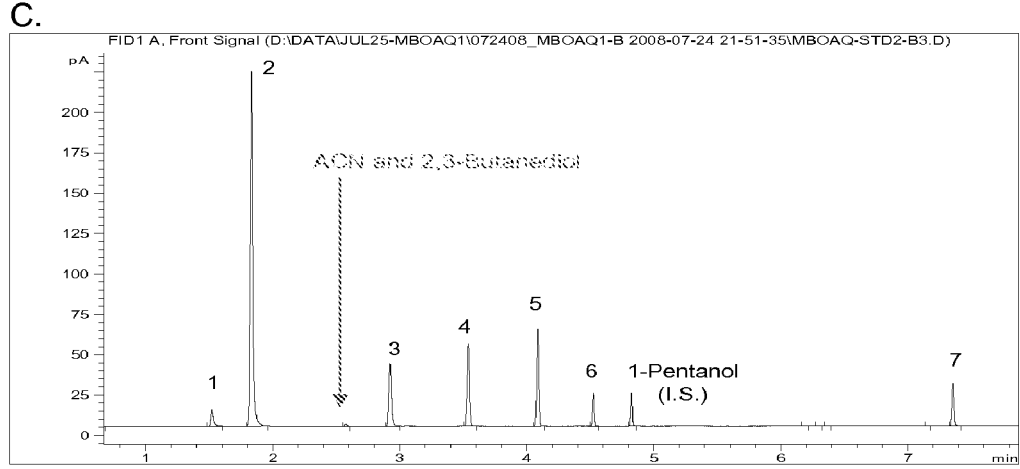

FIGURE 75
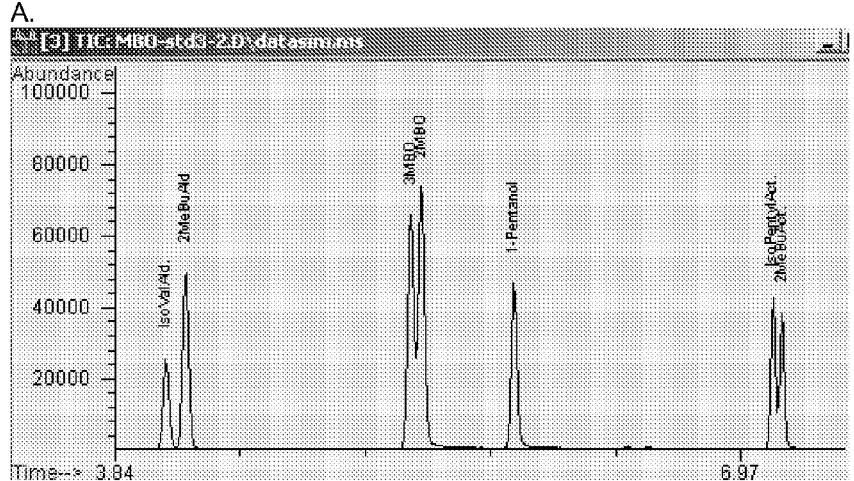
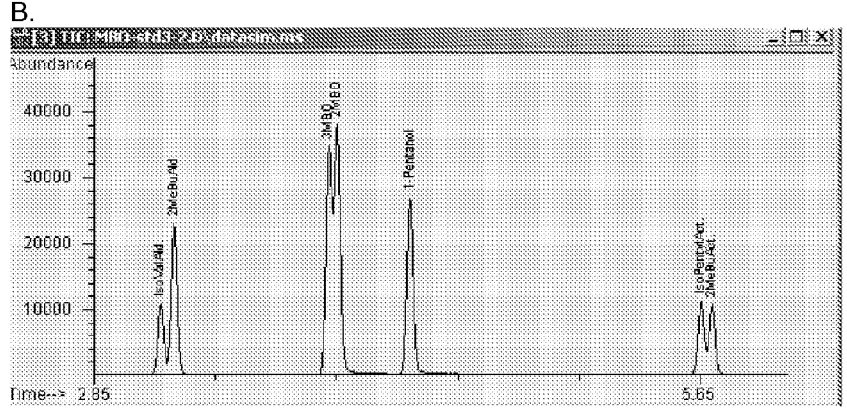
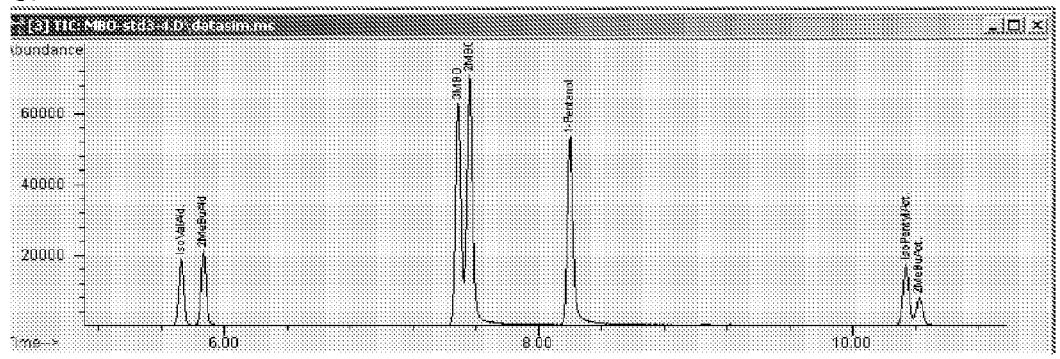

SEQUENCE LISTING

<160> NUMBER OF SEQ ID NOS: 122

<210> SEQ ID NO 1
<211> LENGTH: 377
<212> TYPE: PRT
<213> ORGANISM: Picihia stipitis

<400> SEQUENCE: 1

Met Pro His Ser Val Thr Pro Ser Ile Glu Gln Asp Ser Leu Lys Ile
1               5                   10                  15

Ala Ile Leu Gly Ala Ala Gly Gly Ile Gly Gln Ser Leu Ser Leu Leu
            20                  25                  30

Leu Lys Ala Gln Leu Gln Tyr Gln Leu Lys Glu Ser Asn Arg Ser Val
        35                  40                  45

Thr His Ile His Leu Ala Leu Tyr Asp Val Asn Gln Glu Ala Ile Asn
    50                  55                  60

Gly Val Thr Ala Asp Leu Ser His Ile Asp Thr Pro Ile Ser Val Ser
65                  70                  75                  80

Ser His Ser Pro Ala Gly Gly Ile Glu Asn Cys Leu His Asn Ala Ser
                85                  90                  95

Ile Val Val Ile Pro Ala Gly Val Pro Arg Lys Pro Gly Met Thr Arg
            100                 105                 110

Asp Asp Leu Phe Asn Val Asn Ala Gly Ile Ile Ser Gln Leu Gly Asp
        115                 120                 125

Ser Ile Ala Glu Cys Cys Asp Leu Ser Lys Val Phe Val Leu Val Ile
    130                 135                 140

Ser Asn Pro Val Asn Ser Leu Val Pro Val Met Val Ser Asn Ile Leu
145                 150                 155                 160

Lys Asn His Pro Gln Ser Arg Asn Ser Gly Ile Glu Arg Arg Ile Met
                165                 170                 175

Gly Val Thr Lys Leu Asp Ile Val Arg Ala Ser Thr Phe Leu Arg Glu
            180                 185                 190

Ile Asn Ile Glu Ser Gly Leu Thr Pro Arg Val Asn Ser Met Pro Asp
        195                 200                 205

Val Pro Val Ile Gly Gly His Ser Gly Glu Thr Ile Ile Pro Leu Phe
    210                 215                 220

Ser Gln Ser Asn Phe Leu Ser Arg Leu Asn Glu Asp Gln Leu Lys Tyr
225                 230                 235                 240

Leu Ile His Arg Val Gln Tyr Gly Gly Asp Glu Val Val Lys Ala Lys
                245                 250                 255

Asn Gly Lys Gly Ser Ala Thr Leu Ser Met Ala His Ala Gly Tyr Lys
            260                 265                 270

Cys Val Val Gln Phe Val Ser Leu Leu Leu Gly Asn Ile Glu Gln Ile
        275                 280                 285

His Gly Thr Tyr Tyr Val Pro Leu Lys Asp Ala Asn Asn Phe Pro Ile
    290                 295                 300

Ala Pro Gly Ala Asp Gln Leu Leu Pro Leu Val Asp Gly Ala Asp Tyr
305                 310                 315                 320

Phe Ala Ile Pro Leu Thr Ile Thr Thr Lys Gly Val Ser Tyr Val Asp
                325                 330                 335

Tyr Asp Ile Val Asn Arg Met Asn Asp Met Glu Arg Asn Gln Met Leu
            340                 345                 350

Pro Ile Cys Val Ser Gln Leu Lys Lys Asn Ile Asp Lys Gly Leu Glu
        355                 360                 365

```
Phe Val Ala Ser Arg Ser Ala Ser Ser
    370             375
```

```
<210> SEQ ID NO 2
<211> LENGTH: 346
<212> TYPE: PRT
<213> ORGANISM: Saccharomyces cerevisiae

<400> SEQUENCE: 2

Met Val Lys Val Thr Val Cys Gly Ala Ala Gly Gly Ile Gly Gln Pro
1               5                   10                  15
Leu Ser Leu Leu Leu Lys Leu Asn Pro Ala Val Ser Glu Leu Ala Leu
            20                  25                  30
Phe Asp Ile Val Asn Ala Lys Gly Val Ala Ala Asp Leu Ser His Ile
        35                  40                  45
Asn Thr Pro Ala Val Val Thr Gly His Gln Pro Ala Asn Lys Glu Asp
    50                  55                  60
Lys Thr Ala Ile Val Asp Ala Leu Lys Gly Thr Asp Leu Val Val Ile
65                  70                  75                  80
Pro Ala Gly Val Pro Arg Lys Pro Gly Met Thr Arg Ala Asp Leu Phe
                85                  90                  95
Asn Ile Asn Ala Ser Ile Ile Arg Asp Leu Val Ala Asn Ile Gly Arg
            100                 105                 110
Thr Ala Pro Asn Ala Ala Ile Leu Ile Ile Ser Asn Pro Val Asn Ala
        115                 120                 125
Thr Val Pro Ile Ala Ala Glu Val Leu Lys Lys Leu Gly Val Phe Asn
    130                 135                 140
Pro Gly Lys Leu Phe Gly Val Thr Thr Leu Asp Ser Val Arg Ala Glu
145                 150                 155                 160
Thr Phe Leu Gly Glu Leu Ile Asn Val Asn Pro Ser Gln Leu Gln Gly
                165                 170                 175
Arg Ile Ser Val Val Gly Gly His Ser Gly Asp Thr Ile Val Pro Leu
            180                 185                 190
Ile Asn Val Thr Pro Asp Val Ser Ala Lys Val Ala Asn Ile Ser Lys
        195                 200                 205
Ala Asp Tyr Asp Lys Phe Val Asn Arg Val Gln Phe Gly Gly Asp Glu
    210                 215                 220
Val Val Lys Ala Lys Asn Gly Ala Gly Ser Ala Thr Leu Ser Met Ala
225                 230                 235                 240
Tyr Ala Gly Tyr Arg Phe Ala Ala Gly Val Leu Asn Ser Leu Gly Gly
                245                 250                 255
Ala Ser Thr Ser Ser Ser Gly Val Pro Asp Ser Ser Tyr Val Tyr Leu
            260                 265                 270
Pro Gly Val Pro Gly Gly Lys Glu Phe Ser Ala Lys Tyr Leu Asn Gly
        275                 280                 285
Val Asp Phe Phe Ser Val Pro Ile Val Leu Glu Asn Gly Val Ile Lys
    290                 295                 300
Ser Phe Ile Asn Pro Phe Glu His Met Lys Ile Thr Gln Lys Glu Gln
305                 310                 315                 320
Glu Leu Val Lys Val Ala Leu Gly Gly Leu Glu Lys Ser Ile Glu Gln
                325                 330                 335
Gly Thr Asn Phe Val Lys Gly Ser Lys Leu
            340                 345

<210> SEQ ID NO 3
```

<211> LENGTH: 1179
<212> TYPE: PRT
<213> ORGANISM: Picihia stipitis

<400> SEQUENCE: 3

```
Met Ser Ser Leu Ser Pro His Asp His His Gly Lys Ile Asn Gln Met
 1               5                  10                  15
Arg Arg Asp Ser Thr Val Leu Gly Pro Met Asn Lys Ile Leu Val Ala
            20                  25                  30
Asn Arg Gly Glu Ile Pro Ile Arg Ile Phe Arg Thr Ala His Glu Leu
        35                  40                  45
Ser Met Gln Thr Val Ala Ile Tyr Ser His Glu Asp Arg Leu Ser Met
 50                  55                  60
His Arg Leu Lys Ala Asp Glu Ser Tyr Val Ile Gly Lys Lys Gly Glu
 65                  70                  75                  80
Phe Ser Pro Val Gly Ala Tyr Leu Gln Ile Asp Glu Ile Ile Lys Ile
                85                  90                  95
Ala Lys Thr His Asn Val Asn Met Ile His Pro Gly Tyr Gly Phe Leu
            100                 105                 110
Ser Glu Asn Ser Glu Phe Ala Arg Lys Val Glu Glu Ala Gly Ile Ala
        115                 120                 125
Trp Ile Gly Pro Thr His Glu Thr Ile Asp Ala Val Gly Asp Lys Val
130                 135                 140
Ser Ala Arg Asn Leu Ala Leu Ala Asn Asp Val Pro Val Val Pro Gly
145                 150                 155                 160
Thr Pro Gly Pro Ile Asp Ser Val Glu Glu Ala Glu Ala Phe Val Glu
                165                 170                 175
Lys Tyr Gly Tyr Pro Val Ile Ile Lys Ala Ala Phe Gly Gly Gly Gly
            180                 185                 190
Arg Gly Met Arg Val Val Arg Glu Gly Asp Asp Ile Gly Asp Ala Phe
        195                 200                 205
Lys Arg Ala Thr Ser Glu Ala Lys Thr Ala Phe Gly Asn Gly Thr Cys
210                 215                 220
Phe Ile Glu Arg Phe Leu Asp Lys Pro Lys His Ile Glu Val Gln Leu
225                 230                 235                 240
Leu Ala Asp Gly Tyr Gly Asn Val Ile His Leu Phe Glu Arg Asp Cys
                245                 250                 255
Ser Val Gln Arg Arg His Gln Lys Val Val Glu Ile Ala Pro Ala Lys
            260                 265                 270
Asn Leu Pro Lys Ala Val Arg Asp Ala Ile Leu Thr Asp Ala Val Lys
        275                 280                 285
Leu Ala Lys Ser Ala Asn Tyr Arg Asn Ala Gly Thr Ala Glu Phe Leu
290                 295                 300
Val Asp Glu Gln Asn Arg His Tyr Phe Ile Glu Ile Asn Pro Arg Ile
305                 310                 315                 320
Gln Val Glu His Thr Ile Thr Glu Glu Ile Thr Gly Val Asp Ile Val
                325                 330                 335
Ala Ala Gln Ile Gln Ile Ala Ala Gly Ala Ser Leu Gln Gln Leu Gly
            340                 345                 350
Leu Leu Gln Asp Lys Ile Thr Thr Arg Gly Phe Ala Ile Gln Cys Arg
        355                 360                 365
Ile Thr Thr Glu Asp Pro Ser Lys Asn Phe Gln Pro Asp Thr Gly Lys
370                 375                 380
Ile Glu Val Tyr Arg Ser Ser Gly Gly Asn Gly Val Arg Leu Asp Gly
385                 390                 395                 400
```

```
Gly Asn Gly Phe Ala Gly Ser Ile Ile Ser Pro His Tyr Asp Ser Met
                405                 410                 415
Leu Val Lys Cys Ser Thr Ser Gly Ser Thr Tyr Glu Ile Ala Arg Arg
                420                 425                 430
Lys Met Leu Arg Ala Leu Ile Glu Phe Arg Ile Arg Gly Val Lys Thr
                435                 440                 445
Asn Ile Pro Phe Leu Leu Ala Leu Leu Thr Asn Glu Thr Phe Ile Ser
                450                 455                 460
Gly Ser Cys Trp Thr Thr Phe Ile Asp Asp Thr Pro Ser Leu Phe Gln
465                 470                 475                 480
Met Ile Ser Ser Gln Asn Arg Ala Asn Lys Ile Leu Ser Tyr Leu Ala
                485                 490                 495
Asp Leu Ile Val Asn Gly Ser Ser Ile Lys Gly Gln Val Gly Leu Pro
                500                 505                 510
Lys Leu Asn Glu Glu Ala Glu Ile Pro Thr Ile His Asp Pro Lys Thr
                515                 520                 525
Gly Ile Pro Ile Asp Val Glu Leu Asn Pro Ala Pro Arg Gly Trp Arg
                530                 535                 540
Gln Val Leu Leu Glu Glu Gly Pro Asp Ala Phe Ala Lys Lys Val Arg
545                 550                 555                 560
Asn Phe Asn Gly Thr Leu Ile Thr Asp Thr Thr Trp Arg Asp Ala His
                565                 570                 575
Gln Ser Leu Leu Ala Thr Arg Leu Arg Thr Ile Asp Leu Leu Asn Ile
                580                 585                 590
Ala Pro Thr Thr Ala His Ala Leu Asn Gly Ala Phe Ser Leu Glu Cys
                595                 600                 605
Trp Gly Gly Ala Thr Phe Asp Val Cys Met Arg Phe Leu Tyr Glu Asp
                610                 615                 620
Pro Trp Ala Arg Leu Arg Lys Leu Arg Lys Leu Val Pro Asn Ile Pro
625                 630                 635                 640
Phe Gln Met Leu Leu Arg Gly Ala Asn Gly Val Ala Tyr Ser Ser Leu
                645                 650                 655
Pro Asp Asn Ala Ile Asp Gln Phe Val Lys Gln Ala Lys Asp Asn Gly
                660                 665                 670
Val Asp Ile Phe Arg Val Phe Asp Ala Leu Asn Asp Leu Asp Gln Leu
                675                 680                 685
Lys Val Gly Ile Asp Ala Val Lys Lys Ala Gly Gly Val Val Glu Ala
                690                 695                 700
Thr Val Cys Tyr Ser Gly Asp Met Leu Gln Lys Gly Lys Lys Tyr Asn
705                 710                 715                 720
Leu Ala Tyr Tyr Val Asp Val Val Asp Lys Ile Val Ala Met Gly Thr
                725                 730                 735
His Phe Leu Gly Ile Lys Asp Met Ala Gly Thr Leu Lys Pro Lys Ala
                740                 745                 750
Ala Thr Asp Leu Val Ser Ala Ile Arg Ala Lys Tyr Pro Asp Leu Pro
                755                 760                 765
Ile His Val His Thr His Asp Ser Ala Gly Thr Gly Val Ala Ser Met
                770                 775                 780
Thr Ala Ala Ala Lys Ala Gly Ala Asp Val Val Asp Ala Ala Ser Asn
785                 790                 795                 800
Ser Met Ser Gly Met Thr Ser Gln Pro Ser Ile Ser Ala Ile Leu Ala
                805                 810                 815
Ser Phe Glu Gly Glu Val Glu Thr Gly Leu Ser Glu Arg Leu Val Arg
```

```
                        820                 825                 830
Glu Ile Asp His Tyr Trp Ala Gln Met Arg Leu Leu Tyr Ser Cys Phe
        835                 840                 845

Glu Ala Asp Leu Lys Gly Pro Asp Pro Glu Val Tyr Glu His Glu Ile
850                 855                 860

Pro Gly Gly Gln Leu Thr Asn Leu Leu Phe Gln Ala Gln Gln Leu Gly
865                 870                 875                 880

Leu Gly Ala Lys Trp Leu Gln Thr Lys Glu Thr Tyr Lys Ile Ala Asn
                885                 890                 895

Arg Val Leu Gly Asp Val Val Lys Val Thr Pro Thr Ser Lys Val Val
                900                 905                 910

Gly Asp Leu Ala Gln Phe Met Val Ser Asn Asn Leu Thr Glu Glu Asp
                915                 920                 925

Val Asn Lys Leu Ala Gly Glu Leu Asp Phe Pro Asp Ser Val Leu Asp
        930                 935                 940

Phe Met Glu Gly Leu Met Gly Thr Pro Tyr Gly Gly Phe Pro Glu Pro
945                 950                 955                 960

Leu Arg Thr Asn Met Leu Gly Asn Lys Arg Gln Lys Leu Asn Glu Arg
                965                 970                 975

Pro Gly Leu Ser Leu Ala Pro Val Asp Phe Ser Ala Leu Lys Gln Glu
            980                 985                 990

Leu Val Ser Lys Tyr Gly Asn Ser Ile Lys Glu Val Asp Leu Ala Ser
                995                 1000                1005

Tyr Thr Met Tyr Pro Lys Val Tyr Glu Ser Tyr Arg Lys Ile Val Glu
        1010                1015                1020

Lys Tyr Gly Asp Leu Ser Val Leu Pro Thr Arg Tyr Phe Leu Lys Gly
1025                1030                1035                1040

Ile Asn Val Gly Glu Glu Leu Ser Val Glu Ile Gln Gly Lys Thr
                1045                1050                1055

Leu Ile Val Lys Leu Leu Ala Val Gly Glu Ile Ser Gln Lys Gly
            1060                1065                1070

Thr Arg Glu Val Phe Phe Glu Leu Asn Gly Glu Met Arg Ser Val Thr
        1075                1080                1085

Val Asp Asp Lys Thr Val Ser Val Glu Thr Ile Thr Arg Arg Lys Ala
    1090                1095                1100

Thr Gln Pro Asn Glu Val Gly Ala Pro Met Ala Gly Val Val Ile Glu
1105                1110                1115                1120

Ile Arg Thr Gln Ser Gly Thr Asp Val Lys Lys Gly Asp Pro Ile Ala
                1125                1130                1135

Val Leu Ser Ala Met Lys Met Glu Met Val Ile Ser Ala Pro Val Ser
            1140                1145                1150

Gly Val Val Gly Glu Ile Leu Ile Lys Glu Gly Glu Ser Val Asp Ala
                1155                1160                1165

Ser Asp Leu Ile Thr Ser Ile Leu Lys His Asn
    1170                1175

<210> SEQ ID NO 4
<211> LENGTH: 1178
<212> TYPE: PRT
<213> ORGANISM: Saccharomyces cerevisiae

<400> SEQUENCE: 4

Met Ser Gln Arg Lys Phe Ala Gly Leu Arg Asp Asn Phe Asn Leu Leu
1               5                   10                  15

Gly Glu Lys Asn Lys Ile Leu Val Ala Asn Arg Gly Glu Ile Pro Ile
```

```
                    20                  25                  30
Arg Ile Phe Arg Thr Ala His Glu Leu Ser Met Gln Thr Val Ala Ile
                35                  40                  45
Tyr Ser His Glu Asp Arg Leu Ser Thr His Lys Gln Lys Ala Asp Glu
 50                  55                  60
Ala Tyr Val Ile Gly Glu Val Gly Gln Tyr Thr Pro Val Gly Ala Tyr
 65                  70                  75                  80
Leu Ala Ile Asp Glu Ile Ile Ser Ile Ala Gln Lys His Gln Val Asp
                 85                  90                  95
Phe Ile His Pro Gly Tyr Gly Phe Leu Ser Glu Asn Ser Glu Phe Ala
                100                 105                 110
Asp Lys Val Val Lys Ala Gly Ile Thr Trp Ile Gly Pro Pro Ala Glu
                115                 120                 125
Val Ile Asp Ser Val Gly Asp Lys Val Ser Ala Arg Asn Leu Ala Ala
 130                 135                 140
Lys Ala Asn Val Pro Thr Val Pro Gly Thr Pro Gly Pro Ile Glu Thr
145                 150                 155                 160
Val Glu Glu Ala Leu Asp Phe Val Asn Glu Tyr Gly Tyr Pro Val Ile
                165                 170                 175
Ile Lys Ala Ala Phe Gly Gly Gly Arg Gly Met Arg Val Val Arg
                180                 185                 190
Glu Gly Asp Asp Val Ala Asp Ala Phe Gln Arg Ala Thr Ser Glu Ala
                195                 200                 205
Arg Thr Ala Phe Gly Asn Gly Thr Cys Phe Val Glu Arg Phe Leu Asp
 210                 215                 220
Lys Pro Lys His Ile Glu Val Gln Leu Leu Ala Asp Asn His Gly Asn
225                 230                 235                 240
Val Val His Leu Phe Glu Arg Asp Cys Ser Val Gln Arg Arg His Gln
                245                 250                 255
Lys Val Val Glu Val Ala Pro Ala Lys Thr Leu Pro Arg Glu Val Arg
                260                 265                 270
Asp Ala Ile Leu Thr Asp Ala Val Lys Leu Ala Lys Glu Cys Gly Tyr
 275                 280                 285
Arg Asn Ala Gly Thr Ala Glu Phe Leu Val Asp Asn Gln Asn Arg His
290                 295                 300
Tyr Phe Ile Glu Ile Asn Pro Arg Ile Gln Val Glu His Thr Ile Thr
305                 310                 315                 320
Glu Glu Ile Thr Gly Ile Asp Ile Val Ala Ala Gln Ile Gln Ile Ala
                325                 330                 335
Ala Gly Ala Ser Leu Pro Gln Leu Gly Leu Phe Gln Asp Lys Ile Thr
                340                 345                 350
Thr Arg Gly Phe Ala Ile Gln Cys Arg Ile Thr Thr Glu Asp Pro Ala
                355                 360                 365
Lys Asn Phe Gln Pro Asp Thr Gly Arg Ile Glu Val Tyr Arg Ser Ala
                370                 375                 380
Gly Gly Asn Gly Val Arg Leu Asp Gly Gly Asn Ala Tyr Ala Gly Thr
385                 390                 395                 400
Ile Ile Ser Pro His Tyr Asp Ser Met Leu Val Lys Cys Ser Cys Ser
                405                 410                 415
Gly Ser Thr Tyr Glu Ile Val Arg Arg Lys Met Ile Arg Ala Leu Ile
                420                 425                 430
Glu Phe Arg Ile Arg Gly Val Lys Thr Asn Ile Pro Phe Leu Leu Thr
                435                 440                 445
```

-continued

```
Leu Leu Thr Asn Pro Val Phe Ile Glu Gly Thr Tyr Trp Thr Thr Phe
450                 455                 460

Ile Asp Asp Thr Pro Gln Leu Phe Gln Met Val Ser Ser Gln Asn Arg
465                 470                 475                 480

Ala Gln Lys Leu Leu His Tyr Leu Ala Asp Val Ala Val Asn Gly Ser
                485                 490                 495

Ser Ile Lys Gly Gln Ile Gly Leu Pro Lys Leu Lys Ser Asn Pro Ser
            500                 505                 510

Val Pro His Leu His Asp Ala Gln Gly Asn Val Ile Asn Val Thr Lys
        515                 520                 525

Ser Ala Pro Pro Ser Gly Trp Arg Gln Val Leu Glu Lys Gly Pro
530                 535                 540

Ala Glu Phe Ala Arg Gln Val Arg Gln Phe Asn Gly Thr Leu Leu Met
545                 550                 555                 560

Asp Thr Thr Trp Arg Asp Ala His Gln Ser Leu Leu Ala Thr Arg Val
                565                 570                 575

Arg Thr His Asp Leu Ala Thr Ile Ala Pro Thr Thr Ala His Ala Leu
                580                 585                 590

Ala Gly Arg Phe Ala Leu Glu Cys Trp Gly Ala Thr Phe Asp Val
                595                 600                 605

Ala Met Arg Phe Leu His Glu Asp Pro Trp Glu Arg Leu Arg Lys Leu
        610                 615                 620

Arg Ser Leu Val Pro Asn Ile Pro Phe Gln Met Leu Leu Arg Gly Ala
625                 630                 635                 640

Asn Gly Val Ala Tyr Ser Ser Leu Pro Asp Asn Ala Ile Asp His Phe
                645                 650                 655

Val Lys Gln Ala Lys Asp Asn Gly Val Asp Ile Phe Arg Val Phe Asp
            660                 665                 670

Ala Leu Asn Asp Leu Glu Gln Leu Lys Val Gly Val Asp Ala Val Lys
                675                 680                 685

Lys Ala Gly Gly Val Val Glu Ala Thr Val Cys Phe Ser Gly Asp Met
        690                 695                 700

Leu Gln Pro Gly Lys Lys Tyr Asn Leu Asp Tyr Tyr Leu Glu Ile Ala
705                 710                 715                 720

Glu Lys Ile Val Gln Met Gly Thr His Ile Leu Gly Ile Lys Asp Met
                725                 730                 735

Ala Gly Thr Met Lys Pro Ala Ala Ala Lys Leu Leu Ile Gly Ser Leu
                740                 745                 750

Arg Ala Lys Tyr Pro Asp Leu Pro Ile His Val His Thr His Asp Ser
            755                 760                 765

Ala Gly Thr Ala Val Ala Ser Met Thr Ala Cys Ala Leu Ala Gly Ala
        770                 775                 780

Asp Val Val Asp Val Ala Ile Asn Ser Met Ser Gly Leu Thr Ser Gln
785                 790                 795                 800

Pro Ser Ile Asn Ala Leu Leu Ala Ser Leu Glu Gly Asn Ile Asp Thr
                805                 810                 815

Gly Ile Asn Val Glu His Val Arg Glu Leu Asp Ala Tyr Trp Ala Glu
            820                 825                 830

Met Arg Leu Leu Tyr Ser Cys Phe Glu Ala Asp Leu Lys Gly Pro Asp
        835                 840                 845

Pro Glu Val Tyr Gln His Glu Ile Pro Gly Gly Gln Leu Thr Asn Leu
        850                 855                 860

Leu Phe Gln Ala Gln Gln Leu Gly Leu Gly Glu Gln Trp Ala Glu Thr
865                 870                 875                 880
```

Lys Arg Ala Tyr Arg Glu Ala Asn Tyr Leu Leu Gly Asp Ile Val Lys
                885                 890                 895

Val Thr Pro Thr Ser Lys Val Val Gly Asp Leu Ala Gln Phe Met Val
            900                 905                 910

Ser Asn Lys Leu Thr Ser Asp Asp Val Arg Arg Leu Ala Asn Ser Leu
            915                 920                 925

Asp Phe Pro Asp Ser Val Met Asp Phe Glu Gly Leu Ile Gly Gln
        930                 935                 940

Pro Tyr Gly Gly Phe Pro Glu Pro Phe Arg Ser Asp Val Leu Arg Asn
945                 950                 955                 960

Lys Arg Arg Lys Leu Thr Cys Arg Pro Gly Leu Glu Leu Glu Pro Phe
                965                 970                 975

Asp Leu Glu Lys Ile Arg Glu Asp Leu Gln Asn Arg Phe Gly Asp Val
            980                 985                 990

Asp Glu Cys Asp Val Ala Ser Tyr Asn Met Tyr Pro Arg Val Tyr Glu
            995                 1000                1005

Asp Phe Gln Lys Met Arg Glu Thr Tyr Gly Asp Leu Ser Val Leu Pro
        1010                1015                1020

Thr Arg Ser Phe Leu Ser Pro Leu Glu Thr Asp Glu Ile Glu Val
1025                1030                1035                1040

Val Ile Glu Gln Gly Lys Thr Leu Ile Ile Lys Leu Gln Ala Val Gly
                1045                1050                1055

Asp Leu Asn Lys Lys Thr Gly Glu Arg Glu Val Tyr Phe Asp Leu Asn
            1060                1065                1070

Gly Glu Met Arg Lys Ile Arg Val Ala Asp Arg Ser Gln Lys Val Glu
            1075                1080                1085

Thr Val Thr Lys Ser Lys Ala Asp Met His Asp Pro Leu His Ile Gly
        1090                1095                1100

Ala Pro Met Ala Gly Val Ile Val Glu Val Lys Val His Lys Gly Ser
1105                1110                1115                1120

Leu Ile Lys Lys Gly Gln Pro Val Ala Val Leu Ser Ala Met Lys Met
                1125                1130                1135

Glu Met Ile Ile Ser Ser Pro Ser Asp Gly Gln Val Lys Glu Val Phe
            1140                1145                1150

Val Ser Asp Gly Glu Asn Val Asp Ser Ser Asp Leu Leu Val Leu Leu
            1155                1160                1165

Glu Asp Gln Val Pro Val Glu Thr Lys Ala
        1170                1175

<210> SEQ ID NO 5
<211> LENGTH: 1180
<212> TYPE: PRT
<213> ORGANISM: Saccharomyces cerevisiae

<400> SEQUENCE: 5

Met Ser Ser Ser Lys Lys Leu Ala Gly Leu Arg Asp Asn Phe Ser Leu
1               5                   10                  15

Leu Gly Glu Lys Asn Lys Ile Leu Val Ala Asn Arg Gly Glu Ile Pro
            20                  25                  30

Ile Arg Ile Phe Arg Ser Ala His Glu Leu Ser Met Arg Thr Ile Ala
        35                  40                  45

Ile Tyr Ser His Glu Asp Arg Leu Ser Met His Arg Leu Lys Ala Asp
    50                  55                  60

Glu Ala Tyr Val Ile Gly Glu Gly Gly Gln Tyr Thr Pro Val Gly Ala
65                  70                  75                  80

-continued

```
Tyr Leu Ala Met Asp Glu Ile Ile Glu Ile Ala Lys Lys His Lys Val
                 85                  90                  95

Asp Phe Ile His Pro Gly Tyr Gly Phe Leu Ser Glu Asn Ser Glu Phe
                100                 105                 110

Ala Asp Lys Val Val Lys Ala Gly Ile Thr Trp Ile Gly Pro Pro Ala
                115                 120                 125

Glu Val Ile Asp Ser Val Gly Asp Lys Val Ser Ala Arg His Leu Ala
130                 135                 140

Ala Arg Ala Asn Val Pro Thr Val Pro Gly Thr Pro Gly Pro Ile Glu
145                 150                 155                 160

Thr Val Gln Glu Ala Leu Asp Phe Val Asn Glu Tyr Gly Tyr Pro Val
                165                 170                 175

Ile Ile Lys Ala Ala Phe Gly Gly Gly Gly Arg Gly Met Arg Val Val
                180                 185                 190

Arg Glu Gly Asp Asp Val Ala Asp Ala Phe Gln Arg Ala Thr Ser Glu
                195                 200                 205

Ala Arg Thr Ala Phe Gly Asn Gly Thr Cys Phe Val Glu Arg Phe Leu
                210                 215                 220

Asp Lys Pro Lys His Ile Glu Val Gln Leu Leu Ala Asp Asn His Gly
225                 230                 235                 240

Asn Val Val His Leu Phe Glu Arg Asp Cys Ser Val Gln Arg Arg His
                245                 250                 255

Gln Lys Val Val Glu Val Ala Pro Ala Lys Thr Leu Pro Arg Glu Val
                260                 265                 270

Arg Asp Ala Ile Leu Thr Asp Ala Val Lys Leu Ala Lys Val Cys Gly
                275                 280                 285

Tyr Arg Asn Ala Gly Thr Ala Glu Phe Leu Val Asp Asn Gln Asn Arg
                290                 295                 300

His Tyr Phe Ile Glu Ile Asn Pro Arg Ile Gln Val Glu His Thr Ile
305                 310                 315                 320

Thr Glu Glu Ile Thr Gly Ile Asp Ile Val Ser Ala Gln Ile Gln Ile
                325                 330                 335

Ala Ala Gly Ala Thr Leu Thr Gln Leu Gly Leu Leu Gln Asp Lys Ile
                340                 345                 350

Thr Thr Arg Gly Phe Ser Ile Gln Cys Arg Ile Thr Thr Glu Asp Pro
                355                 360                 365

Ser Lys Asn Phe Gln Pro Asp Thr Gly Arg Leu Glu Val Tyr Arg Ser
                370                 375                 380

Ala Gly Gly Asn Gly Val Arg Leu Asp Gly Gly Asn Ala Tyr Ala Gly
385                 390                 395                 400

Ala Thr Ile Ser Pro His Tyr Asp Ser Met Leu Val Lys Cys Ser Cys
                405                 410                 415

Ser Gly Ser Thr Tyr Glu Ile Val Arg Arg Lys Met Ile Arg Ala Leu
                420                 425                 430

Ile Glu Phe Arg Ile Arg Gly Val Lys Thr Asn Ile Pro Phe Leu Leu
                435                 440                 445

Thr Leu Leu Thr Asn Pro Val Phe Ile Glu Gly Thr Tyr Trp Thr Thr
                450                 455                 460

Phe Ile Asp Asp Thr Pro Gln Leu Phe Gln Met Val Ser Ser Gln Asn
465                 470                 475                 480

Arg Ala Gln Lys Leu Leu His Tyr Leu Ala Asp Leu Ala Val Asn Gly
                485                 490                 495

Ser Ser Ile Lys Gly Gln Ile Gly Leu Pro Lys Leu Lys Ser Asn Pro
```

```
                500             505             510
Ser Val Pro His Leu His Asp Ala Gln Gly Asn Val Ile Asn Val Thr
    515                 520                 525
Lys Ser Ala Pro Pro Ser Gly Trp Arg Gln Val Leu Leu Glu Lys Gly
530                 535                 540
Pro Ser Glu Phe Ala Lys Gln Val Arg Gln Phe Asn Gly Thr Leu Leu
545                 550                 555                 560
Met Asp Thr Thr Trp Arg Asp Ala His Gln Ser Leu Leu Ala Thr Arg
                565                 570                 575
Val Arg Thr His Asp Leu Ala Thr Ile Ala Pro Thr Thr Ala His Ala
            580                 585                 590
Leu Ala Gly Ala Phe Ala Leu Glu Cys Trp Gly Gly Ala Thr Phe Asp
        595                 600                 605
Val Ala Met Arg Phe Leu His Glu Asp Pro Trp Glu Arg Leu Arg Lys
    610                 615                 620
Leu Arg Ser Leu Val Pro Asn Ile Pro Phe Gln Met Leu Leu Arg Gly
625                 630                 635                 640
Ala Asn Gly Val Ala Tyr Ser Ser Leu Pro Asp Asn Ala Ile Asp His
                645                 650                 655
Phe Val Lys Gln Ala Lys Asp Asn Gly Val Asp Ile Phe Arg Val Phe
            660                 665                 670
Asp Ala Leu Asn Asp Leu Glu Gln Leu Lys Val Gly Val Asn Ala Val
        675                 680                 685
Lys Lys Ala Gly Gly Val Val Glu Ala Thr Val Cys Tyr Ser Gly Asp
    690                 695                 700
Met Leu Gln Pro Gly Lys Lys Tyr Asn Leu Asp Tyr Tyr Leu Glu Val
705                 710                 715                 720
Val Glu Lys Ile Val Gln Met Gly Thr His Ile Leu Gly Ile Lys Asp
                725                 730                 735
Met Ala Gly Thr Met Lys Pro Ala Ala Ala Lys Leu Leu Ile Gly Ser
            740                 745                 750
Leu Arg Thr Arg Tyr Pro Asp Leu Pro Ile His Val His Ser His Asp
        755                 760                 765
Ser Ala Gly Thr Ala Val Ala Ser Met Thr Ala Cys Ala Leu Ala Gly
    770                 775                 780
Ala Asp Val Val Asp Val Ala Ile Asn Ser Met Ser Gly Leu Thr Ser
785                 790                 795                 800
Gln Pro Ser Ile Asn Ala Leu Leu Ala Ser Leu Glu Gly Asn Ile Asp
                805                 810                 815
Thr Gly Ile Asn Val Glu His Val Arg Glu Leu Asp Ala Tyr Trp Ala
            820                 825                 830
Glu Met Arg Leu Leu Tyr Ser Cys Phe Glu Ala Asp Leu Lys Gly Pro
        835                 840                 845
Asp Pro Glu Val Tyr Gln His Glu Ile Pro Gly Gly Gln Leu Thr Asn
    850                 855                 860
Leu Leu Phe Gln Ala Gln Gln Leu Gly Leu Gly Glu Gln Trp Ala Glu
865                 870                 875                 880
Thr Lys Arg Ala Tyr Arg Glu Ala Asn Tyr Leu Leu Gly Asp Ile Val
                885                 890                 895
Lys Val Thr Pro Thr Ser Lys Val Val Gly Asp Leu Ala Gln Phe Met
            900                 905                 910
Val Ser Asn Lys Leu Thr Ser Asp Asp Ile Arg Arg Leu Ala Asn Ser
        915                 920                 925
```

```
Leu Asp Phe Pro Asp Ser Val Met Asp Phe Glu Gly Leu Ile Gly
    930                 935                 940

Gln Pro Tyr Gly Gly Phe Pro Glu Pro Leu Arg Ser Asp Val Leu Arg
945                 950                 955                 960

Asn Lys Arg Arg Lys Leu Thr Cys Arg Pro Gly Leu Glu Leu Glu Pro
                965                 970                 975

Phe Asp Leu Glu Lys Ile Arg Glu Asp Leu Gln Asn Arg Phe Gly Asp
            980                 985                 990

Ile Asp Glu Cys Asp Val Ala Ser Tyr Asn Met Tyr Pro Arg Val Tyr
        995                 1000                1005

Glu Asp Phe Gln Lys Ile Arg Glu Thr Tyr Gly Asp Leu Ser Val Leu
    1010                1015                1020

Pro Thr Lys Asn Phe Leu Ala Pro Ala Glu Pro Asp Glu Glu Ile Glu
1025                1030                1035                1040

Val Thr Ile Glu Gln Gly Lys Thr Leu Ile Ile Lys Leu Gln Ala Val
                1045                1050                1055

Gly Asp Leu Asn Lys Lys Thr Gly Gln Arg Glu Val Tyr Phe Glu Leu
            1060                1065                1070

Asn Gly Glu Leu Arg Lys Ile Arg Val Ala Asp Lys Ser Gln Asn Ile
        1075                1080                1085

Gln Ser Val Ala Lys Pro Lys Ala Asp Val His Asp Thr His Gln Ile
    1090                1095                1100

Gly Ala Pro Met Ala Gly Val Ile Ile Glu Val Lys Val His Lys Gly
1105                1110                1115                1120

Ser Leu Val Lys Lys Gly Glu Ser Ile Ala Val Leu Ser Ala Met Lys
                1125                1130                1135

Met Glu Met Val Val Ser Ser Pro Ala Asp Gly Gln Val Lys Asp Val
            1140                1145                1150

Phe Ile Lys Asp Gly Glu Ser Val Asp Ala Ser Asp Leu Leu Val Val
        1155                1160                1165

Leu Glu Glu Glu Thr Leu Pro Pro Ser Gln Lys Lys
    1170                1175                1180

<210> SEQ ID NO 6
<211> LENGTH: 560
<212> TYPE: PRT
<213> ORGANISM: Pichia stipitis

<400> SEQUENCE: 6

Met Thr Ala Ser Ser Leu Asp Asn Gln Leu Asn Tyr Val His Ala Ala
1               5                   10                  15

Phe Asp Glu Glu Asn Asp Gly Leu Leu Pro Ile Ser Leu Gln Asp Leu
            20                  25                  30

Thr Asn Lys His Lys Glu Ala Ser Thr Ser Lys Asn Ser Thr Phe Ala
        35                  40                  45

Pro Lys Asn Thr Ser Leu Pro Ser Ser Thr Lys Ser Ala Ser Leu Leu
    50                  55                  60

Lys Val Asp Arg Pro Ala Phe Phe Val Leu Leu Leu Tyr Leu
65                  70                  75                  80

Gln Gly Val Pro Val Gly Leu Ala Phe Gly Ser Ile Pro Phe Ile Leu
                85                  90                  95

Lys Ser Lys Leu Ser Tyr Ser Gln Val Gly Ile Phe Ser Leu Ala Ala
            100                 105                 110

Tyr Pro Tyr Ser Leu Lys Leu Ile Trp Ser Pro Ile Val Asp Ala Val
        115                 120                 125
```

```
Tyr Ser Pro Lys Leu Gly Arg Arg Ser Trp Ile Pro Ile Gln
130                 135                 140

Thr Ile Ser Gly Val Thr Leu Ile Tyr Leu Gly Ser Leu Ile Asp Gly
145                 150                 155                 160

Leu Met Glu Asp Pro Gln Asn Cys Leu Pro Thr Ile Thr Phe Cys Phe
                165                 170                 175

Phe Met Leu Val Phe Phe Cys Ala Thr Gln Asp Ile Ala Val Asp Gly
                180                 185                 190

Trp Ala Leu Thr Cys Leu Ser Pro Glu Ser Leu Ser Tyr Ala Ser Thr
                195                 200                 205

Ala Gln Thr Ile Gly Ile Asn Thr Gly Tyr Phe Ser Ser Phe Thr Ile
210                 215                 220

Phe Leu Ala Leu Ser Ser Pro Asp Phe Ala Asn Arg Tyr Leu Arg Lys
225                 230                 235                 240

Val Pro Leu Asp Val Gly Leu Phe Ser Leu Gly Ser Tyr Leu Thr Phe
                245                 250                 255

Trp Gly Trp Met Phe Leu Ala Val Thr Ala Leu Leu Trp Phe Val Pro
                260                 265                 270

Glu Asp Pro Pro His Leu Ala Lys Arg Asn Gln Ala Lys Leu Ser Asn
                275                 280                 285

Glu Lys Ile Lys Thr Glu Ser Val Tyr Asn Lys Asp Ser Lys Phe Lys
290                 295                 300

Asp Leu Gln Asn Val Tyr Leu Ala Met Phe Lys Val Leu Lys Leu Pro
305                 310                 315                 320

Asn Val Gln Thr Phe Val Ile Ile Leu Leu Ile Ser Lys Phe Gly Phe
                325                 330                 335

Gln Val Asn Glu Ala Ala Thr Asn Leu Lys Leu Leu Glu Lys Gly Leu
                340                 345                 350

Ser Lys Glu Asp Leu Ser Ile Thr Val Leu Ile Asp Phe Pro Phe Glu
                355                 360                 365

Met Val Phe Gly Tyr Tyr Ala Gly Arg Trp Ser Thr Gly Lys Ser Pro
370                 375                 380

Leu Lys Pro Trp Ile Phe Gly Phe Ala Gly Arg Leu Val Ala Ala Ala
385                 390                 395                 400

Leu Ala Gln Gly Ile Val Tyr Phe Phe Pro Glu Asp Gly Lys Ile Ser
                405                 410                 415

Ser Phe Tyr Phe Leu Leu Val Ile Leu Gln His Leu Leu Gly Ser Phe
                420                 425                 430

Met Ser Thr Ile Gln Phe Val Ser Leu Cys Ala Phe His Thr Lys Ile
                435                 440                 445

Ala Asp Pro Ala Ile Gly Gly Thr Tyr Met Thr Thr Leu Asn Thr Leu
450                 455                 460

Ser Asn Tyr Gly Gly Thr Trp Pro Arg Leu Ile Leu Leu Tyr Leu Ile
465                 470                 475                 480

Asp Lys Leu Thr Ile Glu Glu Cys Lys Val Pro Ser Val Thr Asn Ser
                485                 490                 495

Tyr Tyr Ile Thr Asp Glu Asp Leu Arg Gln Gln Cys Lys Ser Ser Gly
                500                 505                 510

Gly Lys Leu Thr Val Leu Arg Asp Gly Tyr Tyr Thr Asn Thr Ile
                515                 520                 525

Cys Val Ile Ile Gly Ile Phe Thr Leu Leu Trp Val Lys Arg Lys Thr
530                 535                 540

Thr Tyr Leu Gln Ser Leu Pro Asn Ser Ala Trp Arg Val Asn Lys Asp
545                 550                 555                 560
```

<210> SEQ ID NO 7
<211> LENGTH: 415
<212> TYPE: PRT
<213> ORGANISM: Picihia stipitis

<400> SEQUENCE: 7

```
Met Ser Tyr Phe Ala Gly Ile Thr Glu Leu Pro Pro Asp Pro Leu Phe
 1               5                  10                  15

Gly Leu Lys Ala Arg Tyr Val Ala Asp Ser Arg Thr Asp Lys Val Asp
            20                  25                  30

Leu Gly Ile Gly Ala Tyr Arg Asp Asn Asn Gly Lys Pro Trp Ile Leu
        35                  40                  45

Pro Ala Val Lys Leu Ala Glu Ala Lys Leu Val Ser Ser Pro Asp Tyr
    50                  55                  60

Asn His Glu Tyr Leu Ser Ile Ser Gly Phe Glu Pro Phe Leu Lys Gln
65                  70                  75                  80

Ala Ser Lys Val Ile Leu Gly Glu Asn Ser Ala Ala Leu Ala Glu Asn
                85                  90                  95

Arg Val Val Ser Gln Gln Ser Leu Ser Gly Thr Gly Ala Leu His Val
            100                 105                 110

Ala Gly Val Leu Leu Lys Glu Phe Tyr Thr Gly Glu Lys Thr Val Tyr
        115                 120                 125

Leu Ser Lys Pro Thr Trp Ala Asn His Asn Gln Ile Phe Thr Ser Ile
    130                 135                 140

Gly Phe Lys Val Ala Ser Tyr Pro Tyr Trp Asp Asn Asp Thr Lys Ser
145                 150                 155                 160

Leu Asp Leu Lys Gly Phe Leu Ser Thr Ile Arg Thr Ala Pro Ala Gly
                165                 170                 175

Ser Ile Phe Leu Leu His Ala Cys Ala His Asn Pro Thr Gly Leu Asp
            180                 185                 190

Pro Ser Gln Asp Glu Trp Lys Gln Val Leu Lys Glu Leu Glu Ala Lys
        195                 200                 205

Lys His Leu Val Leu Phe Asp Ser Ala Tyr Gln Gly Phe Ala Ser Gly
    210                 215                 220

Asp Leu Asp Lys Asp Ala Tyr Ala Ile Arg Tyr Ala Ile Asp Gln Lys
225                 230                 235                 240

Val Ile Ser Thr Pro Ile Ile Cys Gln Ser Phe Ala Lys Asn Val
                245                 250                 255

Gly Met Tyr Gly Glu Arg Val Gly Ala Ile His Val Ile Pro Ser Thr
            260                 265                 270

Gln Lys Asp Glu Gln Leu Gly Arg Ala Leu Lys Ser Gln Leu Asn Arg
        275                 280                 285

Ile Ile Arg Ser Glu Ile Ser Asn Pro Pro Ala Tyr Gly Ala Lys Ile
    290                 295                 300

Val Ser Thr Ile Leu Asn Asp Arg Ala Leu Arg Gln Gln Trp Glu Ala
305                 310                 315                 320

Asp Leu Val Thr Met Ser Ser Arg Ile His Lys Met Arg Leu Lys Leu
                325                 330                 335

Lys Glu Leu Leu Thr Asn Leu His Thr Pro Gly Thr Trp Asp His Ile
            340                 345                 350

Val Asn Gln Thr Gly Met Phe Ser Phe Thr Gly Leu Ser Pro Asp Met
        355                 360                 365

Val Ala Arg Leu Glu Lys Val His Gly Ile Tyr Leu Val Ser Ser Gly
    370                 375                 380
```

```
Arg Ala Ser Val Ala Gly Leu Asn Asp Gly Asn Val Glu Lys Val Ala
385                 390                 395                 400

Asn Ala Ile Asp Glu Val Val Arg Phe Tyr Ala Lys Pro Lys Leu
            405                 410                 415

<210> SEQ ID NO 8
<211> LENGTH: 451
<212> TYPE: PRT
<213> ORGANISM: Saccharomyces cerevisiae

<400> SEQUENCE: 8

Met Leu Arg Thr Arg Leu Thr Asn Cys Ser Leu Trp Arg Pro Tyr Tyr
1               5                   10                  15

Thr Ser Ser Leu Ser Arg Val Pro Arg Ala Pro Pro Asp Lys Val Leu
            20                  25                  30

Gly Leu Ser Glu His Phe Lys Lys Val Lys Asn Val Asn Lys Ile Asp
        35                  40                  45

Leu Thr Val Gly Ile Tyr Lys Asp Gly Trp Gly Lys Val Thr Thr Phe
50                  55                  60

Pro Ser Val Ala Lys Ala Gln Lys Leu Ile Glu Ser His Leu Glu Leu
65                  70                  75                  80

Asn Lys Asn Leu Ser Tyr Leu Pro Ile Thr Gly Ser Lys Glu Phe Gln
                85                  90                  95

Glu Asn Val Met Lys Phe Leu Phe Lys Glu Ser Cys Pro Gln Phe Gly
            100                 105                 110

Pro Phe Tyr Leu Ala His Asp Arg Ile Ser Phe Val Gln Thr Leu Ser
        115                 120                 125

Gly Thr Gly Ala Leu Ala Val Ala Ala Lys Phe Leu Ala Leu Phe Ile
130                 135                 140

Ser Arg Asp Ile Trp Ile Pro Asp Pro Ser Trp Ala Asn His Lys Asn
145                 150                 155                 160

Ile Phe Gln Asn Asn Gly Phe Glu Asn Ile Tyr Arg Tyr Ser Tyr Tyr
                165                 170                 175

Lys Asp Gly Gln Ile Asp Ile Asp Gly Trp Ile Glu Gln Leu Lys Thr
            180                 185                 190

Phe Ala Tyr Asn Asn Gln Gln Glu Asn Asn Lys Asn Pro Pro Cys Ile
        195                 200                 205

Ile Leu His Ala Cys Cys His Asn Pro Thr Gly Leu Asp Pro Thr Lys
210                 215                 220

Glu Gln Trp Glu Lys Ile Ile Asp Thr Ile Tyr Glu Leu Lys Met Val
225                 230                 235                 240

Pro Ile Val Asp Met Ala Tyr Gln Gly Leu Glu Ser Gly Asn Leu Leu
                245                 250                 255

Lys Asp Ala Tyr Leu Leu Arg Leu Cys Leu Asn Val Asn Lys Tyr Pro
            260                 265                 270

Asn Trp Ser Asn Gly Ile Phe Leu Cys Gln Ser Phe Ala Lys Asn Met
        275                 280                 285

Gly Leu Tyr Gly Glu Arg Val Gly Ser Leu Ser Val Ile Thr Pro Ala
290                 295                 300

Thr Ala Asn Asn Gly Lys Phe Asn Pro Leu Gln Gln Lys Asn Ser Leu
305                 310                 315                 320

Gln Gln Asn Ile Asp Ser Gln Leu Lys Lys Ile Val Arg Gly Met Tyr
                325                 330                 335

Ser Ser Pro Pro Gly Tyr Gly Ser Arg Val Val Asn Val Val Leu Ser
            340                 345                 350
```

```
Asp Phe Lys Leu Lys Gln Gln Trp Phe Lys Asp Val Asp Phe Met Val
        355                 360                 365

Gln Arg Leu His His Val Arg Gln Glu Met Phe Asp Arg Leu Gly Trp
        370                 375                 380

Pro Asp Leu Val Asn Phe Ala Gln Gln His Gly Met Phe Tyr Tyr Thr
385                 390                 395                 400

Arg Phe Ser Pro Lys Gln Val Glu Ile Leu Arg Asn Asn Tyr Phe Val
                405                 410                 415

Tyr Leu Thr Gly Asp Gly Arg Leu Ser Leu Ser Gly Val Asn Asp Ser
                420                 425                 430

Asn Val Asp Tyr Leu Cys Glu Ser Leu Glu Ala Val Ser Lys Met Asp
            435                 440                 445

Lys Leu Ala
        450

<210> SEQ ID NO 9
<211> LENGTH: 439
<212> TYPE: PRT
<213> ORGANISM: Pichia stipitis

<400> SEQUENCE: 9

Met Tyr Arg Thr Ser Leu Leu Lys Gln Thr Ala Arg Pro Ser Val Arg
1               5                   10                  15

Val Ser Thr Arg Gln Phe Ser Val Leu Asn Asn Gln Val Arg Lys Trp
            20                  25                  30

Ser Glu Ile Pro Leu Ala Pro Pro Asp Lys Ile Leu Gly Ile Ser Glu
        35                  40                  45

Ala Tyr Asn Lys Asp Ala Asn Thr Ser Lys Ile Asn Leu Gly Val Gly
    50                  55                  60

Ala Tyr Arg Asp Asn Ser Gly Lys Pro Ile Ile Phe Pro Ser Val Lys
65                  70                  75                  80

Glu Ala Glu Lys Ile Leu Leu Ala Ser Glu Val Glu Lys Glu Tyr Thr
                85                  90                  95

Gly Ile Thr Gly Ser Lys Lys Phe Gln Asn Ala Val Lys Gly Phe Val
            100                 105                 110

Phe Asn Asn Ser Gly Lys Asp Val Asn Gly Gln Gln Leu Ile Glu Gln
        115                 120                 125

Asn Arg Ile Val Thr Ala Gln Thr Ile Ser Gly Thr Gly Ser Leu Arg
    130                 135                 140

Val Ile Gly Asp Phe Leu Asn Arg Phe Tyr Thr Asn Lys Lys Leu Leu
145                 150                 155                 160

Val Pro Lys Pro Thr Trp Ala Asn His Val Ala Val Phe Lys Asp Ala
                165                 170                 175

Gly Leu Glu Pro Glu Phe Tyr Ala Tyr Tyr Glu Thr Ser Lys Asn Asp
            180                 185                 190

Leu Asp Phe Ala Asn Leu Lys Lys Ser Leu Ser Ser Gln Pro Asp Gly
        195                 200                 205

Ser Ile Val Leu Leu His Ala Cys Cys His Asn Pro Thr Gly Met Asp
    210                 215                 220

Leu Thr Pro Glu Gln Trp Glu Glu Val Leu Ala Ile Val Gln Glu Lys
225                 230                 235                 240

Asn Phe Tyr Pro Leu Val Asp Met Ala Tyr Gln Gly Phe Ala Ser Gly
                245                 250                 255

Asn Pro Tyr Lys Asp Ile Gly Leu Ile Arg Arg Leu Asn Glu Leu Val
            260                 265                 270
```

```
Val Gln Asn Lys Leu Lys Ser Tyr Ala Leu Cys Gln Ser Phe Ala Lys
        275                 280                 285

Asn Met Gly Leu Tyr Gly Glu Arg Thr Gly Ser Ile Ser Ile Ile Thr
    290                 295                 300

Glu Ser Ala Glu Ala Ser Gln Ala Ile Glu Ser Gln Leu Lys Lys Leu
305                 310                 315                 320

Ile Arg Pro Ile Tyr Ser Ser Pro Ile His Gly Ser Lys Ile Val
                325                 330                 335

Glu Ile Ile Phe Asp Glu Gln His Asn Leu Leu Asn Ser Trp Leu Gln
            340                 345                 350

Asp Leu Asp Lys Val Val Gly Arg Leu Asn Thr Val Arg Ser Lys Leu
            355                 360                 365

Tyr Glu Asn Leu Asp Lys Ser Ser Tyr Asn Trp Asp His Leu Leu Lys
        370                 375                 380

Gln Arg Gly Met Phe Val Tyr Thr Gly Leu Ser Ala Glu Gln Val Ile
385                 390                 395                 400

Lys Leu Arg Asn Asp Tyr Ser Val Tyr Ala Thr Glu Asp Gly Arg Phe
                405                 410                 415

Ser Ile Ser Gly Ile Asn Asp Asn Val Glu Tyr Leu Ala Asn Ala
            420                 425                 430

Ile Asn Glu Val Val Lys Gln
        435

<210> SEQ ID NO 10
<211> LENGTH: 418
<212> TYPE: PRT
<213> ORGANISM: Saccharomyces cerevisiae

<400> SEQUENCE: 10

Met Ser Ala Thr Leu Phe Asn Asn Ile Glu Leu Leu Pro Pro Asp Ala
1               5                   10                  15

Leu Phe Gly Ile Lys Gln Arg Tyr Gly Gln Asp Gln Arg Ala Thr Lys
            20                  25                  30

Val Asp Leu Gly Ile Gly Ala Tyr Arg Asp Asp Asn Gly Lys Pro Trp
        35                  40                  45

Val Leu Pro Ser Val Lys Ala Ala Glu Lys Leu Ile His Asn Asp Ser
    50                  55                  60

Ser Tyr Asn His Glu Tyr Leu Gly Ile Thr Gly Leu Pro Ser Leu Thr
65              70                  75                  80

Ser Asn Ala Ala Lys Ile Ile Phe Gly Thr Gln Ser Asp Ala Phe Gln
            85                  90                  95

Glu Asp Arg Val Ile Ser Val Gln Ser Leu Ser Gly Thr Gly Ala Leu
            100                 105                 110

His Ile Ser Ala Lys Phe Phe Ser Lys Phe Phe Pro Asp Lys Leu Val
        115                 120                 125

Tyr Leu Ser Lys Pro Thr Trp Ala Asn His Met Ala Ile Phe Glu Asn
    130                 135                 140

Gln Gly Leu Lys Thr Ala Thr Tyr Pro Tyr Trp Ala Asn Glu Thr Lys
145                 150                 155                 160

Ser Leu Asp Leu Asn Gly Phe Leu Asn Ala Ile Gln Lys Ala Pro Glu
                165                 170                 175

Gly Ser Ile Phe Val Leu His Ser Cys Ala His Asn Pro Thr Gly Leu
            180                 185                 190

Asp Pro Thr Ser Glu Gln Trp Val Gln Ile Val Asp Ala Ile Ala Ser
        195                 200                 205
```

Lys Asn His Ile Ala Leu Phe Asp Thr Ala Tyr Gln Gly Phe Ala Thr
210                 215                 220

Gly Asp Leu Asp Lys Asp Ala Tyr Ala Val Arg Leu Gly Val Glu Lys
225                 230                 235                 240

Leu Ser Thr Val Ser Pro Val Phe Val Cys Gln Ser Phe Ala Lys Asn
                245                 250                 255

Ala Gly Met Tyr Gly Glu Arg Val Gly Cys Phe His Leu Ala Leu Thr
            260                 265                 270

Lys Gln Ala Gln Asn Lys Thr Ile Lys Pro Ala Val Thr Ser Gln Leu
        275                 280                 285

Ala Lys Ile Ile Arg Ser Glu Val Ser Asn Pro Pro Ala Tyr Gly Ala
    290                 295                 300

Lys Ile Val Ala Lys Leu Leu Glu Thr Pro Glu Leu Thr Glu Gln Trp
305                 310                 315                 320

His Lys Asp Met Val Thr Met Ser Ser Arg Ile Thr Lys Met Arg His
                325                 330                 335

Ala Leu Arg Asp His Leu Val Lys Leu Gly Thr Pro Gly Asn Trp Asp
            340                 345                 350

His Ile Val Asn Gln Cys Gly Met Phe Ser Phe Thr Gly Leu Thr Pro
        355                 360                 365

Gln Met Val Lys Arg Leu Glu Glu Thr His Ala Val Tyr Leu Val Ala
    370                 375                 380

Ser Gly Arg Ala Ser Ile Ala Gly Leu Asn Gln Gly Asn Val Glu Tyr
385                 390                 395                 400

Val Ala Lys Ala Ile Asp Glu Val Val Arg Phe Tyr Thr Ile Glu Ala
                405                 410                 415

Lys Leu

<210> SEQ ID NO 11
<211> LENGTH: 536
<212> TYPE: PRT
<213> ORGANISM: Pichia stipitis

<400> SEQUENCE: 11

Met Ser Val Ser Pro Pro Leu Ser Ala Lys Ser Tyr Asn Ser Ile Val
1               5                   10                  15

Asp Leu Arg Phe Thr Ala Ser Lys Pro Gln Gly Trp Val Val Gln Lys
            20                  25                  30

Phe Gly Gly Thr Ser Val Gly Lys Phe Pro Glu Asn Ile Val Asp Asp
        35                  40                  45

Ile Val Leu Val Phe Ser Lys Thr Asn Arg Val Ala Val Val Cys Ser
    50                  55                  60

Ala Arg Ser Ser Gln Thr Lys Ser Glu Gly Thr Thr Ser Arg Leu Leu
65                  70                  75                  80

Lys Ala Ala Asp Ile Ala Ala Glu Ser Gly Asp Phe Gln Tyr Met Leu
                85                  90                  95

Asp Val Ile Glu Asp His Val Lys Asn Ala Glu Ala Arg Val Lys
            100                 105                 110

Asn Lys Thr Ile Gln Gln Lys Leu Val Ala Asp Thr Lys Arg Glu Ile
        115                 120                 125

Ala His Ala Ala Glu Leu Leu Arg Ala Cys Gln Val Ile Gly Glu Ile
    130                 135                 140

Ser Ala Arg Ser Leu Asp Ser Val Met Ser Ile Gly Glu Lys Leu Ser
145                 150                 155                 160

```
Cys Leu Phe Met Ala Leu Met Asn Asp His Gly Leu Lys Ala Val
            165                 170                 175

Tyr Ile Asp Leu Ser Asp Val Ile Pro Leu Asp Tyr Asp Phe Thr Asn
            180                 185                 190

Gly Phe Asp Asp Asn Phe Tyr Lys Phe Leu Ser Gln Gln Leu Ser Ser
            195                 200             205

Arg Ala Leu Ala Leu Ser Glu Asp Thr Val Pro Val Leu Thr Gly Tyr
    210                 215                 220

Phe Gly Thr Val Pro Gly Gly Leu Leu Asn Gly Val Gly Arg Gly Tyr
225                 230                 235                 240

Thr Asp Leu Cys Ala Ala Leu Val Ala Val Gly Val Gln Ala Asp Glu
            245                 250                 255

Leu Gln Val Trp Lys Glu Val Asp Gly Ile Phe Thr Ala Asp Pro Arg
            260                 265                 270

Lys Val Pro Thr Ala Arg Leu Leu Asp Ser Val Thr Pro Glu Glu Ala
            275                 280                 285

Ala Glu Leu Thr Tyr Tyr Gly Ser Glu Val Ile His Pro Phe Thr Met
            290                 295                 300

Glu Gln Val Ile Lys Ala Lys Ile Pro Ile Arg Ile Lys Asn Val Val
305                 310                 315                 320

Asn Pro Lys Gly Ser Gly Thr Ile Ile Phe Pro Asp Asn Val Gly Arg
            325                 330                 335

Arg Gly Glu Glu Thr Pro Pro His Pro Pro Glu Ala Tyr Glu Thr Leu
            340                 345                 350

Ser Ser Ser Phe Val Leu Ser His Lys Lys Arg Ser Ala Thr Ala Ile
            355                 360                 365

Thr Ala Lys Gln Asp Ile Val Val Ile Asn Ile His Ser Asn Lys Lys
370                 375                 380

Thr Leu Ser His Gly Phe Leu Ala His Ile Phe Thr Thr Leu Asp Asn
385                 390                 395                 400

Phe Lys Leu Val Val Asp Leu Ile Ser Thr Ser Glu Val His Val Ser
            405                 410                 415

Met Ala Leu Gln Ile Leu Gln Asp Gln Glu Leu Gln Leu Lys Asn Ala
            420                 425                 430

Leu Lys Asp Leu Arg Arg Met Gly Thr Val Asp Ile Thr Arg Asn Met
            435                 440                 445

Thr Ile Ile Ser Leu Val Gly Lys Gln Met Val Asn Phe Ile Asp Ile
450                 455                 460

Ala Gly Asn Met Phe Lys Val Leu Ala Asp Asn Arg Ile Asn Ile Glu
465                 470                 475                 480

Met Ile Ser Gln Gly Ala Asn Glu Ile Asn Ile Ser Ala Val Ile Asn
            485                 490                 495

Glu Lys Asp Thr Ile Arg Ala Leu Gln Ser Ile His Ala Lys Leu Leu
            500                 505                 510

Glu Gly Thr Phe Gly Phe Asp Asp His Val Glu Ser Ala Val Asp Leu
            515                 520                 525

Arg Leu Glu Ser Leu Lys Phe Gln
            530                 535

<210> SEQ ID NO 12
<211> LENGTH: 536
<212> TYPE: PRT
<213> ORGANISM: Saccharomyces cerevisiae

<400> SEQUENCE: 12
```

```
Met Ser Val Ser Pro Leu Ser Ala Lys Ser Tyr Asn Ser Ile Val
1               5                   10                  15

Asp Leu Arg Phe Thr Ala Ser Lys Pro Gln Gly Trp Val Val Gln Lys
            20                  25                  30

Phe Gly Gly Thr Ser Val Gly Lys Phe Pro Glu Asn Ile Val Asp Asp
            35                  40                  45

Ile Val Leu Val Phe Ser Lys Thr Asn Arg Val Ala Val Val Cys Ser
50                  55                  60

Ala Arg Ser Ser Gln Thr Lys Ser Glu Gly Thr Thr Ser Arg Leu Leu
65                  70                  75                  80

Lys Ala Ala Asp Ile Ala Ala Glu Ser Gly Asp Phe Gly Tyr Met Leu
                85                  90                  95

Asp Val Ile Glu Asp Asp His Val Lys Asn Ala Glu Ala Arg Val Lys
            100                 105                 110

Asn Lys Thr Ile Gln Gln Lys Leu Val Ala Asp Thr Lys Arg Glu Ile
            115                 120                 125

Ala His Ala Ala Glu Leu Leu Arg Ala Cys Gln Val Ile Gly Glu Ile
        130                 135                 140

Ser Ala Arg Ser Leu Asp Ser Val Met Ser Ile Gly Glu Lys Leu Ser
145                 150                 155                 160

Cys Leu Phe Met Ala Ala Leu Met Asn Asp His Gly Leu Lys Ala Val
                165                 170                 175

Tyr Ile Asp Leu Ser Asp Val Ile Pro Leu Asp Tyr Asp Phe Thr Asn
            180                 185                 190

Gly Phe Asp Asp Asn Phe Tyr Lys Phe Leu Ser Gln Gln Leu Ser Ser
            195                 200                 205

Arg Ala Leu Ala Leu Ser Glu Asp Thr Val Pro Val Leu Thr Gly Tyr
210                 215                 220

Phe Gly Thr Val Pro Gly Gly Leu Leu Asn Gly Val Gly Arg Gly Tyr
225                 230                 235                 240

Thr Asp Leu Cys Ala Ala Leu Val Ala Val Gly Val Gln Ala Asp Glu
                245                 250                 255

Leu Gln Val Trp Lys Glu Val Asp Gly Ile Phe Thr Ala Asp Pro Arg
            260                 265                 270

Lys Val Pro Thr Ala Arg Leu Leu Asp Ser Val Thr Pro Glu Glu Ala
            275                 280                 285

Ala Glu Leu Thr Tyr Tyr Gly Ser Glu Val Ile His Pro Phe Thr Met
            290                 295                 300

Glu Gln Val Ile Lys Ala Lys Ile Pro Ile Arg Ile Lys Asn Val Val
305                 310                 315                 320

Asn Pro Lys Gly Ser Gly Thr Ile Ile Phe Pro Asp Asn Val Gly Arg
            325                 330                 335

Arg Gly Glu Glu Thr Pro Pro His Pro Pro Glu Ala Tyr Glu Thr Leu
            340                 345                 350

Ser Ser Ser Phe Val Leu Ser His Lys Lys Arg Ser Ala Thr Ala Ile
            355                 360                 365

Thr Ala Lys Gln Asp Ile Val Val Ile Asn Ile His Ser Asn Lys Lys
            370                 375                 380

Thr Leu Ser His Gly Phe Leu Ala His Ile Phe Thr Thr Leu Asp Asn
385                 390                 395                 400

Phe Lys Leu Val Val Asp Leu Ile Ser Thr Ser Glu Val His Val Ser
                405                 410                 415

Met Ala Leu Gln Ile Leu Gln Asp Gln Glu Leu Gln Leu Lys Asn Ala
            420                 425                 430
```

Leu Lys Asp Leu Arg Arg Met Gly Thr Val Asp Ile Thr Arg Asn Met
          435                 440                 445

Thr Ile Ile Ser Leu Val Gly Lys Gln Met Val Asn Phe Ile Asp Ile
          450                 455                 460

Ala Gly Asn Met Phe Lys Val Leu Ala Asp Asn Arg Ile Asn Ile Glu
465                 470                 475                 480

Met Ile Ser Gln Gly Ala Asn Glu Ile Asn Ile Ser Ala Val Ile Asn
          485                 490                 495

Glu Lys Asp Thr Ile Arg Ala Leu Gln Ser Ile His Ala Lys Leu Leu
          500                 505                 510

Glu Gly Thr Phe Gly Phe Asp Asp His Val Glu Ser Ala Val Asp Leu
          515                 520                 525

Arg Leu Glu Ser Leu Lys Phe Gln
          530                 535

<210> SEQ ID NO 13
<211> LENGTH: 363
<212> TYPE: PRT
<213> ORGANISM: Picihia stipitis

<400> SEQUENCE: 13

Met Val Lys Lys Ala Gly Val Leu Gly Ala Thr Gly Ser Val Gly Gln
1               5                   10                  15

Arg Phe Ile Leu Leu Leu Ala Glu His Pro Asp Phe Glu Leu His Val
            20                  25                  30

Leu Gly Ala Ser Pro Arg Ser Ala Gly Lys Gln Tyr Lys Asp Ala Val
        35                  40                  45

Gln Trp Lys Gln Thr Asp Leu Leu Pro Glu Asn Ala Gln Lys Ile Ile
    50                  55                  60

Val Ser Glu Cys Lys Ala Glu Ala Phe Lys Asp Cys Asp Ile Val Phe
65                  70                  75                  80

Ser Gly Leu Asp Ala Asp Tyr Ala Gly Pro Ile Glu Lys Glu Phe Val
                85                  90                  95

Glu Ala Gly Leu Val Val Val Ser Asn Ala Lys Asn Tyr Arg Arg Glu
            100                 105                 110

Pro Gly Val Pro Leu Ile Val Pro Ile Val Asn Ser Glu His Leu Ser
        115                 120                 125

Val Ile Glu Arg Lys Leu Ala Val Ala Lys Glu Gly Lys Ser Lys
130                 135                 140

Pro Gly Tyr Ile Ile Cys Ile Ser Asn Cys Ser Thr Ala Gly Leu Val
145                 150                 155                 160

Ala Pro Leu Lys Pro Leu Ile Asp Ala Phe Gly Pro Ile Asp Ala Leu
                165                 170                 175

Thr Ala Thr Thr Leu Gln Ala Ile Ser Gly Ala Gly Phe Ser Pro Gly
            180                 185                 190

Val Pro Gly Met Asp Val Leu Asp Asn Ile Ile Pro Tyr Ile Gly Gly
        195                 200                 205

Glu Glu Glu Lys Leu Glu Trp Glu Ser Lys Lys Ile Leu Gly Asn Leu
    210                 215                 220

Thr Lys Asp Gly Thr Asp Phe Ala Pro Leu Ser Asn Asp Glu Met Lys
225                 230                 235                 240

Val Ser Ala Gln Cys Asn Arg Val Ala Val Ile Asp Gly His Thr Glu
                245                 250                 255

Cys Ile Ser Phe Arg Phe Ala Lys His Pro Ala Pro Ser Val Ala Gln
            260                 265                 270

```
Val Lys Lys Val Leu Ser Glu Tyr Val Cys Glu Ala Thr Lys Leu Gly
            275                 280                 285

Cys His Ser Ala Pro Lys Gln Thr Ile His Val Leu Glu Gln Gln Asp
        290                 295                 300

Arg Pro Gln Pro Arg Leu Asp Arg Asn Arg Asp Asn Gly Tyr Gly Val
305                 310                 315                 320

Ser Val Gly Arg Ile Arg Glu Asp Ala Val Leu Asp Phe Lys Met Val
                325                 330                 335

Val Leu Ser His Asn Thr Ile Ile Gly Ala Ala Gly Ala Gly Val Leu
            340                 345                 350

Ile Ala Glu Ile Leu Lys Ala Lys Asp Met Ile
355                 360

<210> SEQ ID NO 14
<211> LENGTH: 365
<212> TYPE: PRT
<213> ORGANISM: Saccharomyces cerevisiae

<400> SEQUENCE: 14

Met Ala Gly Lys Lys Ile Ala Gly Val Leu Gly Ala Thr Gly Ser Val
1               5                   10                  15

Gly Gln Arg Phe Ile Leu Leu Leu Ala Asn His Pro His Phe Glu Leu
            20                  25                  30

Lys Val Leu Gly Ala Ser Ser Arg Ser Ala Gly Lys Lys Tyr Val Asp
        35                  40                  45

Ala Val Asn Trp Lys Gln Thr Asp Leu Leu Pro Glu Ser Ala Thr Asp
    50                  55                  60

Ile Ile Val Ser Glu Cys Lys Ser Glu Phe Phe Lys Glu Cys Asp Ile
65                  70                  75                  80

Val Phe Ser Gly Leu Asp Ala Asp Tyr Ala Gly Ala Ile Glu Lys Glu
                85                  90                  95

Phe Met Glu Ala Gly Ile Ala Ile Val Ser Asn Ala Lys Asn Tyr Arg
            100                 105                 110

Arg Glu Gln Asp Val Pro Leu Ile Val Pro Val Asn Pro Glu His
        115                 120                 125

Leu Asp Ile Val Ala Gln Lys Leu Asp Thr Ala Lys Ala Gln Gly Lys
130                 135                 140

Pro Arg Pro Gly Phe Ile Ile Cys Ile Ser Asn Cys Ser Thr Ala Gly
145                 150                 155                 160

Leu Val Ala Pro Leu Lys Pro Leu Ile Glu Lys Phe Gly Pro Ile Asp
                165                 170                 175

Ala Leu Thr Thr Thr Thr Leu Gln Ala Ile Ser Gly Ala Gly Phe Ser
            180                 185                 190

Pro Gly Val Pro Gly Ile Asp Ile Leu Asp Asn Ile Ile Pro Tyr Ile
        195                 200                 205

Gly Gly Glu Glu Asp Lys Met Glu Trp Glu Thr Lys Lys Ile Leu Ala
    210                 215                 220

Pro Leu Ala Glu Asp Lys Thr His Val Lys Leu Leu Thr Pro Glu Glu
225                 230                 235                 240

Ile Lys Val Ser Ala Gln Cys Asn Arg Val Ala Val Ser Asp Gly His
                245                 250                 255

Thr Glu Cys Ile Ser Leu Arg Phe Lys Asn Arg Pro Ala Pro Ser Val
            260                 265                 270

Glu Gln Val Lys Thr Cys Leu Lys Glu Tyr Val Cys Asp Ala Tyr Lys
        275                 280                 285
```

Leu Gly Cys His Ser Ala Pro Lys Gln Thr Ile His Val Leu Glu Gln
        290                 295                 300

Pro Asp Arg Pro Gln Pro Arg Leu Asp Arg Asn Arg Asp Ser Gly Tyr
305                 310                 315                 320

Gly Val Ser Val Gly Arg Ile Arg Glu Asp Pro Leu Leu Asp Phe Lys
                325                 330                 335

Met Val Val Leu Ser His Asn Thr Ile Ile Gly Ala Ala Gly Ser Gly
            340                 345                 350

Val Leu Ile Ala Glu Ile Leu Leu Ala Arg Asn Leu Ile
        355                 360                 365

<210> SEQ ID NO 15
<211> LENGTH: 359
<212> TYPE: PRT
<213> ORGANISM: Picihia stipitis

<400> SEQUENCE: 15

Met Ser Lys Ser Val Asn Val Ala Ile Ile Gly Ser Gly Val Val Gly
1               5                   10                  15

Ser Ala Phe Ile Ser Gln Leu Asn Gly Leu Lys Thr Ala Ile Lys Tyr
            20                  25                  30

Asn Val Val Tyr Leu Ala Lys Thr Ser Glu Ala Leu Tyr Ser Ser
        35                  40                  45

Asp Tyr Gln Ser Val Asp Leu Ser Ser Tyr Lys Thr Ser Ala Thr Lys
50                  55                  60

Pro Thr Leu Gly Leu Asp Glu Leu Leu Lys Phe Leu Gln Gly Ala Lys
65                  70                  75                  80

Lys Ala Thr Ile Leu Val Asp Asn Thr Ser Asn Ala Ser Ile Ala Asp
            85                  90                  95

Tyr Tyr Pro Thr Phe Ile Lys Ala Gly Ile Ser Ile Ala Thr Pro Asn
            100                 105                 110

Lys Lys Ala Phe Ser Ser Asp Leu Lys Thr Trp Asn Glu Ile Phe Ala
        115                 120                 125

Asn Ser Ala Val Pro Gly Ala Gly Leu Val Ala His Glu Ala Thr Val
    130                 135                 140

Gly Ala Gly Leu Pro Ile Ile Gly Pro Leu Arg Asp Leu Ile Thr Thr
145                 150                 155                 160

Gly Asp Lys Val Asp Lys Ile Glu Gly Ile Phe Ser Gly Thr Leu Ser
                165                 170                 175

Tyr Ile Phe Asn Glu Phe Ser Thr Glu Lys Ser Asp Val Lys Phe
            180                 185                 190

Ser Asp Val Val Lys Val Ala Lys Lys Leu Gly Tyr Thr Glu Pro Asp
        195                 200                 205

Pro Arg Asp Asp Leu Asn Gly Leu Asp Val Ala Arg Lys Val Thr Ile
    210                 215                 220

Leu Ala Arg Ile Ser Gly Phe Glu Val Glu Ser Pro Thr Ser Phe Pro
225                 230                 235                 240

Val Glu Ser Leu Ile Pro Lys Gly Leu Glu Gly Ile Glu Ser Ala Ala
                245                 250                 255

Glu Phe Leu Glu Lys Leu Pro Asn Tyr Asp Ala Asp Ile Gln Lys Ile
            260                 265                 270

Lys Asp Glu Ala Phe Ala Glu Asn Lys Thr Leu Arg Phe Val Gly Gln
        275                 280                 285

Val Asp Phe Lys Ala Asn Lys Val Ser Val Gly Ile Gly Lys Tyr Pro
    290                 295                 300

```
Phe Asp His Pro Phe Ser Ala Leu Lys Gly Ser Asp Asn Val Ile Ser
305                 310                 315                 320

Ile Lys Thr Glu Arg Tyr Pro Asn Pro Leu Ile Val Gln Gly Ala Gly
            325                 330                 335

Ala Gly Ser Glu Val Thr Ala His Gly Val Leu Ala Asp Thr Ile Lys
            340                 345                 350

Ile Ala Glu Arg Ile Ala Asn
        355

<210> SEQ ID NO 16
<211> LENGTH: 359
<212> TYPE: PRT
<213> ORGANISM: Saccharomyces cerevisiae

<400> SEQUENCE: 16

Met Ser Thr Lys Val Val Asn Val Ala Val Ile Gly Ala Gly Val Val
1               5                   10                  15

Gly Ser Ala Phe Leu Asp Gln Leu Leu Ala Met Lys Ser Thr Ile Thr
                20                  25                  30

Tyr Asn Leu Val Leu Leu Ala Glu Ala Glu Arg Ser Leu Ile Ser Lys
            35                  40                  45

Asp Phe Ser Pro Leu Asn Val Gly Ser Asp Trp Lys Ala Ala Leu Ala
50                  55                  60

Ala Ser Thr Thr Lys Thr Leu Pro Leu Asp Asp Leu Ile Ala His Leu
65                  70                  75                  80

Lys Thr Ser Pro Lys Pro Val Ile Leu Val Asp Asn Thr Ser Ser Ala
                85                  90                  95

Tyr Ile Ala Gly Phe Tyr Thr Lys Phe Val Glu Asn Gly Ile Ser Ile
            100                 105                 110

Ala Thr Pro Asn Lys Lys Ala Phe Ser Ser Asp Leu Ala Thr Trp Lys
        115                 120                 125

Ala Leu Phe Ser Asn Lys Pro Thr Asn Gly Phe Val Tyr His Glu Ala
130                 135                 140

Thr Val Gly Ala Gly Leu Pro Ile Ile Ser Phe Leu Arg Glu Ile Ile
145                 150                 155                 160

Gln Thr Gly Asp Glu Val Glu Lys Ile Glu Gly Ile Phe Ser Gly Thr
                165                 170                 175

Leu Ser Tyr Ile Phe Asn Glu Phe Ser Thr Ser Gln Ala Asn Asp Val
            180                 185                 190

Lys Phe Ser Asp Val Val Lys Val Ala Lys Lys Leu Gly Tyr Thr Glu
        195                 200                 205

Pro Asp Pro Arg Asp Asp Leu Asn Gly Leu Asp Val Ala Arg Lys Val
210                 215                 220

Thr Ile Val Gly Arg Ile Ser Gly Val Glu Val Glu Ser Pro Thr Ser
225                 230                 235                 240

Phe Pro Val Gln Ser Leu Ile Pro Lys Pro Leu Glu Ser Val Lys Ser
                245                 250                 255

Ala Asp Glu Phe Leu Glu Lys Leu Ser Asp Tyr Asp Lys Asp Leu Thr
            260                 265                 270

Gln Leu Lys Lys Glu Ala Ala Thr Glu Asn Lys Val Leu Arg Phe Ile
        275                 280                 285

Gly Lys Val Asp Val Ala Thr Lys Ser Val Ser Val Gly Ile Glu Lys
290                 295                 300

Tyr Asp Tyr Ser His Pro Phe Ala Ser Leu Lys Gly Ser Asp Asn Val
305                 310                 315                 320
```

```
Ile Ser Ile Lys Thr Lys Arg Tyr Thr Asn Pro Val Val Ile Gln Gly
            325                 330                 335

Ala Gly Ala Gly Ala Ala Val Thr Ala Ala Gly Val Leu Gly Asp Val
            340                 345                 350

Ile Lys Ile Ala Gln Arg Leu
            355

<210> SEQ ID NO 17
<211> LENGTH: 353
<212> TYPE: PRT
<213> ORGANISM: Pichia stipitis

<400> SEQUENCE: 17

Met Thr Ile Arg Ser Phe Glu Val Lys Val Pro Ala Ser Ser Ala Asn
  1               5                  10                  15

Ile Gly Pro Gly Phe Asp Val Leu Gly Val Gly Leu Gln Leu Tyr Leu
                 20                  25                  30

Gln Ile Lys Val Thr Ile Asp Ser Ser Lys Asp Thr Ser His Asp Pro
             35                  40                  45

Tyr His Val Lys Leu Ser Tyr Glu Gly Asp Leu Ala Glu Lys Val Pro
 50                  55                  60

Leu Thr Ser Asp Lys Asn Leu Ile Thr Gln Thr Ala Leu Tyr Ile Leu
 65                  70                  75                  80

Arg Val Asn Gly Met Asp Ser Phe Pro Gln Gly Thr His Ile His Val
                 85                  90                  95

Ile Asn Pro Val Pro Leu Gly Arg Gly Leu Gly Ser Ser Ala Ser Ala
            100                 105                 110

Ile Val Gly Gly Ile Val Leu Gly Asn Glu Ile Gly Glu Phe Lys Phe
            115                 120                 125

Ser Lys Thr Arg Leu Met Asp Tyr Cys Leu Met Ile Glu Arg His Pro
            130                 135                 140

Asp Asn Ile Ala Ala Ala Met Leu Gly Gly Phe Val Gly Ser Tyr Leu
145                 150                 155                 160

His Asp Leu Ser Pro Glu Asp Met Ala Ala Lys Asn Val Pro Leu Asp
                165                 170                 175

Tyr Ile Leu Pro Lys Pro Asp Thr Pro Lys Glu Lys Ile Val Ser Ser
            180                 185                 190

Gln Pro Pro Thr Asn Ile Gly Glu Tyr Leu Gln Tyr Asn Trp Cys His
            195                 200                 205

Lys Ile Lys Cys Val Ala Ile Val Pro Asn Phe Glu Val Ser Thr Asp
            210                 215                 220

Ser Ser Arg Ala Val Leu Pro Glu Lys Tyr Asp Arg Gln Asp Ile Val
225                 230                 235                 240

Phe Asn Leu Gln Arg Leu Ala Ile Leu Thr Asn Ala Leu Thr Gln Glu
                245                 250                 255

Thr Pro Asn Asn Lys Leu Ile Tyr Glu Ser Met Lys Asp Lys Ile His
            260                 265                 270

Gln Pro Tyr Arg Ser Gly Leu Ile Pro Gly Leu Gln Lys Val Leu Ala
            275                 280                 285

Ser Val Thr Pro Asp Thr His Pro Gly Leu Cys Gly Ile Cys Leu Ser
            290                 295                 300

Gly Ala Gly Pro Thr Ile Leu Cys Leu Ala Thr Gly Gly Tyr Asp Ala
305                 310                 315                 320

Ile Ala Glu Thr Val Ile Gly Ile Phe Asn Lys Ala Gly Val Glu Cys
                325                 330                 335
```

Ser Trp Lys Leu Leu Glu Leu Ala Tyr Asp Gly Ala Thr Val Glu Ile
            340                 345                 350

Lys

<210> SEQ ID NO 18
<211> LENGTH: 357
<212> TYPE: PRT
<213> ORGANISM: Saccharomyces cerevisiae

<400> SEQUENCE: 18

Met Val Arg Ala Phe Lys Ile Lys Val Pro Ala Ser Ser Ala Asn Ile
 1               5                  10                  15

Gly Pro Gly Tyr Asp Val Leu Gly Val Gly Leu Ser Leu Phe Leu Glu
            20                  25                  30

Leu Asp Val Thr Ile Asp Ser Ser Gln Ala Gln Glu Thr Asn Asp Asp
        35                  40                  45

Pro Asn Asn Cys Lys Leu Ser Tyr Thr Lys Glu Ser Glu Gly Tyr Ser
    50                  55                  60

Thr Val Pro Leu Arg Ser Asp Ala Asn Leu Ile Thr Arg Thr Ala Leu
65                  70                  75                  80

Tyr Val Leu Arg Cys Asn Asn Ile Arg Asn Phe Pro Ser Gly Thr Lys
                85                  90                  95

Val His Val Ser Asn Pro Ile Pro Leu Gly Arg Gly Leu Gly Ser Ser
            100                 105                 110

Gly Ala Ala Val Val Ala Gly Val Ile Leu Gly Asn Glu Val Ala Gln
        115                 120                 125

Leu Gly Phe Ser Lys Gln Arg Met Leu Asp Tyr Cys Leu Met Ile Glu
130                 135                 140

Arg His Pro Asp Asn Ile Thr Ala Ala Met Met Gly Gly Phe Cys Gly
145                 150                 155                 160

Ser Phe Leu Arg Asp Leu Thr Pro Gln Glu Val Glu Arg Arg Glu Ile
                165                 170                 175

Pro Leu Ala Glu Val Leu Pro Glu Pro Ser Gly Gly Glu Asp Thr Gly
            180                 185                 190

Leu Val Pro Pro Leu Pro Pro Thr Asp Ile Gly Arg His Val Lys Tyr
        195                 200                 205

Gln Trp Asn Pro Ala Ile Lys Cys Ile Ala Ile Pro Gln Phe Glu
    210                 215                 220

Leu Ser Thr Ala Asp Ser Arg Gly Val Leu Pro Lys Ala Tyr Pro Thr
225                 230                 235                 240

Gln Asp Leu Val Phe Asn Leu Gln Arg Leu Ala Val Leu Thr Thr Ala
                245                 250                 255

Leu Thr Met Asp Pro Pro Asn Ala Asp Leu Ile Tyr Pro Ala Met Gln
            260                 265                 270

Asp Arg Val His Gln Pro Tyr Arg Lys Thr Leu Ile Pro Gly Leu Thr
        275                 280                 285

Glu Ile Leu Ser Cys Val Thr Pro Ser Thr Tyr Pro Gly Leu Leu Gly
    290                 295                 300

Ile Cys Leu Ser Gly Ala Gly Pro Thr Ile Leu Ala Leu Ala Thr Glu
305                 310                 315                 320

Asn Phe Glu Glu Ile Ser Gln Glu Ile Ile Asn Arg Phe Ala Lys Asn
                325                 330                 335

Gly Ile Lys Cys Ser Trp Lys Leu Leu Glu Pro Ala Tyr Asp Gly Ala
            340                 345                 350

Ser Val Glu Gln Gln
    355

<210> SEQ ID NO 19
<211> LENGTH: 308
<212> TYPE: PRT
<213> ORGANISM: Corynebacterium glutamicum

<400> SEQUENCE: 19

Met Ala Ile Glu Leu Pro Val Gly Lys Lys Val Thr Val Thr Val Pro
1               5                   10                  15

Ala Ser Ser Ala Asn Leu Gly Pro Gly Phe Asp Thr Leu Gly Leu Ala
            20                  25                  30

Leu Ser Leu Tyr Asp Thr Val Glu Val Glu Val Thr Asp His Gly Leu
        35                  40                  45

Glu Val Glu Val Phe Gly Glu Gly Gln Gly Glu Leu Pro Leu Asp Gly
    50                  55                  60

Ser His Leu Val Val Lys Ala Ile Arg Ala Gly Leu Lys Ala Ala Asp
65                  70                  75                  80

Val Gln Val Pro Gly Leu Arg Val Val Cys His Asn Asn Ile Pro Gln
                85                  90                  95

Ser Arg Gly Leu Gly Ser Ser Ala Ala Ala Val Ala Gly Val Ala
            100                 105                 110

Ala Ala Asn Gly Leu Ala Gly Phe Pro Leu Asp Asp Ala Arg Val Val
        115                 120                 125

Gln Leu Ser Ser Ala Phe Glu Gly His Pro Asp Asn Ala Ala Ala Ser
    130                 135                 140

Val Leu Gly Asn Ala Val Val Ser Trp Thr Glu Ile Pro Val Asp Gly
145                 150                 155                 160

Arg Thr Glu Pro Gln Phe Lys Ala Val Thr Ile Asn Val Asp Ser Arg
                165                 170                 175

Ile Lys Ala Thr Ala Leu Val Pro Asp Phe His Ala Ser Thr Glu Ala
            180                 185                 190

Val Arg Arg Val Leu Pro Ser Asp Val Thr His Leu Asp Ala Arg Phe
        195                 200                 205

Asn Val Ser Arg Cys Ala Val Met Thr Val Ala Leu Gln His His Pro
    210                 215                 220

Glu Leu Leu Trp Glu Gly Thr Arg Asp Arg Leu His Gln Pro Tyr Arg
225                 230                 235                 240

Ala Asp Val Leu Pro Val Thr Ala Glu Trp Val Asn Arg Leu Arg Asn
                245                 250                 255

Arg Gly Tyr Ala Ala Tyr Leu Ser Gly Ala Gly Pro Thr Ile Met Val
            260                 265                 270

Leu His Thr Glu Pro Val Asp Glu Ala Val Leu Asn Asp Ala Arg Glu
        275                 280                 285

Ala Gly Leu Arg Val Leu Ser Leu Asp Val Ala Asp Ala Val Ser Val
    290                 295                 300

Lys Val Asp Ala
305

<210> SEQ ID NO 20
<211> LENGTH: 511
<212> TYPE: PRT
<213> ORGANISM: Picihia stipitis

<400> SEQUENCE: 20

Met Ser Gln Lys Tyr Arg Ser Ser Arg Ser Ala Glu Pro Gln Ala Leu

-continued

```
                1               5                  10                  15
        Ser Phe Glu Asp Val Val Met Thr Gly Leu Ala Asn Asp Gly Gly Leu
                        20                  25                  30

Phe Leu Pro Ser Gln Val Pro Gln Leu Pro Ala Ser Phe Leu Gln Asp
                        35                  40                  45

Trp Ala Asp Leu Ser Phe Gln Glu Leu Ala Phe Asn Val Leu Arg Leu
                        50                  55                  60

Tyr Ile Asn Ala Ala Glu Ile Pro Asp Gln Asp Leu Arg Asp Leu Ile
        65                      70                  75                  80

Ser Lys Ser Tyr Ser Thr Phe Arg Ser Glu Glu Val Thr Pro Leu Lys
                        85                  90                  95

Lys Ile Asp Asp Lys Leu Tyr Leu Leu Glu Leu Phe His Gly Pro Thr
                        100                 105                 110

Tyr Ala Phe Lys Asp Val Ala Leu Gln Phe Val Gly Asn Leu Phe Glu
                        115                 120                 125

Tyr Phe Leu Thr Arg Arg Asn Ala Lys Lys Val Glu Gly Glu Ala Arg
                        130                 135                 140

Asp Val Ile Thr Val Val Gly Ala Thr Ser Gly Asp Thr Gly Ser Ala
        145                     150                 155                 160

Ala Ile Tyr Gly Leu Arg Gly Lys Lys Asp Val Ser Val Phe Ile Leu
                        165                 170                 175

Tyr Pro Thr Gly Arg Ile Ser Pro Ile Gln Glu Glu Gln Met Thr Thr
                        180                 185                 190

Val Glu Asp Ala Asn Val His Thr Leu Ser Val Asn Gly Thr Phe Asp
                        195                 200                 205

Asp Cys Gln Asp Ile Val Lys Ser Ile Phe Gly Asp Arg Glu Phe Asn
                        210                 215                 220

Asp Lys Tyr His Val Gly Ala Val Asn Ser Ile Asn Trp Ala Arg Ile
        225                     230                 235                 240

Leu Ala Gln Gln Thr Tyr Tyr Phe Tyr Ser Tyr Phe Gln Leu Gln Lys
                        245                 250                 255

Lys Leu Asn Asp Thr Ser Ala Lys Val Arg Phe Val Val Pro Ser Gly
                        260                 265                 270

Asn Phe Gly Asp Ile Leu Ala Gly Tyr Tyr Ala Tyr Lys Met Gly Leu
                        275                 280                 285

Pro Val Asp Lys Leu Ile Ile Ala Thr Asn Glu Asn Asp Ile Leu Asp
                        290                 295                 300

Arg Phe Met Lys Thr Gly Arg Tyr Glu Lys Lys Ala Glu Lys Asp Ala
        305                     310                 315                 320

Ser Ala Ala Val Lys Ala Thr Phe Ser Pro Ala Met Asp Ile Leu Ile
                        325                 330                 335

Ser Ser Asn Phe Glu Arg Leu Leu Trp Tyr Leu Ile Arg Asp Ser Val
                        340                 345                 350

Ala Asn Gly Ser Asp Glu Val Ala Gly Lys Thr Leu Asn Ser Trp Met
                        355                 360                 365

Gln Gln Leu Lys Glu Thr Gly Ser Val Val Ala Asp Pro Glu Val Leu
                        370                 375                 380

Ala Gly Ala Arg Ser Ile Phe Asp Ser Glu Arg Val Asp Asp Ala Glu
        385                     390                 395                 400

Thr Val Ala Thr Ile Lys Glu Val Tyr Ser Ala His Pro Glu Ser Tyr
                        405                 410                 415

Val Leu Asp Pro His Ser Ser Val Gly Val Thr Thr Ser Tyr Arg Phe
                        420                 425                 430
```

```
Ile Lys Lys Asp Asp Lys Lys Asp Asn Ile Lys Tyr Ile Ser Leu Ser
            435                 440                 445

Thr Ala His Pro Ala Lys Phe Ser Glu Val Val Asn Lys Ala Leu Asp
        450                 455                 460

Ser Ile Ala Gly Tyr Ser Phe Glu Lys Asp Val Leu Pro Ala Glu Leu
465                 470                 475                 480

Lys Ala Leu Ser Thr Lys Arg Lys Arg Ile Asn Leu Ile Asp Glu Ala
                485                 490                 495

Ser Ile Glu Lys Val Lys Asp Ala Ile Lys Lys Glu Leu Asn Phe
            500                 505                 510

<210> SEQ ID NO 21
<211> LENGTH: 514
<212> TYPE: PRT
<213> ORGANISM: Saccharomyces cerevisiae

<400> SEQUENCE: 21

Met Pro Asn Ala Ser Gln Val Tyr Arg Ser Thr Arg Ser Ser Ser Pro
1               5                   10                  15

Lys Thr Ile Ser Phe Glu Glu Ala Ile Ile Gln Gly Leu Ala Thr Asp
                20                  25                  30

Gly Gly Leu Phe Ile Pro Pro Thr Ile Pro Gln Val Asp Gln Ala Thr
            35                  40                  45

Leu Phe Asn Asp Trp Ser Lys Leu Ser Phe Gln Asp Leu Ala Phe Ala
50                  55                  60

Ile Met Arg Leu Tyr Ile Ala Gln Glu Glu Ile Pro Asp Ala Asp Leu
65                  70                  75                  80

Lys Asp Leu Ile Lys Arg Ser Tyr Ser Thr Phe Arg Ser Asp Glu Val
                85                  90                  95

Thr Pro Leu Val Gln Asn Val Thr Gly Asp Lys Glu Asn Leu His Ile
            100                 105                 110

Leu Glu Leu Phe His Gly Pro Thr Tyr Ala Phe Lys Asp Val Ala Leu
        115                 120                 125

Gln Phe Val Gly Asn Leu Phe Glu Tyr Phe Leu Gln Arg Thr Asn Ala
130                 135                 140

Asn Leu Pro Glu Gly Glu Lys Lys Gln Ile Thr Val Val Gly Ala Thr
145                 150                 155                 160

Ser Gly Asp Thr Gly Ser Ala Ala Ile Tyr Gly Leu Arg Gly Lys Lys
                165                 170                 175

Asp Val Ser Val Phe Ile Leu Tyr Pro Thr Gly Arg Ile Ser Pro Ile
            180                 185                 190

Gln Glu Glu Gln Met Thr Thr Val Pro Asp Glu Asn Val Gln Thr Leu
        195                 200                 205

Ser Val Thr Gly Thr Phe Asp Asn Cys Gln Asp Ile Val Lys Ala Ile
210                 215                 220

Phe Gly Asp Lys Glu Phe Asn Ser Lys His Asn Val Gly Ala Val Asn
225                 230                 235                 240

Ser Ile Asn Trp Ala Arg Ile Leu Ala Gln Met Thr Tyr Tyr Phe Tyr
                245                 250                 255

Ser Phe Phe Gln Ala Thr Asn Gly Lys Asp Ser Lys Lys Val Lys Phe
            260                 265                 270

Val Val Pro Ser Gly Asn Phe Gly Asp Ile Leu Ala Gly Tyr Phe Ala
        275                 280                 285

Lys Lys Met Gly Leu Pro Ile Glu Lys Leu Ala Ile Ala Thr Asn Glu
        290                 295                 300
```

-continued

```
Asn Asp Ile Leu Asp Arg Phe Leu Lys Ser Gly Leu Tyr Glu Arg Ser
305                 310                 315                 320

Asp Lys Val Ala Ala Thr Leu Ser Pro Ala Met Asp Ile Leu Ile Ser
                325                 330                 335

Ser Asn Phe Glu Arg Leu Leu Trp Tyr Leu Ala Arg Glu Tyr Leu Ala
            340                 345                 350

Asn Gly Asp Asp Leu Lys Ala Gly Glu Ile Val Asn Asn Trp Phe Gln
        355                 360                 365

Glu Leu Lys Thr Asn Gly Lys Phe Gln Val Asp Lys Ser Ile Ile Glu
    370                 375                 380

Gly Ala Ser Lys Asp Phe Thr Ser Glu Arg Val Ser Asn Glu Glu Thr
385                 390                 395                 400

Ser Glu Thr Ile Lys Lys Ile Tyr Glu Ser Ser Val Asn Pro Lys His
                405                 410                 415

Tyr Ile Leu Asp Pro His Thr Ala Val Gly Val Cys Ala Thr Glu Arg
            420                 425                 430

Leu Ile Ala Lys Asp Asn Asp Lys Ser Ile Gln Tyr Ile Ser Leu Ser
        435                 440                 445

Thr Ala His Pro Ala Lys Phe Ala Asp Ala Val Asn Asn Ala Leu Ser
    450                 455                 460

Gly Phe Ser Asn Tyr Ser Phe Glu Lys Asp Val Leu Pro Glu Glu Leu
465                 470                 475                 480

Lys Lys Leu Ser Thr Leu Lys Lys Leu Lys Phe Ile Glu Arg Ala
                485                 490                 495

Asp Val Glu Leu Val Lys Asn Ala Ile Glu Glu Leu Ala Lys Met
            500                 505                 510

Lys Leu

<210> SEQ ID NO 22
<211> LENGTH: 539
<212> TYPE: PRT
<213> ORGANISM: Picihia stipitis

<400> SEQUENCE: 22

Met Phe Phe Ser Arg Ser Gly Glu Val Glu Lys Phe Pro Asn Leu Leu
1               5                   10                  15

Asp Ala Asp Phe Asn Glu Asp Gly Asp Pro Asp Tyr Ile Lys Leu Ile
                20                  25                  30

Leu Thr Ser Arg Val Tyr Asp Val Val Glu Arg Ala Gly Thr Pro Leu
            35                  40                  45

Thr His Ala Ile Asn Leu Ser His Lys Cys Asn Ser Asn Ile Tyr Leu
    50                  55                  60

Lys Arg Glu Asp Leu Leu Pro Val Phe Ser Phe Lys Leu Arg Gly Ala
65                  70                  75                  80

Tyr Asn Met Ile Ser His Leu His Ser Asn Ser Lys Met Pro Leu Ser
                85                  90                  95

Gly Val Ile Ala Cys Ser Ala Gly Asn His Ala Gln Gly Val Ala Tyr
            100                 105                 110

Ser Ala Asn Arg Leu Lys Ile Pro Ser Thr Ile Val Met Pro Thr Ala
        115                 120                 125

Thr Pro Ser Ile Lys Tyr Thr Asn Val Ser Arg Leu Gly Ser Gln Val
    130                 135                 140

Val Leu Tyr Gly Asp Asp Phe Asp Ser Ala Lys Gln Glu Cys Ala Arg
145                 150                 155                 160

Leu Ser Ser Leu Asn Asn Leu Thr Asp Val Pro Pro Phe Asp His Pro
```

```
            165                 170                 175
Tyr Val Ile Ala Gly Gln Gly Thr Ile Ala Leu Glu Ile Thr Arg Gln
            180                 185                 190

Leu Arg Leu Asp Lys Leu Asn Ala Leu Phe Val Pro Val Gly Gly Gly
        195                 200                 205

Gly Leu Ile Ala Gly Val Ala Val Tyr Leu Lys Lys Ile Ala Pro His
        210                 215                 220

Val Lys Ile Ile Gly Val Glu Thr Asn Asp Ala Asp Ala Leu Tyr Gln
225                 230                 235                 240

Ser Leu Lys Ala Lys Lys Leu Val Val Leu Asp Gln Val Gly Met Phe
                245                 250                 255

Ala Asp Gly Thr Ala Val Lys Val Leu Gly Lys Glu Thr Trp Arg Leu
            260                 265                 270

Cys Glu Asn Leu Val Asp Glu Val Val Lys Val Ser Thr Asp Glu Leu
        275                 280                 285

Cys Ala Ala Ile Lys Asp Ile Phe Glu Asp Thr Arg Leu Ile Thr Glu
        290                 295                 300

Pro Ser Gly Ala Leu Ser Val Ala Gly Leu Lys Lys Tyr Ile Glu Gln
305                 310                 315                 320

Asn Pro Asp Ile Asp His Arg Asn Lys Phe Tyr Val Pro Ile Leu Ser
                325                 330                 335

Gly Ala Asn Met Asn Phe Asp Arg Leu Arg Phe Val Ser Glu Arg Ala
            340                 345                 350

Val Leu Gly Glu Gly Lys Glu Val Ser Leu Val Val Thr Ile Pro Glu
        355                 360                 365

Lys Pro Gly Glu Phe Ala Lys Leu Gln Ser Ile Ile Asn Pro Arg Ala
370                 375                 380

Ile Thr Glu Phe Ser Tyr Arg Cys Asn Gly Ala Asp Ala Asn Ile Phe
385                 390                 395                 400

Val Ser Phe Asn Val Ile Asp Lys Lys Glu Leu Thr Pro Ile Ile
                405                 410                 415

Glu Asp Met Asn Asn Asn Glu His Gly Tyr Glu Val Val Asp Ile Ser
            420                 425                 430

Asp Asn Glu Leu Ala Lys Thr His Gly Cys Tyr Leu Val Gly Gly Lys
        435                 440                 445

Ser Ser Glu Glu Val Ala Asn Glu Arg Leu Tyr Ser Phe Glu Phe Pro
        450                 455                 460

Glu Lys Pro Gly Ala Leu Phe Asn Phe Leu Gln Ala Leu Lys Ala Asp
465                 470                 475                 480

Trp Asn Ile Thr Leu Phe His Tyr His Asn His Gly His Asp Ile Gly
                485                 490                 495

Lys Val Leu Cys Gly Phe Thr Leu Pro Glu Gly Thr Asp Asp Ala Asp
            500                 505                 510

Phe Gln Ser Phe Leu Asn Glu Leu Gly Tyr Lys Phe Asn Val Glu Asn
        515                 520                 525

Asp Asn Val Val Tyr Lys Lys Phe Leu Arg Ser
    530                 535

<210> SEQ ID NO 23
<211> LENGTH: 529
<212> TYPE: PRT
<213> ORGANISM: Pichia stipitis

<400> SEQUENCE: 23

Met Phe Pro Asn Leu Leu Asp Ala Asp Phe Asn Glu Asp Gly Asp Pro
```

-continued

```
                1               5                   10                  15
        Asp Tyr Ile Lys Leu Ile Leu Thr Ser Arg Val Tyr Asp Val Val Glu
                        20                  25                  30

Arg Ala Gly Thr Pro Leu Thr His Ala Ile Asn Leu Ser His Lys Cys
                    35                  40                  45

Asn Ser Asn Ile Tyr Leu Lys Arg Glu Asp Leu Leu Pro Val Phe Ser
         50                  55                  60

Phe Lys Leu Arg Gly Ala Tyr Asn Met Ile Ser His Leu His Ser Asn
         65                  70                  75                  80

Ser Lys Met Pro Leu Ser Gly Val Ile Ala Cys Ser Ala Gly Asn His
                        85                  90                  95

Ala Gln Gly Val Ala Tyr Ser Ala Asn Arg Leu Lys Ile Pro Ser Thr
                    100                 105                 110

Ile Val Met Pro Thr Ala Thr Pro Ser Ile Lys Tyr Thr Asn Val Ser
                    115                 120                 125

Arg Leu Gly Ser Gln Val Val Leu Tyr Gly Asp Asp Phe Asp Ser Ala
                    130                 135                 140

Lys Gln Glu Cys Ala Arg Leu Ser Ser Leu Asn Asn Leu Thr Asp Val
        145                 150                 155                 160

Pro Pro Phe Asp His Pro Tyr Val Ile Ala Gly Gln Gly Thr Ile Ala
                            165                 170                 175

Leu Glu Ile Thr Arg Gln Leu Arg Leu Asp Lys Leu Asn Ala Leu Phe
                        180                 185                 190

Val Pro Val Gly Gly Gly Gly Leu Ile Ala Gly Val Ala Val Tyr Leu
                        195                 200                 205

Lys Lys Ile Ala Pro His Val Lys Ile Ile Gly Val Glu Thr Asn Asp
        210                 215                 220

Ala Asp Ala Leu Tyr Gln Ser Leu Lys Ala Lys Leu Val Val Leu
        225                 230                 235                 240

Asp Gln Val Gly Met Phe Ala Asp Gly Thr Ala Val Lys Val Leu Gly
                        245                 250                 255

Lys Glu Thr Trp Arg Leu Cys Glu Asn Leu Val Asp Glu Val Val Lys
                        260                 265                 270

Val Ser Thr Asp Glu Leu Cys Ala Ala Ile Lys Asp Ile Phe Glu Asp
                    275                 280                 285

Thr Arg Leu Ile Thr Glu Pro Ser Gly Ala Leu Ser Val Ala Gly Leu
                    290                 295                 300

Lys Lys Tyr Ile Glu Gln Asn Pro Asp Ile Asp His Arg Asn Lys Phe
        305                 310                 315                 320

Tyr Val Pro Ile Leu Ser Gly Ala Asn Met Asn Phe Asp Arg Leu Arg
                        325                 330                 335

Phe Val Ser Glu Arg Ala Val Leu Gly Glu Gly Lys Glu Val Ser Leu
                        340                 345                 350

Val Val Thr Ile Pro Glu Lys Pro Gly Glu Phe Ala Lys Leu Gln Ser
                    355                 360                 365

Ile Ile Asn Pro Arg Ala Ile Thr Glu Phe Ser Tyr Arg Cys Asn Gly
                370                 375                 380

Ala Asp Ala Asn Ile Phe Val Ser Phe Asn Val Ile Asp Lys Lys Lys
        385                 390                 395                 400

Glu Leu Thr Pro Ile Ile Glu Asp Met Asn Asn Glu His Gly Tyr
                        405                 410                 415

Glu Val Val Asp Ile Ser Asp Asn Glu Leu Ala Lys Thr His Gly Cys
                        420                 425                 430
```

```
Tyr Leu Val Gly Gly Lys Ser Ser Glu Glu Val Ala Asn Glu Arg Leu
            435                 440                 445

Tyr Ser Phe Glu Phe Pro Glu Lys Pro Gly Ala Leu Phe Asn Phe Leu
    450                 455                 460

Gln Ala Leu Lys Ala Asp Trp Asn Ile Thr Leu Phe His Tyr His Asn
465                 470                 475                 480

His Gly His Asp Ile Gly Lys Val Leu Cys Gly Phe Thr Leu Pro Glu
                485                 490                 495

Gly Thr Asp Asp Ala Asp Phe Gln Ser Phe Leu Asn Glu Leu Gly Tyr
            500                 505                 510

Lys Phe Asn Val Glu Asn Asp Asn Val Val Tyr Lys Lys Phe Leu Arg
            515                 520                 525

Ser

<210> SEQ ID NO 24
<211> LENGTH: 576
<212> TYPE: PRT
<213> ORGANISM: Saccharomyces cerevisiae

<400> SEQUENCE: 24

Met Ser Ala Thr Leu Leu Lys Gln Pro Leu Cys Thr Val Val Arg Gln
1               5                   10                  15

Gly Lys Gln Ser Lys Val Ser Gly Leu Asn Leu Leu Arg Leu Lys Ala
            20                  25                  30

His Leu His Arg Gln His Leu Ser Pro Ser Leu Ile Lys Leu His Ser
        35                  40                  45

Glu Leu Lys Leu Asp Glu Leu Gln Thr Asp Asn Thr Pro Asp Tyr Val
    50                  55                  60

Arg Leu Val Leu Arg Ser Ser Val Tyr Asp Val Ile Asn Glu Ser Pro
65                  70                  75                  80

Ile Ser Gln Gly Val Gly Leu Ser Arg Leu Asn Thr Asn Val Ile
                85                  90                  95

Leu Lys Arg Glu Asp Leu Leu Pro Val Phe Ser Phe Lys Leu Arg Gly
            100                 105                 110

Ala Tyr Asn Met Ile Ala Lys Leu Asp Asp Ser Gln Arg Asn Gln Gly
        115                 120                 125

Val Ile Ala Cys Ser Ala Gly Asn His Ala Gln Gly Val Ala Phe Ala
    130                 135                 140

Ala Lys His Leu Lys Ile Pro Ala Thr Ile Val Met Pro Val Cys Thr
145                 150                 155                 160

Pro Ser Ile Lys Tyr Gln Asn Val Ser Arg Leu Gly Ser Gln Val Val
                165                 170                 175

Leu Tyr Gly Asn Asp Phe Asp Glu Ala Lys Ala Glu Cys Ala Lys Leu
            180                 185                 190

Ala Glu Glu Arg Gly Leu Thr Asn Ile Pro Pro Phe Asp His Pro Tyr
        195                 200                 205

Val Ile Ala Gly Gln Gly Thr Val Ala Met Glu Ile Leu Arg Gln Val
    210                 215                 220

Arg Thr Ala Asn Lys Ile Gly Ala Val Phe Val Pro Val Gly Gly Gly
225                 230                 235                 240

Gly Leu Ile Ala Gly Ile Gly Ala Tyr Leu Lys Arg Val Ala Pro His
                245                 250                 255

Ile Lys Ile Ile Gly Val Glu Thr Tyr Asp Ala Ala Thr Leu His Asn
            260                 265                 270

Ser Leu Gln Arg Asn Gln Arg Thr Pro Leu Pro Val Val Gly Thr Phe
```

```
              275                 280                 285
Ala Asp Gly Thr Ser Val Arg Met Ile Gly Glu Glu Thr Phe Arg Val
290                 295                 300

Ala Gln Gln Val Val Asp Glu Val Val Leu Val Asn Thr Asp Glu Ile
305                 310                 315                 320

Cys Ala Ala Val Lys Asp Ile Phe Glu Asp Thr Arg Ser Ile Val Glu
            325                 330                 335

Pro Ser Gly Ala Leu Ser Val Ala Gly Met Lys Lys Tyr Ile Ser Thr
            340                 345                 350

Val His Pro Glu Ile Asp His Thr Lys Asn Thr Tyr Val Pro Ile Leu
            355                 360                 365

Ser Gly Ala Asn Met Asn Phe Asp Arg Leu Arg Phe Val Ser Glu Arg
            370                 375                 380

Ala Val Leu Gly Glu Gly Lys Glu Val Phe Met Leu Val Thr Leu Pro
385                 390                 395                 400

Asp Val Pro Gly Ala Phe Lys Lys Met Gln Lys Ile Ile His Pro Arg
                405                 410                 415

Ser Val Thr Glu Phe Ser Tyr Arg Tyr Asn Glu His Arg His Glu Ser
                420                 425                 430

Ser Ser Glu Val Pro Lys Ala Tyr Ile Tyr Thr Ser Phe Ser Val Val
            435                 440                 445

Asp Arg Glu Lys Glu Ile Lys Gln Val Met Gln Gln Leu Asn Ala Leu
            450                 455                 460

Gly Phe Glu Ala Val Asp Ile Ser Asp Asn Glu Leu Ala Lys Ser His
465                 470                 475                 480

Gly Arg Tyr Leu Val Gly Gly Ala Ser Lys Val Pro Asn Glu Arg Ile
                485                 490                 495

Ile Ser Phe Glu Phe Pro Glu Arg Pro Gly Ala Leu Thr Arg Phe Leu
                500                 505                 510

Gly Gly Leu Ser Asp Ser Trp Asn Leu Thr Leu Phe His Tyr Arg Asn
            515                 520                 525

His Gly Ala Asp Ile Gly Lys Val Leu Ala Gly Ile Ser Val Pro Pro
            530                 535                 540

Arg Glu Asn Leu Thr Phe Gln Lys Phe Leu Glu Asp Leu Gly Tyr Thr
545                 550                 555                 560

Tyr His Asp Glu Thr Asp Asn Thr Val Tyr Gln Lys Phe Leu Lys Tyr
                565                 570                 575

<210> SEQ ID NO 25
<211> LENGTH: 576
<212> TYPE: PRT
<213> ORGANISM: Saccharomyces cerevisiae

<400> SEQUENCE: 25

Met Ser Ala Thr Leu Leu Lys Gln Pro Leu Cys Thr Val Val Arg Gln
1               5                   10                  15

Gly Lys Gln Ser Lys Val Ser Gly Leu Asn Leu Leu Arg Leu Lys Ala
                20                  25                  30

His Leu His Arg Gln His Leu Ser Pro Ser Leu Ile Lys Leu His Ser
            35                  40                  45

Glu Leu Lys Leu Asp Glu Leu Gln Thr Asp Asn Thr Pro Asp Tyr Val
            50                  55                  60

Arg Leu Val Leu Arg Ser Ser Val Tyr Asp Val Ile Asn Glu Ser Pro
65                  70                  75                  80

Ile Ser Gln Gly Val Gly Leu Ser Ser Arg Leu Asn Thr Asn Val Ile
```

-continued

```
                85                  90                  95
Leu Lys Arg Glu Asp Leu Leu Pro Val Phe Ser Phe Lys Leu Arg Gly
            100                 105                 110
Ala Tyr Asn Met Ile Ala Lys Leu Asp Asp Ser Gln Arg Asn Gln Gly
            115                 120                 125
Val Ile Ala Cys Ser Ala Gly Asn His Ala Gln Gly Val Ala Phe Ala
            130                 135                 140
Ala Lys His Leu Lys Ile Pro Ala Thr Ile Val Met Pro Val Cys Thr
145                 150                 155                 160
Pro Ser Ile Lys Tyr Gln Asn Val Ser Arg Leu Gly Ser Gln Val Val
                165                 170                 175
Leu Tyr Gly Asn Asp Phe Asp Glu Ala Lys Ala Glu Cys Ala Lys Leu
            180                 185                 190
Ala Glu Glu Arg Gly Leu Thr Asn Ile Pro Pro Phe Asp His Pro Tyr
            195                 200                 205
Val Ile Ala Gly Gln Gly Thr Val Ala Met Glu Ile Leu Arg Gln Val
            210                 215                 220
Arg Thr Ala Asn Lys Ile Gly Ala Val Phe Val Pro Val Gly Gly Gly
225                 230                 235                 240
Gly Leu Ile Ala Gly Ile Gly Ala Tyr Leu Lys Arg Val Ala Pro His
                245                 250                 255
Ile Lys Ile Ile Gly Val Glu Thr Tyr Asp Ala Ala Thr Leu His Asn
            260                 265                 270
Ser Leu Gln Arg Asn Gln Arg Thr Pro Leu Pro Val Val Gly Thr Phe
            275                 280                 285
Ala Asp Gly Thr Ser Val Arg Met Ile Gly Glu Glu Thr Phe Arg Val
            290                 295                 300
Ala Gln Gln Val Val Asp Glu Val Val Leu Val Asn Thr Asp Glu Ile
305                 310                 315                 320
Cys Ala Ala Val Lys Asp Ile Phe Glu Asp Thr Arg Ser Ile Val Glu
            325                 330                 335
Pro Ser Gly Ala Leu Ser Val Ala Gly Met Lys Lys Tyr Ile Ser Thr
            340                 345                 350
Val His Pro Glu Ile Asp His Thr Lys Asn Thr Tyr Val Pro Ile Leu
            355                 360                 365
Ser Gly Ala Asn Met Asn Phe Asp Arg Leu Arg Phe Val Ser Glu Arg
            370                 375                 380
Ala Val Leu Gly Glu Gly Lys Glu Val Phe Met Leu Val Thr Leu Pro
385                 390                 395                 400
Asp Val Pro Gly Ala Phe Lys Lys Met Gln Lys Ile Ile His Pro Arg
                405                 410                 415
Ser Val Thr Glu Phe Ser Tyr Arg Tyr Asn Glu His Arg His Glu Ser
            420                 425                 430
Ser Ser Glu Val Pro Lys Ala Tyr Ile Tyr Thr Ser Phe Ser Val Val
            435                 440                 445
Asp Arg Glu Lys Glu Ile Lys Gln Val Met Gln Gln Leu Asn Ala Leu
450                 455                 460
Gly Phe Glu Ala Val Asp Ile Ser Asp Asn Glu Leu Ala Lys Ser His
465                 470                 475                 480
Gly Cys Tyr Leu Val Gly Gly Ala Ser Lys Val Pro Asn Glu Arg Ile
                485                 490                 495
Ile Ser Phe Glu Phe Pro Glu Arg Pro Gly Ala Leu Thr Arg Phe Leu
            500                 505                 510
```

```
Gly Gly Leu Ser Asp Ser Trp Asn Leu Thr Leu Phe His Tyr His Asn
        515                 520                 525

His Gly Ala Asp Ile Gly Lys Val Leu Ala Gly Ile Ser Val Pro Pro
        530                 535                 540

Arg Glu Asn Leu Thr Phe Gln Lys Phe Leu Glu Asp Leu Gly Tyr Thr
545                 550                 555                 560

Tyr His Asp Glu Thr Asp Asn Thr Val Tyr Gln Lys Phe Leu Lys Tyr
                565                 570                 575

<210> SEQ ID NO 26
<211> LENGTH: 539
<212> TYPE: PRT
<213> ORGANISM: Pichia stipitis

<400> SEQUENCE: 26

Met Phe Phe Ser Arg Ser Gly Glu Val Glu Lys Phe Pro Asn Leu Leu
1               5                   10                  15

Asp Ala Asp Phe Asn Glu Asp Gly Asp Pro Asp Tyr Ile Lys Leu Ile
            20                  25                  30

Leu Thr Ser Arg Val Tyr Asp Val Val Glu Arg Ala Gly Thr Pro Leu
        35                  40                  45

Thr His Ala Ile Asn Leu Ser His Lys Cys Asn Ser Asn Ile Tyr Leu
    50                  55                  60

Lys Arg Glu Asp Leu Leu Pro Val Phe Ser Lys Leu Arg Gly Ala
65                  70                  75                  80

Tyr Asn Met Ile Ser His Leu His Ser Asn Ser Lys Met Pro Leu Ser
                85                  90                  95

Gly Val Ile Ala Cys Ser Ala Gly Asn His Ala Gln Gly Val Ala Tyr
            100                 105                 110

Ser Ala Asn Arg Leu Lys Ile Pro Ser Thr Ile Val Met Pro Thr Ala
        115                 120                 125

Thr Pro Ser Ile Lys Tyr Thr Asn Val Ser Arg Leu Gly Ser Gln Val
    130                 135                 140

Val Leu Tyr Gly Asp Asp Phe Asp Ser Ala Lys Gln Glu Cys Ala Arg
145                 150                 155                 160

Leu Ser Ser Leu Asn Asn Leu Thr Asp Val Pro Pro Phe Asp His Pro
                165                 170                 175

Tyr Val Ile Ala Gly Gln Gly Thr Ile Ala Leu Glu Ile Thr Arg Gln
            180                 185                 190

Leu Arg Leu Asp Lys Leu Asn Ala Leu Phe Val Pro Val Gly Gly Gly
        195                 200                 205

Gly Leu Ile Ala Gly Val Ala Val Tyr Leu Lys Lys Ile Ala Pro His
    210                 215                 220

Val Lys Ile Ile Gly Val Glu Thr Asn Asp Ala Asp Ala Leu Tyr Gln
225                 230                 235                 240

Ser Leu Lys Ala Lys Lys Ser Val Val Leu Asp Gln Val Gly Met Phe
                245                 250                 255

Ala Asp Gly Thr Ala Val Lys Val Leu Gly Lys Glu Thr Trp Arg Leu
            260                 265                 270

Cys Glu Asn Leu Val Asp Glu Val Val Lys Val Ser Thr Asp Glu Leu
        275                 280                 285

Cys Ala Ala Ile Lys Asp Ile Phe Glu Asp Thr Arg Ser Ile Thr Glu
    290                 295                 300

Pro Ser Gly Ala Leu Ser Val Ala Gly Leu Lys Lys Tyr Ile Glu Gln
305                 310                 315                 320
```

-continued

Asn Pro Asp Ile Asp His Arg Asn Lys Phe Tyr Val Pro Ile Leu Ser
              325                 330                 335

Gly Ala Asn Met Asn Phe Asp Arg Leu Arg Phe Val Ser Glu Arg Ala
              340                 345                 350

Val Leu Gly Glu Gly Lys Glu Val Ser Leu Val Val Thr Ile Pro Glu
              355                 360                 365

Lys Pro Gly Glu Phe Ala Lys Leu Gln Ser Ile Ile Asn Pro Arg Ala
370                 375                 380

Ile Thr Glu Phe Ser Tyr Arg Cys Asn Gly Ala Asp Ala Asn Ile Phe
385                 390                 395                 400

Val Ser Phe Asn Val Ile Asp Lys Lys Glu Leu Thr Pro Ile Ile
              405                 410                 415

Glu Asp Met Asn Asn Glu His Gly Tyr Glu Val Val Asp Ile Ser
              420                 425                 430

Asp Asn Glu Leu Ala Lys Thr His Gly Arg Tyr Leu Val Gly Gly Lys
              435                 440                 445

Ser Ser Glu Glu Val Ala Asn Glu Arg Leu Tyr Ser Phe Glu Phe Pro
450                 455                 460

Glu Lys Pro Gly Ala Leu Phe Asn Phe Leu Gln Ala Leu Lys Ala Asp
465                 470                 475                 480

Trp Asn Ile Thr Leu Phe His Tyr Arg Asn His Gly His Asp Ile Gly
              485                 490                 495

Lys Val Leu Cys Gly Phe Thr Leu Pro Glu Gly Thr Asp Asp Ala Asp
              500                 505                 510

Phe Gln Ser Phe Leu Asn Glu Leu Gly Tyr Lys Phe Asn Val Glu Asn
              515                 520                 525

Asp Asn Val Val Tyr Lys Lys Phe Leu Arg Ser
              530                 535

<210> SEQ ID NO 27
<211> LENGTH: 360
<212> TYPE: PRT
<213> ORGANISM: Saccharomyces cerevisiae

<400> SEQUENCE: 27

Met Ser Ile Val Tyr Asn Lys Thr Pro Leu Leu Arg Gln Phe Phe Pro
1               5                   10                  15

Gly Lys Ala Ser Ala Gln Phe Phe Leu Lys Tyr Glu Cys Leu Gln Pro
              20                  25                  30

Ser Gly Ser Phe Lys Ser Arg Gly Ile Gly Asn Leu Ile Met Lys Ser
              35                  40                  45

Ala Ile Arg Ile Gln Lys Asp Gly Lys Arg Ser Pro Gln Val Phe Ala
50                  55                  60

Ser Ser Gly Gly Asn Ala Gly Phe Ala Ala Ala Thr Ala Cys Gln Arg
65                  70                  75                  80

Leu Ser Leu Pro Cys Thr Val Val Pro Thr Ala Thr Lys Lys Arg
              85                  90                  95

Met Val Asp Lys Ile Arg Asn Thr Gly Ala Gln Val Ile Val Ser Gly
              100                 105                 110

Ala Tyr Trp Lys Glu Ala Asp Thr Phe Leu Lys Thr Asn Val Met Asn
              115                 120                 125

Lys Ile Asp Ser Gln Val Ile Glu Pro Ile Tyr Val His Pro Phe Asp
              130                 135                 140

Asn Pro Asp Ile Trp Glu Gly His Ser Ser Met Ile Asp Glu Ile Val
145                 150                 155                 160

```
Gln Asp Leu Lys Ser Gln His Ile Ser Val Asn Lys Val Lys Gly Ile
                165                 170                 175
Val Cys Ser Val Gly Gly Gly Leu Tyr Asn Gly Ile Ile Gln Gly
            180                 185                 190
Leu Glu Arg Tyr Gly Leu Ala Asp Arg Ile Pro Ile Val Gly Val Glu
        195                 200                 205
Thr Asn Gly Cys His Val Phe Asn Thr Ser Leu Lys Ile Gly Gln Pro
    210                 215                 220
Val Gln Phe Lys Lys Ile Thr Ser Ile Ala Thr Ser Leu Gly Thr Ala
225                 230                 235                 240
Val Ile Ser Asn Gln Thr Phe Glu Tyr Ala Arg Lys Tyr Asn Thr Arg
                245                 250                 255
Ser Val Val Ile Glu Asp Lys Asp Val Ile Glu Thr Cys Leu Lys Tyr
            260                 265                 270
Thr His Gln Phe Asn Met Val Ile Glu Pro Ala Cys Gly Ala Ala Leu
        275                 280                 285
His Leu Gly Tyr Asn Thr Lys Ile Leu Glu Asn Ala Leu Gly Ser Lys
    290                 295                 300
Leu Ala Ala Asp Asp Ile Val Ile Ile Ala Cys Gly Gly Ser Ser
305                 310                 315                 320
Asn Thr Ile Lys Asp Leu Glu Glu Ala Leu Asp Ser Met Arg Lys Lys
                325                 330                 335
Asp Thr Pro Val Ile Glu Val Ala Asp Asn Phe Ile Phe Pro Glu Lys
            340                 345                 350
Asn Ile Val Asn Leu Lys Ser Ala
        355                 360

<210> SEQ ID NO 28
<211> LENGTH: 436
<212> TYPE: PRT
<213> ORGANISM: Corynebacterium glutamicum

<400> SEQUENCE: 28

Met Ser Glu Thr Tyr Val Ser Glu Lys Ser Pro Gly Val Met Ala Ser
1               5                   10                  15
Gly Ala Glu Leu Ile Arg Ala Ala Asp Ile Gln Thr Ala Gln Ala Arg
            20                  25                  30
Ile Ser Ser Val Ile Ala Pro Thr Pro Leu Gln Tyr Cys Pro Arg Leu
        35                  40                  45
Ser Glu Glu Thr Gly Ala Glu Ile Tyr Leu Lys Arg Glu Asp Leu Gln
    50                  55                  60
Asp Val Arg Ser Tyr Lys Ile Arg Gly Ala Leu Asn Ser Gly Ala Gln
65                  70                  75                  80
Leu Thr Gln Glu Gln Arg Asp Ala Gly Ile Val Ala Ala Ser Ala Gly
                85                  90                  95
Asn His Ala Gln Gly Val Ala Tyr Val Cys Lys Ser Leu Gly Val Gln
            100                 105                 110
Gly Arg Ile Tyr Val Pro Val Gln Thr Pro Lys Gln Lys Arg Asp Arg
        115                 120                 125
Ile Met Val His Gly Gly Glu Phe Val Ser Leu Val Val Thr Gly Asn
    130                 135                 140
Asn Phe Asp Glu Ala Ser Ala Ala Ala His Glu Asp Ala Glu Arg Thr
145                 150                 155                 160
Gly Ala Thr Leu Ile Glu Pro Phe Asp Ala Arg Asn Thr Val Ile Gly
                165                 170                 175
```

```
Gln Gly Thr Val Ala Ala Glu Ile Leu Ser Gln Leu Thr Ser Met Gly
            180                 185                 190

Lys Ser Ala Asp His Val Met Val Pro Val Gly Gly Gly Leu Leu
        195                 200                 205

Ala Gly Val Val Ser Tyr Met Ala Asp Met Ala Pro Arg Thr Ala Ile
            210                 215                 220

Val Gly Ile Glu Pro Ala Gly Ala Ala Ser Met Gln Ala Ala Leu His
225                 230                 235                 240

Asn Gly Gly Pro Ile Thr Leu Glu Thr Val Asp Pro Phe Val Asp Gly
                245                 250                 255

Ala Ala Val Lys Arg Val Gly Asp Leu Asn Tyr Thr Ile Val Glu Lys
            260                 265                 270

Asn Gln Gly Arg Val His Met Met Ser Ala Thr Glu Gly Ala Val Cys
        275                 280                 285

Thr Glu Met Leu Asp Leu Tyr Gln Asn Glu Gly Ile Ile Ala Glu Pro
    290                 295                 300

Ala Gly Ala Leu Ser Ile Ala Gly Leu Lys Glu Met Ser Phe Ala Pro
305                 310                 315                 320

Gly Ser Val Val Val Cys Ile Ile Ser Gly Gly Asn Asn Asp Val Leu
                325                 330                 335

Arg Tyr Ala Glu Ile Ala Glu Arg Ser Leu Val His Arg Gly Leu Lys
            340                 345                 350

His Tyr Phe Leu Val Asn Phe Pro Gln Lys Pro Gly Gln Leu Arg His
        355                 360                 365

Phe Leu Glu Asp Ile Leu Gly Pro Asp Asp Ile Thr Leu Phe Glu
    370                 375                 380

Tyr Leu Lys Arg Asn Asn Arg Glu Thr Gly Thr Ala Leu Val Gly Ile
385                 390                 395                 400

His Leu Ser Glu Ala Ser Gly Leu Asp Ser Leu Leu Glu Arg Met Glu
                405                 410                 415

Glu Ser Ala Ile Asp Ser Arg Arg Leu Glu Pro Gly Thr Pro Glu Tyr
            420                 425                 430

Glu Tyr Leu Thr
        435

<210> SEQ ID NO 29
<211> LENGTH: 514
<212> TYPE: PRT
<213> ORGANISM: Escherichia coli

<400> SEQUENCE: 29

Met Ala Asp Ser Gln Pro Leu Ser Gly Ala Pro Glu Gly Ala Glu Tyr
1               5                   10                  15

Leu Arg Ala Val Leu Arg Ala Pro Val Tyr Glu Ala Ala Gln Val Thr
            20                  25                  30

Pro Leu Gln Lys Met Glu Lys Leu Ser Ser Arg Leu Asp Asn Val Ile
        35                  40                  45

Leu Val Lys Arg Glu Asp Arg Gln Pro Val His Ser Phe Lys Leu Arg
    50                  55                  60

Gly Ala Tyr Ala Met Met Ala Gly Leu Thr Glu Glu Gln Lys Ala His
65                  70                  75                  80

Gly Val Ile Thr Ala Ser Ala Gly Asn His Ala Gln Gly Val Ala Phe
                85                  90                  95

Ser Ser Ala Arg Leu Gly Val Lys Ala Leu Ile Val Met Pro Thr Ala
            100                 105                 110
```

```
Thr Ala Asp Ile Lys Val Asp Ala Val Arg Gly Phe Gly Gly Glu Val
        115                 120                 125

Leu Leu His Gly Ala Asn Phe Asp Glu Ala Lys Ala Lys Ala Ile Glu
130                 135                 140

Leu Ser Gln Gln Gln Gly Phe Thr Trp Val Pro Pro Phe Asp His Pro
145                 150                 155                 160

Met Val Ile Ala Gly Gln Gly Thr Leu Ala Leu Glu Leu Leu Gln Gln
                165                 170                 175

Asp Ala His Leu Asp Arg Val Phe Val Pro Val Gly Gly Gly Gly Leu
                180                 185                 190

Ala Ala Gly Val Ala Val Leu Ile Lys Gln Leu Met Pro Gln Ile Lys
                195                 200                 205

Val Ile Ala Val Glu Ala Glu Asp Ser Ala Cys Leu Lys Ala Ala Leu
210                 215                 220

Asp Ala Gly His Pro Val Asp Leu Pro Arg Val Gly Leu Phe Ala Glu
225                 230                 235                 240

Gly Val Ala Val Lys Arg Ile Gly Asp Glu Thr Phe Arg Leu Cys Gln
                245                 250                 255

Glu Tyr Leu Asp Asp Ile Ile Thr Val Asp Ser Asp Ala Ile Cys Ala
                260                 265                 270

Ala Met Lys Asp Leu Phe Glu Asp Val Arg Ala Val Ala Glu Pro Ser
                275                 280                 285

Gly Ala Leu Ala Leu Ala Gly Met Lys Lys Tyr Ile Ala Gln His Asn
                290                 295                 300

Ile Arg Gly Glu Arg Leu Ala His Ile Leu Ser Gly Ala Asn Val Asn
305                 310                 315                 320

Phe His Gly Leu Arg Tyr Val Ser Glu Arg Cys Glu Leu Gly Glu Gln
                325                 330                 335

Arg Glu Ala Leu Leu Ala Val Thr Ile Pro Glu Glu Lys Gly Ser Phe
                340                 345                 350

Leu Lys Phe Cys Gln Leu Leu Gly Gly Arg Ser Val Thr Glu Phe Asn
                355                 360                 365

Tyr Arg Phe Ala Asp Ala Lys Asn Ala Cys Ile Phe Val Gly Val Arg
                370                 375                 380

Leu Ser Arg Gly Leu Glu Glu Arg Lys Glu Ile Leu Gln Met Leu Asn
385                 390                 395                 400

Asp Gly Gly Tyr Ser Val Val Asp Leu Ser Asp Asp Glu Met Ala Lys
                405                 410                 415

Leu His Val Arg Tyr Met Val Gly Gly Arg Pro Ser His Pro Leu Gln
                420                 425                 430

Glu Arg Leu Tyr Ser Phe Glu Phe Pro Glu Ser Pro Gly Ala Leu Leu
                435                 440                 445

Arg Phe Leu Asn Thr Leu Gly Thr His Trp Asn Ile Ser Leu Phe His
                450                 455                 460

Tyr Arg Ser His Gly Thr Asp Tyr Gly Arg Val Leu Ala Ala Phe Glu
465                 470                 475                 480

Leu Gly Asp His Glu Pro Asp Phe Glu Thr Arg Leu Asn Glu Leu Gly
                485                 490                 495

Tyr Asp Cys His Asp Glu Thr Ile Asn Pro Ala Phe Arg Phe Phe Leu
                500                 505                 510

Ala Gly

<210> SEQ ID NO 30
<211> LENGTH: 665
```

<212> TYPE: PRT
<213> ORGANISM: Picihia stipitis

<400> SEQUENCE: 30

Met Ala Arg Ala Ala Leu Ser Arg Ser Gly Ser Arg Tyr Ala Ile
1               5                   10                  15

Arg Ala Leu Ser Asn Thr Lys Leu His Asn Ala Thr Met Ser Ala Thr
            20                  25                  30

Ser Arg Pro Thr Pro Ser Pro Ala Phe Asn Ala Ala Asp Ile Arg Gln
        35                  40                  45

Pro Gln Ser Tyr Pro Thr Gln Arg Lys Lys Asn Asp Phe Val Met Asp
50                  55                  60

Asp Ser Phe Ile Gly Leu Thr Gly Gly Glu Ile Phe His Glu Met Met
65                  70                  75                  80

Leu Arg His Asn Val Asp Thr Val Phe Gly Tyr Ala Gly Gly Ala Ile
                85                  90                  95

Leu Pro Val Phe Asp Ala Ile Tyr Asn Ser Asp Lys Phe Lys Phe Val
            100                 105                 110

Leu Pro Arg His Glu Gln Gly Ala Gly His Met Ala Glu Gly Tyr Ala
        115                 120                 125

Arg Ala Thr Gly Lys Pro Gly Val Val Leu Val Thr Ser Gly Pro Gly
130                 135                 140

Ala Thr Asn Val Ile Thr Pro Leu Ala Asp Ala Leu Met Asp Gly Val
145                 150                 155                 160

Pro Leu Val Val Phe Thr Gly Gln Val Pro Thr Thr Ala Ile Gly Thr
                165                 170                 175

Asp Ala Phe Gln Glu Ala Asp Val Val Gly Ile Ser Arg Ser Cys Thr
            180                 185                 190

Lys Trp Asn Val Met Val Lys Asn Val Ala Glu Leu Pro Arg Arg Ile
        195                 200                 205

Asn Glu Ala Phe Glu Ile Ala Thr Ser Gly Arg Pro Gly Pro Val Leu
210                 215                 220

Val Asp Leu Pro Lys Asp Val Thr Ala Ala Ile Leu Arg Glu Ala Ile
225                 230                 235                 240

Pro Ile Asn Ser Thr Leu Pro Ser Asn Ala Leu Gln Gln Ile Thr Lys
                245                 250                 255

Glu Ala Gln Asn Glu Phe Thr Met Gly Ala Ile Ala Arg Ser Ala Asn
            260                 265                 270

Leu Leu Asn Val Ala Lys Lys Pro Ile Ile Tyr Ala Gly Ala Gly Val
        275                 280                 285

Leu Asn His Glu Asp Gly Pro Lys Leu Leu Lys Glu Leu Ser Asp Lys
290                 295                 300

Ala Asn Ile Pro Val Thr Thr Thr Leu Gln Gly Leu Gly Ala Phe Asp
305                 310                 315                 320

Gln Arg Asp Pro Lys Ser Leu Asp Met Leu Gly Met His Gly His Ala
                325                 330                 335

Ala Ala Asn Thr Ala Met Gln Asp Ala Asp Cys Ile Ile Ala Leu Gly
            340                 345                 350

Ala Arg Phe Asp Asp Arg Val Thr Gly Asn Ile Asn Lys Phe Ala Pro
        355                 360                 365

Glu Ala Lys Leu Ala Ala Ser Glu Gly Arg Gly Gly Ile Ile His Phe
370                 375                 380

Glu Ile Ser Pro Lys Asn Ile Asn Lys Val Val Glu Ala Thr Glu Ala
385                 390                 395                 400

```
Val Glu Gly Asp Leu Thr Ala Asn Leu Arg Ser Phe Ile Pro Leu Val
                405                 410                 415

Lys Pro Val Ala Glu Arg Pro Gln Trp Leu Gly Lys Ile Asn Glu Trp
            420                 425                 430

Lys Glu Lys Tyr Pro Tyr Ala Tyr Gln Leu Glu Thr Pro Gly Ser Leu
        435                 440                 445

Ile Lys Pro Gln Thr Leu Ile Lys Glu Ile Ser Glu Gln Ser Ser Thr
    450                 455                 460

Tyr Asn Lys Glu Val Ile Val Thr Gly Val Gly Gln His Gln Met
465                 470                 475                 480

Trp Ala Ala Gln His Phe Thr Trp Thr Lys Pro Arg Thr Met Ile Thr
                485                 490                 495

Ser Gly Gly Leu Gly Thr Met Gly Tyr Gly Leu Pro Ala Ala Ile Gly
            500                 505                 510

Ala Gln Ile Gly Lys Pro Asp Ala Ile Val Ile Asp Ile Asp Gly Asp
        515                 520                 525

Ala Ser Phe Asn Met Thr Leu Thr Glu Leu Ser Ser Ala Val Gln Ala
    530                 535                 540

Gly Ala Pro Val Lys Val Cys Val Leu Asn Asn Glu Glu Gln Gly Met
545                 550                 555                 560

Val Thr Gln Trp Gln Ser Leu Phe Tyr Glu His Arg Tyr Ser His Thr
                565                 570                 575

His Gln Ser Asn Pro Asp Phe Met Lys Leu Ala Asp Ala Met Gly Val
            580                 585                 590

Gln Gly Ile Arg Ile Ser Thr Gln Glu Glu Leu Lys Ser Gly Val Lys
        595                 600                 605

Ala Phe Leu Asp Ala Lys Gly Pro Val Leu Leu Glu Val Ile Val Glu
    610                 615                 620

Lys Lys Val Pro Val Leu Pro Met Val Pro Ala Gly Ser Ala Leu Asp
625                 630                 635                 640

Asp Phe Ile Leu Trp Asp Ala Glu Thr Glu Lys Gln Gln Lys Glu Leu
                645                 650                 655

Arg Asn Glu Arg Thr Gly Gly Lys His
            660                 665

<210> SEQ ID NO 31
<211> LENGTH: 640
<212> TYPE: PRT
<213> ORGANISM: Pichia stipitis

<400> SEQUENCE: 31

Met Ala Thr Met Ser Ala Thr Ser Arg Pro Thr Pro Leu Pro Ala Phe
1               5                   10                  15

Asn Ala Ala Asp Ile Arg Gln Pro Gln Ser Tyr Pro Thr Gln Arg Lys
                20                  25                  30

Lys Asn Asp Phe Val Met Asp Ser Phe Ile Gly Leu Thr Gly Gly
            35                  40                  45

Glu Ile Phe His Glu Met Met Leu Arg His Asn Val Asp Thr Val Phe
    50                  55                  60

Gly Tyr Ala Gly Gly Ala Ile Leu Pro Val Phe Asp Ala Ile Tyr Asn
65                  70                  75                  80

Ser Asp Lys Phe Lys Phe Val Leu Pro Arg His Glu Gln Gly Ala Gly
                85                  90                  95

His Met Ala Glu Gly Tyr Ala Arg Ala Thr Gly Lys Pro Gly Val Val
            100                 105                 110
```

-continued

```
Leu Val Thr Ser Gly Pro Gly Ala Thr Asn Val Ile Thr Pro Leu Ala
            115                 120                 125

Asp Ala Leu Met Asp Gly Val Pro Leu Val Val Phe Thr Gly Gln Val
    130                 135                 140

Pro Thr Thr Ala Ile Gly Thr Asp Ala Phe Gln Glu Ala Asp Val Val
145                 150                 155                 160

Gly Ile Ser Arg Ser Cys Thr Lys Trp Asn Val Met Val Lys Asn Val
                165                 170                 175

Ala Glu Leu Pro Arg Arg Ile Asn Glu Ala Phe Glu Ile Ala Thr Ser
            180                 185                 190

Gly Arg Pro Gly Pro Val Leu Val Asp Leu Pro Lys Asp Val Thr Ala
    195                 200                 205

Ala Ile Leu Arg Glu Ala Ile Pro Ile Asn Ser Thr Leu Pro Ser Asn
210                 215                 220

Ala Leu Gln Gln Ile Thr Lys Glu Ala Gln Asn Glu Phe Thr Met Gly
225                 230                 235                 240

Ala Ile Ala Arg Ser Ala Asn Leu Leu Asn Val Ala Lys Lys Pro Ile
                245                 250                 255

Ile Tyr Ala Gly Ala Gly Val Leu Asn His Glu Asp Gly Pro Lys Leu
            260                 265                 270

Leu Lys Glu Leu Ser Asp Lys Ala Asn Ile Pro Val Thr Thr Thr Leu
    275                 280                 285

Gln Gly Leu Gly Ala Phe Asp Gln Arg Asp Pro Lys Ser Leu Asp Met
290                 295                 300

Leu Gly Met His Gly His Ala Ala Asn Thr Ala Met Gln Asp Ala
305                 310                 315                 320

Asp Cys Ile Ile Ala Leu Gly Ala Arg Phe Asp Asp Arg Val Thr Gly
                325                 330                 335

Asn Ile Asn Lys Phe Ala Pro Glu Ala Lys Leu Ala Ala Ser Glu Gly
            340                 345                 350

Arg Gly Gly Ile Ile His Phe Glu Ile Ser Pro Lys Asn Ile Asn Lys
    355                 360                 365

Val Val Glu Ala Thr Glu Ala Val Glu Gly Asp Leu Thr Ala Asn Leu
370                 375                 380

Arg Ser Phe Ile Pro Leu Val Lys Pro Val Ala Glu Arg Pro Gln Trp
385                 390                 395                 400

Leu Gly Lys Ile Asn Glu Trp Lys Glu Lys Tyr Pro Tyr Ala Tyr Gln
                405                 410                 415

Leu Glu Thr Pro Gly Ser Leu Ile Lys Pro Gln Thr Leu Ile Lys Glu
            420                 425                 430

Ile Ser Glu Gln Ser Ser Thr Tyr Asn Lys Glu Val Ile Val Thr Thr
    435                 440                 445

Gly Val Gly Gln His Gln Met Trp Ala Ala Gln His Phe Thr Trp Thr
450                 455                 460

Lys Pro Arg Thr Met Ile Thr Ser Gly Gly Leu Gly Thr Met Gly Tyr
465                 470                 475                 480

Gly Leu Pro Ala Ala Ile Gly Ala Gln Ile Gly Lys Pro Asp Ala Ile
                485                 490                 495

Val Ile Asp Ile Asp Gly Asp Ala Ser Phe Asn Met Thr Leu Thr Glu
            500                 505                 510

Leu Ser Ser Ala Val Gln Ala Gly Ala Pro Val Lys Val Cys Val Leu
    515                 520                 525

Asn Asn Glu Glu Gln Gly Met Val Thr Gln Trp Gln Ser Leu Phe Tyr
530                 535                 540
```

```
Glu His Arg Tyr Ser His Thr His Gln Ser Asn Pro Asp Phe Met Lys
545                 550                 555                 560

Leu Ala Asp Ala Met Gly Val Gln Gly Ile Arg Ile Ser Thr Gln Glu
            565                 570                 575

Glu Leu Lys Ser Gly Val Lys Ala Phe Leu Asp Ala Lys Gly Pro Val
        580                 585                 590

Leu Leu Glu Val Ile Val Glu Lys Lys Val Pro Val Leu Pro Met Val
    595                 600                 605

Pro Ala Gly Ser Ala Leu Asp Asp Phe Ile Leu Trp Asp Ala Glu Thr
610                 615                 620

Glu Lys Gln Gln Lys Glu Leu Arg Asn Glu Arg Thr Gly Gly Lys His
625                 630                 635                 640

<210> SEQ ID NO 32
<211> LENGTH: 687
<212> TYPE: PRT
<213> ORGANISM: Saccharomyces cerevisiae

<400> SEQUENCE: 32

Met Ile Arg Gln Ser Thr Leu Lys Asn Phe Ala Ile Lys Arg Cys Phe
1               5                   10                  15

Gln His Ile Ala Tyr Arg Asn Thr Pro Ala Met Arg Ser Val Ala Leu
            20                  25                  30

Ala Gln Arg Phe Tyr Ser Ser Ser Arg Tyr Tyr Ser Ala Ser Pro
        35                  40                  45

Leu Pro Ala Ser Lys Arg Pro Glu Pro Ala Pro Ser Phe Asn Val Asp
    50                  55                  60

Pro Leu Glu Gln Pro Ala Glu Pro Ser Lys Leu Ala Lys Lys Leu Arg
65                  70                  75                  80

Ala Glu Pro Asp Met Asp Thr Ser Phe Val Gly Leu Thr Gly Gly Gln
                85                  90                  95

Ile Phe Asn Glu Met Met Ser Arg Gln Asn Val Asp Thr Val Phe Gly
            100                 105                 110

Tyr Pro Gly Gly Ala Ile Leu Pro Val Tyr Asp Ala Ile His Asn Ser
        115                 120                 125

Asp Lys Phe Asn Phe Val Leu Pro Lys His Glu Gln Gly Ala Gly His
    130                 135                 140

Met Ala Glu Gly Tyr Ala Arg Ala Ser Gly Lys Pro Gly Val Val Leu
145                 150                 155                 160

Val Thr Ser Gly Pro Gly Ala Thr Asn Val Val Thr Pro Met Ala Asp
                165                 170                 175

Ala Phe Ala Asp Gly Ile Pro Met Val Val Phe Thr Gly Gln Val Pro
            180                 185                 190

Thr Ser Ala Ile Gly Thr Asp Ala Phe Gln Glu Ala Asp Val Val Gly
        195                 200                 205

Ile Ser Arg Ser Cys Thr Lys Trp Asn Val Met Val Lys Ser Val Glu
    210                 215                 220

Glu Leu Pro Leu Arg Ile Asn Glu Ala Phe Glu Ile Ala Thr Ser Gly
225                 230                 235                 240

Arg Pro Gly Pro Val Leu Val Asp Leu Pro Lys Asp Val Thr Ala Ala
                245                 250                 255

Ile Leu Arg Asn Pro Ile Pro Thr Lys Thr Thr Leu Pro Ser Asn Ala
            260                 265                 270

Leu Asn Gln Leu Thr Ser Arg Ala Gln Asp Glu Phe Val Met Gln Ser
        275                 280                 285
```

```
Ile Asn Lys Ala Ala Asp Leu Ile Asn Leu Ala Lys Lys Pro Val Leu
            290                 295                 300
Tyr Val Gly Ala Gly Ile Leu Asn His Ala Asp Gly Pro Arg Leu Leu
305                 310                 315                 320
Lys Glu Leu Ser Asp Arg Ala Gln Ile Pro Val Thr Thr Thr Leu Gln
                325                 330                 335
Gly Leu Gly Ser Phe Asp Gln Glu Asp Pro Lys Ser Leu Asp Met Leu
            340                 345                 350
Gly Met His Gly Cys Ala Thr Ala Asn Leu Ala Val Gln Asn Ala Asp
                355                 360                 365
Leu Ile Ile Ala Val Gly Ala Arg Phe Asp Asp Arg Val Thr Gly Asn
370                 375                 380
Ile Ser Lys Phe Ala Pro Glu Ala Arg Arg Ala Ala Glu Gly Arg
385                 390                 395                 400
Gly Gly Ile Ile His Phe Glu Val Ser Pro Lys Asn Ile Asn Lys Val
                405                 410                 415
Val Gln Thr Gln Ile Ala Val Glu Gly Asp Ala Thr Thr Asn Leu Gly
            420                 425                 430
Lys Met Met Ser Lys Ile Phe Pro Val Lys Glu Arg Ser Glu Trp Phe
435                 440                 445
Ala Gln Ile Asn Lys Trp Lys Lys Glu Tyr Pro Tyr Ala Tyr Met Glu
450                 455                 460
Glu Thr Pro Gly Ser Lys Ile Lys Pro Gln Thr Val Ile Lys Lys Leu
465                 470                 475                 480
Ser Lys Val Ala Asn Asp Thr Gly Arg His Val Ile Val Thr Thr Gly
                485                 490                 495
Val Gly Gln His Gln Met Trp Ala Ala Gln His Trp Thr Trp Arg Asn
            500                 505                 510
Pro His Thr Phe Ile Thr Ser Gly Gly Leu Gly Thr Met Gly Tyr Gly
                515                 520                 525
Leu Pro Ala Ala Ile Gly Ala Gln Val Ala Lys Pro Glu Ser Leu Val
530                 535                 540
Ile Asp Ile Asp Gly Asp Ala Ser Phe Asn Met Thr Leu Thr Glu Leu
545                 550                 555                 560
Ser Ser Ala Val Gln Ala Gly Thr Pro Val Lys Ile Leu Ile Leu Asn
                565                 570                 575
Asn Glu Glu Gln Gly Met Val Thr Gln Trp Gln Ser Leu Phe Tyr Glu
            580                 585                 590
His Arg Tyr Ser His Thr His Gln Leu Asn Pro Asp Phe Ile Lys Leu
                595                 600                 605
Ala Glu Ala Met Gly Leu Lys Gly Leu Arg Val Lys Lys Gln Glu Glu
610                 615                 620
Leu Asp Ala Lys Leu Lys Glu Phe Val Ser Thr Lys Gly Pro Val Leu
625                 630                 635                 640
Leu Glu Val Glu Val Asp Lys Lys Val Pro Val Leu Pro Met Val Ala
                645                 650                 655
Gly Gly Ser Gly Leu Asp Glu Phe Ile Asn Phe Asp Pro Glu Val Glu
            660                 665                 670
Arg Gln Gln Thr Glu Leu Arg His Lys Arg Thr Gly Gly Lys His
                675                 680                 685

<210> SEQ ID NO 33
<211> LENGTH: 309
<212> TYPE: PRT
```

<213> ORGANISM: Saccharomyces cerevisiae

<400> SEQUENCE: 33

Met Leu Arg Ser Leu Leu Gln Ser Gly His Arg Arg Val Val Ala Ser
1               5                   10                  15

Ser Cys Ala Thr Met Val Arg Cys Ser Ser Ser Thr Ser Ala Leu
            20                  25                  30

Ala Tyr Lys Gln Met His Arg His Ala Thr Arg Pro Pro Leu Pro Thr
        35                  40                  45

Leu Asp Thr Pro Ser Trp Asn Ala Asn Ser Ala Val Ser Ser Ile Ile
    50                  55                  60

Tyr Glu Thr Pro Ala Pro Ser Arg Gln Pro Arg Lys Gln His Val Leu
65                  70                  75                  80

Asn Cys Leu Val Gln Asn Glu Pro Gly Val Leu Ser Arg Val Ser Gly
                85                  90                  95

Thr Leu Ala Ala Arg Gly Phe Asn Ile Asp Ser Leu Val Val Cys Asn
            100                 105                 110

Thr Glu Val Lys Asp Leu Ser Arg Met Thr Ile Val Leu Gln Gly Gln
        115                 120                 125

Asp Gly Val Val Glu Gln Ala Arg Arg Gln Ile Glu Asp Leu Val Pro
    130                 135                 140

Val Tyr Ala Val Leu Asp Tyr Thr Asn Ser Glu Ile Ile Lys Arg Glu
145                 150                 155                 160

Leu Val Met Ala Arg Ile Ser Leu Leu Gly Thr Glu Tyr Phe Glu Asp
                165                 170                 175

Leu Leu Leu His His His Thr Ser Thr Asn Ala Gly Ala Ala Asp Ser
            180                 185                 190

Gln Glu Leu Val Ala Glu Ile Arg Glu Lys Gln Phe His Pro Ala Asn
        195                 200                 205

Leu Pro Ala Ser Glu Val Leu Arg Leu Lys His Glu His Leu Asn Asp
    210                 215                 220

Ile Thr Asn Leu Thr Asn Asn Phe Gly Gly Arg Val Val Asp Ile Ser
225                 230                 235                 240

Glu Thr Ser Cys Ile Val Glu Leu Ser Ala Lys Pro Thr Arg Ile Ser
                245                 250                 255

Ala Phe Leu Lys Leu Val Glu Pro Phe Gly Val Leu Gly Cys Ala Arg
            260                 265                 270

Ser Gly Met Met Ala Leu Pro Arg Thr Pro Leu Lys Thr Ser Thr Glu
        275                 280                 285

Glu Ala Ala Asp Glu Asp Glu Lys Ile Ser Glu Ile Val Asp Ile Ser
    290                 295                 300

Gln Leu Pro Pro Gly
305

<210> SEQ ID NO 34
<211> LENGTH: 303
<212> TYPE: PRT
<213> ORGANISM: Pichia stipitis

<400> SEQUENCE: 34

Met Phe Ala Lys Gln Thr Leu Arg Arg Ser Ala Ser Ser Ala Tyr Lys
1               5                   10                  15

Gln Gly Val Arg Asn Lys Gln Thr Ser Ser Thr Ser Ala Leu Ala
            20                  25                  30

Tyr Lys Thr Leu His Arg Asn Gln Lys Arg Pro Pro Leu Pro Thr Leu
        35                  40                  45

```
Glu Thr Pro Asn Trp Ser Ala Asp Ala Val Ser Ser Ile Leu Tyr
     50                  55                  60

Glu Thr Pro Met Pro Ser Lys Ala Pro Arg Lys Gln His Val Leu Asn
 65                  70                  75                  80

Cys Leu Val Gln Asn Glu Pro Gly Val Leu Ser Val Ser Gly Thr
                 85                  90                  95

Leu Ala Ala Arg Gly Phe Asn Ile Asp Ser Leu Val Val Cys Asn Thr
                100                 105                 110

Glu Val Lys Asp Leu Ser Arg Met Thr Ile Val Leu Ala Gly Gln Asp
            115                 120                 125

Ala Val Val Glu Gln Ala Arg Arg Gln Ile Glu Asp Leu Val Pro Val
        130                 135                 140

Tyr Ala Val Leu Asp Tyr Thr Asn Ala Glu Ile Ile Lys Arg Glu Leu
145                 150                 155                 160

Leu Leu Ala Arg Val Ser Leu Leu Gly Pro Glu Tyr Phe Gln Glu Leu
                165                 170                 175

Ile Ala Thr His Lys Leu His Ile Ser Asp Gly Ser Ala Val Pro Asp
            180                 185                 190

Leu Ser Ala Thr Asp Ser Ala Tyr His Pro Asn Asn Leu Ala Pro Ser
        195                 200                 205

Glu Ala Leu Arg Gln Lys His Ile His Leu Asp His Ile Asn Thr Ile
210                 215                 220

Thr Glu Lys Phe Gly Gly Lys Ile Val Asp Leu Ser Asp Arg Asn Val
225                 230                 235                 240

Ile Val Glu Leu Ser Ala Lys Pro Ser Arg Ile Thr Ser Phe Leu His
                245                 250                 255

Leu Leu Gln Pro Phe Gly Ile Leu Glu Leu Ala Arg Ser Gly Met Met
            260                 265                 270

Ala Leu Pro Arg Thr Pro Leu Asp Ala Ala Val Glu Glu Asp Glu Pro
        275                 280                 285

Val Glu Ala Ala Asp Val Val Asp Ala Ser Gln Leu Pro Pro Gly
    290                 295                 300

<210> SEQ ID NO 35
<211> LENGTH: 626
<212> TYPE: PRT
<213> ORGANISM: Corynebacterium glutamicum

<400> SEQUENCE: 35

Met Asn Val Ala Ala Ser Gln Gln Pro Thr Pro Ala Thr Val Ala Ser
  1               5                  10                  15

Arg Gly Arg Ser Ala Ala Pro Glu Arg Met Thr Gly Ala Lys Ala Ile
                 20                  25                  30

Val Arg Ser Leu Glu Glu Leu Asn Ala Asp Ile Val Phe Gly Ile Pro
             35                  40                  45

Gly Gly Ala Val Leu Pro Val Tyr Asp Pro Leu Tyr Ser Ser Thr Lys
         50                  55                  60

Val Arg His Val Leu Val Arg His Glu Gln Gly Ala Gly His Ala Ala
 65                  70                  75                  80

Thr Gly Tyr Ala Gln Val Thr Gly Arg Val Gly Val Cys Ile Ala Thr
                 85                  90                  95

Ser Gly Pro Gly Ala Thr Asn Leu Val Thr Pro Ile Ala Asp Ala Asn
                100                 105                 110

Leu Asp Ser Val Pro Met Val Ala Ile Thr Gly Gln Val Gly Ser Gly
            115                 120                 125
```

```
Leu Leu Gly Thr Asp Ala Phe Gln Glu Ala Asp Ile Arg Gly Ile Thr
        130                 135                 140
Met Pro Val Thr Lys His Asn Phe Met Val Thr Asn Pro Asn Asp Ile
145                 150                 155                 160
Pro Gln Ala Leu Ala Glu Ala Phe His Leu Ala Ile Thr Gly Arg Pro
                165                 170                 175
Gly Pro Val Leu Val Asp Ile Pro Lys Asp Val Gln Asn Ala Glu Leu
                180                 185                 190
Asp Phe Val Trp Pro Pro Lys Ile Asp Leu Pro Gly Tyr Arg Pro Val
            195                 200                 205
Ser Thr Pro His Ala Arg Gln Ile Glu Gln Ala Val Lys Leu Ile Gly
        210                 215                 220
Glu Ala Lys Lys Pro Val Leu Tyr Val Gly Gly Gly Val Ile Lys Ala
225                 230                 235                 240
Asp Ala His Glu Glu Leu Arg Ala Phe Ala Glu Tyr Thr Gly Ile Pro
                245                 250                 255
Val Val Thr Thr Leu Met Ala Leu Gly Thr Phe Pro Glu Ser His Glu
                260                 265                 270
Leu His Met Gly Met Pro Gly Met His Gly Thr Val Ser Ala Val Gly
        275                 280                 285
Ala Leu Gln Arg Ser Asp Leu Leu Ile Ala Ile Gly Ser Arg Phe Asp
        290                 295                 300
Asp Arg Val Thr Gly Asp Val Asp Thr Phe Ala Pro Asp Ala Lys Ile
305                 310                 315                 320
Ile His Ala Asp Ile Asp Pro Ala Glu Ile Gly Lys Ile Lys Gln Val
                325                 330                 335
Glu Val Pro Ile Val Gly Asp Ala Arg Glu Val Leu Ala Arg Leu Leu
                340                 345                 350
Glu Thr Thr Lys Ala Ser Lys Ala Glu Thr Glu Asp Ile Ser Glu Trp
            355                 360                 365
Val Asp Tyr Leu Lys Gly Leu Lys Ala Arg Phe Pro Arg Gly Tyr Asp
        370                 375                 380
Glu Gln Pro Gly Asp Leu Leu Ala Pro Gln Phe Val Ile Glu Thr Leu
385                 390                 395                 400
Ser Lys Glu Val Gly Pro Asp Ala Ile Tyr Cys Ala Gly Val Gly Gln
                405                 410                 415
His Gln Met Trp Ala Ala Gln Phe Val Asp Phe Glu Lys Pro Arg Thr
            420                 425                 430
Trp Leu Asn Ser Gly Gly Leu Gly Thr Met Gly Tyr Ala Val Pro Ala
        435                 440                 445
Ala Leu Gly Ala Lys Ala Gly Ala Pro Asp Lys Glu Val Trp Ala Ile
        450                 455                 460
Asp Gly Asp Gly Cys Phe Gln Met Thr Asn Gln Glu Leu Thr Thr Ala
465                 470                 475                 480
Ala Val Glu Gly Phe Pro Ile Lys Ile Ala Leu Ile Asn Asn Gly Asn
                485                 490                 495
Leu Gly Met Val Arg Gln Trp Gln Thr Leu Phe Tyr Glu Gly Arg Tyr
            500                 505                 510
Ser Asn Thr Lys Leu Arg Asn Gln Gly Glu Tyr Met Pro Asp Phe Val
        515                 520                 525
Thr Leu Ser Glu Gly Leu Gly Cys Val Ala Ile Arg Val Thr Lys Ala
        530                 535                 540
Glu Glu Val Leu Pro Ala Ile Gln Lys Ala Arg Glu Ile Asn Asp Arg
```

-continued

```
            545                 550                 555                 560
Pro Val Ile Asp Phe Ile Val Gly Glu Asp Ala Gln Val Trp Pro
                    565                 570                 575
Met Val Ser Ala Gly Ser Ser Asn Ser Asp Ile Gln Tyr Ala Leu Gly
                580                 585                 590
Leu Arg Pro Phe Phe Asp Gly Asp Glu Ser Ala Ala Glu Asp Pro Ala
                595                 600                 605
Asp Ile His Glu Ala Val Ser Asp Ile Asp Ala Ala Val Glu Ser Thr
    610                 615                 620
Glu Ala
625

<210> SEQ ID NO 36
<211> LENGTH: 172
<212> TYPE: PRT
<213> ORGANISM: Corynebacterium glutamicum

<400> SEQUENCE: 36

Met Ala Asn Ser Asp Val Thr Arg His Ile Leu Ser Val Leu Val Gln
1               5                   10                  15
Asp Val Asp Gly Ile Ile Ser Arg Val Ser Gly Met Phe Thr Arg Arg
                20                  25                  30
Ala Phe Asn Leu Val Ser Leu Val Ser Ala Lys Thr Glu Thr His Gly
            35                  40                  45
Ile Asn Arg Ile Thr Val Val Asp Ala Asp Glu Leu Asn Ile Glu
        50                  55                  60
Gln Ile Thr Lys Gln Leu Asn Lys Leu Ile Pro Val Leu Lys Val Val
65                  70                  75                  80
Arg Leu Asp Glu Glu Thr Thr Ile Ala Arg Ala Ile Met Leu Val Lys
                85                  90                  95
Val Ser Ala Asp Ser Thr Asn Arg Pro Gln Ile Val Asp Ala Ala Asn
            100                 105                 110
Ile Phe Arg Ala Arg Val Val Asp Val Ala Pro Asp Ser Val Val Ile
        115                 120                 125
Glu Ser Thr Gly Thr Pro Gly Lys Leu Arg Ala Leu Leu Asp Val Met
    130                 135                 140
Glu Pro Phe Gly Ile Arg Glu Leu Ile Gln Ser Gly Gln Ile Ala Leu
145                 150                 155                 160
Asn Arg Gly Pro Lys Thr Met Ala Pro Ala Lys Ile
                165                 170

<210> SEQ ID NO 37
<211> LENGTH: 562
<212> TYPE: PRT
<213> ORGANISM: Escherichia coli

<400> SEQUENCE: 37

Met Ala Ser Ser Gly Thr Thr Ser Thr Arg Lys Arg Phe Thr Gly Ala
1               5                   10                  15
Glu Phe Ile Val His Phe Leu Glu Gln Gln Gly Ile Lys Ile Val Thr
                20                  25                  30
Gly Ile Pro Gly Gly Ser Ile Leu Pro Val Tyr Asp Ala Leu Ser Gln
            35                  40                  45
Ser Thr Gln Ile Arg His Ile Leu Ala Arg His Glu Gln Gly Ala Gly
        50                  55                  60
Phe Ile Ala Gln Gly Met Ala Arg Thr Asp Gly Lys Pro Ala Val Cys
65                  70                  75                  80
```

```
Met Ala Cys Ser Gly Pro Gly Ala Thr Asn Leu Val Thr Ala Ile Ala
                85                  90                  95

Asp Ala Arg Leu Asp Ser Ile Pro Leu Ile Cys Ile Thr Gly Gln Val
            100                 105                 110

Pro Ala Ser Met Ile Gly Thr Asp Ala Phe Gln Glu Val Asp Thr Tyr
            115                 120                 125

Gly Ile Ser Ile Pro Ile Thr Lys His Asn Tyr Leu Val Arg His Ile
130                 135                 140

Glu Leu Pro Gln Val Met Ser Asp Ala Phe Arg Ile Ala Gln Ser
145                 150                 155                 160

Gly Arg Pro Gly Pro Val Trp Ile Asp Ile Pro Lys Asp Val Gln Thr
                165                 170                 175

Ala Val Phe Glu Ile Glu Thr Gln Pro Ala Met Ala Glu Lys Ala Ala
            180                 185                 190

Ala Pro Ala Phe Ser Glu Glu Ser Ile Arg Asp Ala Ala Ala Met Ile
            195                 200                 205

Asn Ala Ala Lys Arg Pro Val Leu Tyr Leu Gly Gly Gly Val Ile Asn
210                 215                 220

Ala Pro Ala Arg Val Arg Glu Leu Ala Glu Lys Ala Gln Leu Pro Thr
225                 230                 235                 240

Thr Met Thr Leu Met Ala Leu Gly Met Leu Pro Lys Ala His Pro Leu
                245                 250                 255

Ser Leu Gly Met Leu Gly Met His Gly Val Arg Ser Thr Asn Tyr Ile
                260                 265                 270

Leu Gln Glu Ala Asp Leu Leu Ile Val Leu Gly Ala Arg Phe Asp Asp
            275                 280                 285

Arg Ala Ile Gly Lys Thr Glu Gln Phe Cys Pro Asn Ala Lys Ile Ile
            290                 295                 300

His Val Asp Ile Asp Arg Ala Glu Leu Gly Lys Ile Lys Gln Pro His
305                 310                 315                 320

Val Ala Ile Gln Ala Asp Val Asp Val Leu Ala Gln Leu Ile Pro
                325                 330                 335

Leu Val Glu Ala Gln Pro Arg Ala Glu Trp His Gln Leu Val Ala Asp
                340                 345                 350

Leu Gln Arg Glu Phe Pro Cys Pro Ile Pro Lys Ala Cys Asp Pro Leu
                355                 360                 365

Ser His Tyr Gly Leu Ile Asn Ala Val Ala Ala Cys Val Asp Asp Asn
    370                 375                 380

Ala Ile Ile Thr Thr Asp Val Gly Gln His Gln Met Trp Thr Ala Gln
385                 390                 395                 400

Ala Tyr Pro Leu Asn Arg Pro Arg Gln Trp Leu Thr Ser Gly Gly Leu
                405                 410                 415

Gly Thr Met Gly Phe Gly Leu Pro Ala Ala Ile Gly Ala Ala Leu Ala
                420                 425                 430

Asn Pro Asp Arg Lys Val Leu Cys Phe Ser Gly Asp Gly Ser Leu Met
            435                 440                 445

Met Asn Ile Gln Glu Met Ala Thr Ala Ser Glu Asn Gln Leu Asp Val
    450                 455                 460

Lys Ile Ile Leu Met Asn Asn Glu Ala Leu Gly Leu Val His Gln Gln
465                 470                 475                 480

Gln Ser Leu Phe Tyr Glu Gln Gly Val Phe Ala Ala Thr Tyr Pro Gly
                485                 490                 495

Lys Ile Asn Phe Met Gln Ile Ala Ala Gly Phe Gly Leu Glu Thr Cys
```

-continued

```
                    500                 505                 510
Asp Leu Asn Asn Glu Ala Asp Pro Gln Ala Ser Leu Gln Glu Ile Ile
            515                 520                 525

Asn Arg Pro Gly Pro Ala Leu Ile His Val Arg Ile Asp Ala Glu Glu
        530                 535                 540

Lys Val Tyr Pro Met Val Pro Pro Gly Ala Ala Asn Thr Glu Met Val
545                 550                 555                 560

Gly Glu

<210> SEQ ID NO 38
<211> LENGTH: 96
<212> TYPE: PRT
<213> ORGANISM: Escherichia coli

<400> SEQUENCE: 38

Met Gln Asn Thr Thr His Asp Asn Val Ile Leu Glu Leu Thr Val Arg
1               5                   10                  15

Asn His Pro Gly Val Met Thr His Val Cys Gly Leu Phe Ala Arg Arg
            20                  25                  30

Ala Phe Asn Val Glu Gly Ile Leu Cys Leu Pro Ile Gln Asp Ser Asp
        35                  40                  45

Lys Ser His Ile Trp Leu Leu Val Asn Asp Asp Gln Arg Leu Glu Gln
    50                  55                  60

Met Ile Ser Gln Ile Asp Lys Leu Glu Asp Val Val Lys Val Gln Arg
65                  70                  75                  80

Asn Gln Ser Asp Pro Thr Met Phe Asn Lys Ile Ala Val Phe Phe Gln
                85                  90                  95

<210> SEQ ID NO 39
<211> LENGTH: 548
<212> TYPE: PRT
<213> ORGANISM: Escherichia coli

<400> SEQUENCE: 39

Met Asn Gly Ala Gln Trp Val Val His Ala Leu Arg Ala Gln Gly Val
1               5                   10                  15

Asn Thr Val Phe Gly Tyr Pro Gly Gly Ala Ile Met Pro Val Tyr Asp
            20                  25                  30

Ala Leu Tyr Asp Gly Gly Val Glu His Leu Leu Cys Arg His Glu Gln
        35                  40                  45

Gly Ala Ala Met Ala Ala Ile Gly Tyr Ala Arg Ala Thr Gly Lys Thr
    50                  55                  60

Gly Val Cys Ile Ala Thr Ser Gly Pro Gly Ala Thr Asn Leu Ile Thr
65                  70                  75                  80

Gly Leu Ala Asp Ala Leu Leu Asp Ser Ile Pro Val Val Ala Ile Thr
                85                  90                  95

Gly Gln Val Ser Ala Pro Phe Ile Gly Thr Asp Ala Phe Gln Glu Val
                100                 105                 110

Asp Ile Leu Gly Leu Ser Leu Ala Cys Thr Lys His Ser Phe Leu Val
            115                 120                 125

Gln Ser Leu Glu Glu Leu Pro Arg Ile Met Ala Glu Ala Phe Asp Val
        130                 135                 140

Ala Ser Ser Gly Arg Pro Gly Pro Val Leu Val Asp Ile Pro Lys Asp
145                 150                 155                 160

Ile Gln Leu Ala Ser Gly Asp Leu Glu Pro Trp Phe Thr Thr Val Glu
                165                 170                 175
```

Asn Glu Val Thr Phe Pro His Ala Glu Val Gln Ala Arg Gln Met
            180                 185                 190

Leu Ala Lys Ala Gln Lys Pro Met Leu Tyr Val Gly Gly Val Gly
        195                 200                 205

Met Ala Gln Ala Val Ser Ala Leu Arg Glu Phe Leu Ala Ala Thr Lys
210                 215                 220

Met Pro Ala Thr Cys Thr Leu Lys Gly Leu Gly Ala Val Glu Ala Asp
225                 230                 235                 240

Tyr Pro Tyr Tyr Leu Gly Met Leu Gly Met His Gly Thr Lys Ala Ala
                245                 250                 255

Asn Phe Ala Val Gln Glu Cys Asp Leu Leu Ile Ala Val Gly Ala Arg
            260                 265                 270

Phe Asp Asp Arg Val Thr Gly Lys Leu Asn Thr Phe Ala Pro His Ala
        275                 280                 285

Ser Val Ile His Met Asp Ile Asp Pro Ala Glu Met Asn Lys Leu Arg
290                 295                 300

Gln Ala His Val Ala Leu Gln Gly Asp Leu Asn Ala Leu Leu Pro Ala
305                 310                 315                 320

Leu Gln Gln Pro Leu Asn Ile Asn Asp Trp Gln Gln Tyr Cys Ala Gln
                325                 330                 335

Leu Arg Asp Glu His Thr Trp Arg Tyr Asp His Pro Gly Asp Ala Ile
            340                 345                 350

Tyr Ala Pro Leu Leu Leu Lys Gln Leu Ser Asp Arg Lys Pro Ala Asp
        355                 360                 365

Cys Val Val Thr Thr Asp Val Gly Gln His Gln Met Trp Ala Ala Gln
370                 375                 380

His Ile Ala His Thr Arg Pro Glu Asn Phe Ile Thr Ser Ser Gly Leu
385                 390                 395                 400

Gly Thr Met Gly Phe Gly Leu Pro Ala Ala Val Gly Ala Gln Val Ala
                405                 410                 415

Arg Pro Asn Asp Thr Val Val Cys Ile Ser Gly Asp Gly Ser Phe Met
            420                 425                 430

Met Asn Val Gln Glu Leu Gly Thr Val Lys Arg Lys Gln Leu Pro Leu
        435                 440                 445

Lys Ile Val Leu Leu Asp Asn Gln Arg Leu Gly Met Val Arg Gln Trp
450                 455                 460

Gln Gln Leu Phe Phe Gln Glu Arg Tyr Ser Glu Thr Thr Leu Thr Asp
465                 470                 475                 480

Asn Pro Asp Phe Leu Met Leu Ala Ser Ala Phe Gly Ile Pro Gly Gln
                485                 490                 495

His Ile Thr Arg Lys Asp Gln Val Glu Ala Ala Leu Asp Thr Met Leu
            500                 505                 510

Asn Ser Asp Gly Pro Tyr Leu Leu His Val Ser Ile Asp Glu Leu Glu
        515                 520                 525

Asn Val Trp Pro Leu Val Pro Pro Gly Ala Ser Asn Ser Glu Met Leu
530                 535                 540

Glu Lys Leu Ser
545

<210> SEQ ID NO 40
<211> LENGTH: 87
<212> TYPE: PRT
<213> ORGANISM: Escherichia coli

<400> SEQUENCE: 40

```
Met Met Gln His Gln Val Asn Val Ser Ala Arg Phe Asn Pro Glu Thr
1               5                   10                  15

Leu Glu Arg Val Leu Arg Val Val Arg His Arg Gly Phe His Val Cys
            20                  25                  30

Ser Met Asn Met Ala Ala Ala Ser Asp Ala Gln Asn Ile Asn Ile Glu
            35                  40                  45

Leu Thr Val Ala Ser Pro Arg Ser Val Asp Leu Leu Phe Ser Gln Leu
        50                  55                  60

Asn Lys Leu Val Asp Val Ala His Val Ala Ile Cys Gln Ser Thr Thr
65              70                  75                  80

Thr Ser Gln Gln Ile Arg Ala
                85
```

<210> SEQ ID NO 41
<211> LENGTH: 574
<212> TYPE: PRT
<213> ORGANISM: Escherichia coli

<400> SEQUENCE: 41

```
Met Glu Met Leu Ser Gly Ala Glu Met Val Arg Ser Leu Ile Asp
1               5                   10                  15

Gln Gly Val Lys Gln Val Phe Gly Tyr Pro Gly Gly Ala Val Leu Asp
            20                  25                  30

Ile Tyr Asp Ala Leu His Thr Val Gly Gly Ile Asp His Val Leu Val
            35                  40                  45

Arg His Glu Gln Ala Ala Val His Met Ala Asp Gly Leu Ala Arg Ala
        50                  55                  60

Thr Gly Glu Val Gly Val Val Leu Val Thr Ser Gly Pro Gly Ala Thr
65              70                  75                  80

Asn Ala Ile Thr Gly Ile Ala Thr Ala Tyr Met Asp Ser Ile Pro Leu
                85                  90                  95

Val Val Leu Ser Gly Gln Val Ala Thr Ser Leu Ile Gly Tyr Asp Ala
                100                 105                 110

Phe Gln Glu Cys Asp Met Val Gly Ile Ser Arg Pro Val Val Lys His
            115                 120                 125

Ser Phe Leu Val Lys Gln Thr Glu Asp Ile Pro Gln Val Leu Lys Lys
    130                 135                 140

Ala Phe Trp Leu Ala Ala Ser Gly Arg Pro Gly Pro Val Val Val Asp
145                 150                 155                 160

Leu Pro Lys Asp Ile Leu Asn Pro Ala Asn Lys Leu Pro Tyr Val Trp
                165                 170                 175

Pro Glu Ser Val Ser Met Arg Ser Tyr Asn Pro Thr Thr Thr Gly His
            180                 185                 190

Lys Gly Gln Ile Lys Arg Ala Leu Gln Thr Leu Val Ala Ala Lys Lys
        195                 200                 205

Pro Val Val Tyr Val Gly Gly Gly Ala Ile Thr Ala Gly Cys His Gln
    210                 215                 220

Gln Leu Lys Glu Thr Val Glu Ala Leu Asn Leu Pro Val Val Cys Ser
225                 230                 235                 240

Leu Met Gly Leu Gly Ala Phe Pro Ala Thr His Arg Gln Ala Leu Gly
                245                 250                 255

Met Leu Gly Met His Gly Thr Tyr Glu Ala Asn Met Thr Met His Asn
            260                 265                 270

Ala Asp Val Ile Phe Ala Val Gly Val Arg Phe Asp Asp Arg Thr Thr
        275                 280                 285
```

Asn Asn Leu Ala Lys Tyr Cys Pro Asn Ala Thr Val Leu His Ile Asp
            290                 295                 300

Ile Asp Pro Thr Ser Ile Ser Lys Thr Val Thr Ala Asp Ile Pro Ile
305                 310                 315                 320

Val Gly Asp Ala Arg Gln Val Leu Glu Gln Met Leu Glu Leu Leu Ser
                325                 330                 335

Gln Glu Ser Ala His Gln Pro Leu Asp Glu Ile Arg Asp Trp Trp Gln
            340                 345                 350

Gln Ile Glu Gln Trp Arg Ala Arg Gln Cys Leu Lys Tyr Asp Thr His
            355                 360                 365

Ser Glu Lys Ile Lys Pro Gln Ala Val Ile Glu Thr Leu Trp Arg Leu
    370                 375                 380

Thr Lys Gly Asp Ala Tyr Val Thr Ser Asp Val Gly Gln His Gln Met
385                 390                 395                 400

Phe Ala Ala Leu Tyr Tyr Pro Phe Asp Lys Pro Arg Arg Trp Ile Asn
                405                 410                 415

Ser Gly Gly Leu Gly Thr Met Gly Phe Gly Leu Pro Ala Ala Leu Gly
            420                 425                 430

Val Lys Met Ala Leu Pro Glu Glu Thr Val Val Cys Val Thr Gly Asp
            435                 440                 445

Gly Ser Ile Gln Met Asn Ile Gln Glu Leu Ser Thr Ala Leu Gln Tyr
    450                 455                 460

Glu Leu Pro Val Leu Val Asn Leu Asn Asn Arg Tyr Leu Gly Met
465                 470                 475                 480

Val Lys Gln Trp Gln Asp Met Ile Tyr Ser Gly Arg His Ser Gln Ser
                485                 490                 495

Tyr Met Gln Ser Leu Pro Asp Phe Val Arg Leu Ala Glu Ala Tyr Gly
            500                 505                 510

His Val Gly Ile Gln Ile Ser His Pro His Glu Leu Glu Ser Lys Leu
            515                 520                 525

Ser Glu Ala Leu Glu Gln Val Arg Asn Asn Arg Leu Val Phe Val Asp
    530                 535                 540

Val Thr Val Asp Gly Ser Glu His Val Tyr Pro Met Gln Ile Arg Gly
545                 550                 555                 560

Gly Gly Met Asp Glu Met Trp Leu Ser Lys Thr Glu Arg Thr
                565                 570

<210> SEQ ID NO 42
<211> LENGTH: 163
<212> TYPE: PRT
<213> ORGANISM: Escherichia coli

<400> SEQUENCE: 42

Met Arg Arg Ile Leu Ser Val Leu Leu Glu Asn Glu Ser Gly Ala Leu
1               5                   10                  15

Ser Arg Val Ile Gly Leu Phe Ser Gln Arg Gly Tyr Asn Ile Glu Ser
                20                  25                  30

Leu Thr Val Ala Pro Thr Asp Asp Pro Thr Leu Ser Arg Met Thr Ile
            35                  40                  45

Gln Thr Val Gly Asp Glu Lys Val Leu Glu Gln Ile Glu Lys Gln Leu
    50                  55                  60

His Lys Leu Val Asp Val Leu Arg Val Ser Glu Leu Gly Gln Gly Ala
65                  70                  75                  80

His Val Glu Arg Glu Ile Met Leu Val Lys Ile Gln Ala Ser Gly Tyr
                85                  90                  95

Gly Arg Asp Glu Val Lys Arg Asn Thr Glu Ile Phe Arg Gly Gln Ile
            100                 105                 110

Ile Asp Val Thr Pro Ser Leu Tyr Thr Val Gln Leu Ala Gly Thr Ser
        115                 120                 125

Gly Lys Leu Ser Ala Phe Leu Ala Ser Ile Arg Asp Val Ala Lys Ile
    130                 135                 140

Val Glu Val Ala Arg Ser Gly Val Val Gly Leu Ser Arg Gly Asp Lys
145                 150                 155                 160

Ile Met Arg

<210> SEQ ID NO 43
<211> LENGTH: 399
<212> TYPE: PRT
<213> ORGANISM: Picihia stipitis

<400> SEQUENCE: 43

Met Ser Phe Arg Arg Ser Ser Leu Arg Met Ala Lys Met Ala Ser Ala
1               5                   10                  15

Ala Ala Ser Lys Gln Ile Ala Ser Lys Arg Ala Met Ser Ala Leu Ala
            20                  25                  30

Ser Ala Ala Lys Pro Val Val Ser Lys Gln Ser Met Ala Pro Leu Ala
        35                  40                  45

Val Arg Gly Ile Lys Thr Ile Asn Phe Gly Gly Thr Glu Glu Val Val
    50                  55                  60

His Glu Arg Ala Asp Trp Pro Arg Glu Lys Leu Leu Glu Tyr Phe Lys
65                  70                  75                  80

Asn Asp Thr Leu Ala Leu Ile Gly Tyr Gly Ser Gln Gly Tyr Gly Gln
                85                  90                  95

Gly Leu Asn Leu Arg Asp Asn Gly Leu Asn Val Ile Ile Gly Val Arg
            100                 105                 110

Lys Asn Gly Ala Ser Trp Lys Ala Ala Ile Glu Asp Gly Trp Val Pro
        115                 120                 125

Gly Glu Asn Leu Phe Asp Val Asn Glu Ala Ile Ser Lys Gly Thr Tyr
    130                 135                 140

Ile Met Asn Leu Leu Ser Asp Ala Ala Gln Ser Glu Thr Trp Ala Ser
145                 150                 155                 160

Ile Lys Pro Gln Leu Thr Glu Gly Lys Thr Leu Tyr Phe Ser His Gly
                165                 170                 175

Phe Ser Pro Val Phe Lys Glu Leu Thr His Val Glu Pro Pro Thr Asn
            180                 185                 190

Ile Asp Val Ile Leu Ala Ala Pro Lys Gly Ser Gly Arg Thr Val Arg
        195                 200                 205

Ser Leu Phe Lys Glu Gly Arg Gly Ile Asn Ser Ser Tyr Ala Val Trp
    210                 215                 220

Asn Asp Val Thr Gly Lys Ala Glu Glu Lys Ala Ile Ala Leu Ala Val
225                 230                 235                 240

Ala Ile Gly Ser Gly Tyr Val Tyr Gln Thr Thr Phe Glu Arg Glu Val
                245                 250                 255

Asn Ser Asp Leu Tyr Gly Glu Arg Gly Cys Leu Met Gly Gly Ile His
            260                 265                 270

Gly Met Phe Leu Ala Gln Tyr Glu Val Leu Arg Glu Asn Gly His Thr
        275                 280                 285

Pro Ser Glu Ala Phe Asn Glu Thr Val Glu Glu Ala Thr Gln Ser Leu
    290                 295                 300

Tyr Pro Leu Ile Gly Lys Tyr Gly Met Asp Tyr Met Tyr Asp Ala Cys

```
            305                 310                 315                 320
Ser Thr Thr Ala Arg Arg Gly Ala Leu Asp Trp Tyr Pro Arg Phe Lys
                    325                 330                 335

Asp Ala Leu Lys Pro Val Phe Asn Asp Leu Tyr Glu Ser Val Lys Asn
                340                 345                 350

Gly Ser Glu Thr Gln Arg Ser Leu Asp Phe Asn Ser Gln Pro Asp Tyr
            355                 360                 365

Arg Glu Lys Leu Glu Glu Leu Gln Val Ile Arg Asn Met Glu Ile
        370                 375                 380

Trp Arg Val Gly Lys Glu Val Arg Lys Leu Arg Pro Glu Asn Gln
385                 390                 395

<210> SEQ ID NO 44
<211> LENGTH: 360
<212> TYPE: PRT
<213> ORGANISM: Pichia stipitis

<400> SEQUENCE: 44

Met Lys Gln Ser Met Ala Pro Leu Ala Val Arg Gly Ile Lys Thr Ile
1               5                   10                  15

Asn Phe Gly Gly Thr Glu Glu Val Val His Glu Arg Ala Asp Trp Pro
            20                  25                  30

Arg Glu Lys Leu Leu Glu Tyr Phe Lys Asn Asp Thr Leu Ala Leu Ile
        35                  40                  45

Gly Tyr Gly Ser Gln Gly Tyr Gly Gln Gly Leu Asn Leu Arg Asp Asn
    50                  55                  60

Gly Leu Asn Val Ile Ile Gly Val Arg Lys Asn Gly Ala Ser Trp Lys
65                  70                  75                  80

Ala Ala Ile Glu Asp Gly Trp Val Pro Gly Asn Leu Phe Asp Val
                85                  90                  95

Asn Glu Ala Ile Ser Lys Gly Thr Tyr Ile Met Asn Leu Leu Ser Asp
            100                 105                 110

Ala Ala Gln Ser Glu Thr Trp Ala Ser Ile Lys Pro Gln Leu Thr Glu
        115                 120                 125

Gly Lys Thr Leu Tyr Phe Ser His Gly Phe Ser Pro Val Phe Lys Glu
    130                 135                 140

Leu Thr His Val Glu Pro Pro Thr Asn Ile Asp Val Ile Leu Ala Ala
145                 150                 155                 160

Pro Lys Gly Ser Gly Arg Thr Val Arg Ser Leu Phe Lys Glu Gly Arg
                165                 170                 175

Gly Ile Asn Ser Ser Tyr Ala Val Trp Asn Asp Val Thr Gly Lys Ala
            180                 185                 190

Glu Glu Lys Ala Ile Ala Leu Ala Val Ala Ile Gly Ser Gly Tyr Val
        195                 200                 205

Tyr Gln Thr Thr Phe Glu Arg Glu Val Asn Ser Asp Leu Tyr Gly Glu
    210                 215                 220

Arg Gly Cys Leu Met Gly Gly Ile His Gly Met Phe Leu Ala Gln Tyr
225                 230                 235                 240

Glu Val Leu Arg Glu Asn Gly His Thr Pro Ser Glu Ala Phe Asn Glu
                245                 250                 255

Thr Val Glu Glu Ala Thr Gln Ser Leu Tyr Pro Leu Ile Gly Lys Tyr
            260                 265                 270

Gly Met Asp Tyr Met Tyr Asp Ala Cys Ser Thr Thr Ala Arg Arg Gly
        275                 280                 285

Ala Leu Asp Trp Tyr Pro Arg Phe Lys Asp Ala Leu Lys Pro Val Phe
```

```
                    290                 295                 300

Asn Asp Leu Tyr Glu Ser Val Lys Asn Gly Ser Glu Thr Gln Arg Ser
305                 310                 315                 320

Leu Asp Phe Asn Ser Gln Pro Asp Tyr Arg Glu Lys Leu Glu Glu Glu
                325                 330                 335

Leu Gln Val Ile Arg Asn Met Glu Ile Trp Arg Val Gly Lys Glu Val
            340                 345                 350

Arg Lys Leu Arg Pro Glu Asn Gln
            355                 360

<210> SEQ ID NO 45
<211> LENGTH: 395
<212> TYPE: PRT
<213> ORGANISM: Saccharomyces cerevisiae

<400> SEQUENCE: 45

Met Leu Arg Thr Gln Ala Ala Arg Leu Ile Cys Asn Ser Arg Val Ile
1               5                   10                  15

Thr Ala Lys Arg Thr Phe Ala Leu Ala Thr Arg Ala Ala Ala Tyr Ser
            20                  25                  30

Arg Pro Ala Ala Arg Phe Val Lys Pro Met Ile Thr Thr Arg Gly Leu
        35                  40                  45

Lys Gln Ile Asn Phe Gly Gly Thr Val Glu Thr Val Tyr Glu Arg Ala
    50                  55                  60

Asp Trp Pro Arg Glu Lys Leu Leu Asp Tyr Phe Lys Asn Asp Thr Phe
65                  70                  75                  80

Ala Leu Ile Gly Tyr Gly Ser Gln Gly Tyr Gly Gln Gly Leu Asn Leu
                85                  90                  95

Arg Asp Asn Gly Leu Asn Val Ile Gly Val Arg Lys Asp Gly Ala
            100                 105                 110

Ser Trp Lys Ala Ala Ile Glu Asp Gly Trp Val Pro Gly Lys Asn Leu
        115                 120                 125

Phe Thr Val Glu Asp Ala Ile Lys Arg Gly Ser Tyr Val Met Asn Leu
    130                 135                 140

Leu Ser Asp Ala Ala Gln Ser Glu Thr Trp Pro Ala Ile Lys Pro Leu
145                 150                 155                 160

Leu Thr Lys Gly Lys Thr Leu Tyr Phe Ser His Gly Phe Ser Pro Val
                165                 170                 175

Phe Lys Asp Leu Thr His Val Glu Pro Pro Lys Asp Leu Asp Val Ile
            180                 185                 190

Leu Val Ala Pro Lys Gly Ser Gly Arg Thr Val Arg Ser Leu Phe Lys
        195                 200                 205

Glu Gly Arg Gly Ile Asn Ser Ser Tyr Ala Val Trp Asn Asp Val Thr
    210                 215                 220

Gly Lys Ala His Glu Lys Ala Gln Ala Leu Ala Val Ala Ile Gly Ser
225                 230                 235                 240

Gly Tyr Val Tyr Gln Thr Thr Phe Glu Arg Glu Val Asn Ser Asp Leu
                245                 250                 255

Tyr Gly Glu Arg Gly Cys Leu Met Gly Gly Ile His Gly Met Phe Leu
            260                 265                 270

Ala Gln Tyr Asp Val Leu Arg Glu Asn Gly His Ser Pro Ser Glu Ala
        275                 280                 285

Phe Asn Glu Thr Val Glu Glu Ala Thr Gln Ser Leu Tyr Pro Leu Ile
    290                 295                 300

Gly Lys Tyr Gly Met Asp Tyr Met Tyr Asp Ala Cys Ser Thr Thr Ala
```

```
            305                 310                 315                 320
Arg Arg Gly Ala Leu Asp Trp Tyr Pro Ile Phe Lys Asn Ala Leu Lys
                325                 330                 335

Pro Val Phe Gln Asp Leu Tyr Glu Ser Thr Lys Asn Gly Thr Glu Thr
            340                 345                 350

Lys Arg Ser Leu Glu Phe Asn Ser Gln Pro Asp Tyr Arg Glu Lys Leu
        355                 360                 365

Glu Lys Glu Leu Asp Thr Ile Arg Asn Met Glu Ile Trp Lys Val Gly
370                 375                 380

Lys Glu Val Arg Lys Leu Arg Pro Glu Asn Gln
385                 390                 395

<210> SEQ ID NO 46
<211> LENGTH: 338
<212> TYPE: PRT
<213> ORGANISM: Corynebacterium glutamicum

<400> SEQUENCE: 46

Met Ala Ile Glu Leu Leu Tyr Asp Ala Asp Ala Asp Leu Ser Leu Ile
1               5                   10                  15

Gln Gly Arg Lys Val Ala Ile Val Gly Tyr Gly Ser Gln Gly His Ala
            20                  25                  30

His Ser Gln Asn Leu Arg Asp Ser Gly Val Glu Val Ile Gly Leu
        35                  40                  45

Arg Glu Gly Ser Lys Ser Ala Glu Lys Ala Lys Glu Ala Gly Phe Glu
    50                  55                  60

Val Lys Thr Thr Ala Glu Ala Ala Trp Ala Asp Val Ile Met Leu
65                  70                  75                  80

Leu Ala Pro Asp Thr Ser Gln Ala Glu Ile Phe Thr Asn Asp Ile Glu
                85                  90                  95

Pro Asn Leu Asn Ala Gly Asp Ala Leu Leu Phe Gly His Gly Leu Asn
            100                 105                 110

Ile His Phe Asp Leu Ile Lys Pro Ala Asp Asp Ile Ile Val Gly Met
        115                 120                 125

Val Ala Pro Lys Gly Pro Gly His Leu Val Arg Arg Gln Phe Val Asp
    130                 135                 140

Gly Lys Gly Val Pro Cys Leu Ile Ala Val Asp Gln Asp Pro Thr Gly
145                 150                 155                 160

Thr Ala Gln Ala Leu Thr Leu Ser Tyr Ala Ala Ile Gly Gly Ala
                165                 170                 175

Arg Ala Gly Val Ile Pro Thr Thr Phe Glu Ala Glu Thr Val Thr Asp
            180                 185                 190

Leu Phe Gly Glu Gln Ala Val Leu Cys Gly Gly Thr Glu Glu Leu Val
        195                 200                 205

Lys Val Gly Phe Glu Val Leu Thr Glu Ala Gly Tyr Glu Pro Glu Met
    210                 215                 220

Ala Tyr Phe Glu Val Leu His Glu Leu Lys Leu Ile Val Asp Leu Met
225                 230                 235                 240

Phe Glu Gly Gly Ile Ser Asn Met Asn Tyr Ser Val Ser Asp Thr Ala
                245                 250                 255

Glu Phe Gly Gly Tyr Leu Ser Gly Pro Arg Val Ile Asp Ala Asp Thr
            260                 265                 270

Lys Ser Arg Met Lys Asp Ile Leu Thr Asp Ile Gln Asp Gly Thr Phe
        275                 280                 285

Thr Lys Arg Leu Ile Ala Asn Val Glu Asn Gly Asn Thr Glu Leu Glu
```

```
                290                 295                 300
Gly Leu Arg Ala Ser Tyr Asn Asn His Pro Ile Glu Glu Thr Gly Ala
305                 310                 315                 320

Lys Leu Arg Asp Leu Met Ser Trp Val Lys Val Asp Ala Arg Ala Glu
                325                 330                 335

Thr Ala

<210> SEQ ID NO 47
<211> LENGTH: 491
<212> TYPE: PRT
<213> ORGANISM: Escherichia coli

<400> SEQUENCE: 47

Met Ala Asn Tyr Phe Asn Thr Leu Asn Leu Arg Gln Gln Leu Ala Gln
  1               5                  10                  15

Leu Gly Lys Cys Arg Phe Met Gly Arg Asp Glu Phe Ala Asp Gly Ala
                 20                  25                  30

Ser Tyr Leu Gln Gly Lys Lys Val Ile Val Gly Cys Gly Ala Gln
                 35                  40                  45

Gly Leu Asn Gln Gly Leu Asn Met Arg Asp Ser Gly Leu Asp Ile Ser
 50                  55                  60

Tyr Ala Leu Arg Lys Glu Ala Ile Ala Glu Lys Arg Ala Ser Trp Arg
 65                  70                  75                  80

Lys Ala Thr Glu Asn Gly Phe Lys Val Gly Thr Tyr Glu Glu Leu Ile
                 85                  90                  95

Pro Gln Ala Asp Leu Val Ile Asn Leu Thr Pro Asp Lys Gln His Ser
                100                 105                 110

Asp Val Val Arg Thr Val Gln Pro Leu Met Lys Asp Gly Ala Ala Leu
                115                 120                 125

Gly Tyr Ser His Gly Phe Asn Ile Val Glu Val Gly Glu Gln Ile Arg
130                 135                 140

Lys Asp Ile Thr Val Val Met Val Ala Pro Lys Cys Pro Gly Thr Glu
145                 150                 155                 160

Val Arg Glu Glu Tyr Lys Arg Gly Phe Gly Val Pro Thr Leu Ile Ala
                165                 170                 175

Val His Pro Glu Asn Asp Pro Lys Gly Glu Gly Met Ala Ile Ala Lys
                180                 185                 190

Ala Trp Ala Ala Ala Thr Gly Gly His Arg Ala Gly Val Leu Glu Ser
            195                 200                 205

Ser Phe Val Ala Glu Val Lys Ser Asp Leu Met Gly Glu Gln Thr Ile
210                 215                 220

Leu Cys Gly Met Leu Gln Ala Gly Ser Leu Leu Cys Phe Asp Lys Leu
225                 230                 235                 240

Val Glu Glu Gly Thr Asp Pro Ala Tyr Ala Glu Lys Leu Ile Gln Phe
                245                 250                 255

Gly Trp Glu Thr Ile Thr Glu Ala Leu Lys Gln Gly Gly Ile Thr Leu
                260                 265                 270

Met Met Asp Arg Leu Ser Asn Pro Ala Lys Leu Arg Ala Tyr Ala Leu
                275                 280                 285

Ser Glu Gln Leu Lys Glu Ile Met Ala Pro Leu Phe Gln Lys His Met
            290                 295                 300

Asp Asp Ile Ile Ser Gly Glu Phe Ser Ser Gly Met Met Ala Asp Trp
305                 310                 315                 320

Ala Asn Asp Asp Lys Lys Leu Leu Thr Trp Arg Glu Glu Thr Gly Lys
                325                 330                 335
```

```
Thr Ala Phe Glu Thr Ala Pro Gln Tyr Glu Gly Lys Ile Gly Glu Gln
                340                 345                 350

Glu Tyr Phe Asp Lys Gly Val Leu Met Ile Ala Met Val Lys Ala Gly
                355                 360                 365

Val Glu Leu Ala Phe Glu Thr Met Val Asp Ser Gly Ile Ile Glu Glu
    370                 375                 380

Ser Ala Tyr Tyr Glu Ser Leu His Glu Leu Pro Leu Ile Ala Asn Thr
385                 390                 395                 400

Ile Ala Arg Lys Arg Leu Tyr Glu Met Asn Val Val Ile Ser Asp Thr
                405                 410                 415

Ala Glu Tyr Gly Asn Tyr Leu Phe Ser Tyr Ala Cys Val Pro Leu Leu
                420                 425                 430

Lys Pro Phe Met Ala Glu Leu Gln Pro Gly Asp Leu Gly Lys Ala Ile
                435                 440                 445

Pro Glu Gly Ala Val Asp Asn Gly Gln Leu Arg Asp Val Asn Glu Ala
                450                 455                 460

Ile Arg Ser His Ala Ile Glu Gln Val Gly Lys Lys Leu Arg Gly Tyr
465                 470                 475                 480

Met Thr Asp Met Lys Arg Ile Ala Val Ala Gly
                485                 490

<210> SEQ ID NO 48
<211> LENGTH: 604
<212> TYPE: PRT
<213> ORGANISM: Picihia stipitis

<400> SEQUENCE: 48

Met Ser Phe Leu Phe Lys Ala Ala Ala Arg Arg Val Ala Ser Lys
  1               5                  10                  15

Ser Pro Ala Ala Val Ala Arg Ser Phe Ser Val Ser Ala Thr Gln Cys
                20                  25                  30

Glu Lys Lys Leu Asn Lys Tyr Ser Ile Val Thr Gly Asp Pro Ser
            35                  40                  45

Gln Gly Ala Ser Gln Ala Met Leu Tyr Ala Thr Gly Phe Asp Asp Ala
    50                  55                  60

Asp Phe Asn Arg Ala Gln Ile Gly Val Gly Ser Val Trp Trp Ser Gly
65                  70                  75                  80

Asn Pro Cys Asn Met His Leu Met Glu Leu Asn Asn Lys Cys Thr Glu
                85                  90                  95

Ser Val Asn Arg Ala Gly Leu Lys Gly Met Gln Phe Asn Ser Ile Gly
                100                 105                 110

Ile Ser Asp Gly Ile Thr Asn Gly Thr Glu Gly Met Arg Tyr Ser Leu
            115                 120                 125

Gln Ser Arg Glu Ile Ile Ala Asp Ser Phe Glu Ser Met Met Leu Gly
    130                 135                 140

Gln Leu Tyr Asp Gly Asn Ile Ala Ile Pro Ser Cys Asp Lys Asn Met
145                 150                 155                 160

Pro Gly Val Leu Ile Ala Met Ala Arg His Asn Arg Pro Ser Ile Met
                165                 170                 175

Val Tyr Gly Gly Thr Ile Leu Pro Gly Gln Thr Thr Cys Gly Thr Asn
                180                 185                 190

Asn Pro Ala Ile Ala Asp Lys Ile Asp Ile Ile Ser Ala Phe Gln Ser
            195                 200                 205

Tyr Gly Gln Tyr Leu Thr Lys Ser Ile Thr Asn Glu Glu Arg Lys Asp
    210                 215                 220
```

Ile Val Arg His Ala Cys Pro Gly Pro Gly Ala Cys Gly Gly Met Tyr
225                 230                 235                 240

Thr Ala Asn Thr Met Ala Ser Ala Ala Glu Cys Leu Gly Met Ser Leu
            245                 250                 255

Pro Tyr Ser Ser Ser Ala Pro Ala Val Ser Lys Glu Lys Asp Ala Glu
        260                 265                 270

Cys Ala Asn Ile Gly Gln Ala Ile Lys His Leu Leu Glu Ile Asp Leu
    275                 280                 285

Lys Pro Arg Asp Ile Leu Thr Lys Lys Ser Phe Glu Asn Ala Ile Ala
290                 295                 300

Tyr Ile Ile Ala Thr Gly Gly Ser Thr Asn Ala Val Leu His Leu Ile
305                 310                 315                 320

Ala Ile Ala Ser Ser Ala Asp Ile Asp Leu Thr Val Asp Asp Phe Gln
            325                 330                 335

Arg Ile Ser Asp Ser Thr Pro Leu Leu Ala Asp Phe Lys Pro Ser Gly
        340                 345                 350

Gln Phe Val Met Ala Asp Leu Gln Lys Tyr Gly Gly Thr Pro Ala Val
    355                 360                 365

Met Lys Phe Leu Met Asn Glu Gly Phe Ile Asp Gly Asp Gln Tyr Thr
370                 375                 380

Val Thr Gly Lys Thr Ile Lys Glu Asn Leu Ala Ser Val Lys Asp Leu
385                 390                 395                 400

Pro Ala Asp Gln Pro Ile Ile Arg Pro Val Ser Asn Pro Leu Lys Thr
            405                 410                 415

Ser Gly His Leu Gln Ile Leu Lys Gly Ser Leu Ala Pro Gly Ser Ala
        420                 425                 430

Val Gly Lys Ile Thr Gly Lys Glu Gly Thr Tyr Phe Lys Gly Lys Ala
    435                 440                 445

Arg Val Phe Asp Asp Glu Gly Asp Phe Ile Val Ala Leu Glu Lys Gly
450                 455                 460

Glu Ile Lys Lys Gly Glu Lys Thr Val Cys Val Ile Arg Tyr Glu Gly
465                 470                 475                 480

Pro Lys Gly Gly Pro Gly Met Pro Glu Met Leu Lys Pro Ser Ser Ala
            485                 490                 495

Leu Met Gly Tyr Gly Leu Gly Lys Asp Val Ala Leu Leu Thr Asp Gly
        500                 505                 510

Arg Phe Ser Gly Gly Ser His Gly Phe Leu Ile Gly His Ile Val Pro
    515                 520                 525

Glu Ala Ala Glu Gly Gly Pro Ile Gly Leu Val Tyr Asp Gly Asp Glu
530                 535                 540

Ile Val Ile Asp Ala Glu Asn Asn Lys Ile Asp Leu Leu Val Asp Glu
545                 550                 555                 560

Ala Val Leu Ala Glu Arg Arg Lys Leu Trp Thr Ala Pro Glu Pro Arg
            565                 570                 575

Tyr Thr Arg Gly Thr Leu Ala Lys Tyr Ala Arg Leu Val Ser Asp Ala
        580                 585                 590

Ser Ala Gly Cys Val Thr Asp Leu Pro Ile Lys Asn
    595                 600

<210> SEQ ID NO 49
<211> LENGTH: 572
<212> TYPE: PRT
<213> ORGANISM: Pichia stipitis

<400> SEQUENCE: 49

```
Met Lys Lys Leu Asn Lys Tyr Ser Ser Ile Val Thr Gly Asp Pro Ser
 1               5                  10                  15

Gln Gly Ala Ser Gln Ala Met Leu Tyr Ala Thr Gly Phe Asp Asp Ala
            20                  25                  30

Asp Phe Asn Arg Ala Gln Ile Gly Val Gly Ser Val Trp Trp Ser Gly
        35                  40                  45

Asn Pro Cys Asn Met His Leu Met Glu Leu Asn Asn Lys Cys Thr Glu
50                  55                  60

Ser Val Asn Arg Ala Gly Leu Lys Gly Met Gln Phe Asn Ser Ile Gly
65                  70                  75                  80

Ile Ser Asp Gly Ile Thr Asn Gly Thr Glu Gly Met Arg Tyr Ser Leu
                85                  90                  95

Gln Ser Arg Glu Ile Ile Ala Asp Ser Phe Glu Ser Met Met Leu Gly
            100                 105                 110

Gln Leu Tyr Asp Gly Asn Ile Ala Ile Pro Ser Cys Asp Lys Asn Met
            115                 120                 125

Pro Gly Val Leu Ile Ala Met Ala Arg His Asn Arg Pro Ser Ile Met
        130                 135                 140

Val Tyr Gly Gly Thr Ile Leu Pro Gly Gln Thr Thr Cys Gly Thr Asn
145                 150                 155                 160

Asn Pro Ala Ile Ala Asp Lys Ile Asp Ile Ser Ala Phe Gln Ser
                165                 170                 175

Tyr Gly Gln Tyr Leu Thr Lys Ser Ile Thr Asn Glu Glu Arg Lys Asp
            180                 185                 190

Ile Val Arg His Ala Cys Pro Gly Pro Gly Ala Cys Gly Gly Met Tyr
        195                 200                 205

Thr Ala Asn Thr Met Ala Ser Ala Ala Glu Cys Leu Gly Met Ser Leu
        210                 215                 220

Pro Tyr Ser Ser Ala Pro Ala Val Ser Lys Glu Lys Asp Ala Glu
225                 230                 235                 240

Cys Ala Asn Ile Gly Gln Ala Ile Lys His Leu Leu Glu Ile Asp Leu
                245                 250                 255

Lys Pro Arg Asp Ile Leu Thr Lys Lys Ser Phe Glu Asn Ala Ile Ala
            260                 265                 270

Tyr Ile Ile Ala Thr Gly Gly Ser Thr Asn Ala Val Leu His Leu Ile
        275                 280                 285

Ala Ile Ala Ser Ser Ala Asp Ile Asp Leu Thr Val Asp Asp Phe Gln
        290                 295                 300

Arg Ile Ser Asp Ser Thr Pro Leu Leu Ala Asp Phe Lys Pro Ser Gly
305                 310                 315                 320

Gln Phe Val Met Ala Asp Leu Gln Lys Tyr Gly Gly Thr Pro Ala Val
            325                 330                 335

Met Lys Phe Leu Met Asn Glu Gly Phe Ile Asp Gly Asp Gln Tyr Thr
            340                 345                 350

Val Thr Gly Lys Thr Ile Lys Glu Asn Leu Ala Ser Val Lys Asp Leu
        355                 360                 365

Pro Ala Asp Gln Pro Ile Ile Arg Pro Val Ser Asn Pro Leu Lys Thr
        370                 375                 380

Ser Gly His Leu Gln Ile Leu Lys Gly Ser Leu Ala Pro Gly Ser Ala
385                 390                 395                 400

Val Gly Lys Ile Thr Gly Lys Glu Gly Thr Tyr Phe Lys Gly Lys Ala
            405                 410                 415

Arg Val Phe Asp Asp Glu Gly Asp Phe Ile Val Ala Leu Glu Lys Gly
```

```
                    420             425             430
Glu Ile Lys Lys Gly Lys Thr Val Cys Val Ile Arg Tyr Glu Gly
            435             440             445

Pro Lys Gly Gly Pro Gly Met Pro Glu Met Leu Lys Pro Ser Ser Ala
450             455             460

Leu Met Gly Tyr Gly Leu Gly Lys Asp Val Ala Leu Leu Thr Asp Gly
465             470             475             480

Arg Phe Ser Gly Gly Ser His Gly Phe Leu Ile Gly His Ile Val Pro
                485             490             495

Glu Ala Ala Glu Gly Gly Pro Ile Gly Leu Val Tyr Asp Gly Asp Glu
                500             505             510

Ile Val Ile Asp Ala Glu Asn Asn Lys Ile Asp Leu Leu Val Asp Glu
            515             520             525

Ala Val Leu Ala Glu Arg Arg Lys Leu Trp Thr Ala Pro Glu Pro Arg
530             535             540

Tyr Thr Arg Gly Thr Leu Ala Lys Tyr Ala Arg Leu Val Ser Asp Ala
545             550             555             560

Ser Ala Gly Cys Val Thr Asp Leu Pro Ile Lys Asn
                565             570

<210> SEQ ID NO 50
<211> LENGTH: 585
<212> TYPE: PRT
<213> ORGANISM: Saccharomyces cerevisiae

<400> SEQUENCE: 50

Met Gly Leu Leu Thr Lys Val Ala Thr Ser Arg Gln Phe Ser Thr Thr
1               5                   10                  15

Arg Cys Val Ala Lys Lys Leu Asn Lys Tyr Ser Tyr Ile Ile Thr Glu
                20                  25                  30

Pro Lys Gly Gln Gly Ala Ser Gln Ala Met Leu Tyr Ala Thr Gly Phe
            35                  40                  45

Lys Lys Glu Asp Phe Lys Lys Pro Gln Val Gly Val Gly Ser Cys Trp
        50                  55                  60

Trp Ser Gly Asn Pro Cys Asn Met His Leu Leu Asp Leu Asn Asn Arg
65                  70                  75                  80

Cys Ser Gln Ser Ile Glu Lys Ala Gly Leu Lys Ala Met Gln Phe Asn
                85                  90                  95

Thr Ile Gly Val Ser Asp Gly Ile Ser Met Gly Thr Lys Gly Met Arg
            100                 105                 110

Tyr Ser Leu Gln Ser Arg Glu Ile Ile Ala Asp Ser Phe Glu Thr Ile
        115                 120                 125

Met Met Ala Gln His Tyr Asp Ala Asn Ile Ala Ile Pro Ser Cys Asp
130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
            180                 185                 190

Ser Tyr Gly Glu Tyr Ile Ser Lys Gln Phe Thr Glu Glu Arg Glu
        195                 200                 205

Asp Val Val Glu His Ala Cys Pro Gly Pro Gly Ser Cys Gly Gly Met
210                 215                 220

Tyr Thr Ala Asn Thr Met Ala Ser Ala Ala Glu Val Leu Gly Leu Thr
```

```
                225                 230                 235                 240
Ile Pro Asn Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
            260                 265                 270

Ile Leu Pro Arg Asp Ile Leu Thr Lys Glu Ala Phe Glu Asn Ala Ile
            275                 280                 285

Thr Tyr Val Val Ala Thr Gly Ser Thr Asn Ala Val Leu His Leu
            290                 295                 300

Val Ala Val Ala His Ser Ala Gly Val Lys Leu Ser Pro Asp Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
            340                 345                 350

Val Ile Lys Tyr Leu Tyr Glu Asn Asn Met Leu His Gly Asn Thr Met
            355                 360                 365

Thr Val Thr Gly Asp Thr Leu Ala Glu Arg Ala Lys Lys Ala Pro Ser
370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
            420                 425                 430

Ala Arg Val Phe Glu Glu Gly Ala Phe Ile Glu Ala Leu Glu Arg
            435                 440                 445

Gly Glu Ile Lys Lys Gly Glu Lys Thr Val Val Ile Arg Tyr Glu
450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
                500                 505                 510

Pro Glu Ala Ala Glu Gly Gly Pro Ile Gly Leu Val Arg Asp Gly Asp
                515                 520                 525

Glu Ile Ile Ile Asp Ala Asp Asn Asn Lys Ile Asp Leu Leu Val Ser
            530                 535                 540

Asp Lys Glu Met Ala Gln Arg Lys Gln Ser Trp Val Ala Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
            580                 585

<210> SEQ ID NO 51
<211> LENGTH: 613
<212> TYPE: PRT
<213> ORGANISM: Corynebacterium glutamicum

<400> SEQUENCE: 51

Met Ile Pro Leu Arg Ser Lys Val Thr Thr Val Gly Arg Asn Ala Ala
1               5                   10                  15

Gly Ala Arg Ala Leu Trp Arg Ala Thr Gly Thr Lys Glu Asn Glu Phe
```

```
                     20                  25                  30
Gly Lys Pro Ile Val Ala Ile Val Asn Ser Tyr Thr Gln Phe Val Pro
             35                  40                  45
Gly His Val His Leu Lys Asn Val Gly Asp Ile Val Ala Asp Ala Val
             50                  55                  60
Arg Lys Ala Gly Gly Val Pro Lys Glu Phe Asn Thr Ile Ala Val Asp
 65                  70                  75                  80
Asp Gly Ile Ala Met Gly His Gly Gly Met Leu Tyr Ser Leu Pro Ser
                 85                  90                  95
Arg Glu Ile Ile Ala Asp Ser Val Glu Tyr Met Val Asn Ala His Thr
            100                 105                 110
Ala Asp Ala Met Val Cys Ile Ser Asn Cys Asp Lys Ile Thr Pro Gly
            115                 120                 125
Met Leu Asn Ala Ala Met Arg Leu Asn Ile Pro Val Val Phe Val Ser
    130                 135                 140
Gly Gly Pro Met Glu Ala Gly Lys Ala Val Val Val Asp Gly Val Ala
145                 150                 155                 160
His Ala Pro Thr Asp Leu Ile Thr Ala Ile Ser Ala Ser Ala Ser Asp
                165                 170                 175
Ala Val Asp Asp Ala Gly Leu Ala Ala Val Glu Ala Ser Ala Cys Pro
            180                 185                 190
Thr Cys Gly Ser Cys Ser Gly Met Phe Thr Ala Asn Ser Met Asn Cys
        195                 200                 205
Leu Thr Glu Ala Leu Gly Leu Ser Leu Pro Gly Asn Gly Ser Thr Leu
    210                 215                 220
Ala Thr His Ala Ala Arg Arg Ala Leu Phe Glu Lys Ala Gly Glu Thr
225                 230                 235                 240
Val Val Glu Leu Cys Arg Arg Tyr Tyr Gly Glu Glu Asp Glu Ser Val
                245                 250                 255
Leu Pro Arg Gly Ile Ala Thr Lys Lys Ala Phe Glu Asn Ala Met Ala
            260                 265                 270
Leu Asp Met Ala Met Gly Gly Ser Thr Asn Thr Ile Leu His Ile Leu
    275                 280                 285
Ala Ala Ala Gln Glu Gly Glu Val Asp Phe Asp Leu Ala Asp Ile Asp
290                 295                 300
Glu Leu Ser Lys Asn Val Pro Cys Leu Ser Lys Val Ala Pro Asn Ser
305                 310                 315                 320
Asp Tyr His Met Glu Asp Val His Arg Ala Gly Gly Ile Pro Ala Leu
                325                 330                 335
Leu Gly Glu Leu Asn Arg Gly Gly Leu Leu Asn Lys Asp Val His Ser
            340                 345                 350
Val His Ser Asn Asp Leu Glu Gly Trp Leu Asp Asp Trp Asp Ile Arg
        355                 360                 365
Ser Gly Lys Thr Thr Glu Val Ala Thr Glu Leu Phe His Ala Ala Pro
    370                 375                 380
Gly Gly Ile Arg Thr Thr Glu Ala Phe Ser Thr Glu Asn Arg Trp Asp
385                 390                 395                 400
Glu Leu Asp Thr Asp Ala Ala Lys Gly Cys Ile Arg Asp Val Glu His
                405                 410                 415
Ala Tyr Thr Ala Asp Gly Gly Leu Val Val Leu Arg Gly Asn Ile Ser
            420                 425                 430
Pro Asp Gly Ala Val Ile Lys Ser Ala Gly Ile Glu Glu Glu Leu Trp
        435                 440                 445
```

```
Asn Phe Thr Gly Pro Ala Arg Val Val Glu Ser Gln Glu Glu Ala Val
    450                 455                 460

Ser Val Ile Leu Thr Lys Thr Ile Gln Ala Gly Glu Val Leu Val Val
465                 470                 475                 480

Arg Tyr Glu Gly Pro Ser Gly Pro Gly Met Gln Glu Met Leu His
                    485                 490                 495

Pro Thr Ala Phe Leu Lys Gly Ser Gly Leu Gly Lys Lys Cys Ala Leu
                500                 505                 510

Ile Thr Asp Gly Arg Phe Ser Gly Gly Ser Ser Gly Leu Ser Ile Gly
                515                 520                 525

His Val Ser Pro Glu Ala Ala His Gly Gly Val Ile Gly Leu Ile Glu
                530                 535                 540

Asn Gly Asp Ile Val Ser Ile Asp Val His Asn Arg Lys Leu Glu Val
545                 550                 555                 560

Gln Val Ser Asp Glu Glu Leu Gln Arg Arg Arg Asp Ala Met Asn Ala
                565                 570                 575

Ser Glu Lys Pro Trp Gln Pro Val Asn Arg Asn Arg Val Val Thr Lys
                580                 585                 590

Ala Leu Arg Ala Tyr Ala Lys Met Ala Thr Ser Ala Asp Lys Gly Ala
                595                 600                 605

Val Arg Gln Val Asp
        610

<210> SEQ ID NO 52
<211> LENGTH: 616
<212> TYPE: PRT
<213> ORGANISM: Escherichia coli

<400> SEQUENCE: 52

Met Pro Lys Tyr Arg Ser Ala Thr Thr Thr His Gly Arg Asn Met Ala
1               5                   10                  15

Gly Ala Arg Ala Leu Trp Arg Ala Thr Gly Met Thr Asp Ala Asp Phe
            20                  25                  30

Gly Lys Pro Ile Ile Ala Val Val Asn Ser Phe Thr Gln Phe Val Pro
        35                  40                  45

Gly His Val His Leu Arg Asp Leu Gly Lys Leu Val Ala Glu Gln Ile
    50                  55                  60

Glu Ala Ala Gly Gly Val Ala Lys Glu Phe Asn Thr Ile Ala Val Asp
65                  70                  75                  80

Asp Gly Ile Ala Met Gly His Gly Gly Met Leu Tyr Ser Leu Pro Ser
                85                  90                  95

Arg Glu Leu Ile Ala Asp Ser Val Glu Tyr Met Val Asn Ala His Cys
                100                 105                 110

Ala Asp Ala Met Val Cys Ile Ser Asn Cys Asp Lys Ile Thr Pro Gly
            115                 120                 125

Met Leu Met Ala Ser Leu Arg Leu Asn Ile Pro Val Ile Phe Val Ser
        130                 135                 140

Gly Gly Pro Met Glu Ala Gly Lys Thr Lys Leu Ser Asp Gln Ile Ile
145                 150                 155                 160

Lys Leu Asp Leu Val Asp Ala Met Ile Gln Gly Ala Asp Pro Lys Val
                165                 170                 175

Ser Asp Ser Gln Ser Asp Gln Val Glu Arg Ser Ala Cys Pro Thr Cys
                180                 185                 190

Gly Ser Cys Ser Gly Met Phe Thr Ala Asn Ser Met Asn Cys Leu Thr
            195                 200                 205
```

```
Glu Ala Leu Gly Leu Ser Gln Pro Gly Asn Gly Ser Leu Leu Ala Thr
    210                 215                 220

His Ala Asp Arg Lys Gln Leu Phe Leu Asn Ala Gly Lys Arg Ile Val
225                 230                 235                 240

Glu Leu Thr Lys Arg Tyr Tyr Glu Gln Asn Asp Glu Ser Ala Leu Pro
                245                 250                 255

Arg Asn Ile Ala Ser Lys Ala Ala Phe Glu Asn Ala Met Thr Leu Asp
            260                 265                 270

Ile Ala Met Gly Gly Ser Thr Asn Thr Val Leu His Leu Leu Ala Ala
        275                 280                 285

Ala Gln Glu Ala Glu Ile Asp Phe Thr Met Ser Asp Ile Asp Lys Leu
    290                 295                 300

Ser Arg Lys Val Pro Gln Leu Cys Lys Val Ala Pro Ser Thr Gln Lys
305                 310                 315                 320

Tyr His Met Glu Asp Val His Arg Ala Gly Gly Val Ile Gly Ile Leu
                325                 330                 335

Gly Glu Leu Asp Arg Ala Gly Leu Leu Asn Arg Asp Val Lys Asn Val
            340                 345                 350

Leu Gly Leu Thr Leu Pro Gln Thr Leu Glu Gln Tyr Asp Val Met Leu
        355                 360                 365

Thr Gln Asp Asp Ala Val Lys Asn Met Phe Arg Ala Gly Pro Ala Gly
370                 375                 380

Ile Arg Thr Thr Gln Ala Phe Ser Gln Asp Cys Arg Trp Asp Thr Leu
385                 390                 395                 400

Asp Asp Asp Arg Ala Asn Gly Cys Ile Arg Ser Leu Glu His Ala Tyr
                405                 410                 415

Ser Lys Asp Gly Gly Leu Ala Val Leu Tyr Gly Asn Phe Ala Glu Asn
            420                 425                 430

Gly Cys Ile Val Lys Thr Ala Gly Val Asp Asp Ser Ile Leu Lys Phe
        435                 440                 445

Thr Gly Pro Ala Lys Val Tyr Glu Ser Gln Asp Asp Ala Val Glu Ala
    450                 455                 460

Ile Leu Gly Gly Lys Val Val Ala Gly Asp Val Val Val Ile Arg Tyr
465                 470                 475                 480

Glu Gly Pro Lys Gly Gly Pro Gly Met Gln Glu Met Leu Tyr Pro Thr
                485                 490                 495

Ser Phe Leu Lys Ser Met Gly Leu Gly Lys Ala Cys Ala Leu Ile Thr
            500                 505                 510

Asp Gly Arg Phe Ser Gly Gly Thr Ser Gly Leu Ser Ile Gly His Val
        515                 520                 525

Ser Pro Glu Ala Ala Ser Gly Gly Ser Ile Gly Leu Ile Glu Asp Gly
    530                 535                 540

Asp Leu Ile Ala Ile Asp Ile Pro Asn Arg Gly Ile Gln Leu Gln Val
545                 550                 555                 560

Ser Asp Ala Glu Leu Ala Ala Arg Arg Glu Ala Gln Asp Ala Arg Gly
                565                 570                 575

Asp Lys Ala Trp Thr Pro Lys Asn Arg Glu Arg Gln Val Ser Phe Ala
            580                 585                 590

Leu Arg Ala Tyr Ala Ser Leu Ala Thr Ser Ala Asp Lys Gly Ala Val
        595                 600                 605

Arg Asp Lys Ser Lys Leu Gly Gly
610                 615

<210> SEQ ID NO 53
```

<211> LENGTH: 623
<212> TYPE: PRT
<213> ORGANISM: Pichia stipitis

<400> SEQUENCE: 53

```
Met Thr Pro Val Gln Glu Thr Ile Arg Leu Pro Gly Thr Ser Ser Pro
 1               5                  10                  15

Thr Val Pro Glu Asn Val Thr Leu Gly Glu Tyr Leu Phe Leu Arg Ile
             20                  25                  30

Ser Gln Ala Asn Pro Lys Leu Arg Ser Ile Phe Gly Ile Pro Gly Asp
         35                  40                  45

Phe Asn Val Asp Leu Leu Glu His Leu Tyr Ser Pro Val Val Ala Gly
     50                  55                  60

Arg Asp Ile Lys Phe Ile Gly Leu Cys Asn Glu Leu Asn Gly Ala Tyr
 65                  70                  75                  80

Thr Ala Asp Gly Tyr Ser Arg Ala Ile Gly Gly Leu Ser Thr Phe Ile
                 85                  90                  95

Ser Thr Phe Gly Val Gly Glu Leu Ser Ala Ile Asn Gly Ile Ala Gly
            100                 105                 110

Ser Phe Ala Glu Phe Ser Pro Val Leu His Ile Val Gly Thr Thr Ser
        115                 120                 125

Leu Pro Gln Arg Asp His Ala Ile Asn Gly Ser Asp Val Arg Asn His
    130                 135                 140

His Leu Ile Gln Asn Lys Asn Pro Leu Cys Gln Pro Asn His Ala
145                 150                 155                 160

Val Tyr Lys Lys Met Ile Glu Pro Ile Ser Val Ile Gln Glu Ser Leu
                165                 170                 175

Asp Ser Asp Leu Gln Arg Asn Met Glu Lys Ile Asp Arg Val Leu Val
            180                 185                 190

Lys Ile Leu Gln Glu Ser Arg Pro Gly Tyr Leu Phe Ile Pro Cys Asp
        195                 200                 205

Ile Thr Asn Leu Ile Val Pro Ser Tyr Arg Leu Tyr Glu Thr Pro Leu
    210                 215                 220

Pro Leu Glu Ile Gln Leu Thr Thr Ser Gly Val Glu Val Leu Glu Asp
225                 230                 235                 240

Val Val Asp Ala Ile Leu Phe Arg Leu Tyr Lys Ser Lys Asn Pro Ser
                245                 250                 255

Leu Leu Ser Asp Cys Leu Thr Thr Arg Phe Asn Leu Gln Asp Lys Leu
            260                 265                 270

Asn Thr Leu Val Ala Lys Leu Pro Ser Asn Phe Val Lys Leu Phe Ser
        275                 280                 285

Thr Asn Met Ala Arg Asn Ile Asp Glu Ser Leu Ser Asn Phe Val Gly
    290                 295                 300

Leu Tyr Phe Gly Ile Gly Ser Ser Ser Lys Glu Val Ser Arg Gln Leu
305                 310                 315                 320

Glu Arg Asn Thr Asp Phe Leu Ile Asn Leu Gly Tyr Phe Asn Ala Glu
                325                 330                 335

Thr Thr Thr Ala Gly Tyr Ser Asn Asp Phe Ser Asn Ile Glu Glu Tyr
            340                 345                 350

Ile Glu Ile Asn Pro Asp Tyr Ile Lys Val Asn Glu His Ile Ile Asn
        355                 360                 365

Ile Lys Asn Pro Glu Ser Gly Lys Arg Leu Phe Ser Met Gly Gln Leu
    370                 375                 380

Leu Asp Ala Leu Leu Phe Lys Leu Asp Leu Asn Lys Ile Glu Asn Ile
385                 390                 395                 400
```

```
Asn Asn Asn Asn Ile Ser Tyr Lys Phe Phe Pro Pro Thr Leu Tyr Glu
            405                 410                 415

Gln Asp Asn Asn Thr Asp Tyr Ile Pro Gln Thr Lys Leu Val Asp Tyr
            420                 425                 430

Leu Asn Glu Asn Leu Gln Pro Gly Asp Leu Leu Val Met Asp Thr Met
            435                 440                 445

Ser Phe Cys Phe Ala Leu Pro Asp Ile Met Leu Pro Gln Gly Val Gln
            450                 455                 460

Leu Leu Thr Gln Asn Tyr Tyr Gly Ser Ile Gly Tyr Ala Leu Pro Ser
465                 470                 475                 480

Thr Phe Gly Ala Thr Met Ala Val Asn Asp Leu Gly Ser Asp Arg Arg
                    485                 490                 495

Ile Ile Leu Ile Glu Gly Asp Gly Ala Ala Gln Met Thr Ile Gln Glu
                500                 505                 510

Leu Ser Ser Phe Leu Lys Tyr Lys Glu Phe Leu Pro Asn Met Pro Lys
            515                 520                 525

Ile Phe Leu Ile Asn Asn Asp Gly Tyr Thr Val Glu Arg Met Ile Lys
            530                 535                 540

Gly Pro Thr Arg Ser Tyr Asn Asp Ile Asn Gly Glu Trp Ser Trp Thr
545                 550                 555                 560

Gln Leu Leu Gly Val Phe Gly Asp Lys Glu Gln Lys Tyr His Ser Thr
                    565                 570                 575

Ala Leu Leu Arg Asn Val Asn Glu Phe Asn Lys Tyr Phe Glu Phe Gln
                580                 585                 590

Arg Gln Thr Asp Asn Ser Lys Leu Glu Phe Ile Glu Leu Ile Ala Gly
            595                 600                 605

Lys Tyr Asp Cys Pro Leu Arg Phe Ser Glu Met Phe Cys Lys Lys
            610                 615                 620

<210> SEQ ID NO 54
<211> LENGTH: 563
<212> TYPE: PRT
<213> ORGANISM: Saccharomyces cerevisiae

<400> SEQUENCE: 54

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Phe Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
    50                  55                  60

Lys Gly Met Ser Cys Ile Ile Thr Thr Phe Gly Val Gly Glu Leu Ser
65                  70                  75                  80

Ala Leu Asn Gly Ile Ala Gly Ser Tyr Ala Glu His Val Gly Val Leu
                85                  90                  95

His Val Val Gly Val Pro Ser Ile Ser Ala Gln Ala Lys Gln Leu Leu
            100                 105                 110

Leu His His Thr Leu Gly Asn Gly Asp Phe Thr Val Phe His Arg Met
        115                 120                 125

Ser Ala Asn Ile Ser Glu Thr Thr Ala Met Ile Thr Asp Ile Ala Thr
    130                 135                 140

Ala Pro Ala Glu Ile Asp Arg Cys Ile Arg Thr Thr Tyr Val Thr Gln
145                 150                 155                 160
```

```
Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
        195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
        355                 360                 365

Trp Met Trp Asn Gln Leu Gly Asn Phe Leu Gln Glu Gly Asp Val Val
370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Ile
            420                 425                 430

Asp Pro Lys Lys Arg Val Ile Leu Phe Ile Gly Asp Gly Ser Leu Gln
        435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro Lys Ala Gln Tyr Asn Glu Ile Gln Gly Trp Asp His Leu
                485                 490                 495

Ser Leu Leu Pro Thr Phe Gly Ala Lys Asp Tyr Glu Thr His Arg Val
            500                 505                 510

Ala Thr Thr Gly Glu Trp Asp Lys Leu Thr Gln Asp Lys Ser Phe Asn
        515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 55
```

```
<211> LENGTH: 596
<212> TYPE: PRT
<213> ORGANISM: Pichia stipitis

<400> SEQUENCE: 55

Met Ala Glu Val Ser Leu Gly Arg Tyr Leu Phe Glu Arg Leu Tyr Gln
1               5                   10                  15

Leu Gln Val Gln Thr Ile Phe Gly Val Pro Gly Asp Phe Asn Leu Ser
            20                  25                  30

Leu Leu Asp Lys Ile Tyr Glu Val Glu Asp Ala His Gly Lys Asn Ser
        35                  40                  45

Phe Arg Trp Ala Gly Asn Ala Asn Glu Leu Asn Ala Ser Tyr Ala Ala
50                  55                  60

Asp Gly Tyr Ser Arg Val Lys Arg Leu Gly Cys Leu Val Thr Thr Phe
65                  70                  75                  80

Gly Val Gly Glu Leu Ser Ala Leu Asn Gly Ile Ala Gly Ser Tyr Ala
                85                  90                  95

Glu His Val Gly Leu Leu His Val Val Gly Val Pro Ser Ile Ser Ser
            100                 105                 110

Gln Ala Lys Gln Leu Leu Leu His His Thr Leu Gly Asn Gly Asp Phe
        115                 120                 125

Thr Val Phe His Arg Met Ser Asn Asn Ile Ser Gln Thr Thr Ala Phe
130                 135                 140

Ile Ser Asp Ile Asn Ser Ala Pro Ala Glu Ile Asp Arg Cys Ile Arg
145                 150                 155                 160

Glu Ala Tyr Val Lys Gln Arg Pro Val Tyr Ile Gly Leu Pro Ala Asn
                165                 170                 175

Leu Val Asp Leu Asn Val Pro Ala Ser Leu Leu Glu Ser Pro Ile Asn
            180                 185                 190

Leu Ser Leu Glu Lys Asn Asp Pro Glu Ala Gln Asp Glu Val Ile Asp
        195                 200                 205

Ser Val Leu Asp Leu Ile Lys Lys Ser Leu Asn Pro Ile Ile Leu Val
210                 215                 220

Asp Ala Cys Ala Ser Arg His Asp Cys Lys Ala Glu Val Thr Gln Leu
225                 230                 235                 240

Ile Glu Gln Thr Gln Phe Pro Val Phe Val Thr Pro Met Gly Lys Gly
                245                 250                 255

Thr Val Asp Glu Gly Gly Val Asp Gly Glu Leu Leu Glu Asp Asp Pro
            260                 265                 270

His Leu Ile Ala Lys Val Ala Ala Arg Leu Ser Ala Gly Lys Asn Ala
        275                 280                 285

Ala Ser Arg Phe Gly Gly Val Tyr Val Gly Thr Leu Ser Lys Pro Glu
290                 295                 300

Val Lys Asp Ala Val Glu Ser Ala Asp Leu Ile Leu Ser Val Gly Ala
305                 310                 315                 320

Leu Leu Ser Asp Phe Asn Thr Gly Ser Phe Ser Tyr Ser Tyr Arg Thr
                325                 330                 335

Lys Asn Ile Val Glu Phe His Ser Asp Tyr Thr Lys Ile Arg Gln Ala
            340                 345                 350

Thr Phe Pro Gly Val Gln Met Lys Glu Ala Leu Gln Glu Leu Asn Lys
        355                 360                 365

Lys Val Ser Ser Ala Ala Ser His Tyr Glu Val Lys Pro Val Pro Lys
370                 375                 380

Ile Lys Leu Ala Asn Thr Pro Ala Thr Arg Glu Val Lys Leu Thr Gln
385                 390                 395                 400
```

```
Glu Trp Leu Trp Thr Arg Val Ser Ser Trp Phe Arg Glu Gly Asp Ile
            405                 410                 415
Ile Ile Thr Glu Thr Gly Thr Ser Ser Phe Gly Ile Val Gln Ser Arg
            420                 425                 430
Phe Pro Asn Asn Thr Ile Gly Ile Ser Gln Val Leu Trp Gly Ser Ile
            435                 440                 445
Gly Phe Ser Val Gly Ala Thr Leu Gly Ala Ala Met Ala Ala Gln Glu
        450                 455                 460
Leu Asp Pro Asn Lys Arg Thr Ile Leu Phe Val Gly Asp Gly Ser Leu
465                 470                 475                 480
Gln Leu Thr Val Gln Glu Ile Ser Thr Met Ile Arg Trp Gly Thr Thr
                485                 490                 495
Pro Tyr Leu Phe Val Leu Asn Asn Asp Gly Tyr Thr Ile Glu Arg Leu
            500                 505                 510
Ile His Gly Val Asn Ala Ser Tyr Asn Asp Ile Gln Pro Trp Gln Asn
            515                 520                 525
Leu Glu Ile Leu Pro Thr Phe Ser Ala Lys Asn Tyr Asp Ala Val Arg
        530                 535                 540
Ile Ser Asn Ile Gly Glu Ala Glu Asp Ile Leu Lys Asp Lys Glu Phe
545                 550                 555                 560
Gly Lys Asn Ser Lys Ile Arg Leu Ile Glu Val Met Leu Pro Arg Leu
                565                 570                 575
Asp Ala Pro Ser Asn Leu Ala Lys Gln Ala Ala Ile Thr Ala Ala Thr
            580                 585                 590
Asn Ala Glu Ala
        595

<210> SEQ ID NO 56
<211> LENGTH: 563
<212> TYPE: PRT
<213> ORGANISM: Saccharomyces cerevisiae

<400> SEQUENCE: 56

Met Ser Glu Ile Thr Leu Gly Lys Tyr Leu Phe Glu Arg Leu Ser Gln
1               5                   10                  15
Val Asn Cys Asn Thr Val Phe Gly Leu Pro Gly Asp Phe Asn Leu Ser
            20                  25                  30
Leu Leu Asp Lys Leu Tyr Glu Val Lys Gly Met Arg Trp Ala Gly Asn
        35                  40                  45
Ala Asn Glu Leu Asn Ala Ala Tyr Ala Ala Asp Gly Tyr Ala Arg Ile
    50                  55                  60
Lys Gly Met Ser Cys Ile Ile Thr Thr Phe Gly Val Gly Glu Leu Ser
65              70                  75                  80
Ala Leu Asn Gly Ile Ala Gly Ser Tyr Ala Glu His Val Gly Val Leu
                85                  90                  95
His Val Val Gly Val Pro Ser Ile Ser Ser Gln Ala Lys Gln Leu Leu
            100                 105                 110
Leu His His Thr Leu Gly Asn Gly Asp Phe Thr Val Phe His Arg Met
        115                 120                 125
Ser Ala Asn Ile Ser Glu Thr Thr Ala Met Ile Thr Asp Ile Ala Asn
    130                 135                 140
Ala Pro Ala Glu Ile Asp Arg Cys Ile Arg Thr Thr Tyr Thr Thr Gln
145                 150                 155                 160
Arg Pro Val Tyr Leu Gly Leu Pro Ala Asn Leu Val Asp Leu Asn Val
                165                 170                 175
```

Pro Ala Lys Leu Leu Glu Thr Pro Ile Asp Leu Ser Leu Lys Pro Asn
            180                 185                 190

Asp Ala Glu Ala Glu Ala Val Val Arg Thr Val Val Glu Leu Ile
            195                 200                 205

Lys Asp Ala Lys Asn Pro Val Ile Leu Ala Asp Ala Cys Ala Ser Arg
210                 215                 220

His Asp Val Lys Ala Glu Thr Lys Lys Leu Met Asp Leu Thr Gln Phe
225                 230                 235                 240

Pro Val Tyr Val Thr Pro Met Gly Lys Gly Ala Ile Asp Glu Gln His
            245                 250                 255

Pro Arg Tyr Gly Gly Val Tyr Val Gly Thr Leu Ser Arg Pro Glu Val
            260                 265                 270

Lys Lys Ala Val Glu Ser Ala Asp Leu Ile Leu Ser Ile Gly Ala Leu
275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Ile Lys Ile Arg Asn Ala Thr
305                 310                 315                 320

Phe Pro Gly Val Gln Met Lys Phe Ala Leu Gln Lys Leu Leu Asp Ala
            325                 330                 335

Ile Pro Glu Val Val Lys Asp Tyr Lys Pro Val Ala Val Pro Ala Arg
            340                 345                 350

Val Pro Ile Thr Lys Ser Thr Pro Ala Asn Thr Pro Met Lys Gln Glu
            355                 360                 365

Trp Met Trp Asn His Leu Gly Asn Phe Leu Arg Glu Gly Asp Ile Val
            370                 375                 380

Ile Ala Glu Thr Gly Thr Ser Ala Phe Gly Ile Asn Gln Thr Thr Phe
385                 390                 395                 400

Pro Thr Asp Val Tyr Ala Ile Val Gln Val Leu Trp Gly Ser Ile Gly
            405                 410                 415

Phe Thr Val Gly Ala Leu Leu Gly Ala Thr Met Ala Ala Glu Glu Leu
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Ile Phe Val Leu Asn Asn Asn Gly Tyr Thr Ile Glu Lys Leu Ile
465                 470                 475                 480

His Gly Pro His Ala Glu Tyr Asn Glu Ile Gln Gly Trp Asp His Leu
            485                 490                 495

Ala Leu Leu Pro Thr Phe Gly Ala Arg Asn Tyr Glu Thr His Arg Val
            500                 505                 510

Ala Thr Thr Gly Glu Trp Glu Lys Leu Thr Gln Asp Lys Asp Phe Gln
            515                 520                 525

Asp Asn Ser Lys Ile Arg Met Ile Glu Val Met Leu Pro Val Phe Asp
530                 535                 540

Ala Pro Gln Asn Leu Val Lys Gln Ala Gln Leu Thr Ala Ala Thr Asn
545                 550                 555                 560

Ala Lys Gln

<210> SEQ ID NO 57
<211> LENGTH: 563
<212> TYPE: PRT
<213> ORGANISM: Saccharomyces cerevisiae

```
<400> SEQUENCE: 57

Met Ser Glu Ile Thr Leu Gly Lys Tyr Leu Phe Glu Arg Leu Lys Gln
  1               5                  10                  15

Val Asn Val Asn Thr Ile Phe Gly Leu Pro Gly Asp Phe Asn Leu Ser
             20                  25                  30

Leu Leu Asp Lys Ile Tyr Glu Val Asp Gly Leu Arg Trp Ala Gly Asn
         35                  40                  45

Ala Asn Glu Leu Asn Ala Ala Tyr Ala Ala Asp Gly Tyr Ala Arg Ile
     50                  55                  60

Lys Gly Leu Ser Val Leu Val Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ser Met Ile Thr Asp Ile Ala Thr
    130                 135                 140

Ala Pro Ser Glu Ile Asp Arg Leu Ile Arg Thr Thr Phe Ile Thr Gln
145                 150                 155                 160

Arg Pro Ser Tyr Leu Gly Leu Pro Ala Asn Leu Val Asp Leu Lys Val
                165                 170                 175

Pro Gly Ser Leu Leu Glu Lys Pro Ile Asp Leu Ser Leu Lys Pro Asn
            180                 185                 190

Asp Pro Glu Ala Glu Lys Glu Val Ile Asp Thr Val Leu Glu Leu Ile
        195                 200                 205

Gln Asn Ser Lys Asn Pro Val Ile Leu Ser Asp Ala Cys Ala Ser Arg
    210                 215                 220

His Asn Val Lys Lys Glu Thr Gln Lys Leu Ile Asp Leu Thr Gln Phe
225                 230                 235                 240

Pro Ala Phe Val Thr Pro Leu Gly Lys Gly Ser Ile Asp Glu Gln His
                245                 250                 255

Pro Arg Tyr Gly Gly Val Tyr Val Gly Thr Leu Ser Lys Gln Asp Val
            260                 265                 270

Lys Gln Ala Val Glu Ser Ala Asp Leu Ile Leu Ser Val Gly Ala Leu
        275                 280                 285

Leu Ser Asp Phe Asn Thr Gly Ser Phe Ser Tyr Ser Tyr Lys Thr Lys
    290                 295                 300

Asn Val Val Glu Phe His Ser Asp Tyr Val Lys Val Lys Asn Ala Thr
305                 310                 315                 320

Phe Leu Gly Val Gln Met Lys Phe Ala Leu Gln Asn Leu Leu Lys Val
                325                 330                 335

Ile Pro Asp Val Val Lys Gly Tyr Lys Ser Val Pro Val Pro Thr Lys
            340                 345                 350

Thr Pro Ala Asn Lys Gly Val Pro Ala Ser Thr Pro Leu Lys Gln Glu
        355                 360                 365

Trp Leu Trp Asn Glu Leu Ser Lys Phe Leu Gln Glu Gly Asp Val Ile
    370                 375                 380

Ile Ser Glu Thr Gly Thr Ser Ala Phe Gly Ile Asn Gln Thr Ile Phe
385                 390                 395                 400

Pro Lys Asp Ala Tyr Gly Ile Ser Gln Val Leu Trp Gly Ser Ile Gly
                405                 410                 415
```

```
Phe Thr Thr Gly Ala Thr Leu Gly Ala Ala Phe Ala Ala Glu Glu Ile
                420                 425                 430

Asp Pro Asn Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
450                 455                 460

Tyr Leu Phe Val Leu Asn Asn Asp Gly Tyr Thr Ile Glu Lys Leu Ile
465                 470                 475                 480

His Gly Pro His Ala Glu Tyr Asn Glu Ile Gln Thr Trp Asp His Leu
                485                 490                 495

Ala Leu Leu Pro Ala Phe Gly Ala Lys Lys Tyr Glu Asn His Lys Ile
            500                 505                 510

Ala Thr Thr Gly Glu Trp Asp Ala Leu Thr Thr Asp Ser Glu Phe Gln
        515                 520                 525

Lys Asn Ser Val Ile Arg Leu Ile Glu Leu Lys Leu Pro Val Phe Asp
530                 535                 540

Ala Pro Glu Ser Leu Ile Lys Gln Ala Gln Leu Thr Ala Ala Thr Asn
545                 550                 555                 560

Ala Lys Gln

<210> SEQ ID NO 58
<211> LENGTH: 609
<212> TYPE: PRT
<213> ORGANISM: Saccharomyces cerevisiae

<400> SEQUENCE: 58

Met Asn Ser Ser Tyr Thr Gln Arg Tyr Ala Leu Pro Lys Cys Ile Ala
1               5                   10                  15

Ile Ser Asp Tyr Leu Phe His Arg Leu Asn Gln Leu Asn Ile His Thr
            20                  25                  30

Ile Phe Gly Leu Ser Gly Glu Phe Ser Met Pro Leu Leu Asp Lys Leu
        35                  40                  45

Tyr Asn Ile Pro Asn Leu Arg Trp Ala Gly Asn Ser Asn Glu Leu Asn
50                  55                  60

Ala Ala Tyr Ala Ala Asp Gly Tyr Ser Arg Leu Lys Gly Leu Gly Cys
65                  70                  75                  80

Leu Ile Thr Thr Phe Gly Val Gly Glu Leu Ser Ala Ile Asn Gly Val
                85                  90                  95

Ala Gly Ser Tyr Ala Glu His Val Gly Ile Leu His Ile Val Gly Met
            100                 105                 110

Pro Pro Thr Ser Ala Gln Thr Lys Gln Leu Leu Leu His His Thr Leu
        115                 120                 125

Gly Asn Gly Asp Phe Thr Val Phe His Arg Ile Ala Ser Asp Val Ala
130                 135                 140

Cys Tyr Thr Thr Leu Ile Ile Asp Ser Glu Leu Cys Ala Asp Glu Val
145                 150                 155                 160

Asp Lys Cys Ile Lys Lys Ala Trp Ile Glu Gln Arg Pro Val Tyr Met
                165                 170                 175

Gly Met Pro Val Asn Gln Val Asn Leu Pro Ile Glu Ser Ala Arg Leu
            180                 185                 190

Asn Thr Pro Leu Asp Leu Gln Leu His Lys Asn Asp Pro Asp Val Glu
        195                 200                 205

Lys Glu Val Ile Ser Arg Ile Leu Ser Phe Ile Tyr Lys Ser Gln Asn
210                 215                 220
```

```
Pro Ala Ile Ile Val Asp Ala Cys Thr Ser Arg Gln Asn Leu Ile Glu
225                 230                 235                 240

Glu Thr Lys Glu Leu Cys Asn Arg Leu Lys Phe Pro Val Phe Val Thr
            245                 250                 255

Pro Met Gly Lys Gly Thr Val Asn Glu Thr Asp Pro Gln Phe Gly Gly
        260                 265                 270

Val Phe Thr Gly Ser Ile Ser Ala Pro Glu Val Arg Glu Val Val Asp
    275                 280                 285

Phe Ala Asp Phe Ile Ile Val Ile Gly Cys Met Leu Ser Glu Phe Ser
290                 295                 300

Thr Ser Thr Phe His Phe Gln Tyr Lys Thr Lys Asn Cys Ala Leu Leu
305                 310                 315                 320

Tyr Ser Thr Ser Val Lys Leu Lys Asn Ala Thr Tyr Pro Asp Leu Ser
            325                 330                 335

Ile Lys Leu Leu Leu Gln Lys Ile Leu Ala Asn Leu Asp Glu Ser Lys
        340                 345                 350

Leu Ser Tyr Gln Pro Ser Glu Gln Pro Ser Met Met Val Pro Arg Pro
    355                 360                 365

Tyr Pro Ala Gly Asn Val Leu Leu Arg Gln Glu Trp Val Trp Asn Glu
370                 375                 380

Ile Ser His Trp Phe Gln Pro Gly Asp Ile Ile Ile Thr Glu Thr Gly
385                 390                 395                 400

Ala Ser Ala Phe Gly Val Asn Gln Thr Arg Phe Pro Val Asn Thr Leu
            405                 410                 415

Gly Ile Ser Gln Ala Leu Trp Gly Ser Val Gly Tyr Thr Met Gly Ala
        420                 425                 430

Cys Leu Gly Ala Glu Phe Ala Val Gln Glu Ile Asn Lys Asp Lys Phe
    435                 440                 445

Pro Ala Thr Lys His Arg Val Ile Leu Phe Met Gly Asp Gly Ala Phe
450                 455                 460

Gln Leu Thr Val Gln Glu Leu Ser Thr Ile Val Lys Trp Gly Leu Thr
465                 470                 475                 480

Pro Tyr Ile Phe Val Met Asn Asn Gln Gly Tyr Ser Val Asp Arg Phe
            485                 490                 495

Leu His His Arg Ser Asp Ala Ser Tyr Tyr Asp Ile Gln Pro Trp Asn
        500                 505                 510

Tyr Leu Gly Leu Leu Arg Val Phe Gly Cys Thr Asn Tyr Glu Thr Lys
    515                 520                 525

Lys Ile Ile Thr Val Gly Glu Phe Arg Ser Met Ile Ser Asp Pro Asn
530                 535                 540

Phe Ala Thr Asn Asp Lys Ile Arg Met Ile Glu Ile Met Leu Pro Pro
545                 550                 555                 560

Arg Asp Val Pro Gln Ala Leu Leu Asp Arg Trp Val Val Glu Lys Glu
            565                 570                 575

Gln Ser Lys Gln Val Gln Glu Glu Asn Glu Asn Ser Ser Ala Val Asn
        580                 585                 590

Thr Pro Thr Pro Glu Phe Gln Pro Leu Leu Lys Lys Asn Gln Val Gly
    595                 600                 605

Tyr

<210> SEQ ID NO 59
<211> LENGTH: 635
<212> TYPE: PRT
<213> ORGANISM: Saccharomyces cerevisiae
```

-continued

```
<400> SEQUENCE: 59

Met Ala Pro Val Thr Ile Glu Lys Phe Val Asn Gln Glu Glu Arg His
1               5                   10                  15

Leu Val Ser Asn Arg Ser Ala Thr Ile Pro Phe Gly Glu Tyr Ile Phe
            20                  25                  30

Lys Arg Leu Leu Ser Ile Asp Thr Lys Ser Val Phe Gly Val Pro Gly
        35                  40                  45

Asp Phe Asn Leu Ser Leu Leu Glu Tyr Leu Tyr Ser Pro Ser Val Glu
    50                  55                  60

Ser Ala Gly Leu Arg Trp Val Gly Thr Cys Asn Glu Leu Asn Ala Ala
65                  70                  75                  80

Tyr Ala Ala Asp Gly Tyr Ser Arg Tyr Ser Asn Lys Ile Gly Cys Leu
                85                  90                  95

Ile Thr Thr Tyr Gly Val Gly Glu Leu Ser Ala Leu Asn Gly Ile Ala
            100                 105                 110

Gly Ser Phe Ala Glu Asn Val Lys Val Leu His Ile Val Gly Val Ala
        115                 120                 125

Lys Ser Ile Asp Ser Arg Ser Ser Asn Phe Ser Asp Arg Asn Leu His
    130                 135                 140

His Leu Val Pro Gln Leu His Asp Ser Asn Phe Lys Gly Pro Asn His
145                 150                 155                 160

Lys Val Tyr His Asp Met Val Lys Asp Arg Val Ala Cys Ser Val Ala
                165                 170                 175

Tyr Leu Glu Asp Ile Glu Thr Ala Cys Asp Gln Val Asp Asn Val Ile
            180                 185                 190

Arg Asp Ile Tyr Lys Tyr Ser Lys Pro Gly Tyr Ile Phe Val Pro Ala
        195                 200                 205

Asp Phe Ala Asp Met Ser Val Thr Cys Asp Asn Leu Val Asn Val Pro
    210                 215                 220

Arg Ile Ser Gln Gln Asp Cys Ile Val Tyr Pro Ser Glu Asn Gln Leu
225                 230                 235                 240

Ser Asp Ile Ile Asn Lys Ile Thr Ser Trp Ile Tyr Ser Ser Lys Thr
                245                 250                 255

Pro Ala Ile Leu Gly Asp Val Leu Thr Asp Arg Tyr Gly Val Ser Asn
            260                 265                 270

Phe Leu Asn Lys Leu Ile Cys Lys Thr Gly Ile Trp Asn Phe Ser Thr
        275                 280                 285

Val Met Gly Lys Ser Val Ile Asp Glu Ser Asn Pro Thr Tyr Met Gly
    290                 295                 300

Gln Tyr Asn Gly Lys Glu Gly Leu Lys Gln Val Tyr Glu His Phe Glu
305                 310                 315                 320

Leu Cys Asp Leu Val Leu His Phe Gly Val Asp Ile Asn Glu Ile Asn
                325                 330                 335

Asn Gly His Tyr Thr Phe Thr Tyr Lys Pro Asn Ala Lys Ile Ile Gln
            340                 345                 350

Phe His Pro Asn Tyr Ile Arg Leu Val Asp Thr Arg Gln Gly Asn Glu
        355                 360                 365

Gln Met Phe Lys Gly Ile Asn Phe Ala Pro Ile Leu Lys Glu Leu Tyr
    370                 375                 380

Lys Arg Ile Asp Val Ser Lys Leu Ser Leu Gln Tyr Asp Ser Asn Val
385                 390                 395                 400

Thr Gln Tyr Thr Asn Glu Thr Met Arg Leu Glu Asp Pro Thr Asn Gly
                405                 410                 415
```

```
Gln Ser Ser Ile Ile Thr Gln Val His Leu Gln Lys Thr Met Pro Lys
                420                 425                 430

Phe Leu Asn Pro Gly Asp Val Val Cys Glu Thr Gly Ser Phe Gln
            435                 440                 445

Phe Ser Val Arg Asp Phe Ala Phe Pro Ser Gln Leu Lys Tyr Ile Ser
        450                 455                 460

Gln Gly Phe Phe Leu Ser Ile Gly Met Ala Leu Pro Ala Ala Leu Gly
465                 470                 475                 480

Val Gly Ile Ala Met Gln Asp His Ser Asn Ala His Ile Asn Gly Gly
                485                 490                 495

Asn Val Lys Glu Asp Tyr Lys Pro Arg Leu Ile Leu Phe Glu Gly Asp
                500                 505                 510

Gly Ala Ala Gln Met Thr Ile Gln Glu Leu Ser Thr Ile Leu Lys Cys
            515                 520                 525

Asn Ile Pro Leu Glu Val Ile Ile Trp Asn Asn Gly Tyr Thr Ile
        530                 535                 540

Glu Arg Ala Ile Met Gly Pro Thr Arg Ser Tyr Asn Asp Val Met Ser
545                 550                 555                 560

Trp Lys Trp Thr Lys Leu Phe Glu Ala Phe Gly Asp Phe Asp Gly Lys
                565                 570                 575

Tyr Thr Asn Ser Thr Leu Ile Gln Cys Pro Ser Lys Leu Ala Leu Lys
            580                 585                 590

Leu Glu Glu Leu Lys Asn Ser Asn Lys Arg Ser Gly Ile Glu Leu Leu
        595                 600                 605

Glu Val Lys Leu Gly Glu Leu Asp Phe Pro Glu Gln Leu Lys Cys Met
610                 615                 620

Val Glu Ala Ala Ala Leu Lys Arg Asn Lys Lys
625                 630                 635

<210> SEQ ID NO 60
<211> LENGTH: 560
<212> TYPE: PRT
<213> ORGANISM: Mycobacterium smegmatis

<400> SEQUENCE: 60

Met Thr Pro Gln Lys Ser Asp Ala Cys Ser Asp Pro Val Tyr Thr Val
1               5                   10                  15

Gly Asp Tyr Leu Leu Asp Arg Leu Ala Glu Leu Gly Val Ser Glu Ile
                20                  25                  30

Phe Gly Val Pro Gly Asp Tyr Asn Leu Gln Phe Leu Asp His Ile Val
            35                  40                  45

Ala His Pro Thr Ile Arg Trp Val Gly Ser Ala Asn Glu Leu Asn Ala
        50                  55                  60

Gly Tyr Ala Ala Asp Gly Tyr Gly Arg Leu Arg Gly Met Ser Ala Val
65                  70                  75                  80

Val Thr Thr Phe Gly Val Gly Glu Leu Ser Val Thr Asn Ala Ile Ala
                85                  90                  95

Gly Ser Tyr Ala Glu His Val Pro Val Val His Ile Val Gly Gly Pro
            100                 105                 110

Thr Lys Asp Ala Gln Gly Thr Arg Arg Ala Leu His His Ser Leu Gly
        115                 120                 125

Asp Gly Asp Phe Glu His Phe Leu Arg Ile Ser Arg Glu Ile Thr Cys
        130                 135                 140

Ala Gln Ala Asn Leu Met Pro Ala Thr Ala Gly Arg Glu Ile Asp Arg
145                 150                 155                 160
```

```
Val Leu Ser Glu Val Arg Glu Gln Lys Arg Pro Gly Tyr Ile Leu Leu
            165                 170                 175

Ser Ser Asp Val Ala Arg Phe Pro Thr Glu Pro Ala Ala Pro Leu
        180                 185                 190

Pro Arg Tyr Pro Gly Gly Thr Ser Pro Arg Ala Leu Ser Leu Phe Thr
            195                 200                 205

Lys Ala Ala Ile Glu Leu Ile Ala Asp His Gln Leu Thr Val Leu Ala
210                 215                 220

Asp Leu Leu Val His Arg Leu Gln Ala Val Lys Glu Leu Glu Ala Leu
225                 230                 235                 240

Leu Ala Ala Asp Val Val Pro His Ala Thr Leu Met Trp Gly Lys Ser
                245                 250                 255

Leu Leu Asp Glu Ser Ser Pro Asn Phe Leu Gly Ile Tyr Ala Gly Ala
            260                 265                 270

Ala Ser Ala Glu Arg Val Arg Ala Ala Ile Glu Gly Ala Pro Val Leu
        275                 280                 285

Val Thr Ala Gly Val Val Phe Thr Asp Met Val Ser Gly Phe Phe Ser
    290                 295                 300

Gln Arg Ile Asp Pro Ala Arg Thr Ile Asp Ile Gly Gln Tyr Gln Ser
305                 310                 315                 320

Ser Val Ala Asp Gln Val Phe Ala Pro Leu Glu Met Ser Ala Ala Leu
                325                 330                 335

Gln Ala Leu Ala Thr Ile Leu Thr Gly Arg Gly Ile Ser Ser Pro Pro
            340                 345                 350

Val Val Pro Pro Pro Ala Glu Pro Pro Ala Met Pro Ala Arg Asp
        355                 360                 365

Glu Pro Leu Thr Gln Gln Met Val Trp Asp Arg Val Cys Ser Ala Leu
    370                 375                 380

Thr Pro Gly Asn Val Val Leu Ala Asp Gln Gly Thr Ser Phe Tyr Gly
385                 390                 395                 400

Met Ala Asp His Arg Leu Pro Gln Gly Val Thr Phe Ile Gly Gln Pro
                405                 410                 415

Leu Trp Gly Ser Ile Gly Tyr Thr Leu Pro Ala Ala Val Gly Ala Ala
            420                 425                 430

Val Ala His Pro Asp Arg Arg Thr Val Leu Leu Ile Gly Asp Gly Ala
        435                 440                 445

Ala Gln Leu Thr Val Gln Glu Leu Gly Thr Phe Ser Arg Glu Gly Leu
    450                 455                 460

Ser Pro Val Ile Val Val Asn Asn Asp Gly Tyr Thr Val Glu Arg
465                 470                 475                 480

Ala Ile His Gly Glu Thr Ala Pro Tyr Asn Asp Ile Val Ser Trp Asn
                485                 490                 495

Trp Thr Glu Leu Pro Ser Ala Leu Gly Val Thr Asn His Leu Ala Phe
            500                 505                 510

Arg Ala Gln Thr Tyr Gly Gln Leu Asp Asp Ala Leu Thr Val Ala Ala
        515                 520                 525

Ala Arg Arg Asp Arg Met Val Leu Val Glu Val Leu Pro Arg Leu
    530                 535                 540

Glu Ile Pro Arg Leu Leu Gly Gln Leu Val Gly Ser Met Ala Pro Gln
545                 550                 555                 560

<210> SEQ ID NO 61
<211> LENGTH: 547
<212> TYPE: PRT
<213> ORGANISM: Lactococcus lactis
```

<400> SEQUENCE: 61

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Ser Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
            340                 345                 350

Pro Leu Ser Gln Asp Arg Leu Trp Gln Ala Val Glu Ser Leu Thr Gln
        355                 360                 365

Ser Asn Glu Thr Ile Val Ala Glu Gln Gly Thr Ser Phe Phe Gly Ala
    370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

```
Ala Asp Lys Glu Ser Arg His Leu Leu Phe Ile Gly Asp Gly Ser Leu
            420                 425                 430

Gln Leu Thr Val Gln Glu Leu Gly Leu Ser Ile Arg Glu Lys Leu Asn
        435                 440                 445

Pro Ile Cys Phe Ile Ile Asn Asn Asp Gly Tyr Thr Val Glu Arg Glu
    450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
                485                 490                 495

Lys Ile Val Arg Thr Glu Asn Glu Phe Val Ser Val Met Lys Glu Ala
                500                 505                 510

Gln Ala Asp Val Asn Arg Met Tyr Trp Ile Glu Leu Val Leu Glu Lys
            515                 520                 525

Glu Asp Ala Pro Lys Leu Leu Lys Lys Met Gly Lys Leu Phe Ala Glu
        530                 535                 540

Gln Asn Lys
545

<210> SEQ ID NO 62
<211> LENGTH: 547
<212> TYPE: PRT
<213> ORGANISM: Lactococcus lactis

<400> SEQUENCE: 62

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240
```

```
Phe Gly Lys Ser Ala Val Asp Glu Ser Leu Pro Ser Phe Leu Gly Ile
                245                 250                 255
Tyr Asn Gly Lys Leu Ser Glu Ile Ser Leu Lys Asn Phe Val Glu Ser
            260                 265                 270
Ala Asp Phe Ile Leu Met Leu Gly Val Lys Leu Thr Asp Tyr Ser Thr
        275                 280                 285
Gly Ala Phe Thr His His Leu Asp Glu Asn Lys Met Ile Ser Leu Asn
    290                 295                 300
Ile Asp Glu Gly Ile Ile Phe Asn Lys Val Val Glu Asp Phe Asp Phe
305                 310                 315                 320
Arg Ala Val Val Ser Ser Leu Ser Glu Leu Lys Gly Ile Glu Tyr Glu
                325                 330                 335
Gly Gln Tyr Ile Asp Lys Gln Tyr Glu Glu Phe Ile Pro Ser Ser Ala
            340                 345                 350
Pro Leu Ser Gln Asp Arg Leu Trp Gln Ala Val Glu Ser Leu Thr Gln
        355                 360                 365
Ser Asn Glu Thr Ile Val Ala Glu Gln Gly Thr Ser Phe Phe Gly Ala
    370                 375                 380
Ser Thr Ile Phe Leu Lys Ser Asn Ser Arg Phe Ile Gly Gln Pro Leu
385                 390                 395                 400
Trp Gly Ser Ile Gly Tyr Thr Phe Pro Ala Ala Leu Gly Ser Gln Ile
                405                 410                 415
Ala Asp Lys Glu Ser Arg His Leu Leu Phe Ile Gly Asp Gly Ser Leu
            420                 425                 430
Gln Leu Thr Val Gln Glu Leu Gly Leu Ser Ile Arg Glu Lys Leu Asn
        435                 440                 445
Pro Ile Cys Phe Ile Ile Asn Asn Asp Gly Tyr Thr Val Glu Arg Glu
    450                 455                 460
Ile His Gly Pro Thr Gln Ser Tyr Asn Asp Ile Pro Met Trp Asn Tyr
465                 470                 475                 480
Ser Lys Leu Pro Glu Thr Phe Gly Ala Thr Glu Asp Arg Val Val Ser
                485                 490                 495
Lys Ile Val Arg Thr Glu Asn Glu Phe Val Ser Val Met Lys Glu Ala
            500                 505                 510
Gln Ala Asp Val Asn Arg Met Tyr Trp Ile Glu Leu Val Leu Glu Lys
        515                 520                 525
Glu Asp Ala Pro Lys Leu Leu Lys Lys Met Gly Lys Leu Phe Ala Glu
    530                 535                 540
Gln Asn Lys
545

<210> SEQ ID NO 63
<211> LENGTH: 547
<212> TYPE: PRT
<213> ORGANISM: Lactococcus lactis

<400> SEQUENCE: 63

Met Tyr Thr Val Gly Asp Tyr Leu Leu Asp Arg Leu His Glu Leu Gly
 1               5                  10                  15
Ile Glu Glu Ile Phe Gly Val Pro Gly Asp Tyr Asn Leu Gln Phe Leu
             20                  25                  30
Asp Gln Ile Ile Ser Arg Glu Asp Met Lys Trp Ile Gly Asn Ala Asn
         35                  40                  45
Glu Leu Asn Ala Ser Tyr Met Ala Asp Gly Tyr Ala Arg Thr Lys Lys
     50                  55                  60
```

```
Ala Ala Ala Phe Leu Thr Thr Phe Gly Val Gly Glu Leu Ser Ala Ile
 65                  70                  75                  80

Asn Gly Leu Ala Gly Ser Tyr Ala Glu Asn Leu Pro Val Val Glu Ile
                 85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ala Leu Ser Leu Glu Lys Glu Ser Ser Thr Thr Asn Thr Thr Glu Gln
                180                 185                 190

Val Ile Leu Ser Lys Ile Glu Glu Ser Leu Lys Asn Ala Gln Lys Pro
                195                 200                 205

Val Val Ile Ala Gly His Glu Val Ile Ser Phe Gly Leu Glu Lys Thr
210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
                260                 265                 270

Ala Asp Phe Ile Leu Met Leu Gly Val Lys Leu Thr Asp Ser Ser Thr
            275                 280                 285

Gly Ala Phe Thr His His Leu Asp Glu Asn Lys Met Ile Ser Leu Asn
290                 295                 300

Ile Asp Glu Gly Ile Ile Phe Asn Lys Val Val Glu Asp Phe Asp Phe
305                 310                 315                 320

Arg Ala Val Val Ser Ser Leu Ser Glu Leu Lys Gly Ile Glu Tyr Glu
                325                 330                 335

Gly Gln Tyr Ile Asp Lys Gln Tyr Glu Glu Phe Ile Pro Ser Ser Ala
                340                 345                 350

Pro Leu Ser Gln Asp Arg Leu Trp Gln Ala Val Glu Ser Leu Thr Gln
                355                 360                 365

Ser Asn Glu Thr Ile Val Ala Glu Gln Gly Thr Ser Trp Phe Gly Ala
370                 375                 380

Ser Thr Ile Phe Leu Lys Ser Asn Ser Arg Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
                420                 425                 430

Gln Leu Thr Val Gln Glu Leu Gly Leu Ser Ile Arg Glu Lys Leu Asn
            435                 440                 445

Pro Ile Cys Phe Ile Ile Asn Asn Asp Gly Tyr Thr Val Glu Arg Glu
        450                 455                 460

Ile His Gly Pro Thr Gln Ser Tyr Asn Asp Ile Pro Met Trp Asn Tyr
465                 470                 475                 480

Ser Lys Leu Pro Glu Thr Phe Gly Ala Thr Glu Asp Arg Val Val Ser
```

```
                        485                 490                 495
Lys Ile Val Arg Thr Glu Asn Glu Phe Val Ser Val Met Lys Glu Ala
                500                 505                 510

Gln Ala Asp Val Asn Arg Met Tyr Trp Ile Glu Leu Val Leu Glu Lys
            515                 520                 525

Glu Asp Ala Pro Lys Leu Leu Lys Met Gly Lys Leu Phe Ala Glu
        530                 535                 540

Gln Asn Lys
545

<210> SEQ ID NO 64
<211> LENGTH: 547
<212> TYPE: PRT
<213> ORGANISM: Lactococcus lactis

<400> SEQUENCE: 64

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Val Ala Ala Lys Ala Glu Lys Pro
                165                 170                 175

Ala Leu Ser Leu Glu Lys Glu Ser Ser Thr Thr Asn Thr Thr Glu Gln
            180                 185                 190

Val Ile Leu Ser Lys Ile Glu Glu Ser Leu Lys Asn Ala Gln Lys Pro
        195                 200                 205

Val Val Ile Ala Gly His Glu Val Ile Ser Phe Gly Leu Glu Lys Thr
    210                 215                 220

Val Thr Gln Phe Val Ser Glu Thr Lys Leu Pro Ile Thr Thr Leu Asn
225                 230                 235                 240

Phe Gly Lys Ser Ala Val Asp Glu Ser Leu Pro Ser Phe Leu Gly Ile
                245                 250                 255

Tyr Asn Gly Lys Leu Ser Glu Ile Ser Leu Lys Asn Phe Val Glu Ser
            260                 265                 270

Ala Asp Phe Ile Leu Met Leu Gly Val Lys Leu Thr Asp Tyr Ser Thr
        275                 280                 285

Gly Ala Phe Thr His His Leu Asp Glu Asn Lys Met Ile Ser Leu Asn
    290                 295                 300

Ile Asp Glu Gly Ile Ile Phe Asn Lys Val Val Glu Asp Phe Asp Phe
```

```
            305                 310                 315                 320
Arg Ala Val Val Ser Ser Leu Ser Glu Leu Lys Gly Ile Glu Tyr Glu
                    325                 330                 335
Gly Gln Tyr Ile Asp Lys Gln Tyr Glu Glu Phe Ile Pro Ser Ser Ala
                340                 345                 350
Pro Leu Ser Gln Asp Arg Leu Trp Gln Ala Val Glu Ser Leu Thr Gln
            355                 360                 365
Ser Asn Glu Thr Ile Val Ala Glu Gln Gly Thr Ser Trp Phe Gly Ala
        370                 375                 380
Ser Thr Ile Phe Leu Lys Ser Asn Ser Arg Phe Ile Gly Gln Pro Leu
385                 390                 395                 400
Trp Gly Ser Ile Gly Tyr Thr Phe Pro Ala Ala Leu Gly Ser Gln Ile
                    405                 410                 415
Ala Asp Lys Glu Ser Arg His Leu Leu Phe Ile Gly Asp Gly Ser Leu
                420                 425                 430
Gln Leu Thr Val Gln Glu Leu Gly Leu Ser Ile Arg Glu Lys Leu Asn
            435                 440                 445
Pro Ile Cys Phe Ile Ile Asn Asn Asp Gly Tyr Thr Val Glu Arg Glu
        450                 455                 460
Ile His Gly Pro Thr Gln Ser Tyr Asn Asp Ile Pro Met Trp Asn Tyr
465                 470                 475                 480
Ser Lys Leu Pro Glu Thr Phe Gly Ala Thr Glu Asp Arg Val Val Ser
                    485                 490                 495
Lys Ile Val Arg Thr Glu Asn Glu Phe Val Ser Val Met Lys Glu Ala
                500                 505                 510
Gln Ala Asp Val Asn Arg Met Tyr Trp Ile Glu Leu Val Leu Glu Lys
            515                 520                 525
Glu Asp Ala Pro Lys Leu Leu Lys Lys Met Gly Lys Leu Phe Ala Glu
        530                 535                 540
Gln Asn Lys
545

<210> SEQ ID NO 65
<211> LENGTH: 570
<212> TYPE: PRT
<213> ORGANISM: Pichia stipitis

<400> SEQUENCE: 65

Met Val Ser Thr Tyr Pro Glu Ser Glu Val Thr Leu Gly Arg Tyr Leu
1               5                   10                  15
Phe Glu Arg Leu His Gln Leu Lys Val Asp Thr Ile Phe Gly Leu Pro
                20                  25                  30
Gly Asp Phe Asn Leu Ser Leu Leu Asp Lys Val Tyr Glu Val Pro Asp
            35                  40                  45
Met Arg Trp Ala Gly Asn Ala Asn Glu Leu Asn Ala Ala Tyr Ala Ala
        50                  55                  60
Asp Gly Tyr Ser Arg Ile Lys Gly Leu Ser Cys Leu Val Thr Thr Phe
65                  70                  75                  80
Gly Val Gly Glu Leu Ser Ala Leu Asn Gly Val Gly Gly Ala Tyr Ala
                85                  90                  95
Glu His Val Gly Leu Leu His Val Gly Val Pro Ser Ile Ser Ser
                100                 105                 110
Gln Ala Lys Gln Leu Leu Leu His His Thr Leu Gly Asn Gly Asp Phe
            115                 120                 125
Thr Val Phe His Arg Met Ser Asn Ser Ile Ser Gln Thr Thr Ala Phe
```

```
                130                 135                 140
Leu Ser Asp Ile Ser Ile Ala Pro Gly Gln Ile Asp Arg Cys Ile Arg
145                 150                 155                 160

Glu Ala Tyr Val His Gln Arg Pro Val Tyr Val Gly Leu Pro Ala Asn
                165                 170                 175

Met Val Asp Leu Lys Val Pro Ser Ser Leu Glu Thr Pro Ile Asp
                180                 185                 190

Leu Lys Leu Lys Gln Asn Asp Pro Glu Ala Gln Glu Val Val Glu
                195                 200                 205

Thr Val Leu Lys Leu Val Ser Gln Ala Thr Asn Pro Ile Ile Leu Val
210                 215                 220

Asp Ala Cys Ala Leu Arg His Asn Cys Lys Glu Val Lys Gln Leu
225                 230                 235                 240

Val Asp Ala Thr Asn Phe Gln Val Phe Thr Thr Pro Met Gly Lys Ser
                245                 250                 255

Gly Ile Ser Glu Ser His Pro Arg Phe Gly Val Tyr Val Gly Thr
                260                 265                 270

Met Ser Ser Pro Gln Val Lys Lys Ala Val Glu Asn Ala Asp Leu Ile
                275                 280                 285

Leu Ser Val Gly Ser Leu Leu Ser Asp Phe Asn Thr Gly Ser Phe Ser
                290                 295                 300

Tyr Ser Tyr Lys Thr Lys Asn Val Val Glu Phe His Ser Asp Tyr Met
305                 310                 315                 320

Lys Ile Arg Gln Ala Thr Phe Pro Gly Val Gln Met Lys Glu Ala Leu
                325                 330                 335

Gln Gln Leu Ile Lys Arg Val Ser Ser Tyr Ile Asn Pro Ser Tyr Ile
                340                 345                 350

Pro Thr Arg Val Pro Lys Arg Lys Gln Pro Leu Lys Ala Pro Ser Glu
                355                 360                 365

Ala Pro Leu Thr Gln Glu Tyr Leu Trp Ser Lys Val Ser Gly Trp Phe
                370                 375                 380

Arg Glu Gly Asp Ile Ile Val Thr Glu Thr Gly Thr Ser Ala Phe Gly
385                 390                 395                 400

Ile Ile Gln Ser His Phe Pro Ser Asn Thr Ile Gly Ile Ser Gln Val
                405                 410                 415

Leu Trp Gly Ser Ile Gly Phe Thr Val Gly Ala Thr Val Gly Ala Ala
                420                 425                 430

Met Ala Ala Gln Glu Ile Asp Pro Ser Arg Arg Val Ile Leu Phe Val
                435                 440                 445

Gly Asp Gly Ser Leu Gln Leu Thr Val Gln Glu Ile Ser Thr Leu Cys
450                 455                 460

Lys Trp Asp Cys Asn Asn Thr Tyr Leu Tyr Val Leu Asn Asn Asp Gly
465                 470                 475                 480

Tyr Thr Ile Glu Arg Leu Ile His Gly Lys Ser Ala Ser Tyr Asn Asp
                485                 490                 495

Ile Gln Pro Trp Asn His Leu Ser Leu Leu Arg Leu Phe Asn Ala Lys
                500                 505                 510

Lys Tyr Gln Asn Val Arg Val Ser Thr Ala Gly Glu Leu Asp Ser Leu
                515                 520                 525

Phe Ser Asp Lys Lys Phe Ala Ser Pro Asp Arg Ile Arg Met Ile Glu
                530                 535                 540

Val Met Leu Ser Arg Leu Asp Ala Pro Ala Asn Leu Val Ala Gln Ala
545                 550                 555                 560
```

```
Lys Leu Ser Glu Arg Val Asn Leu Glu Asn
            565                 570

<210> SEQ ID NO 66
<211> LENGTH: 360
<212> TYPE: PRT
<213> ORGANISM: Saccharomyces cerevisiae

<400> SEQUENCE: 66

Met Ser Tyr Pro Glu Lys Phe Glu Gly Ile Ala Ile Gln Ser His Glu
 1               5                  10                  15

Asp Trp Lys Asn Pro Lys Lys Thr Lys Tyr Asp Pro Lys Pro Phe Tyr
            20                  25                  30

Asp His Asp Ile Asp Ile Lys Ile Glu Ala Cys Gly Val Cys Gly Ser
        35                  40                  45

Asp Ile His Cys Ala Ala Gly His Trp Gly Asn Met Lys Met Pro Leu
    50                  55                  60

Val Val Gly His Glu Ile Val Gly Lys Val Val Lys Leu Gly Pro Lys
65                  70                  75                  80

Ser Asn Ser Gly Leu Lys Val Gly Gln Arg Val Gly Val Gly Ala Gln
                85                  90                  95

Val Phe Ser Cys Leu Glu Cys Asp Arg Cys Lys Asn Asp Asn Glu Pro
            100                 105                 110

Tyr Cys Thr Lys Phe Val Thr Thr Tyr Ser Gln Pro Tyr Glu Asp Gly
        115                 120                 125

Tyr Val Ser Gln Gly Gly Tyr Ala Asn Tyr Val Arg Val His Glu His
    130                 135                 140

Phe Val Val Pro Ile Pro Glu Asn Ile Pro Ser His Leu Ala Ala Pro
145                 150                 155                 160

Leu Leu Cys Gly Gly Leu Thr Val Tyr Ser Pro Leu Val Arg Asn Gly
                165                 170                 175

Cys Gly Pro Gly Lys Lys Val Gly Ile Val Gly Leu Gly Gly Ile Gly
            180                 185                 190

Ser Met Gly Thr Leu Ile Ser Lys Ala Met Gly Ala Glu Thr Tyr Val
        195                 200                 205

Ile Ser Arg Ser Ser Arg Lys Arg Glu Asp Ala Met Lys Met Gly Ala
    210                 215                 220

Asp His Tyr Ile Ala Thr Leu Glu Glu Gly Asp Trp Gly Glu Lys Tyr
225                 230                 235                 240

Phe Asp Thr Phe Asp Leu Ile Val Val Cys Ala Ser Ser Leu Thr Asp
                245                 250                 255

Ile Asp Phe Asn Ile Met Pro Lys Ala Met Lys Val Gly Gly Arg Ile
            260                 265                 270

Val Ser Ile Ser Ile Pro Glu Gln His Glu Met Leu Ser Leu Lys Pro
        275                 280                 285

Tyr Gly Leu Lys Ala Val Ser Ile Ser Tyr Ser Ala Leu Gly Ser Ile
    290                 295                 300

Lys Glu Leu Asn Gln Leu Leu Lys Leu Val Ser Glu Lys Asp Ile Lys
305                 310                 315                 320

Ile Trp Val Glu Thr Leu Pro Val Gly Glu Ala Gly Val His Glu Ala
                325                 330                 335

Phe Glu Arg Met Glu Lys Gly Asp Val Arg Tyr Arg Phe Thr Leu Val
            340                 345                 350

Gly Tyr Asp Lys Glu Phe Ser Asp
        355                 360
```

<210> SEQ ID NO 67
<211> LENGTH: 348
<212> TYPE: PRT
<213> ORGANISM: Saccharomyces cerevisiae

<400> SEQUENCE: 67

| Met | Ser | Ile | Pro | Glu | Thr | Gln | Lys | Gly | Val | Ile | Phe | Tyr | Glu | Ser | His |
|---|---|---|---|---|---|---|---|---|---|---|---|---|---|---|---|
| 1 | | | | 5 | | | | | 10 | | | | | 15 | |

Gly Lys Leu Glu Tyr Lys Asp Ile Pro Val Pro Lys Pro Lys Ala Asn
            20                  25                  30

Glu Leu Leu Ile Asn Val Lys Tyr Ser Gly Val Cys His Thr Asp Leu
        35                  40                  45

His Ala Trp His Gly Asp Trp Pro Leu Pro Val Lys Leu Pro Leu Val
    50                  55                  60

Gly Gly His Glu Gly Ala Gly Val Val Val Gly Met Gly Glu Asn Val
65                  70                  75                  80

Lys Gly Trp Lys Ile Gly Asp Tyr Ala Gly Ile Lys Trp Leu Asn Gly
                85                  90                  95

Ser Cys Met Ala Cys Glu Tyr Cys Glu Leu Gly Asn Glu Ser Asn Cys
            100                 105                 110

Pro His Ala Asp Leu Ser Gly Tyr Thr His Asp Gly Ser Phe Gln Gln
        115                 120                 125

Tyr Ala Thr Ala Asp Ala Val Gln Ala Ala His Ile Pro Gln Gly Thr
    130                 135                 140

Asp Leu Ala Gln Val Ala Pro Ile Leu Cys Ala Gly Ile Thr Val Tyr
145                 150                 155                 160

Lys Ala Leu Lys Ser Ala Asn Leu Met Ala Gly His Trp Val Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Glu Gly Lys Glu
        195                 200                 205

Glu Leu Phe Arg Ser Ile Gly Gly Glu Val Phe Ile Asp Phe Thr Lys
    210                 215                 220

Glu Lys Asp Ile Val Gly Ala Val Leu Lys Ala Thr Asp Gly Gly Ala
225                 230                 235                 240

His Gly Val Ile Asn Val Ser Val Ser Glu Ala Ala Ile Glu Ala Ser
                245                 250                 255

Thr Arg Tyr Val Arg Ala Asn Gly Thr Thr Val Leu Val Gly Met Pro
            260                 265                 270

Ala Gly Ala Lys Cys Cys Ser Asp Val Phe Asn Gln Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Thr Leu Pro Glu Ile Tyr Glu Lys Met Glu Lys Gly
                325                 330                 335

Gln Ile Val Gly Arg Tyr Val Val Asp Thr Ser Lys
            340                 345

<210> SEQ ID NO 68
<211> LENGTH: 348
<212> TYPE: PRT
<213> ORGANISM: Saccharomyces cerevisiae

<400> SEQUENCE: 68

```
Met Ser Ile Pro Glu Thr Gln Lys Ala Ile Ile Phe Tyr Glu Ser Asn
 1               5                  10                  15

Gly Lys Leu Glu His Lys Asp Ile Pro Val Pro Lys Pro Lys Pro Asn
                20                  25                  30

Glu Leu Leu Ile Asn Val Lys Tyr Ser Gly Val Cys His Thr Asp Leu
             35                  40                  45

His Ala Trp His Gly Asp Trp Pro Leu Pro Thr Lys Leu Pro Leu Val
         50                  55                  60

Gly Gly His Glu Gly Ala Gly Val Val Val Gly Met Gly Glu Asn Val
 65                  70                  75                  80

Lys Gly Trp Lys Ile Gly Asp Tyr Ala Gly Ile Lys Trp Leu Asn Gly
                 85                  90                  95

Ser Cys Met Ala Cys Glu Tyr Cys Glu Leu Gly Asn Glu Ser Asn Cys
                100                 105                 110

Pro His Ala Asp Leu Ser Gly Tyr Thr His Asp Gly Ser Phe Gln Glu
            115                 120                 125

Tyr Ala Thr Ala Asp Ala Val Gln Ala Ala His Ile Pro Gln Gly Thr
        130                 135                 140

Asp Leu Ala Glu Val Ala Pro Ile Leu Cys Ala Gly Ile Thr Val Tyr
145                 150                 155                 160

Lys Ala Leu Lys Ser Ala Asn Leu Arg Ala Gly His Trp Ala Ala Ile
                165                 170                 175

Ser Gly Ala Ala Gly Gly Leu Gly Ser Leu Ala Val Gln Tyr Ala Lys
            180                 185                 190

Ala Met Gly Tyr Arg Val Leu Gly Ile Asp Gly Gly Pro Gly Lys Glu
        195                 200                 205

Glu Leu Phe Thr Ser Leu Gly Gly Glu Val Phe Ile Asp Phe Thr Lys
    210                 215                 220

Glu Lys Asp Ile Val Ser Ala Val Val Lys Ala Thr Asn Gly Gly Ala
225                 230                 235                 240

His Gly Ile Ile Asn Val Ser Val Ser Glu Ala Ala Ile Glu Ala Ser
                245                 250                 255

Thr Arg Tyr Cys Arg Ala Asn Gly Thr Val Val Leu Val Gly Leu Pro
            260                 265                 270

Ala Gly Ala Lys Cys Ser Ser Asp Val Phe Asn His Val Val Lys Ser
        275                 280                 285

Ile Ser Ile Val Gly Ser Tyr Val Gly Asn Arg Ala Asp Thr Arg Glu
    290                 295                 300

Ala Leu Asp Phe Phe Ala Arg Gly Leu Val Lys Ser Pro Ile Lys Val
305                 310                 315                 320

Val Gly Leu Ser Ser Leu Pro Glu Ile Tyr Glu Lys Met Glu Lys Gly
                325                 330                 335

Gln Ile Ala Gly Arg Tyr Val Val Asp Thr Ser Lys
            340                 345
```

<210> SEQ ID NO 69
<211> LENGTH: 375
<212> TYPE: PRT
<213> ORGANISM: Saccharomyces cerevisiae

<400> SEQUENCE: 69

```
Met Leu Arg Thr Ser Thr Leu Phe Thr Arg Arg Val Gln Pro Ser Leu
 1               5                  10                  15

Phe Ser Arg Asn Ile Leu Arg Leu Gln Ser Thr Ala Ala Ile Pro Lys
```

```
                        20                  25                  30
Thr Gln Lys Gly Val Ile Phe Tyr Glu Asn Lys Gly Lys Leu His Tyr
                35                  40                  45
Lys Asp Ile Pro Val Pro Glu Pro Lys Pro Asn Glu Ile Leu Ile Asn
            50                  55                  60
Val Lys Tyr Ser Gly Val Cys His Thr Asp Leu His Ala Trp His Gly
65                  70                  75                  80
Asp Trp Pro Leu Pro Val Lys Leu Pro Leu Val Gly Gly His Glu Gly
                85                  90                  95
Ala Gly Val Val Val Lys Leu Gly Ser Asn Val Lys Gly Trp Lys Val
                100                 105                 110
Gly Asp Leu Ala Gly Ile Lys Trp Leu Asn Gly Ser Cys Met Thr Cys
            115                 120                 125
Glu Phe Cys Glu Ser Gly His Glu Ser Asn Cys Pro Asp Ala Asp Leu
    130                 135                 140
Ser Gly Tyr Thr His Asp Gly Ser Phe Gln Gln Phe Ala Thr Ala Asp
145                 150                 155                 160
Ala Ile Gln Ala Ala Lys Ile Gln Gln Gly Thr Asp Leu Ala Glu Val
                165                 170                 175
Ala Pro Ile Leu Cys Ala Gly Val Thr Val Tyr Lys Ala Leu Lys Glu
            180                 185                 190
Ala Asp Leu Lys Ala Gly Asp Trp Val Ala Ile Ser Gly Ala Ala Gly
            195                 200                 205
Gly Leu Gly Ser Leu Ala Val Gln Tyr Ala Thr Ala Met Gly Tyr Arg
    210                 215                 220
Val Leu Gly Ile Asp Ala Gly Glu Glu Lys Glu Lys Leu Phe Lys Lys
225                 230                 235                 240
Leu Gly Gly Glu Val Phe Ile Asp Phe Thr Lys Thr Lys Asn Met Val
                245                 250                 255
Ser Asp Ile Gln Glu Ala Thr Lys Gly Gly Pro His Gly Val Ile Asn
            260                 265                 270
Val Ser Val Ser Glu Ala Ala Ile Ser Leu Ser Thr Glu Tyr Val Arg
        275                 280                 285
Pro Cys Gly Thr Val Val Leu Val Gly Leu Pro Ala Asn Ala Tyr Val
    290                 295                 300
Lys Ser Glu Val Phe Ser His Val Val Lys Ser Ile Asn Ile Lys Gly
305                 310                 315                 320
Ser Tyr Val Gly Asn Arg Ala Asp Thr Arg Glu Ala Leu Asp Phe Phe
                325                 330                 335
Ser Arg Gly Leu Ile Lys Ser Pro Ile Lys Ile Val Gly Leu Ser Glu
            340                 345                 350
Leu Pro Lys Val Tyr Asp Leu Met Glu Lys Gly Lys Ile Leu Gly Arg
        355                 360                 365
Tyr Val Asp Thr Ser Lys
    370                 375

<210> SEQ ID NO 70
<211> LENGTH: 374
<212> TYPE: PRT
<213> ORGANISM: Pichia stipitis

<400> SEQUENCE: 70

Met Ser Lys Ser Thr Ser Thr Thr Val Pro Ala Lys Phe Ser Gly Phe
1               5                   10                  15

Ala Val Asp Lys Pro Glu Asn Trp Asn Lys Ala Lys Leu Val Gln Tyr
```

```
                          20                  25                  30
Asp Pro Lys Pro Phe Lys Pro Tyr Asp Ile Thr Ile Lys Val Ile Cys
            35                  40                  45

Cys Gly Val Cys Gly Ser Asp Cys His Thr Val Leu Gly Ser Trp Gly
        50                  55                  60

Pro Leu Asn Arg Asp Asp Leu Val Val Gly His Glu Ile Val Gly Glu
65                  70                  75                  80

Val Ile Glu Ile Gly Ser Glu Val Thr Asn His Lys Leu Gly Asp Ile
                85                  90                  95

Val Ala Val Gly Ala Gln Ser Asp Ser Cys Gly Glu Cys Glu Leu Cys
            100                 105                 110

Glu Asn Asn Glu Gln Tyr Cys Arg Asp Gly Ile Ala Ala Thr Tyr
        115                 120                 125

Asn Phe Pro Asn Lys Arg Cys Gly Gly Tyr Val Thr Gln Gly Gly Tyr
    130                 135                 140

Ala Ser His Leu Arg Val Asn Ser Tyr Phe Ala Ala Ser Val Pro Lys
145                 150                 155                 160

Asn Leu Asp Val His Tyr Ala Ala Pro Leu Leu Cys Gly Gly Leu Thr
                165                 170                 175

Val Tyr Ser Pro Ile Val Arg His Gly Gly Tyr Asp Leu Lys Asp Lys
            180                 185                 190

Arg Ile Gly Ile Val Gly Ile Gly Gly Leu Gly Ser Met Ala Ile Gln
        195                 200                 205

Ile Ala Asn Ala Leu Gly Ala Lys Glu Val Val Ala Phe Ser Arg Thr
    210                 215                 220

Ser Asp Lys Lys Glu Asp Ala Leu Lys Leu Gly Ala Ser Arg Ile Ile
225                 230                 235                 240

Ala Thr Lys Glu Asp Pro Asp Trp Ser Lys Ser Asn Ala Ala Thr Phe
                245                 250                 255

Asp Ile Ile Leu Asn Cys Ala Ser Phe Gly Lys Gly Val Asn Phe Asp
            260                 265                 270

Ser Phe Phe Gly Ala Leu Lys Leu Gly Gly Lys Tyr Val Asn Val Ser
        275                 280                 285

Ala Pro Pro Ser Asp Glu Leu Ile Ser Leu Ser Pro Arg Asn Leu Ile
    290                 295                 300

Phe Gly Gly Phe Ser Ile Val Gly Ser Val Ile Gly Ser Met Lys Glu
305                 310                 315                 320

Ala Asn Glu Leu Leu Lys Leu Tyr Ala Asp Asn Leu Ala Pro Trp
                325                 330                 335

Ile Glu Lys Val Pro Ile Ser Glu Glu Gly Val His Thr Val Met Asn
            340                 345                 350

Arg Ile Asn Val Ser Asp Val Lys Tyr Arg Phe Val Leu Thr Asp Tyr
        355                 360                 365

Asp Lys Ala Phe Asn Asn
    370

<210> SEQ ID NO 71
<211> LENGTH: 374
<212> TYPE: PRT
<213> ORGANISM: Pichia stipitis

<400> SEQUENCE: 71

Met Thr Thr Ser Arg Thr Val Pro Glu Lys Phe Ser Gly Phe Gly Val
1               5                   10                  15

Asp Lys Ala Glu Asn Trp Asn Lys Ala Arg Leu Val Arg Phe Asp Pro
```

```
                    20                  25                  30
Lys Pro Leu Met Pro Tyr Asp Ile Thr Ile Lys Val Ile Ala Cys Ala
                35                  40                  45

Val Cys Gly Ser Asp Cys His Thr Val Thr Gly Asn Phe Gly Pro Ile
 50                  55                  60

Asn Arg Asp Asp Leu Val Val Gly His Glu Ile Val Gly Glu Val Ile
 65                  70                  75                  80

Glu Val Gly Pro Glu Val Thr Lys His Lys Leu Gly Asp Val Val Ala
                85                  90                  95

Ile Gly Ala Gln Ser Asp Ser Cys Gly Glu Cys Asn Arg Cys Lys Ser
            100                 105                 110

Asn Asn Glu Gln Tyr Cys Gln Lys Gly Thr Val Gly Thr Tyr Asn Ser
        115                 120                 125

Leu Ser Lys Lys Cys Gly Gly Tyr Ile Thr Gln Gly Gly Tyr Ala Ser
    130                 135                 140

His Val Arg Val Asn Ser His Phe Ala Ala Arg Val Pro Ala Asn Leu
145                 150                 155                 160

Asp Val His His Ala Ala Pro Leu Leu Cys Gly Gly Leu Thr Val Tyr
                165                 170                 175

Ser Pro Ile Val Arg His Ala Gly Tyr Asp Leu Lys Glu Lys Val Ile
            180                 185                 190

Gly Ile Val Gly Ile Gly Gly Leu Gly Ser Met Ala Ile Gln Ile Ala
        195                 200                 205

Lys Ala Leu Gly Ala Lys Glu Val Val Ala Phe Ser Arg Ser Ser Ser
    210                 215                 220

Lys Lys Glu Asp Ala Phe Lys Met Gly Ala Ser Lys Tyr Ile Ala Thr
225                 230                 235                 240

Lys Glu Asp Thr Glu Trp Ala Asn Ser Asn Leu Asp Thr Phe Asp Met
                245                 250                 255

Ile Leu Asn Cys Ala Ser Phe Gly Lys Gly Val Asp Tyr Asp Ser Phe
            260                 265                 270

Ile Arg Thr Leu Lys Leu Gly Gly Lys Tyr Val Thr Val Ser Ala Pro
        275                 280                 285

Pro Ala Asp Glu Ser Ile Thr Ile Ala Pro Phe Asn Leu Leu Ile Gly
    290                 295                 300

Gly Gly Ile Ile Ala Gly Ser Gly Ile Gly Ser Met Lys Glu Ala Asp
305                 310                 315                 320

Glu Leu Leu Lys Leu Tyr Ala Asp Asn Asn Leu Ala Pro Trp Ile Glu
                325                 330                 335

Lys Val Pro Ile Ser Glu Glu Gly Val His Lys Val Met Asn Arg Ile
            340                 345                 350

Ser Val Gly Asp Val Arg Tyr Arg Phe Val Leu Thr Asp Phe Asp Gln
        355                 360                 365

Ala Phe Asp Ser Lys Trp
    370

<210> SEQ ID NO 72
<211> LENGTH: 361
<212> TYPE: PRT
<213> ORGANISM: Saccharomyces cerevisiae

<400> SEQUENCE: 72

Met Leu Tyr Pro Glu Lys Phe Gln Gly Ile Gly Ile Ser Asn Ala Lys
 1               5                  10                  15

Asp Trp Lys His Pro Lys Leu Val Ser Phe Asp Pro Lys Pro Phe Gly
```

```
            20                  25                  30
Asp His Asp Val Asp Val Glu Ile Glu Ala Cys Gly Ile Cys Gly Ser
    35                  40                  45

Asp Phe His Ile Ala Val Gly Asn Trp Gly Pro Val Pro Glu Asn Gln
50                  55                  60

Ile Leu Gly His Glu Ile Gly Arg Val Lys Val Gly Ser Lys
65                  70                  75                  80

Cys His Thr Gly Val Lys Ile Gly Asp Arg Val Gly Val Gly Ala Gln
                85                  90                  95

Ala Leu Ala Cys Phe Glu Cys Glu Arg Cys Lys Ser Asp Asn Glu Gln
            100                 105                 110

Tyr Cys Thr Asn Asp His Val Leu Thr Met Trp Thr Pro Tyr Lys Asp
        115                 120                 125

Gly Tyr Ile Ser Gln Gly Gly Phe Ala Ser His Val Arg Leu His Glu
    130                 135                 140

His Phe Ala Ile Gln Ile Pro Glu Asn Ile Pro Ser Pro Leu Ala Ala
145                 150                 155                 160

Pro Leu Leu Cys Gly Gly Ile Thr Val Phe Ser Pro Leu Leu Arg Asn
                165                 170                 175

Gly Cys Gly Pro Gly Lys Arg Val Gly Ile Val Gly Ile Gly Gly Ile
            180                 185                 190

Gly His Met Gly Ile Leu Leu Ala Lys Ala Met Gly Ala Glu Val Tyr
        195                 200                 205

Ala Phe Ser Arg Gly His Ser Lys Arg Glu Asp Ser Met Lys Leu Gly
    210                 215                 220

Ala Asp His Tyr Ile Ala Met Leu Glu Asp Lys Gly Trp Thr Glu Gln
225                 230                 235                 240

Tyr Ser Asn Ala Leu Asp Leu Val Val Cys Ser Ser Ser Leu Ser
                245                 250                 255

Lys Val Asn Phe Asp Ser Ile Val Lys Ile Met Lys Ile Gly Gly Ser
            260                 265                 270

Ile Val Ser Ile Ala Ala Pro Glu Val Asn Glu Lys Leu Val Leu Lys
        275                 280                 285

Pro Leu Gly Leu Met Gly Val Ser Ile Ser Ser Ala Ile Gly Ser
    290                 295                 300

Arg Lys Glu Ile Glu Gln Leu Leu Lys Leu Val Ser Lys Asn Val
305                 310                 315                 320

Lys Ile Trp Val Glu Lys Leu Pro Ile Ser Glu Glu Gly Val Ser His
                325                 330                 335

Ala Phe Thr Arg Met Glu Ser Gly Asp Val Lys Tyr Arg Phe Thr Leu
            340                 345                 350

Val Asp Tyr Asp Lys Lys Phe His Lys
        355                 360

<210> SEQ ID NO 73
<211> LENGTH: 357
<212> TYPE: PRT
<213> ORGANISM: Pichia stipitis

<400> SEQUENCE: 73

Met Gly Tyr Pro Asp Thr Phe Gln Gly Phe Ala Val Asn Asp Thr Ser
1               5                   10                  15

Lys Trp Ser Glu Val Glu Lys Met Asp Phe Lys Pro Lys Thr Phe Gly
            20                  25                  30

Pro Leu Asp Ile Asp Ile Lys Ile Lys Ala Cys Gly Val Cys Gly Ser
```

```
                35                  40                  45
Asp Val His Thr Val Thr Gly Gly Trp Asp Gln Pro Arg Leu Pro Val
 50                  55                  60

Ile Val Gly His Glu Ile Val Gly Glu Val Val Lys Val Gly Asp Asn
 65                  70                  75                  80

Val Ser Ser Phe Lys Ile Gly Asp Arg Val Met Gly Ala Gln Ala
                 85                  90                  95

Trp Ala Cys Leu Glu Cys Asp Val Cys Lys Asn Gly Asp Glu Ile Tyr
                100                 105                 110

Cys Pro Lys Trp Val Asp Thr Tyr Asn Asp Val Tyr Pro Asp Gly Ser
                115                 120                 125

Leu Ala Tyr Gly Gly Tyr Ser Ser His Val Arg Val His Glu His Phe
                130                 135                 140

Ala Phe Pro Ile Pro Glu Ala Leu Ser Thr Glu Gly Val Ala Pro Met
145                 150                 155                 160

Leu Cys Ala Gly Ile Thr Thr Tyr Ser Pro Leu Val Arg Asn Gly Ala
                165                 170                 175

Gly Pro Gly Lys Lys Val Gly Val Val Gly Val Gly Gly Leu Gly His
                180                 185                 190

Phe Ala Ile Met Trp Ala Arg Ala Leu Gly Cys Glu Val Tyr Val Phe
                195                 200                 205

Ser Arg Ser Leu Ser Lys Lys Asp Asp Ala Ile Lys Leu Gly Ala Asp
                210                 215                 220

His Tyr Ile Ala Thr Gly Glu Glu Asn Trp Asn Glu Pro Tyr Lys Tyr
225                 230                 235                 240

Lys Leu Asp Leu Ile Leu Ser Thr Ala Asn Ser Asn Ser Gly Phe Asp
                245                 250                 255

Met Gly Ala Tyr Leu Ser Thr Leu Arg Val His Gly Lys Tyr Ile Ala
                260                 265                 270

Leu Gly Leu Pro Glu Asp Asp Phe Lys Val Ser Pro Gly Ser Leu Leu
                275                 280                 285

Lys Asn Gly Cys Phe Val Gly Ser Ser His Leu Gly Asn Arg Gln Glu
                290                 295                 300

Met Ile Asp Met Leu Asn Leu Ala Ala Glu Lys Gly Ile Glu Ala Trp
305                 310                 315                 320

Tyr Glu Ala Val Pro Ile Gly Lys Gln Gly Ile Lys Glu Ala Leu Glu
                325                 330                 335

Arg Cys Gln Ser Gly Lys Val Leu Tyr Arg Phe Thr Leu Thr Asp Tyr
                340                 345                 350

Glu Lys Gln Phe Glu
                355

<210> SEQ ID NO 74
<211> LENGTH: 342
<212> TYPE: PRT
<213> ORGANISM: Saccharomyces cerevisiae

<400> SEQUENCE: 74

Met Ser Val Phe Val Ser Gly Ala Asn Gly Phe Ile Ala Gln His Ile
 1               5                  10                  15

Val Asp Leu Leu Leu Lys Glu Asp Tyr Lys Val Ile Gly Ser Ala Arg
                20                  25                  30

Ser Gln Glu Lys Ala Glu Asn Leu Thr Glu Ala Phe Gly Asn Asn Pro
                35                  40                  45

Lys Phe Ser Met Glu Val Val Pro Asp Ile Ser Lys Leu Asp Ala Phe
```

```
                    50                  55                  60
Asp His Val Phe Gln Lys His Gly Lys Asp Ile Lys Ile Val Leu His
 65                  70                  75                  80

Thr Ala Ser Pro Phe Cys Phe Asp Ile Thr Asp Ser Glu Arg Asp Leu
                 85                  90                  95

Leu Ile Pro Ala Val Asn Gly Val Lys Gly Ile Leu His Ser Ile Lys
                100                 105                 110

Lys Tyr Ala Ala Asp Ser Val Glu Arg Val Val Leu Thr Ser Ser Tyr
            115                 120                 125

Ala Ala Val Phe Asp Met Ala Lys Glu Asn Asp Lys Ser Leu Thr Phe
        130                 135                 140

Asn Glu Glu Ser Trp Asn Pro Ala Thr Trp Glu Ser Cys Gln Ser Asp
145                 150                 155                 160

Pro Val Asn Ala Tyr Cys Gly Ser Lys Lys Phe Ala Glu Lys Ala Ala
                165                 170                 175

Trp Glu Phe Leu Glu Glu Asn Arg Asp Ser Val Lys Phe Glu Leu Thr
                180                 185                 190

Ala Val Asn Pro Val Tyr Val Phe Gly Pro Gln Met Phe Asp Lys Asp
            195                 200                 205

Val Lys Lys His Leu Asn Thr Ser Cys Glu Leu Val Asn Ser Leu Met
210                 215                 220

His Leu Ser Pro Glu Asp Lys Ile Pro Glu Leu Phe Gly Gly Tyr Ile
225                 230                 235                 240

Asp Val Arg Asp Val Ala Lys Ala His Leu Val Ala Phe Gln Lys Arg
                245                 250                 255

Glu Thr Ile Gly Gln Arg Leu Ile Val Ser Glu Ala Arg Phe Thr Met
                260                 265                 270

Gln Asp Val Leu Asp Ile Leu Asn Glu Asp Phe Pro Val Leu Lys Gly
            275                 280                 285

Asn Ile Pro Val Gly Lys Pro Gly Ser Gly Ala Thr His Asn Thr Leu
290                 295                 300

Gly Ala Thr Leu Asp Asn Lys Lys Ser Lys Lys Leu Leu Gly Phe Lys
305                 310                 315                 320

Phe Arg Asn Leu Lys Glu Thr Ile Asp Asp Thr Ala Ser Gln Ile Leu
                325                 330                 335

Lys Phe Glu Gly Arg Ile
            340

<210> SEQ ID NO 75
<211> LENGTH: 337
<212> TYPE: PRT
<213> ORGANISM: Pichia stipitis

<400> SEQUENCE: 75

Met Thr Ser Val Phe Val Ser Gly Ala Thr Gly Phe Ile Ala Gln His
  1               5                  10                  15

Val Val Lys Asp Leu Leu Ala Lys Asn Tyr Thr Val Ile Gly Ser Val
             20                  25                  30

Arg Ser Ala Ser Lys Gly Asp His Leu Ala Glu Leu Leu Gly Ser Lys
         35                  40                  45

Lys Phe Ser Tyr Glu Val Val Glu Asp Ile Glu Lys Glu Gly Ala Phe
     50                  55                  60

Asp Ala Ala Leu Glu Lys His Pro Glu Val Ser Val Phe Leu His Thr
 65                  70                  75                  80

Ala Ser Pro Phe His Phe Lys Ala Thr Asp Asn Glu Lys Glu Leu Leu
```

-continued

```
                85                  90                  95
Leu Pro Ala Val Asn Gly Thr Lys Asn Ala Phe Arg Ala Ile Gln Leu
                100                 105                 110

His Gly Lys Asn Val Thr Asn Val Leu Thr Ser Ser Tyr Ala Ala
                115                 120                 125

Val Gly Thr Ala Ser Lys Asp Ala Asn Lys Asp Glu Val Ile Asn Glu
                130                 135                 140

Glu Ser Trp Asn Glu Ile Thr Trp Glu Ala Leu Lys Asp Pro Val
145                 150                 155                 160

Ser Gly Tyr Arg Gly Ser Lys Thr Phe Ala Glu Lys Ala Ala Trp Glu
                165                 170                 175

Phe Leu Lys Glu Asn Asn Pro Lys Phe Val Leu Ser Val Val Asn Pro
                180                 185                 190

Thr Phe Val Phe Gly Pro Gln Ala Phe Asp Ser Glu Val Lys Asp Ser
                195                 200                 205

Leu Asn Thr Ser Ser Glu Val Ile Asn Ala Leu Leu Lys Ser Gly Ala
                210                 215                 220

Asn Gly Val Val Pro Pro Val Lys Gly Phe Val Asp Val Arg Asp
225                 230                 235                 240

Val Ser Ser Ala His Ile Thr Ala Phe Glu Lys Glu Ala Ala Tyr Gly
                245                 250                 255

Gln Arg Leu Ile Leu Asn Ser Thr Arg Phe Thr Ala Gln Glu Ile Val
                260                 265                 270

Asp Ile Leu Asn Lys Arg Phe Pro Glu Leu Val Gly Lys Ile Pro Val
                275                 280                 285

Gly Glu Pro Gly Thr Gly Pro Ser Leu Arg Ala Asn Asn Ala Thr Ile
                290                 295                 300

Asp Asn Thr Lys Thr Lys Lys Ile Leu Gly Val Ser Glu Phe Ile Gly
305                 310                 315                 320

Leu Glu Lys Ser Val Val Asp Ser Val Ser Gln Ile Leu Arg Thr Arg
                325                 330                 335

Lys

<210> SEQ ID NO 76
<211> LENGTH: 386
<212> TYPE: PRT
<213> ORGANISM: Saccharomyces cerevisiae

<400> SEQUENCE: 76

Met Ser Ala Ala Thr Val Gly Lys Pro Ile Lys Cys Ile Ala Ala Val
  1               5                  10                  15

Ala Tyr Asp Ala Lys Lys Pro Leu Ser Val Glu Glu Ile Thr Val Asp
                20                  25                  30

Ala Pro Lys Ala His Glu Val Arg Ile Lys Ile Glu Tyr Thr Ala Val
                35                  40                  45

Cys His Thr Asp Ala Tyr Thr Leu Ser Gly Ser Asp Pro Glu Gly Leu
                50                  55                  60

Phe Pro Cys Val Leu Gly His Glu Gly Ala Gly Ile Val Glu Ser Val
 65                  70                  75                  80

Gly Asp Asp Val Ile Thr Val Lys Pro Gly Asp His Val Ile Ala Leu
                85                  90                  95

Tyr Thr Ala Glu Cys Gly Lys Cys Lys Phe Cys Thr Ser Gly Lys Thr
                100                 105                 110

Asn Leu Cys Gly Ala Val Arg Ala Thr Gln Gly Lys Gly Val Met Pro
                115                 120                 125
```

-continued

```
Asp Gly Thr Thr Arg Phe His Asn Ala Lys Gly Glu Asp Ile Tyr His
    130                 135                 140

Phe Met Gly Cys Ser Thr Phe Ser Glu Tyr Thr Val Val Ala Asp Val
145                 150                 155                 160

Ser Val Val Ala Ile Asp Pro Lys Ala Pro Leu Asp Ala Ala Cys Leu
                165                 170                 175

Leu Gly Cys Gly Val Thr Thr Gly Phe Gly Ala Ala Leu Lys Thr Ala
            180                 185                 190

Asn Val Gln Lys Gly Asp Thr Val Ala Val Phe Gly Cys Gly Thr Val
        195                 200                 205

Gly Leu Ser Val Ile Gln Gly Ala Lys Leu Arg Gly Ala Ser Lys Ile
    210                 215                 220

Ile Ala Ile Asp Ile Asn Asn Lys Lys Gln Tyr Cys Ser Gln Phe
225                 230                 235                 240

Gly Ala Thr Asp Phe Val Asn Pro Lys Glu Asp Leu Ala Lys Asp Gln
                245                 250                 255

Thr Ile Val Glu Lys Leu Ile Glu Met Thr Asp Gly Gly Leu Asp Phe
            260                 265                 270

Thr Phe Asp Cys Thr Gly Asn Thr Lys Ile Met Arg Asp Ala Leu Glu
        275                 280                 285

Ala Cys His Lys Gly Trp Gly Gln Ser Ile Ile Ile Gly Val Ala Ala
    290                 295                 300

Ala Gly Glu Glu Ile Ser Thr Arg Pro Phe Gln Leu Val Thr Gly Arg
305                 310                 315                 320

Val Trp Lys Gly Ser Ala Phe Gly Gly Ile Lys Gly Arg Ser Glu Met
                325                 330                 335

Gly Gly Leu Ile Lys Asp Tyr Gln Lys Gly Ala Leu Lys Val Glu Glu
            340                 345                 350

Phe Ile Thr His Arg Arg Pro Phe Lys Glu Ile Asn Gln Ala Phe Glu
        355                 360                 365

Asp Leu His Asn Gly Asp Cys Leu Arg Thr Val Leu Lys Ser Asp Glu
    370                 375                 380

Ile Lys
385

<210> SEQ ID NO 77
<211> LENGTH: 312
<212> TYPE: PRT
<213> ORGANISM: Saccharomyces cerevisiae

<400> SEQUENCE: 77

Met Pro Ala Thr Leu Lys Asn Ser Ser Ala Thr Leu Lys Leu Asn Thr
1               5                   10                  15

Gly Ala Ser Ile Pro Val Leu Gly Phe Gly Thr Trp Arg Ser Val Asp
            20                  25                  30

Asn Asn Gly Tyr His Ser Val Ile Ala Ala Leu Lys Ala Gly Tyr Arg
        35                  40                  45

His Ile Asp Ala Ala Ala Ile Tyr Leu Asn Glu Glu Glu Val Gly Arg
    50                  55                  60

Ala Ile Lys Asp Ser Gly Val Pro Arg Glu Glu Ile Phe Ile Thr Thr
65                  70                  75                  80

Lys Leu Trp Gly Thr Glu Gln Arg Asp Pro Glu Ala Ala Leu Asn Lys
                85                  90                  95

Ser Leu Lys Arg Leu Gly Leu Asp Tyr Val Asp Leu Tyr Leu Met His
            100                 105                 110
```

```
Trp Pro Val Pro Leu Lys Thr Asp Arg Val Thr Asp Gly Asn Val Leu
            115                 120                 125

Cys Ile Pro Thr Leu Glu Asp Gly Thr Val Asp Ile Asp Thr Lys Glu
        130                 135                 140

Trp Asn Phe Ile Lys Thr Trp Glu Leu Met Gln Glu Leu Pro Lys Thr
145                 150                 155                 160

Gly Lys Thr Lys Ala Val Gly Val Ser Asn Phe Ser Ile Asn Asn Ile
                165                 170                 175

Lys Glu Leu Leu Glu Ser Pro Asn Asn Lys Val Val Pro Ala Thr Asn
            180                 185                 190

Gln Ile Glu Ile His Pro Leu Leu Pro Gln Asp Glu Leu Ile Ala Phe
        195                 200                 205

Cys Lys Glu Lys Gly Ile Val Glu Ala Tyr Ser Pro Phe Gly Ser
        210                 215                 220

Ala Asn Ala Pro Leu Leu Lys Glu Gln Ala Ile Ile Asp Met Ala Lys
225                 230                 235                 240

Lys His Gly Val Glu Pro Ala Gln Leu Ile Ile Ser Trp Ser Ile Gln
                245                 250                 255

Arg Gly Tyr Val Val Leu Ala Lys Ser Val Asn Pro Glu Arg Ile Val
            260                 265                 270

Ser Asn Phe Lys Ile Phe Thr Leu Pro Glu Asp Asp Phe Lys Thr Ile
        275                 280                 285

Ser Asn Leu Ser Lys Val His Gly Thr Lys Arg Val Val Asp Met Lys
290                 295                 300

Trp Gly Ser Phe Pro Ile Phe Gln
305                 310

<210> SEQ ID NO 78
<211> LENGTH: 378
<212> TYPE: PRT
<213> ORGANISM: Mycobacterium smegmatis

<400> SEQUENCE: 78

Met Pro Ala Pro Asp Thr Ile Arg Pro His Ser Thr Ser Ile Arg Ala
 1                5                  10                  15

Ala Val Phe Asp Gly Thr Ile Ser Val Glu Pro Val Asp Leu Ala Asp
                20                  25                  30

Pro Arg Pro Gly Glu Val Arg Val Lys Ile Ala Ala Gly Val Cys
            35                  40                  45

His Ser Asp Leu His Val Thr Thr Gly Ala Trp Asp Val Pro Ala Pro
 50                 55                  60

Val Val Leu Gly His Glu Gly Ser Gly Val Val Thr Ala Val Gly Glu
65                  70                  75                  80

Gly Val Asp Asp Leu Glu Pro Gly Asp His Val Val Leu Ser Trp Val
                85                  90                  95

Pro Gly Cys Gly Glu Cys Arg Tyr Cys Lys Ala Gly Arg Pro Ala Gln
            100                 105                 110

Cys Ser Leu Val Ala Ser Val Val Ala Val Lys Gly Thr Leu Tyr Asp
        115                 120                 125

Gly Thr Thr Arg Leu Ser Asn Glu Arg Gly Thr Val His His Tyr Leu
    130                 135                 140

Gly Val Ser Ser Tyr Ala Glu Gln Val Val Pro Arg Asn Gly Ala
145                 150                 155                 160

Ile Lys Val Arg Lys Asp Ala Pro Leu Glu Asp Ile Ala Ile Val Gly
                165                 170                 175
```

```
Cys Ala Ile Ala Thr Gly Val Gly Ala Val Arg Asn Thr Ala Gly Val
            180                 185                 190

Glu Pro Gly Ser Thr Val Ala Val Ile Gly Cys Gly Gly Val Gly Leu
            195                 200                 205

Ala Cys Val Gln Gly Ala Arg Leu Ala Gly Ala Ser Arg Ile Val Ala
210                 215                 220

Val Asp Val Val Ala Glu Lys Leu Glu Leu Ala Arg Lys Leu Gly Ala
225                 230                 235                 240

Thr Asp Ala Val Asp Ala Ser Ala Thr Asp Val Val Ala Ala Met
            245                 250                 255

Arg Glu Val Leu Pro Asp Gly Tyr Asp Tyr Val Phe Asp Ala Ile Gly
            260                 265                 270

Lys Ile Ala Thr Thr Glu Gln Ala Ile Ala Ala Leu Gly Leu Gly Gly
            275                 280                 285

Ala Ala Val Ile Val Gly Leu Pro Pro Gln Glu Arg Ala Ser Phe
290                 295                 300

Asp Pro Leu Thr Leu Ala Glu Ala Asp Gln Arg Ile Leu Gly Ser Asn
305                 310                 315                 320

Tyr Gly Ser Ala Val Pro Glu Arg Asp Ile Pro Ala Leu Val Asp Glu
                325                 330                 335

Val Met Ala Gly Asn Leu Asp Leu Ala Ser Met Ile Ser Gly Arg Arg
            340                 345                 350

Pro Leu Glu Glu Ala Ala Ala Leu Asp Asp Leu Ala Ala Gly His
            355                 360                 365

Ala Leu Arg Gln Leu Leu Ile Pro Ser Ala
            370                 375

<210> SEQ ID NO 79
<211> LENGTH: 278
<212> TYPE: PRT
<213> ORGANISM: Mycobacterium smegmatis

<400> SEQUENCE: 79

Met Arg Ala Val Asp Gly Phe Pro Gly Arg Gly Ala Val Ile Thr Gly
1               5                   10                  15

Gly Ala Ser Gly Ile Gly Leu Ala Thr Gly Thr Glu Phe Ala Arg Arg
            20                  25                  30

Gly Ala Arg Val Val Leu Gly Asp Val Asp Lys Pro Gly Leu Arg Gln
        35                  40                  45

Ala Val Asn His Leu Arg Ala Glu Gly Phe Asp Val His Ser Val Met
50                  55                  60

Cys Asp Val Arg His Arg Glu Glu Val Thr His Leu Ala Asp Glu Ala
65                  70                  75                  80

Phe Arg Leu Leu Gly His Val Asp Val Val Phe Ser Asn Ala Gly Ile
                85                  90                  95

Val Val Gly Gly Pro Ile Val Glu Met Thr His Asp Asp Trp Arg Trp
            100                 105                 110

Val Ile Asp Val Asp Leu Trp Gly Ser Ile His Thr Val Glu Ala Phe
        115                 120                 125

Leu Pro Arg Leu Leu Glu Gln Gly Thr Gly His Val Val Phe Thr
130                 135                 140

Ala Ser Phe Ala Gly Leu Val Pro Asn Ala Gly Leu Gly Ala Tyr Gly
145                 150                 155                 160

Val Ala Lys Tyr Gly Val Val Gly Leu Ala Glu Thr Leu Ala Arg Glu
                165                 170                 175
```

```
Val Thr Ala Asp Gly Ile Gly Val Ser Val Leu Cys Pro Met Val Val
            180                 185                 190

Glu Thr Asn Leu Val Ala Asn Ser Glu Arg Ile Arg Gly Ala Ala Cys
        195                 200                 205

Ala Gln Ser Ser Thr Thr Gly Ser Pro Gly Pro Leu Pro Leu Gln Asp
    210                 215                 220

Asp Asn Leu Gly Val Asp Asp Ile Ala Gln Leu Thr Ala Asp Ala Ile
225                 230                 235                 240

Leu Ala Asn Arg Leu Tyr Val Leu Pro His Ala Ala Ser Arg Ala Ser
                245                 250                 255

Ile Arg Arg Arg Phe Glu Arg Ile Asp Arg Thr Phe Asp Glu Gln Ala
            260                 265                 270

Ala Glu Gly Trp Arg His
            275

<210> SEQ ID NO 80
<211> LENGTH: 375
<212> TYPE: PRT
<213> ORGANISM: Mycobacterium smegmatis

<400> SEQUENCE: 80

Met Lys Thr Lys Gly Ala Leu Ile Trp Glu Phe Asn Gln Pro Trp Ser
1               5                   10                  15

Val Glu Glu Ile Glu Ile Gly Asp Pro Arg Lys Asp Glu Val Lys Ile
                20                  25                  30

Gln Met Glu Ala Ala Gly Met Cys Arg Ser Asp His His Leu Val Thr
            35                  40                  45

Gly Asp Ile Pro Met Ala Gly Phe Pro Val Leu Gly Gly His Glu Gly
        50                  55                  60

Ala Gly Ile Val Thr Glu Val Gly Pro Gly Val Asp Asp Phe Ala Pro
65                  70                  75                  80

Gly Asp His Val Val Leu Ala Phe Ile Pro Ser Cys Gly Lys Cys Pro
                85                  90                  95

Ser Cys Gln Ala Gly Met Arg Asn Leu Cys Asp Leu Gly Ala Gly Leu
            100                 105                 110

Leu Ala Gly Glu Ser Val Thr Asp Gly Ser Phe Arg Ile Gln Ala Arg
        115                 120                 125

Gly Gln Asn Val Tyr Pro Met Thr Leu Leu Gly Thr Phe Ser Pro Tyr
    130                 135                 140

Met Val Val His Arg Ser Ser Val Val Lys Ile Asp Pro Ser Val Pro
145                 150                 155                 160

Phe Glu Val Ala Cys Leu Val Gly Cys Gly Val Thr Thr Gly Tyr Gly
                165                 170                 175

Ser Ala Val Arg Thr Ala Asp Val Arg Pro Gly Asp Val Ala Ile
            180                 185                 190

Val Gly Leu Gly Gly Val Gly Met Ala Ala Leu Gln Gly Ala Val Ser
        195                 200                 205

Ala Gly Ala Arg Tyr Val Phe Ala Val Glu Pro Val Glu Trp Lys Arg
    210                 215                 220

Asp Gln Ala Leu Lys Phe Gly Ala Thr His Val Tyr Pro Asp Ile Asn
225                 230                 235                 240

Ala Ala Leu Met Gly Ile Ala Glu Val Thr Tyr Gly Leu Met Ala Gln
                245                 250                 255

Lys Val Ile Ile Thr Val Gly Lys Leu Asp Gly Ala Asp Val Asp Ser
            260                 265                 270
```

```
Tyr Leu Thr Ile Thr Ala Lys Gly Gly Thr Cys Val Leu Thr Ala Ile
            275                 280                 285

Gly Ser Leu Val Asp Thr Gln Val Thr Leu Asn Leu Ala Met Leu Thr
    290                 295                 300

Leu Leu Gln Lys Asn Ile Gln Gly Thr Ile Phe Gly Gly Gly Asn Pro
305                 310                 315                 320

His Tyr Asp Ile Pro Lys Leu Leu Ser Met Tyr Lys Ala Gly Lys Leu
                325                 330                 335

Asn Leu Asp Asp Met Val Thr Thr Ala Tyr Lys Leu Glu Gln Ile Asn
            340                 345                 350

Asp Gly Tyr Gln Asp Met Leu Asn Gly Lys Asn Ile Arg Gly Val Ile
        355                 360                 365

Arg Tyr Thr Asp Asp Arg
    370                 375

<210> SEQ ID NO 81
<211> LENGTH: 375
<212> TYPE: PRT
<213> ORGANISM: Equus caballus

<400> SEQUENCE: 81

Met Ser Thr Ala Gly Lys Val Ile Lys Cys Lys Ala Ala Val Leu Trp
1               5                   10                  15

Glu Glu Lys Lys Pro Phe Ser Ile Glu Val Glu Val Ala Pro Pro
            20                  25                  30

Lys Ala His Glu Val Arg Ile Lys Met Val Ala Thr Gly Ile Cys Arg
    35                  40                  45

Ser Asp Asp His Val Val Ser Gly Thr Leu Val Thr Pro Leu Pro Val
50                  55                  60

Ile Ala Gly His Glu Ala Ala Gly Ile Val Glu Ser Ile Gly Glu Gly
65                  70                  75                  80

Val Thr Thr Val Arg Pro Gly Asp Lys Val Ile Pro Leu Phe Thr Pro
                85                  90                  95

Gln Cys Gly Lys Cys Arg Val Cys Lys His Pro Glu Gly Asn Phe Cys
            100                 105                 110

Leu Lys Asn Asp Leu Ser Met Pro Arg Gly Thr Met Gln Asp Gly Thr
        115                 120                 125

Ser Arg Phe Thr Cys Arg Gly Lys Pro Ile His His Phe Leu Gly Thr
    130                 135                 140

Ser Thr Phe Ser Gln Tyr Thr Val Val Asp Glu Ile Ser Val Ala Lys
145                 150                 155                 160

Ile Asp Ala Ala Ser Pro Leu Glu Lys Val Cys Leu Ile Gly Cys Gly
                165                 170                 175

Phe Ser Thr Gly Tyr Gly Ser Ala Val Lys Val Ala Lys Val Thr Gln
            180                 185                 190

Gly Ser Thr Cys Ala Val Phe Gly Leu Gly Gly Val Gly Leu Ser Val
        195                 200                 205

Ile Met Gly Cys Lys Ala Ala Gly Ala Ala Arg Ile Ile Gly Val Asp
    210                 215                 220

Ile Asn Lys Asp Lys Phe Ala Lys Ala Lys Glu Val Gly Ala Thr Glu
225                 230                 235                 240

Cys Val Asn Pro Gln Asp Tyr Lys Lys Pro Ile Gln Glu Val Leu Thr
                245                 250                 255

Glu Met Ser Asn Gly Gly Val Asp Phe Ser Phe Glu Val Ile Gly Arg
            260                 265                 270
```

-continued

```
Leu Asp Thr Met Val Thr Ala Leu Ser Cys Cys Gln Glu Ala Tyr Gly
            275                 280                 285

Val Ser Val Ile Val Gly Val Pro Pro Asp Ser Gln Asn Leu Ser Met
        290                 295                 300

Asn Pro Met Leu Leu Ser Gly Arg Thr Trp Lys Gly Ala Ile Phe
305                 310                 315                 320

Gly Gly Phe Lys Ser Lys Asp Ser Val Pro Lys Leu Val Ala Asp Phe
                325                 330                 335

Met Ala Lys Lys Phe Ala Leu Asp Pro Leu Ile Thr His Val Leu Pro
            340                 345                 350

Phe Glu Lys Ile Asn Glu Gly Phe Asp Leu Leu Arg Ser Gly Glu Ser
        355                 360                 365

Ile Arg Thr Ile Leu Thr Phe
    370                 375

<210> SEQ ID NO 82
<211> LENGTH: 538
<212> TYPE: PRT
<213> ORGANISM: Thermatoga maritima

<400> SEQUENCE: 82

Met Ser Ile Lys Val Tyr Asp Thr Thr Leu Arg Asp Gly Ala Gln Ala
1               5                   10                  15

Phe Gly Val Ser Phe Ser Leu Glu Asp Lys Ile Arg Ile Ala Glu Ala
            20                  25                  30

Leu Asp Asp Leu Gly Val His Tyr Leu Glu Gly Gly Trp Pro Gly Ser
        35                  40                  45

Asn Pro Lys Asp Ile Ala Phe Phe Glu Ala Val Lys Gly Met Asn Phe
    50                  55                  60

Lys Asn Leu Lys Val Ala Ala Phe Ser Ser Thr Arg Arg Pro Asp Val
65                  70                  75                  80

Lys Ile Glu Glu Asp Ala Asn Ile Gln Thr Leu Ile Lys Ala Glu Thr
                85                  90                  95

Pro Val Tyr Thr Ile Phe Gly Lys Ser Trp Asp Leu His Val Glu Lys
            100                 105                 110

Ala Leu Arg Thr Thr Leu Glu Glu Asn Leu Lys Met Ile Tyr Asp Thr
        115                 120                 125

Val Ser Tyr Leu Lys Arg Phe Ala Asp Glu Val Ile Tyr Asp Ala Glu
    130                 135                 140

His Phe Phe Asp Gly Tyr Lys Ala Asn Arg Glu Tyr Ala Leu Lys Thr
145                 150                 155                 160

Leu Lys Val Ala Glu Glu Ala Gly Ala Asp Cys Leu Val Leu Ala Asp
                165                 170                 175

Thr Asn Gly Gly Thr Leu Pro His Glu Ile Glu Glu Ile Ile Glu Asp
            180                 185                 190

Val Lys Lys His Val Lys Ala Pro Leu Gly Ile His Ala His Asn Asp
        195                 200                 205

Ser Asp Val Ala Val Ala Asn Thr Leu Ala Ala Val Arg Lys Gly Ala
    210                 215                 220

Val His Val Gln Gly Thr Ile Asn Gly Leu Gly Glu Arg Cys Gly Asn
225                 230                 235                 240

Ala Asn Leu Cys Ser Val Ile Pro Asn Leu Val Leu Lys Met Gly Leu
                245                 250                 255

Glu Val Ile Pro Lys Glu Asn Leu Lys Lys Leu Phe Asp Val Ala His
            260                 265                 270
```

Leu Val Ala Glu Leu Ser Gly Arg Pro His Ile Glu Asn Met Pro Tyr
            275                 280                 285

Val Gly Asp Tyr Ala Phe Ala His Lys Gly Val His Val Ser Ala
        290                 295                 300

Ile Lys Arg Asp Pro Arg Thr Tyr Glu His Ile Asp Pro Glu Leu Val
305                 310                 315                 320

Gly Asn Arg Arg Ile Ile Ser Ile Ser Glu Leu Ser Gly Lys Ser Asn
                325                 330                 335

Val Leu Glu Lys Ile Lys Glu Met Gly Phe Glu Ile Asp Glu Ser Ser
            340                 345                 350

Pro Lys Val Arg Glu Ile Leu Lys Ile Lys Glu Leu Glu Ala Gln
        355                 360                 365

Gly Tyr His Phe Glu Gly Ala Glu Ala Ser Phe Glu Leu Leu Val Arg
        370                 375                 380

Asp Met Leu Gly Lys Arg Lys Tyr Phe Glu Phe Leu Gly Phe Thr
385                 390                 395                 400

Val Met Thr Ile Lys Asn Arg Asp Glu Glu Ser Phe Ser Glu Ala Thr
                405                 410                 415

Val Lys Val Arg Val Pro Asp Glu Val Ala Lys Arg Leu Gly His Asp
            420                 425                 430

Glu Pro Phe Glu His Thr Ala Ala Glu Gly Gly Pro Val Glu Ala
        435                 440                 445

Leu Asp Arg Ala Val Arg Lys Ala Leu Glu Lys Phe Tyr Pro Ser Leu
        450                 455                 460

Lys Asp Thr Lys Leu Thr Asp Tyr Lys Val Arg Ile Leu Asn Glu Gln
465                 470                 475                 480

Ala Gly Thr Lys Ala Thr Thr Arg Val Leu Ile Glu Ser Ser Asp Gly
                485                 490                 495

Lys Arg Arg Trp Gly Thr Val Gly Val Ser Pro Asn Ile Ile Glu Ala
            500                 505                 510

Ser Trp Thr Ala Leu Leu Glu Ser Leu Glu Tyr Lys Leu His Lys Asp
        515                 520                 525

Glu Glu Glu Met Arg Asn Asp Glu Glu Asn
        530                 535

<210> SEQ ID NO 83
<211> LENGTH: 382
<212> TYPE: PRT
<213> ORGANISM: Thermatoga maritima

<400> SEQUENCE: 83

Met Ser Ile Lys Val Tyr Asp Thr Thr Leu Arg Asp Gly Ala Gln Ala
1               5                   10                  15

Phe Gly Val Ser Phe Ser Leu Glu Asp Lys Ile Arg Ile Ala Glu Ala
            20                  25                  30

Leu Asp Asp Leu Gly Val His Tyr Leu Glu Gly Gly Trp Pro Gly Ser
        35                  40                  45

Asn Pro Lys Asp Ile Ala Phe Phe Glu Ala Val Lys Gly Met Asn Phe
    50                  55                  60

Lys Asn Leu Lys Val Ala Ala Phe Ser Ser Thr Arg Arg Pro Asp Val
65                  70                  75                  80

Lys Ile Glu Glu Asp Ala Asn Ile Gln Thr Leu Ile Lys Ala Glu Thr
                85                  90                  95

Pro Val Tyr Thr Ile Phe Gly Lys Ser Trp Asp Leu His Val Glu Lys
            100                 105                 110

```
Ala Leu Arg Thr Thr Leu Glu Glu Asn Leu Lys Met Ile Tyr Asp Thr
            115                 120                 125

Val Ser Tyr Leu Lys Arg Phe Ala Asp Glu Val Ile Tyr Asp Ala Glu
    130                 135                 140

His Phe Phe Asp Gly Tyr Lys Ala Asn Arg Glu Tyr Ala Leu Lys Thr
145                 150                 155                 160

Leu Lys Val Ala Glu Glu Ala Gly Ala Asp Cys Leu Val Leu Ala Asp
                165                 170                 175

Thr Asn Gly Gly Thr Leu Pro His Glu Ile Glu Ile Ile Glu Asp
            180                 185                 190

Val Lys Lys His Val Lys Ala Pro Leu Gly Ile His Ala His Asn Asp
    195                 200                 205

Ser Asp Val Ala Val Ala Asn Thr Leu Ala Ala Val Arg Lys Gly Ala
    210                 215                 220

Val His Val Gln Gly Thr Ile Asn Gly Leu Gly Glu Arg Cys Gly Asn
225                 230                 235                 240

Ala Asn Leu Cys Ser Val Ile Pro Asn Leu Val Leu Lys Met Gly Leu
                245                 250                 255

Glu Val Ile Pro Lys Glu Asn Leu Lys Leu Phe Asp Val Ala His
        260                 265                 270

Leu Val Ala Glu Leu Ser Gly Arg Pro His Ile Glu Asn Met Pro Tyr
            275                 280                 285

Val Gly Asp Tyr Ala Phe Ala His Lys Gly Gly Val His Val Ser Ala
    290                 295                 300

Ile Lys Arg Asp Pro Arg Thr Tyr Glu His Ile Asp Pro Glu Leu Val
305                 310                 315                 320

Gly Asn Arg Arg Ile Ile Ser Ile Ser Glu Leu Ser Gly Lys Ser Asn
                325                 330                 335

Val Leu Glu Lys Ile Lys Glu Met Gly Phe Glu Ile Asp Glu Ser Ser
            340                 345                 350

Pro Lys Val Arg Glu Ile Leu Lys Lys Ile Lys Glu Leu Glu Ala Gln
            355                 360                 365

Gly Tyr His Phe Glu Gly Ala Glu Ala Ser Phe Glu Leu Leu
            370                 375                 380

<210> SEQ ID NO 84
<211> LENGTH: 316
<212> TYPE: PRT
<213> ORGANISM: Thermatoga maritima

<400> SEQUENCE: 84

Met Ser Ile Lys Val Tyr Asp Thr Thr Leu Arg Asp Gly Ala Gln Ala
1               5                   10                  15

Phe Gly Val Ser Phe Ser Leu Glu Asp Lys Ile Arg Ile Ala Glu Ala
            20                  25                  30

Leu Asp Asp Leu Gly Val His Tyr Leu Glu Gly Gly Trp Pro Gly Ser
        35                  40                  45

Asn Pro Lys Asp Ile Ala Phe Phe Glu Ala Val Lys Gly Met Asn Phe
    50                  55                  60

Lys Asn Leu Lys Val Ala Ala Phe Ser Ser Thr Arg Arg Pro Asp Val
65                  70                  75                  80

Lys Ile Glu Glu Asp Ala Asn Ile Gln Thr Leu Ile Lys Ala Glu Thr
                85                  90                  95

Pro Val Tyr Thr Ile Phe Gly Lys Ser Trp Asp Leu His Val Glu Lys
            100                 105                 110
```

```
Ala Leu Arg Thr Thr Leu Glu Glu Asn Leu Lys Met Ile Tyr Asp Thr
            115                 120                 125

Val Ser Tyr Leu Lys Arg Phe Ala Asp Glu Val Ile Tyr Asp Ala Glu
        130                 135                 140

His Phe Phe Asp Gly Tyr Lys Ala Asn Arg Glu Tyr Ala Leu Lys Thr
145                 150                 155                 160

Leu Lys Val Ala Glu Ala Gly Ala Asp Cys Leu Val Leu Ala Asp
                165                 170                 175

Thr Asn Gly Gly Thr Leu Pro His Glu Ile Glu Ile Ile Glu Asp
            180                 185                 190

Val Lys Lys His Val Lys Ala Pro Leu Gly Ile His Ala His Asn Asp
        195                 200                 205

Ser Asp Val Ala Val Ala Asn Thr Leu Ala Ala Val Arg Lys Gly Ala
210                 215                 220

Val His Val Gln Gly Thr Ile Asn Gly Leu Gly Glu Arg Cys Gly Asn
225                 230                 235                 240

Ala Asn Leu Cys Ser Val Ile Pro Asn Leu Val Leu Lys Met Gly Leu
                245                 250                 255

Glu Val Ile Pro Lys Glu Asn Leu Lys Lys Leu Phe Asp Val Ala His
            260                 265                 270

Leu Val Ala Glu Leu Ser Gly Arg Pro His Ile Glu Asn Met Pro Tyr
        275                 280                 285

Val Gly Asp Tyr Ala Phe Ala His Lys Gly Val His Val Ser Ala
            290                 295                 300

Ile Lys Arg Asp Pro Arg Thr Tyr Glu His Ile Asp
305                 310                 315

<210> SEQ ID NO 85
<211> LENGTH: 547
<212> TYPE: PRT
<213> ORGANISM: Synechocystis sp.

<400> SEQUENCE: 85

Met Ala Thr Lys Lys Thr Ser Leu Trp Leu Tyr Asp Thr Thr Leu Arg
1               5                   10                  15

Asp Gly Ala Gln Arg Glu Gly Ile Ser Leu Ser Leu Thr Asp Lys Leu
            20                  25                  30

Thr Ile Ala Arg Arg Leu Asp Gln Leu Gly Ile Pro Phe Ile Glu Gly
        35                  40                  45

Gly Trp Pro Gly Ala Asn Pro Lys Asp Val Gln Phe Phe Trp Gln Leu
    50                  55                  60

Gln Glu Glu Pro Leu Glu Gln Ala Glu Ile Val Ala Phe Cys Ser Thr
65                  70                  75                  80

Arg Arg Pro His Lys Ala Val Glu Thr Asp Lys Met Leu Gln Ala Ile
                85                  90                  95

Leu Ser Ala Gly Thr Arg Trp Val Thr Ile Phe Gly Lys Ser Trp Asp
            100                 105                 110

Leu His Val Leu Glu Gly Leu Gln Thr Ser Leu Ala Glu Asn Leu Ala
        115                 120                 125

Met Ile Ser Asp Thr Ile Ala Tyr Leu Arg Ser Gln Gly Arg Arg Val
    130                 135                 140

Ile Tyr Asp Ala Glu His Trp Phe Asp Gly Tyr Arg Ala Asn Pro Asp
145                 150                 155                 160

Tyr Ala Leu Ala Thr Leu Ala Thr Ala Gln Gln Ala Gly Ala Glu Trp
                165                 170                 175
```

```
Leu Val Met Cys Asp Thr Asn Gly Gly Thr Leu Pro Gly Gln Ile Ser
            180                 185                 190

Glu Ile Thr Thr Lys Val Arg Arg Ser Leu Gly Leu Asp Gly Gln Ser
            195                 200                 205

Asp Arg Gln Pro Gln Leu Gly Ile His Ala His Asn Asp Ser Gly Thr
210                 215                 220

Ala Val Ala Asn Ser Leu Leu Ala Val Glu Ala Gly Ala Thr Met Val
225                 230                 235                 240

Gln Gly Thr Ile Asn Gly Tyr Gly Glu Arg Cys Gly Asn Ala Asn Leu
            245                 250                 255

Cys Thr Leu Ile Pro Asn Leu Gln Leu Lys Leu Asp Tyr Asp Cys Ile
            260                 265                 270

Glu Pro Glu Lys Leu Ala His Leu Thr Ser Thr Ser Arg Leu Ile Ser
            275                 280                 285

Glu Ile Val Asn Leu Ala Pro Asp Asp His Ala Pro Phe Val Gly Arg
            290                 295                 300

Ser Ala Phe Ala His Lys Gly Gly Ile His Val Ser Ala Val Gln Arg
305                 310                 315                 320

Asn Pro Phe Thr Tyr Glu His Ile Ala Pro Asn Leu Val Gly Asn Glu
            325                 330                 335

Arg Arg Ile Val Val Ser Glu Gln Ala Gly Leu Ser Asn Val Leu Ser
            340                 345                 350

Lys Ala Glu Leu Phe Gly Ile Ala Leu Asp Arg Gln Asn Pro Ala Cys
            355                 360                 365

Arg Thr Ile Leu Ala Thr Leu Lys Asp Leu Glu Gln Gln Gly Tyr Gln
            370                 375                 380

Phe Glu Ala Ala Glu Ala Ser Phe Glu Leu Leu Met Arg Gln Ala Met
385                 390                 395                 400

Gly Asp Arg Gln Pro Leu Phe Leu Val Gln Gly Phe Gln Val His Cys
            405                 410                 415

Asp Leu Leu Thr Pro Ala Glu Asn Pro Ala Tyr Arg Asn Ala Leu Ala
            420                 425                 430

Thr Val Lys Val Thr Val Asn Gly Gln Asn Ile Leu Glu Val Ala Glu
            435                 440                 445

Gly Asn Gly Pro Val Ser Ala Leu Asp Gln Ala Leu Arg Lys Ala Leu
            450                 455                 460

Thr Arg Phe Tyr Pro Gln Ile Ala Asp Phe His Leu Thr Asp Tyr Lys
465                 470                 475                 480

Val Arg Ile Leu Asp Gly Gly Ala Gly Thr Ser Ala Lys Thr Arg Val
            485                 490                 495

Leu Val Glu Ser Ser Asn Gly Asp Arg Arg Trp Thr Thr Val Gly Val
            500                 505                 510

Ser Gly Asn Ile Leu Glu Ala Ser Tyr Gln Ala Val Val Glu Gly Ile
            515                 520                 525

Glu Tyr Gly Leu Arg Leu Leu Thr Cys Gly Leu Thr Asn Gln Glu Ala
            530                 535                 540

Ile Ser Ser
545

<210> SEQ ID NO 86
<211> LENGTH: 528
<212> TYPE: PRT
<213> ORGANISM: Geobacter sulfurreducens

<400> SEQUENCE: 86
```

```
Met Ser Leu Val Lys Leu Tyr Asp Thr Thr Leu Arg Asp Gly Thr Gln
  1               5                   10                  15

Ala Glu Asp Ile Ser Phe Leu Val Glu Asp Lys Ile Arg Ile Ala His
             20                  25                  30

Lys Leu Asp Glu Ile Gly Ile His Tyr Ile Glu Gly Gly Trp Pro Gly
         35                  40                  45

Ser Asn Pro Lys Asp Val Ala Phe Phe Lys Asp Ile Lys Lys Glu Lys
     50                  55                  60

Leu Ser Gln Ala Lys Ile Ala Ala Phe Gly Ser Thr Arg Arg Ala Lys
 65              70                  75                      80

Val Thr Pro Asp Lys Asp His Asn Leu Lys Thr Leu Ile Gln Ala Glu
                 85                  90                  95

Pro Asp Val Cys Thr Ile Phe Gly Lys Thr Trp Asp Phe His Val His
                100                 105                 110

Glu Ala Leu Arg Ile Ser Leu Glu Glu Asn Leu Glu Leu Ile Phe Asp
             115                 120                 125

Ser Leu Glu Tyr Leu Lys Ala Asn Val Pro Glu Val Phe Tyr Asp Ala
         130                 135                 140

Glu His Phe Phe Asp Gly Tyr Lys Ala Asn Pro Asp Tyr Ala Ile Lys
145                 150                 155                 160

Thr Leu Lys Ala Ala Gln Asp Ala Lys Ala Asp Cys Ile Val Leu Cys
                 165                 170                 175

Asp Thr Asn Gly Gly Thr Met Pro Phe Glu Leu Val Glu Ile Ile Arg
             180                 185                 190

Glu Val Arg Lys His Ile Thr Ala Pro Leu Gly Ile His Thr His Asn
         195                 200                 205

Asp Ser Glu Cys Ala Val Ala Asn Ser Leu His Ala Val Ser Glu Gly
     210                 215                 220

Ile Val Gln Val Gln Gly Thr Ile Asn Gly Phe Gly Glu Arg Cys Gly
225                 230                 235                 240

Asn Ala Asn Leu Cys Ser Ile Ile Pro Ala Leu Lys Leu Lys Met Lys
                 245                 250                 255

Arg Glu Cys Ile Gly Asp Asp Gln Leu Arg Lys Leu Arg Asp Leu Ser
             260                 265                 270

Arg Phe Val Tyr Glu Leu Ala Asn Leu Ser Pro Asn Lys His Gln Ala
         275                 280                 285

Tyr Val Gly Asn Ser Ala Phe Ala His Lys Gly Gly Val His Val Ser
     290                 295                 300

Ala Ile Gln Arg His Pro Glu Thr Tyr Glu His Leu Arg Pro Glu Leu
305                 310                 315                 320

Val Gly Asn Met Thr Arg Val Leu Val Ser Asp Leu Ser Gly Arg Ser
                 325                 330                 335

Asn Ile Leu Ala Lys Ala Glu Glu Phe Asn Ile Lys Met Asp Ser Lys
             340                 345                 350

Asp Pro Val Thr Leu Glu Ile Leu Glu Asn Ile Lys Glu Met Glu Asn
         355                 360                 365

Arg Gly Tyr Gln Phe Glu Gly Ala Glu Ala Ser Phe Glu Leu Leu Met
     370                 375                 380

Lys Arg Ala Leu Gly Thr His Arg Lys Phe Phe Ser Val Ile Gly Phe
385                 390                 395                 400

Arg Val Ile Asp Glu Lys Arg His Glu Asp Gln Lys Pro Leu Ser Glu
                 405                 410                 415

Ala Thr Ile Met Val Lys Val Gly Gly Lys Ile Glu His Thr Ala Ala
```

-continued

```
                        420                 425                 430
Glu Gly Asn Gly Pro Val Asn Ala Leu Asp Asn Ala Leu Arg Lys Ala
                435                 440                 445
Leu Glu Lys Phe Tyr Pro Arg Leu Lys Glu Val Lys Leu Leu Asp Tyr
        450                 455                 460
Lys Val Arg Val Leu Pro Ala Gly Gln Gly Thr Ala Ser Ser Ile Arg
465                 470                 475                 480
Val Leu Ile Glu Ser Gly Asp Lys Glu Ser Arg Trp Gly Thr Val Gly
                485                 490                 495
Val Ser Glu Asn Ile Val Asp Ala Ser Tyr Gln Ala Leu Leu Asp Ser
                500                 505                 510
Val Glu Tyr Lys Leu His Lys Ser Glu Glu Ile Glu Gly Ser Lys Lys
        515                 520                 525

<210> SEQ ID NO 87
<211> LENGTH: 424
<212> TYPE: PRT
<213> ORGANISM: Methanococcus jannaschii

<400> SEQUENCE: 87

Met Gly Met Thr Ile Val Glu Lys Ile Leu Ala Lys Ala Ser Gly Lys
1               5                   10                  15
Lys Glu Val Ser Pro Gly Asp Ile Val Met Ala Asn Ile Asp Val Ala
                20                  25                  30
Met Val His Asp Ile Thr Gly Pro Leu Thr Val Asn Thr Leu Lys Glu
        35                  40                  45
Tyr Gly Ile Glu Lys Val Trp Asn Pro Glu Lys Ile Val Ile Leu Phe
    50                  55                  60
Asp His Gln Val Pro Ala Asp Ser Ile Lys Ala Ala Glu Asn His Ile
65                  70                  75                  80
Leu Met Arg Lys Phe Val Lys Glu Gln Gly Ile Lys Tyr Phe Tyr Asp
                85                  90                  95
Ile Arg Glu Gly Val Cys His Gln Val Leu Pro Glu Lys Gly His Val
                100                 105                 110
Ala Pro Gly Glu Val Val Gly Ala Asp Ser His Thr Cys Thr His
            115                 120                 125
Gly Ala Phe Gly Ala Phe Ala Thr Gly Ile Gly Ser Thr Asp Met Ala
        130                 135                 140
His Val Phe Ala Thr Gly Lys Leu Trp Phe Lys Val Pro Glu Thr Ile
145                 150                 155                 160
Tyr Phe Asn Ile Thr Gly Asp Leu Gln Pro Tyr Val Thr Ser Lys Asp
                165                 170                 175
Val Ile Leu Ser Ile Ile Gly Glu Val Gly Val Asp Gly Ala Thr Tyr
                180                 185                 190
Lys Ala Cys Gln Phe Gly Gly Glu Thr Val Lys Lys Met Ser Ile Ala
        195                 200                 205
Ser Arg Met Thr Met Thr Asn Met Ala Ile Glu Met Gly Gly Lys Thr
    210                 215                 220
Gly Ile Ile Glu Pro Asp Glu Lys Thr Ile Gln Tyr Val Lys Glu Ala
225                 230                 235                 240
Met Lys Lys His Gly Thr Glu Arg Pro Phe Glu Val Ile Lys Gly Asp
                245                 250                 255
Glu Asp Ala Glu Phe Ala Glu Val Tyr Glu Ile Glu Ala Asp Lys Ile
                260                 265                 270
Glu Pro Val Phe Ala Cys Pro His Asn Val Asp Asn Val Lys Gln Ala
```

```
                      275                 280                 285
Arg Glu Val Ala Gly Lys Pro Ile Asp Gln Val Phe Ile Gly Ser Cys
    290                 295                 300

Thr Asn Gly Arg Leu Glu Asp Leu Arg Met Ala Ile Lys Ile Ile Glu
305                 310                 315                 320

Lys His Gly Gly Ile Ala Asp Asp Val Arg Val Val Thr Pro Ala
                325                 330                 335

Ser Arg Glu Glu Tyr Leu Lys Ala Leu Lys Gly Ile Ile Glu Lys
                340                 345                 350

Phe Leu Lys Tyr Gly Cys Val Val Thr Asn Pro Ser Cys Ser Ala Cys
            355                 360                 365

Met Gly Ser Leu Tyr Gly Val Leu Gly Pro Gly Glu Val Cys Val Ser
    370                 375                 380

Thr Ser Asn Arg Asn Phe Arg Gly Arg Gln Gly Ser Leu Glu Ala Glu
385                 390                 395                 400

Ile Tyr Leu Ala Ser Pro Ile Thr Ala Ala Cys Ala Val Lys Gly
                405                 410                 415

Glu Leu Val Asp Pro Arg Asp Leu
                420

<210> SEQ ID NO 88
<211> LENGTH: 168
<212> TYPE: PRT
<213> ORGANISM: Methanococcus jannaschii

<400> SEQUENCE: 88

Met Arg Ser Ile Ile Lys Gly Arg Val Trp Lys Phe Gly Asn Asn Val
1               5                   10                  15

Asp Thr Asp Ala Ile Leu Pro Ala Arg Tyr Leu Val Tyr Thr Lys Pro
            20                  25                  30

Glu Glu Leu Ala Gln Phe Val Met Thr Gly Ala Asp Pro Asp Phe Pro
        35                  40                  45

Lys Lys Val Lys Pro Gly Asp Ile Ile Val Gly Gly Lys Asn Phe Gly
    50                  55                  60

Cys Gly Ser Ser Arg Glu His Ala Pro Leu Gly Leu Lys Gly Ala Gly
65                  70                  75                  80

Ile Ser Cys Val Ile Ala Glu Ser Phe Ala Arg Ile Phe Tyr Arg Asn
                85                  90                  95

Ala Ile Asn Val Gly Leu Pro Leu Ile Glu Cys Lys Gly Ile Ser Glu
            100                 105                 110

Lys Val Asn Glu Gly Asp Glu Leu Glu Val Asn Leu Glu Thr Gly Glu
        115                 120                 125

Ile Lys Asn Leu Thr Thr Gly Glu Val Leu Lys Gly Gln Lys Leu Pro
    130                 135                 140

Glu Phe Met Met Glu Ile Leu Glu Ala Gly Gly Leu Met Pro Tyr Leu
145                 150                 155                 160

Lys Lys Lys Met Ala Glu Ser Gln
                165

<210> SEQ ID NO 89
<211> LENGTH: 333
<212> TYPE: PRT
<213> ORGANISM: Methanococcus jannaschii

<400> SEQUENCE: 89

Met His Lys Ile Cys Val Ile Glu Gly Asp Gly Ile Gly Lys Glu Val
1               5                   10                  15
```

Val Pro Ala Thr Ile Gln Val Leu Glu Ala Thr Gly Leu Pro Phe Glu
            20                  25                  30

Phe Val Tyr Ala Glu Ala Gly Asp Glu Val Tyr Lys Arg Thr Gly Lys
        35                  40                  45

Ala Leu Pro Glu Glu Thr Ile Glu Thr Ala Leu Asp Cys Asp Ala Val
    50                  55                  60

Leu Phe Gly Ala Ala Gly Glu Thr Ala Ala Asp Val Ile Val Lys Leu
65                  70                  75                  80

Arg His Ile Leu Asp Thr Tyr Ala Asn Ile Arg Pro Val Lys Ala Tyr
                85                  90                  95

Lys Gly Val Lys Cys Leu Arg Pro Asp Ile Asp Tyr Val Ile Val Arg
            100                 105                 110

Glu Asn Thr Glu Gly Leu Tyr Lys Gly Ile Glu Ala Glu Ile Asp Glu
        115                 120                 125

Gly Ile Thr Ile Ala Thr Arg Val Ile Thr Glu Lys Ala Cys Glu Arg
    130                 135                 140

Ile Phe Arg Phe Ala Phe Asn Leu Ala Arg Glu Arg Lys Lys Met Gly
145                 150                 155                 160

Lys Glu Gly Lys Val Thr Cys Ala His Lys Ala Asn Val Leu Lys Leu
                165                 170                 175

Thr Asp Gly Leu Phe Lys Lys Ile Phe Tyr Lys Val Ala Glu Glu Tyr
            180                 185                 190

Asp Asp Ile Lys Ala Glu Asp Tyr Tyr Ile Asp Ala Met Asn Met Tyr
        195                 200                 205

Ile Ile Thr Lys Pro Gln Val Phe Asp Val Val Thr Ser Asn Leu
    210                 215                 220

Phe Gly Asp Ile Leu Ser Asp Gly Ala Ala Gly Thr Val Gly Gly Leu
225                 230                 235                 240

Gly Leu Ala Pro Ser Ala Asn Ile Gly Asp Glu His Gly Leu Phe Glu
                245                 250                 255

Pro Val His Gly Ser Ala Pro Asp Ile Ala Gly Lys Lys Ile Ala Asn
            260                 265                 270

Pro Thr Ala Thr Ile Leu Ser Ala Val Leu Met Leu Arg Tyr Leu Gly
        275                 280                 285

Glu Tyr Glu Ala Ala Asp Lys Val Glu Lys Ala Leu Glu Glu Val Leu
    290                 295                 300

Ala Leu Gly Leu Thr Thr Pro Asp Leu Gly Gly Asn Leu Asn Thr Phe
305                 310                 315                 320

Glu Met Ala Glu Glu Val Ala Lys Arg Val Arg Glu Glu
                325                 330

<210> SEQ ID NO 90
<211> LENGTH: 281
<212> TYPE: PRT
<213> ORGANISM: Saccharomyces cerevisiae

<400> SEQUENCE: 90

Met Ser Glu Tyr Gln Pro Ser Leu Phe Ala Leu Asn Pro Met Gly Phe
 1               5                  10                  15

Ser Pro Leu Asp Gly Ser Lys Ser Thr Asn Glu Asn Val Ser Ala Ser
            20                  25                  30

Thr Ser Thr Ala Lys Pro Met Val Gly Gln Leu Ile Phe Asp Lys Phe
        35                  40                  45

Ile Lys Thr Glu Glu Asp Pro Ile Ile Lys Gln Asp Thr Pro Ser Asn
    50                  55                  60

```
Leu Asp Phe Asp Phe Ala Leu Pro Gln Thr Ala Thr Ala Pro Asp Ala
 65                  70                  75                  80

Lys Thr Val Leu Pro Ile Pro Glu Leu Asp Asp Ala Val Val Glu Ser
                 85                  90                  95

Phe Phe Ser Ser Ser Thr Asp Ser Thr Pro Met Phe Glu Tyr Glu Asn
            100                 105                 110

Leu Glu Asp Asn Ser Lys Glu Trp Thr Ser Leu Phe Asp Asn Asp Ile
        115                 120                 125

Pro Val Thr Thr Asp Asp Val Ser Leu Ala Asp Lys Ala Ile Glu Ser
    130                 135                 140

Thr Glu Glu Val Ser Leu Val Pro Ser Asn Leu Glu Val Ser Thr Thr
145                 150                 155                 160

Ser Phe Leu Pro Thr Pro Val Leu Glu Asp Ala Lys Leu Thr Gln Thr
                165                 170                 175

Arg Lys Val Lys Lys Pro Asn Ser Val Val Lys Lys Ser His His Val
            180                 185                 190

Gly Lys Asp Asp Glu Ser Arg Leu Asp His Leu Gly Val Val Ala Tyr
        195                 200                 205

Asn Arg Lys Gln Arg Ser Ile Pro Leu Ser Pro Ile Val Pro Glu Ser
210                 215                 220

Ser Asp Pro Ala Ala Leu Lys Arg Ala Arg Asn Thr Glu Ala Ala Arg
225                 230                 235                 240

Arg Ser Arg Ala Arg Lys Leu Gln Arg Met Lys Gln Leu Glu Asp Lys
                245                 250                 255

Val Glu Glu Leu Leu Ser Lys Asn Tyr His Leu Glu Asn Glu Val Ala
                260                 265                 270

Arg Leu Lys Lys Leu Val Gly Glu Arg
                275                 280

<210> SEQ ID NO 91
<211> LENGTH: 30
<212> TYPE: DNA
<213> ORGANISM: Artificial Sequence
<220> FEATURE:
<223> OTHER INFORMATION: Primer

<400> SEQUENCE: 91
atgtatactg tgggggatta tttgttggat                                              30

<210> SEQ ID NO 92
<211> LENGTH: 30
<212> TYPE: DNA
<213> ORGANISM: Artificial Sequence
<220> FEATURE:
<223> OTHER INFORMATION: Primer

<400> SEQUENCE: 92
ttatttgttt tgctcagcaa atagtttccc                                              30

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
atggattctg aggttgctgc tt                                                      22
```

```
<210> SEQ ID NO 94
<211> LENGTH: 26
<212> TYPE: DNA
<213> ORGANISM: Artificial Sequence
<220> FEATURE:
<223> OTHER INFORMATION: Primer

<400> SEQUENCE: 94
ttagaaacac ttgtggtgaa cgatag                                          26

<210> SEQ ID NO 95
<211> LENGTH: 28
<212> TYPE: DNA
<213> ORGANISM: Artificial Sequence
<220> FEATURE:
<223> OTHER INFORMATION: Primer

<400> SEQUENCE: 95
atgtcttatc ctgagaaatt tgaaggta                                        28

<210> SEQ ID NO 96
<211> LENGTH: 25
<212> TYPE: DNA
<213> ORGANISM: Artificial Sequence
<220> FEATURE:
<223> OTHER INFORMATION: Primer

<400> SEQUENCE: 96
ctagtctgaa aattctttgt cgtag                                           25

<210> SEQ ID NO 97
<211> LENGTH: 13812
<212> TYPE: DNA
<213> ORGANISM: Saccharomyces cerevisiae

<400> SEQUENCE: 97
atagcttcaa aatgtttcta ctcctttttt actcttccag attttctcgg actccgcgca     60
tcgccgtacc acttcaaaac acccaagcac agcatactaa atttcccctc tttcttcctc    120
tagggtgtcg ttaattaccc gtactaaagg tttggaaaag aaaaaagaga ccgcctcgtt    180
tctttttctt cgtcgaaaaa ggcaataaaa attttttatca cgtttctttt tcttgaaaat    240
ttttttttg attttttttct ctttcgatga cctcccattg atatttaagt taataaacgg    300
tcttcaattt ctcaagtttc agtttcattt ttcttgttct attacaactt tttttacttc    360
ttgctcatta gaaagaaagc atagcaatct aatctaagtt ttctagaact agtggatccc    420
ccatggctga ctcgcaaccc ctgtccggtg ctccggaagg tgccgaatat ttaagagcag    480
tgctgcgcgc gccggtttac gaggcggcgc aggttacgcc gctacaaaaa atggaaaaac    540
tgtcgtcgcg tcttgataac gtcattctgg tgaagcgcga agatcgccag ccagtgcaca    600
gctttaagct gcgcggcgca tacgccatga tggcgggcct gacggaagaa cagaaagcgc    660
acggcgtgat cactgcttct gcgggtaacc acgcgcaggg cgtcgcgttt tcttctgcgc    720
ggttaggcgt gaaggccctg atcgttatgc caaccgccac cgccgacatc aaagtcgacg    780
cggtgcgcgg cttcggcggc gaagtgctgc tccacgcgc gaactttgat gaagcgaaag    840
ccaaagcgat cgaactgtca cagcagcagg ggttcacctg ggtgccgccg ttcgaccatc    900
cgatggtgat tgccgggcaa ggcacgctgg cgctggaact gctccagcag gacgccatc     960
tcgaccgcgt atttgtgcca gtcggcggcg gcggtctggc tgctggcgtg gcggtgctga   1020
tcaaacaact gatgccgcaa atcaaagtga tcgccgtaga agcggaagac tccgcctgcc   1080
tgaaagcagc gctggatgcg ggtcatccgg ttgatctgcc gcgcgtaggg ctatttgctg   1140
```

```
aaggcgtagc ggtaaaacgc atcggtgacg aaaccttccg tttatgccag gagtatctcg    1200
acgacatcat caccgtcgat agcgatgcga tctgtgcggc gatgaaggat ttattcgaag    1260
atgtgcgcgt ggtggcggaa ccctctggcg cgctggcgct ggcgggaatg aaaaaatata    1320
tcgccctgca caacattcgc ggcgaacggc tggcgcatat tctttccggt gccaacgtga    1380
acttccacgg cctgcgctac gtctcagaac gctgcgaact gggcgaacag cgtgaagcgt    1440
tgttggcggt gaccattccg gaagaaaaag gcagcttcct caaattctgc caactgcttg    1500
gcgggcgttc ggtcaccgag ttcaactacc gttttgccga tgccaaaaac gcctgcatct    1560
ttgtcggtgt gcgcctgagc cgcggcctcg aagagcgcaa agaaattttg cagatgctca    1620
acgacggcgg ctacagcgtg gttgatctct ccgacgacga aatggcgaag ctacacgtgc    1680
gctatatggt cggcggacgt ccatcgcatc cgttgcagga acgcctctac agcttcgaat    1740
tcccggaatc accgggcgcg ctgctgcgct tcctcaacac gctgggtacg tactggaaca    1800
tttctttgtt ccactatcac agccatggca ccgactacgg cgcgtactg gcggcgttcg    1860 aacttggcga ccatgaaccg gatttcgaaa cccggctgaa tgagctgggc tacgattgcc    1920
acgacgaaac caataacccg cgcgttcaggt tcttttttggc gggttagggg gctgcaggaa    1980
ttcgatatca agcttatcga taccgtcgac ctcgagtcat gtaattagtt atgtcacgct    2040
tacattcacg ccctccccc acatccgctc taaccgaaaa ggaaggagtt agacaacctg    2100
aagtctaggt ccctatttat tttttataag ttatgttagt attaagaacg ttatttatat    2160
ttcaaatttt tctttttttt ctgtacagac gcgtgtacgc atgtaacatt atactgaaaa    2220
ccttgcttga aaggtttttg ggacgctcga aggctttaat ttgcggccgg tacccaattc    2280
gccctatagt gagtcgtatt acgcgcgcat agcttcaaaa tgtttctact cctttttttac    2340 tcttccagat tttctcggac tccgcgcatc gccgtaccac ttcaaaacac ccaagcacag    2400
catactaaat ttcccctctt tcttcctcta gggtgtcgtt aattacccgt actaaaggtt    2460
tggaaaagaa aaagagacc gcctcgtttc ttttttcttcg tcgaaaaagg caataaaaat    2520
ttttatcacg tttcttttttc ttgaaaattt tttttttgat ttttttctct ttcgatgacc    2580
tcccattgat atttaagtta ataaacggtc ttcaatttct caagtttcag tttcatttttt    2640 cttgttctat tacaactttt tttacttctt gctcattaga aagaaagcat agcaatctaa    2700
tctaagtttt ctagaactag tggatccccc atgaatggcg cacagtgggt ggtacatgcg    2760
ttgcgggcac agggtgtgaa caccgttttc ggttatccgg gtggcgcaat tatgccggtt    2820
tacgatgcat tgtatgacgg cggcgtggag cacttgctat gccgacatga gcagggtgcg    2880
gcaatggcgg ctatcggtta tgctcgtgct accggcaaaa ctggcgtatg tatcgccacg    2940
tctggtccgg gcgcaaccaa cctgataacc gggcttgcgg acgcactgtt agattccatc    3000
cctgttgttg ccatcaccgg tcaagtgtcc gcaccgttta tcggcactga cgcatttcag    3060
gaagtggatg tcctgggatt gtcgttagcc tgtaccaagc acagctttct ggtgcagtcg    3120
ctggaagagt tgccgcgcat catggctgaa gcattcgacg ttgcctgctc aggtcgtcct    3180
ggtccggttc tggtcgatat cccaaaagat atccagttag ccagcggtga cctggaaccg    3240
tggttcacca ccgttgaaaa cgaagtgact ttcccacatg ccgaagttga gcaagcgcgc    3300
cagatgctgg caaaagcgca aaaccgatg ctgtacgttg gcggtggcgt tggtatggcg    3360
caggcagttc cggctttgcg tgaatttctc gctgccacaa aaatgcctgc cacctgtacg    3420
ctgaaagggc tgggcgcagt agaagcagat tatccgtact atctgggcat gctgggaatg    3480
catggcacca aagcggcgaa cttcgcggtg caggagtgcg acttgctgat cgccgtgggt    3540
```

```
gcacgttttg atgaccgggt gaccggcaaa ctgaacacct tcgcaccaca cgccagtgtt   3600
atccatatgg atatcgaccc ggcagaaatg aacaagctgc gtcaggcaca tgtggcatta   3660
caaggtgatt taaatgctct gttaccagca tttacagcagc cgttaaatat caatgactgg   3720
cagctacact gcgcgcagct gcgtgatgaa catgcctggc gttacgacca tcccggtgac   3780
gctatctacg cgccgttgtt gttaaaacaa ctgtcagatc gtaaacctgc ggattgcgtc   3840
gtgaccacag atgtggggca gcaccagatg tgggctgcgc agcacatcgc ccacactcgc   3900
ccggaaaatt tcatcacctc cagcggctta ggcaccatgg gttttggttt accggcggcg   3960
gttggcgcgc aagtcgcgcg accaaacgat accgtcgtct gtatctccgg tgacggctct   4020
ttcatgatga atgtgcaaga gctgggcacc gtaaaacgca agcagttacc gttgaaaatc   4080
gtcttactcg ataaccaacg gttagggatg gttcgacaat ggcagcaact gttttttccag   4140
gaacgatata gcgaaaccac ccttaccgat aaccccgatt tcctcatgtt agccagcgcc   4200
ttcggcatcc ctggccaaca catcacccgt aaagaccagg ttgaagcggc actcgacacc   4260
atgctgaaca gtgatgggcc ataccctgctt catgtctcaa tcgacgaact tgagaacgtc   4320
tggccgctgg tgccgcctgg tgccagtaat tcagaaatgt tggagaaatt atcatgatgc   4380
aacatcaggt caatgtatcg gctctgaggg ctgcaggaat tcgatatcaa gcttatcgat   4440
accgtcgacc tcgagtcatg taattagtta tgtcacgctt acattcacgc cctcccccca   4500
catccgctct aaccgaaaag gaaggagtta gacaacctga agtctaggtc cctatttatt   4560
tttttatagt tatgttagta ttaagaacgt tatttatatt tcaaattttt cttttttttc   4620
tgtacagacg cgtgtacgca tgtaacatta tactgaaaac cttgcttgag aaggttttgg   4680
gacgctcgaa ggctttaatt tgcggcctca ctggccgtcg ttttacaacg tcgtgactgg   4740
gaaaaccata gcttcaaaat gtttctactc cttttttact cttccagatt ttctcggact   4800
ccgcgcatcg ccgtaccact tcaaaacacc caagcacagc atactaaatt tcccctcttt   4860
cttcctctag ggtgtcgtta attacccgta ctaaaggttt ggaaagaaaa aagagaccg   4920
cctcgttttct ttttcttcgt cgaaaaaggc aataaaaatt tttatcacgt ttcttttttct   4980
tgaaaatttt ttttttgatt ttttttctctt tcgatgacct cccattgata tttaagttaa   5040
taaacggtct tcaatttctc aagtttcagt ttcattttttc ttgttctatt acaacttttt   5100
ttacttcttg ctcattagaa agaaagcata gcaatctaat ctaagttttc tagaactagt   5160
ggatccccca tggctaacta cttcaataca ctgaatctgc gccaacagct ggcacagctg   5220
ggcaaatgtc gctttatggg ccgcgatgaa ttcgccgatg gcgcgagcta ccttcagggt   5280
aaaaaagtag tcatcgtcgg ctgtggcgca cagggtctga accagggcct gaacatgcgt   5340
gattctggtc tcgatatctc ctacgctctg cgtaaagaag cgattgccga gaagcgcgcg   5400
tcctggcgta aagcgaccga aaatggtttt aaagtgggta cttacgaaga actgatccca   5460
caggcggatc tggtgattaa cctgacgccg gacaagcagc actctgatgt agtgcgcacc   5520
gtacagccac tgatgaaaga cggcgcggcg ctgggctact cgcacggttt caacatcgtc   5580
gaagtgggcg agcagatccg taagatatc accgtagtga tggttgcgcc gaaatgccca   5640
ggcaccgaag tgcgtgaaga gtacaaacgt gggttcggcg taccgacgct gattgccctt   5700
cacccggaaa acgatccgaa aggcgaaggc atggcgattg ccaaagcctg gcggctgca   5760
accggtggtc accgtgcggg tgtgctggaa tcgtccttcg ttgcggaagt gaaatctgac   5820
ctgatgggcg agcaaaccat cctgtgcggt atgttgcagg ctggctctct gctgtgcttc   5880
gacaagctgg tggaagaagg taccgatcca gcatacgcag aaaaactgat tcagttcggt   5940
```

```
tgggaaaccca tcaccgaagc actgaaacag ggcggcatca ccctgatgat ggaccgtctc    6000
tctaacccgg cgaaactgcg tgcttatgcg ctttctgaac agctgaaaga gatcatggca    6060
cccctgttcc agaaacatat ggacgacatc atctccggcg aattctcttc cggtatgatg    6120
gcggactggg ccaacgatga taagaaactg ctgacctggc gtgaagagac cggcaaaacc    6180
gcgtttgaaa ccgcgccgca gtatgaaggc aaaatcggcg agcaggagta cttcgataaa    6240
ggcgtactga tgattgcgat ggtgaaagcg ggcgttgaac tggcgttcga aaccatggtc    6300
gattccggca tcattgaaga gtctgcatat tatgaatcac tgcacgagct gccgctgatt    6360
gccaacacca tcgcccgtaa gcgtttgtac gaaatgaacg tggttatctc tgataccgct    6420
gagtacggta actatctgtt ctcttacgct tgtgtgccgt tgctgaaacc gtttatggca    6480
gagctgcaac cgggcgacct gggtaaagct attccggaag cgcggtaga taacgggcaa    6540
ctgcgtgatg tgaacgaagc gattcgcagc catgcgattg agcaggtagg taagaaactg    6600
cgcggctata tgacagatat gaaacgtatt gctgttgcgg gttaagtggg ctgcaggaat    6660
tcgatatcaa gcttatcgat accgtcgacc tcgagtcatg taattagtta tgtcacgctt    6720
acattcacgc cctcccccca catccgctct aaccgaaaag gaaggagtta gacaacctga    6780
agtctaggtc cctatttatt ttttatagt tatgttagta ttaagaacgt tatttatatt    6840
tcaaattttt ctttttttc tgtacagacg cgtgtacgca tgtaacatta tactgaaaac    6900
cttgcttgag aaggttttgg gacgctcgaa ggctttaatt tgcggccctg cgttaccca    6960
acttaatcgc cttgcagcac atcccccata gcttcaaaat gtttctactc cttttttact    7020
cttccagatt ttctcggact ccgcgcatcg ccgtaccact tcaaaacacc caagcacagc    7080
atactaaatt tccctctttt cttcctctag ggtgtcgtta attacccgta ctaaggtttt    7140
ggaaagaaa aaagagaccg cctcgtttct ttttcttcgt cgaaaaaggc aataaaaatt    7200
tttatcacgt ttcttttttct tgaaaatttt tttttgatt tttttctctt tcgatgacct    7260
cccattgata tttaagttaa taaacggtct tcaatttctc aagtttcagt ttcatttttc    7320
ttgttctatt acaactttttt ttacttcttg ctcattagaa agaaagcata gcaatctaat    7380
ctaagttttc tagaactagt ggatccccca tgcctaagta ccgttccgcc accaccactc    7440
atggtcgtaa tatggcgggt gctcgtgcgc tgtggcgcgc caccggaatg accgacgccg    7500
atttcggtaa gccgattatc gcggttgtga actcgttcac ccaatttgta ccgggtcacg    7560
tccatctgcg cgatctcggt aaactggtcg ccgaacaaat tgaagcggct ggcggcgttg    7620
ccaaagagtt caacaccatt gcggtggatg atgggattgc catgggccac gggggatgc    7680
tttattcact gccatctcgc gaactgatcg ctgattccgt tgagtatatg gtcaacgccc    7740
actgcgccga cgccatggtc tgcatctcta actgcgacaa aatcacccg gggatgctga    7800
tggcttccct gcgcctgaat attccggtga tctttgtttc cggcggcccg atggaggccg    7860
ggaaaaccaa actttccgat cagatcatca agctcgatct ggttgatgcg atgatccagg    7920
gcgcagaccc gaaagtatct gactcccaga gcgatcaggt tgaacgttcc gcgtgtccga    7980
cctgcggttc ctgctccggg atgtttaccg ctaactcaat gaactgcctg accgaagcgc    8040
tgggcctgtc gcagccgggc aacggctcgc tgctggcaac ccacgccgac cgtaagcagc    8100
tgttccttaa tgctggtaaa cgcattgttg aattgaccaa acgttattac gagcaaaacg    8160
acgaaagtgc actgccgcgt aatatcgcca gtaaggcggc gtttgaaaac gccatgacgc    8220
tggatatcgc gatgggtgga tcgactaaca ccgtacttca cctgctggcg gcggcgcagg    8280
aagcggaaat cgacttcacc atgagtgata tcgataagct ttcccgcaag gttccacagc    8340
```

```
tgtgtaaagt tgcgccgagc acccagaaat accatatgga agatgttcac cgtgctggtg   8400
gtgttatcgg tattctcggc gaactggatc gcgcggggtt actgaaccgt gatgtgaaaa   8460
acgtacttgg cctgacgttg ccgcaaacgc tggaacaata cgacgttatg ctgacccagg   8520
atgacgcggt aaaaaatatg ttccgcgcag gtcctgcagg cattcgtacc acacaggcat   8580
tctcgcaaga ttgccgttgg gatacgctgg acgacgatcg cgccaatggc tgtatccgct   8640
cgctggaaca cgcctacagc aaagacggcg gcctggcggt gctctacggt aactttgcgg   8700
aaaacggctg catcgtgaaa acggcaggcg tcgatgacag catcctcaaa ttcaccggcc   8760
cggcgaaagt gtacgaaagc caggacgatg cggtagaagc gattctcggc ggtaaagttg   8820
tcgccggaga tgtggtagta attgctatg aaggcccgaa aggcggtccg gggatgcagg   8880
aaatgctcta cccaaccagc ttcctgaaat caatgggtct cggcaaagcc tgtgcgctga   8940
tcaccgacgg tcgtttctct ggtggcacct ctggtctttc catcggccac gtctcaccgg   9000
aagcggcaag cggcggcagc attggcctga ttgaagatgg tgacctgatc gctatcgaca   9060
tcccgaaccg tggcattcag ttacaggtaa gcgatgccga actggcggcg cgtcgtgaag   9120
cgcaggacgc tcgaggtgac aaagcctgga cgccgaaaaa tcgtgaacgt caggtctcct   9180
ttgccctgcg tgcttatgcc agcctggcaa ccagcgccga caaggcgcg gtgcgcgata   9240
aatcgaaact gggggggttaa gggctgcagg aattcgatat caagcttatc gataccgtcg   9300
acctcgagtc atgtaattag ttatgtcacg cttacattca cgccctcccc ccacatccgc   9360
tctaaccgaa aaggaaggag ttagacaacc tgaagtctag gtccctattt atttttttat   9420
agttatgtta gtattaagaa cgttatttat atttcaaatt tttctttttt ttctgtacag   9480
acgcgtgtac gcatgtaaca ttatactgaa aaccttgctt gagaaggttt tgggacgctc   9540
gaaggcttta atttgcggcc tttcgccagc tggcgtaata gcgaagaggc cccgcaccga   9600
tatagcttca aaatgtttct actccttttt tactcttcca gattttctcg gactccgcgc   9660
atcgccgtac cacttcaaaa cacccaagca cagcatacta aatttcccct ctttcttcct   9720
ctagggtgtc gttaattacc cgtactaaag gtttggaaaa gaaaaaagag accgcctcgt   9780
ttctttttct tcgtcgaaaa aggcaataaa aatttttatc acgtttcttt tcttgaaaa   9840
tttttttttt gattttttc tctttcgatg acctcccatt gatatttaag ttaataaacg   9900
gtcttcaatt tctcaagttt cagtttcatt tttcttgttc tattacaact tttttactt   9960
cttgctcatt agaaagaaag catagcaatc taatctaagt tttctagaac tagtggatcc  10020
cccatgtata ctgtggggga ttatttgttg ataggttgc atgaattagg catcgaggaa  10080
atctttggtg tacctggaga ttacaatttg caatttctgg accagatcat atcgagagag  10140
gatatgaaat ggattggtaa cgccaatgaa ttaaatgcca gctatatggc cgatggctat  10200
gctcgtacca agaaagctgc tgcttttctg acaacttttg gtgtcggtga attgtctgct  10260
attaacggac tggccggtag ttatgctgaa aatttgccag tagttaaat agtcggaagc  10320
ccaacttcta aagtgcaaaa cgatggcaaa ttcgtgcatc atactctggc agatggtgat  10380
tttaagcact tcatgaaaat gcatgaaccc gtaacggctg ccagaactct tttaacagcc  10440
gagaatgcga catatgaaat tgatcgtgta ctttctcagc tttaaaggga gagaaaacct  10500
gtttacataa acttacctgt cgatgttgct gctgccaaag cagagaagcc agccctgtct  10560
cttgaaaaag aaagctccac caccaacact accgaacaag tgatattatc taaaattgag  10620
gaatcactta aaaacgctca gaaccagta gtcatagcgg gtcatgaagt cataagtttc  10680
ggtcttgaaa agactgtaac acaatttgtc agcgaaacaa aattgcctat cactactttg  10740
```

```
aactttggca aaagtgcggt cgacgagtcg ttgccatcat ttttgggtat ctacaatggc   10800
aaactatcag aaatctcatt gaaaaatttc gtagaaagtg cggatttcat tctgatgttg   10860
ggcgtcaagc tgacggattc ttctacgggg gctttcactc accatttgga tgaaaacaaa   10920
atgatttcat tgaacatcga tgaagggatc atctttaata aggtagtgga agatttcgat   10980
tttagagccg tggtttcctc cttatcagag ttaaaaggta ttgagtacga agggcagtat   11040
attgataagc agtacgagga atttattcct tcttctgctc cactttctca agatcgttta   11100
tggcaagcag tcgagtccct gacacaaagc aacgagacta tagttgcaga gcaggggacc   11160
tcattctttg gtgcctctac aattttttctg aaatccaaca gcagatttat aggacaaccc   11220
ctttggggct ctattggata tacttttccc gcagcccttg gttcacaaat cgcagataag   11280
gagtcaagac atctgttatt cataggtgat ggtagtctac aattaacagt tcaagaatta   11340
ggcctatcaa taagggagaa gttaaaccca atctgtttca taattaacaa tgacggctac   11400
actgttgaaa gggagatcca cggaccaaca caatcataca atgatattcc catgtggaac   11460
tatagcaaat taccggagac tttcggcgca accgaggata gagtagtttc gaagatcgtt   11520
aggactgaga atgaatttgt tagcgttatg aaggaagccc aggctgatgt caatagaatg   11580
tattggattg aattagtttt ggaaaaggaa gatgcaccta aattactaaa aaagatgggg   11640
aaactatttg ctgagcaaaa caaataaggg ctgcaggaat tcgatatcaa gcttatcgat   11700
accgtcgacc tcgagtcatg taattagtta tgtcacgctt acattcacgc cctccccca   11760 catccgctct aaccgaaaag gaaggagtta gacaacctga agtctaggtc cctatttatt   11820
tttttatagt tatgttagta ttaagaacgt tatttatatt tcaaattttt ctttttttc   11880 tgtacagacg cgtgtacgca tgtaacatta tactgaaaac cttgcttgag aaggttttgg   11940
gacgctcgaa ggctttaatt tgcggcccgc ccttcccaac agttgcgcag cctgaatggc   12000
gaatggcata gcttcaaaat gtttctactc ctttttttact cttccagatt ttctcggact   12060
ccgcgcatcg ccgtaccact tcaaaacacc caagcacagc atactaaatt tcccctcttt   12120
cttcctctag ggtgtcgtta attcccgta ctaaaggttt ggaaaagaaa aaagagaccg   12180
cctcgtttct ttttcttcgt cgaaaaggc aataaaaatt tttatcacgt ttctttttct   12240
tgaaaatttt ttttttgatt ttttttctctt tcgatgacct cccattgata tttaagttaa   12300
taaacggtct tcaatttctc aagtttcagt ttcatttttc ttgttctatt acaactttt   12360 ttacttcttg ctcattagaa agaaagcata gcaatctaat ctaagttttc tagaactagt   12420
ggatccccca tgtcttatcc tgagaaattt gaaggtatcg ctattcaatc acacgaagat   12480 tggaaaacc caaagaagac aaagtatgac ccaaaaccat tttacgatca tgacattgac   12540
attaagatcg aagcatgtgg tgtctgcggt agtgatattc attgtgcagc tggtcattgg   12600
ggcaatatga agatgccgct agtcgttggt catgaaatcg ttggtaaagt tgtcaagcta   12660
gggcccaagt caaacagtgg gttgaaagtc ggtcaacgtg ttggtgtagg tgctcaagtc   12720
ttttcatgct tggaatgtga ccgttgtaag aatgataatg aaccatactg caccaagttt   12780
gttaccacat acagtcagcc ttatgaagac ggctatgtgt cgcagggtgg ctatgcaaac   12840
tacgtcagag ttcatgaaca ttttgtggtg cctatcccag agaatattcc atcacatttg   12900
gctgctccac tattatgtgg tggtttgact gtgtactctc cattggttcg taacggttgc   12960
ggtccaggta aaaagttgg tatagttggt cttggtggta tcggcagtat gggtacattg   13020
atttccaaag ccatggggc agagacgtat gttatttctc gttcttcgag aaaaagagaa   13080
gatgcaatga aagatgggcgc cgatcactac attgctacat tagaagaagg tgattggggt   13140
```

```
gaaaagtact tgacacctt cgacctgatt gtagtctgtg cttcctccct taccgacatt   13200
gacttcaaca ttatgccaaa ggctatgaag gttggtggta gaattgtctc aatctctata   13260
ccagaacaac acgaaatgtt atcgctaaag ccatatggct taaaggctgt ctccatttct   13320
tacagtgctt taggttccat caaagaattg aaccaactct tgaaattagt ctctgaaaaa   13380
gatatcaaaa tttgggtgga aacattacct gttggtgaag ccggcgtcca tgaagccttc   13440
gaaaggatgg aaaagggtga cgttagatat agatttacct tagtcggcta cgacaaagaa   13500
ttttcagact aggggctgca ggaattcgat atcaagctta tcgataccgt cgacctcgag   13560
tcatgtaatt agttatgtca cgcttacatt cacgccctcc ccccacatcc gctctaaccg   13620
aaaaggaagg agttagacaa cctgaagtct aggtccctat ttattttttt atagttatgt   13680
tagtattaag aacgttattt atatttcaaa ttttctttt ttttctgtac agacgcgtgt   13740
acgcatgtaa cattatactg aaaaccttgc ttgagaaggt tttgggacgc tcgaaggctt   13800
taatttgcgg cc                                                       13812
```

<210> SEQ ID NO 98
<211> LENGTH: 546
<212> TYPE: PRT
<213> ORGANISM: Lactococcus lactis
<220> FEATURE:
<223> OTHER INFORMATION: Primer

<400> SEQUENCE: 98

```
Met Tyr Thr Val Gly Asp Tyr Leu Leu Asp Arg Leu His Glu Leu Gly
 1               5                  10                  15

Ile Glu Glu Ile Phe Gly Val Pro Gly Asp Tyr Asn Leu Gln Phe Leu
            20                  25                  30

Asp Gln Ile Ile Ser Arg Glu Asp Met Lys Trp Ile Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Ile
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Asp Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Tyr
    130                 135                 140

Glu Ile Asp Arg Val Leu Ser Gln Leu Leu Lys Glu Arg Lys Pro Val
145                 150                 155                 160

Tyr Ile Asn Leu Pro Val Asp Ala Ala Lys Ala Glu Lys Pro Ala
                165                 170                 175

Leu Ser Leu Glu Lys Glu Ser Ser Thr Thr Asn Thr Thr Glu Gln Val
            180                 185                 190

Ile Leu Ser Lys Ile Glu Glu Ser Leu Lys Asn Ala Gln Lys Pro Val
        195                 200                 205

Val Ile Ala Gly His Glu Val Ile Ser Phe Gly Leu Glu Lys Thr Val
    210                 215                 220

Thr Gln Phe Val Ser Glu Thr Lys Leu Pro Ile Thr Thr Leu Asn Phe
225                 230                 235                 240
```

-continued

```
Gly Lys Ser Ala Val Asp Glu Ser Leu Pro Ser Phe Leu Gly Ile Tyr
                245                 250                 255

Asn Gly Lys Leu Ser Glu Ile Ser Leu Lys Asn Phe Val Glu Ser Ala
            260                 265                 270

Asp Phe Ile Leu Met Leu Gly Val Lys Leu Thr Asp Ser Ser Thr Gly
        275                 280                 285

Ala Phe Thr His His Leu Asp Glu Asn Lys Met Ile Ser Leu Asn Ile
    290                 295                 300

Asp Glu Gly Ile Ile Phe Asn Lys Val Val Glu Asp Phe Asp Phe Arg
305                 310                 315                 320

Ala Val Val Ser Ser Leu Ser Glu Leu Lys Gly Ile Glu Tyr Glu Gly
                325                 330                 335

Gln Tyr Ile Asp Lys Gln Tyr Glu Glu Phe Ile Pro Ser Ser Ala Pro
            340                 345                 350

Leu Ser Gln Asp Arg Leu Trp Gln Ala Val Glu Ser Leu Thr Gln Ser
        355                 360                 365

Asn Glu Thr Ile Val Ala Glu Gln Gly Thr Ser Phe Phe Gly Ala Ser
    370                 375                 380

Thr Ile Phe Leu Lys Ser Asn Ser Arg Phe Ile Gly Gln Pro Leu Trp
385                 390                 395                 400

Gly Ser Ile Gly Tyr Thr Phe Pro Ala Ala Leu Gly Ser Gln Ile Ala
                405                 410                 415

Asp Lys Glu Ser Arg His Leu Leu Phe Ile Gly Asp Gly Ser Leu Gln
            420                 425                 430

Leu Thr Val Gln Glu Leu Gly Leu Ser Ile Arg Glu Lys Leu Asn Pro
        435                 440                 445

Ile Cys Phe Ile Ile Asn Asn Asp Gly Tyr Thr Val Glu Arg Glu Ile
    450                 455                 460

His Gly Pro Thr Gln Ser Tyr Asn Asp Ile Pro Met Trp Asn Tyr Ser
465                 470                 475                 480

Lys Leu Pro Glu Thr Phe Gly Ala Thr Glu Asp Arg Val Val Ser Lys
                485                 490                 495

Ile Val Arg Thr Glu Asn Glu Phe Val Ser Val Met Lys Glu Ala Gln
            500                 505                 510

Ala Asp Val Asn Arg Met Tyr Trp Ile Glu Leu Val Leu Glu Lys Glu
        515                 520                 525

Asp Ala Pro Lys Leu Leu Lys Lys Met Gly Lys Leu Phe Ala Glu Gln
    530                 535                 540

Asn Lys
545

<210> SEQ ID NO 99
<211> LENGTH: 563
<212> TYPE: PRT
<213> ORGANISM: Saccharomyces cerevisiase
<220> FEATURE:
<223> OTHER INFORMATION: Primer

<400> SEQUENCE: 99

Met Ser Glu Ile Thr Leu Gly Lys Tyr Leu Phe Glu Arg Leu Lys Gln
1               5                   10                  15

Val Asn Val Asn Thr Val Phe Gly Leu Pro Gly Asp Glu Asn Leu Ser
            20                  25                  30

Leu Leu Asp Lys Ile Tyr Glu Val Glu Gly Met Arg Trp Ala Gly Asn
        35                  40                  45

Ala Asn Glu Leu Asn Ala Ala Tyr Ala Ala Asp Gly Tyr Ala Arg Ile
```

```
              50                  55                  60
Lys Gly Met Ser Cys Ile Ile Thr Thr Phe Gly Val Gly Glu Leu Ser
 65                  70                  75                  80

Ala Leu Asn Gly Ile Ala Gly Ser Tyr Ala Glu His Val Gly Val Leu
                 85                  90                  95

His Val Val Gly Val Pro Ser Ile Ser Ala Gln Ala Lys Gln Leu Leu
                100                 105                 110

Leu His His Thr Leu Gly Asn Gly Asp Phe Thr Val Phe His Arg Met
            115                 120                 125

Ser Ala Asn Ile Ser Glu Thr Thr Ala Met Ile Thr Asp Ile Ala Thr
            130                 135                 140

Ala Pro Ala Glu Ile Asp Arg Cys Ile Arg Thr Thr Tyr Val Thr Gln
145                 150                 155                 160

Arg Pro Val Tyr Leu Gly Leu Pro Ala Asn Leu Val Asp Leu Asn Val
                165                 170                 175

Pro Ala Lys Leu Leu Gln Thr Pro Ile Asp Met Ser Leu Lys Pro Asn
            180                 185                 190

Asp Ala Glu Ser Glu Lys Glu Val Ile Asp Thr Ile Leu Ala Leu Val
            195                 200                 205

Lys Asp Ala Lys Asn Pro Val Ile Leu Ala Asp Ala Cys Cys Ser Arg
210                 215                 220

His Asp Val Lys Ala Glu Thr Lys Lys Leu Ile Asp Leu Thr Gln Phe
225                 230                 235                 240

Pro Ala Phe Val Thr Pro Met Gly Lys Gly Ser Ile Asp Glu Gln His
                245                 250                 255

Pro Arg Tyr Gly Gly Val Tyr Val Gly Thr Leu Ser Lys Pro Glu Val
            260                 265                 270

Lys Glu Ala Val Glu Ser Ala Asp Leu Ile Leu Ser Val Gly Ala Leu
            275                 280                 285

Leu Ser Asp Phe Asn Thr Gly Ser Phe Ser Tyr Ser Tyr Lys Thr Lys
            290                 295                 300

Asn Ile Val Glu Phe His Ser Asp His Met Lys Ile Arg Asn Ala Thr
305                 310                 315                 320

Phe Pro Gly Val Gln Met Lys Phe Val Leu Gln Lys Leu Leu Thr Thr
                325                 330                 335

Ile Ala Asp Ala Ala Lys Gly Tyr Lys Pro Val Ala Val Pro Ala Arg
            340                 345                 350

Thr Pro Ala Asn Ala Ala Val Pro Ala Ser Thr Pro Leu Lys Gln Glu
            355                 360                 365

Trp Met Trp Asn Gln Leu Gly Asn Phe Leu Gln Glu Gly Asp Val Val
            370                 375                 380

Ile Ala Glu Thr Gly Thr Ser Ala Phe Gly Ile Asn Gln Thr Thr Phe
385                 390                 395                 400

Pro Asn Asn Thr Tyr Gly Ile Ser Gln Val Leu Trp Gly Ser Ile Gly
                405                 410                 415

Phe Thr Thr Gly Ala Thr Leu Gly Ala Ala Phe Ala Ala Glu Glu Ile
            420                 425                 430

Asp Pro Lys Lys Arg Val Ile Leu Phe Ile Gly Asp Gly Ser Leu Gln
            435                 440                 445

Leu Thr Val Gln Glu Ile Ser Thr Met Ile Arg Trp Gly Leu Lys Pro
            450                 455                 460

Tyr Leu Phe Val Leu Asn Asn Asp Gly Tyr Thr Ile Glu Lys Leu Thr
465                 470                 475                 480
```

```
His Gly Pro Lys Ala Gln Tyr Asn Glu Ile Gln Gly Trp Asp His Leu
            485                 490                 495

Ser Leu Leu Pro Thr Phe Gly Ala Lys Asp Tyr Glu Thr His Arg Val
        500                 505                 510

Ala Thr Thr Gly Glu Trp Asp Lys Leu Thr Gln Asp Lys Ser Phe Asn
    515                 520                 525

Asp Asn Ser Lys Ile Arg Met Ile Glu Ile Met Leu Pro Val Phe Asp
530                 535                 540

Ala Pro Gln Asn Leu Val Glu Gln Ala Lys Leu Thr Ala Ala Thr Asn
545                 550                 555                 560

Ala Lys Gln

<210> SEQ ID NO 100
<211> LENGTH: 50
<212> TYPE: DNA
<213> ORGANISM: Artificial Sequence
<220> FEATURE:
<223> OTHER INFORMATION: Primer

<400> SEQUENCE: 100
ctagaactag tggatccccc atgtatactg tggggggatta tttgttggat               50

<210> SEQ ID NO 101
<211> LENGTH: 50
<212> TYPE: DNA
<213> ORGANISM: Artificial Sequence
<220> FEATURE:
<223> OTHER INFORMATION: Primer

<400> SEQUENCE: 101
atatcgaatt cctgcagccc ttatttgttt tgctcagcaa atagtttccc               50

<210> SEQ ID NO 102
<211> LENGTH: 53
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 27, 28
<223> OTHER INFORMATION: n = A,T,C or G

<400> SEQUENCE: 102
tcagaaaaat tgtagaggca ccaaaknntg aggtcccttg ctctgcaact ata          53

<210> SEQ ID NO 103
<211> LENGTH: 48
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 25, 26
<223> OTHER INFORMATION: n = A,T,C or G

<400> SEQUENCE: 103
atgttgggcg tcaagctgac ggatnnktct acgggggctt tcactcac                 48

<210> SEQ ID NO 104
<211> LENGTH: 50
<212> TYPE: DNA
<213> ORGANISM: Artificial Sequence
<220> FEATURE:
<223> OTHER INFORMATION: Primer
```

-continued

<400> SEQUENCE: 104
ctagaactag tggatccacc atgtctgaaa ttactttggg taaatatttg            50

<210> SEQ ID NO 105
<211> LENGTH: 40
<212> TYPE: DNA
<213> ORGANISM: Artificial Sequence
<220> FEATURE:
<223> OTHER INFORMATION: Primer

<400> SEQUENCE: 105
atatcgaatt cctgcagccc ttaaatcgct tattgcttag            40

<210> SEQ ID NO 106
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 25, 26, 27
<223> OTHER INFORMATION: n = A,T,C or G

<400> SEQUENCE: 106
gaaagtggtt tggttgatac cgaannngga ggtaccggtt tcagcaatga            50

<210> SEQ ID NO 107
<211> LENGTH: 50
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: 24, 25, 26
<223> OTHER INFORMATION: n = A,T,C or G

<400> SEQUENCE: 107
ctgtcggtgc tttgttgtct gatnnnaaca ccggttcttt ctcttactct            50

<210> SEQ ID NO 108
<211> LENGTH: 568
<212> TYPE: PRT
<213> ORGANISM: Lactococcus lactis
<220> FEATURE:
<223> OTHER INFORMATION: Primer

<400> SEQUENCE: 108

Met Gly Ser Ser His His His His His His Ser Ser Gly Leu Val Pro
1               5                 10               15

Arg Gly Ser His Met Ala Ser Met Tyr Thr Val Gly Asp Tyr Leu Leu
            20               25                 30

Asp Arg Leu His Glu Leu Gly Ile Glu Glu Ile Phe Gly Val Pro Gly
35               40                 45

Asp Tyr Asn Leu Gln Phe Leu Asp Gln Ile Ile Ser Arg Glu Asp Met
    50                 55                 60

Lys Trp Ile Gly Ala Asn Glu Leu Asn Ala Ser Tyr Met Ala Asp Gly
65               70               75               80

Tyr Ala Arg Thr Lys Lys Ala Ala Ala Phe Leu Thr Thr Phe Gly Val
               85               90               95

Gly Glu Leu Ser Ala Ile Asn Gly Leu Ala Gly Ser Tyr Ala Glu Asn
                 100              105              110

```
Leu Pro Val Val Glu Ile Val Gly Ser Pro Thr Ser Lys Val Gln Asn
            115                 120                 125

Asp Gly Lys Phe Val His His Thr Leu Ala Asp Gly Asp Phe Lys His
        130                 135                 140

Phe Met Lys Met His Glu Pro Val Thr Ala Ala Arg Thr Leu Leu Thr
145                 150                 155                 160

Ala Glu Asn Ala Thr Tyr Glu Ile Asp Arg Val Leu Ser Gln Leu Leu
                165                 170                 175

Lys Glu Arg Lys Pro Val Ile Asn Leu Pro Val Asp Val Ala Ala
            180                 185                 190

Lys Ala Glu Lys Pro Ala Leu Ser Leu Glu Lys Glu Ser Ser Thr Thr
            195                 200                 205

Asn Thr Thr Glu Gln Val Ile Leu Ser Lys Ile Glu Glu Ser Leu Lys
210                 215                 220

Asn Ala Gln Lys Pro Val Val Ile Ala Gly His Glu Val Ile Ser Phe
225                 230                 235                 240

Gly Leu Glu Lys Thr Val Thr Gln Phe Val Ser Glu Thr Lys Leu Pro
            245                 250                 255

Ile Thr Thr Lys Asn Phe Gly Lys Ser Ala Val Asp Glu Ser Leu Pro
            260                 265                 270

Ser Phe Leu Gly Ile Tyr Asn Gly Lys Leu Ser Glu Ile Ser Leu Lys
        275                 280                 285

Asn Phe Val Glu Ser Ala Asp Phe Ile Leu Met Leu Gly Val Lys Leu
290                 295                 300

Thr Asp Ser Ser Thr Gly Ala Phe Thr His His Lys Asp Glu Asn Lys
305                 310                 315                 320

Met Ile Ser Leu Asn Ile Asp Glu Gly Ile Ile Phe Asn Lys Val Val
                325                 330                 335

Glu Asp Phe Asp Phe Arg Ala Val Val Ser Ser Leu Ser Glu Leu Lys
            340                 345                 350

Gly Ile Glu Tyr Glu Gly Gln Tyr Ile Asp Lys Gln Tyr Glu Glu Phe
        355                 360                 365

Ile Pro Ser Ser Ala Pro Leu Ser Gln Asp Arg Leu Trp Gln Ala Val
        370                 375                 380

Glu Ser Leu Thr Gln Ser Asn Glu Thr Ile Val Ala Glu Gln Gly Thr
385                 390                 395                 400

Ser Phe Phe Gly Ala Ser Thr Ile Phe Leu Lys Ser Asn Ser Arg Phe
                405                 410                 415

Ile Gly Gln Pro Leu Trp Gly Ser Ile Gly Tyr Thr Phe Pro Ala Ala
            420                 425                 430

Leu Gly Ser Gln Ile Ala Asp Lys Glu Ser Arg His Leu Leu Phe Ile
        435                 440                 445

Gly Asp Gly Ser Leu Gln Thr Val Gln Glu Leu Gly Leu Ser Ile Arg
450                 455                 460

Glu Lys Leu Asn Pro Ile Cys Phe Ile Ile Asn Asn Asp Gly Tyr Thr
465                 470                 475                 480

Val Glu Arg Glu Ile His Gly Pro Thr Gln Ser Tyr Asn Asp Ile Pro
                485                 490                 495

Met Trp Asn Tyr Ser Lys Leu Pro Glu Thr Phe Gly Ala Thr Glu Asp
            500                 505                 510

Arg Val Val Ser Lys Ile Val Arg Thr Glu Asn Glu Phe Val Ser Val
            515                 520                 525

Met Lys Glu Ala Gln Ala Asp Val Ile Asn Arg Met Tyr Trp Ile Glu
530                 535                 540
```

```
Leu Val Leu Glu Lys Glu Asp Ala Pro Lys Leu Leu Lys Lys Met Gly
545                 550                 555                 560

Lys Leu Phe Ala Glu Gln Asn Lys
                565
```

<210> SEQ ID NO 109
<211> LENGTH: 555
<212> TYPE: PRT
<213> ORGANISM: Saccharomyces cerevisiae
<220> FEATURE:
<223> OTHER INFORMATION: Primer

<400> SEQUENCE: 109

```
Ser Glu Ile Thr Leu Gly Lys Tyr Leu Phe Glu Arg Leu Lys Gln Val
1               5                   10                  15

Asn Val Asn Thr Val Phe Gly Leu Pro Gly Asp Phe Asn Leu Ser Leu
                20                  25                  30

Leu Asp Lys Ile Tyr Glu Val Glu Gly Met Arg Trp Ala Gly Asn Ala
            35                  40                  45

Asn Glu Leu Asn Ala Ala Tyr Ala Ala Asp Gly Tyr Ala Arg Ile Lys
        50                  55                  60

Gly Met Ser Cys Ile Ile Thr Thr Phe Gly Val Gly Glu Leu Ser Ala
65                  70                  75                  80

Leu Asn Gly Ile Ala Gly Ser Tyr Ala Glu His Val Gly Val Leu His
                85                  90                  95

Val Val Gly Val Pro Ser Ile Ser Ser Gln Ala Lys Gln Leu Leu Leu
                100                 105                 110

His His Thr Leu Gly Asn Gly Asp Phe Thr Val Phe His Arg Met Ser
            115                 120                 125

Ala Asn Ile Ser Glu Thr Thr Ala Met Ile Thr Asp Ile Ala Thr Ala
        130                 135                 140

Pro Ala Glu Ile Asp Arg Cys Ile Arg Thr Thr Tyr Val Thr Gln Arg
145                 150                 155                 160

Pro Val Tyr Leu Gly Leu Pro Ala Asn Leu Val Asp Leu Asn Val Pro
                165                 170                 175

Ala Lys Leu Leu Gln Thr Pro Ile Asp Met Ser Leu Lys Pro Asn Asp
            180                 185                 190

Ala Glu Ser Glu Lys Glu Val Ile Asp Thr Ile Leu Ala Leu Val Lys
        195                 200                 205

Asp Ala Lys Asn Pro Val Ile Leu Ala Asp Ala Cys Cys Ser Arg His
210                 215                 220

Asp Val Lys Ala Glu Thr Lys Lys Leu Ile Asp Leu Thr Gln Phe Pro
225                 230                 235                 240

Ala Phe Val Thr Pro Met Gly Lys Gly Ser Ile Ser Glu Gln His Pro
                245                 250                 255

Arg Tyr Gly Gly Val Tyr Val Gly Thr Leu Ser Lys Pro Glu Val Lys
            260                 265                 270

Glu Ala Val Glu Ser Ala Asp Leu Ile Leu Ser Val Gly Ala Leu Leu
        275                 280                 285

Ser Asp Phe Asn Thr Cys Ser Phe Ser Tyr Tyr Lys Thr Lys Asn
        290                 295                 300

Ile Val Glu Phe His Ser Asp His Met Lys Ile Arg Asn Ala Thr Phe
305                 310                 315                 320

Pro Gly Val Gln Met Lys Phe Val Leu Gln Lys Leu Leu Thr Asn Ile
                325                 330                 335
```

-continued

```
Ala Asp Ala Ala Lys Gly Tyr Lys Pro Val Ala Val Pro Ala Arg Thr
        340                 345                 350

Pro Ala Asn Ala Ala Val Pro Ala Ser Thr Pro Leu Lys Gln Glu Trp
            355                 360                 365

Met Trp Asn Gln Leu Gly Asn Phe Leu Gln Glu Gly Asp Val Val Ile
370                 375                 380

Ala Glu Thr Gly Thr Ser Ala Phe Gly Ile Asn Gln Thr Thr Phe Pro
385                 390                 395                 400

Asn Asn Thr Tyr Gly Ile Ser Gln Val Leu Trp Gly Ser Ile Gly Phe
                405                 410                 415

Thr Thr Gly Ala Thr Leu Gly Ala Ala Phe Ala Ala Glu Glu Ile Asp
            420                 425                 430

Pro Lys Lys Arg Val Ile Leu Phe Ile Gly Asp Gly Ser Leu Gln Leu
        435                 440                 445

Thr Val Gln Glu Ile Ser Thr Met Ile Arg Trp Gly Leu Lys Pro Tyr
450                 455                 460

Leu Phe Val Leu Asn Asn Asp Gly Tyr Thr Ile Glu Lys Leu Ile His
465                 470                 475                 480

Gly Pro Lys Ala Gln Tyr Asn Glu Ile Gln Gly Trp Asp His Leu Ser
                485                 490                 495

Leu Leu Pro Thr Phe Gly Ala Lys Asp Tyr Glu Thr His Arg Val Ala
            500                 505                 510

Thr Thr Gly Glu Trp Asp Lys Leu Thr Gln Asp Lys Ser Phe Asn Asp
        515                 520                 525

Asn Ser Lys Ile Arg Met Ile Glu Ile Met Leu Pro Val Phe Asp Ala
530                 535                 540

Pro Gln Asn Leu Val Lys Gln Ala Lys Leu Thr
545                 550                 555

<210> SEQ ID NO 110
<211> LENGTH: 3300
<212> TYPE: DNA
<213> ORGANISM: Lactococcus lactis

<400> SEQUENCE: 110
atgtctgaaa ttactttggg taaatatttg ttcgaaagat taaagcaagt caacgttaac     60
accgttttcg gtttgccagg tgacttcaac ttgtccttgt tggacaagat ctacgaagtt    120
gaaggtatga gatgggctgg taacgccaac gaattgaacg ctgcttacgc cgctgatggt    180
tacgctcgta tcaagggtat gtcttgtatc atcaccacct tcggtgtcgg tgaattgtct    240
gctattaacg gactggccgg tagttatgct gaaaatttgc cagtagttga atagtcgga    300 agcccaactt ctaaagtgca aaacgatggc aaattcgtgc atcatactct ggcagatggt    360
gattttaagc acttcatgaa aatgcatgaa cccgtaacgg ctgccagaac tcttttaaca    420
gccgagaatg cgacatatga aattgatcgt gtactttctc agcttttaaa ggagagaaaa    480
cctgtttaca taaacttacc tgtcgatgtt gctgctgcca aagcagagaa gccagccctg    540
tctcttgaaa aagaaagctc caccaccaac actaccgaac aagtgatatt atctaaaatt    600
gaggaatcac ttaaaaacgc tcagaaacca gtagtcatag cgggtcatga agtcataagt    660
ttcggtcttg aaaagactgt aacacaattt gtcagcgaaa caaaattgcc tatcactact    720
ttgaactttg gcaaagtgc ggtcgacgag tcgttgccat cattttttggg tatctacaat    780 ggcaaactat cagaaatctc attgaaaaat ttcgtagaaa gtgcggattt cattctgatg    840
ttgggcgtca agctgacgga ttcttctacg ggggctttca ctcaccattt ggatgaaaac    900
```

```
aaaatgattt cattgaacat cgatgaaggg atcatcttta ataaggtagt ggaagatttc      960
gattttagag ccgtggtttc ctccttatca gagttaaaag gtattgagta cgaagggcag     1020
tatattgata agcagtacga ggaatttatt ccttcttctg ctccactttc tcaagatcgt     1080
ttatggcaag cagtcgagtc cctgacacaa agcaacgaga ctatagttgc agagcaaggg     1140
acctcattct ttggtgcctc tacaattttt ctgaaatcca acagcagatt tataggacaa     1200
cccctttggg gctctattgg atatactttt cccgcagccc ttggttcaca aatcgcagat     1260
aaggagtcaa gacatctgtt attcataggt gatggtagtc tacaattaac agttcaagaa     1320
ttaggcctat caataaggga gaagttaaac ccaatctgtt tcataattaa caatgacggc     1380
tacactgttg aaagggagat ccacggacca acacaatcat acaatgatat tcccatgtgg     1440
aactatagca aattaccgga gactttcggc gcaaccgagg atagagtagt ttcgaagatc     1500
gttaggactg agaatgaatt tgttagcgtt atgaaggaag cccaggctga tgtcaataga     1560
atgtattgga ttgaattagt tttggaaaag gaagatgcac ctaaaattact aaaaaagatg     1620 gggaaactat ttgctgagca aaacaaataa atgtctgaaa ttactttggg taaatatttg     1680
ttcgaaagat taaagcaagt caacgttaac accgttttcg gtttgccagg tgacttcaac     1740
ttgtccttgt tggacaagat ctacgaagtt gaaggtatga gatgggctgg taacgccaac     1800
gaattgaacg ctgcttacgc cgctgatggt tacgctcgta tcaagggtat gtcttgtatc     1860
atcaccacct tcggtgtcgg tgaattgtct gctattaacg gactggccgg tagttatgct     1920
gaaaatttgc cagtagttga atagtcgga agcccaactt ctaaagtgca aaacgatggc     1980
aaattcgtgc atcatactct ggcagatggt gattttaagc acttcatgaa aatgcatgaa     2040
cccgtaacgg ctgccagaac tcttttaaca gccgagaatg cgacatatga aattgatcgt     2100
gtactttctc agctttttaaa ggagagaaaa cctgtttaca taaacttacc tgtcgatgtt     2160
gctgctgcca agcagagaa gccagccctg tctcttgaaa agaaagctc caccaccaac     2220 actaccgaac aagtgatatt atctaaaatt gaggaatcac ttaaaaacgc tcagaaacca     2280
gtagtcatag cgggtcatga agtcataagt ttcggtcttg aaaagactgt aacacaattt     2340
gtcagcgaaa caaaattgcc tatcactact ttgaactttg gcaaagtgc ggtcgacgag     2400 tcgttgccat cattttggg tatctacaat ggcaaactat cagaaatctc attgaaaaat     2460
ttcgtagaaa gtgcggattt cattctgatg ttgggcgtca agctgacgga ttcttctacg     2520
ggggctttca ctcaccattt ggatgaaaac aaaatgattt cattgaacat cgatgaaggg     2580
atcatcttta ataaggtagt ggaagatttc gattttagag ccgtggtttc ctccttatca     2640
gagttaaaag gtattgagta cgaagggcag tatattgata agcagtacga ggaatttatt     2700
ccttcttctg ctccactttc tcaagatcgt ttatggcaag cagtcgagtc cctgacacaa     2760
agcaacgaga ctatagttgc agagcaaggg acctcattct ttggtgcctc tacaattttt     2820
ctgaaatcca acagcagatt tataggacaa cccctttggg gctctattgg atatactttt     2880
cccgcagccc ttggttcaca aatcgcagat aaggagtcaa gacatctgtt attcataggt     2940
gatggtagtc tacaattaac agttcaagaa ttaggcctat caataaggga gaagttaaac     3000
ccaatctgtt tcataattaa caatgacggc tacactgttg aaagggagat ccacggacca     3060
acacaatcat acaatgatat tcccatgtgg aactatagca aattaccgga gactttcggc     3120
gcaaccgagg atagagtagt ttcgaagatc gttaggactg agaatgaatt tgttagcgtt     3180
atgaaggaag cccaggctga tgtcaataga atgtattgga ttgaattagt tttggaaaag     3240
gaagatgcac ctaaaattact aaaaaagatg gggaaactat ttgctgagca aaacaaataa     3300
```

<210> SEQ ID NO 111
<211> LENGTH: 1701
<212> TYPE: DNA
<213> ORGANISM: Saccharomyces cerevisiae

<400> SEQUENCE: 111

```
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctctgctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact tgaacgtccc agctaagttg     540
ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720
ccagctttcg tcaccccaat gggtaagggt tccattgacg aacaacaccc aagatacggt     780
ggtgtttacg tcggtacctt gtccaagcca gaagttaagg aagccgttga atctgctgac     840
ttgattttgt ctgtcggtgc tttgttgtct gatttcaaca ccggttcttt ctcttactct     900
tacaagacca gaacattgt cgaattccac tccgaccaca tgaagatcag aaacgccact     960
ttcccaggtg tccaaatgaa attcgttttg caaaagttgt tgaccactat tgctgacgcc    1020
gctaagggtt acaagccagt tgctgtcggg cagtatattg ataagcagta cgaggaattt    1080
attccttctt ctgctccact ttctcaagat cgtttatggc aagcagtcga gtccctgaca    1140
caaagcaacg agactatagt tgcagagcaa gggacctcat tctttggtgc ctctacaatt    1200
tttctgaaat ccaacagcag atttatagga caacccctt ggggctctat tggatatact    1260
tttcccgcag cccttggttc acaaatcgca gataaggagt caagacatct gttattcata    1320
ggtgatggta gtctacaatt aacagttcaa gaattaggcc tatcaataag ggagaagtta    1380
aacccaatct gtttcataat taacaatgac ggctacactg ttgaaaggga gatccacgga    1440
ccaacacaat catacaatga tattcccatg tggaactata gcaaattacc ggagactttc    1500
ggcgcaaccg aggatagagt agtttcgaag atcgttagga ctgagaatga atttgttagc    1560
gttatgaagg aagcccaggc tgatgtcaat agaatgtatt ggattgaatt agttttggaa    1620
aaggaagatg cacctaaatt actaaaaaag atggggaaac tatttgctga gcaaaacaaa    1680
catcaccatc accatcacta a                                              1701
```

<210> SEQ ID NO 112
<211> LENGTH: 1695
<212> TYPE: DNA
<213> ORGANISM: Saccharomyces cerevisiae

<400> SEQUENCE: 112

```
atgtctgaaa ttactttggg taaatatttg ttcgaaagat taaagcaagt caacgttaac      60
accgttttcg gtttgccagg tgacttcaac ttgtccttgt tggacaagat ctacgaagtt     120
gaaggtatga gatgggctgg taacgccaac gaattgaacg ctgcttacgc cgctgatggt     180
```

```
tacgctcgta tcaagggtat gtcttgtatc atcaccacct tcggtgtcgg tgaattgtct     240
gctttgaacg gtattgccgg ttcttacgct gaacacgtcg gtgttttgca cgttgttggt     300
gtcccatcca tctctgctca agctaagcaa ttgttgttgc accacacctt gggtaacggt     360
gacttcactg ttttccacag aatgtctgcc aacatttctg aaaccactgc tatgatcact     420
gacattgcta ccgccccagc tgaaattgac agatgtatca gaaccactta cgtcacccaa     480
agaccagtct acttaggttt gccagctaac ttggtcgact tgaacgtccc agctaagttg     540
ttgcaaactc caattgacat gtctttgaag ccaaacgatg ctgaatccga aaaggaagtc     600
attgacacca tcttggcttt ggtcaaggat gctaagaacc cagttatctt ggctgatgct     660
tgttgttcca gacacgacgt caaggctgaa actaagaagt tgattgactt gactcaattc     720
ccagctttcg tcaccccaat gggtaagggt tccattgacg aacaacaccc aagatacggt     780
ggtgtttacg tcggtacctt gtccaagcca gaagttaagg aagccgttga atctgctgac     840
ttgattttgt ctgtcggtgc tttgttgtct gatttcaaca ccggttcttt ctcttactct     900
tacaagacca agaacattgt cgaattccac tccgaccaca tgaagatcag aaacgccact     960
ttcccaggtg tccaaatgaa attcgttttg caaaagttgt tgaccactat tgctgacgcc    1020
gctaagggtt acaagccagt tgctgtccca gctagaactc cagctaacgc ttttattcct    1080
tcttctgctc cactttctca agatcgttta tggcaagcag tcgagtccct gacacaaagc    1140
aacgagacta tagttgcaga gcaagggacc tcattctttg gtgcctctac aattttctg    1200 aaatccaaca gcagatttat aggacaaccc ctttgggct ctattggata ctttttccc     1260 gcagcccttg gttcacaaat cgcagataag gagtcaagac atctgttatt cataggtgat    1320
ggtagtctac aattaacagt tcaagaatta ggcctatcaa taagggagaa gttaaaccca    1380
atctgtttca taattaacaa tgacggctac actgttgaaa gggagatcca cggaccaaca    1440
caatcataca atgatattcc catgtggaac tatagcaaat taccggagac tttcggcgca    1500
accgaggata gagtagtttc gaagatcgtt aggactgaga atgaatttgt tagcgttatg    1560
aaggaagccc aggctgatgt caatagaatg tattggattg aattagtttt ggaaaaggaa    1620
gatgcaccta aattactaaa aaagatgggg aaactatttg ctgagcaaaa caaacatcac    1680
catcaccatc actaa                                                     1695
```

<210> SEQ ID NO 113  
<211> LENGTH: 50  
<212> TYPE: DNA  
<213> ORGANISM: Artificial Sequence  
<220> FEATURE:  
<223> OTHER INFORMATION: Primer

<400> SEQUENCE: 113

```
ctagaactag tggatccccc atgtatacag taggagatta cctgttagac                 50
```

<210> SEQ ID NO 114  
<211> LENGTH: 110  
<212> TYPE: DNA  
<213> ORGANISM: Artificial Sequence  
<220> FEATURE:  
<223> OTHER INFORMATION: Primer

<400> SEQUENCE: 114

```
ttactcttgt acaatctgaa caaaatagcg tcaacaacgt cttctaatac ttcgacgcca      60
gaagtggtca attggatttc ttctaaagat aatgcaggct tctctgcttt                110
```

<210> SEQ ID NO 115

```
<211> LENGTH: 110
<212> TYPE: DNA
<213> ORGANISM: Artificial Sequence
<220> FEATURE:
<223> OTHER INFORMATION: Primer

<400> SEQUENCE: 115
atgagaattt gcagcctggt gatcttttgg taatggacac catgtcattc tgctttgctt      60
tacctgacat aatgcttcca gaatttattc catcaagtgc tcccttatca                110

<210> SEQ ID NO 116
<211> LENGTH: 50
<212> TYPE: DNA
<213> ORGANISM: Artificial Sequence
<220> FEATURE:
<223> OTHER INFORMATION: Primer

<400> SEQUENCE: 116
atatcgaatt cctgcagccc ctatttattt tgctcagcaa ataatttacc                 50

<210> SEQ ID NO 117
<211> LENGTH: 50
<212> TYPE: DNA
<213> ORGANISM: Artificial Sequence
<220> FEATURE:
<223> OTHER INFORMATION: Primer

<400> SEQUENCE: 117
ctagaactag tggatccccc atgacccctg tgcaagaaac aatacgcctt                 50

<210> SEQ ID NO 118
<211> LENGTH: 110
<212> TYPE: DNA
<213> ORGANISM: Artificial Sequence
<220> FEATURE:
<223> OTHER INFORMATION: Primer

<400> SEQUENCE: 118
ggtttttggg cattttcaa actttcttca atcttactca aaatcacttg ttcagttgta       60
tttgttgtag agctttcttt agaagtggtc aattggattt caagaggtaa                110

<210> SEQ ID NO 119
<211> LENGTH: 110
<212> TYPE: DNA
<213> ORGANISM: Artificial Sequence
<220> FEATURE:
<223> OTHER INFORMATION: Primer

<400> SEQUENCE: 119
attttagagc agtggtttct tctttatcag aattaaaagg aatagaatat gaaggacaat      60
atattgataa gcaatatgaa tactatggat ccattggcta tgcattgcca                110

<210> SEQ ID NO 120
<211> LENGTH: 50
<212> TYPE: DNA
<213> ORGANISM: Artificial Sequence
<220> FEATURE:
<223> OTHER INFORMATION: Primer

<400> SEQUENCE: 120
atatcgaatt cctgcagccc ctatttcttg caaaacattt cgctaaatct                 50

<210> SEQ ID NO 121
<211> LENGTH: 1854
<212> TYPE: DNA
```

<213> ORGANISM: Pichia stipitis

<400> SEQUENCE: 121

```
tatcacaaga ccgtctatgg caggcagttg aaagtttgac tcaaagcaat gaaacaatcg      60
ttgctgaaca aggaacctca ttttttggag cttcaacaat tttcttaaaa tcaaatagtc     120
gttttattgg acaaccttta tggggttcta ttggatatac ttttccagcg gctttaggaa     180
gccaaattgc ggataaagag agcagacacc tttatttat tggtgatggt tcacttcaac      240
ttaccgtaca agaattagga ctatcaatca gagaaaaact caatccaatt tgttttatca     300
taaataatga tggttataca gttgaaagag aaatccacgg acctactcaa agttataacg     360
acattccaat gtggaattac tcgaaattac agaaacatt tggagcaaca gaagatcgtg      420
tagtatcaaa aattgttaga acagagaatg aatttgtgtc tgtcatgaaa gaagcccaag     480
cagatgtcaa tagaatgtat tggatagaac tagttttgga aaaagaagat gcgccaaaat     540
tactgaaaaa aatgggtaaa ttatttgctg agcaaaataa atagatgtat acagtaggag     600
attacctgtt agaccgatta cacgagttgg gaattgaaga aattttttgga gttcctggtg    660
actataactt acaattttta gatcaaatta tttcacgcga agatatgaaa tggattggaa     720
atgctaatga attaaatgct tcttatatgg ctgatggtta tgctcgtact aaaaaagctg     780
ccgcatttct caccacattt ggagtcggcg aattgagtgc gatcaatgga ctggcaggaa     840
gttatgccga aaatttacca gtagtagaaa ttgttggttc accaacttca aaagtacaaa     900
atgacggaaa atttgtccat catacactag cagatggtga ttttaaacac tttatgaaga     960
tgcatgaacc tgttacagca gcgcggactt tactgacagc agaaaatgcc acatatgaaa    1020
ttgaccgagt actttctcaa ttactaaaag aaagaaaacc agtctatatt aacttaccag    1080
tcgatgttgc tgcagcaaaa gcagagaagc ctgcattatc tttagaagaa atccaattga    1140
ccacttctgg cgtcgaagta ttagaagacg ttgttgacgc tatttttgttc agattgtaca    1200
agagtaagaa cccatcgttg ttgtcggatt gcttgactac cagattcaat cttcaagaca    1260
agttgaatac acttgttgct aaattacctt ccaacttcgt caagttgttt tcgacaaaca    1320
tggctagaaa catagatgag tcgctcagca actttgtagg tctttacttt ggcattggtt    1380
cttcaagcaa ggaagtgtcc agacaattgg agagaaacac cgatttcttg atcaatttgg    1440
gatactttaa tgctgaaact acgactgctg ttattccaa tgacttctcc aatatcgagg     1500
agtatattga aatcaacct gattacatca aggtcaatga acacatcatt aacattaaaa     1560
atcctgagtc tggaaagagg ttgttctcta tgggccagtt gttggatgca ttactcttta    1620
aattagacct caacaagatt gagaacataa acaacaataa tattagctac aagttcttcc    1680
caccaacttt atatgagcaa gacaacaata ccgattacat tccacaaaca aaactagtgg    1740
actatttgaa tgagaatttg cagcctggtg atcttttggt aatggacacc atgtcattct    1800
gctttgcttt acctgacata atgcttccag aatttattcc atcaagtgct ccct          1854
```

<210> SEQ ID NO 122
<211> LENGTH: 1656
<212> TYPE: DNA
<213> ORGANISM: Pichia stipitis

<400> SEQUENCE: 122

```
atgacccctg tgcaagaaac aatacgcctt ccaggcactt cttctcctac ggttcctgaa      60
aacgtcactt gggcgagta tctcttcctc agaatctctc aggctaatcc aaagttgagg     120
tccatctttg gtattcctgg cgacttcaat gtcgatttgt tggaacactt gtactctcca    180
```

-continued

```
gttgtcgctg gaagagacat aaagtttatt ggcttatgta acgaattgaa tggtgcctac      240
actgctgatg gatactccag ggccattgga ggtttgagca cttttatttc tacattcggt      300
gttggtgaat tgtcggccat taacggaatc gctggatcgt ttgctgagtt ttctcctgtg      360
cttcacattg taggcaccac ctccttacca caacgtgacc atgccattaa cggcagcgac      420
gttagaaacc accaccactt aattcaaaac aagaatcctt tgtgtcagcc aaatcatgat      480
gtctacaaga agatgattga acctatctca gttattcagg aatctttaga cagtgatttg      540
caaaggaaca tggaaaagat tgatagagtt ttggttaaga ttctccagga atctagacct      600
ggatacctct ttatcccttg tgatattacc aacttaatag tcccaagcta tagattatat      660
gaaaccccat tacctcttga aatccaattg accacttcta aagaaagctc tacaacaaat      720
acaactgaac aagtgatttt gagtaagatt gaagaaagtt tgaaaaatgc ccaaaaacca      780
gtagtgattg caggacacga agtaattagt tttggtttag aaaaaacggt aactcagttt      840
gtttcagaaa caaaactacc gattacgaca ctaaattttg gtaaaagtgc tgttgatgaa      900
tctttgccct cattttagg aatatataac gggaaacttt cagaaatcag tcttaaaaat       960
tttgtggagt ccgcagactt tatcctaatg cttggagtga agcttacgga ctcctcaaca     1020
ggtgcattca cacatcattt agatgaaaat aaaatgattt cactaaacat agatgaagga     1080
ataattttca ataaagtggt agaagatttt gattttagag cagtggtttc ttctttatca     1140
gaattaaaag gaatagaata tgaaggacaa tatattgata agcaatatga atactatgga     1200
tccattggct atgcattgcc atccactttc ggtgctacca tggcagtcaa tgaccttggt     1260
agtgatagaa gaatcatctt aattgaaggt gatggggcag cccagatgac tatccaggaa     1320
ttgtcttcgt tcctcaaata caaggaattt ttgccaaaca tgcctaagat cttcttgatc     1380
aataacgatg gttacactgt cgagagaatg attaagggac caaccagatc atacaatgac     1440
atcaatggtg aatggagttg gacacaattg cttggtgtgt ttggagataa agagcaaaag     1500
taccactcta ctgccttgtt gcgcaatgtc aacgaattca caagtatttt tgaatttcaa     1560
aggcagactg acaattctaa gttggagttc attgagttga tagccggcaa atacgattgt     1620
cctcttagat ttagcgaaat gttttgcaag aaatag                               1656
```

METHYLBUTANOL AS AN ADVANCED BIOFUEL

RELATED APPLICATIONS

This application claims the benefit of priority of U.S. Provisional Application No. 60/012,749, filed Dec. 10, 2007, which is hereby incorporated by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 616872000600Seqlist.txt | Jul. 27, 2009 | 409,600 bytes |

TECHNICAL FIELD

This invention describes genes, polypeptides and expression constructs therefor, metabolic pathways, microbial strains and methods to biologically produce methylbutanol and derivatives thereof for a variety of uses including as an advanced biofuel.

BACKGROUND ART

Some oxygenate fuels produced by fermentation, like ethanol, have lower energy density than gasoline and absorb water, a property that prevents such fuels from being distributed with gasoline in existing pipelines. These fuels must be transported separately by rail or trucks to "splash" blending terminals, increasing the cost of blended fuels. Methylbutanol (MBO) has higher energy content than ethanol and because it does not absorb water, can be distributed on existing pipelines, avoiding additional transportation costs. Methylbutanol and its derivatives can be useful as a neat fuel or blend stock for gasoline, diesel, kerosene and jet fuels. Its relatively low volatility also minimizes environmental contamination.

SUMMARY OF THE INVENTION

This invention describes genes, polypeptides and expression constructs therefor, metabolic pathways, microbial strains and methods to biologically produce methylbutanol and derivatives thereof for a variety of uses including as an advanced biofuel. One embodiment of the invention relates to a recombinant microorganism comprising at least one DNA molecule, wherein said at least one DNA molecule encodes at least three polypeptides that catalyze a substrate to product conversion selected from the group consisting of: malate to pyruvate, pyruvate to oxaloacetic acid, oxaloacetic acid to L-aspartate, L-aspartate to L-aspartyl-4-phospate, L-aspartyl-4-phospate to L-aspartate-semialdehyde, L-aspartate-semialdehyde to homoserine, homoserine to O-phospho-L-homoserine, and O-phospho-L-homoserine to L-threonine; and wherein said recombinant microorganism produces 2-methylbutanol.

In one embodiment, the at least three polypeptides are selected from the group consisting of: a) a malate dehydrogenase [EC 1.1.1.37], b) a pyruvate carboxylase [EC 6.4.1.1], c) an aspartate aminotransferase [EC 2.6.1.1], d) an aspartate kinase [EC 2.7.2.4], e) an aspartic beta semi-aldehyde dehydrogenase [EC 1.2.1.11], f) a homoserine dehydrogenase [EC 1.1.1.3], g) a homoserine kinase [EC 2.7.1.39], and h) a threonine synthase [EC 4.2.99.2].

The polypeptides used with the invention can be derived from a variety of sources, such as *Picihia*, *Saccharomyces*, or *Corynebacterium*. For example, the malate dehydrogenase may be a *Picihia stipitis* malate dehydrogenase MDH2 gene product, the pyruvate carboxylase can be a *Picihia stipitis* pyruvate carboxylase PYC1 gene product, can be a *Pichia stipitis* aspartate aminotransferase gene AAT2 gene product, and the aspartate kinase can a *Pichia stipitis* aspartate kinase HOM3 gene product. The invention encompasses the use of enzymes, such as HOM3 that have been modified to become resistant to feedback inhibition.

In another embodiment, the aspartate kinase is derived from the genus *Saccharomyces*, for example, the aspartate kinase can be a *Saccharomyces cerevisiae* aspartate kinase HOM3 gene product, and further, it can be modified to become resistant to feedback inhibition (SEQ ID NO:). The aspartic beta semi-aldehyde dehydrogenase can be a *Pichia stipitis* aspartic beta semi-aldehyde dehydrogenase HOM2 gene product, the homoserine dehydrogenase can be a *Pichia stipitis* homoserine dehydrogenase HOM6 gene product, and the homoserine kinase is a *Pichia stipitis* homoserine kinase THR1 gene product. In still another embodiment, the homoserine kinase can be derived from the genus *Corynebacterium*, and the threonine synthase is a *Pichia stipitis* threonine synthase THR4 gene product.

Another embodiment of the invention relates to a recombinant microorganism comprising at least one DNA molecule, wherein said at least one DNA molecule encodes at least two polypeptides that catalyze a substrate to product conversion selected from the group consisting of a) L-threonine to 2-oxobutanate, b) 2-oxobutanate to 2-aceto-hydroxy-butyrate, c) 2-aceto-hydroxy-butyrate to 2,3-dihydroxy-3-methylvalerate, and d) 2,3-dihydroxy-3-methylvalerate to 2-keto-3-methylvalerate; and wherein said recombinant microorganism produces 2-methylbutanol.

In a preferred embodiment, the at least two polypeptides are selected from the group consisting of: a threonine deaminase or a threonine dehydratase [EC 4.3.1.19], an acetolactate synthase [EC 2.2.1.6], or a subunit thereof, a ketol-acid reductoisomerase or an acetohydroxyacid reductoisomerase [EC 1.1.1.86], and a dihydroxyacid dehydratase [EC 4.2.1.9]. In one aspect of the invention, the polypeptides are directed to the in the cytoplasm of the recombinant microorganism.

The polypeptides used with the invention can be derived from a variety of sources, such as *Picihia*, *Escherichia*, *Saccharomyces*, or *Corynebacterium*.

For example, the threonine deaminase can be a *Pichia stipitis* threonine deaminase ILV1 gene product, it can also be a *Pichia stipitis* threonine deaminase ILV1 gene product that has been modified to become resistant to feedback inhibition, or modified to optimize cytoplasmic expression. In one embodiment, the threonine deaminase can be derived from the genus *Saccharomyces*, such as a *Saccharomyces cerevisiae* ILV1 gene product that has been modified to become resistant to feedback inhibition. In other embodiments, the threonine deaminase can be derived from the genus *Escherichia* or *Corynebacterium*.

In one aspect of the invention, the acetolactate synthase or an acetolactate synthase subunit is derived from the genus Pichia. For example, the acetolactate synthase can be a *Pichia stipitis* acetolactate synthase ILV2 gene product, or a *Pichia stipitis* acetolactate synthase ILV2 gene product that has been modified to optimize cytoplasmic expression. In another embodiment, the acetolactate synthase is a *Pichia stipitis* acetolactate synthase ILV6 gene product. In another embodiment, the acetolactate synthase or an acetolactate synthase subunit is derived from the genus *Escherichia* or *Corynebacterium*.

In another embodiment of the invention, the ketol-acid reductoisomerase can be derived from the genus *Pichia, Escherichia*, or *Corynebacterium*. For example, the *Pichia stipitis* ketol-acid reductoisomerase ILV5 gene product or an ILV5 gene product that has been modified to optimize cytoplasmic expression.

In another embodiment of the invention, the dihydroxyacid dehydratase derived from the genus *Pichia, Escherichia*, or *Corynebacterium*, such as a dihyroxyacid dehydratase is a *Pichia stipitis* dihydroxyacid dehydratase ILV3 gene product or an ILV3 gene product that has been modified to optimize cytoplasmic expression.

Another embodiment of the invention relates to a recombinant microorganism comprising at least one DNA molecule, wherein said at least one DNA molecule encodes (i) a polypeptide that catalyzes a 2-keto-3-methyl-valerate to 2-methylbutanal conversion, and (ii) a polypeptide that catalyzes a 2-methylbutanal to 2-methylbutanol conversion; and wherein said recombinant microorganism produces 2-methylbutanol. In one aspect, the at least one DNA molecule encodes a pyruvate decarboxylase or a pyruvate decarboxylase isoform derived from the genus *Pichia*. For example, the pyruvate decarboxylase can be a *Pichia stipitis* pyruvate decarboxylase PDC3-6 gene product. In another aspect, the alpha-ketoacid decarboxylase derived from the genus *Mycobacterium*, the genus *Lactococcus*. In one embodiment, the alcohol dehydrogenase is derived from the genus *Saccharomyces*, or the genus *Pichia*. For example, the alcohol dehydrogenase can be a *Saccharomyces cerevisiase* alcohol dehydrogenase ADH6 gene product. In another embodiment, the methylglyoxal reductase derived from the genus *Pichia* or the genus *Saccharomyces*.

Another embodiment of the invention relates to a recombinant microorganism comprising at least one DNA molecule, wherein said at least one DNA molecule encodes at least two polypeptides that catalyze a substrate to product conversion selected from the group consisting of: pyruvate to citramalate, citramalate to erythro-beta-methyl-D-malate, and erythro-beta-methyl-D-malate to 2-oxobutanoate; and wherein said recombinant microorganism produces 2-methylbutanol. The polypeptides can be selected from the group consisting of: a 2-isopropylmalate synthase [EC 2.3.3.13], a citramalate synthase [EC 4.1.3.22], an isopropylmalate isomerase [EC 4.2.1.33], and an isopropylmalate dehydrogenase [EC 1.1.1.85].

The polypeptides can be derived from a number of sources, for example, in one embodiment, the 2-isopropylmalate synthase derived from the genus *Thermatoga* or the genus *Synechocystis*. In one embodiment, the polypeptide is derived from a *Thermotoga maritima* 2-isopropylmalate synthase leuA gene product. In another embodiment, the citramalate synthase can be derived from the genus *Geobacter* and the isopropymalate isomerase can be derived from the genus *Methanococcus*, for example the isopropylmalate isomerase can be a *Methanococcus jannaschii* isopropylmalate isomerase leuC gene product and/or leuD gene product. The isopropymalate dehydrogenase can be derived from the genus *Methanococcus*, such as the *Methanococcus jannaschii* isopropylmalate dehydrogenase leuB gene product.

Various embodiments of the invention also contemplate a nucleic acid encoding an amino acid biosynthesis regulatory protein, such as a regulatory protein derived from the genus *Saccharomyces*. In one embodiment, the regulatory protein can be a *Saccharomyces cerevisiae* GCN4 gene product.

Another aspect of the invention relates to methods for producing compounds. For example, one embodiment of the invention relates to a recombinant method for producing 2-methylbutanol, comprising: providing a culture medium, wherein the culture medium comprises a carbon source; contacting said culture medium with the recombinant microorganism of the invention, wherein the recombinant microorganism produces spent culture medium from the culture medium by metabolizing the carbon source to 2-methylbutanol; and recovering said 2-methylbutanol from the spent culture medium. In one embodiment, the 2-methylbutanol in the culture medium is produced at the rate of at least 1500 $\mu M/OD_{600}/h$ at 16 h EFT. In another embodiment of the method, the recovering step comprises extracting 2-methylbutanol using liquid-liquid extraction, wherein a solvent is used to continuously extract at least 2-methylbutanol from the spent culture medium. Examples of solvents include diisopropyl ether, heptane or isooctane. In certain embodiments the solvent is diisopropyl ether; and at least 90% of 2-methylbutanol is extracted from the spent culture medium.

In other embodiments of the invention, the 2-methylbutanol is converted to bis(2-methyl)butyl ether or 3,3,5-trimethylheptane. In some embodiments, the conversion step of converting 2-methylbutanol to bis(2-methyl)butyl ether comprises treating the 2-methylbutanol with an acid resulting in the formation of bis(2-methyl)butyl ether. An example of a suitable acid is trifluoromethanesulfonic acid. In another embodiment of the invention, the conversion step of converting 2-methylbutanol to bis(2-methyl)butyl ether comprises: refluxing a solution comprising 2-methylbutanol and a catalytic amount of acid; removal of water generated from the solution; and neutralizing the solution and isolating the ether product.

Examples of products produced include: a compound of formula I, II, III, IV, V or any combination thereof:

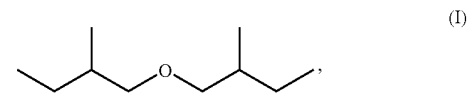

(I)

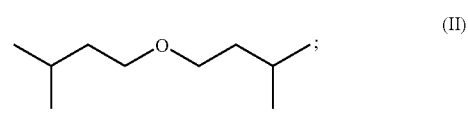

(II)

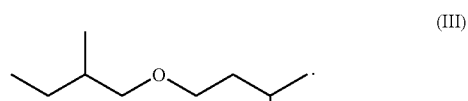

(III)

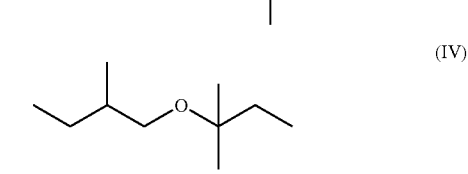

(IV)

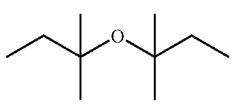
(V)

In other embodiments of the invention, the conversion step of converting 2-methylbutanol is to 3,3,5-trimethylheptane comprises: treating 2-methylbutanol with an acid to form 2-methylbutene; hydrogenating 2-methylbutene to form 2-methylbutane; and combining 2-methylbutane with 2-methylbutene in the presence of acid to form 3,3,5-trimethylheptane.

The disclosed invention also relates to a number of compositions produced from biological sources. Preferred embodiments include a composition comprising a compound of the formula I and/or II:

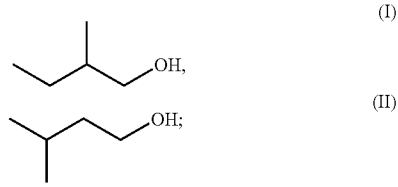

(I)

(II)

wherein the compound comprises a fraction of modern carbon ($f_M$ $^{14}C$) of at least about 1.003.

In another embodiment, the composition comprising a compound of the formula I, II, III, IV and/or V:

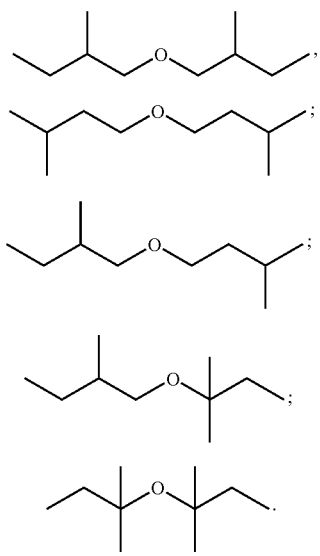

(I)

(II)

(III)

(IV)

(V)

wherein the compound comprises a fraction of modern carbon ($f_M$ $^{14}C$) of at least about 1.003.

Embodiments of the invention also include fuel compositions comprising a compound discussed above. Embodiments of these fuel compositions can further comprises a petroleum-based fuel, such as gasoline, diesel, jet fuel, kerosene, heating oil, and any combinations thereof. Embodiments of the fuel composition can further comprises another biofuel. In another embodiment, the compounds of the invention can make up approximately 100% of the composition, or less, such as 1-99% of the weight of the composition or, in another embodiment, 1-99% of the volume of the composition. In another embodiment, the composition can be a fuel additive or it can comprise a fuel additive.

| Strain genotype | Strain number |
|---|---|
| BY4741 (wild-type) | 7766 |
| BY4741 + p415Tefllv1fbr | 7746 |
| Ilv1::ilv1fbr | 7767 |
| Ilv1::ilv1fbr + p415Tefilv1fbr | 7747 |

Figure 22:
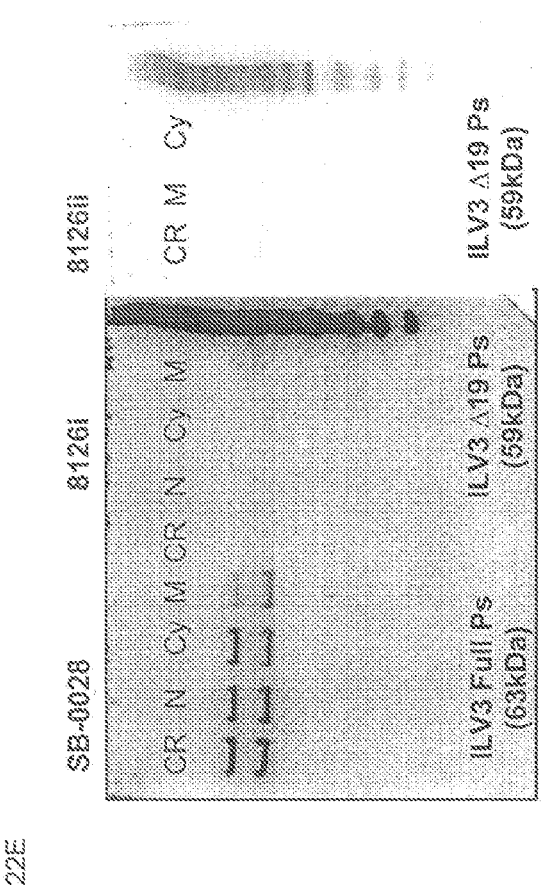
Figure 22:
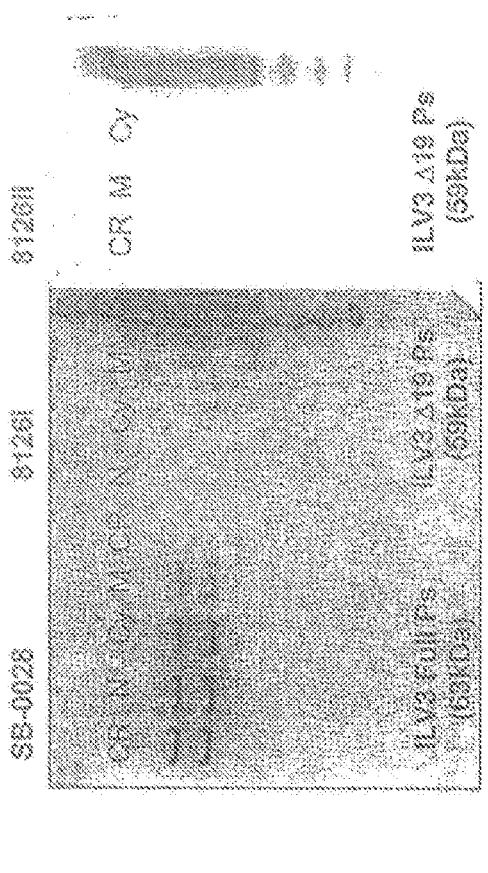

FIG. 22 (a-e) Data showing the intracellular localization of expressed polypeptides. The recombinant proteins carry a C-terminal 6×His tag for identification by the anti-His antibody using immunoblots of specific cell fractions. a) 7541 background ILV1Δ strain with p415TEF ILV1, p415TEF ILV1Δ45 & p415TEF ILV1FBR45; b) 7123 strain with p415TEF ILV2, p415TEF ILV2 Δ45; c) 7123 strain with p415TEF ILV5, p415TEF ILV5 Δ35; d) 7123 strain with p415TEF ILV3, p415TEF ILV3 Δ35, e) 7123 strain with p415TEF ILV3, p415TEF ILV3 Δ19 *Pichia stipidis* (panel ii for ILV3 Δ19 is a crude fractionation method showing expression in all 3 fractions). 7.0 ug of protein was loaded in each well to all gel results below. A 1:2000 dilution of primary antibody was used for each lane. (CR=Crude extract; N=Nuclei fraction; M=Mitochondrial fraction; and Cy=Cytosolic fraction.)

FIG. 23 (a-d.) Endpoint assays for acetolactate synthase activity were carried out using pyruvate as substrate. The resulting acetolactate was converted to acetone under acidic conditions. Acetone was reacted with α-naphtha for colorimetric detection at 546 nm. *E. coli* ilvB was found to the highest activity on pyruvate and *E. coli* ilvG showed minimum activity (a). The reaction was only moderately subject to feedback inhibition by leucine, isoleucine and valine (b, c and d) which could be due to longer reaction times. Strain information is provided below:

| Strain | Description | Strain number |
|---|---|---|
| S7209 | p416TEF | 7209 |
| B | p415TEF ilvB (Ec) | 7302 |
| B + N | p415TEF ilvB (Ec) p414TEFilvN (Ec) | 8129 |
| G | p413TEF ilvG' (Ec) p415TEF | 7307 |
| G + M | p415TEF ilvG' (Ec) p416TEFilvM (Ec) | 7558 |
| I | p415TEF ilvI (Ec) | 7560 |
| I + H | p415TEF ilvI (Ec) p416TEF ilvH (Ec) | 7559 |
| S ce2 | p414TEF ILV2 p415TEF | 7309 |
| 2 + 6 | p415 TEF ILV6 p414TEF ILV2 | 7313 |
| B (C glu) | p415TEF ilvB (Cg) | 7306 |

Figure 24:
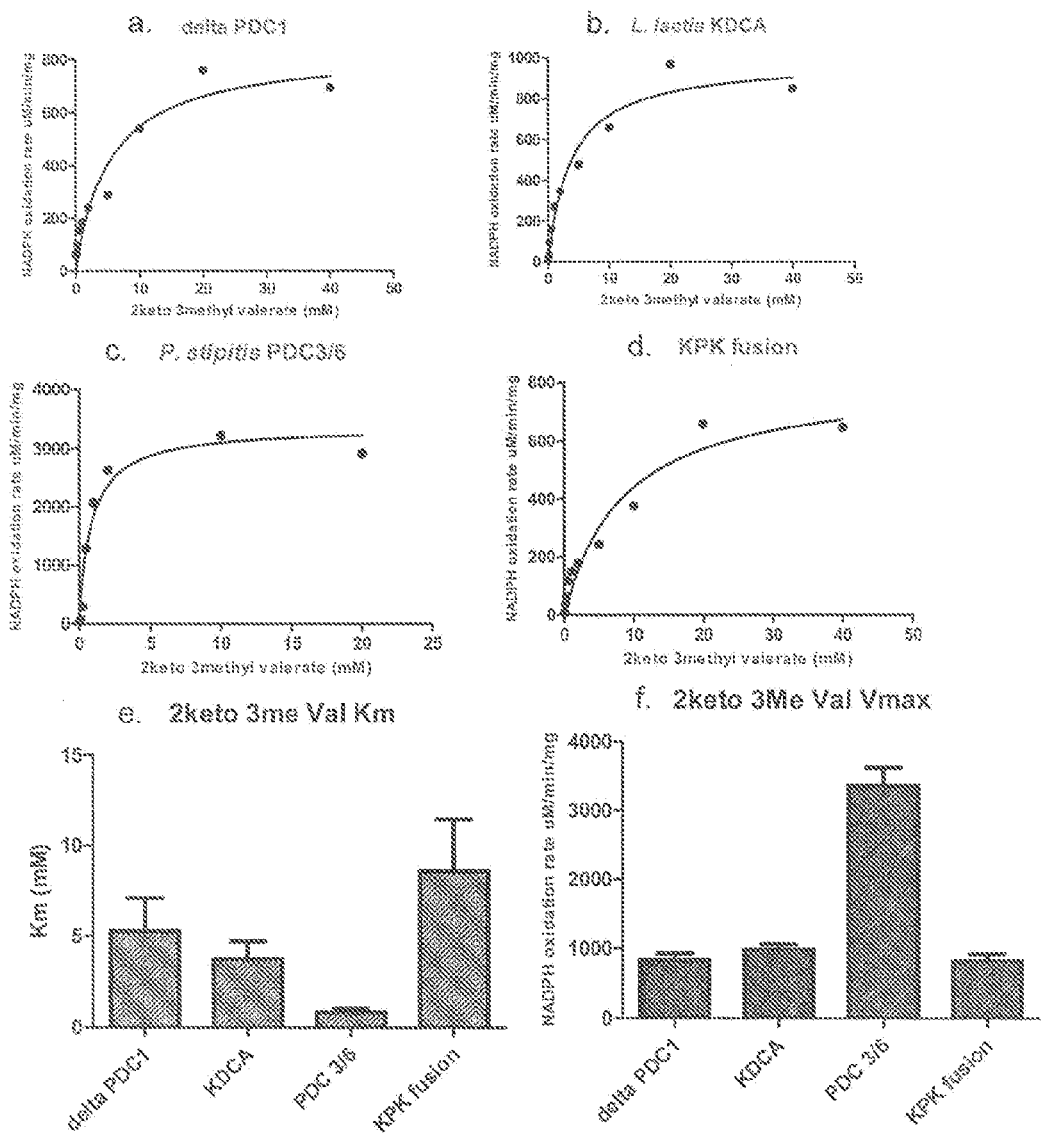

FIG. 24 (a-f.) Kinetic curves of keto acid decarboxylases on 2-keto-3-methyulvalerate a. ΔPDC1 strain; *L. lactis* KdcA; c. *Pichia stipitis* PDC3-6; d. ES1 (KdcA PDC1 (KPK) fusion 1); e. $K_m$ values of the four enzymes (a to d) on 2-keto-3-methylvalerate; f. $V_{max}$ values of the four enzymes (a to d) on 2-keto-3-methylvalerate.

Figure 25:
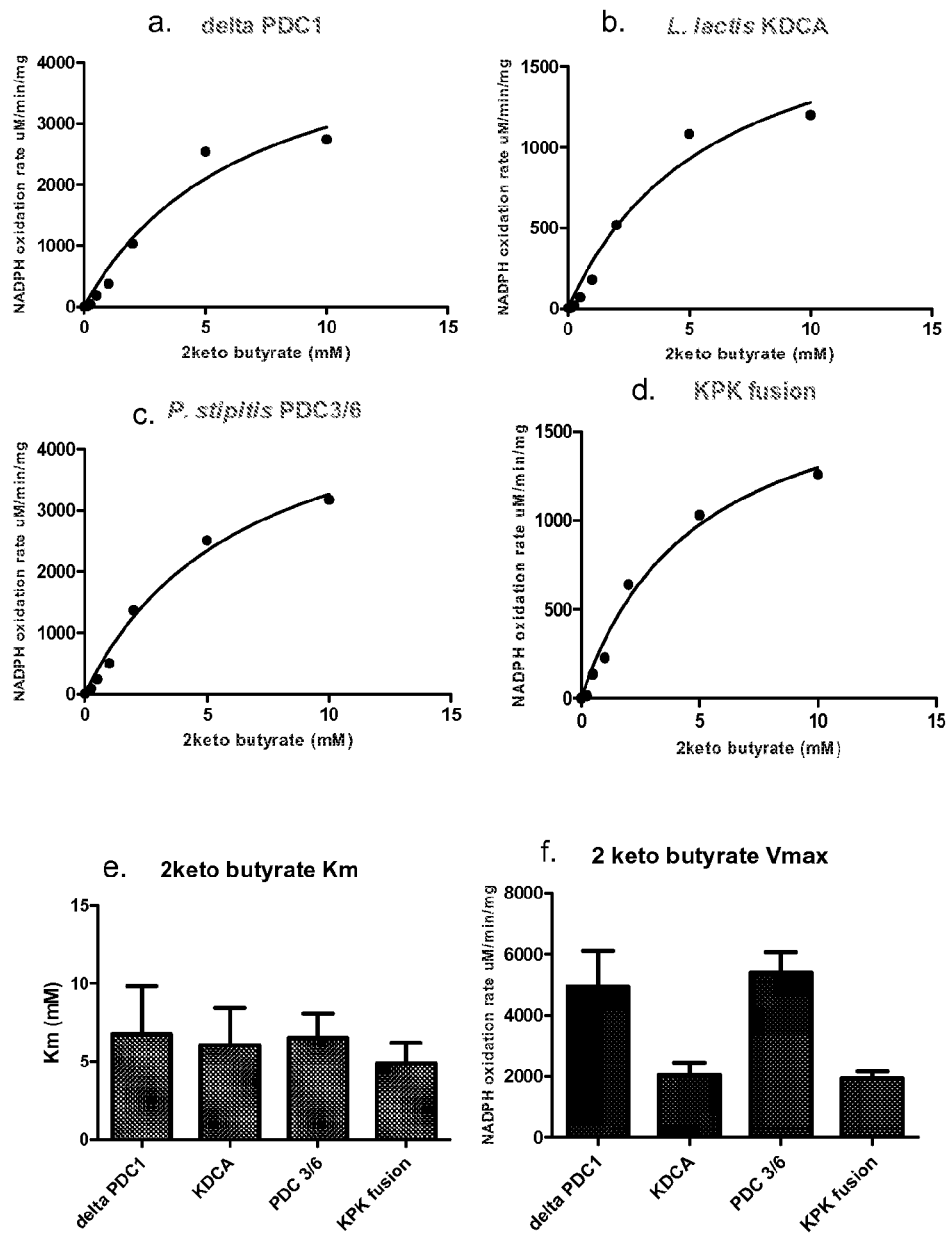

FIG. 25 (a-f) Kinetic curves of keto acid decarboxylases on 2-keto butyrate a. ΔPDC1 strain; b. *L. lactis* KdcA; c. *Pichia stipitis* PDC3-6; d. ES1 (KdcA-PDC1 (KPK) fusion 1); e. $K_m$ values of the four enzymes (a to d) on 2-keto butyrate; f. $V_{max}$ values of the four enzymes (a to d) on 2keto butyrate.

Figure 26:
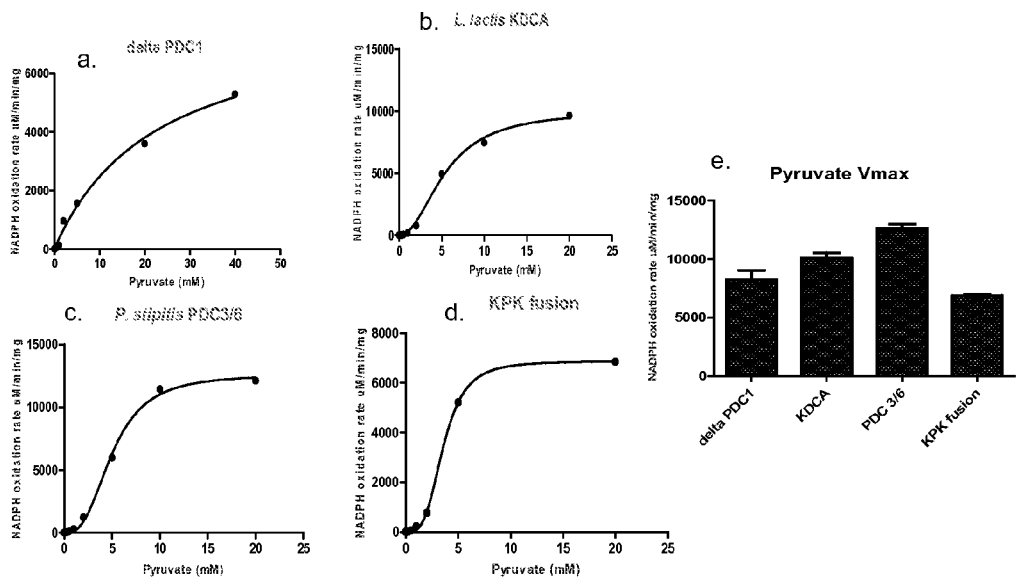

FIG. 26 (a-e.) Kinetic curves of keto acid decarboxylases on pyruvate a. ΔPDC1 strain; b. *L. lactic* KdcA; c. *Pichia stipitis* PDC3-6; d. ES1 (KDCA-PDC1 (KPK) fusion 1); e. $V_{max}$ values of the four enzymes (a to d) on pyruvate.

Figure 27:
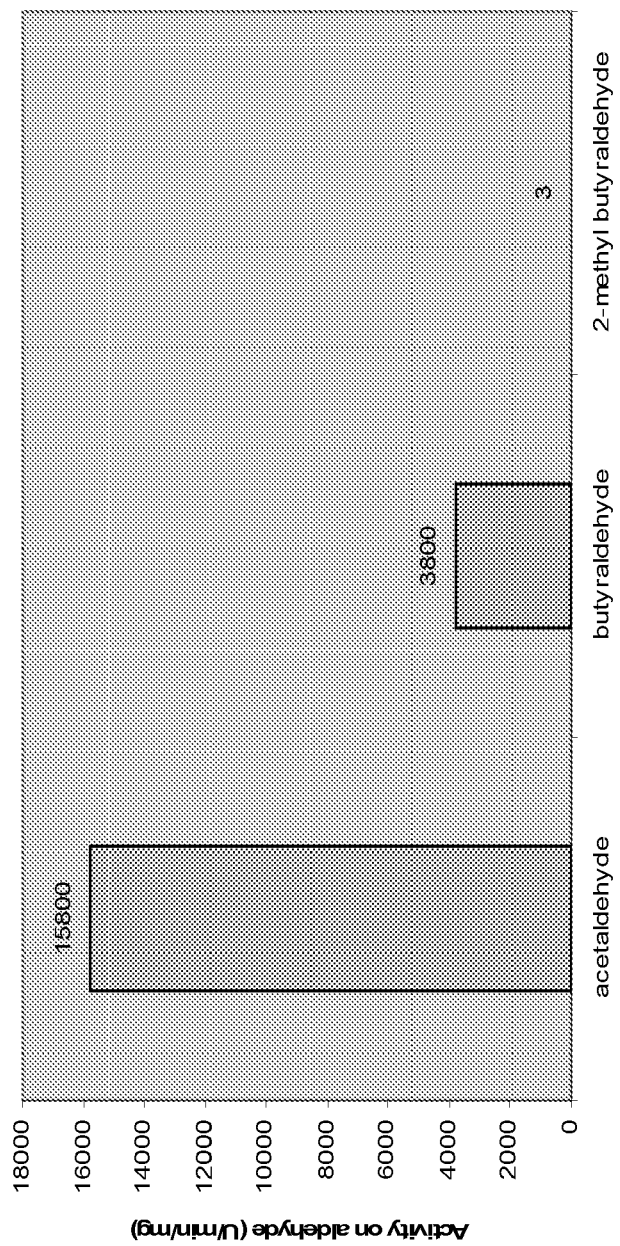

FIG. 27. Activity of *S. cerevisiae* ADH1 on various aldehydes.

FIG. 28 (A and B). Kinetic curves of ADH6 on 2-methylbutyraldehye (A) and acetaldehyde (B).

Figure 29:
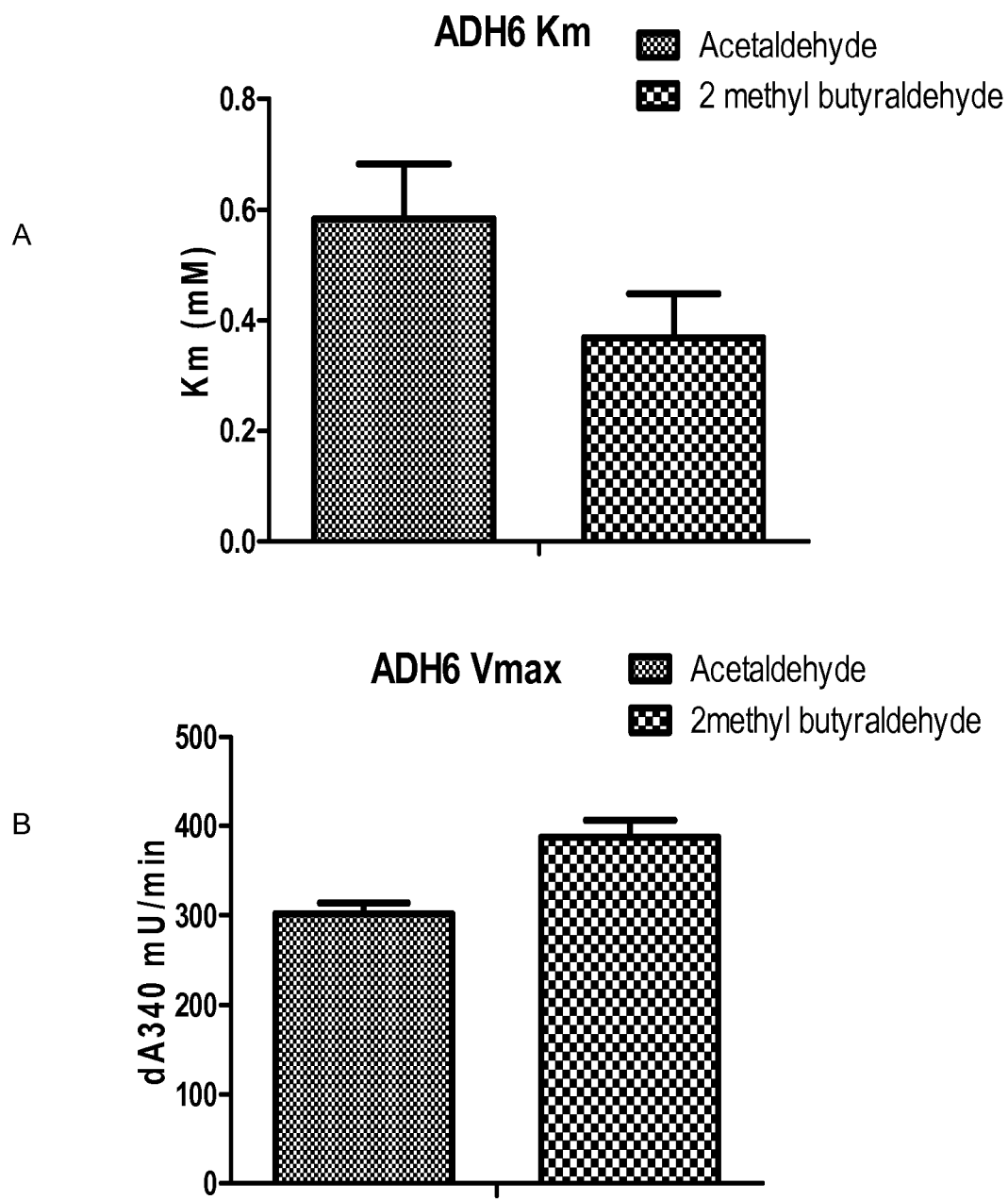

FIG. 29 (a and b). $K_m$ and $V_{max}$ values of *S. cerevisiae* ADH6 on the substrates acetaldehyde and 2-methylbutyraldehyde FIG. 30. Co-factor oxidation of GRE2 (alcohol dehydrogenase) on methylbutyraldhyde substrates.

Figure 31:
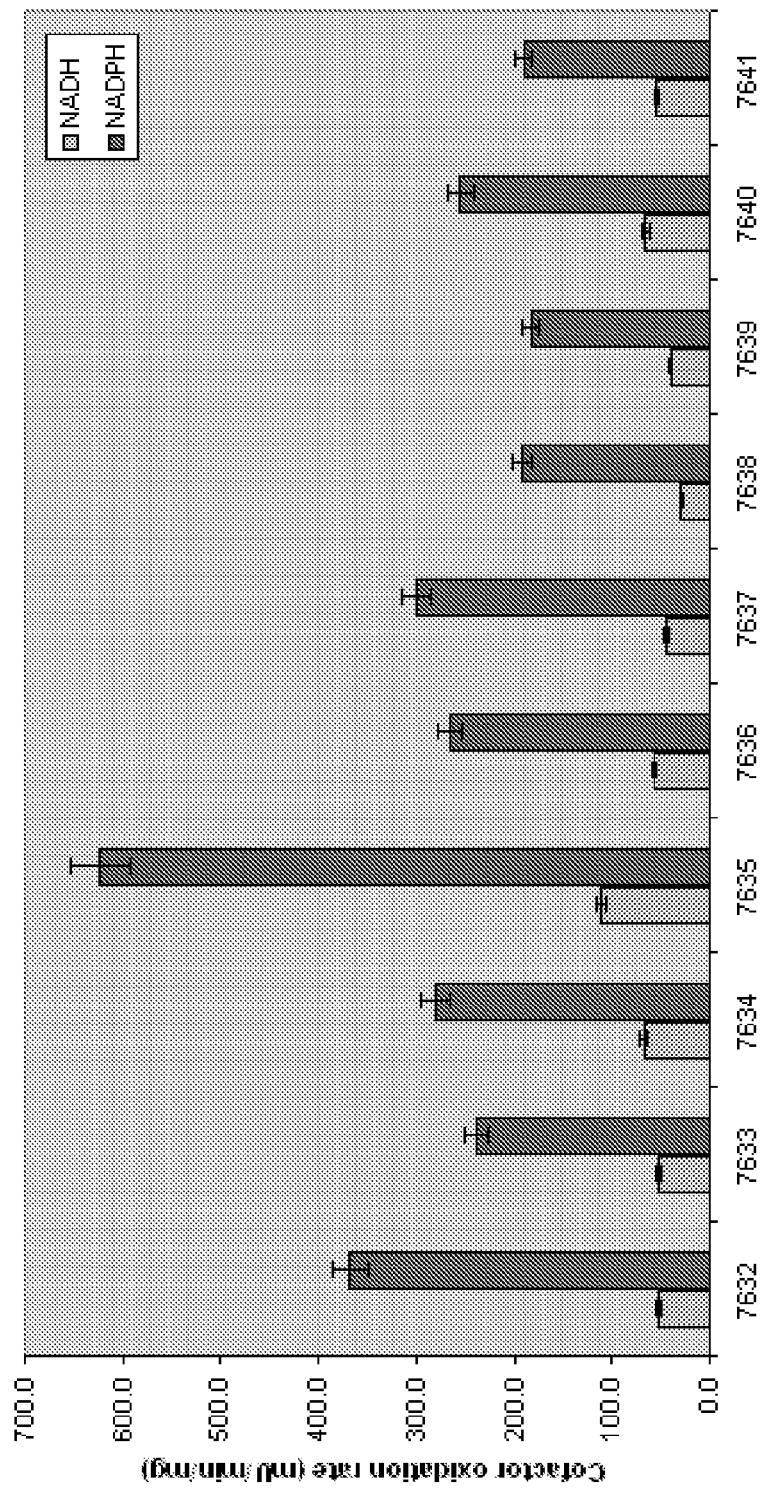

FIG. 31. Co-factor oxidation of decarboxylase and alcohol dehydrogenase combinations. Strains 7632 (p416TEF-ADH6, p415TEF-PDC1); 7633 (p416TEF-His:GRE2), pTEF-PDC5); 7634 (ΔPDC1, p416TEF-ADH6, p415TEF-PDC1); 7635 (p416TEF-His:GRE2, p415TEF-PDC1); 7636 (p416TEF-ADH6, p415TEF-KdcA(Ll)); 7637 (p416TEF-ADH6, p415TEF-KdcA(Ll)-S286Y); 7638 (p416TEF-ADH6, p415TEF-KdcA(Mt); 7639 (p416TEF-ADH6, p415TEF-PDC5); 7640 (p416TEF-His:GRE2, p415TEF-KdcA(Ll)); 7641 (p416TEF-His:GRE2, p415TEF-KdcA (Ll)-S286Y).

Figure 32:
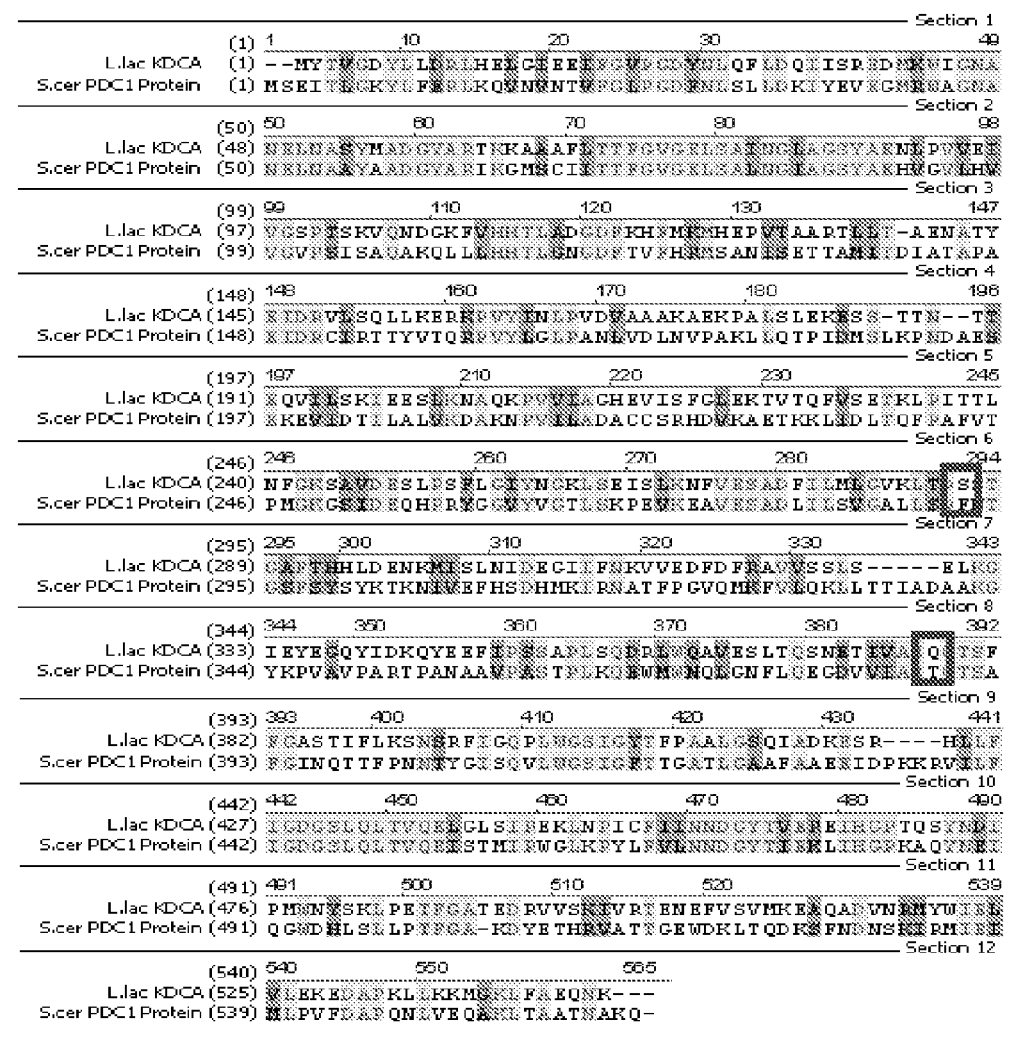

FIG. 32. Alignment of KdcAp and Pdc1p from *Lactococcus lactis* and *Saccharomyces cerevisiae*, respectively. Amino acids identified for site saturation mutagenesis are outlined by the boxes.

FIG. 33. Schematic for making mutant library. Amplification 1 and 2 were completed separately via PCR then combined in one PCR round to attain Amplification 3. Amplification 3 could have both mutations as well as single mutations. These mutations could also be stop codons.

Figure 34:
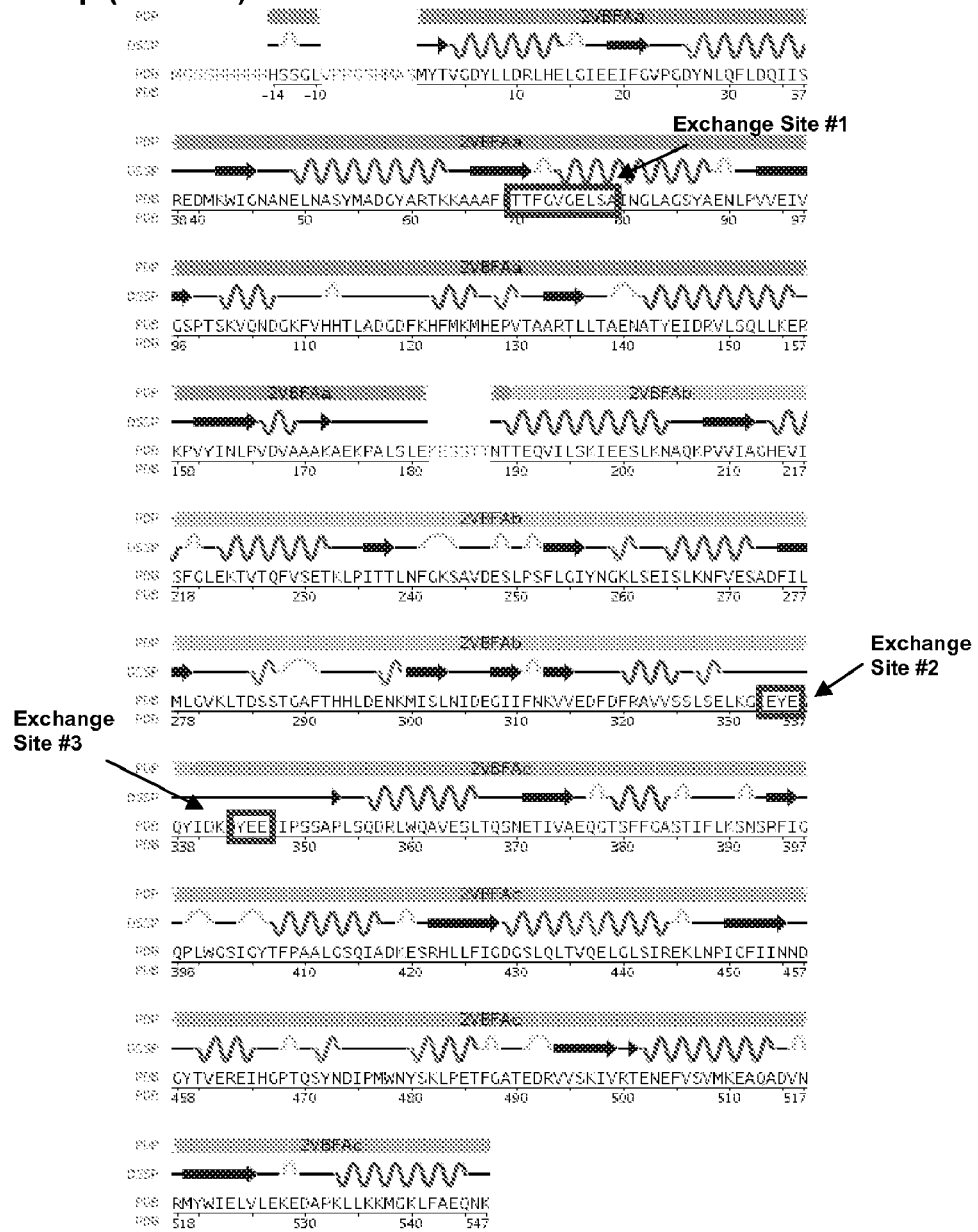

FIG. 34. Schematic of KdcAp structure. The boxed regions are those that were fusion sites when combining KdcAp to Pdc1p (Exchange Sites).

Figure 35:
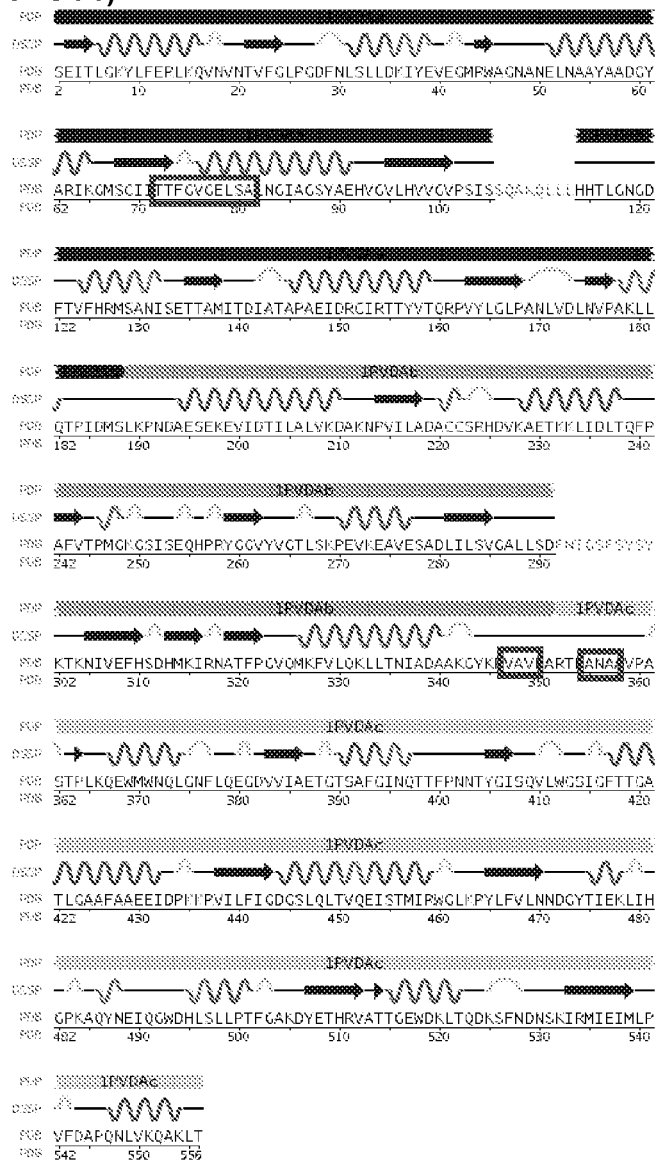

FIG. 35. Schematic of Pdc1p structure. The boxed regions are those that were fusion sites when combining KdcAp to Pdc1p (Exchange Sites).

FIG. 36. Schematic of the KdcAp and Pdc1p fusion protein at Exchange Site #1 as indicated in FIG. 35. This Exchange Site is in a conserved region for both proteins in domain 1.

FIG. 37. Schematic of the KdcAp and Pdc1p fusion protein at Exchange Site #2 as indicated in FIG. 35. This Exchange Site is in a conserved region for both proteins in between domain 2 and domain 3.

FIG. 38. Schematic of the KdcAp and Pdc1p fusion protein at Exchange Site 3. This Exchange Site is in a conserved region for both proteins in between domain 2 and domain 3.

FIG. 39. Diagrammatic representation of strategy for creating fusion proteins between *Lactococcus lactis* KDCA and *Pichia stipitis* PDC 3-6 to increase the affinity for branched keto acids.

FIG. 40. A schematic of KdcA-PDC 3-6 fusion 1 for increasing the affinity for brance keto acids.

FIG. 41. A schematic of KdcA-PDC 3-6 fusion 2 for increasing the affinity for brance keto acids.

Figure 42:
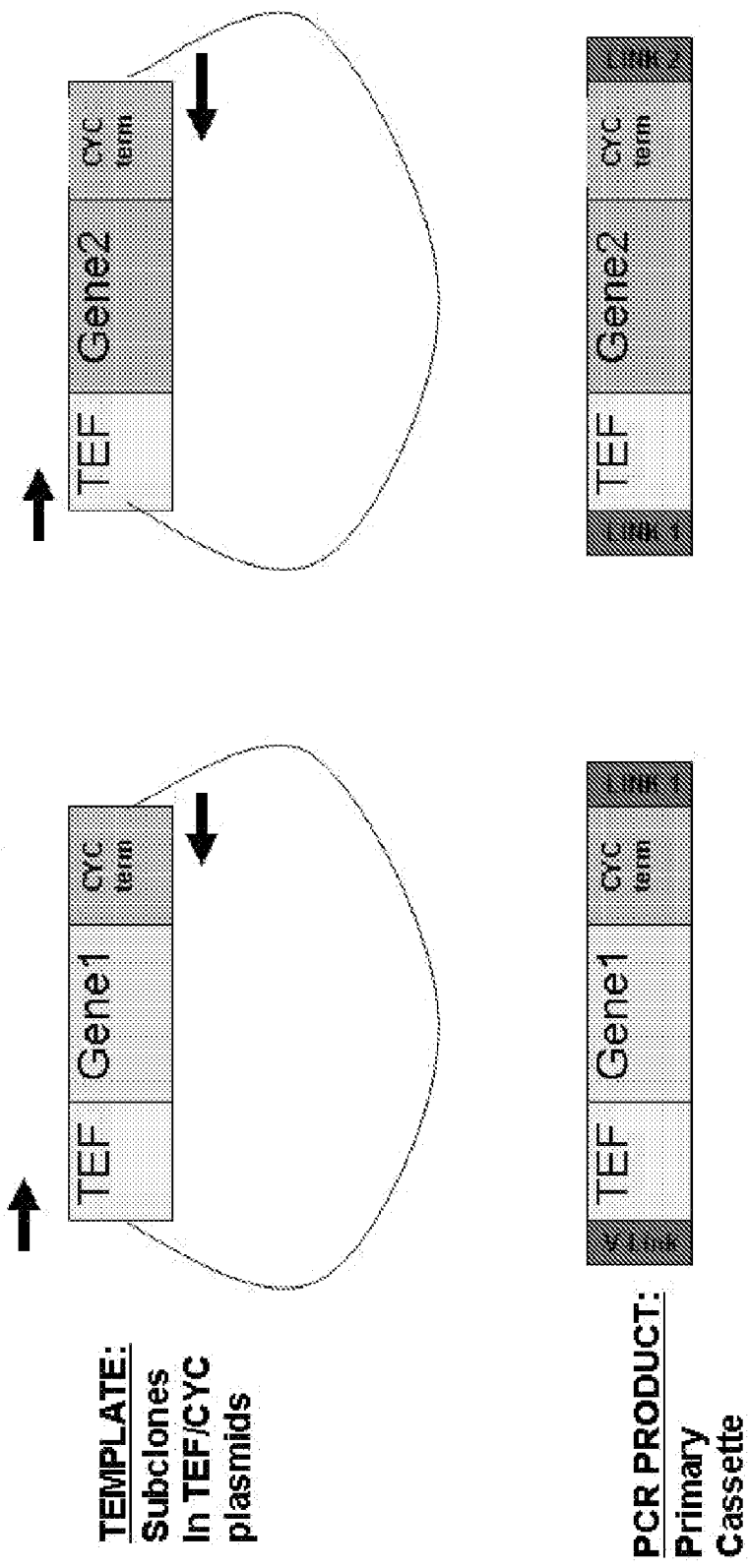

FIG. 42. A schematic of PCR amplification of cassettes. Primers give 40 base overlaps between primary cassettes.

Figure 43:
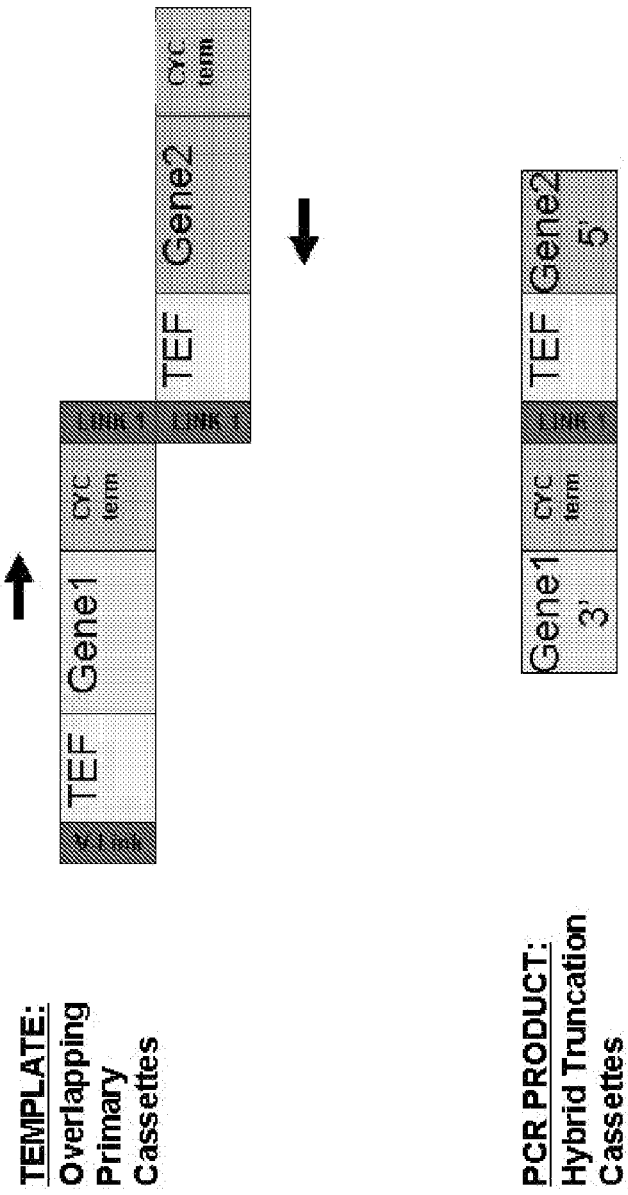

FIG. 43. A schematic of amplification of Truncated-Hybrid Cassettes from Overlapping Primary Cassettes.

Figure 44:
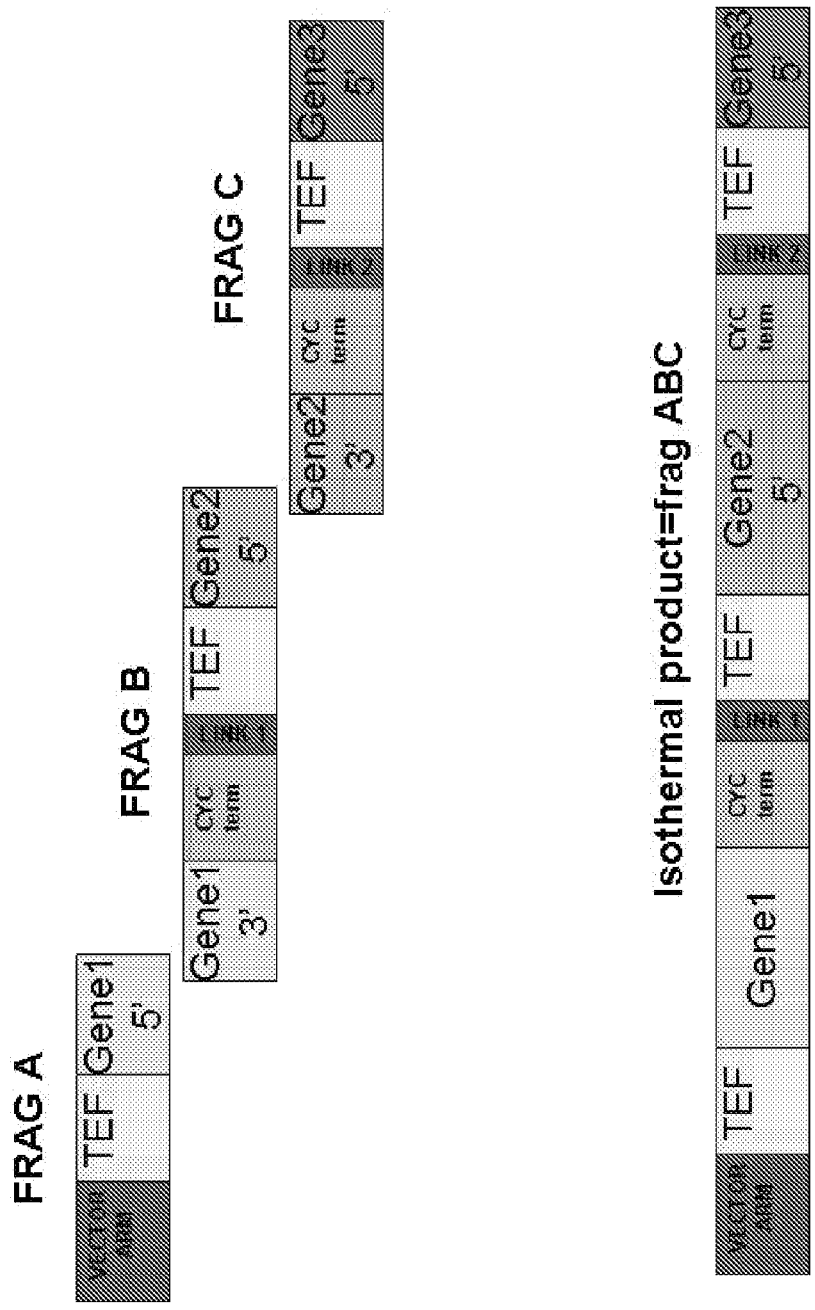

FIG. 44. A schematic of fragments used in an isothermal reaction that creates 7 kb fragment. Note there are 40 base overlaps between the fragments.

FIG. 45. A schematic of fragments used in an isothermal reaction creates 8 kb fragment. Note there are 40 base overlaps between the fragments.

Figure 46:
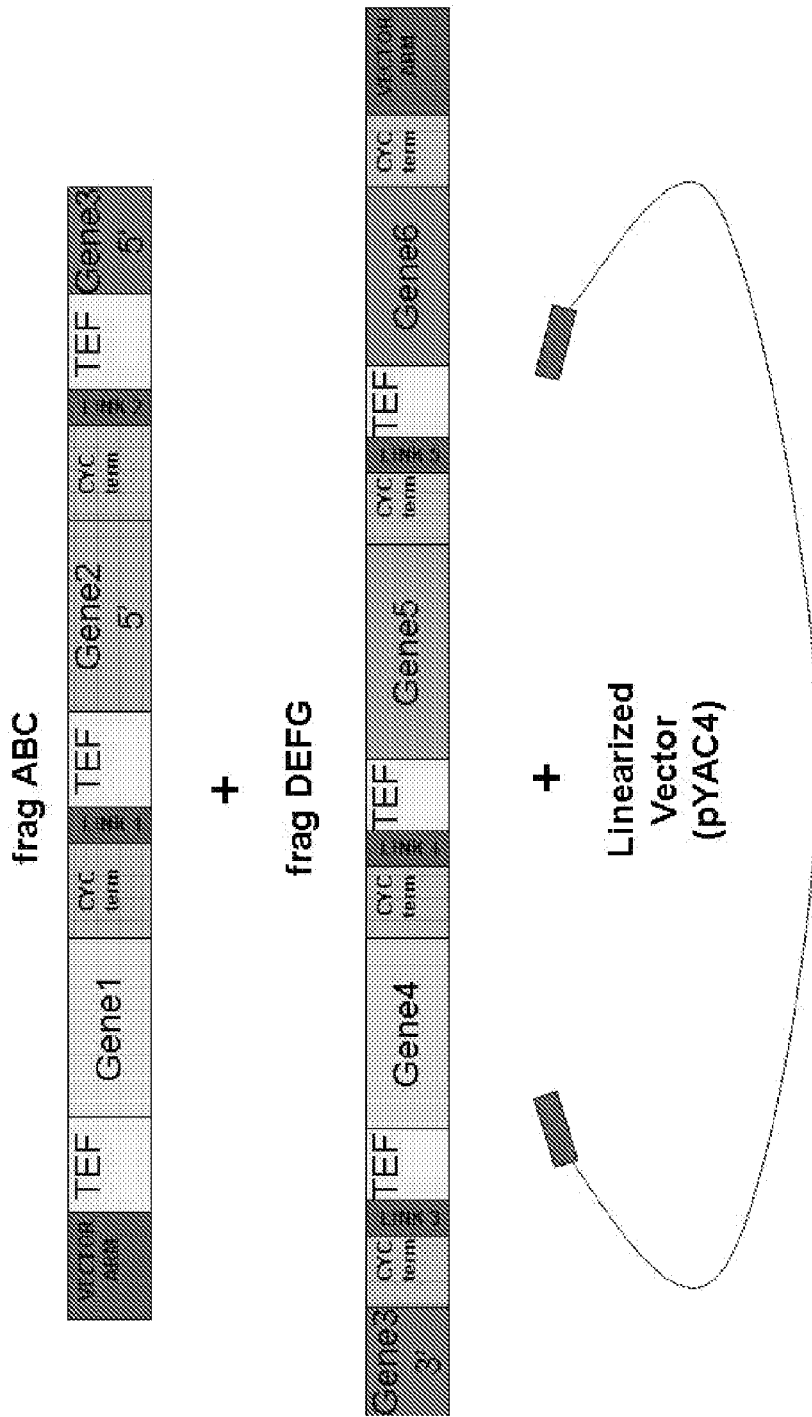

FIG. 46. A schematic of fragments used in an isothermal reaction or In-vivo recombination by Yeast. Note there are 40 base overlaps between the fragments. These was used for both isothermal assembly, and In-vivo recombination by yeast.

Figure 47:
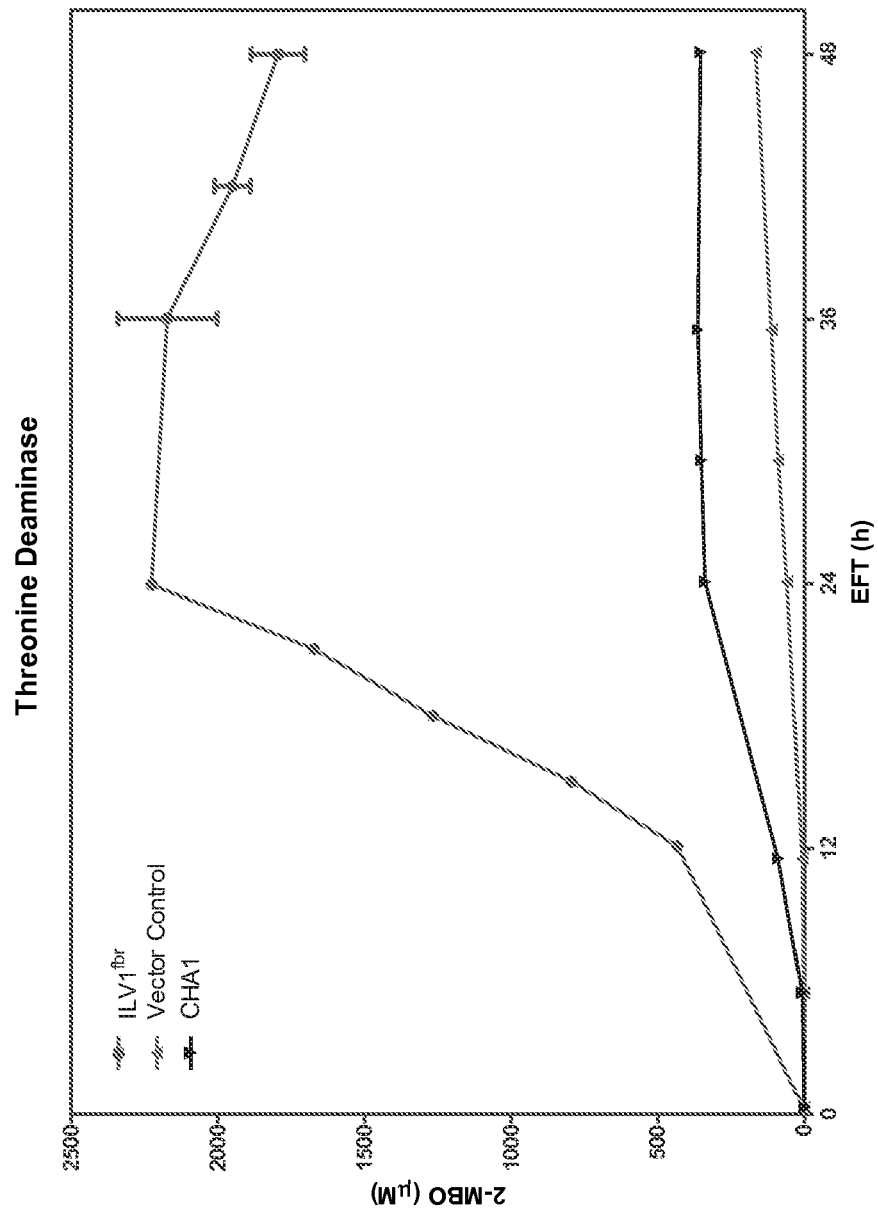

FIG. 47. A graph of 2-MBO production during fermentation of strains expressing threonine deaminase (TD). Fermentation were performed under standard conditions (aerobic, 30° C., pH 4.5) in YNB medium containing 50 g 1-1 glucose and supplemented with nutrients to complement remaining auxotrophies.

Figure 48:
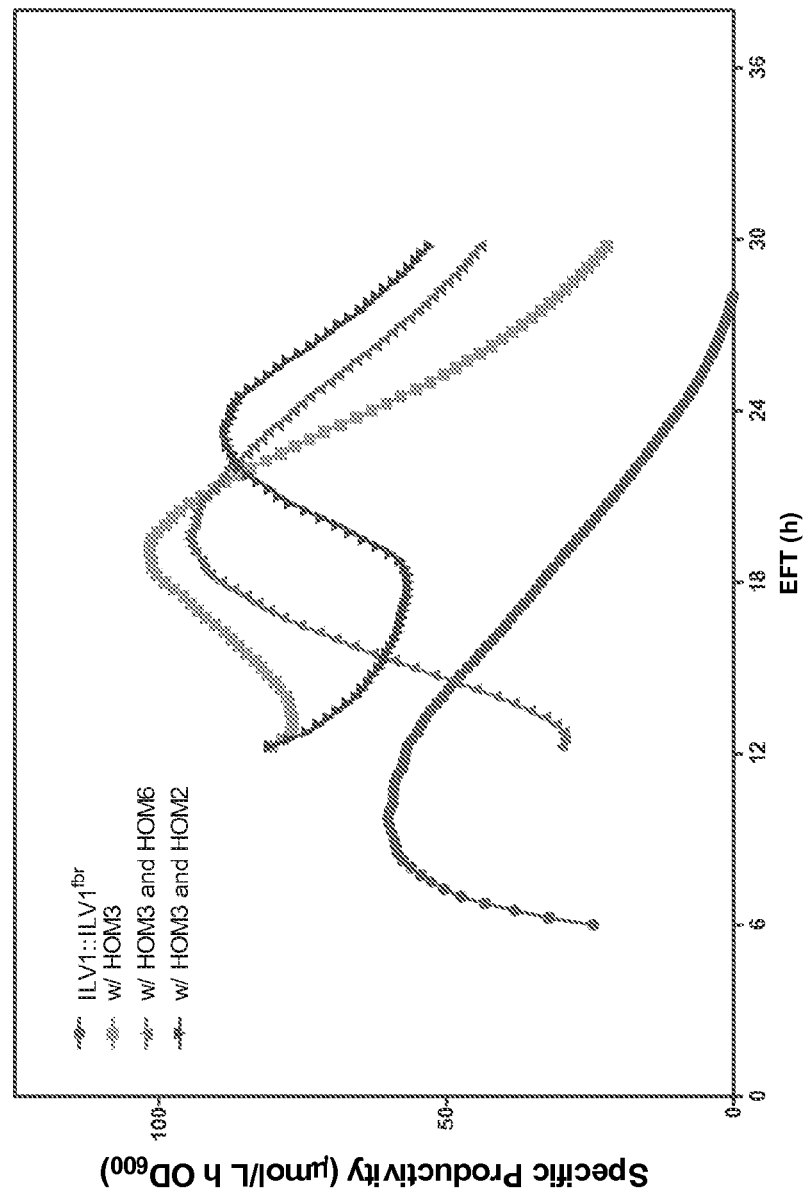

FIG. 48. A graph of specific 2-MBO production in strains expressing TD and AK. Fermentations were preformed under standard conditions (aerobic, 30° C., pH4.5). Specific productivity was calculated from interpolated values for biomass and 2-MBO. The average of 2 independent replicates are reported.

Figure 49:
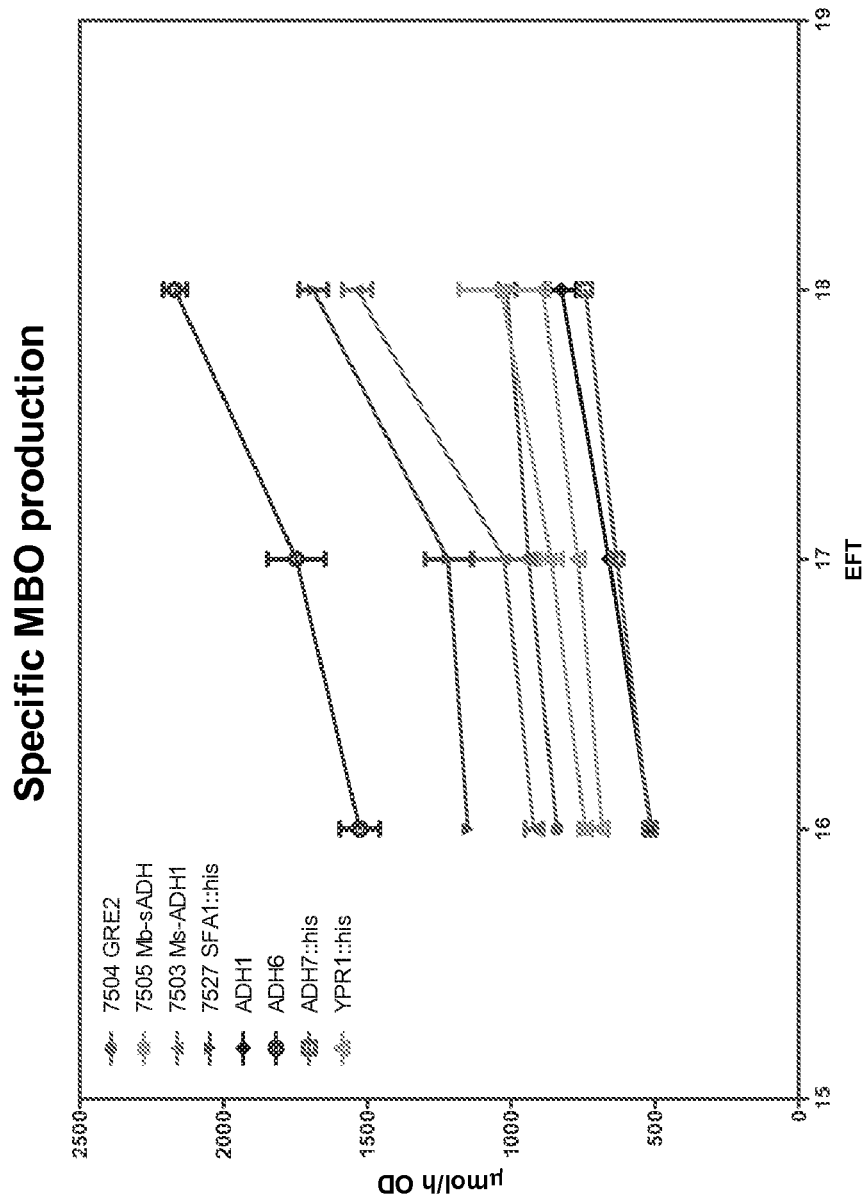

FIG. 49. A graph of specific productivity of 2-MBO with excess 2-MBA. Fermentations were performed under standard conditions (aerobic, 30° C., pH 4.5) in YNB medium containing 50 g 1-1 glucose and supplemented with nutrients to complement auxotrophies. A bolus of 2-MBA was added and samples collects hourly thereafter. Specific productivity was calculated from interpolated values for 2-MBO and biomass.

Figure 50:
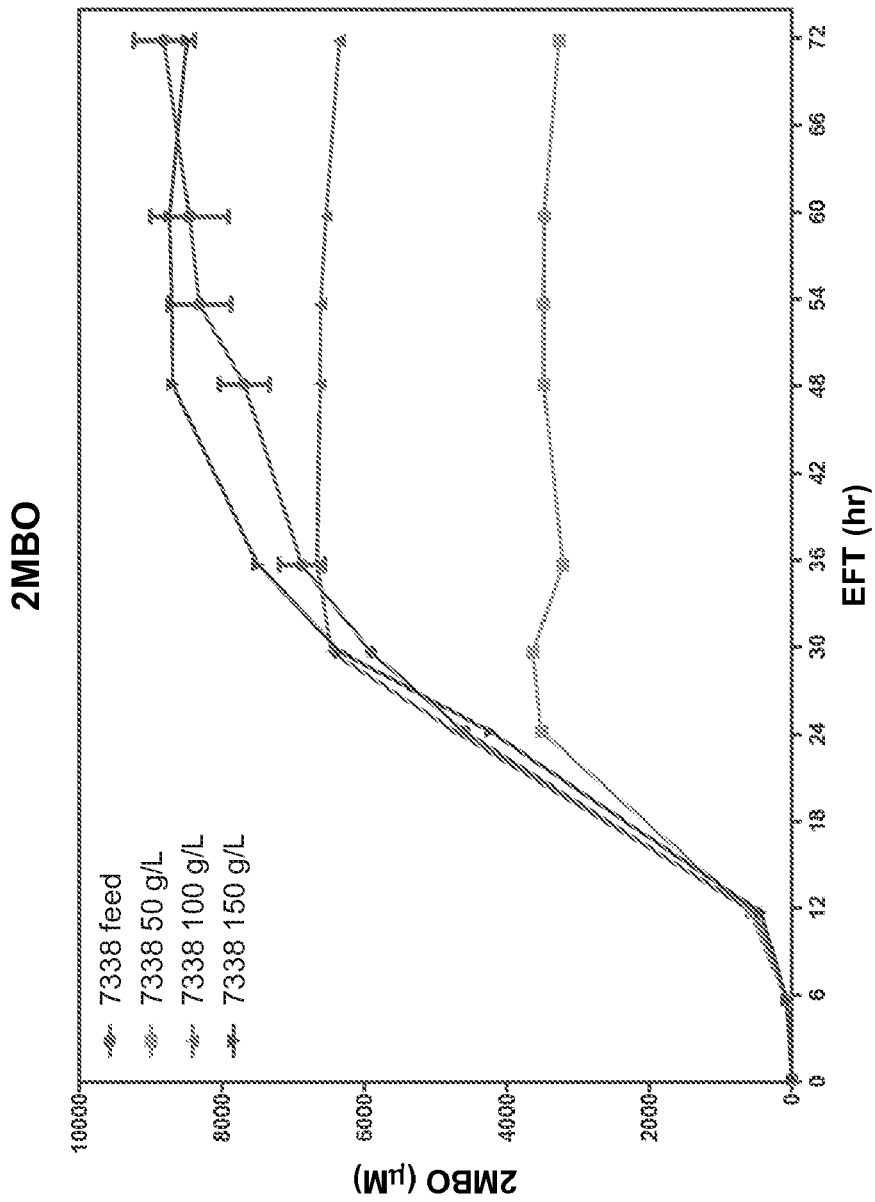

FIG. 50. A graph of 2-MBO production by strain 7338 (p415TEF ILV1FBR) in medium with increased glucose. Fermentations were performed under standard conditions (aerobic, 30° C., pH 4.5) in YNB medium containing the indicated amount of glucose. In one set of experiments, a constant glucose feed was employed. The data shown represent the average of two independent replicates.

Figure 51:
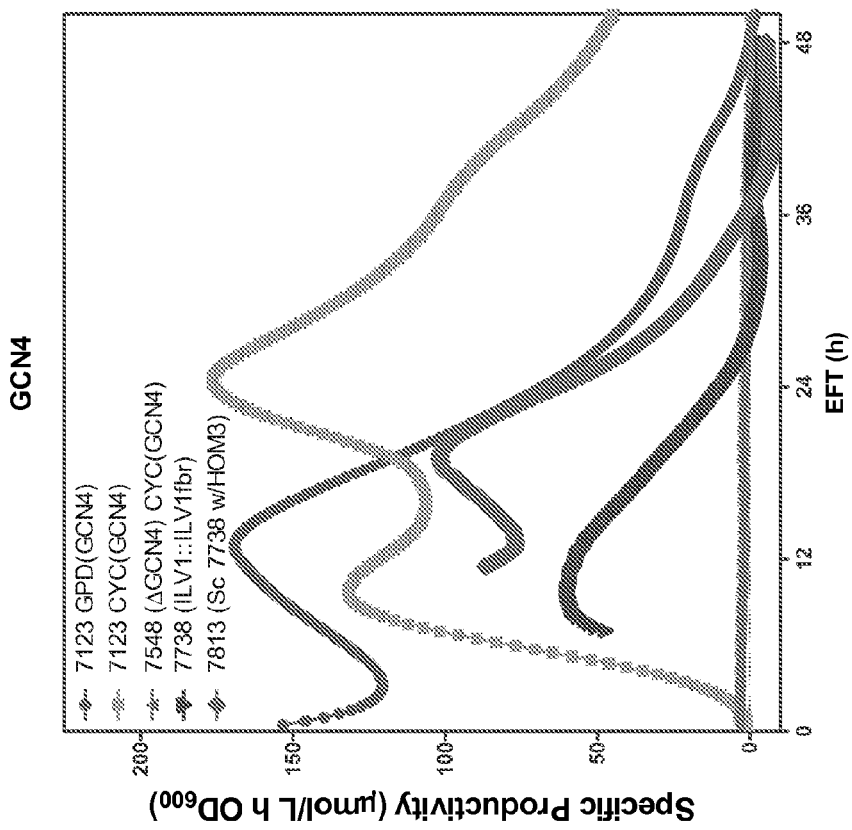

FIG. 51. A graph of 2-MBO specific productivity in strains expressing GCN4. Fermentations were performed under standard conditions (aerobic, 30° C., pH 4.5) in YNB containing 50 g 1-1 glucose and supplemented with nutrients to complement auxotrophies.

Figure 52:
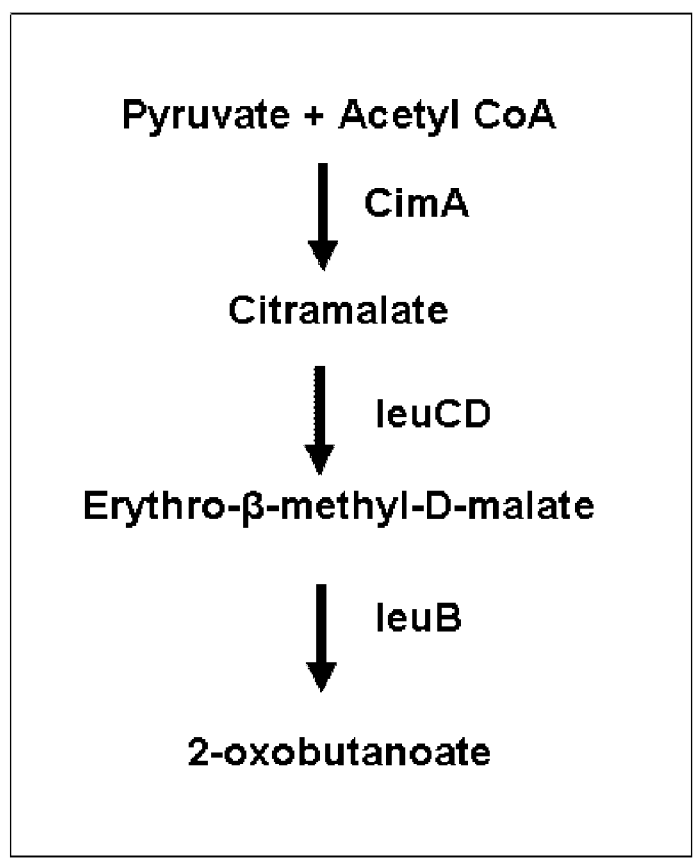

FIG. 52. The heterologous citramalate pathway composed of cimA/leuA, leuB, leuC, and leuD is expressed in the cytoplasm of *S. cerevisiae*.

Figure 53:
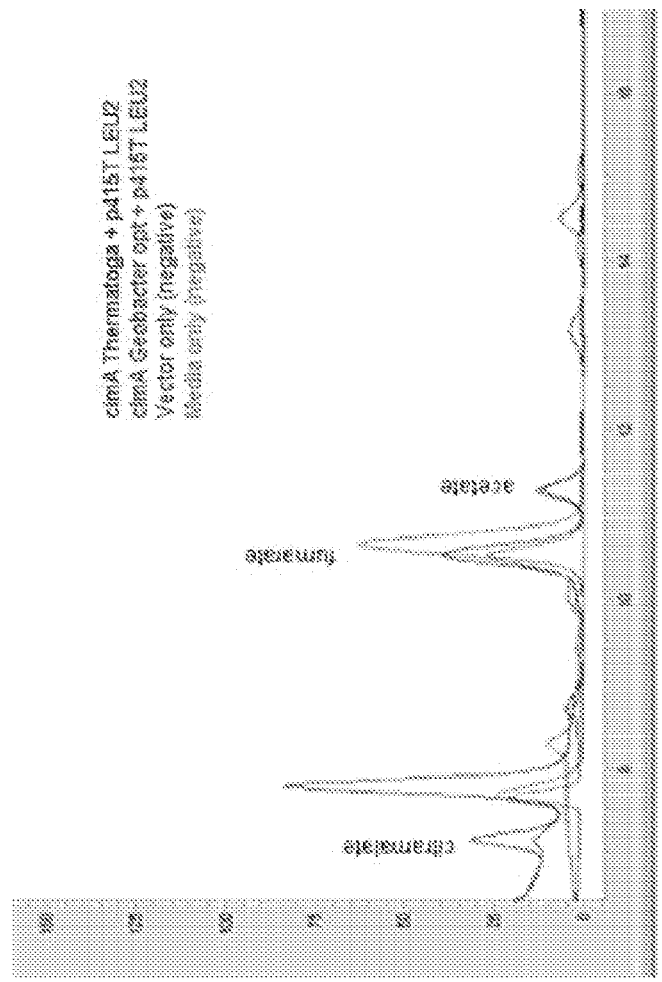

FIG. 53. A graph showing results of detection of citramalate via HPLC.

Figure 54:
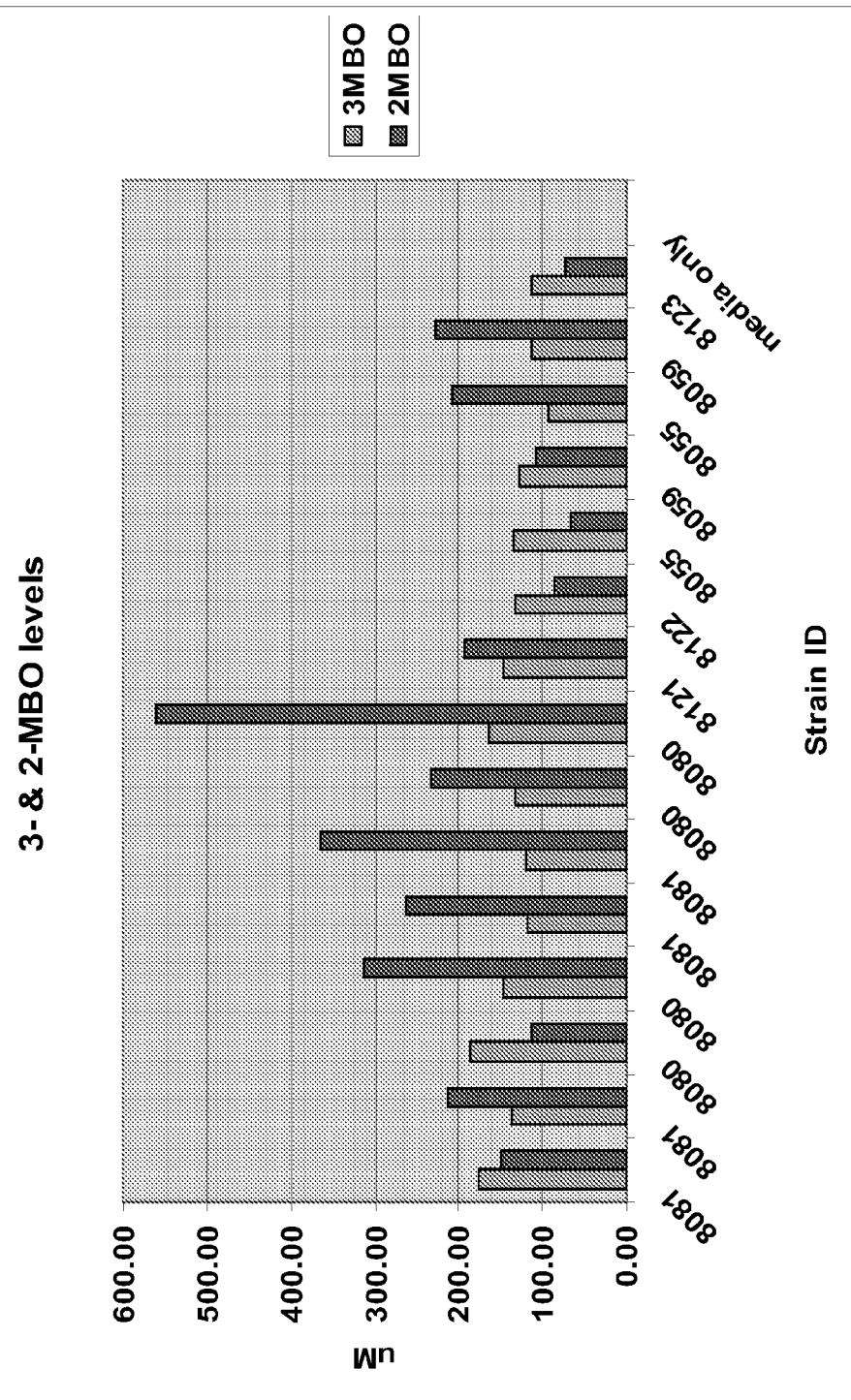

FIG. 54. A bar graph showing MBO production of cimA/leuA 1 clones. A 3- to 8-fold increase in 2-MBO was observed for strains containing cimA/leuA, leuB, and leuCD and grown in +Ile SD medium. Strain information shown in Table 10.

Figure 55:
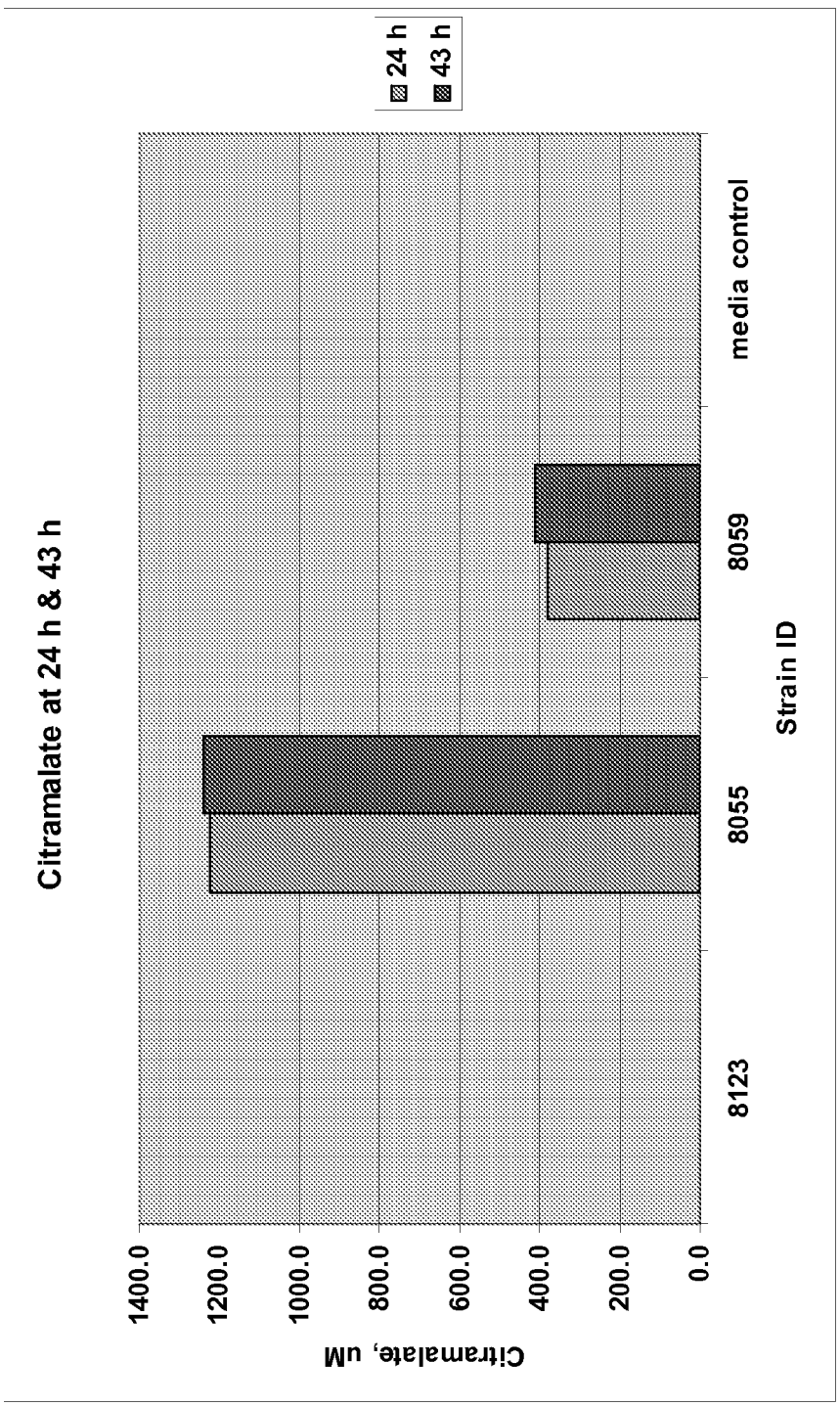

FIG. 55. A bar graph showing citramalate production of various heterologous genes in *Saccharomyces*. Strains 8123 control strain (empty vector); 8055 p416GPD-cimA (Tm)+p415TEF1; 8059 p416GPD-cimA (Gs), p415TEF1.

Figure 56:
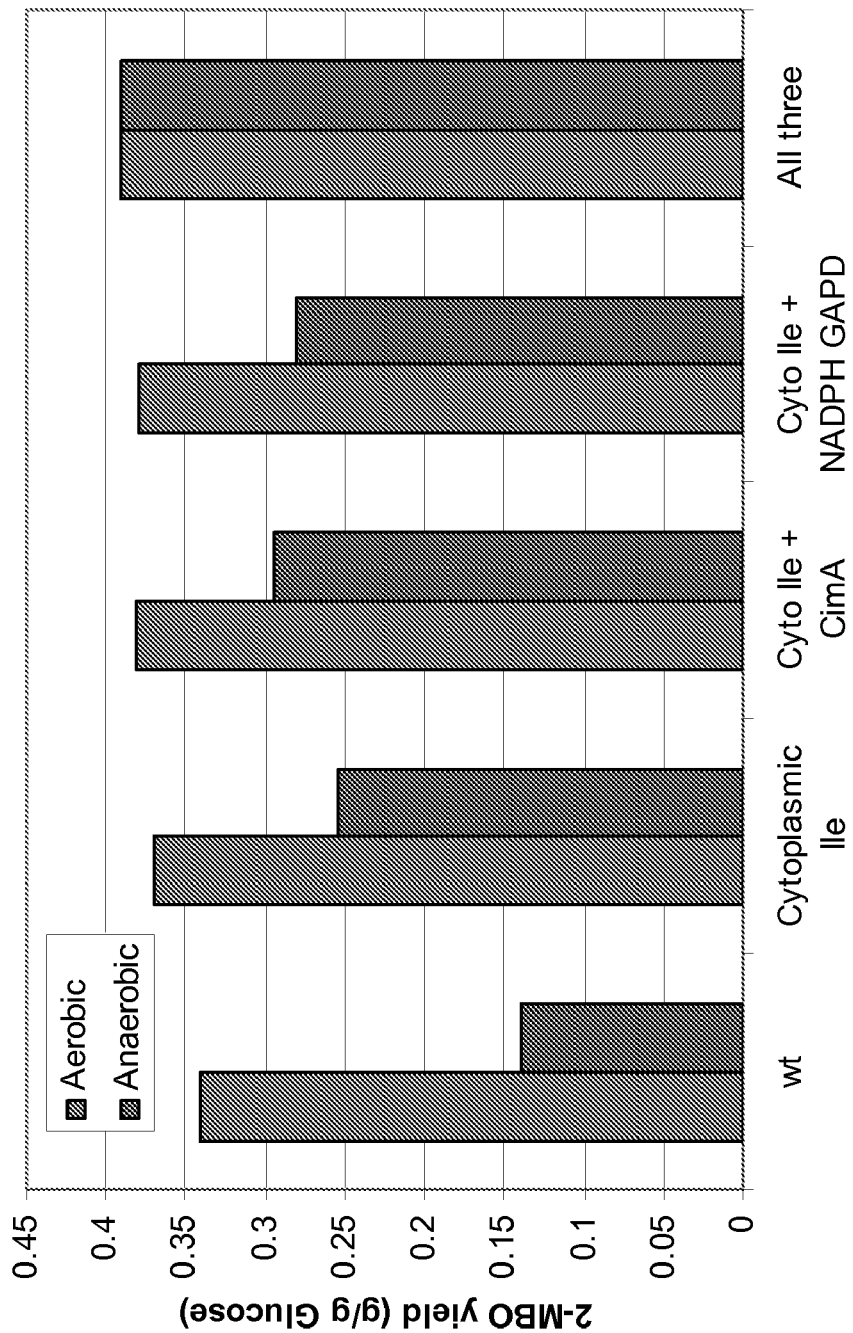

FIG. 56. A bar graph showing calculated maximum theoretical yields of 2-MBO from glucose in yeast resulting from different genetic manipulations.

Figure 57:
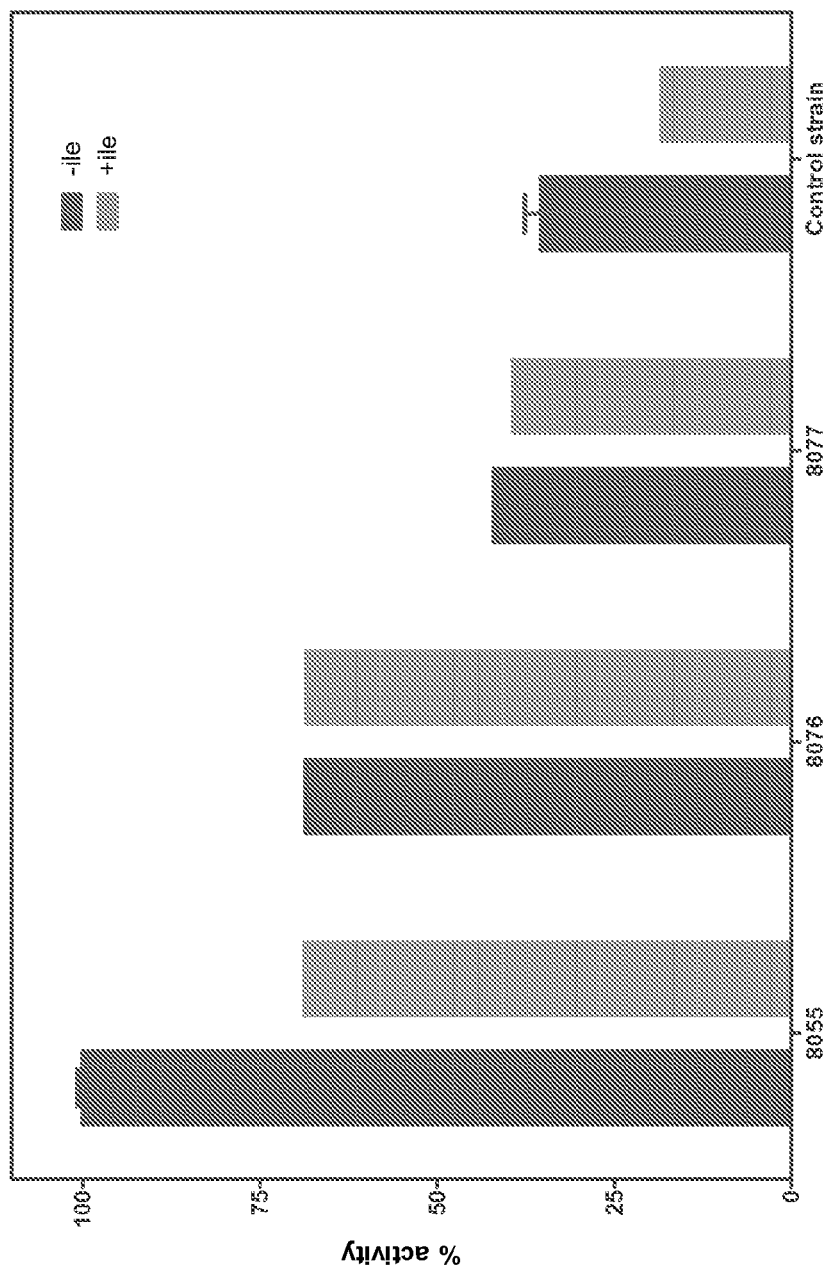

FIG. 57. Effect of Isoleucine on the putative leuA activity and variants. Isoleucine was added to 10 mM.

FIG. 58 (*a-c*). Shows tracings of GCMS analysis of MBO production.

Figure 59:
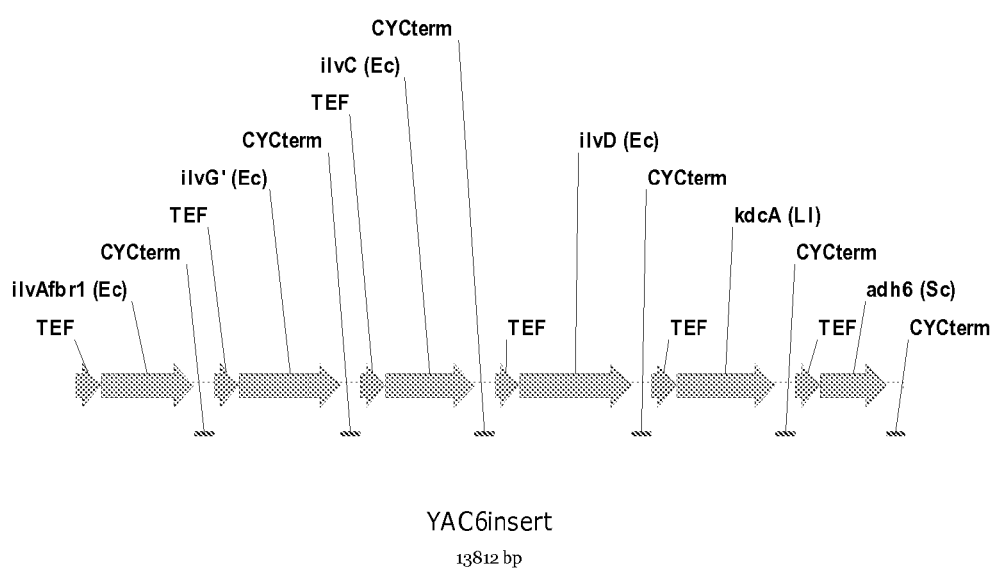

FIG. 59. Shows a map of YAC6 comprising the following genes: ilvAfbr (Ec), ilvG' (Ec), ilvC (Ec), ilvD (Ec), kdcA (Ll), adh6.

Figure 60:
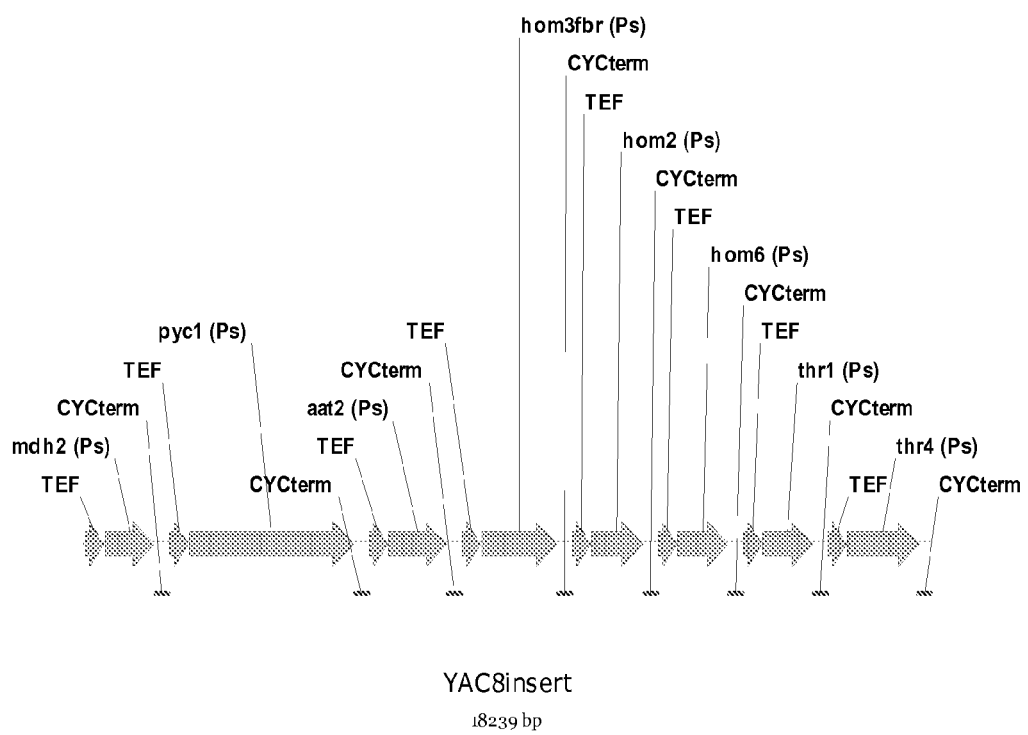

FIG. 60. Shows a map of YAC8 comprising the following genes: mdh2 (Ps), pyc1 (Ps), aat2 (Ps), hom3fbr (Ps), hom2 (Ps), hom6 (Ps), thr1 (Ps), thr4 (Ps).

Figure 61:
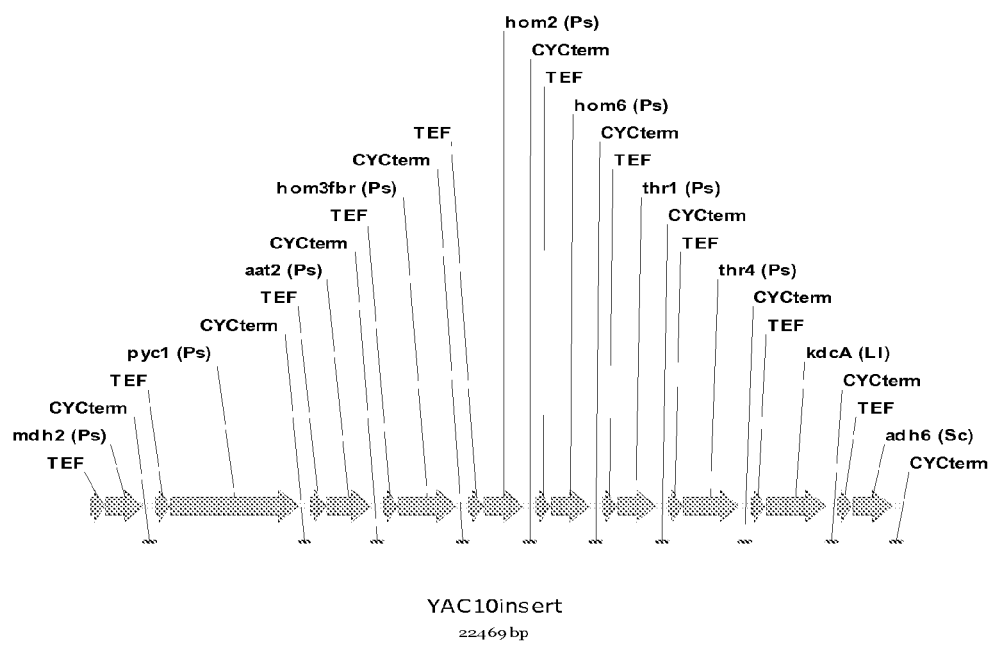

FIG. 61. Shows a map of YAC10 comprising the following genes: mdh2 (Ps), pyc1 (Ps), aat2 (Ps), hom3fbr (Ps), hom2 (Ps), hom6 (Ps), thr1 (Ps), thr4 (Ps), kdcA (Ll), adh6.

Figure 62:
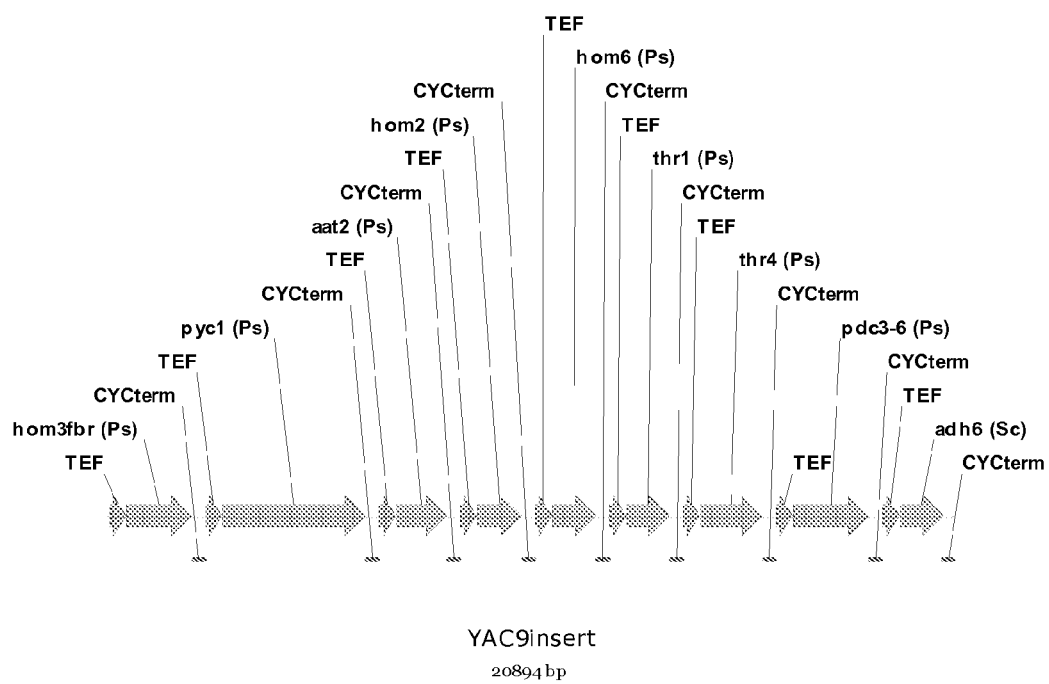

FIG. 62. Shows a map of YAC9 comprising the following genes: hom3fbr (Ps), pyc1 (Ps), aat2 (Ps), hom3fbr (Ps), hom2 (Ps), hom6 (Ps), thr1 (Ps), thr4 (Ps), pdc3-6 (Ps), adh6.

Figure 63:
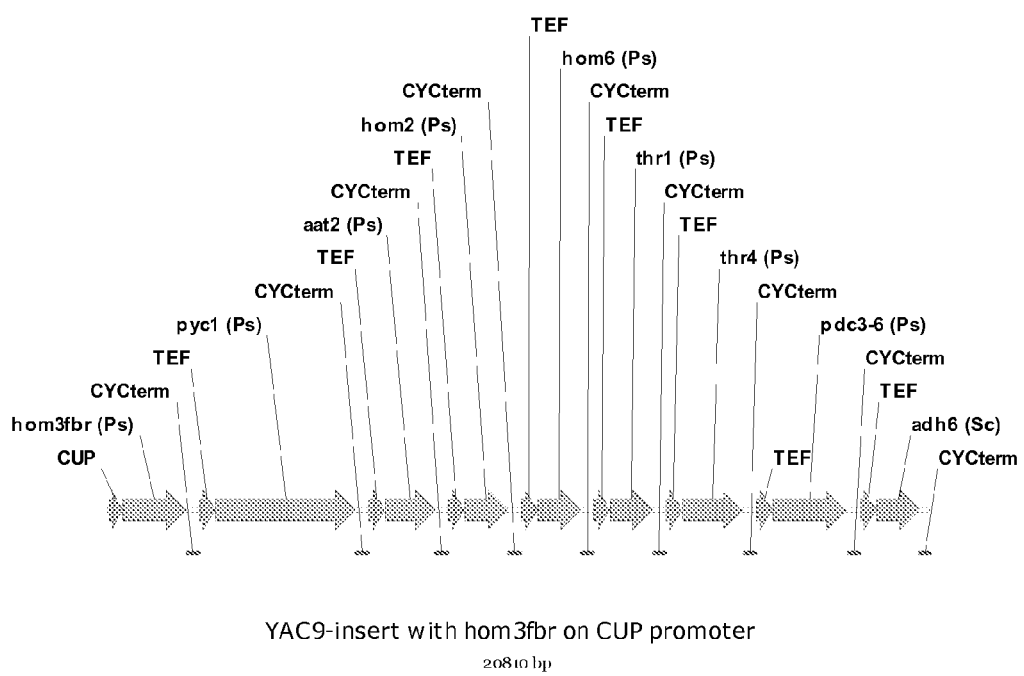

FIG. 63. Shows a map of YAC9 with hom3fbr on CUP promoter comprising the following genes: hom3fbr (Ps), pyc1 (Ps), aat2 (Ps), hom3fbr (Ps), hom2 (Ps), hom6 (Ps), thr1 (Ps), thr4 (Ps), pdc3-6 (Ps), adh6

Figure 64:
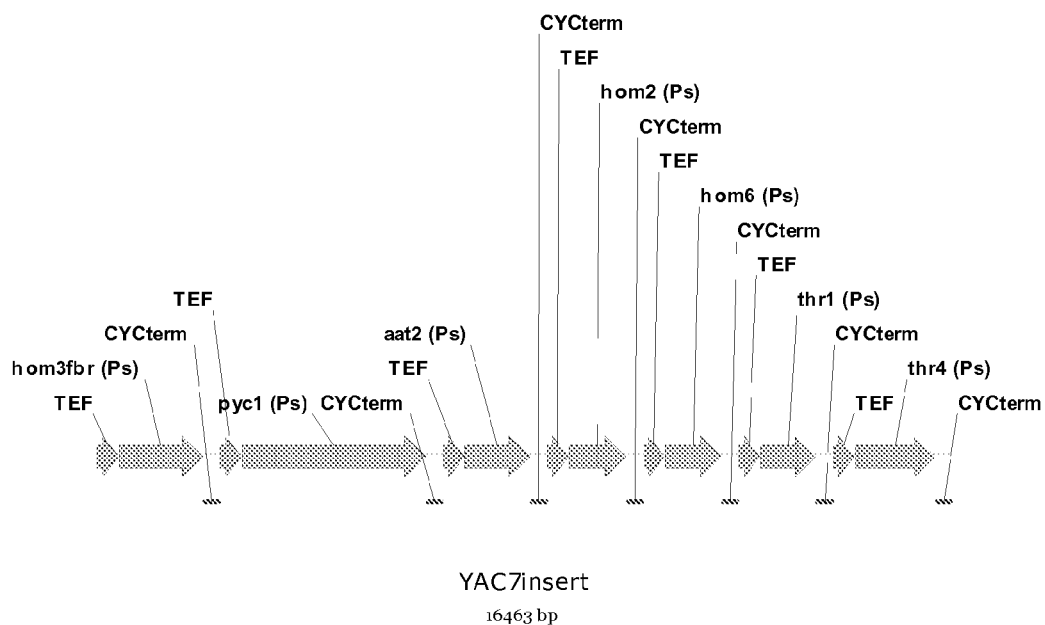

FIG. 64. Shows a map of YAC7 comprising the following genes: hom3fbr (Ps), pyc1 (Ps), aat2 (Ps), hom3fbr (Ps), hom2 (Ps), hom6 (Ps), thr1 (Ps), thr4 (Ps)

Figure 65:
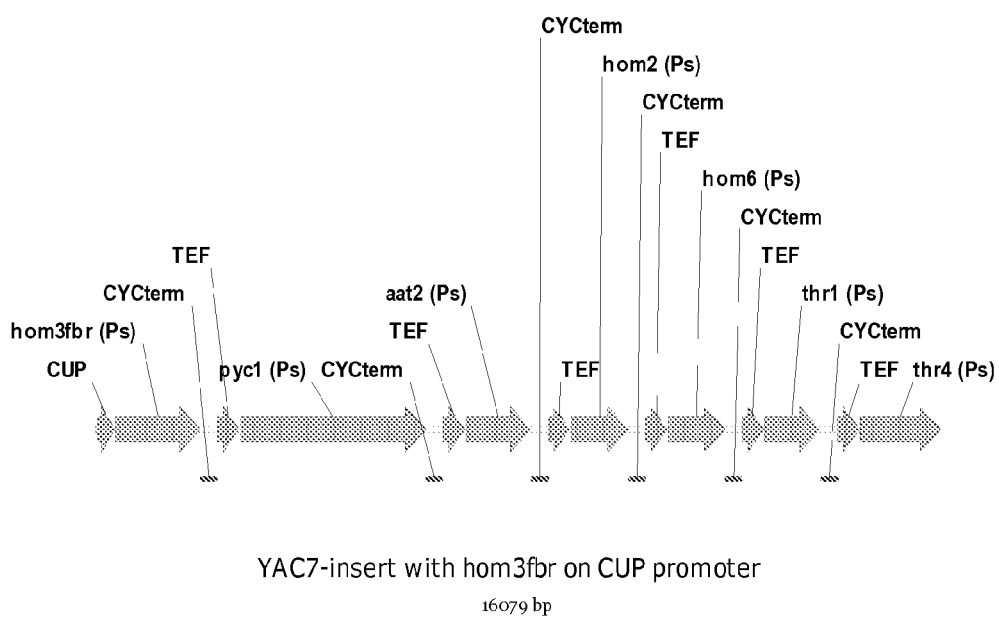

FIG. 65. Shows a map of YAC7 with hom3fbr on CUP promoter comprising the following genes: hom3fbr (Ps), pyc1 (Ps), aat2 (Ps), hom3fbr (Ps), hom2 (Ps), hom6 (Ps), thr1 (Ps), thr4 (Ps).

Figure 66:
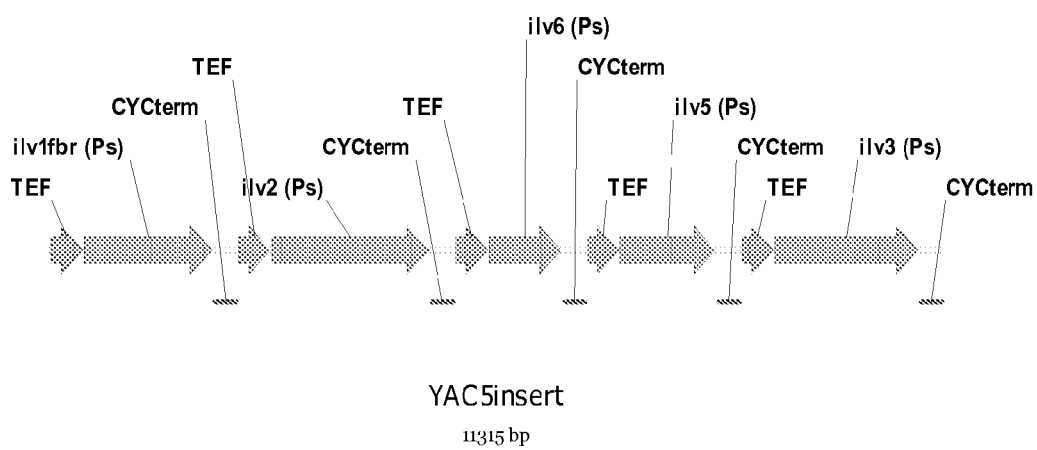

FIG. 66. Shows a map of YAC5 comprising the following genes: ilv1fbr (Ps), ilv2 (Ps), ilv6 (Ps), ilv5 (Ps), ilv3 (Ps).

Figure 67:
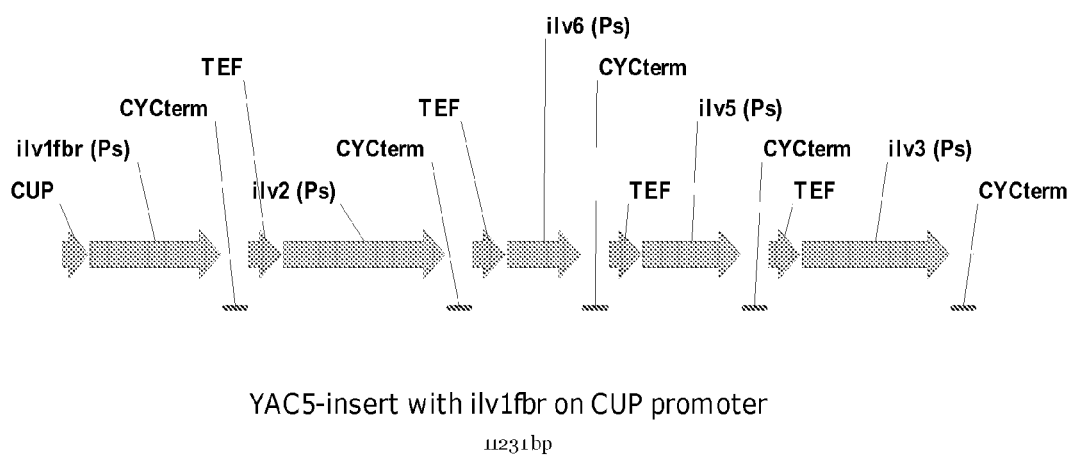

FIG. 67. Shows a map of YAC5 with ilv1fbr on CUP promoter comprising the following genes: ilv1fbr (Ps), ilv2 (Ps), ilv6 (Ps), ilv5 (Ps), ilv3 (Ps).

Figure 68:
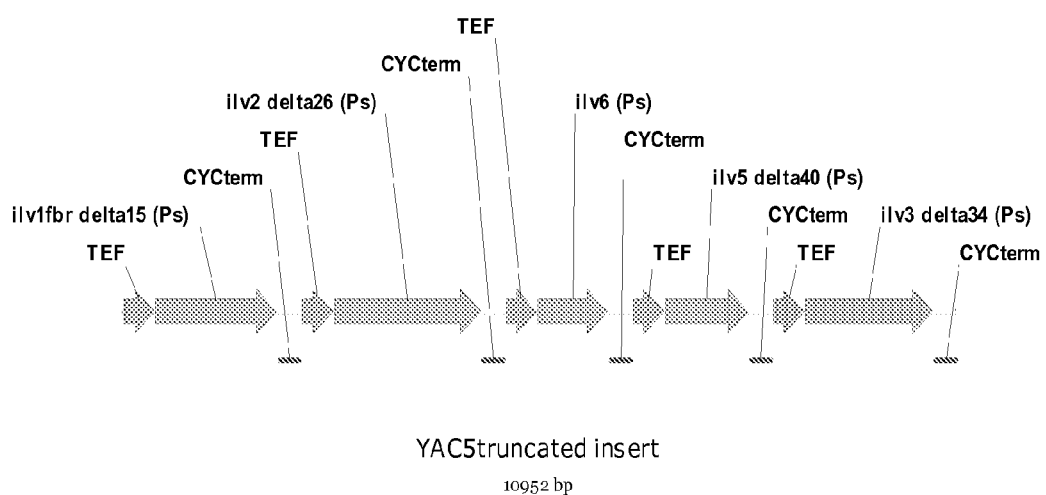

FIG. 68. Shows a map of YAC5 truncated comprising the following genes: ilv1fbrΔ15 (Ps), ilv2Δ26 (Ps), ilv6 (Ps), ilv5Δ40 (Ps), ilv3Δ34 (Ps).

Figure 69:
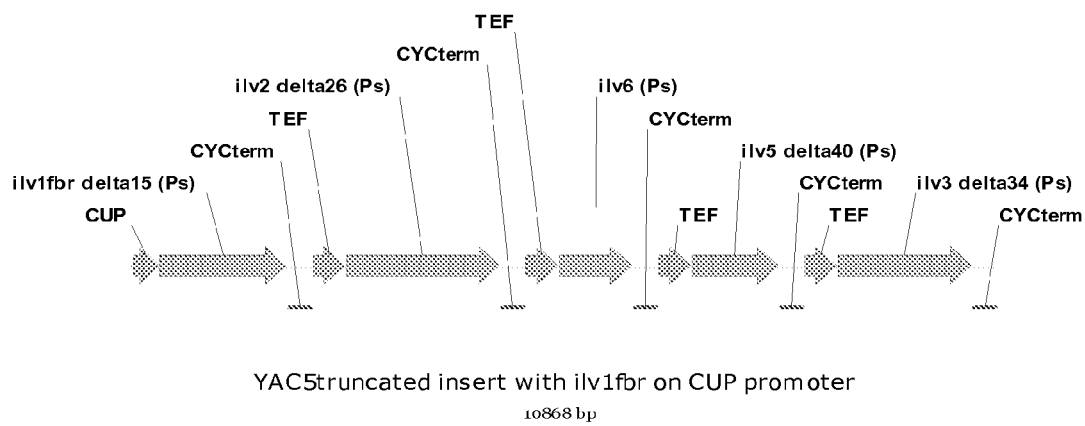

FIG. 69. Shows a map of YAC5 truncated with ilv1fbr on CUP promoter ilv1fbrΔ15 (Ps), ilv2Δ26 (Ps), ilv6 (Ps), ilv5Δ40 (Ps), ilv3Δ34 (Ps).

Figure 70:
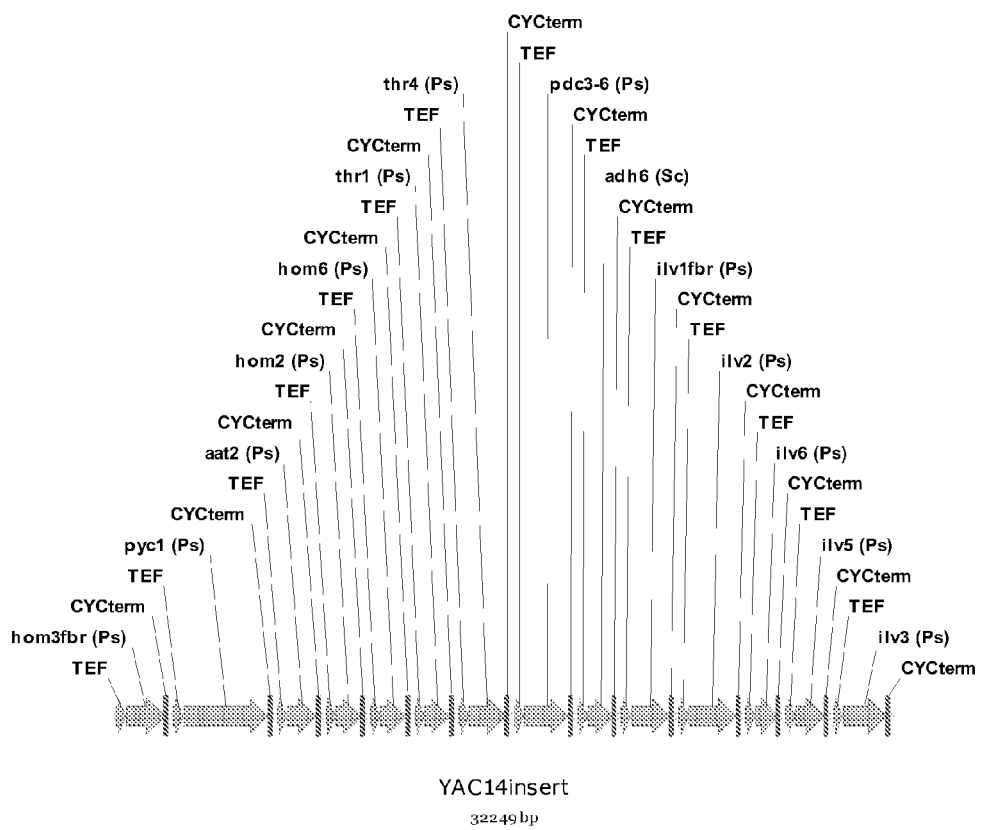

FIG. 70. Shows a map of YAC14 comprising the following genes: hom3fbr (Ps), pyc1 (Ps), aat2 (Ps), hom3fbr (Ps), hom2 (Ps), hom6 (Ps), thr1 (Ps), thr4 (Ps), pdc3-6 (Ps), adh6, ilv1fbr (Ps), ilv2 (Ps), ilv6 (Ps), ilv5 (Ps), ilv3 (Ps).

Figure 71:
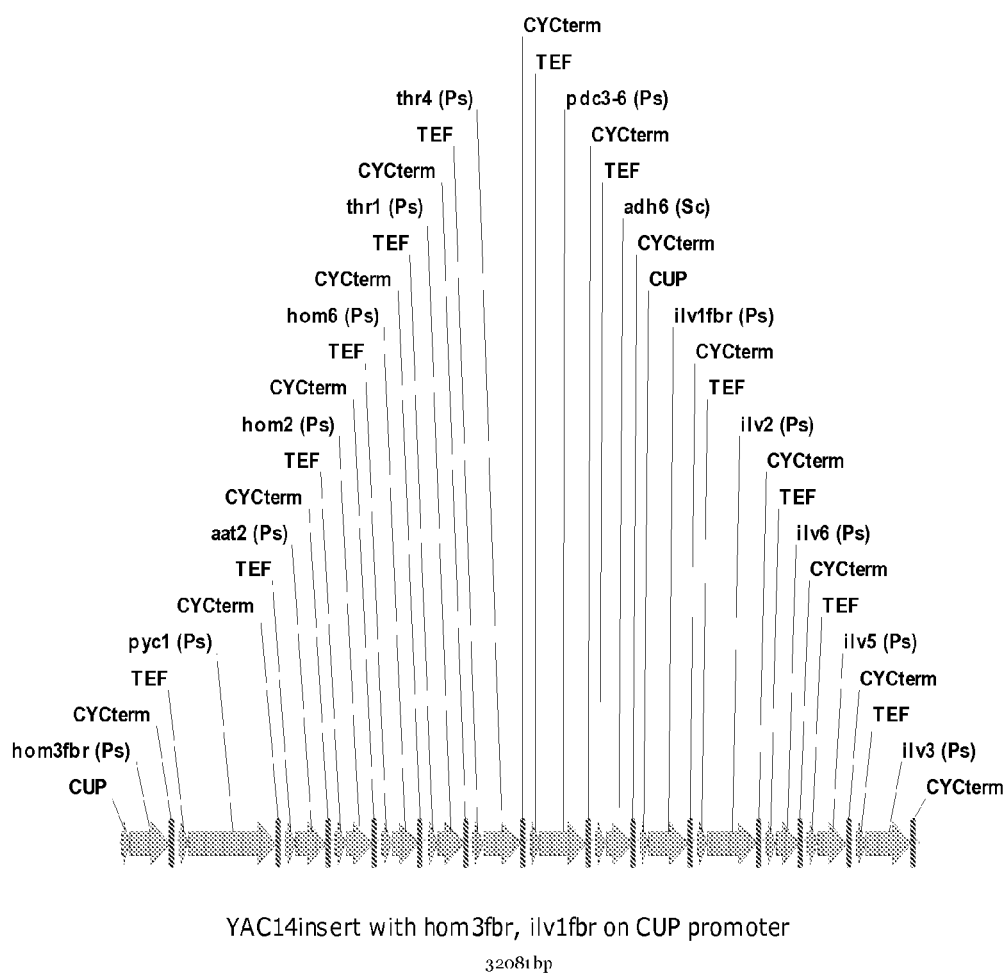

FIG. 71. Shows a map of YAC14 with hom3fbr, ilv1fbr on CUP promoter comprising the following genes: hom3fbr (Ps), pyc1 (Ps), aat2 (Ps), hom3fbr (Ps), hom2 (Ps), hom6 (Ps), thr1 (Ps), thr4 (Ps), pdc3-6 (Ps), adh6, ilv1fbr (Ps), ilv2 (Ps), ilv6 (Ps), ilv5 (Ps), ilv3 (Ps).

Figure 72:
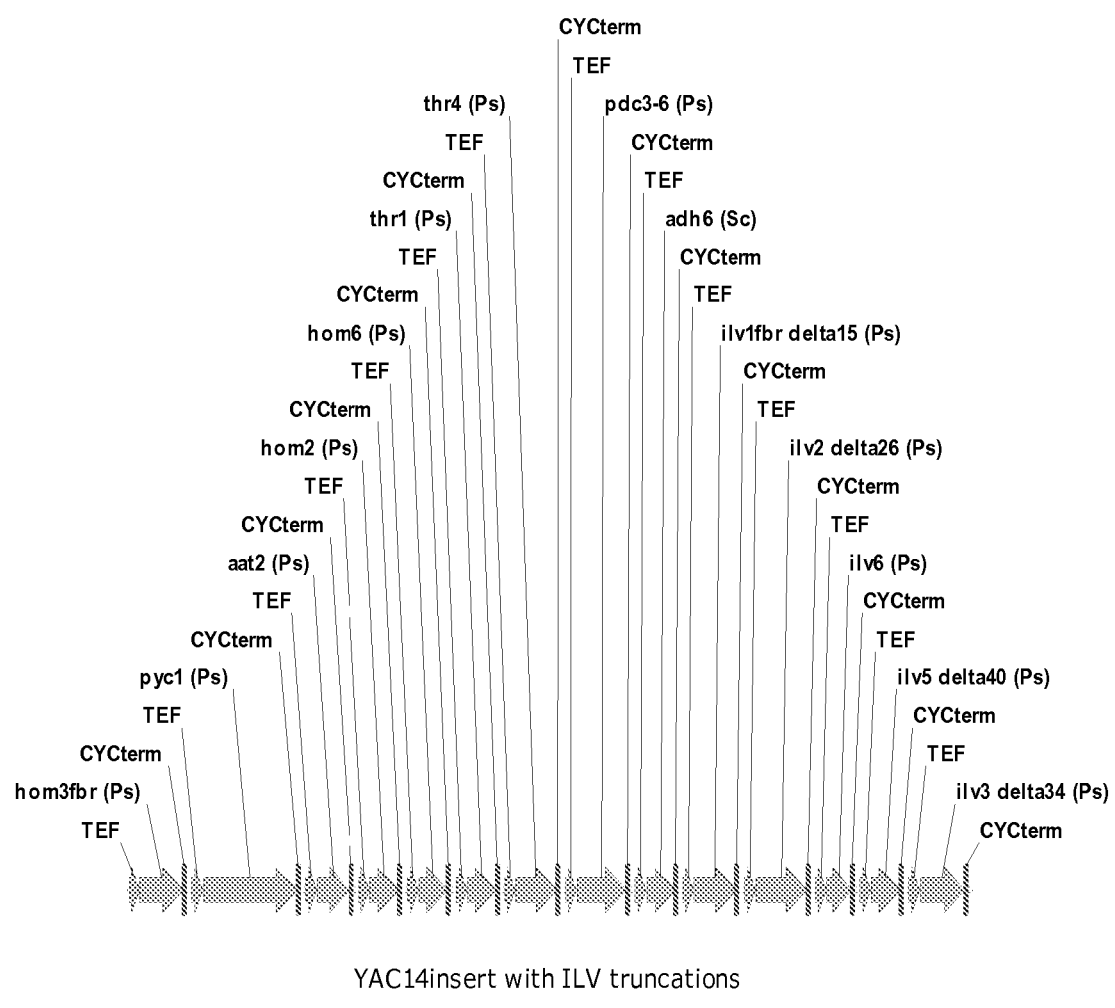

FIG. 72. Shows a map of YAC14 with ILV truncations comprising the following genes: hom3fbr (Ps), pyc1 (Ps), aat2 (Ps), hom3fbr (Ps), hom2 (Ps), hom6 (Ps), thr1 (Ps), thr4 (Ps), pdc3-6 (Ps), adh6, ilv1fbrΔ15 (Ps), ilv2Δ26 (Ps), ilv6 (Ps), ilv5Δ40 (Ps), ilv3Δ34 (Ps).

Figure 73:
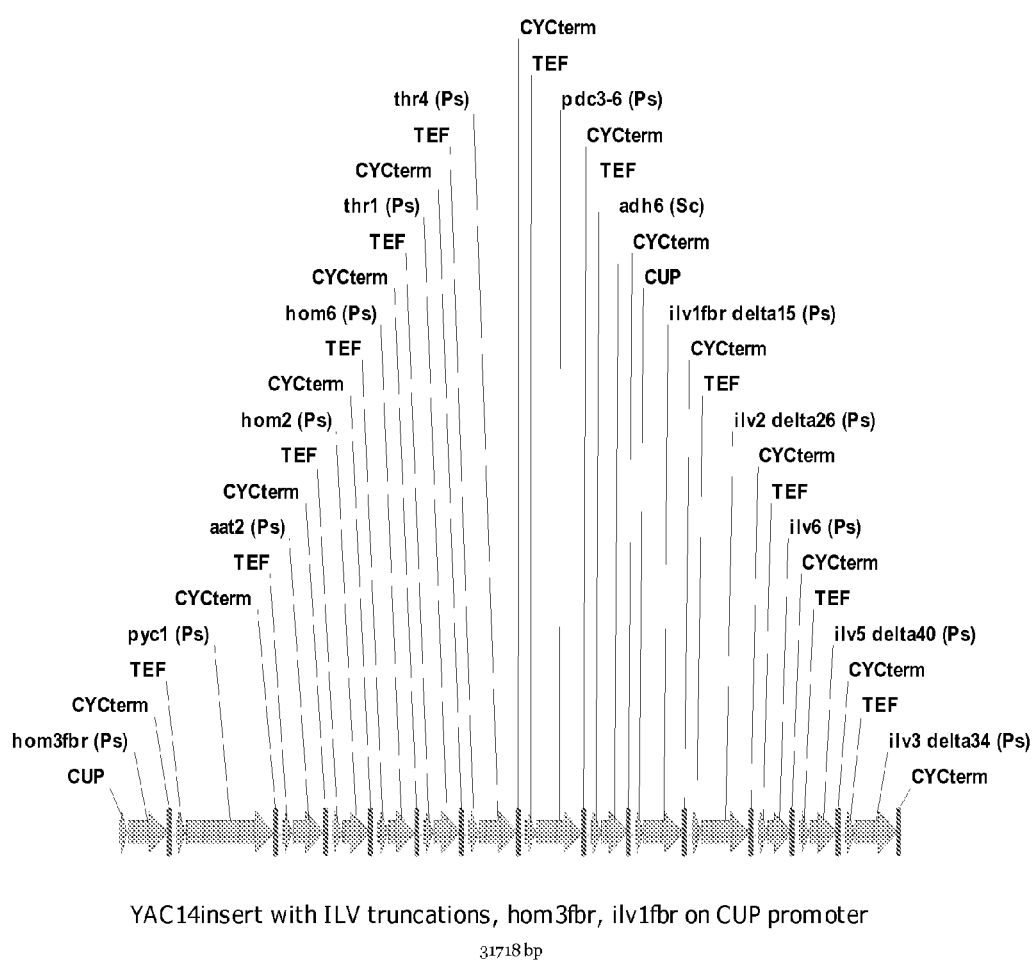

FIG. 73. Shows a map of YAC14 with ILV truncations, hom3fbr, ilv1fbr on CUP promoter comprising the following genes: hom3fbr (Ps), pyc1 (Ps), aat2 (Ps), hom3fbr (Ps), hom2 (Ps), hom6 (Ps), thr1 (Ps), thr4 (Ps), pdc3-6 (Ps), adh6, ilv1fbrΔ15 (Ps), ilv2Δ26 (Ps), ilv6 (Ps), ilv5Δ40 (Ps), ilv3Δ34 (Ps).

FIG. 74 (*a-c*). a) Shows a representative chromatogram for the array of C1-C4 alcohols, 2-MBO and isovaleric acid. The internal standard 1-pentanol. c) Shows a representative chromatogram for the alcohols and MBOs in a fermentation broth sample The internal standard 1-pentanol. Since the relative response factor for 3-MBO is similar to that for 2-MBO, the quantification of 3-MBO is based on the calibration curve set for 2-MBO. c) Shows a representative chromatogram: 1-Methanol; 2-Ethanol; 3-n-Propanol; 4-iso-Butanol; 5-n-Butanol; 6-2 MBO (partial separation from 3 MBO); 7-2MeBu Acid (co-elution with isovaleric acid).

FIG. 75 (*a-c*). Shows representative chromatograms. a) Short run, after improving resolution (Rtx-624 20×0.18, 1 um, MBOorg2), b) Short run (Rtx-624 20×0.18, 1 um, MBOorg1), and c) long run (Rtx-624 30×0.25, 1.4 um, MBO-FASTC/GC1).

DETAILED DESCRIPTION OF THE INVENTION

The invention described herein relates to recombinant microorganisms capable of metabolizing a variety of carbon sources to a number of commercially valuable compounds, including isoamyl alcohol, propanol, methylbutanols (MBO) such as 2-methyl-1-butanol (2-MBO), 3-methyl-1-butanol (3-MBO), and isobutanol. Derivatives of these compounds are also contemplated, and may be synthesized either biologically or chemically. For example, derivatives of methylbutanol include 2-methyl-1-(2-methylbutoxy) butane and 1-(isopentyloxy)-3-methylbutane, 1-(isopentyloxy)-2-methylbutane, 2-methyl-1-(tert-pentyloxy)butane, and, 2-methyl-2-(tert-pentyloxy)butane. The recombinant microorganisms are engineered to include a variety of heterologous genes encoding enzymes which complement or replace endogenous enzymatic systems. The invention also describes fuel compositions containing the compounds produced by the recombinant microorganisms and derivatives thereof, as well as methods of using such compositions.

Figure 1:
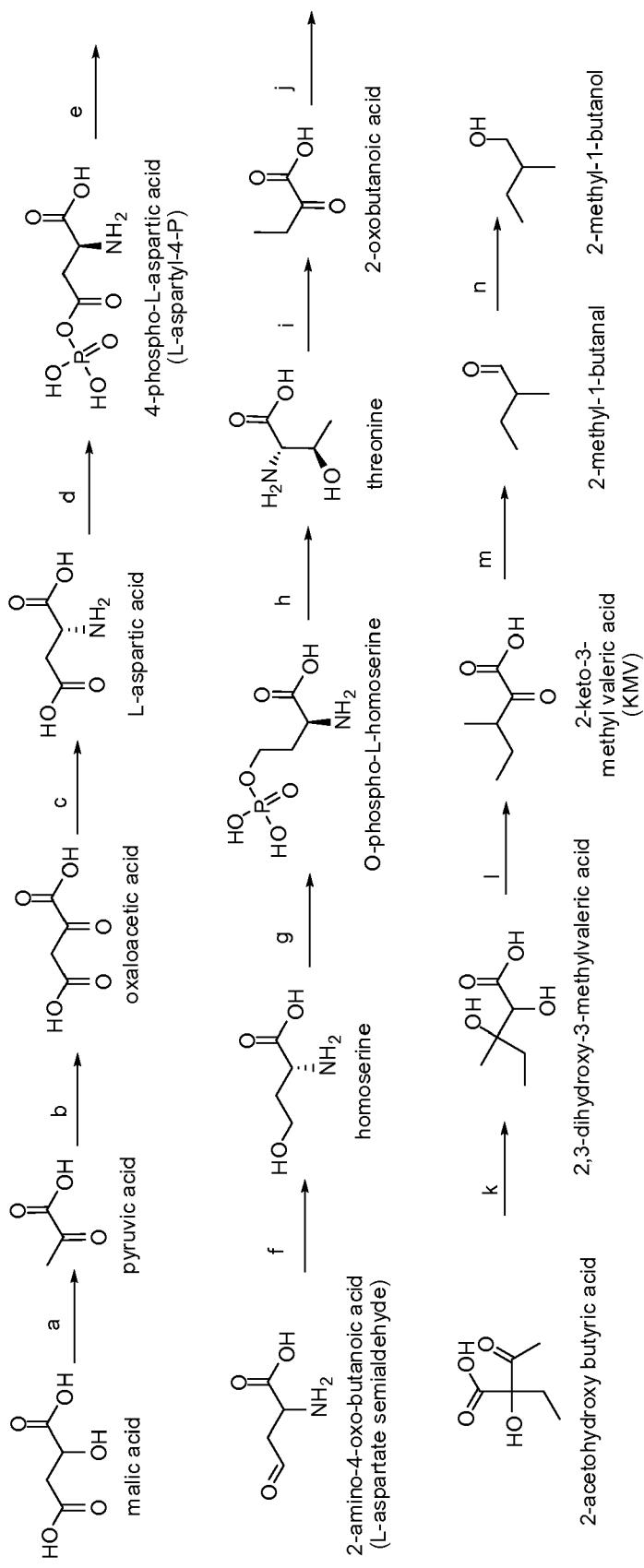
FIG. 1 depicts a metabolic pathway for the preparation of 2-methyl-1-butanol. Each enzymatic step of the pathway is provided a letter designation, which corresponds to polypeptides with the following enzymatic activities: a) malate dehydrogenase; b) pyruvate carboxylase; c) aspartate aminotransferase; d) aspartate kinase; e) aspartic beta semi-aldehyde dehydrogenase; f) homoserine dehydrogenase; g) homoserine kinase; h) threonine synthase; i) threonine deaminase or threonine dehydratase; j) acetolactate synthase; k) ketol-acid reductoisomerase or acetohydroxyacid reductoisomerase; l) dihydroxy-acid dehydratase; m) pyruvate decarboxylase; and n) alcohol dehydrogenase.

FIG. 1 shows a proposed pathway for the generation of MBO with malate as the starting material. Each step of the enzymatic pathway is provided with a letter designation which corresponds to an polypeptide with the following enzymatic activity.

Step a) corresponds to the conversion of malic acid to pyruvic acid,

Step b) corresponds to the conversion of pyruvic acid to oxaloacetic acid,

Step c) corresponds to the conversion of oxaloacetic acid to L-aspartic acid,

Step d) corresponds to the conversion of L-aspartic acid to L-aspartyl-4-phospate, Step e) corresponds to the conversion of L-aspartyl-4-phospate to 2-amino-4-oxo-butanoic acid (L-aspartate semialdehyde), step f) corresponds to the conversion of 2-amino-4-oxo-butanoic acid (L-aspartate semialdehyde) to homoserine, Step g) corresponds to the conversion of homoserine to O-phospho-L-homoserine, Step h) corresponds to the conversion of O-phospho-L-homoserine to L-threonine, Step i) corresponds to the conversion of L-threonine to 2-oxobutanic acid, Step j) corresponds to the conversion of 2-oxobutanic acid to 2-aceto-hydroxy-butyric acid, Step k) corresponds to the conversion of 2-aceto-hydroxy-butyric acid to 2,3-dihydroxy-3-methylvaleric acid, Step l) corresponds to the conversion of 2,3-dihydroxy-3-methylvaleric acid to 2-keto-3-methylvaleric acid, Step m) corresponds to the conversion of 2-keto-3-methylvaleric acid to 2-methylbutanal, and Step n) corresponds to the conversion of 2-methylbutanal to 2-methylbutanol.

The designations provide examples of enzymatic activities that catalyze particular reactions in the overall pathway. For example, malate dehydrogenase is an example of a designation for the enzyme that catalyzes the conversion of malate to pyruvate. Because enzymatic nomenclature various between organisms, it should be noted that the names provided above are merely illustrative of a class of enzymes that catalyze the particular steps of the pathway. The enzymes contemplated for use with the invention are those that catalyze the reactions illustrated and are not limited to the enzymatic names provided.

Polypeptides providing the following enzymatic activities corresponding to the steps of FIG. 1 are:

Step a) malate dehydrogenase [EC 1.1.1.37]

Step b) pyruvate carboxylase [EC 6.4.1.1]

Step c) aspartate aminotransferase [EC 2.6.1.1];

Step d) aspartate kinase or L-aspartate-4-P-transferase [EC 2.7.2.4];

Step e) aspartic beta semi-aldehyde dehydrogenase [EC 1.2.1.11];

Step f) homoserine dehydrogenase [EC 1.1.1.3];

Step g) homoserine kinase [EC 2.7.1.39];

Step h) threonine synthase [EC 4.2.99.2];

Step i) threonine deaminase or threonine dehydratase [EC 4.3.1.19];

Step j) acetolactate synthase or a subunit thereof [EC 2.2.1.6];

Step k) ketol-acid reductoisomerase or acetohydroxyacid reductoisomerase [EC 1.1.1.86];

Step l) dihydroxy-acid dehydratase [EC 4.2.1.9];

Step m) pyruvate decarboxylase [EC 4.1.1.1] or alpha-keto acid decarboxylase [4.1.1.72]; and Step n) alcohol dehydrogenase [EC 1.1.1.1]. The EC numbers provided use the enzyme nomenclature of the Nomenclature Committee of the International Union of Biochemistry and Molecular Biology.

A first aspect of the invention provides a recombinant microorganism comprising at least one DNA molecule, wherein said at least one DNA molecule encodes at least three polypeptides that catalyze a substrate to product conversion selected from the group consisting of steps a) through h), wherein said recombinant microorganism produces 2-methylbutanol.

In particular embodiments of the invention, the polypeptide catalyzing the conversion of malate to pyruvate is derived from a yeast. An example of a suitable source for this enzyme is the genus *Pichia*, a preferred source is *Picihia stipitis*. A specific example of a suitable sequence is:

*Pichia stipitis* MDH2 (Ps) amino acid sequence:

```
                                          (SEQ ID NO: 1)
MPHSVTPSIEQDSLKIAILGAAGGIGQSLSLLLKAQLQYQLKESNRSVTH

IHLALYDVNQEAINGVTADLSHIDTPISVSSHSPAGGIENCLHNASIVVI

PAGVPRKPGMTRDDLFNVNAGIISQLGDSIAECCDLSKVFVLVISNPVNS

LVPVMVSNILKNHPQSRNSGIERRIMGVTKLDIVRASTFLREINIESGLT

PRVNSMPDVPVIGGHSGETIIPLFSQSNFLSRLNEDQLKYLIHRVQYGGD

EVVKAKNGKGSATLSMAHAGYKCVVQFVSLLLGNIEQIHGTYYVPLKDAN

NFPIAPGADQLLPLVDGADYFAIPLTITTKGVSYVDYDIVNRMNDMERNQ

MLPICVSQLKKNIDKGLEFVASRSASS.
```

Another exemplary sequence is:
*Saccharomyces cerevisiae* MDH2 amino acid sequence:

```
                                          (SEQ ID NO: 2)
MVKVTVCGAAGGIGQPLSLLLKLNPAVSELALFDIVNAKGVAADLSHINT

PAVVTGHQPANKEDKTAIVDALKGTDLVVIPAGVPRKPGMTRADLFNINA

SIIRDLVANIGRTAPNAAILIISNPVNATVPIAAEVLKKLGVFNPGKLFG

VTTLDSVRAETFLGELINVNPSQLQGRISVVGGHSGDTIVPLINVTPDVS

AKVANISKADYDKFVNRVQFGGDEVVKAKNGAGSATLSMAYAGYRFAAGV
```

LNSLGGASTSSSGVPDSSYVYLPGVPGGKEFSAKYLNGVDFFSVPIVLEN

GVIKSFINPFEHMKITQKEQELVKVALGGLEKSIEQGTNFVKGSKL

In particular embodiments of the invention, the polypeptide catalysing the conversion of pyruvate to oxaloacetic acid is derived from a yeast. An example of a suitable source for this enzyme is the genus Pichia, a preferred source is Picihia stipitis. A specific example of a suitable sequence is:

Pichia stipitis PYC1 (Ps) amino acid sequence:

(SEQ ID NO: 3)
MSSLSPHDHHGKINQMRRDSTVLGPMNKILVANRGEIPIRIFRTAHELSM

QTVAIYSHEDRLSMHRLKADESYVIGKKGEFSPVGAYLQIDEIIKIAKTH

NVNMIHPGYGFLSENSEFARKVEEAGIAWIGPTHETIDAVGDKVSARNLA

LANDVPVVPGTPGPIDSVEEAEAFVEKYGYPVIIKAAFGGGGRGMRVVRE

GDDIGDAFKRATSEAKTAFGNGTCFIERFLDKPKHIEVQLLADGYGNVIH

LFERDCSVQRRHQKVVEIAPAKNLPKAVRDAILTDAVKLAKSANYRNAGT

AEFLVDEQNRHYFIEINPRIQVEHTITEEITGVDIVAAQIQIAAGASLQQ

LGLLQDKITTRGFAIQCRITTEDPSKNFQPDTGKIEVYRSSGGNGVRLDG

GNGFAGSIISPHYDSMLVKCSTSGSTYEIARRKMLRALIEFRIRGVKTNI

PFLLALLTNETFISGSCWTTFIDDTPSLFQMISSQNRANKILSYLADLIV

NGSSIKGQVGLPKLNEEAEIPTIHDPKTGIPIDVELNPAPRGWRQVLLEE

GPDAFAKKVRNFNGTLITDTTWRDAHQSLLATRLRTIDLLNIAPTTAHAL

NGAFSLECWGGATFDVCMRFLYEDPWARLRKLRKLVPNIPFQMLLRGANG

VAYSSLPDNAIDQFVKQAKDNGVDIFRVFDALNDLDQLKVGIDAVKKAGG

VVEATVCYSGDMLQKGKKYNLAYYVDVVDKIVAMGTHFLGIKDMAGTLKP

KAATDLVSAIRAKYPDLPIHVHTHDSAGTGVASMTAAAKAGADVVDAASN

SMSGMTSQPSISAILASFEGEVETGLSERLVREIDHYWAQMRLLYSCFEA

DLKGPDPEVYEHEIPGGQLTNLLFQAQQLGLGAKWLQTKETYKIANRVLG

DVVKVTPTSKVVGDLAQFMVSNNLTEEDVNKLAGELDFPDSVLDFMEGLM

GTPYGGFPEPLRTNMLGNKRQKLNERPGLSLAPVDFSALKQELVSKYGNS

IKEVDLASYTMYPKVYESYRKIVEKYGDLSVLPTRYFLKGINVGEELSVE

IEQGKTLIVKLLAVGEISQQKGTREVFFELNGEMRSVTVDDKTVSVETIT

RRKATQPNEVGAPMAGVVIEIRTQSGTDVKKGDPIAVLSAMKMEMVISAP

VSGVVGEILIKEGESVDASDLITSILKHN

Other exemplary sequences are:

Saccharomyces cerevisiae PYC1 amino acid sequence:

(SEQ ID NO: 4)
MSQRKFAGLRDNFNLLGEKNKILVANRGEIPIRIFRTAHELSMQTVAIYS

HEDRLSTHKQKADEAYVIGEVGQYTPVGAYLAIDEIISIAQKHQVDFIHP

GYGFLSENSEFADKVVKAGITWIGPPAEVIDSVGDKVSARNLAAKANVPT

VPGTPGPIETVEEALDFVNEYGYPVIIKAAFGGGGRGMRVVREGDDVADA

FQRATSEARTAFGNGTCFVERFLDKPKHIEVQLLADNHGNVVHLFERDCS

VQRRHQKVVEVAPAKTLPREVRDAILTDAVKLAKECGYRNAGTAEFLVDN

QNRHYFIEINPRIQVEHTITEEITGDIVAAQIQIAAGASLPQLGLFQDK

ITTRGFAIQCRITTEDPAKNFQPDTGRIEVYRSAGGNGVRLDGGNAYAGT

IISPHYDSMLVKCSCSGSTYEIVRRKMIRALIEFRIRGVKTNIPFLLTLL

TNPVFIEGTYWTTFIDDTPQLFQMVSSQNRAQKLLHYLADVAVNGSSIKG

QIGLPKLKSNPSVPHLHDAQGNVINVTKSAPPSGWRQVLLEKGPAEFARQ

VRQFNGTLLMDTTWRDAHQSLLATRVRTHDLATIAPTTAHALAGRFALEC

WGGATFDVAMRFLHEDPWERLRKLRSLVPNIPFQMLLRGANGVAYSSLPD

NAIDHFVKQAKDNGVDIFRVFDALNDLEQLKVGVDAVKKAGGVVEATVCF

SGDMLQPGKKYNLDYYLEIAEKIVQMGTHILGIKDMAGTMKPAAAKLLIG

SLRAKYPDLPIHVHTHDSAGTAVASMTACALAGADVVDVAINSMSGLTSQ

PSINALLASLEGNIDTGINVEHVRELDAYWAEMRLLYSCFEADLKGPDPE

VYQHEIPGGQLTNLLFQAQQLGLGEQWAETKRAYREANYLLGDIVKVTPT

SKVVGDLAQFMVSNKLTSDDVRRLANSLDFPDSVMDFFEGLIGQPYGGFP

EPFRSDVLRNKRRKLTCRPGLELEPFDLEKIREDLQNRFGDVDECDVASY

NMYPRVYEDFQKMRETYGDLSVLPTRSFLSPLETDEEIEVVIEQGKTLII

KLQAVGDLNKKTGEREVYFDLNGEMRKIRVADRSQKVETVTKSKADMHDP

LHIGAPMAGVIVEVKVHKGSLIKKGQPVAVLSAMKMEMIISSPSDGQVKE

VFVSDGENVDSSDLLVLLEDQVPVETKA

Saccharomyces cerevisiae PYC2 amino acid sequence:

(SEQ ID NO: 5)
MSSSKKLAGLRDNFSLLGEKNKILVANRGEIPIRIFRSAHELSMRTIAIY

SHEDRLSMHRLKADEAYVIGEEGQYTPVGAYLAMDEIIEIAKKHKVDFIH

PGYGFLSENSEFADKVVKAGITWIGPPAEVIDSVGDKVSARHLAARANVP

TVPGTPGPIETVQEALDFVNEYGYPVIIKAAFGGGGRGMRVVREGDDVAD

AFQRATSEARTAFGNGTCFVERFLDKPKHIEVQLLADNHGNVVHLFERDC

SVQRRHQKVVEVAPAKTLPREVRDAILTDAVKLAKVCGYRNAGTAEFLVD

NQNRHYFIEINPRIQVEHTITEEITGDIVSAQIQIAAGATLTQLGLLQD

KITTRGFSIQCRITTEDPSKNFQPDTGRLEVYRSAGGNGVRLDGGNAYAG

ATISPHYDSMLVKCSCSGSTYEIVRRKMIRALIEFRIRGVKTNIPFLLTL

LTNPVFIEGTYWTTFIDDTPQLFQMVSSQNRAQKLLHYLADLAVNGSSIK

GQIGLPKLKSNPSVPHLHDAQGNVINVTKSAPPSGWRQVLLEKGPSEFAK

QVRQFNGTLLMDTTWRDAHQSLLATRVRTHDLATIAPTTAHALAGAFALE

CWGGATFDVAMRFLHEDPWERLRKLRSLVPNIPFQMLLRGANGVAYSSLP

DNAIDHFVKQAKDNGVDIFRVFDALNDLEQLKVGVNAVKKAGGVVEATVC

YSGDMLQPGKKYNLDYYLEVVEKIVQMGTHILGIKDMAGTMKPAAAKLLI

GSLRTRYPDLPIHVHSHDSAGTAVASMTACALAGADVVDVAINSMSGLTS

QPSINALLASLEGNIDTGINVEHVRELDAYWAEMRLLYSCFEADLKGPDP

EVYQHEIPGGQLTNLLFQAQQLGLGEQWAETKRAYREANYLLGDIVKVTP

TSKVVGDLAQFMVSNKLTSDDIRRLANSLDFPDSVMDFFEGLIGQPYGGF

PEPLRSDVLRNKRRKLTCRPGLELEPFDLEKIREDLQNRFGDIDECDVAS

YNMYPRVYEDFQKIRETYGDLSVLPTKNFLAPAEPDEEIEVTIEQOKTLI

IKLQAVGDLNKKTGQREVYFELNGELRKIRVADKSQNIQSVAKPKADVHD

THQIGAPMAGVIIEVKVHKGSLVKKGESIAVLSAMKMEMVVSSPADGQVK

DVFIKDGESVDASDLLVVLEEETLPPSQKK

Pichia stipitis PYC2 (Ps) amino acid sequence:

(SEQ ID NO: 6)
MTASSLDNQLNYVHAAFDEENDGLLPISLQDLTNKHKEASTSKNSTFAPK

NTSLPSSTKSASLLKVDRPAFFVLVLLYLLQGVPVGLAFGSIPFILKSKL

SYSQVGIFSLAAYPYSLKLIWSPIVDAVYSPKLGRRRSWIIPIQTISGVT

LIYLGSLIDGLMEDPQNCLPTITFCFFMLVFFCATQDIAVDGWALTCLSP

ESLSYASTAQTIGINTGYFSSFTIFLALSSPDFANRYLRKVPLDVGLFSL

GSYLTFWGWMFLAVTALLWFVPEDPPHLAKRNQAKLSNEKIKTESVYNKD

SKFKDLQNVYLAMFKVLKLPNVQTFVIILLISKFGFQVNEAATNLKLLEK

GLSKEDLSITVLIDFPFEMVFGYYAGRWSTGKSPLKPWIFGFAGRLVAAA

LAQGIVYFFPEDGKISSFYFLLVILQHLLGSFMSTIQFVSLCAFHTKIAD

PAIGGTYMTTLNTLSNYGGTWPRLILLYLIDKLTIEECKVPSVTNSYYIT

DEDLRQQCKSSGGKLTVLRDGYYYTNTICVIIGIFTLLWVKRKTTYLQSL

PNSAWRVNKD

In particular embodiments of the invention, the polypeptide catalyzing the conversion of oxaloacetic acid to L-aspartate is derived from a yeast. An example of a suitable source for this enzyme is the genus Pichia, a preferred source is Picihia stipitis. A specific example of a suitable sequence is:
Pichia stipitis AAT2 (Ps) amino acid sequence:

(SEQ ID NO: 7)
MSYFAGITELPPDPLFGLKARYVADSRTDKVDLGIGAYRDNNGKPWILPA

VKLAEAKLVSSPDYNHEYLSISGFEPFLKQASKVILGENSAALAENRVVS

QQSLSGTGALHVAGVLLKEFYTGEKTVYLSKPTWANHNQIFTSIGFKVAS

YPYWDNDTKSLDLKGFLSTIRTAPASGIFLLHACAHNPTGLDPSQDEWKQ

VLKELEAKKHLVLFDSAYQGFASGDLDKDAYAIRYAIDQKVISTPIIICQ

SFAKNVGMYGERVGAIHVIPSTQKDEQLGRALKSQLNRIIRSEISNPPAY

GAKIVSTILNDRALRQQWEADLVTMSSRIHKMRLKLKELLTNLHTPGTWD

HIVNQTGMFSFTGLSPDMVARLEKVHGIYLVSSGRASVAGLNDGNVEKVA

NAIDEVVRFYAKPKL

Other exemplary sequences are:
Saccharomyces cerevisiae AAT1 amino acid sequence:

(SEQ ID NO: 8)
MLRTRLTNCSLWRPYYTSSLSRVPRAPPDKVLGLSEHFKKVKNVNKIDLT

VGIYKDGWGKVTTFPSVAKAQKLIESHLELNKNLSYLPITGSKEFQENVM

KFLFKESCPQFGPFYLAHDRISFVQTLSGTGALAVAAKFLALFISRDIWI

PDPSWANHKNIFQNNGFENIYRYSYYKDGQIDIDGWIEQLKTFAYNNQQE

NNKNPPCIILHACCHNPTGLDPTKEQWEKIIDTIYELKMVPIVDMAYQGL

ESGNLLKDAYLLRLCLNVNKYPNWSNGIFLCQSFAKNMGLYGERVGSLSV

ITPATANNGKFNPLQQKNSLQQNIDSQLKKIVRGMYSSPPGYGSRVVNVV

LSDFKLKQQWFKDVDFMVQRLHHVRQEMFDRLGWPDLVNFAQQHGMFYYT

RFSPKQVEILRNNYFVYLTGDGRLSLSGVNDSNVDYLCESLEAVSKMDKL

A

Pichia stipitis AAT1 (Ps) amino acid sequence:

(SEQ ID NO: 9)
MYRTSLLKQTARPSVRVSTRQFSVLNNQVRKWSEIPLAPPDKILGISEAY

NKDANTSKINLGVGAYRDNSGKPIIFPSVKEAEKILLASEVEKEYTGITG

SKKFQNAVKGFVFNNSGKDVNGQQLIEQNRIVTAQTISGTGSLRVIGDFL

NRFYTNKKLLVPKPTWANHVAVFKDAGLEPEFYAYYETSKNDLDFANLKK

SLSSQPDGSIVLLHACCHNPTGMDLTPEQWEEVLAIVQEKNFYPLVDMAY

QGFASGNPYKDIGLIRRLNELVVQNKLKSYALCQSFAKNMGLYGERTGSI

SIITESAEASQAIESQLKKLIRPIYSSPPIHGSKIVEIIFDEQHNLLNSW

LQDLDKVVGRLNTVRSKLYENLDKSSYNWDHLLKQRGMFVYTGLSAEQVI

KLRNDYSVYATEDGRFSISGINDNNVEYLANAINEVVKQ

Saccharomyces cerevisiae AAT2 amino acid sequence:

(SEQ ID NO: 10)
MSATLFNNIELLPPDALFGIKQRYGQDQRATKVDLGIGAYRDDNGKPWVL

PSVKAAEKLIHNDSSYNHEYLGITGLPSLTSNAAKIIFGTQSDAFQEDRV

ISVQSLSGTGALHISAKFFSKFFPDKLVYLSKPTWANHMAIFENQGLKTA

TYPYWANETKSLDLNGFLNAIQKAPEGSIFVLHSCAHNPTGLDPTSEQWV

QIVDAIASKNHIALFDTAYQGFATGDLDKDAYAVRLGVEKLSTVSPVFVC

QSFAKNAGMYGERVGCFHLALTKQAQNKTIKPAVTSQLAKIIRSEVSNPP

AYGAKIVAKLLETPELTEQWHKDMVTMSSRITKMRHALRDHLVKLGTPGN

WDHIVNQCGMFSFTGLTPQMVKRLEETHAVYLVASGRASIAGLNQGNVEY

VAKAIDEVVRFYTIEAKL

In particular embodiments of the invention, the polypeptide catalyzing the conversion of L-aspartate to L-aspartyl-4-phospate is derived from a yeast. An example of a suitable source for this enzyme is the genus Pichia, a preferred source is Picihia stipitis. Another example of a suitable source is the appropriate gene derived from the genus Saccharomyces, a preferred source is S. cerevisiae. The invention further contemplates the use of an aspartate kinase that has been modified to become resistant to feedback inhibition. A specific example of a suitable sequence is:
Pichia stipitis HOM3$^{FBR}$ (Ps) amino acid sequence:

(SEQ ID NO: 11)
MSVSPPLSAKSYNSIVDLRFTASKPQGWVVQKFGGTSVGKFPENIVDDIV

LVFSKTNRVAVVCSARSSQTKSEGTTSRLLKAADIAAESGDFQYMLDVIE

DDHVKNAEARVKNKTIQQKLVADTKREIAHAAELLRACQVIGEISARSLD

SVMSIGEKLSCLFMAALMNDHGLKAVYIDLSDVIPLDYDFTNGFDDNFYK

-continued
FLSQQLSSRALALSEDTVPVLTGYFGTVPGGLLNGVGRGYTDLCAALVAV

GVQADELQVWKEVDGIFTADPRKVPTARLLDSVTPEEAAELTYYGSEVIH

PFTMEQVIKAKIPIRIKNVVNPKGSGTIIFPDNVGRRGEETPPHPPEAYE

TLSSSFVLSHKKRSATAITAKQDIVVINIHSNKKTLSHGFLAHIFTTLDN

FKLVVDLISTSEVHVSMALQILQDQELQLKNALKDLRRMGTVDITRNMTI

ISLVGKQMVNFIDIAGNMFKVLADNRINIEMISQGANEINISAVINEKDT

IRALQSIHAKLLEGTFGFDDHVESAVDLRLESLKFQ

Another exemplary sequence is:
Saccharomyces cerevisiae HOM3<sup>FBR</sup> amino acid sequence:

(SEQ ID NO: 12)
MSVSPPLSAKSYNSIVDLRFTASKPQGWVVQKFGGTSVGKFPENIVDDIV

LVFSKTNRVAVVCSARSSQTKSEGTTSRLLKAADIAAESGDFQYMLDVIE

DDHVKNAEARVKNKTIQQKLVADTKREIAHAAELLRACQVIGEISARSLD

SVMSIGEKLSCLFMAALMNDHGLKAVYIDLSDVIPLDYDFTNGFDDNFYK

FLSQQLSSRALALSEDTVPVLTGYFGTVPGGLLNGVGRGYTDLCAALVAV

GVQADELQVWKEVDGIFTADPRKVPTARLLDSVTPEEAAELTYYGSEVIH

PFTMEQVIKAKIPIRIKNVVNPKGSGTIIFPDNVGRRGEETPPHPPEAYE

TLSSSFVLSHKKRSATAITAKQDIVVINIHSNKKTLSHGFLAHIFTTLDN

FKLVVDLISTSEVHVSMALQILQDQELQLKNALKDLRRMGTVDITRNMTI

ISLVGKQMVNFIDIAGNMFKVLADNRINIEMISQGANEINISAVINEKDT

IRALQSIHAKLLEGTFGFDDHVESAVDLRLESLKFQ

In particular embodiments of the invention, the polypeptide catalyzing the conversion of L-aspartyl-4-phospate to 2-amino-4-oxo-butanoic acid (L-aspartate semialdehyde) is derived from a yeast. An example of a suitable source for this enzyme is the genus Pichia, a preferred source is Picihia stipitis. A specific example of a suitable sequence is:
Pichia stipitis HOM2 (Ps) amino acid sequence:

(SEQ ID NO: 13)
MVKKAGVLGATGSVGQRFILLLAEHPDFELHVLGASPRSAGKQYKDAVQW

KQTDLLPENAQKIIVSECKAEAFKDCDIVFSGLDADYAGPIEKEFVEAGL

VVVSNAKNYRREPGVPLIVPIVNSEHLSVIERKLAVAKAEGKSKPGYIIC

ISNCSTAGLVAPLKPLIDAFGPIDALTATTLQAISGAGFSPGVPGMDVLD

NIIPYIGGEEEKLEWESKKILGNLTKDGTDFAPLSNDEMKVSAQCNRVAV

IDGHTECISFRFAKHPAPSVAQVKKVLSEYVCEATKLGCHSAPKQTIHVL

EQQDRPQPRLDRNRDNGYGVSVGRIREDAVLDFKMVVLSHNTIIGAAGAG

VLIAEILKAKDMI

Another exemplary sequence is:
Saccharomyces cerevisiae HOM2 (Sc) amino acid sequence:

(SEQ ID NO: 14)
MAGKKIAGVLGATGSVGQRFILLLANHPHFELKVLGASSRSAGKKYVDAV

NWKQTDLLPESATDIIVSECKSEFFKECDIVFSGLDADYAGAIEKEFMEA

GIAIVSNAKNYRREQDVPLIVPVVNPEHLDIVAQKLDTAKAQGKPRPGFI

ICISNCSTAGLVAPLKPLIEKFGPIDALTTTTLQAISGAGFSPGVPGIDI

LDNIIPYIGGEEDKMEWETKKILAPLAEDKTHVKLLTPEEIKVSAQCNRV

AVSDGHTECISLRFKNRPAPSVEQVKTCLKEYVCDAYKLGCHSAPKQTIH

VLEQPDRPQPRLDRNRDSGYGVSVGRIREDPLLDFKMVVLSHNTIIGAAG

SGVLIAEILLARNLI

In particular embodiments of the invention, the polypeptide catalyzing the conversion of 2-amino-4-oxo-butanoic acid (L-aspartate semialdehyde) to homoserine is derived from a yeast. An example of a suitable source for this enzyme is the genus Pichia, a preferred source is Picihia stipitis. A specific example of a suitable sequence is:
Pichia stipitis HOM6 (Ps) amino acid sequence:

(SEQ ID NO: 15)
MSKSVNVAIIGSGVVGSAFISQLNGLKTAIKYNVVYLAKTSSEALYSSDY

QSVDLSSYKTSATKPTLGLDELLKFLQGAKKATILVDNTSNASIADYYPT

FIKAGISIATPNKKAFSSDLKTWNEIFANSAVPGAGLVAHEATVGAGLPI

IGPLRDLITTGDKVDKIEGIFSGTLSYIFNEFSTTEKSDVKFSDVVKVAK

KLGYTEPDPRDDLNGLDVARKVTILARISGFEVESPTSFPVESLIPKELE

GIESAAEFLEKLPNYDADIQKIKDEAFAENKTLRFVGQVDFKANKVSVGI

GKYPFDHPFSALKGSDNVISIKTERYPNPLIVQGAGAGSEVTAHGVLADT

IKIAERIAN

Another exemplary sequence is:
Saccharomyces cerevisiae HOM6 amino acid sequence:

(SEQ ID NO: 16)
MSTKVVNVAVIGAGVVGSAFLDQLLAMKSTITYNLVLLAEAERSLISKDF

SPLNVGSDWKAALAASTTKTLPLDDLIAHLKTSPKPVILVDNTSSAYIAG

FYTKFVENGISIATPNKKAFSSDLATWKALFSNKPTNGFVYHEATVGAGL

PIISFLREIIQTGDEVEKIEGIFSGTLSYIFNEFSTSQANDVKFSDVVKV

AKKLGYTEPDPRDDLNGLDVARKVTIVGRISGVEVESPTSFPVQSLIPKP

LESVKSADEFLEKLSDYDKDLTQLKKEAATENKVLRFIGKVDVATKSVSV

GIEKYDYSHPFASLKGSDNVISIKTKRYTNPVVIQGAGAGAAVTAAGVLG

DVIKIAQRL

In particular embodiments of the invention, the polypeptide catalyzing the conversion of homoserine to O-phospho-L-homoserine is derived from a yeast. An example of a suitable source for this enzyme is the genus Pichia, a preferred source is Picihia stipitis. A specific example of a suitable sequence is:
Pichia stipitis THR1 (Ps) amino acid sequence:

(SEQ ID NO: 17)
MTIRSFEVKVPASSANIGPGFDVLGVGLQLYLQIKVTIDSSKDTSHDPYH

VKLSYEGDLAEKVPLTSDKNLITQTALYILRVNGMDSFPQGTHIHVINPV

PLGRGLGSSASAIVGGIVLGNEIGEFKFSKTRLMDYCLMIERHPDNIAAA

-continued

```
MLGGFVGSYLHDLSPEDMAAKNVPLDYILPKPDTPKEKIVSSQPPTNIGE

YLQYNWCHKIKCVAIVPNFEVSTDSSRAVLPEKYDRQDIVFNLQRLAILT

NALTQETPNNKLIYESMKDKIHQPYRSGLIPGLQKVLASVTPDTHPGLCG

ICLSGAGPTILCLATGGYDAIAETVIGIFNKAGVECSWKLLELAYDGATV

EIK
```

Other exemplary sequences are:
Saccharomyces cerevisiae THR1 amino acid sequence:

```
                                         (SEQ ID NO: 18)
MVRAFKIKVPASSANIGPGYDVLGVGLSLFLELDVTIDSSQAQETNDDPN

NCKLSYTKESEGYSTVPLRSDANLITRTALYVLRCNNIRNFPSGTKVHVS

NPIPLGRGLGSSGAAVVAGVILGNEVAQLGFSKQRMLDYCLMIERHPDNI

TAAMMGGFCGSFLRDLTPQEVERREIPLAEVLPEPSGGEDTGLVPPLPPT

DIGRHVKYQWNPAIKCIAIIPQFELSTADSRGVLPKAYPTQDLVFNLQRL

AVLTTALTMDPPNADLIYPAMQDRVHQPYRKTLIPGLTEILSCVTPSTYP

GLLGICLSGAGPTILALATENFEEISQEIINRFAKNGIKCSWKLLEPAYD

GASVEQQ
```

Corynebacterium glutamicum KhsE (Cg) amino acid sequence:

```
                                         (SEQ ID NO: 19)
MAIELPVGKKVTVTVPASSANLGPGFDTLGLALSLYDTVEVEVTDHGLEV

EVFGEGQGELPLDGSHLVVKAIRAGLKAADVQVPGLRVVCHNNIPQSRGL

GSSAAAAVAGVAAANGLAGFPLDDARVVQLSSAFEGHPDNAAASVLGNAV

VSWTEIPVDGRTEPQFKAVTINVDSRIKATALVPDFHASTEAVRRVLPSD

VTHLDARFNVSRCAVMTVALQHHPELLWEGTRDRLHQPYRADVLPVTAEW

VNRLRNRGYAAYLSGAGPTIMVLHTEPVDEAVLNDAREAGLRVLSLDVAD

AVSVKVDA
```

In particular embodiments of the invention, the polypeptide catalyzing the conversion of O-phospho-L-homoserine to L-threonine is derived from a yeast. An example of a suitable source for this enzyme is the genus Pichia, a preferred source is Picihia stipitis. A specific example of a suitable sequence is:
Pichia stipitis THR4 (Ps) amino acid sequence:

```
                                         (SEQ ID NO: 20)
MSQKYRSSRSAEPQALSFEDVVMTGLANDGGLFLPSQVPQLPASFLQDWA

DLSFQELAFNVLRLYINAAEIPDQDLRDLISKSYSTFRSEEVTPLKKIDD

KLYLLELFHGPTYAFKDVALQFVGNLFEYFLTRRNAKKVEGEARDVITVV

GATSGDTGSAAIYGLRGKKDVSVFILYPTGRISPIQEEQMTTVEDANVHT

LSVNGTFDDCQDIVKSIFGDREFNDKYHVGAVNSINWARILAQQTYYFYS

YFQLQKKLNDTSAKVRFVVPSGNFGDILAGYYAYKMGLPVDKLIIATNEN

DILDRFMKTGRYEKKAEKDASAAVKATFSPAMDILISSNFERLLWYLIRD

SVANGSDEVAGKTLNSWMQQLKETGSVVADPEVLAGARSIFDSERVDDAE

TVATIKEVYSAHPESYVLDPHSSVGVTTSYRFIKKDDKKDNIKYISLSTA

HPAKFSEVVNKALDSIAGYSFEKDVLPAELKALSTKRKRINLIDEASIEK

VKDAIKKELNF
```

Another exemplary sequence is:
Saccharomyces cerevisiae THR4 amino acid sequence:

```
                                         (SEQ ID NO: 21)
MPNASQVYRSTRSSSPKTISFEEAI-
IQGLATDGGLFIPPTIPQVDQATLFNDWSKLSFQDLAFAIMRLYI

AQEEIPDADLKDLIKRSYSTFRSDEVT-
PLVQNVTGDKENLHILELFHGPTYAFKDVALQFVGNLFEYFLQ

RTNANLPEGEKKQITVVGATSGDTG-
SAAIYGLRGKKDVSVFILYPTGRISPIQEEQMTTVPDENVQTLSV

TGTFDNCQDIVKAIFGDKEFNSKHNV-
GAVNSINWARILAQMTYYFYSFFQATNGKDSKKVKFVVPSGNFG

DILAGYFAKKMGLPIEKLAIAT-
NENDILDRFLKSGLYERSDKVAATLSPAMDILISSNFERLLWYLAREY

LANGDDLKAGEIVNNWFQELKTNGK-
FQVDKSIIEGASKDFTSERVSNEETSETIKKIYESSVNPKHYILD

PHTAVGVCATERLIAKDNDKSIQYISLS-
TAHPAKFADAVNNALSGFSNYSFEKDVLPEELKKLSTLKKKL

KFIERADVELVKNAIEEELAKMKL
```

A second aspect of the invention provides a recombinant microorganism comprising at least one DNA molecule, wherein said at least one DNA molecule encodes at least two polypeptides that catalyze a substrate to product conversion selected from the group consisting of steps i) through l), wherein said recombinant microorganism produces 2-methylbutanol.

In particular embodiments of the invention, the polypeptide catalyzing the conversion of L-threonine to 2-oxobutanate is derived from a yeast. An example of a suitable source for this enzyme is the genus Pichia, a preferred source is Picihia stipitis. The invention further contemplates the use of a threonine deaminase or threonine dehydratase that has been modified to become resistant to feedback inhibition. A specific example of a suitable sequence is:
Pichia stipitis ILV1 (Ps)$^{FBR}$ amino acid sequence:

```
                                         (SEQ ID NO: 22)
MFFSRSGEVEKFPNLLDADFNEDGDPDYIKLILTSRVYDVVERAGTPLTH

AINLSHKCNSNIYLKREDLLPVFSFKLRGAYNMISHLHSNSKMPLSGVIA

CSAGNHAQGVAYSANRLKIPSTIVMPTATPSIKYTNVSRLGSQVVLYGDD

FDSAKQECARLSSLNNLTDVPPFDHPYVIAGQGTIALEITRQLRLDKLNA

LFVPVGGGGLIAGVAVYLKKIAPHVKIIGVETNDADALYQSLKAKKLVVL

DQVGMFADGTAVKVLGKETWRLCENLVDEVVKVSTDELCAAIKDIFEDTR

LITEPSGALSVAGLKKYIEQNPDIDHRNKFYVPILSGANMNFDRLRFVSE

RAVLGEGKEVSLVVTIPEKPGEFAKLQSIINPRAITEFSYRCNGADANIF

VSFNVIDKKKELTPIIEDMNNNEHGYEVVDISDNELAKTHGCYLVGGKSS

EEVANERLYSFEFPEKPGALFNFLQALKADWNITLFHYHNHGHDIGKVLC

GFTLPEGTDDADFQSFLNELGYKFNVENDNVVYKKFLRS
```

Another exemplary sequence that contemplates the use of a threonine deaminase that has been modified to optimize cytoplasmic expression is:

*Pichia stipitis* ILV1 (Ps) Δ15 amino acid sequence:

(SEQ ID NO: 23)
MFPNLLDADFNEDGDPDYIKLILTSRVYDVVERAGTPLTHAINLSHKCNS
NIYLKREDLLPVFSFKLRGAYNMISHLHSNSKMPLSGVIACSAGNHAQGV
AYSANRLKIPSTIVMPTATPSIKYTNVSRLGSQVVLYGDDFDSAKQECAR
LSSLNNLTDVPPFDHPYVIASQSTIALEITRQLRLDKLNALFVPVGGGGL
IAGVAVYLKKIAPHVKIISVETNDADALYQSLKAKKLVVLDQVSMFADST
AVKVLGKETWRLCENLVDEVVKVSTDELCAAIKDIFEDTRLITEPSGALS
VASLKKYIEQNPDIDHRNKFYVPILSGANMNFDRLRFVSERAVLGEGKEV
SLVVTIPEKPGEFAKLQSIINPRAITEFSYRCNSADANIFVSFNVIDKKK
ELTPIIEDMNNNEHGYEVVDISDNELAKTHGCYLVGGKSSEEVANERLYS
FEFPEKPGALFNFLQALKADWNITLFHYHNHGHDIGKVLCGFTLPEGTDD
ADFQSFLNELGYKFNVENDNVVYKKFLRS

Other exemplary sequences are:
*Saccharomyces cerevisiae* ILV1 amino acid sequence:

(SEQ ID NO: 24)
MSATLLKQPLCTVVRQGKQSKVSGLNLLRLKAHLRQHLSPSLIKLHSEL
KLDELQTDNTPDYVRLVLRSSVYDVINESPISQGVGLSSRLNTNVILKRE
DLLPVFSFKLRGAYNMIAKLDDSQRNQGVIACSAGNHAQGVAFAAKHLKI
PATIVMPVCTPSIKYQNVSRLGSQVVLYGNDFDEAKAECAKLAEERGLTN
IPPFDHPYVIAGQGTVAMEILRQVRTANKIGAVFVPVGGGGLIAGIGAYL
KRVAPHIKIIGVETYDAATLHNSLQRNQRTPLPVVGTFADGTSVRMIGEE
TFRVAQQVVDEVVLVNTDEICAAVKDIFEDTRSIVEPSGALSVAGMKKYI
STVHPEIDHTKNTYVPILSGANMNFDRLRFVSERAVLGEGKEVFMLVTLP
DVPGAFKKMQKIIHPRSVTEFSYRYNEHRHESSSEVPKAYIYTSFSVVDR
EKEIKQVMQQLNALGFEAVDISDNELAKSHGRYLVGGASKVPNERIISFE
FPERPGALTRFLGGLSDSWNLTLFHYRNHGADIGKVLAGISVPPRENLTF
QKFLEDLGYTYHDETDNTVYQKFLKY

*Saccharomyces cerevisiae* ILV1^FBR amino acid sequence:

(SEQ ID NO: 25)
MSATLLKQPLCTVVRQGKQSKVSGLNLLRLKAHLRQHLSPSLIKLHSEL
KLDELQTDNTPDYVRLVLRSSVYDVINESPISQGVGLSSRLNTNVILKRE
DLLPVFSFKLRGAYNMIAKLDDSQRNQGVIACSAGNHAQGVAFAAKHLKI
PATIVMPVCTPSIKYQNVSRLGSQVVLYGNDFDEAKAECAKLAEERGLTN
IPPFDHPYVIAGQGTVAMEILRQVRTANKIGAVFVPVGGGGLIAGIGAYL
KRVAPHIKIIGVETYDAATLHNSLQRNQRTPLPVVGTFADGTSVRMIGEE
TFRVAQQVVDEVVLVNTDEICAAVKDIFEDTRSIVEPSGALSVAGMKKYI
STVHPEIDHTKNTYVPILSGANMNFDRLRFVSERAVLGEGKEVFMLVTLP
DVPGAFKKMQKIIHPRSVTEFSYRYNEHRHESSSEVPKAYIYTSFSVVDR
EKEIKQVMQQLNALGFEAVDISDNELAKSHGCYLVGGASKVPNERIISFE
FPERPGALTRFLGGLSDSWNLTLFHYHNHGADIGKVLAGISVPPRENLTF
QKFLEDLGYTYHDETDNTVYQKFLKY

*Pichia stipitis* ILV1 (Ps) amino acid sequence:

(SEQ ID NO: 26)
MFFSRSGEVEKFPNLLDADFNEDGDPDY-
IKLILTSRVYDVVERAGTPLTHAINLSHKCNSNIYLKREDLL
PVFSFKLRGAYNMISHLHSNSKMPLS-
GVIACSAGNHAQGVAYSANRLKIPSTIVMPTATPSIKYTNVSRL
GSQVVLYGDDFDSAKQECARLSSLNNLT-
DVPPFDHPYVIAGQGTIALEITRQLRLDKLNALFVPVGGGGL
IAGVAVYLKKIAPHVKIIGVETNDADA-
LYQSLKAKKSVVLDQVGMFADGTAVKVLGKETWRLCENLVDEV
VKVSTDELCAAIKDIFEDTRSITEPS-
GALSVAGLKKYIEQNPDIDHRNKFYVPILSGANMNFDRLRFVSE
RAVLGEGKEVSLVVTIPEKPGEFAK-
LQSIINPRAITEFSYRCNGADANIFVSFNVIDKKKELTPIIEDMN
NNEHGYEVVDISDNELAKTHGRYLVG-
GKSSEEVANERLYSFEFPEKPGALFNFLQALKADWNITLFHYRN
HGHDIGKVLCGFTLPEGTDDADFQSFLNELGYKFNVENDNVVYKKFLRS

*Saccharomyces cerevisiae* CHA1 amino acid sequence:

(SEQ ID NO: 27)
MSIVYNKTPLLRQFFPGKASAQFFLKYECLQPSGSFKSRGIGNLIMKSAI
RIQKDGKRSPQVFASSGGNAGFAAATACQRLSLPCTVVVPTATKKRMVDK
IRNTGAQVIVSGAYWKEADTFLKTNVMNKIDSQVIEPIYVHPFDNPDIWE
GHSSMIDEIVQDLKSQHISVNKVKGIVCSVGGGGLYNGIIQGLERYGLAD
RIPIVGVETNGCHVFNTSLKIGQPVQFKKITSIATSLGTAVISNQTFEYA
RKYNTRSVVIEDKDVIETCLKYTHQFNMVIEPACGAALHLGYNTKILENA
LGSKLAADDIVIIACGGSSNTIKDLEEALDSMRKKDTPVIEVADNFIFP
EKNIVNLKSA

*Corynebacterium glutamicum* IlvA (Cg) amino acid sequence:

(SEQ ID NO: 28)
MSETYVSEKSPGVMASGAELIRAADIQTAQARISSVIAPTPLQYCPRLSE
ETGAEIYLKREDLQDVRSYKIRGALNSGAQLTQEQRDAGIVAASAGNHAQ
GVAYVCKSLGVQGRIYVPVQTPKQKRDRIMVHGGEFVSLVVTGNNFDEAS
AAAHEDAERTGATLIEPFDARNTVIGQGTVAAEILSQLTSMGKSADHVMV
PVGGGGLLAGVVSYMADMAPRTAIVGIEPAGAASMQAALHNGGPITLETV
DPFVDGAAVKRVGDLNYTIVEKNQGRVHMMSATEGAVCTEMLDLYQNEGI
IAEPAGALSIAGLKEMSFAPGSVVVCIISGGNNDVLRYAEIAERSLVHRG
LKHYFLVNFPQKPGQLRHFLEDILGPDDDITLFEYLKRNNRETGTALVGI
HLSEASGLDSLLERMEESAIDSRRLEPGTPEYEYLT

*Escherichia coli* ilvA (Ec) amino acid sequence:

(SEQ ID NO: 29)
MADSQPLSGAPEGAEYLRAVLRAPVYEAAQVTPLQKMEKLSSRLDNVILV

KREDRQPVHSFKLRGAYAMMAGLTEEQKAHGVITASAGNHAQGVAFSSAR

LGVKALIVMPTATADIKVDAVRGFGGEVLLHGANFDEAKAKAIELSQQQG

FTWVPPFDHPMVIAGQGTLALELLQQDAHLDRVFVPVGGGGLAAGVAVLI

KQLMPQIKVIAVEAEDSACLKAALDAGHPVDLPRVGLFAEGVAVKRIGDE

TFRLCQEYLDDIITVDSDAICAAMKDLFEDVRAVAEPSGALALAGMKKYI

AQHNIRGERLAHILSGANVNFHGLRYVSERCELGEQREALLAVTIPEEKG

SFLKFCQLLGGRSVTEFNYRFADAKNACIFVGVRLSRGLEERKEILQMLN

DGGYSVVDLSDDEMAKLHVRYMVGGRPSHPLQERLYSFEFPESPGALLRF

LNTLGTHWNISLFHYRSHGTDYGRVLAAFELGDHEPDFETRLNELGYDCH

DETINPAFRFFLAG

In particular embodiments of the invention, the polypeptide catalyzing the conversion of 2-oxobutanate to 2-acetohydroxy-butyrate is derived from a yeast. An example of a suitable source for this enzyme is the genus Pichia, a preferred source is Picihia stipitis. A specific example of a suitable sequence is:

*Pichia stipitis* ILV2 (Ps) amino acid sequence:

(SEQ ID NO: 30)
MARAALSRSSGSRYAIRALSNTKLHNATMSATSRPTPSPAFNAADIRQPQ

SYPTQRKKNDFVMDDSFIGLTGGEIFHEMMLRHNVDTVFGYAGGAILPVF

DAIYNSDKFKFVLPRHEQGAGHMAEGYARATGKPGVVLVTSGPGATNVIT

PLADALMDGVPLVVFTGQVPTTAIGTDAFQEADVVGISRSCTKWNVMVKN

VAELPRRINEAFEIATSGRPGPVLVDLPKDVTAAILREAIPINSTLPSNA

LQQITKEAQNEFTMGAIARSANLLNVAKKPIIYAGAGVLNHEDGPKLLKE

LSDKANIPVTTTLQGLGAFDQRDPKSLDMLGMHGHAAANTAMQDADCIIA

LGARFDDRVTGNINKFAPEAKLAASEGRGGIIHFEISPKNINKVVEATEA

VEGDLTANLRSFIPLVKPVAERPQWLGKINEWKEKYPYAYQLETPGSLIK

PQTLIKEISEQSSTYNKEVIVTTGVGQHQMWAAQHFTWTKPRIMITSGGL

GTMGYGLPAAIGAQIGKPDAIVIDIDGDASFNMTLTELSSAVQAGAPVKV

CVLNNEEQGMVTQWQSLFYEHRYSHTHQSNPDFMKLADAMGVQGIRISTQ

EELKSGVKAFLDAKGPVLLEVIVEKKVPVLPMVPAGSALDDFILWDAETE

KQQKELRNERTGGKH

Another exemplary sequence that contemplates the use of An acetolactate synthase that has been modified to optimize cytoplasmic expression is:

*Pichia stipitis* ILV2 (Ps) Δ26 amino acid sequence:

(SEQ ID NO: 31)
MATMSATSRPTPLPAFNAADIRQPQSYPTQRKKNDFVMDDSFIGLTGGEI

FHEMMLRHNVDTVFGYAGGAILPVFDAIYNSDKFKFVLPRHEQGAGHMAE

GYARATGKPGVVLVTSGPGATNVITPLADALMDGVPLVVFTGQVPTTAIG

TDAFQEADVVGISRSCTKWNVMVKNVAELPRRINEAFEIATSGRPGPVLV

DLPKDVTAAILREAIPINSTLPSNALQQITKEAQNEFTMGAIARSANLLN

VAKKPIIYAGAGVLNHEDGPKLLKELSDKANIPVTTTLQGLGAFDQRDPK

SLDMLGMHGHAAANTAMQDADCIIALGARFDDRVTGNINKFAPEAKLAAS

EGRGGIIHFEISPKNINKVVEATEAVEGDLTANLRSFIPLVKPVAERPQW

LGKINEWKEKYPYAYQLETPGSLIKPQTLIKEISEQSSTYNKEVIVTTGV

GQHQMWAAQHFTWTKPRTMITSGGLGTMGYGLPAAIGAQIGKPDAIVIDI

DGDASFNMTLTELSSAVQAGAPVKVCVLNNEEQGMVTQWQSLFYEHRYSH

THQSNPDFMKLADAMGVQGIRISTQEELKSGVKAFLDAKGPVLLEVIVEK

KVPVLPMVPAGSALDDFILWDAETEKQQKELRNERTGGKH

Other exemplary sequences are:
*Saccharomyces cerevisiae* ILV2 amino acid sequence:

(SEQ ID NO: 32)
MIRQSTLKNFAIKRCFQHIAYRNTPAMRSVALAQRFYSSSSRYYSASPLP

ASKRPEPAPSFNVDPLEQPAEPSKLAKKLRAEPDMDTSFVGLTGGQIFNE

MMSRQNVDTVFGYPGGAILPVYDAIHNSDKFNFVLPKHEQGAGHMAEGYA

RASGKPGVVLVTSGPGATNVVTPMADAFADGIPMVVFTGQVPTSAIGTDA

FQEADVVGISRSCTKWNVMVKSVEELPLRINEAFEIATSGRPGPVLVDLP

KDVTAAILRNPIPTKTTLPSNALNQLTSRAQDEFVMQSINKAADLINLAK

KPVLYVGAGILNHADGPRLLKELSDRAQIPVTTTLQGLGSFDQEDPKSLD

MLGMHGCATANLAVQNADLIIAVGARFDDRVTGNISKFAPEARRAAAEGR

GGIIHFEVSPKNINKVVQTQIAVEGDATTNLGKMMSKIFPVKERSEWFAQ

INKWKKEYPYAYMEETPGSKIKPQTVIKKLSKVANDTGRHVIVTTGVGQH

QMWAAQHWTWRNPHTFITSGGLGTMGYGLPAAIGAQVAKPESLVIDIDGD

ASFNMTLTELSSAVQAGTPVKILILNNEEQGMVTQWQSLFYEHRYSHTHQ

LNPDFIKLAEAMGLKGLRVKKQEELDAKLKEFVSTKGPVLLEVEVDKKVP

VLPMVAGGSGLDEFINFDPEVERQQTELRHKRTGGKH

*Saccharomyces cerevisiae* ILV6 amino acid sequence:

(SEQ ID NO: 33)
MLRSLLQSGHRRVVASSCATMVRCSSSSTSALAYKQMHRHATRPPLPTLD

TPSWNANSAVSSIIYETPAPSRQPRKQHVLNCLVQNEPGVLSRVSGTLAA

RGFNIDSLVVCNTEVKDLSRMTIVLQGQDGVVEQARRQIEDLVPVYAVLD

YTNSEIIKRELVMARISLLGTEYFEDLLLHHHTSTNAGAADSQELVAEIR

EKQFHPANLPASEVLRLKHEHLNDITNLTNNFGGRVVDISETSCIVELSA

KPTRISAFLKLVEPFGVLECARSGMMALPRTPLKTSTEEAADEDEKISEI

VDISQLPPG

*Pichia stipitis* LV6 (Ps) amino acid sequence:

(SEQ ID NO: 34)
MFAKQTLRRSASSAYKQGVRNKQTSSSTSALAYKTLHRNQKRPPLPTLET

PNWSADAAVSSILYETPMPSKAPRKQHVLNCLVQNEPGVLSSVSGTLAAR

GFNIDSLVVCNTEVKDLSRMTIVLAGQDAVVEQARRQIEDLVPVYAVLDY

TNAEIIKRELLLARVSLLGPEYFQELIATHKLHISDGSAVPDLSATDSAY

HPNNLAPSEALRQKHIHLDHINTITEKFGGKIVDLSDRNVIVELSAKPSR

*Corynebacterium glutamicum* IlvB (Cg) amino acid sequence:

(SEQ ID NO: 35)
MNVAASQQPTPATVASRGRSAAPERMTGAKAIVRSLEELNADIVFGIPGG
AVLPVYDPLYSSTKVRHVLVRHEQGAGHAATGYAQVTGRVGVCIATSGPG
ATNLVTPIADANLDSVPMVAITGQVGSGLLGTDAFQEADIRGITMPVTKH
NFMVTNPNDIPQALAEAFHLAITGRPGPVLVDIPKDVQNAELDFVWPPKI
DLPGYRPVSTPHARQIEQAVKLIGEAKKPVLYVGGGVIKADAHEELRAFA
EYTGIPVVTTLMALGTFPESHELHMGMPGMHGTVSAVGALQRSDLLIAIG
SRFDDRVTGDVDTFAPDAKIIHADIDPAEIGKIKQVEVPIVGDAREVLAR
LLETTKASKAETEDISEWVDYLKGLKARFPRGYDEQPGDLLAPQFVIETL
SKEVGPDAIYCAGVGQHQMWAAQFVDFEKPRTWLNSGGLGTMGYAVPAAL
GAKAGAPDKEVWAIDGDGCFQMTNQELTTAAVEGFPIKIALINNGNLGMV
RQWQTLFYEGRYSNTKLRNQGEYMPDFVTLSEGLGCVAIRVTKAEEVLPA
IQKAREINDRPVVIDFIVGEDAQVWPMVSAGSSNSDIQYALGLRPFFDGD
ESAAEDPADIHEAVSDIDAAVESTEA

*Corynebacterium glutamicum* ilvN (Cg) amino acid sequence:

(SEQ ID NO: 36)
MANSDVTRHILSVLVQDVDGIISRVSGMFTRRAFNLVSLVSAKTETHGIN
RITVVVDADELNIEQITKQLNKLIPVLKVVRLDEETTIARAIMLVKVSAD
STNRPQIVDAANIFRARVVDVAPDSVVIESTGTPGKLRALLDVMEPFGIR
ELIQSGQIALNRGPKTMAPAKI

*Escherichia coli* ilvB (Ec) amino acid sequence:

(SEQ ID NO: 37)
MASSGTTSTRKRFTGAEFIVHFLEQQGIKIVTGIPGGSILPVYDALSQST
QIRHILARHEQGAGFIAQGMARTDGKPAVCMACSGPGATNLVTAIADARL
DSIPLICITGQVPASMIGTDAFQEVDTYGISIPITKHNYLVRHIEELPQV
MSDAFRIAQSGRPGPVWIDIPKDVQTAVFEIETQPAMAEKAAAPAFSEES
IRDAAAMINAAKRPVLYLGGGVINAPARVRELAEKAQLPTTMTLMALGML
PKAHPLSLGMLGMHGVRSTNYILQEADLLIVLGARFDDRAIGKTEQFCPN
AKIIHVDIDRAELGKIKQPHVAIQADVDDVLAQLIPLVEAQPRAEWHQLV
ADLQREFPCPIPKACDPLSHYGLINAVAACVDDNAIITTDVGQHQMWTAQ
AYPLNRPRQWLTSGGLGTMGFGLPAAIGAALANPDRKVLCFSGDGSLMMN
IQEMATASENQLDVKIILMNNEALGLVHQQQSLFYEQGVFAATYPGKINF
MQIAAGFGLETCDLNNEADPQASLQEIINRPGPALIHVRIDAEEKVYPMV
PPGAANTEMVGE

*Escherichia coli* ilvN (Ec) amino acid sequence:

(SEQ ID NO: 38)
MQNTTHDNVILELTVRNHPGVMTHVCGLFARRAFNVEGILCLPIQDSDKS
HIWLLVNDDQRLEQMISQIDKLEDVVKVQRNQSDPTMFNKIAVFFQ

*Escherichia coli* ilvG (Ec) amino acid sequence:

(SEQ ID NO: 39)
MNGAQWVVHALRAQGVNTVFGYPGGAIMPVYDALYDGGVEHLLCRHEQGA
AMAAIGYARATGKTGVCIATSGPGATNLITGLADALLDSIPVVAITGQVS
APFIGTDAFQEVDILGLSLACTKHSFLVQSLEELPRIMAEAFDVASSGRP
GPVLVDIPKDIQLASGDLEPWFTTVENEVTFPHAEVEQARQMLAKAQKPM
LYVGGGVGMAQAVSALREFLAATKMPATCTLKGLGAVEADYPYYLGMLGM
HGTKAANFAVQECDLLIAVGARFDDRVTGKLNTFAPHASVIHMDIDPAEM
NKLRQAHVALQGDLNALLPALQQPLNINDWQQYCAQLRDEHTWRYDHPGD
AIYAPLLLKQLSDRKPADCVVTTDVGQHQMWAAQHIAHTRPENFITSSGL
GTMGFGLPAAVGAQVARPNDTVVCISGDGSFMMNVQELGTVKRKQLPLKI
VLLDNQRLGMVRQWQQLFFQERYSETTLTDNPDFLMLASAFGIPGQHITR
KDQVEAALDTMLNSDGPYLLHVSIDELENVWPLVPPGASNSEMLEKLS

*Escherichia coli* ilvM (Ec) amino acid sequence:

(SEQ ID NO: 40)
MMQHQVNVSARFNPETLERVLRVVRHRGFHVCSMNMAAASDAQNINIELT
VASPRSVDLLFSQLNKLVDVAHVAICQSTTTSQQIRA

*Escherichia coli* ilvI (Ec) amino acid sequence:

(SEQ ID NO: 41)
MEMLSGAEMVVRSLIDQGVKQVFGYPGGAVLDIYDALHTVGGIDHVLVRH
EQAAVHMADGLARATGEVGVVLVTSGPGATNAITGIATAYMDSIPLVVLS
GQVATSLIGYDAFQECDMVGISRPVVKHSFLVKQTEDIPQVLKKAFWLAA
SGRPGPVVVDLPKDILNPANKLPYVWPESVSMRSYNPTTTGHKGQIKRAL
QTLVAAKKPVVYVGGGAITAGCHQQLKETVEALNLPVVCSLMGLGAFPAT
HRQALGMLGMHGTYEANMTMHNADVIFAVGVRFDDRTTNNLAKYCPNATV
LHIDIDPTSISKTVTADIPIVGDARQVLEQMLELLSQESAHQPLDEIRDW
WQQIEQWRARQCLKYDTHSEKIKPQAVIETLWRLTKGDAYVTSDVGQHQM
FAALYYPFDKPRRWINSGGLGTMGFGLPAALGVKMALPEETVVCVTGDGS
IQMNIQELSTALQYELPVLVVNLNNRYLGMVKQWQDMIYSGRHSQSYMQS
LPDFVRLAEAYGHVGIQISHPHELESKLSEALEQVRNNRLVFVDVTVDGS
EHVYPMQIRGGGMDEMWLSKTERT

*Escherichia coli* ilvIH (Ec) amino acid sequence:

(SEQ ID NO: 42)
MRRILSVLLENESGALSRVIGLFSQRGYNIESLTVAPTDDPTLSRMTIQT
VGDEKVLEQIEKQLHKLVDVLRVSELGQGAHVEREIMLVKIQASGYGRDE
VKRNTEIFRGQIIDVTPSLYTVQLAGTSGKLSAFLASIRDVAKIVEVARS
GVVGLSRGDKIMR

In particular embodiments of the invention, the polypeptide catalyzing the conversion of 2-aceto-hydroxy-butyrate to 2,3-dihydroxy-3-methylvalerate is derived from a yeast. An example of a suitable source for this enzyme is the genus *Pichia*, a preferred source is *Picihia stipitis*. A specific example of a suitable sequence is:

*Pichia stipitis* ILV5 (Ps) amino acid sequence:

(SEQ ID NO: 43)
MSFRRSSLRMAKMASAAASKQIASKRAMSALASAAKPVVSKQSMAPLAVR

GIKTINFGGTEEVVHERADWPREKLLEYFKNDTLALIGYGSQGYGQGLNL

RDNGLNVIIGVRKNGASWKAAIEDGWVPGENLFDVNEAISKGTYIMNLLS

DAAQSETWASIKPQLTEGKTLYFSHGFSPVFKELTHVEPPTNIDVILAAP

KGSGRTVRSLFKEGRGINSSYAVWNDVTGKAEEKAIALAVAIGSGYVYQT

TFEREVNSDLYGERGCLMGGIHGMFLAQYEVLRENGHTPSEAFNETVEEA

TQSLYPLIGKYGMDYMYDACSTTARRGALDWYPRFKDALKPVFNDLYESV

KNGSETQRSLDFNSQPDYREKLEEELQVIRNMEIWRVGKEVRKLRPENQ

Another exemplary sequence that contemplates the use of a ketol-acid reductoismorease that has been modified to optimize cytoplasmic expression is:

*Pichia stipitis* ILV5 (Ps) Δ40 amino acid sequence:

(SEQ ID NO: 44)
MKQSMAPLAVRGIKTINFGGTEEVVHERADWPREKLLEYFKNDTLALIGY

GSQGYGQGLNLRDNGLNVIIGVRKNGASWKAAIEDGWVPGENLFDVNEAI

SKGTYIMNLLSDAAQSETWASIKPQLTEGKTLYFSHGFSPVFKELTHVEP

PTNIDVILAAPKGSGRTVRSLFKEGRGINSSYAVWNDVTGKAEEKAIALA

VAIGSGYVYQTTFEREVNSDLYGERGCLMGGIHGMFLAQYEVLRENGHTP

SEAFNETVEEATQSLYPLIGKYGMDYMYDACSTTARRGALDWYPRFKDAL

KPVFNDLYESVKNGSETQRSLDFNSQPDYREKLEEELQVIRNMEIWRVGK

EVRKLRPENQ

Other exemplary sequences are:
*Saccharomyces cerevisiae* ILV5 amino acid sequence:

(SEQ ID NO: 45)
MLRTQAARLICNSRVITAKRTFALATRAAAYSRPAARFVKPMITTRGLKQ

INFGGTVETVYERADWPREKLLDYFKNDTFALIGYGSQGYGQGLNLRDNG

LNVIIGVRKDGASWKAAIEDGWVPGKNLFTVEDAIKRGSYVMNLLSDAAQ

SETWPAIKPLLTKGKTLYFSHGFSPVFKDLTHVEPPKDLDVILVAPKGSG

RTVRSLFKEGRGINSSYAVWNDVTGKAHEKAQALAVAIGSGYVYQTTFER

EVNSDLYGERGCLMGGIHGMFLAQYDVLRENGHSPSEAFNETVEEATQSL

YPLIGKYGMDYMYDACSTTARRGALDWYPIFKNALKPVFQDLYESTKNGT

ETKRSLEFNSQPDYREKLEKELDTIRNMEIWKVGKEVRKLRPENQ

*Corynebacterium glutamicum* IlvC (cg) amino acid sequence:

(SEQ ID NO: 46)
MAIELLYDADADLSLIQGRKVAIVGYGSQSHAHSQNLRDSGVEVVIGLRE

GSKSAEKAKEAGFEVKTTAEAAAWADVIMLLAPDTSQAEIFTNDIEPNLN

AGDALLFGHGLNIHFDLIKPADDIIVGMVAPKGPGHLVRRQFVDGKGVPC

LIAVDQDPTGTAQALTLSYAAAIGGARAGVIPTTFEAETVTDLFGEQAVL

CGGTEELVKVGFEVLTEAGYEPEMAYFEVLHELKLIVDLMFEGGISNMNY

SVSDTAEFGGYLSGPRVIDADTKSRMKDILTDIQDGTFTKRLIANVENGN

TELEGLRASYNNHPIEETGAKLRDLMSWVKVDARAETA

*Escherichia coli* ilvC (Ec) amino acid sequence:

(SEQ ID NO: 47)
MANYFNTLNLRQQLAQLGKCRFMGRDEFADGASYLQGKKVVIVGCGAQGL

NQGLNMRDSGLDISYALRKEAIAEKRASWRKATENGFKVGTYEELIPQAD

LVINLTPDKQHSDVVRTVQPLMKDGAALGYSHGFNIVEVGEQIRKDITVV

MVAPKCPGTEVREEYKRGFGVPTLIAVHPENDPKGEGMAIAKAWAAATGG

HRAGVLESSFVAEVKSDLMGEQTILCGMLQAGSLLCFDKLVEEGTDPAYA

EKLIQFGWETITEALKQGGITLMMDRLSNPAKLRAYALSEQLKEIMAPLF

QKHMDDIISGEFSSGMMADWANDDKKLLTWREETGKTAFETAPQYEGKIG

EQEYFDKGVLMIAMVKAGVELAFETMVDSGIIEESAYYESLHELPLIANT

IARKRLYEMNVVISDTAEYGNYLFSYACVPLLKPFMAELQPGDLGKAIPE

GAVDNGQLRDVNEAIRSHAIEQVGKKLRGYMTDMKRIAVAG

In particular embodiments of the invention, the polypeptide catalyzing the conversion of 2,3-dihydroxy-3-methylvalerate to 2-keto-3-methylvalerate is derived from a yeast. An example of a suitable source for this enzyme is the genus *Pichia*, a preferred source is *Picihia stipitis*. A specific example of a suitable sequence is:

*Pichia stipitis* ILV3 (Ps) amino acid sequence:

(SEQ ID NO: 48)
MSFLFKAAAARRVASKSPAAVARSFSVSATQCEKKLNKYSSIVTGDPSQGASQAMLYATGFDDADFNRAQ

IGVGSVWWSGNPCNMHLMELNNKCTESVNRAGLKGMQFNSIGISDGITNGTEGMRYSLQSREIIADSFES

MMLGQLYDGNIAIPSCDKNMPGVLIAMARHNRPSIMVYGGTILPSQTTCSTNNPAIADKIDIISAFQSYS

QYLIKSITNEERKDIVRHACPSPSACSSMYTANTMASAAECLSMSLPYSSSAPAVSKEKDAECANISQAI

```
KHLLEIDLKPRDILTKKSFENAIAYIIATSSSTNAVLHLIAIASSADIDLTVDDFQRISDSTPLLADFKP

SSQFVMADLQKYSSTPAVMKFLMNESFIDSDQYTVTSKTIKENLASVKDLPADQPIIRPVSNPLKTSSHL

QILKSSLAPSSAVSKITSKESTYFKSKARVFDDESDFIVALEKOFIKKSEKTVCVIRYESPKSSPSMPEM

LKPSSALMSYSLSKDVALLTDSRFSSSSHSFLISHIVPEAAESSPISLVYDSDEIVIDAENNKIDLLVDE

AVLAERRKLWTAPEPRYTRSTLAKYARLVSDASASCVTDLPIKN
```

Another exemplary sequence that contemplates the use of a dihydroxyacid dehydratase that has been modified to optimize cytoplasmic expression is:
*Pichia stipitis* ILV3 (Ps)Δ34 amino acid sequence:

```
                                                          (SEQ ID NO: 49)
MKKLNKYSSIVTGDPSQGASQAMLYATGFDDADFNRAQIGVGSVWWSGNPCNMHLMELNNKCTESVNRAGLKGMQFN

SIGISDGITNGTEGMRYSLQSREIIADSFESMMLGQLYDGNIAIPSCDKNMPGVLIAMARHNRPSIMVYGGTILPGQ

TTCGTNNPAIADKIDIISAFQSYGQYLTKSITNEERKDIVRHACPGPGACGGMYTANTMASAAECLGMSLPYSSSAP

AVSKEKDAECANIGQAIKHLLEIDLKPRDILTKKSFENAIAYIIATGGSTNAVLHLIAIASSADIDLTVDDFQRISD

STPLLADFKPSGQFVMADLQKYGGTPAVMKFLMNEGFIDGDQYTVTGKTIKENLASVKDLPADQPIIRPVSNPLKTS

GHLQILKGSLAPGSAVGKITGKEGTYFKGKARVFDDEGDFIVALEKGEIKKGEKTVCVIRYEGPKGGPGMPEMLKPS

SALMSYGLGKDVALLTDGRFSGGSHSFLIGHIVPEAAEGGPIGLVYDGDEIVIDAENNKIDLLVDEAVLAERRKLWT

APEPRYTRGTLAKYARLVSDASAGCVTDLPIKN
```

Other exemplary sequences are:
*Saccharomyces cerevisiae* ILV3 amino acid sequence:

```
                                                          (SEQ ID NO: 50)
MGLLTKVATSRQFSTTRCVAKKLNKYSYIITEPKGQGASQAMLYATGFKKEDFKKPQVGVGSCWWSGNPC

NMHLLDLNNRCSQSIEKAGLKAMQFNTIGVSDGISMGTKGMRYSLQSREIIADSFETIMMAQHYDANIAI

PSCDKNMPGVMMAMGRHNRPSIMVYGGTILPGHPTCGSSKISKNIDIVSAFQSYGEYISKQFTEEEREDV

VEHACPGPGSCGGMYTANTMASAAEVLGLTIPNSSSFPAVSKEKLAECDNIGEYIKKTMELGILPRDILT

KEAFENAITYVVATGGSTNAVLHLVAVAHSAGVKLSPDDFQRISDTTPLIGDFKPSGKYVMADLINVGGT

QSVIKYLYENNMLHGNTMTVTGDTLAERAKKAPSLPEGQEIIKPLSHPIKANGHLQILYGSLAPGGAVGK

ITGKEGTYFKGRARVFEEEGAFIEALERGEIKKGEKTVVVIRYEGPRGAPGMPEMLKPSSALMGYGLGKD

VALLTDGRFSGGSHGFLIGHIVPEAAEGGPIGLVRDGDEIIIDADNNKIDLLVSDKEMAQRKQSWVAPPP

RYTRGTLSKYAKLVSNASNGCVLDA
```

*Corynebacterium glutamicum* IlvD (Cg) amino acid sequence:

```
                                                          (SEQ ID NO: 51)
MIPLRSKVTTVGRNAAGARALWRATGTKENEFGKPIVAIVNSYTQFVPGHVHLKNVGDIVADAVRKAGGV

PKEFNTIAVDDGIAMGHGGMLYSLPSREIIADSVEYMVNAHTADAMVCISNCDKITPGMLNAAMRLNIPV

VFVSGGPMEAGKAVVVDSVAHAPTDLITAISASASDAVDDAGLAAVEASACPTCGSCSGMFTANSMNCLT

EALGLSLPGNGSTLATHAARRALFEKAGETVVELCRRYYGEEDESVLPRGIATKKAFENAMALDMAMGGS

TNTILHILAAAQEGEVDFDLADIDELSKNVPCLSKVAPNSDYHMEDVHRAGGIPALLGELNRGGLLNKDV

HSVHSNDLEGWLDDWDIRSGKTTEVATELFHAAPGGIRTTEAFSTENRWDELDTDAAKSCIRDVEHAYTA

DGGLVVLRGNISPDGAVIKSAGIEEELWNFTGPARVVESQEEAVSVILTKTIQAGEVLVVRYEGPSGGPG
```

```
MQEMLHPTAFLKGSGLGKKCALITDGRFSGGSSGLSIGHVSPEAAHGGVIGLIENGDIVSIDVHNRKLEV

QVSDEELQRRRDAMNASEKPWQPVNRNRVVTKALRAYAKMATSADKGAVRQVD
```

*Escherichia coli* ilvD (Ec) amino acid sequence:

(SEQ ID NO: 52)
```
MPKYRSATTTHGRNMAGARALWRATGMTDADFGKPIIAVVNSFTQFVPGHVHLRDLGKLVAEQIEAAGGV

AKEFNTIAVDDGIAMGHGGMLYSLPSRELIADSVEYMVNAHCADAMVCISNCDKITPGMLMASLRLNIPV

IFVSGGPMEAGKTKLSDQIIKLDLVDAMIQGADPKVSDSQSDQVERSACPTCGSCSGMFTANSMNCLTEA

LGLSQPGNGSLLATHADRKQLFLNAGKRIVELTKRYYEQNDESALPRNIASKAAFENAMTLDIAMGGSTN

TVLHLLAAAQEAEIDFTMSDIDKLSRKVPQLCKVAPSTQKYHMEDVHRAGGVIGILGELDRAGLLNRDVK

NVLGLTLPQTLEQYDVMLTQDDAVKNMFRAGPAGIRTTQAFSQDCRWDTLDDDRANSCIRSLEHAYSKDG

GLAVLYGNFAENGCIVKTAGVDDSILKFTGPAKVYESQDDAVEAILGGKVVASDVVVIRYEGPKGGPGMQ

EMLYPTSFLKSMGLGKACALITDGRFSGGTSGLSIGHVSPEAASGGSIGLIEDGDLIAIDIPNRGIQLQV

SDAELAARREAQDARGDKAWTPKNRERQVSFALRAYASLATSADKGAVRDKSKLGG
```

*Saccharomyces cerevisiae* PDC1 amino acid sequence:

A third aspect of the invention provides a recombinant microorganism comprising at least one DNA molecule, wherein said at least one DNA molecule encodes (i) a polypeptide that catalyzes a 2-keto-3-methyl-valerate to 2-methylbutanal conversion, and (ii) a polypeptide that catalyzes a 2-methylbutanal to 2-methylbutanol conversion, wherein said recombinant microorganism produces 2-methylbutanol.

In particular embodiments of the invention, the polypeptide catalyzing the conversion of 2-keto-3-methylvalerate to 2-methylbutanal is derived from a yeast. An example of a suitable source for this enzyme is the genus *Pichia*, a preferred source is *Pichia stipitis*. A specific example of a suitable sequence is:

*Pichia stipitis* PDC 3-6 (Ps) amino acid sequence:

(SEQ ID NO: 53)
```
MTPVQETIRLPGTSSPTVPENVTLGEYLFLRISQANPKLRSIFGIPGDFNVDLLEHLYSPVVAGRDIKFI

GLCNELNGAYTADGYSRAIGGLSTFISTFGVGELSAINGIAGSFAEFSPVLHIVGTTSLPQRDHAINGSD

VRNHHHLIQNKNPLCQPNHDVYKKMIEPISVIQESLDSDLQRNMEKIDRVLVKILQESRPGYLFIPCDIT

NLIVPSYRLYETPLPLEIQLTTSGVEVLEDVVDAILFRLYKSKNPSLLSDCLTTRFNLQDKLNTLVAKLP

SNFVKLFSTNMARNIDESLSNFVGLYFGIGSSSKEVSRQLERNTDFLINLGYFNAETTTAGYSNDFSNIE

EYIEINPDYIKVNEHIINIKNPESGKRLFSMGQLLDALLFKLDLNKIENINNNNISYKFFPPTLYEQDNN

TDYIPQTKLVDYLNENLQPGDLLVMDTMSFCFALPDIMLPQGVQLLTQNYYGSIGYALPSTFGATMAVND

LGSDRRIILIEGDGAAQMTIQELSSFLKYKEFLPNMPKIFLINNDGYTVERMIKGPTRSYNDINGEWSWT

QLLGVFGDKEQKYHSTALLRNVNEFNKYFEFQRQTDNSKLEFIELIAGKYDCPLRFSEMFCKK
```

Other exemplary sequences are:

(SEQ ID NO: 54)
```
MSEITLGKYLFERLKQVNVNTVFGLPGDFNLSLLDKIYEVEGMRWAGNANELNAAYAADGYARIKGMSCI

ITTFGVGELSALNGIAGSYAEHVGVLHVVGVPSISAQAKQLLLHHTLGNGDFTVFHRMSANISETTAMIT

DIATAPAEIDRCIRTTYVTQRPVYLGLPANLVDLNVPAKLLQTPIDMSLKPNDAESEKEVIDTILALVKD
```

-continued

AKNPVILADACCSRHDVKAETKKLIDLTQFPAFVTPMGKGSIDEQHPRYGGVYVGTLSKPEVKEAVESAD

LILSVGALLSDFNTGSFSYSYKTKNIVEFHSDHMKIRNATFPGVQMKFVLQKLLTTIADAAKGYKPVAVP

ARTPANAAVPASTPLKQEWMWNQLGNFLQEGDVVIAETGTSAFGINQTTFPNNTYGISQVLWGSIGFITG

ATLGAAFAAEEIDPKKRVILFIGDGSLQLTVQEISTMIRWGLKPYLFVLNNDGYTIEKLIHSPKAQYNEI

QGWDHLSLLPTFGAKDYETHRVATTGEWDKLTQDKSFNDNSKIRMIEIMLPVFDAPQNLVEQAKLTAATN

AKQ

*Pichia stipitis* PDC1 (Ps) amino acid sequence:

(SEQ ID NO: 55)

MAEVSLGRYLFERLYQLQVQTIFGVPGDFNLSLLDKIYEVEDAHGKNSFRWAGNANELNASYAADGYSRV

KRLGCLVTTFGVGELSALNGIAGSYAEHVGLLHVVGVPSISSQAKQLLLHHTLGNGDFTVFHRMSNNISQ

TTAFISDINSAPAEIDRCIREAYVKQRPVYIGLPANLVDLNVPASLLESPINLSLEKNDPEAQDEVIDSV

LDLIKKSLNPIILVDACASRHDCKAEVTQLIEQTQFPVFVTPMGKGTVDEGGVDGELLEDDPHLIAKVAA

RLSAGKNAASRFGGVYVGTLSKPEVKDAVESADLILSVGALLSDFNTGSFSYSYRTKNIVEFHSDYTKIR

QATFPGVQMKEALQELNKKVSSAASHYEVKPVPKIKLANTPATREVKLTQEWLWTRVSSWFREGDIIITE

TGTSSFGIVQSRFPNNTIGISQVLWGSIGFSVGATLGAAMAAQELDPNKRTILFVGDGSLQLTVQEISTM

IRWGTTPYLFVLNNDGYTIERLIHGVNASYNDIQPWQNLEILPTFSAKNYDAVRISNIGEAEDILKDKEF

GKNSKIRLIEVMLPRLDAPSNLAKQAAITAATNAEA

*Saccharomyces cerevisiae* PDC5 amino acid sequence:

(SEQ ID NO: 56)

MSEITLGKYLFERLSQVNCNTVFGLPGDFNLSLLDKLYEVKGMRWAGNANELNAAYAADGYARIKGMSCI

ITTFGVGELSALNGIAGSYAEHVGVLHVVGVPSISSQAKQLLLHHTLGNGDFTVFHRMSANISETTAMIT

DIANAPAEIDRCIRTTYTTQRPVYLGLPANLVDLNVPAKLLETPIDLSLKPNDAEAEAEVVRTVVELIKD

AKNPVILADACASRHDVKAETKKLMDLTQFPVYVTPMGKGAIDEQHPRYGGVYVGTLSRPEVKKAVESAD

LILSIGALLSDFNTGSFSYSYKTKNIVEFHSDHIKIRNATFPGVQMKFALQKLLDAIPEVVKDYKPVAVP

ARVPITKSTPANTPMKQEWMWNHLGNFLREGDIVIAETGTSAFGINQTTFPTDVYAIVQVLWGSIGFIVG

ALLGATMAAEELDPKKRVILFIGDGSLQLTVQEISTMIRWGLKPYIFVLNNNGYTIEKLIHGPHAEYNEI

QGWDHLALLPTFGARNYETHRVATTGEWEKLTQDKDFQDNSKIRMIEVMLPVFDAPQNLVKQAQLTAATN

AKQ

*Saccharomyces cerevisiae* PDC6 amino acid sequence:

(SEQ ID NO: 57)

MSEITLGKYLFERLKQVNVNTIFGLPGDFNLSLLDKIYEVDGLRWAGNANELNAAYAADGYARIKGLSVL

VTTFGVGELSALNGIAGSYAEHVGVLHVVGVPSISAQAKQLLLHHTLGNGDFTVFHRMSANISETTSMIT

DIATAPSEIDRLIRTTFITQRPSYLGLPANLVDLKVPGSLLEKPIDLSLKPNDPEAEKEVIDTVLELIQN

SKNPVILSDACASRHNVKKETQKLIDLTQFPAFVTPLGKGSIDEQHPRYGGVYVGTLSKQDVKQAVESAD

LILSVGALLSDFNTGSFSYSYKTKNVVEFHSDYVKVKNATFLGVQMKFALQNLLKVIPDVVKGYKSVPVP

TKTPANKGVPASTPLKQEWLWNELSKFLQEGDVIISETGTSAFGINQTIFPKDAYGISQVLWGSIGFTTG

ATLGAAFAAEEIDPNKRVILFIGDGSLQLTVQEISTMIRWGLKPYLFVLNNDGYTIEKLIHGPHAEYNEI

QTWDHLALLPAFGAKKYENHKIATTGEWDALTTDSEFQKNSVIRLIELKLPVFDAPESLIKQAQLTAATN

AKQ

*Saccharomyces cerevisiae* THI3 amino acid sequence:

```
                                                          (SEQ ID NO: 58)
MNSSYTQRYALPKCIAISDYLFHRLNQLNIHTIFGLSGEFSMPLLDKLYNIPNLRWAGNSNELNAAYAAD

GYSRLKGLGCLITTFGVGELSAINGVAGSYAEHVGILHIVGMPPTSAQTKQLLLHHTLGNGDFTVFHRIA

SDVACYTTLIIDSELCADEVDKCIKKAWIEQRPVYMGMPVNQVNLPIESARLNTPLDLQLHKNDPDVEKE

VISRILSFIYKSQNPAIIVDACTSRQNLIEETKELCNRLKFPVFVTPMGKTVNETDPQFGGVFTGSISA

PEVREVVDFADFIIVIGCMLSEFSTSTFHFQYKTKNCALLYSTSVKLKNATYPDLSIKLLLQKILANLDE

SKLSYQPSEQPSMMVPRPYPAGNVLLRQEWVWNEISHWFQPGDIIITETGASAFGVNQTRFPVNTLGISQ

ALWGSVGYTMGACLGAEFAVQEINKDKFPATKHRVILFMGDGAFQLTVQELSTIVKWGLTPYIFVMNNQG

YSVDRFLHHRSDASYYDIQPWNYLGLLRVFGCTNYETKKIITVGEFRSMISDPNFATNDKIRMIEIMLPP

RDVPQALLDRWVVEKEQSKQVQEENENSSAVNTPTPEFQPLLKKNQVGY
```

*Saccharomyces cerevisiae* ARO10 amino acid sequence:

```
                                                          (SEQ ID NO: 59)
MAPVTIEKFVNQEERHLVSNRSATIPFGEYIFKRLLSIDTKSVFGVPGDFNLSLLEYLYSPSVESAGLRW

VGTCNELNAAYAADGYSRYSNKIGCLITTYGVGELSALNGIAGSFAENVKVLHIVGVAKSIDSRSSNFSD

RNLHHLVPQLHDSNFKGPNHKVYHDMVKDRVACSVAYLEDIETACDQVDNVIRDIYKYSKPGYIFVPADF

ADMSVTCDNLVNVPRISQQDCIVYPSENQLSDIINKITSWIYSSKTPAILSDVLTDRYSVSNFLNKLICK

TSIWNFSTVMSKSVIDESNPTYMSQYNSKESLKQVYEHFELCDLVLHFSVDINEINNSHYTFTYKPNAKI

IQFHPNYIRLVDTRQSNEQMFKSINFAPILKELYKRIDVSKLSLQYDSNVTQYTNETMRLEDPTNSQSSI

ITQVHLQKTMPKFLNPSDVVVCETSSFQFSVRDFAFPSQLKYISQSFFLSISMALPAALSVSIAMQDHSN

AHINSSNVKEDYKPRLILFESDSAAQMTIQELSTILKCNIPLEVIIWNNNSYTIERAIMSPTRSYNDVMS

WKWTKLFEAFSDFDSKYTNSTLIQCPSKLALKLEELKNSNKRSSIELLEVKLSELDFPEQLKCMVEAAAL

KRNKK
```

*Mycobacterium* Kdc (Mt) amino acid sequence:

```
                                                          (SEQ ID NO: 60)
MTPQKSDACSDPVYTVGDYLLDRLAELGVSEIFGVPGDYNLQFLDHIVAHPTIRWVGSANELNAGYAADG

YGRLRGMSAVVTTFGVGELSVTNAIAGSYAEHVPVVHIVGGPTKDAQGTRRALHHSLGDGDFEHFLRISR

EITCAQANLMPATAGREIDRVLSEVREQKRPGYILLSSDVARFPTEPPAAPLPRYPGGTSPRALSLFTKA

AIELIADHQLTVLADLLVHRLQAVKELEALLAADVVPHATLMWGKSLLDESSPNFLGIYAGAASAERVRA

AIEGAPVLVTAGVVFTDMVSGFFSQRIDPARTIDIGQYQSSVADQVFAPLEMSAALQALATILTGRGISS

PPVVPPPAEPPPAMPARDEPLTQQMVWDRVCSALTPGNVVLADQGTSFYGMADHRLPQGVTFIGQPLWGS

IGYTLPAAVGAAVAHPDRRTVLLIGDGAAQLTVQELGTFSREGLSPVIVVVNNDGYTVERAIHGETAPYN

DIVSWNWTELPSALGVTNHLAFRAQTYGQLDDALTVAAARRDRMVLVEVVLPRLEIPRLLGQLVGSMAPQ
```

*Lactococcus lactis* KdcA (Ll) amino acid sequence:

```
                                                          (SEQ ID NO: 61)
            MYTVGDYLLDRLHELGIEEIFGVPGDYNLQFLDQIISREDMKWIGNANELNASYMADGYARTKKAAAFLTTFGVGEL

SAINGLAGSYAENLPVVEIVGSPTSKVQNDGKFVHHTLADGDFKHFMKMHEPVTAARTLLTAENATYEIDRVLSQLL

KERKPVYINLPVDVAAAKAEKPALSLEKESSTTNTTEQVILSKIEESLKNAQKPVVIAGHEVISFGLEKTVTQFVSE

TKLPITTLNFGKSAVDESLPSFLGIYNGKLSEISLKNFVESADFILMLGVKLTDSSTGAFTHHLDENKMISLNIDEG

IIFNKVVEDFDFRAVVSSLSELKGIEYEGQYIDKQYEEFIPSSAPLSQDRLWQAVESLTQSNETIVAEQGTSFFGAS
```

-continued

```
TIFLKSNSRFIGQPLWGSIGYTFPAALGSQIADKESRHLLFIGDGSLQLTVQELGLSIREKLNPICFIINNDGYTVE
REIHGPTQSYNDIPMWNYSKLPETFGATEDRVVSKIVRTENEFVSVMKEAQADVNRMYWIELVLEKEDAPKLLKKMG
KLFAEQNK
```

*Lactococcus lactis* KdcA-S286Y (Ll) amino acid sequence:

(SEQ ID NO: 62)
```
MYTVGDYLLDRLHELGIEEIFGVPGDYNLQFLDQIISREDMKWIGNANELNASYMADGYARTKKAAAFLTTFGVGEL
SAINGLAGSYAENLPVVEIVGSPTSKVQNDGKFVHHTLADGDFKHFMKMHEPVTAARTLLTAENATYEIDRVLSQLL
KERKPVYINLPVDVAAAKAEKPALSLEKESSTTNTTEQVILSKIEESLKNAQKPVVIAGHEVISFGLEKTVTQFVSE
TKLPITTLNFGKSAVDESLPSFLGIYNGKLSEISLKNFVESADFILMLGVKLTDYSTGAFTHHLDENKMISLNIDEG
IIFNKVVEDFDFRAVVSSLSELKGIEYEGQYIDKQYEEFIPSSAPLSQDRLWQAVESLTQSNETIVAEQGTSFFGAS
TIFLKSNSRFIGQPLWGSIGYTFPAALGSQIADKESRHLLFIGDGSLQLTVQELGLSIREKLNPICFIINNDGYTVE
REIHGPTQSYNDIPMWNYSKLPETFGATEDRVVSKIVRTENEFVSVMKEAQADVNRMYWIELVLEKEDAPKLLKKMG
KLFAEQNK
```

*Lactococcus lactis* KdcA-F381W (Ll) amino acid sequence:

(SEQ ID NO: 63)
```
MYTVGDYLLDRLHELGIEEIFGVPGDYNLQFLDQIISREDMKWIGNANELNASYMADGYARTKKAAAFLTTFGVGEL
SAINGLAGSYAENLPVVEIVGSPTSKVQNDGKFVHHTLADGDFKHFMKMHEPVTAARTLLTAENATYEIDRVLSQLL
KERKPVYINLPVDVAAAKAEKPALSLEKESSTTNTTEQVILSKIEESLKNAQKPVVIAGHEVISFGLEKTVTQFVSE
TKLPITTLNFGKSAVDESLPSFLGIYNGKLSEISLKNFVESADFILMLGVKLTDSSTGAFTHHLDENKMISLNIDEG
IIFNKVVEDFDFRAVVSSLSELKGIEYEGQYIDKQYEEFIPSSAPLSQDRLWQAVESLTQSNETIVAEQGTSWFGAS
TIFLKSNSRFIGQPLWGSIGYTFPAALGSQIADKESRHLLFIGDGSLQLTVQELGLSIREKLNPICFIINNDGYTVE
REIHGPTQSYNDIPMWNYSKLPETFGATEDRVVSKIVRTENEFVSVMKEAQADVNRMYWIELVLEKEDAPKLLKKMG
KLFAEQNK
```

*Lactococcus lactis* KdcAS286Y, F381W (Ll) amino acid sequence:

(SEQ ID NO: 64)
```
MYTVGDYLLDRLHELGIEEIFGVPGDYNLQFLDQIISREDMKWIGNANELNASYMADGYARTKKAAAFLTTFGVGEL
SAINGLAGSYAENLPVVEIVGSPTSKVQNDGKFVHHTLADGDFKHFMKMHEPVTAARTLLTAENATYEIDRVLSQLL
KERKPVYINLPVDVAAAKAEKPALSLEKESSTTNTTEQVILSKIEESLKNAQKPVVIAGHEVISFGLEKTVTQFVSE
TKLPITTLNFGKSAVDESLPSFLGIYNGKLSEISLKNFVESADFILMLGVKLTDYSTGAFTHHLDENKMISLNIDEG
IIFNKVVEDFDFRAVVSSLSELKGIEYEGQYIDKQYEEFIPSSAPLSQDRLWQAVESLTQSNETIVAEQGTSWFGAS
TIFLKSNSRFIGQPLWGSIGYTFPAALGSQIADKESRHLLFIGDGSLQLTVQELGLSIREKLNPICFIINNDGYTVE
REIHGPTQSYNDIPMWNYSKLPETFGATEDRVVSKIVRTENEFVSVMKEAQADVNRMYWIELVLEKEDAPKLLKKMG
KLFAEQNK
```

*Pichia stipitis* PDC2 (Ps) amino acid sequence:

(SEQ ID NO: 65)
```
MVSTYPESEVTLGRYLFERLHQLKVDTIFGLPGDFNLSLLDKVYEVPDMRWAGNANELNAAYAADGYSRI
```

-continued

```
KGLSCLVTTFGVGELSALNGVGGAYAEHVGLLHVVGVPSISSQAKQLLLHHTLGNGDFTVFHRMSNSISQ

TTAFLSDISIAPGQIDRCIREAYVHQRPVYVGLPANMVDLKVPSSLLETPIDLKLKQNDPEAQEEVVETV

LKLVSQATNPIILVDACALRHNCKEEVKQLVDATNFQVFTTPMGKSGISESHPRFGGVYVGTMSSPQVKK

AVENADLILSVGSLLSDFNTGSFSYSYKTKNVVEFHSDYMKIRQATFPGVQMKEALQQLIKRVSSYINPS

YIPTRVPKRKQPLKAPSEAPLTQEYLWSKVSGWFREGDIIVTETGTSAFGIIQSHFPSNTIGISQVLWGS

IGFTVGATVGAAMAAQEIDPSRRVILFVGDGSLQLTVQEISTLCKWDCNNTYLYVLNNDGYTIERLIHGK

SASYNDIQPWNHLSLLRLFNAKKYQNVRVSTAGELDSLFSDKKFASPDRIRMIEVMLSRLDAPANLVAQA

KLSERVNLEN
```

In particular embodiments of the invention, polypeptide catalyzing the conversion of 2-methylbutanal to 2-methylbutanol is derived from a yeast. An example of a suitable source for this enzyme is the genus *Saccharomyces*, a preferred source is *Saccharomyces cerevisiae*. A specific example of a suitable sequence is:

*Saccharomyces cerevisiae* ADH6 amino acid sequence:

```
                                                        (SEQ ID NO: 66)
MSYPEKFEGIAIQSHEDWKNPKKTKYDPKPFYDHDIDIKIEACGVCGSDIHCAAGHWGNMKMPLVVGHEI

VGKVVKLGPKSNSGLKVGQRVGVGAQVFSCLECDRCKNDNEPYCTKFVTTYSQPYEDGYVSQGGYANYVR

VHEHFVVPIPENIPSHLAAPLLCGGLTVYSPLVRNGCGPGKKVGIVGLGGIGSMGTLISKAMGAETYVIS

RSSRKREDAMKMGADHYIATLEEGDWGEKYFDTFDLIVVCASSLTDIDFNIMPKAMKVGGRIVSISIPEQ

HEMLSLKPYGLKAVSISYSALGSIKELNQLLKLVSEKDIKIWVETLPVGEAGVHEAFERMEKGDVRYRFT

LVGYDKEFSD
```

Other exemplary sequences are:
*Saccharomyces cerevisiae* ADH1 amino acid sequence:

```
                                                        (SEQ ID NO: 67)
MSIPETQKGVIFYESHGKLEYKDIPVPKPKANELLINVKYSGVCHTDLHAWHGDWPLPVKLPLVGGHEGA

GVVVGMGENVKGWKIGDYAGIKWLNGSCMACEYCELGNESNCPHADLSGYTHDGSFQQYATADAVQAAHI

PQGTDLAQVAPILCAGITVYKALKSANLMAGHWVAISGAAGGLGSLAVQYAKAMGYRVLGIDGGEGKEEL

FRSIGGEVFIDFTKEKDIVGAVLKATDGGAHGVINVSVSEAAIEASTRYVRANGTTVLVGMPAGAKCCSD

VFNQVVKSISIVGSYVGNRADTREALDFFARGLVKSPIKVVGLSTLPEIYEKMEKGQIVGRYVVDTSK
```

*Saccharomyces cerevisiae* ADH2 amino acid sequence:

```
                                                        (SEQ ID NO: 68)
MSIPETQKAIIFYESNGKLEHKDIPVPKPKPNELLINVKYSGVCHTDLHAWHGDWPLPTKLPLVGGHEGA

GVVVGMGENVKGWKIGDYAGIKWLNGSCMACEYCELGNESNCPHADLSGYTHDGSFQEYATADAVQAAHI

PQGTDLAEVAPILCAGITVYKALKSANLRAGHWAAISGAAGGLGSLAVQYAKAMGYRVLGIDGGPGKEEL

FTSLGGEVFIDFTKEKDIVSAVVKATNGGAHGIINVSVSEAAIEASTRYCRANGTVVLVGLPAGAKCSSD

VFNHVVKSISIVGSYVGNRADTREALDFFARGLVKSPIKVVGLSSLPEIYEKMEKGQIAGRYVVDTSK
```

*Saccharomyces cerevisiae* ADH3 amino acid sequence:

```
                                                        (SEQ ID NO: 69)
MLRTSTLFTRRVQPSLFSRNILRLQSTAAIPKTQKGVIFYENKGKLHYKDIPVPEPKPNEILINVKYSGV

CHTDLHAWHGDWPLPVKLPLVGGHEGAGVVVKLGSNVKGWKVGDLAGIKWLNGSCMTCEFCESGHESNCP
```

-continued

```
DADLSGYTHDGSFQQFATADAIQAAKIQQGTDLAEVAPILCAGVTVYKALKEADLKAGDWVAISGAAGGL

GSLAVQYATAMGYRVLGIDAGEEKEKLFKKLGGEVFIDFTKTKNMVSDIQEATKGGPHGVINVSVSEAAI

SLSTEYVRPCGTVVLVGLPANAYVKSEVFSHVVKSINIKGSYVGNRADTREALDFFSRGLIKSPIKIVGL

SELPKVYDLMEKGKILGRYVVDTSK
```

*Pichia stipitis* ADH3 (Ps) amino acid sequence:

(SEQ ID NO: 70)
```
MSKSTSTTVPAKFSGFAVDKPENWNKAKLVQYDPKPFKPYDITIKVICCGVCGSDCHTVLGSWGPLNRDD

LVVSHEIVGEVIEIGSEVTNHKLGDIVAVGAQSDSCGECELCENNNEQYCRDGIAATYNFPNKRCGGYVT

QGGYASHLRVNSYFAASVPKNLDVHYAAPLLCGGLTVYSPIVRHGGYDLKDKRIGIVGIGGLGSMAIQIA

NALGAKEVVAFSRTSDKKEDALKLGASRIIATKEDPDWSKSNAATFDIILNCASFGKGVNFDSFFGALKL

GGKYVNVSAPPSDELISLSPRNLIFGGFSIVGSVIGSMKEANELLKLYADNNLAPWIEKVPISEEGVHTV

MNRINVSDVKYRFVLTDYDKAFNN
```

*Pichia stipitis* ADH6 (Ps) amino acid sequence:

(SEQ ID NO: 71)
```
MTTSRTVPEKFSGFGVDKAENWNKARLVRFDPKPLMPYDITIKVIACAVCGSDCHTVTGNFGPINRDDLV

VGHEIVGEVIEVSPEVTKHKLGDVVAIGAQSDSCGECNRCKSNNEQYCQKSTVGTYNSLSKKCGGYITQG

GYASHVRVNSHFAARVPANLDVHHAAPLLCGGLTVYSPIVRHAGYDLKEKVIGIVGIGGLGSMAIQIAKA

LGAKEVVAFSRSSSKKEDAFKMGASKYIATKEDTEWANSNLDTFDMILNCASFGKGVDYDSFIRTLKLGG

KYVTVSAPPADESITIAPFNLLIGGGIIAGSGIGSMKEADELLKLYADNNLAPWIEKVPISEEGVHKVMN

RISVSDVRYRFVLTDFDQAFDSKW
```

*Saccharomyces cerevisiae* ADH7 amino acid sequence:

(SEQ ID NO: 72)
```
MLYPEKFQGIGISNAKDWKHPKLVSFDPKPFGDHDVDVEIEACGICGSDFHIAVGNWGPVPENQILGHEI

IGRVVKVGSKCHTGVKIGDRVGVGAQALACFECERCKSDNEQYCTNDHVLTMWTPYKDGYISQGGFASHV

RLHEHFAIQIPENIPSPLAAPLLCGGITVFSPLLRNGCGPGKRVGIVGIGGIGHMGILLAKAMGAEVYAF

SRGHSKREDSMKLGADHYIAMLEDKGWTEQYSNALDLLVVCSSSLSKVNFDSIVKIMKIGGSIVSIAAPE

VNEKLVLKPLGLMGVSISSSAIGSRKEIEQLLKLVSEKNVKIWVEKLPISEEGVSHAFTRMESGDVKYRF

TLVDYDKKFHK
```

*Pichia stipitis* ADH7 (Ps) amino acid sequence:

(SEQ ID NO: 73)
```
MGYPDTFQGFAVNDTSKWSEVEKMDFKPKTFGPLDIDIKIKACGVCGSDVHTVTGGWDQPRLPVIVGHEI

VGEVVKVGDNVSSFKIGDRVGMGAQAWACLECDVCKNGDEIYCPKWVDTYNDVYPDGSLAYGGYSSHVRV

HEHFAFPIPEALSTESVAPMLCAGITTYSPLVRNGAGPGKKVSVVSVGGLGHFAIMWARALSCEVYVFSR

SLSKKDDAIKLGADHYIATGEENWNEPYKYKLDLILSTANSNSGFDMGAYLSTLRVHGKYIALGLPEDDF

KVSPESLLKNGCFVGSSHLGNRQEMIDMLNLAAEKGIEAWYEAVPIGKQGIKEALERCQSGKVKYRFTLT

DYEKQFE
```

*Saccharomyces cerevisiae* GRE2 amino acid sequence:

(SEQ ID NO: 74)
MSVFVSGANGFIAQHIVDLLLKEDYKVIGSARSQEKAENLTEAFGNNPKFSMEVVPDISKLDAFDHVFQK
HGKDIKIVLHTASPFCFDITDSERDLLIPAVNGVKGILHSIKKYAADSVERVVLTSSYAAVFDMAKENDK
SLTFNEESWNPATWESCQSDPVNAYCGSKKFAEKAAWEFLEENRDSVKFELTAVNPVYVFGPQMFDKDVK
KHLNTSCELVNSLMHLSPEDKIPELFGGYIDVRDVAKAHLVAFQKRETIGQRLIVSEARFTMQDVLDILN
EDFPVLKGNIPVGKPGSGATHNTLGATLDNKKSKKLLGFKFRNLKETIDDTASQILKFESRI

*Pichia stipitis* GRE2 (Ps) amino acid sequence:

(SEQ ID NO: 75)
MTSVFVSGATGFIAQHVVKDLLAKNYTVIGSVRSASKGDHLAELLGSKKFSYEVVEDIEKEGAFDAALEK
HPEVSVFLHTASPFHFKATDNEKELLLPAVNGTKNAFRAIQLHGKNVTNVVLTSSYAAVGTASKDANKDE
VINEESWNEITWEEALKDPVSGYRSSKTFAEKAAWEFLKENNPKFVLSVVNPTFVFGPQAFDSEVKDSLN
TSSEVINALLKSGANGVVPPVKGGFVDVRDVSSAHITAFEKEAAYGQRLILNSTRFTAQEIVDILNKRFP
ELVSKIPVGEPGTGPSLRANNATIDNTKTKKILGVSEFIGLEKSVVDSVSQILRTRK

*Saccharomyces cerevisiae* SFA1 amino acid sequence:

(SEQ ID NO: 76)
MSAATVGKPIKCIAAVAYDAKKPLSVEEITVDAPKAHEVRIKIEYTAVCHTDAYTLSGSDPEGLFPCVLG
HEGAGIVESVGDDVITVKPGDHVIALYTAECGKCKFCTSGKTNLCGAVRATQGKGVMPDGTTRFHNAKGE
DIYHFMGCSTFSEYTVVADVSVVAIDPKAPLDAACLLGCVTTGFGAALKTANVQKGDTVAVFGCGTVGL
SVIQGAKLRGASKIIAIDINNKKKQYCSQFGATDFVNPKEDLAKDQTIVEKLIEMTDGGLDFTFDCTGNT
KIMRDALEACHKGWGQSIIIGVAAAGEEISTRPFQLVTGRVWKGSAFGGIKGRSEMGGLIKDYQKGALKV
EEFITHRRPFKEINQAFEDLHNGDCLRTVLKSDEIK

*Saccharomyces cerevisiae* YPR1 amino acid sequence:

(SEQ ID NO: 77)
MPATLKNSSATLKLNTGASIPVLGFGTWRSVDNNGYHSVIAALKAGYRHIDAAAIYLNEEEVGRAIKDSG
VPREEIFITTKLWGTEQRDPEAALNKSLKRLGLDYVDLYLMHWPVPLKTDRVTDGNVLCIPTLEDGTVDI
DTKEWNFIKTWELMQELPKTGKTKAVGVSNFSINNIKELLESPNNKVVPATNQIEIHPLLPQDELIAFCK
EKGIVVEAYSPFGSANAPLLKEQAIIDMAKKHGVEPAQLIISWSIQRGYVVLAKSVNPERIVSNFKIFTL
PEDDFKTISNLSKVHGTKRVVDMKWGSFPIFQ

*Mycobacterium* ADH1 (Mt) amino acid sequence:

(SEQ ID NO: 78)
MPAPDTIRPHSTSIRAAVFDGTISVEPVDLADPRPGEVRVKIAAAGVCHS
DLHVTTGAWDVPAPVVLGHEGSGVVTAVGEGVDDLEPGDHVVLSWVPGCG
ECRYCKAGRPAQCSLVASVVAVKSTLYDGTTRLSNERGTVHHYLGVSSYA
EQVVVPRNGAIKVRKDAPLEDIAIVGCAIATGVGAVRNTAGVEPGSTVAV
IGCGGVGLACVQGARLAGASRIVAVDVVAEKLELARKLGATDAVDASATD
DVVAAMREVLPDGYDYVFDAIGKIATTEQAIAALGLGGAAVIVGLPPQGE
RASFDPLTLAEADQRILGSNYGSAVPERDIPALVDEVMAGNLDLASMISG
RRPLEEAAAALDDLAAGHALRQLLIPSA

*Mycobacterium* ADHs (Mt) amino acid sequence (SEQ ID NO: 79)
MRAVDGFPGRGAVITGGASGIGLATGTEFARRGARVVLGDVDKPGLRQAV
NHLRAEGFDVHSVMCDVRHREEVTHLADEAFRLLGHVDVVFSNAGIVVGG
PIVEMTHDDWRWVIDVDLWGSIHTVEAFLPRLLEQGTGGHVVFTASFAGL
VPNAGLGAYGVAKYGVVGLAETLAREVTADGIGVSVLCPMVVETNLVANS
ERIRGAACAQSSTTGSPGPLPLQDDNLGVDDIAQLTADAILANRLYVLPH
AASRASIRRRFERIDRTFDEQAAEGWRH

*Mycobacterium* dhb (Mt) amino acid sequence:

(SEQ ID NO: 80)
MKTKGALIWEFNQPWSVEEIEIGDPRKDEVKIQMEAAGMCRSDHHLVTSD
IPMAGFPVLGGHEGAGIVTEVGPGVDDFAPGDHVVLAFIPSCGKCPSCQA

```
GMRNLCDLGAGLLAGESVTDGSFRIQARGQNVYPMTLLGTFSPYMVVHRS

SVVKIDPSVPFEVACLVGCGVTTGYGSAVRTADVRPGDDVAIVGLGGVGM

AALQGAVSAGARYVFAVEPVEWKRDQALKFGATHVYPDINAALMGIAEVT

YGLMAQKVIITVGKLDGADVDSYLTITAKGGTCVLTAIGSLVDTQVTLNL

AMLTLLQKNIQGTIFGGGNPHYDIPKLLSMYKAGKLNLDDMVTTAYKLEQ

INDGYQDMLNGKNIRGVIRYTDDDR
```

*Equus caballus* ADHE (Horse) amino acid sequence:

```
                                        (SEQ ID NO: 81)
MSTAGKVIKCKAAVLWEEKKPFSIEEVEVAPPKAHEVRIKMVATGICRSD

DHVVSGTLVTPLPVIAGHEAAGIVESIGEGVTTVRPGDKVIPLFTPQCGK

CRVCKHPEGNFCLKNDLSMPRGTMQDGTSRFTCRGKPIHHFLGTSTFSQY

TVVDEISVAKIDAASPLEKVCLIGCGFSTGYGSAVKVAKVTQGSTCAVFG

LGGVGLSVIMGCKAAGAARIIGVDINKDKFAKAKEVGATECVNPQDYKKP

IQEVLTEMSNGGVDFSFEVIGRLDTMVTALSCCQEAYGVSVIVGVPPDSQ

NLSMNPMLLLSGRTWKGAIFGGFKSKDSVPKLVADFMAKKFALDPLITHV

LPFEKINEGFDLLRSGESIRTILTF
```

Figure 2:
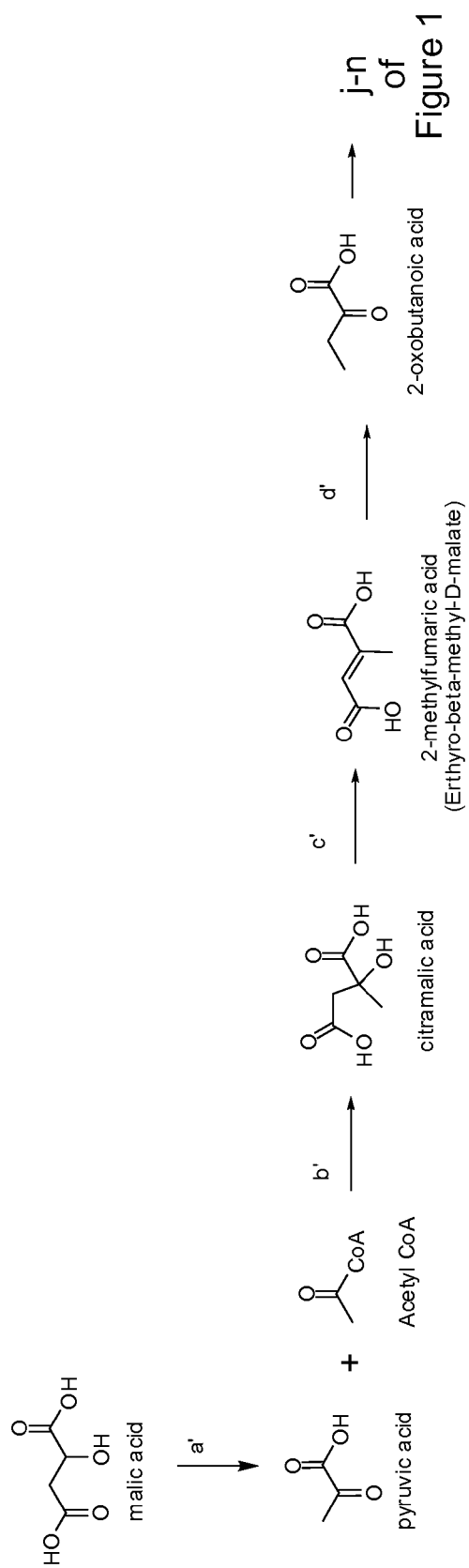
FIG. 2 describes an alternative pathway for converting pyruvate to methylbutanol, wherein steps j) to m) correspond to FIG. 1. Each enzymatic step of the pathway is provided a letter designation, which corresponds to polypeptides with the following enzymatic activities: a') isopropylmalate synthase or citramalate synthase; b') isopropylmalate isomerase; and c') isopropylmalate dehydrogenase.

Steps a) to i) discussed above, converting malate to threonine, can be achieved through an alternative pathway, which is illustrated in FIG. 2. This pathway describes the conversion of pyruvate (and acetal CoA) to citramalate (step a'), citramalate to erythro-beta-methyl-D-malate (2-methylfumaric acid) (step b'), and erythro-beta-methyl-D-malate to 2-oxobutanoate (step c'). The product of step c' enters the pathway shown in FIG. 1 at step j.

The designations provide examples of enzymes that catalyze particular reactions in the overall pathway. For example, citramalate synthase is an example of a designation for the enzyme that catalyzes step a'. Because enzymatic nomenclature various between organisms, it should be noted that the names provided below are merely illustrative of a class of enzymes that catalyze the particular steps of the pathway. The enzymes contemplated for use with the invention are those that catalyze the reactions illustrated and are not limited to the enzymatic names provided.

The designations in the figure are:

Step a') citramalate synthase [EC 4.1.3.22] or 2-isopropylmalate synthase [EC 2.3.3.13];

Step b') an isopropylmalate isomerase [EC 4.2.1.33]; and

Step c') isopropylmalate dehydrogenase [EC 1.1.1.85].

A fourth aspect of the invention provides a recombinant microorganism comprising at least one DNA molecule, wherein said at least one DNA molecule encodes at least two polypeptides that catalyze a substrate to product conversion selected from the group consisting of steps a') through c'), and wherein said recombinant microorganism produces 2-methylbutanol.

In particular embodiments of the invention, the polypeptide catalyzing the conversion of pyruvate (and acetal CoA) to citramalate is derived from a bacterium. An example of a suitable source for this enzyme is the genus *Thermotoga*, a preferred source is *Thermotoga maritima*. A specific example of a suitable sequence is:

*Thermotoga maritima* leuA amino acid sequence:

```
                                        (SEQ ID NO: 82)
MSIKVYDTTLRDGAQAFGVSFSLEDKIRIAEALDDLGVHYLEGGWPGSNP

KDIAFFEAVKGMNFKNLKVAAFSSTRRPDVKIEEDANIQTLIKAETPVYT

IFGKSWDLHVEKALRTTLEENLKMIYDTVSYLKRFADEVIYDAEHFFDGY

KANREYALKTLKVAEEAGADCLVLADTNGGTLPHEIEEIIEDVKKHVKAP

LGIHAHNDSDVAVANTLAAVRKGAVHVQSTINGLGERCGNANLCSVIPNL

VLKMGLEVIPKENLKKLFDVAHLVAELSGRPHIENMPYVGDYAFAHKGGV

HVSAIKRDPRTYEHIDPELVGNRRIISISELSGKSNVLEKIKEMGFEIDE

SSPKVREILKKIKELEAQGYHFEGAEASFELLVRDMLGKRKKYFEFLGFT

VMTIKNRDEESFSEATVKVRVPDEVAKRLGHDEPFEHTAAEGEGPVEALD

RAVRKALEKFYPSLKDTKLTDYKVRILNEQAGTKATTRVLIESSDGKRRW

GTVGVSPNIIEASWTALLESLEYKLHKDEEEMRNDEEN
```

Other exemplary sequences are:

*Thermatoga maritima* leuA truncated (i) amino acid sequence:

```
                                        (SEQ ID NO: 83)
MSIKVYDTTLRDSAQAFGVSFSLEDKIRIAEALDDLGVHYLEGGWPGSNP

KDIAFFEAVKGMNFKNLKVAAFSSTRRPDVKIEEDANIQTLIKAETPVYT

IFGKSWDLHVEKALRTTLEENLKMIYDTVSYLKRFADEVIYDAEHFFDGY

KANREYALKTLKVAEEAGADCLVLADTNGGTLPHEIEEIIEDVKKHVKAP

LGIHAHNDSDVAVANTLAAVRKGAVHVQGTINGLGERCGNANLCSVIPNL

VLKMSLEVIPKENLKKLFDVAHLVAELSGRPHIENMPYVSDYAFAHKSSV

HVSAIKRDPRTYEHIDPELVGNRRIISISELSGKSNVLEKIKEMGFEIDE

SSPKVREILKKIKELEAQGYHFESAEASFELL
```

*Thermatoga maritima* leuA truncated (ii) amino acid sequence:

```
                                        (SEQ ID NO: 84)
MSIKVYDTTLRDGAQAFGVSFSLEDKIRIAEALDDLGVHYLEGGWPGSNP

KDIAFFEAVKGMNFKNLKVAAFSSTRRPDVKIEEDANIQTLIKAETPVYT

IFGKSWDLHVEKALRTTLEENLKMIYDTVSYLKRFADEVIYDAEHFFDGY

KANREYALKTLKVAEEAGADCLVLADTNGGTLPHEIEEIIEDVKKHVKAP

LGIHAHNDSDVAVANTLAAVRKGAVHVQGTINGLGERCGNANLCSVIPNL

VLKMGLEVIPKENLKKLFDVAHLVAELSGRPHIENMPYVSDYAFAHKGGV

HVSAIKRDPRTYEHID
```

*Synechocystis* leuA amino acid sequence:

```
                                        (SEQ ID NO: 85)
MATKKTSLWLYDTTLRDGAQRESISLSLTDKLTIARRLDQLGIPFIEGGW

PGANPKDVQFFWQLQEEPLEQAEIVAFCSTRRPHKAVETDKMLQAILSAG

TRWVTIFGKSWDLHVLEGLQTSLAENLAMISDTIAYLRSQGRRVIYDAEH

WFDGYRANPDYALATLATAQQAGAEWLVMCDTNGGTLPGQISEITTKVRR

SLGLDSQSDRQPQLGIHAHNDSGTAVANSLLAVEAGATMVQGTINGYGER
```

```
CGNANLCTLIPNLQLKLDYDCIEPEKLAHLTSTSRLISEIVNLAPDDHAP

FVGRSAFAHKGGIHVSAVQRNPFTYEHIAPNLVGNERRIVVSEQAGLSNV

LSKAELFGIALDRQNPACRTILATLKDLEQQGYQFEAAEASFELLMRQAM

GDRQPLFLVQGFQVHCDLLTPAENPAYRNALATVKVTVNGQNILEVAEGN

GPVSALDQALRKALTRFYPQIADFHLTDYKVRILDGGAGTSAKTRVLVES

SNGDRRWTTVGVSGNILEASYQAVVEGIEYGLRLLTCGLTNQEAISS
```

*Geobacter sulfurreducens* cimA amino acid sequence:

(SEQ ID NO: 86)
```
MSLVKLYDTTLRDGTQAEDISFLVEDKIRIAHKLDEIGIHYIEGGWPGSN

PKDVAFFKDIKKEKLSQAKIAAFGSTRRAKVTPDKDHNLKTLIQAEPDVC

TIFGKTWDFHVHEALRISLEENLELIFDSLEYLKANVPEVFYDAEHFFDG

YKANPDYAIKTLKAAQDAKADCIVLCDTNGGTMPFELVEIIREVRKHITA

PLGIHTHNDSECAVANSLHAVSEGIVQVQGTINGFGERCGNANLCSIIPA

LKLKMKRECIGDDQLRKLRDLSRFVYELANLSPNKHQAYVGNSAFAHKGG

VHVSAIQRHPETYEHLRPELVGNMTRVLVSDLSGRSNILAKAEEFNIKMD

SKDPVTLEILENIKEMENRGYQFEGAEASFELLMKRALGTHRKFFSVIGF

RVIDEKRHEDQKPLSEATIMVKVGGKIEHTAAEGNGPVNALDNALRKALE

KFYPRLKEVKLLDYKVRVLPAGQGTASSIRVLIESGDKESRWGTVGVSEN

IVDASYQALLDSVEYKLHKSEEIEGSKK
```

In particular embodiments of the invention, the polypeptide catalyzing the conversion of citramalate to erythro-beta-methyl-D-malate (2-methylfumaric acid) is derived from a bacterium. An example of a suitable source for this enzyme is the genus *Methanococcus*, a preferred source is *Methanococcus jannaschii*. Specific examples of suitable sequences are:

*Methanococcus jannaschii* leuC amino acid sequence:

(SEQ ID NO: 87)
```
MGMTIVEKILAKASGKKEVSPGDIVMANIDVAMVHDITGPLTVNTLKEYG

IEKVWNPEKIVILFDHQVPADSIKAAENHILMRKFVKEQGIKYFYDIREG

VCHQVLPEKGHVAPGEVVVGADSHTCTHGAFGAFATGIGSTDMAHVFATG

KLWFKVPETIYFNITGDLQPYVTSKDVILSIIGEVGVDGATYKACQFGGE

TVKKMSIASRMTMTNMAIEMGGKTGIIEPDEKTIQYVKEAMKKHGTERPF

EVIKGDEDAEFAEVYEIEADKIEPVFACPHNVDNVKQAREVAGKPIDQVF

IGSCTNGRLEDLRMAIKIIEKHGGIADDVRVVVTPASREEYLKALKEGII

EKFLKYGCVVTNPSCSACMGSLYGVLGPGEVCVSTSNRNFRGRQGSLEAE

IYLASPITAAACAVKGELVDPRDL
```

*Methanococcus jannaschii* leuD amino acid sequence:

(SEQ ID NO: 88)
```
MRSIIKGRVWKFGNNVDTDAILPARYLVYTKPEELAQFVMTGADPDFPKK

VKPGDIIVGGKNFGCGSSREHAPLGLKGAGISCVIAESFARIFYRNAINV

GLPLIECKGISEKVNEGDELEVNLETGEIKNLTTGEVLKGQKLPEFMMEI

LEAGGLMPYLKKKMAESQ
```

In particular embodiments of the invention, the polypeptide catalyzing the conversion of erythro-beta-methyl-D-malate to 2-oxobutanoate is derived from a bacterium. An example of a suitable source for this enzyme is the genus *Methanococcus*, a preferred source is *Methanococcus jannaschii*. A specific example of a suitable sequence is:

*Methanococcus jannaschii* leuB amino acid sequence:

(SEQ ID NO: 89)
```
MHKICVIEGDGIGKEVVPATIQVLEATGLPFEFVYAEAGDEVYKRTGKAL

PEETIETALDCDAVLFGAAGETAADVIVKLRHILDTYANIRPVKAYKGVK

CLRPDIDYVIVRENTEGLYKGIEAEIDEGITIATRVITEKACERIFRFAF

NLARERKKMGKEGKVTCAHKANVLKLTDGLFKKIFYKVAEEYDDIKAEDY

YIDAMNMYIITKPQVFDVVVTSNLFGDILSDGAAGTVGGLGLAPSANIGD

EHGLFEPVHGSAPDIAGKKIANPTATILSAVLMLRYLGEYEAADKVEKAL

EEVLALGLTTPDLGGNLNTFEMAEEVAKRVREE
```

Any of the foregoing recombinant microorganisms may further comprise a nucleic acid encoding an amino acid biosynthesis regulatory protein. A specific example of a suitable sequence is:

*Saccharomyces cerevisiae* GCN4 amino acid sequence:

(SEQ ID NO: 90)
```
MSEYQPSLFALNPMGFSPLDGSKSTNENVSASTSTAKPMVGQLIFDKFIK

TEEDPIIKQDTPSNLDFDFALPQTATAPDAKTVLPIPELDDAVVESFFSS

STDSTPMFEYENLEDNSKEWTSLFDNDIPVTTDDVSLADKAIESTEEVSL

VPSNLEVSTTSFLPTPVLEDAKLTQTRKVKKPNSVVKKSHHVGKDDESRL

DHLGVVAYNRKQRSIPLSPIVPESSDPAALKRARNTEAARRSRARKLQRM

KQLEDKVEELLSKNYHLENEVARLKKLVGER
```

The genes of these pathways are well studied and many examples for each step of the pathway are available in the literature. Table 1 below provides a number of exemplars.

TABLE 1

List of recombinant enzymes evaluated for the enhanced production of MBO

| EC# | Protein Accession # | Enzyme Name [Genus species] | GENE |
|---|---|---|---|
| | | Malate to Pyruvate | |
| 1.1.1.37 | ABN66921 | Malate Dehydrogenase [*Pichia stipitis*] | MDH2 (Ps) |
| | AAA34766 | Malate Dehydrogenase [*Saccharomyces cerevisiae*] | MDH2 |
| | | Pyruvate to Threonine | |

TABLE 1-continued

List of recombinant enzymes evaluated for the enhanced production of MBO

| EC# | Protein Accession # | Enzyme Name [Genus species] | GENE |
|---|---|---|---|
| 6.4.1.1 | CAA96765 | Pyruvate carboxylase [Saccharomyces cerevisiae] | PYC1 |
| | ABN68200 | Pyruvate carboxylase [Pichia stipitis] | PYC1 (Ps) |
| | CAA85182 | Pyruvate carboxylase [Saccharomyces cerevisiae] | PYC2 |
| | ABN68195 | Acetyl-CoA transporter [Pichia stipitis] | PYC2 (Ps) |
| 2.6.1.1 | CAA50451 | Aspartate aminotransferase [Saccharomyces cerevisiae] | AAT1 |
| | EAZ63967 | Aspartate aminotransferase [Pichia stipitis] | AAT1 (Ps) |
| | P23542 | Aspartate aminotransferase [Saccharomyces cerevisiae] | AAT2 |
| | ABN68070 | Aspartate aminotransferase [Pichia stipitis] | AAT2 (Ps) |
| 2.7.2.4 | AAB64587 | Aspartate kinase (L-aspartate 4-P-transferase) [Saccharomyces cerevisiae] | HOM3$^{FBR}$ |
| | EAZ63309 | Aspartate kinase (L-aspartate 4-P-transferase) [Pichia stipitis] | HOM3$^{FBR}$ (Ps) |
| 1.2.1.11 | AAS56024 | HOM2 Aspartic beta semi-aldehyde dehydrogenase [Saccharomyces cerevisiae] | HOM2 (Sc) |
| | ABN66253 | HOM2 Aspartic beta semi-aldehyde dehydrogenase [Pichia stipitis] | HOM2 (Ps) |
| 1.1.1.3 | CAA45787 | Homoserine dehydrogenase [Saccharomyces cerevisiae] | HOM6 |
| | ABN65351 | Homoserine dehydrogenase [Pichia stipitis] | HOM6 (Ps) |
| 2.7.1.39 | AAA35154 | Homoserine kinase [Saccharomyces cerevisiae] | THR1 |
| | ABN68112 | Homoserine kinase [Pichia stipitis] | THR1 (Ps) |
| | NP600410 | Homoserine kinase [Corynebacterium glutamicum] | KhsE (Cg) |
| 4.2.99.2 | CAA42284 | Threonine synthase [Saccharomyces cerevisiae] | THR4 |
| | ABN67095 | Threonine synthase [Pichia stipitis] | THR4 (Ps) |
| | | Threonine to KMV | |
| 4.3.1.19 | AAB64641 | Threonine deaminase [Saccharomyces cerevisiae] | ILV1 |
| | AAB64641 | Threonine deaminase [Saccharomyces cerevisiae] | ILV1$^{FBR}$ |
| | ABN67213 | Threonine deaminase [Pichia stipitis] | ILV1 (Ps)$^{FBR}$ |
| | ABN67213 | Threonine deaminase [Pichia stipitis] | ILV1 (Ps) Δ15 |
| | ABN67213 | Threonine deaminase [Pichia stipitis] | ILV1 (Ps) |
| | CAA42403 | Catabolic L-serine (L-threonine) deaminase [Saccharomyces cerevisiae] | CHA1 |
| | CAF20464 | Threonine dehydratase [Corynebacterium glutamicum] | IlvA (Cg) |
| | AAB59054 | Threonine deaminase [Escherichia coli] | ilvA (Ec) |
| 2.2.1.6 | CAA89744 | Acetolactate synthase [Saccharomyces cerevisiae] | ILV2 |
| | ABN66585 | Acetolactate synthase [Pichia stipitis] | ILV2 (Ps) |
| | ABN66585 | Acetolactate synthase [Pichia stipitis] | ILV2 (Ps)Δ26 |
| | CAA42350 | Acetolactate synthase regulatory subunit [Saccharomyces cerevisiae] | ILV6 |
| | EAZ63909 | Acetolactate synthase regulatory subunit [Pichia stipitis] | ILV6 (Ps) |
| | BAB98664 | Acetolactate synthase 1 catalytic subunit [Corynebacterium glutamicum] | IlvB (Cg) |
| | CAF19975 | Acetolactate synthase I, small subunit [Corynebacterium glutamicum] | ilvN (Cg) |
| | BAE77622 | Acetolactate synthase I, large subunit [Escherichia coli] | ilvB(Ec) |
| | BAE77623 | Acetolactate synthase I, small subunit [Escherichia coli] | ilvN (Ec) |
| | AAA67571 | Acetolactate synthase II, large subunit [Escherichia coli] | ilvG(Ec) |
| | BAE77528 | Acetolactate synthase II, small subunit [Escherichia coli] | ilvM(Ec) |
| | BAB96646 | Acetolactate synthase III, large subunit [Escherichia coli] | ilvI(Ec) |
| | BAB96647 | Acetolactate synthase III, thiamin-dependent [Escherichia coli] | ilvIH(Ec) |
| 1.1.1.86 | CAA28643 | Acetohydroxyacid reductoisomerase [Saccharomyces cerevisiae] | ILV5 |
| | ABN66666 | Mitochondrial ketol-acid reductoisomerase [Pichia stipitis] | ILV5 (Ps) |
| | ABN66666 | Mitochondrial ketol-acid reductoisomerase [Pichia stipitis] | ILV5 (Ps) Δ40 |
| | CAF19976 | Ketol-acid reductoisomerase [Corynebacterium glutamicum] | IlvC (cg) |
| | BAE77523 | Ketol-acid reductoisomerase, NAD(P)-binding [Escherichia coli] | ilvC (Ec) |
| 4.2.1.9 | CAA60939 | Dihydroxyacid dehydratase [Saccharomyces cerevisiae] | ILV3 |
| | ABN65237 | Dihydroxyacid dehydratase [Pichia stipitis] | ILV3 (Ps) |

TABLE 1-continued

List of recombinant enzymes evaluated for the enhanced production of MBO

| EC# | Protein Accession # | Enzyme Name [Genus species] | GENE |
|---|---|---|---|
| | ABN65237 | Dihydroxyacid dehydratase [*Pichia stipitis*] | ILV3 (Ps)Δ34 |
| | CAF19971 | Dihydroxyacid dehydratase [*Corynebacterium glutamicum*] | IlvD (Cg) |
| | BAE77526 | Dihydroxyacid dehydratase [*Escherichia coli*] | ilvD (Ec) |
| | | KMV to 2MBO | |
| 4.1.1.72 | CAA97573 | Major of three pyruvate decarboxylase isozymes [*Saccharomyces cerevisiae*] | PDC1 |
| | EAZ63546 | Pyruvate decarboxylase [*Pichia stipitis*] | PDC1 (Ps) |
| | CAA97705 | Minor isoform of pyruvate decarboxylase [*Saccharomyces cerevisiae*] | PDC5 |
| | CAA39398 | Minor isoform of pyruvate decarboxylase [*Saccharomyces cerevisiae*] | PDC6 |
| | CAA98646 | Probable alpha-ketoisocaproate decarboxylase [*Saccharomyces cerevisiae*] | THI3 |
| | AAB64816 | Pyruvate decarboxylase [*Saccharomyces cerevisiae*] | ARO10 |
| | ABN67867 | Pyruvate decarboxylase (PDC6) (PDC3) [*Pichia stipitis*] | PDC 3-6 (Ps) |
| | O53865 | Branched-chain alpha-ketoacid decarboxylase [*Mycobacterium*] | Kdc(Mt) |
| | AAS49166 | Branched-chain alpha-ketoacid decarboxylase [*Lactococcus lactis*] | KdcA (Ll) |
| | AAS49166 | Branched-chain alpha-ketoacid decarboxylase [*Lactococcus lactis*] | KdcA-S286Y (Ll) |
| | AAS49166 | Branched-chain alpha-ketoacid decarboxylase [*Lactococcus lactis*] | KdcA-F381W (Ll) |
| | AAS49166 | Branched-chain alpha-ketoacid decarboxylase [*Lactococcus lactis*] | KdcAS286Y, F381W (Ll) |
| | EAZ63682 | Pyruvate decarboxylase [*Pichia stipitis*] | PDC2 (Ps) |
| 1.1.1.1 | CAA58193 | Alcohol dehydrogenase [*Saccharomyces cerevisiae*] | ADH1 |
| | AAA34408 | Alcohol dehydrogenase [*Saccharomyces cerevisiae*] | ADH2 |
| | CAA89229 | Alcohol dehydrogenase [*Saccharomyces cerevisiae*] | ADH3 |
| | ABN65575 | Alcohol dehydrogenase (NADP dependent) [*Pichia stipitis*] | ADH3 (Ps) |
| | CAA90836 | Alcohol dehydrogenase [*Saccharomyces cerevisiae*] | ADH6 |
| | EAZ62840 | NADP-dependent alcohol dehydrogenase [*Pichia stipitis*] | ADH6 (Ps) |
| | CAA42237 | NADPH-dependent alcohol dehydrogenase [*Saccharomyces cerevisiae*] | ADH7 |
| | ABN66271 | NADPH-dependent alcohol dehydrogenase [*Pichia stipitis*] | ADH7 (Ps) |
| | CAA88277 | NADPH-dependent methylglyoxal reductase [*Saccharomyces cerevisiae*] | GRE2 |
| | ABN66052 | NADPH-dependent methylglyoxal reductase GRE2 [*Pichia stipitis*] | GRE2 (Ps) |
| | CAA91578 | Bifunctional enzyme-alcohol dehydrogenase and glutathione-dependent formaldehyde dehydrogenase activities [*Saccharomyces cerevisiae*] | SFA1 |
| | CAA56686 | 2-methylbutyraldehyde reductase [*Saccharomyces cerevisiae*] | YPR1 |
| | ABK75278 | Alcohol dehydrogenase 1 [*Mycobacterium*] | ADH1 (Mt) |
| | AAK45115 | Alcohol dehydrogenase small [*Mycobacterium*] | ADHs (Mt) |
| | CAE55322 | Zinc-containing alcohol dehydrogenase NAD dependent ADHB [*Mycobacterium*] | Adhb (Mt) |
| | P00327 | Alcohol dehydrogenase-E-isoenzyme [*Equus caballus*] | ADHE (Horse) |
| | | Citramalate | |
| 2.3.3.13 | AAD35638 | 2-isopropylmalate synthase [*Thermatoga maritima*] | leuA |
| | | 2-isopropylmalate synthase [*Thermatoga maritima*] | leuA truncated |
| | NP442009 | 2-isopropylmalate synthase [*Synechocystis*] | leuA |
| 4.1.3.22 | GSU1798 | Citramalate synthase [*Geobacter sulfurreducens*] | cimA |
| 4.2.1.33 | MJ0499 | Isopropylmalate isomerase [*Methanococcus jannaschii*] | leuC |
| | MJ1277 | Isopropylmalate isomerase [*Methanococcus jannaschii*] | leuD |
| 1.1.1.85 | MJ0720 | Isopropylmalate dehydrogenase [*Methanococcus jannaschii*] | leuB |
| | | Nitrogen regulation | |
| NA | P03069 | Amino acid biosynthesis regulatory protein [*Saccharomyces cerevisiae*] | GCN4 |

Figure 3:
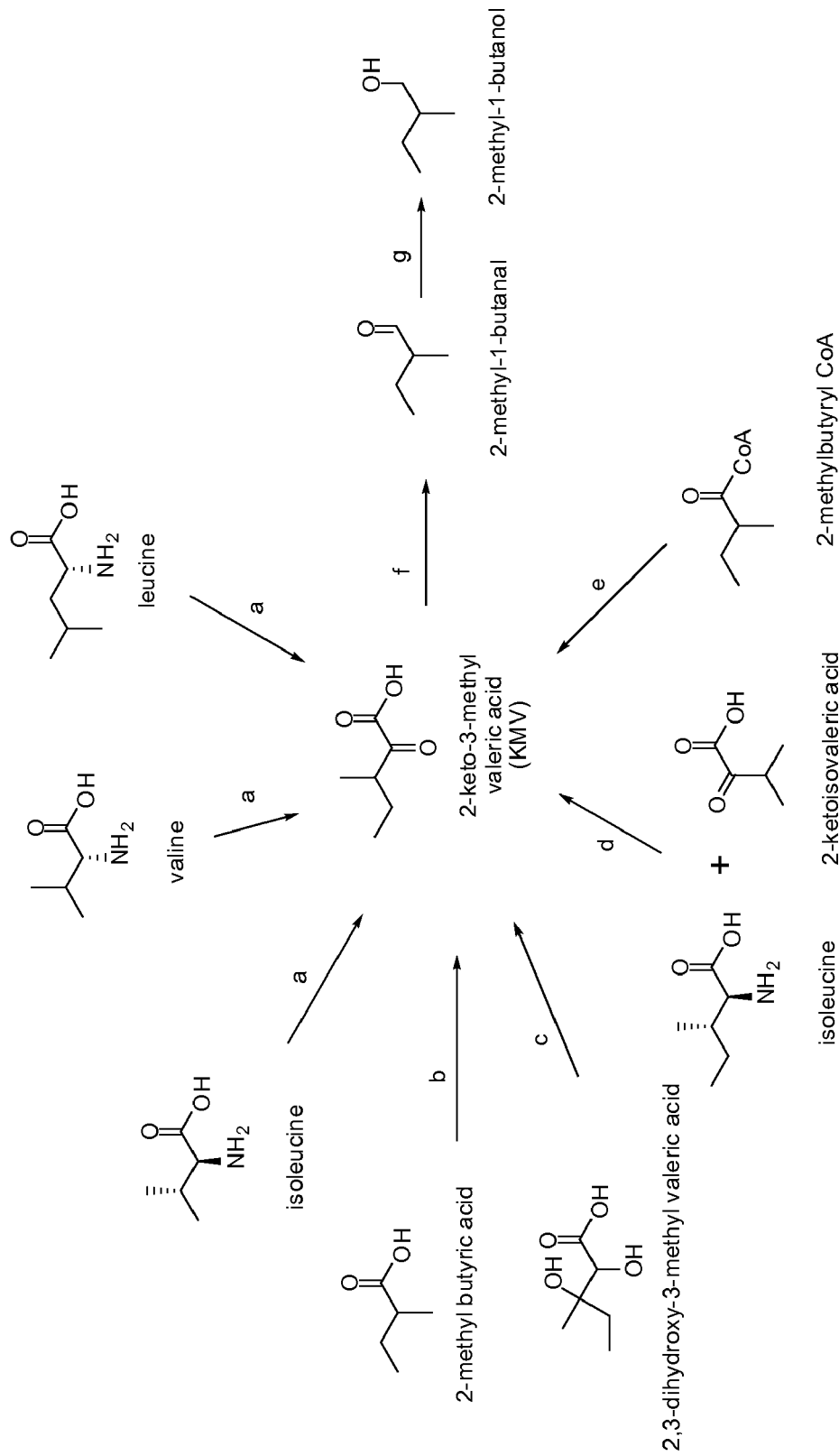
FIG. 3 depicts a metabolic pathway for the preparation of 2-methyl-1-butanol starting from amino acids and other substrates, including leucine, valine, isoleucine, 2-methyl butyric acid, 2,3-dihydroxy-3-methyl valeric acid, isoleucine, 2-ketoisovaleric acid, or 2-methylbutyryl CoA. Each enzymatic step of the pathway is provided a letter designation, which corresponds to polypeptides with the following enzymatic activities: o) or t) valine-isoleucine aminotransferase; u) 2-methylbutyrate decarboxylase; v) dihydroxyacid dehydratase; d) 2-oxo-acid decarboxylase; e) 2-keto-3-methylvalerate decarboxylase; f) alcohol dehydrogenase; and g) branched chain-alpha-ketoacid dehydrogenase complex.

FIG. 3 shows a proposed pathway for the generation of 2-MBO with leucine, valine, isoleucine, 2-methyl butyric acid, 2,3-dihydroxy-3-methyl valeric acid, isoleucine, 2-ketoisovaleric acid, or 2-methylbutyryl CoA as the starting material. Each step of the enzymatic pathway is provided with a letter designation which corresponds to an enzyme.

Step a) corresponds to the conversion of leucine, to 2-keto-3-methyl valeric acid (KMV), Step b) corresponds to the conversion of valine to 2-keto-3-methyl valeric acid (KMV), Step c) corresponds to the conversion of isoleucine to 2-keto-3-methyl valeric acid (KMV), Step d) corresponds to the conversion of 2-methylbutyryl CoA to KMV, Step e) corresponds to the conversion of 2,3-dihydroxy-3-methyl valeric acid to KMV, step f) corresponds to the conversion of isoleucine and 2-ketoisovaleric acid to KMV, Step g) corresponds to the conversion of 2-methylbutyryl CoA to KMV, Step h) corresponds to the conversion of KMV to 2-methyl-1-butanal, and Step i) corresponds to the conversion of 2-methyl-1-butanal to 2-methyl-1-butanol.

The designations provide examples of enzymes that catalyze particular reactions in the overall pathway. For example, valine-isoleucine amniotransferase is an example of a designation for the enzyme that catalyzes the conversion of leucine, valine, and isoleucine to 2-keto-3-methyl valeric acid (KMV). Because enzymatic nomenclature various between organisms, it should be noted that the names provided above are merely illustrative of a class of enzymes that catalyze the particular steps of the pathway. The enzymes contemplated for use with the invention are those that catalyze the reactions illustrated and are not limited to the enzymatic names provided.

The conversion of isoleucine to 2-keto-3-methylvalerate is catalyzed by valine-isoleucine aminotransferase (EC 2.6.1.32) or branched-chain amino acid transaminase (EC 2.6.1.42), which may be encoded by, but not limited to, one or more of the following genes: O14370; P38891; P47176; Q93Y32; P54687; P24288; P54690; Q9GKM4; Q9M439; Q5EA40; O15382; O35855; O19098; Q5REP0; O35854; Q9M401; Q9FYA6; Q9LPM9; P54688; O67733; O29329; P39576; P0AB82; P0AB81; P0AB80; P54689; Q9ZJF1; O26004; Q58414; O27481; O32954; Q10399; O86428; Q1RIJ2; Q92I26; Q4ULR3; O05970; Q9AKE5; P0A1A6; P0A1A5; Q5HIC1; P63512; P99138; Q6GJB4; Q6GBT3; P63513; Q5HRJ8; Q8CQ78; O86505; P54691; P74921; Q9Y885; and O31461.

The conversion of 2-methylbutyrate to 2-keto-3-methylvalerate is catalyzed by 2-methylbutyrate decarboxylase, which may be encoded by, but not limited to, genes occurring naturally in anaerobic microorganisms.

The conversion of 2,3-dihydroxy-3-methylvalerate to 2-keto-3-methylvalerate is catalyzed by dihydroxyacid dehydratase (EC 4.2.1.9), which may be encoded by, but not limited to, one or more of the following genes:

Q10318; P39522; Q6FCR9; Q5P8J4; Q7WQA2; Q7WC98; Q7W069; Q89LK8; Q394V3; Q8FPX6; Q8TPV2; Q5Z0M2; Q3IJH1; Q475B2; Q98BZ8; Q49Z08; Q6F6Q0; Q5P6F1; Q7WJP7; Q7W497; Q7VUN6; Q89KY5; Q39DS9; Q8FMR1; Q8TKM8; Q5YX61; Q3ID04; Q46YI9; Q98LB3; Q49UX2; Q5NY71; Q7WFQ5; Q89HA2; Q5YRV8; Q9YG88; Q8UE43; Q8YTE6; O67009; O29248; Q81S26; Q9XBI3; Q81F26; Q63CV3; Q5L918; Q64PS6; Q9K8E4; Q6HKA0; Q65IB0; Q5WEM9; P51785; Q8A608; Q6G543; Q8G3H2; Q7VRL8; Q491Z0; Q57FS2; Q8YEN0; Q8G353; P57656; O51887; P59426; Q9RQ56; Q9RQ48; Q9RQ52; Q62LG7; Q3JV12; Q63WB9; Q9PJ98; Q5HXE4; Q3AER0; P55186; Q3APB9; Q8KER4; Q7NYJ7; Q97EE3; P31959; Q47UN7; Q6NHN6; Q8NQZ9; Q4JUN3; Q47JC0; Q3Z888; Q3ZXH9; Q9RV97; Q317H9; Q725Q1; Q8XAV1; Q8FBR5; P05791; Q6CZC7; Q5NH32; Q5KYA5; Q74BW7; Q7NGK1; Q5FN26; Q4QMF8; P44851; Q5V545; Q7VHW3; Q02139; Q6AEN9; Q72TC0; Q8F219; Q92A32; Q71Y38; Q8Y5S2; Q65QD4; Q46AU2; Q606D6; Q58672; Q8TW40; Q8Q078; Q6M0F3; O27498; P65155; O06069; Q73TT7; P65154; Q3IMV2; Q5F8G6; Q9JUE0; Q9JS61; Q82XY7; Q3J9N3; Q3SW60; Q8EN63; P57957; Q3A3A5; Q4FM19; Q7MYJ5; Q6LLH7; Q6KZ30; Q7VC95; Q7TV16; Q7V1T1; Q46LF6; Q48PA6; Q916E0; Q4K498; Q3K559; Q88CQ2; Q87V83; Q4ZZ83; Q4FS54; Q9UZ03; Q8ZYU6; Q8U297; Q8XWR1; Q92M28; Q7UJ69; P31874; Q6N9S5; Q31XP4; Q57HU7; Q5PK00; Q8Z377; P40810; Q8E9D9; Q31UL3; Q329V0; Q83PI6; Q3YVJ3; Q5LN98; Q5HEE8; P65156; P65157; Q6GF19; Q6G7Q4; P65158; Q5HMG3; Q8CNL6; Q4L7T6; Q82E99; O69198; Q8DRT7; P65159; P65160; Q5LYH1; Q5M334; Q4J860; Q97UB2; Q96YK0; Q67KX6; Q8DK13; Q5N3N2; Q7U763; P74689; Q47MS7; Q9WZ21; Q72JA8; Q5SIY0; Q8RDJ9; Q8KTS9; Q83HI6; Q83GP9; Q9KVW0; Q5E1P2; Q87KB6; Q8DDG1; Q7MGI8; Q7MAN4; Q8PQI0; Q3BYS5; Q4UZT2; Q8PDJ3; Q5GUY8; Q9PH47; Q87F63; Q8ZAB3; Q66G45; and Q5NLJ4.

The conversion of 2-methyl-butyryl-CoA to 2-keto-3-methylvalerate is catalyzed by branched-chain α-ketoacid dehydrogenase complex (EC 1.2.4.4; EC 2.3.1.268; EC 1.8.1.4), which may be encoded by, but not limited to, one or more of the following genes: P37940; P11178; P12694; Q8HXY4; P50136; A5A6H9; Q9I1M2; P09060; P11960; Q72GU1; Q5SLR4; P37941; P21839; P21953; Q9I1M1; P09061; P35738; Q72GU2; Q5SLR3; P37942; P11181; P11182; P53395; Q9I1M0; P09062; Q9M5K3; P11959; P21880; Q9I1L9; P09063; Q9M5K2; P54533; Q5UYG6; Q913D1; P31052; O34324; Q5UWH2; Q9HUY1; P31046; P35484; P18925; P57303; Q8K9T7; Q89AQ8; P49819; Q9PJI3; Q9Z773; Q8KCW2; O84561; O50311; Q8CIZ7; P0A9P2; P0A9P1; P0A9P0; P43784; Q9HN74; Q04829; P09622; P80647; Q60HG3; O18480; O08749; P66005; P47513; Q50068; P75393; P66004; P31023; P09623; Q5R4B1; P84545; P14218; P52992; Q6P6R2; O05940; P95596; O00087; P0A9P3; P80503; Q5HGY8; P0A0E6; P99084; Q6 GHY9; Q6GAB8; P0A0E8; P0A0E7; P72740; Q04933; P90597; Q9KPF6; O50286; P09624; and P50970.

The conversion of 2-keto-3-methylvalerate to 2-methyl-1-butanal is catalyzed by 2-oxo-acid decarboxylase (EC 4.1.1.72) or 2-keto-3-methylvalerate decarboxylase (EC 4.1.1.1), which may be encoded by, but not limited to, one or more of the following genes: P83779; Q6FJA3; Q12629; P33149; P28516; A2Y5L9; Q0DHF6; P51850; Q09737; P51845; P06169; Q05326; A2XFI3; Q10MW3; P51851; Q92345; P51846; Q05327; A2YQ76; Q0D3D2; Q9P7P6; P16467; P26263; Q4WXX9; Q2UKV4; P51844; Q0CNV1; P87208; P34734; P33287; and P06672.

The conversion of 2-methyl-1-butanal to 2-methyl-1-butanol is catalyzed by alcohol dehydrogenase (EC 1.1.1.1), which may be encoded by, but not limited to, one or more of the following genes: P07327; P28469; Q5RBP7; P25405; P00325; Q5R1W2; P14139; P25406; P00327; P00326; O97959; P00328; P80222; P30350; P49645; P06525; P41747; P12311; Q17334; P43067; P48814; Q70UN9; P23991; P19631; P23236; P48586; P09370; P22246; P07161; P12854; P08843; P26325; Q9Z2M2; Q64413;

Q64415; P05336; P20369; Q07288; P00333; P00329; P80512; Q9P6C8; Q75ZX4; Q2R8Z5; P12886; P14219; P41680; P25141; O00097; Q03505; P22797; P06757; P14673; P80338; P13603; P00330; Q07264; P20368; P42327; O45687; O94038; P48815; Q70UP5; Q70UP6; P27581; P25720; P23237; P48587; P09369; P07160; P24267; P37686; P54202; Q24803; P10847; P49383; Q9P4C2; P04707; Q4R1E8; Q0ITW7; O13309; P28032; P14674; P00331; P06758; P42328; P25437; P07754; P44557; P10848; P49384; P39450; P14675; P73138; P07246; P08319; P49385; Q9QYY9; Q64563; Q09669; P80468; P10127; Q6XQ67; P38113; P28332; P41681; Q5R7Z8; Q5×195; P40394; Q64437; P41682; O31186; Q7U1B9; P71818; P33744; P0A9Q8; P0A9Q7; P81600; P72324; Q9SK86; Q9SK87; A1L4Y2; Q8VZ49; Q0V7W6; Q8LEB2; Q9FH04; P81601; P39451; O46649; O46650; Q96533; Q3ZC42; Q17335; P46415; P19854; P11766; P93629; P28474; P80360; P81431; A2XAZ3; Q0DWH1; P80572; O19053; P12711; P79896; P80467; Q9NAR7; Q00669; P21518; P25139; P48584; Q00670; P22245; Q9NG42; P28483; P48585; P51551; Q09009; P51549; P21898; Q07588; Q9NG40; Q27404; P10807; P07162; Q09010; P00334; Q00671; P25721; Q00672; P07159; P84328; P37473; P23361; P23277; Q6LCE4; Q9U8S9; Q9GN94; Q24641; P23278; Q03384; P28484; P51550; Q05114; P26719; P17648; P48977; P81786; P14940; P25988; P00332; Q2FJ31; Q2G0G1; Q2YSX0; Q5HI63; Q99W07; Q7A742; Q6GJ63; Q6 GBM4; Q8NXU1; Q5HRD6; Q8CQ56; Q4J781; P39462; P50381; Q96XE0; P51552; P32771; P71017; and P33010.

Figure 4:
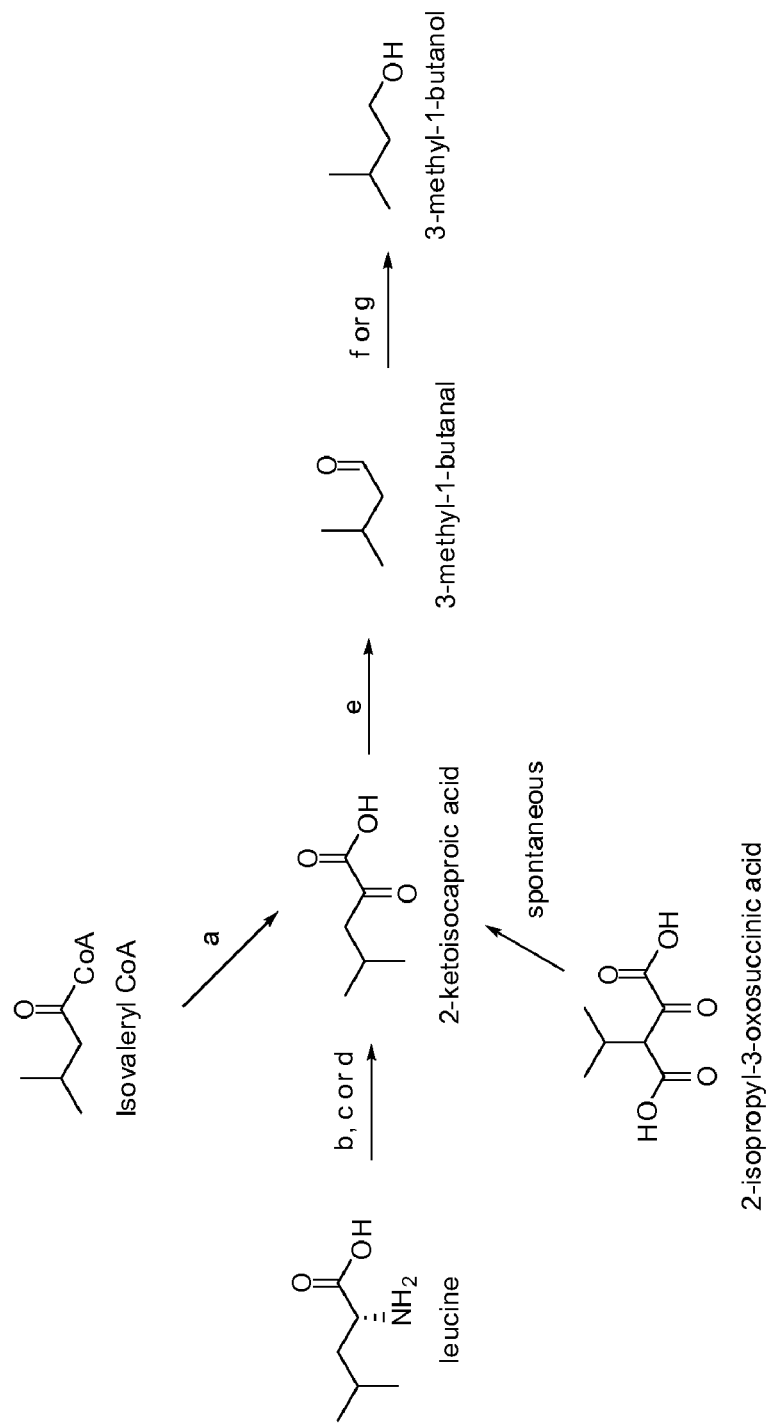
FIG. 4 depicts a pathway for the preparation of 3-methyl-1-butanol starting from isovaleryl CoA, leucine, or 2-isopropyl-3-oxosuccinic acid. Each enzymatic step of the pathway is provided a letter designation, which corresponds to polypeptides with the following enzymatic activities: n) ketoisovalerate dehydrogenase complex; o) branched-chain amino acid transaminase; p) leucine aminotransferase; q) leucine dehydrogenase; r) 2-ketoisocaproaste decarboxylase; s) 3-methyl-1-butanal reductase; and t) alcohol dehydrogenase.

FIG. 4 shows a proposed pathway for the generation of 3-MBO with isovaleryl CoA, leucine, and 2-isopropyl-3-oxosuccinic acid as the starting material. Each step of the enzymatic pathway is provided with a letter designation which corresponds to an enzyme.

Step a) corresponds to the conversion of isovaleryl CoA to 2-ketoisocaproic acid, Step b) corresponds to the conversion of leucine to 2-ketoisocaproic acid, Step c) corresponds to the conversion of 2-isopropyl-3-oxosuccinic acid to 2-ketoisocaproic acid, Step d) corresponds to the conversion of 2-ketoisocaproic acid to 3-methyl-1-butanal, and Step e) corresponds to the conversion of 3-methyl-1-butanal to 3-methyl-1-butanol.

The conversion of isovaleryl-CoA to 2-ketoisocaproate is catalyzed by the ketoisovalerate dehydrogenase complex (EC 1.2.4.4; EC 2.3.1.268; EC 1.8.1.4), which may be encoded by, but not limited to, one or more of the following genes: P37940; P11178; P12694; Q8HXY4; P50136; A5A6H9; Q9I1M2; P09060; P11960; Q72GU1; Q5SLR4; P37941; P21839; P21953; Q9I1M1; P09061; P35738; Q72GU2; Q5SLR3; P37942; P11181; P11182; P53395; Q9I1M0; P09062; Q9M5K3; P11959; P21880; Q9I1L9; P09063; Q9M5K2; P54533; Q5UYG6; Q913D1; P31052; O34324; Q5UWH2; Q9HUY1; P31046; P35484; P18925; P57303; Q8K9T7; Q89AQ8; P49819; Q9PJI3; Q9Z773; Q8KCW2; O84561; O50311; Q8CIZ7; P0A9P2; P0A9P1; P0A9P0; P43784; Q9HN74; Q04829; P09622; P80647; Q60HG3; O18480; O08749; P66005; P47513; Q50068; P75393; P66004; P31023; P09623; Q5R4B1; P84545; P14218; P52992; Q6P6R2; O05940; P95596; O00087; P0A9P3; P80503; Q5HGY8; P0A0E6; P99084; Q6 GHY9; Q6GAB8; P0A0E8; P0A0E7; P72740; Q04933; P90597; Q9KPF6; O50286; P09624; and P50970.

The conversion of L-leucine to 2-ketoisocaproate is catalyzed by the branched-chain amino acid transaminase (EC 2.6.1.42), which may be encoded by, but not limited to, one or more of the following genes: O14370; P38891; P47176; Q93Y32; P54687; P24288; P54690; Q9GKM4; Q9M439; Q5EA40; O15382; O35855; O19098; Q5REP0; O35854; Q9M401; Q9FYA6; Q9LPM9; P54688; O67733; O29329; P39576; P0AB82; P0AB81; P0AB80; P54689; Q9ZJF1; O26004; Q58414; O27481; O32954; Q10399; O86428; Q1RIJ2; Q92126; Q4ULR3; O05970; Q9AKE5; P0A1A6; P0A1A5; Q5HIC1; P63512; P99138; Q6GJB4; Q6 GBT3; P63513; Q5HRJ8; Q8CQ78; O86505; P54691; P74921; Q9Y885; and O31461.

The conversion of L-leucine to 2-ketoisocaproate is catalyzed by leucine aminotransferase (EC 2.6.1.6) or leucine dehydrogenase (EC 1.4.1.9), which may be encoded by, but not limited to, one or more of the following genes: P0A393; P0A392; Q53560; P13154; P54531; Q60030.

The conversion of 2-isopropyl-3-oxosuccinate to 2-ketoisocaproate may occur spontaneously.

The conversion of 2-ketoisocaproate to 3-methyl-1-butanal is catalyzed by 2-ketoisocaproate decarboxylase (EC 4.1.1.1), which may be encoded by, but not limited to, one or more of the genes discussed above.

The conversion of 3-methyl-1-butanal to 3-methyl-1-butanol is catalyzed by 3-methyl-1-butanal reductase (EC 1.1.1.265) or alcohol dehydrogenase (EC 1.1.1.1), which may be encoded by, but not limited to, one or more of the genes discussed above.

The recombinant microorganisms disclosed are engineered to contain a plurality of the enzymes illustrated in FIGS. 1 to 4 and discussed above, with the goal of producing a particular compound or compounds of interest. The entire pathway may be introduced exogenously to a host cell or select portions of the pathway may be introduced to complement existing enzymatic systems in the host cell. One of skill in the art could readily engineer polypeptides providing similar enzymatic function for any particular step of the pathways. For example, in addition to the sequences provided herein, one could provide comparable enzymatic activity with a homolog of any of the polypeptides disclosed sharing at least about 50%, 55%, 60% or 65% amino acid sequence identity, or preferably at least about 70%, 75%, 80%, 85%, 90% or 95% amino acid sequence identity.

The genes encoding these enzymes are introduced to the host cell using standard molecular biology techniques, such as standard expression vectors. One or more vectors may be used, where one or more of the genes encoding enzymes of the pathway are present.

Figure 5:
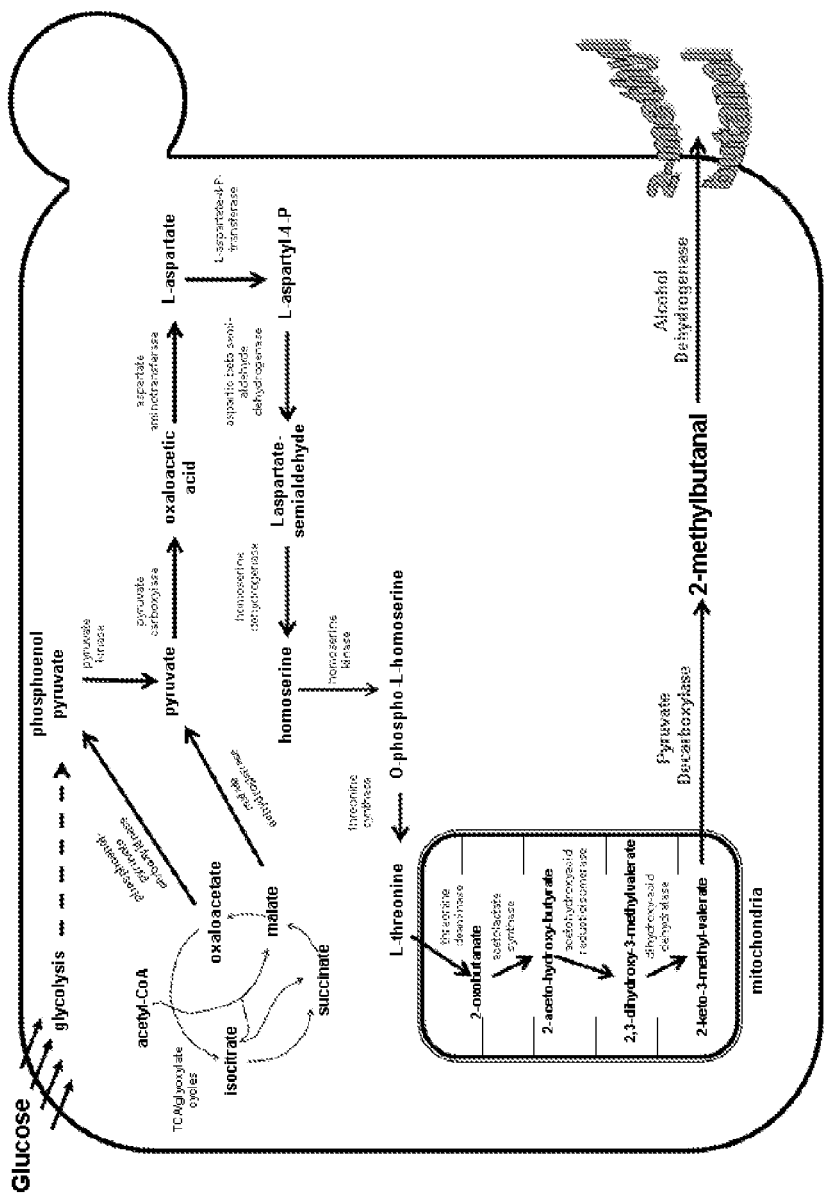
FIG. 5. Representation of a eukaryotic cell, highlighting the route from glucose to 2-methylbutanol (2-MBO). The pathway is similar in prokaryotes with the exception that the isoleucine pathway is not confined to the mitochondria.

FIG. 5 shows an overview of some exemplary pathways that can be exploited to produce compounds of interest.

DEFINITIONS

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, cyclohexyl, cyclopentylethyl, 2-propenyl, 3-butynyl, and the like. The total number of carbon atoms in each such group is sometimes described herein, e.g., when the group can contain up to ten carbon atoms it can be represented as C1-10 or as C1-C10 or C1-10. In certain embodiments, alkyl contains 1-10, 1-8, 1-6, 1-4, or 1-2 carbons.

As used herein, "hydrocarbyl residue" refers to a residue which contains only carbon and hydrogen. The residue may be aliphatic or aromatic, straight-chain, cyclic, branched, saturated or unsaturated, or any combination of these. The hydrocarbyl residue, when so stated however, may contain heteroatoms in addition to or instead of the carbon and hydrogen members of the hydrocarbyl group itself.

As used herein, "acyl" encompasses groups comprising an alkyl, alkenyl, alkynyl, aryl or arylalkyl radical attached at one of the two available valence positions of a carbonyl carbon atom.

"Aromatic" moiety or "aryl" moiety refers to a monocyclic or fused bicyclic moiety having the well-known characteristics of aromaticity; examples include phenyl and naphthyl. Similarly, "arylalkyl" refers to an aromatic ring system which is bonded to their attachment point through a linking group such as an alkylene. In certain embodiments, aryl is a 5-6 membered aromatic ring, optionally containing one or more heteroatoms selected from the group consisting of N, O, and S.

"Alkylene" as used herein refers to a divalent hydrocarbyl group; because it is divalent, it can link two other groups together. Typically it refers to —$(CH_2)_n$— where n is 1-10, 1-8, 1-6, 1-4, or 1-2. The open valences need not be at opposite ends of a chain. Thus —CH(Me)- and —C(Me)$_2$- may also be referred to as alkylenes, as can a cyclic group such as cyclopropan-1,1-diyl.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Arylalkyl" refers to an aromatic ring system bonded to their attachment point through a linking group such as an alkylene, including substituted or unsubstituted, saturated or unsaturated, cyclic or acyclic linkers. Typically the linker is C1-C8 alkylene or a hetero form thereof. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences.

In certain embodiments, optional substituents are selected from the group consisting of halo, =O, OR, NR$_2$, NO$_2$, and CN; wherein each R is independently H, C1-C6 alkyl, C2-C6 alkenyl, or C2-C6 alkynyl.

"Halo", as used herein includes fluoro, chloro, bromo and iodo. In certain embodiments, halo is fluoro or chloro.

"Attenuate" as used herein means to reduce expression levels of a gene product. For example, functional deletion of the gene encoding an enzyme can be used to attenuate an enzyme. A functional deletion is typically a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knock out mutation.

One of ordinary skill in the art will appreciate that there are many methods of attenuating enzyme activity. For example, attenuation can be accomplished by introducing amino acid sequence changes via altering the nucleic acid sequence, placing the gene under the control of a less active promoter, expressing interfering RNA, ribozymes or antisense sequences that targeting the gene of interest, or through any other technique known in the art.

"Carbon source" as used herein generally refers to a substrate or compound suitable to be used as a source of carbon for prokaryotic or simple eukaryotic cell growth. Carbon sources can be in various forms, including, but not limited to carboxylic acids (such as succinic acid, lactic acid, acetic acid), alcohols (e.g., ethanol), sugar alcohols (e.g., glycerol), aldehydes, amino acids, carbohydrates, saturated or unsaturated fatty acids, ketones, peptides, proteins, and mixtures thereof. Examples of carbohydrates include monosaccharides (such as glucose, galactose, xylose, arabinose, and fructose), disaccharides (such as sucrose and lactose), oligosaccharides, and polysaccharides (e.g., starch). Polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., Microb. Growth C1 Compd., [Int. Symp.], 7th (1993), 415-32. Editor(s): Murrell, J. Collin; Kelly, Don P. Publisher: Intercept, Andover, UK). Similarly, various species of *Candida* will metabolize alanine or oleic acid (Sulter et al., Arch. Microbiol. 153:485-489 (1990)). Hence it is contemplated that the source of carbon utilized in the present invention may encompass a wide variety of carbon containing substrates and will only be limited by the choice of organism. Lignocellulosic material is contemplated as a suitable carbon source, i.e., plant biomass that is composed of cellulose, hemicellulose, and lignin. Biomass may include (1) wood residues (including sawmill and paper mill discards), (2) municipal paper waste, (3) agricultural residues (including corn stover and sugarcane bagasse), and (4) dedicated energy crops (which are mostly composed of fast growing tall, woody grasses). Carbon dioxide ($CO_2$), and coal are also contemplated as suitable carbon sources.

"Culture medium" as used herein includes any medium which supports microorganism life (i.e. a microorganism that is actively metabolizing carbon). A culture medium usually contains a carbon source. The carbon source can be anything that can be utilized, with or without additional enzymes, by the microorganism for energy.

"Deletion" as used herein refers to the removal of one or more nucleotides from a nucleic acid molecule or one or more amino acids from a protein, the regions on either side being joined together.

"Detectable" as used herein refers to be capable of having an existence or presence ascertained.

"Methylbutanol" refers to a hydrogen carbon of the formula C5H12, and the term includes stereoisomers thereof. Non-limiting examples of structural isomers of 2-methyl-1-butanol and 3-methyl-1-butanol.

"Endogenous" as used herein in reference to a nucleic acid molecule and a particular cell or microorganism refers to a nucleic acid sequence or peptide that is in the cell and was not introduced into the cell using recombinant engineering techniques. For example, a gene that was present in the cell when the cell was originally isolated from nature. A gene is still considered endogenous if the control sequences, such as a promoter or enhancer sequences that activate transcription or translation have been altered through recombinant techniques.

"Exogenous" as used herein with reference to a nucleic acid molecule and a particular cell refers to any nucleic acid molecule that does not originate from that particular cell as found in nature. Thus, a non-naturally-occurring nucleic acid molecule is considered to be exogenous to a cell once introduced into the cell. A nucleic acid molecule that is naturally-occurring also can be exogenous to a particular cell. For example, an entire coding sequence isolated from cell X is an exogenous nucleic acid with respect to cell Y once that coding sequence is introduced into cell Y, even if X and Y are the same cell type.

"Expression" as used herein refers to the process by which a gene's coded information is converted into the structures and functions of a cell, such as a protein, transfer RNA, or ribosomal RNA. Expressed genes include those that are transcribed into mRNA and then translated into protein and those that are transcribed into RNA but not translated into protein (for example, transfer and ribosomal RNAs).

"Hydrocarbon" as used herein includes chemical compounds that containing the elements carbon (C) and hydrogen (H). Hydrocarbons consist of a carbon backbone and atoms of hydrogen attached to that backbone. Sometimes, the term is used as a shortened form of the term "aliphatic hydrocarbon." There are essentially three types of hydrocarbons: (1) aromatic hydrocarbons, which have at least one aromatic ring; (2) saturated hydrocarbons, also known as alkanes, which lack double, triple or aromatic bonds; and (3) unsaturated hydrocarbons, which have one or more double or triple bonds between carbon atoms. Alkenes are chemical compounds containing at least one double bond between carbon atoms and alkynes are chemical compounds containing at least one triple bond between carbon atoms.

"Isolated" as in "isolated" biological component (such as a nucleic acid molecule, protein, or cell) refers to the component that has been substantially separated or purified away from other biological components in which the component naturally occurs, such as other chromosomal and extrachromosomal DNA and RNA, and proteins. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

"Microorganism" as used herein includes prokaryotic and eukaryotic microbial species. The terms "microbial cells" and "microbes" are used interchangeably with the term microorganism.

"Nucleic Acid Molecule" as used herein encompasses both RNA and DNA molecules including, without limitation, cDNA, genomic DNA and mRNA. Includes synthetic nucleic acid molecules, such as those that are chemically synthesized or recombinantly produced. The nucleic acid molecule can be double-stranded or single-stranded. Where single-stranded, the nucleic acid molecule can be the sense strand or the antisense strand. In addition, nucleic acid molecule can be circular or linear.

"Over-expressed" as used herein refers to when a gene is caused to be transcribed at an elevated rate compared to the endogenous transcription rate for that gene. In some examples, over-expression additionally includes an elevated rate of translation of the gene compared to the endogenous translation rate for that gene. Methods of testing for over-expression are well known in the art, for example transcribed RNA levels can be assessed using rtPCR and protein levels can be assessed using SDS page gel analysis.

"Purified" as used herein does not require absolute purity; rather, it is intended as a relative term.

"Recombinant" as used herein in reference to a recombinant nucleic acid molecule or protein is one that has a sequence that is not naturally occurring, has a sequence that is made by an artificial combination of two otherwise separated segments of sequence, or both. This artificial combination can be achieved, for example, by chemical synthesis or by the artificial manipulation of isolated segments of nucleic acid molecules or proteins, such as genetic engineering techniques. Recombinant is also used to describe nucleic acid molecules that have been artificially manipulated, but contain the same regulatory sequences and coding regions that are found in the organism from which the nucleic acid was isolated. A recombinant cell or microorganism is one that contains an exogenous nucleic acid molecule, such as a recombinant nucleic acid molecule.

"Spent medium" or "spent culture medium" as used herein refers to culture medium that has been used to support the growth of a microorganism.

"Stereoisomers" as used herein are isomeric molecules that have the same molecular formula and connectivity of bonded atoms, but which differ in the three dimensional orientations of their atoms in space. Non-limiting examples of stereoisomers are enantiomers, diastereomers, cis-trans isomers and conformers.

"Transformed or recombinant cell" as used herein refers to a cell into which a nucleic acid molecule has been introduced, such as an acyl-CoA synthase encoding nucleic acid molecule, for example by molecular biology techniques. Transformation encompasses all techniques by which a nucleic acid molecule can be introduced into such a cell, including, but not limited to, transfection with viral vectors, conjugation, transformation with plasmid vectors, and introduction of naked DNA by electroporation, lipofection, and particle gun acceleration.

"Fermentation conditions" referred to herein usually include temperature ranges, levels of aeration, and media selection, which when combined allow the microorganism to grow. Exemplary media include broths or gels. Generally, the medium includes a carbon source such as glucose, fructose, cellulose, or the like that can be metabolized by the microorganism directly, or enzymes can be used in the medium to facilitate metabolizing the carbon source. To determine if culture conditions permit product production, the microorganism can be cultured for 24, 36, or 48 hours and a sample can be obtained and analyzed. For example, the cells in the sample or the medium in which the cells were grown can be tested for the presence of the desired product.

"Vector" as used herein refers to a nucleic acid molecule as introduced into a cell, thereby producing a transformed cell. A vector can include nucleic acid sequences that permit it to replicate in the cell, such as an origin of replication. A vector can also include one or more selectable marker genes and other genetic elements known in the art.

"Finished fuel" is defined as a chemical compound or a mix of chemical compounds (produced through chemical, thermochemical or biological routes) that is in an adequate chemical and physical state to be used directly as a neat fuel or fuel additive in an engine. In many cases, but not always, the suitability of a finished fuel for use in an engine application is determined by a specification which describes the necessary physical and chemical properties that need to be met. Some examples of engines are: internal combustion engine, gas turbine, steam turbine, external combustion engine, and steam boiler. Some examples of finished fuels include: diesel fuel to be used in a compression-ignited (diesel) internal combustion engine, jet fuel to be used in an aviation turbine, fuel oil to be used in a boiler to generate steam or in an external combustion engine, ethanol to be used in a flex-fuel engine. Examples of fuel specifications are ASTM standards, mainly used ion the US, and the EN standards, mainly used in Europe.

"Fuel additive" refers to a compound or composition that is used in combination with another fuel for a variety of reasons, which include but are not limited to complying with mandates on the use of biofuels, reducing the consumption of fossil fuel-derived products or enhancing the performance of a fuel or engine. For example, fuel additives can be used to alter the freezing/gelling point, cloud point, lubricity, viscosity, oxidative stability, ignition quality, octane level, and flash point. Additives can further function as antioxidants, demulsifiers, oxygenates, thermal stability improvers, cetane improvers, stabilizers, cold flow improvers, combustion improvers, antifoams, anti-haze additives, icing inhibitors, injector cleanliness additives, smoke suppressants, drag reducing additives, metal deactivators, dispersants, detergents, demulsifiers, dyes, markers, static dissipaters, biocides, and/or corrosion inhibitors. One of ordinary skill in the art will appreciate that MBO and MBO derivatives described herein can be mixed with one or more fuel or such fuel additives to reduce the dependence on fossil fuel-derived products and/or to impart a desired quality and specific additives are well known in the art. In addition, MBO and MBO derivatives can be used themselves as additives in blends with other fuels to impart a desired quality.

Non-limiting examples of additives to the fuel composition of the invention include: Hybrid compound blends such as combustion catalyst (organo-metallic compound which lowers the ignition point of fuel in the combustion chamber reducing the temperature burn from 1200 degrees to 800° F.), Burn rate modifier (increases the fuel burn time result in an approx. 30% increase of the available BTUs from the fuel), ethanol as an octane enhancer to reduce engine knock, biodiesel, polymerization (increases fuel ignition surface area resulting in increased power from ignition), Stabilizer/Demulsifier (prolongs life of fuel and prevents water vapor contamination), Corrosion inhibitor (prevents tank corrosion), Detergent agent (clean both gasoline and diesel engines with reduced pollution emissions), Catalyst additive (prolongs engine life and increases fuel economy), and Detergent (cleans engine); oxygenates, such as methanol, ethanol, isopropyl alcohol, n-butanol, gasoline grade t-butanol, methyl t-butyl ether, tertiary amyl methyl ether, tertiary hexyl methyl ether, ethyl tertiary butyl ether, tertiary amyl ethyl ether, and diisopropyl ether; antioxidants, such as, Butylated hydroxytoluene (BHT), 2,4-Dimethyl-6-tert-butylphenol, 2,6-Di-tert-butylphenol (2,6-DTBP), Phenylene diamine, and Ethylene diamine; antiknock agents, such as, Tetra-ethyl lead, Methylcyclopentadienyl manganese tricarbonyl (MMT), Ferrocene, and Iron pentacarbonyl, Toluene, isooctane; Lead scavengers (for leaded gasoline), such as, Tricresyl phosphate (TCP) (also an AW additive and EP additive), 1,2-Dibromo-ethane, and 1,2-Dichloroethane; and Fuel dyes, such as, Solvent Red 24, Solvent Red 26, Solvent Yellow 124, and Solvent Blue 35. Other additives include, Nitromethane (increases engine power, "nitro"), Acetone (vaporization additive, mainly used with methanol racing fuel to improve vaporisation at start up), Butyl rubber (as polyisobutylene succinimide, detergent to prevent fouling of diesel fuel injectors), Ferox (catalyst additive that increases fuel economy, cleans engine, lowers emission of pollutants, prolongs engine life), Ferrous picrate (improves combustion, increases mileage), Silicones (anti-foaming agents for diesel, damage oxygen sensors in gasoline engines), and Tetranitromethane (to increase cetane number of diesel fuel).

In certain embodiments, the invention provides for a fuel composition comprising MBO or a derivative thereof as described herein and one or more additives. In certain embodiments, the additives are at least 1-5%, 1-10%, 1-15%, 1-20%, 1-25%, 1-30%, 1-35%, 1-40%, 1-45%, 1-50%, 1-55%, 1-60%, 1-65%, 1-70%, 1-75%, 1-80%, 1-85%, 1-90%, 1-95%, or 1-100% of the weight of the composition. In certain embodiments, the additives comprise 1-5%, 1-10%, 1-15%, 1-20%, 1-25%, 1-30%, 1-35%, 1-40%, 1-45%, 1-50%, 1-55%, 1-60%, 1-65%, 1-70%, 1-75%, 1-80%, 1-85%, 1-90%, 1-95%, or 1-100% of the volume of the composition. In certain embodiments, the additives comprise 5-10%, 10-30%, or 25-40% of the weight of the composition. In certain embodiments, the additives comprise 5-10%, 10-30%, or 25-40% of the volume of the composition.

In certain embodiments, the additives are at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the weight of the composition.

In certain embodiments, the additives are at least 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of the volume of the composition.

One of ordinary skill in the art will also appreciate that the MBO and MBO derivatives described herein are can be mixed with other fuels such as bio-diesel, various alcohols such as ethanol and butanol, and petroleum-based products such as gasoline. In certain embodiments, the conventional petroleum-based fuel is at least 10%, 20%, 30%, 40%, 50%, 60%, 75%, 85%, 95%, or 99% of the weight or volume of the composition.

In one embodiment, the compounds of the present invention and derivatives thereof can themselves provide a fuel composition, wherein the compound or a combination of compounds of the present invention comprise approximately 100% of the fuel composition. In various other embodiments the compounds of the present invention and derivatives thereof are combined with other fuels or biofuels to provide a fuel composition, wherein the compound of a combination of compounds of the present invention comprise 1-99% of the weight or 1-99% or the volume of the composition, any specific percentage in the given range, or any percentage subrange within the given range.

In one embodiment the compounds of the present invention are combined with a petroleum-based fuel, for example, gasoline, diesel, jet fuel, kerosene, heating oil or any combinations thereof, to provide a fuel composition. In a specific embodiment, MBO is combined with gasoline, with the purpose of providing oxygen and increasing the octane content of the fuel composition. In another specific embodiment, an MBO ether is combined with a petroleum-based diesel, e.g., a distillate, with the purpose of providing oxygen and increasing cetane content.

In another embodiment the compounds of the present invention are combined with another biofuel, for example, methanol, ethanol, propanol, butanol or any combinations thereof, to provide a fuel composition.

In another embodiment the compounds of the present invention are combined with a petroleum-based fuel and another biofuel. In a specific embodiment, MBO is combined with ethanol to reduce the Reid vapor pressure (RVP) of an ethanol-gasoline mixture.

Bio-crudes are biologically produced compounds or a mix of different biologically produced compounds that are used as a feedstock for petroleum refineries in replacement of, or in complement to, crude oil. In general, but not necessarily, these feedstocks have been pre-processed through biological, chemical, mechanical or thermal processes in order to be in a liquid state that is adequate for introduction in a petroleum refinery.

Microbial Hosts

Microbial hosts of the invention may be selected from but not limited to archaea, bacteria, cyanobacteria, fungi, yeasts, thraustochytrids and photosynthetic microorganisms. In certain embodiments, examples of criteria for selection of suitable microbial hosts include the following: intrinsic tolerance to desired product, high rate of glucose or alternative carbon substrate utilization, availability of genetic tools for gene manipulation, and the ability to generate stable chromosomal alterations. However, the present invention should not be interpreted to be limited by these criteria.

The microbial host used for MBO or MBO derivative production is preferably tolerant to MBO or MBO derivatives so that the yield is not limited by product toxicity. Suitable host strains with a tolerance for MBO or MBO derivatives may be identified by screening based on the intrinsic tolerance of the strain. The intrinsic tolerance of microbes to MBO or MBO derivatives may be measured by determining the concentration of MBO or MBO derivatives that is responsible for 50% inhibition of the growth rate ($IC_{50}$) when grown in a minimal culture medium. The $IC_{50}$ values may be determined using methods known in the art. For example, the microbes of interest may be grown in the presence of various amounts of MBO or MBO derivatives and the growth rate monitored by measuring the optical density. The doubling time may be calculated from the logarithmic part of the growth curve and used as a measure of the growth rate. The concentration of MBO or of the MBO derivative that produces 50% inhibition of growth may be determined from a graph of the percent inhibition of growth versus the concentration of MBO or MBO derivative. In some embodiments, the host strain should have an $IC_{50}$ for MBO or MBO derivative of greater than 0.5%. The $IC_{50}$ value can be similarly calculated for microbes in contact with compounds other than MBO.

The ability to genetically modify the host is essential for the production of any recombinant microorganism. The mode of gene transfer technology may be by electroporation, conjugation, transduction or natural transformation. A broad range of host conjugative plasmids and drug resistance and nutritional markers are available. The cloning vectors are tailored to the host organisms based on the nature of antibiotic resistance markers that can function in that host.

In some embodiments, the microbial host also may be manipulated in order to inactivate competing pathways for carbon flow by deleting various genes. This may require the ability to direct chromosomal integration events. Additionally, the production host should be amenable to chemical mutagenesis so that mutations to improve intrinsic product tolerance may be obtained.

Microbial hosts of the invention may be selected from but not limited to archaea, bacteria, cyanobacteria, fungi, yeasts, thraustochytrids and photosynthetic microorganisms. Examples of suitable microbial hosts for use with the disclosed invention include, but are not limited to, members of the genera *Clostridium, Zymomonas, Escherichia, Salmonella, Rhodococcus, Pseudomonas, Bacillus, Lactobacillus, Enterococcus, Alcaligenes, Klebsiella, Paenibacillus, Arthrobacter, Corynebacterium, Brevibacterium, Pichia, Candida, Hansenula,* and *Saccharomyces*. Examples of particular bacteria hosts include but are not limited to *Escherichia coli, Corynebacterium glutamicum, Pseudomonas putida, Bacillus subtilis, Rhodopseudomonas palustris, Rhodobacter sphaeroides, Micrococcus luteus, Streptomyces coelicolor, Streptomyces griseus, Lactobacillus fermentum, Lactococcus lactis, Lactobacillus bulgaricus, Acetobacter xylinum, Streptococcus lactis, Bacillus stearothermophilus, Propionibacter shermanii, Streptococcus thermophilus, Deinococcus radiodurans, Delftia acidovorans, Enterococcus faecium, Pseudomonas mendocina,* and *Serratia marcescens*. Examples of particular yeast hosts include but are not limited to *Saccharomyces cerevisiae, Saccharomyces carlsbergensis, Kluyveromyces lactis, Kluyveromyces marxianus, Yarrowia lipolytica, Debaryomyces hansenii, Ashbya gossypii, ZygoSaccharomyces rouxii, ZygoSaccharomyces bailii, Brettanomyces bruxellensis, SchizoSaccharomyces pombe, Rhodotorula glutinis, Pichia stipitis, Pichia pastoris, Candida tropicalis, Candida utilis* and *Candida guilliermondii*. Examples of particular fungal hosts include but are not limited to *Aspergillus niger, Aspergillus oryzae, Neurospora crassa, Fusarium venenatum* and *Penicillium chrysogenum*. Examples of particular photosynthetic microorganism hosts include but are not limited to *Anabaena* sp., *Chlamydomonas reinhardtii, Chlorella* sp., *Cyclotella* sp., *Gloeobacter violaceus, Nannochloropsis* sp., *Nodularia* sp., *Nostoc* sp., *Prochlorococcus* sp., *Synechococcus* sp., *Oscillatoria* sp., *Arthrospira* sp., *Lyngbya* sp., *Dunaliella* sp., and *Synechocystis* sp. Examples of particular thraustochytrid hosts include but are not limited to *Schizochytrium* sp. and *Thraustochytrium* sp.

Construction of Production Host

Recombinant organisms containing the necessary genes that will encode the enzymatic pathway for the conversion of a carbon source to MBO or another compound of interest may be constructed using techniques well known in the art. In the present invention, genes encoding the enzymes of one of the MBO biosynthetic pathways of the invention may be isolated from various sources. Non-limiting examples of enzymes which can be used are discussed above.

Methods of obtaining desired genes from a bacterial genome are common and well known in the art of molecular biology. For example, if the sequence of the gene is known, suitable genomic libraries may be created by restriction endonuclease digestion and may be screened with probes complementary to the desired gene sequence. Once the sequence is isolated, the DNA may be amplified using standard primer-directed amplification methods such as polymerase chain reaction (U.S. Pat. No. 4,683,202) to obtain amounts of DNA suitable for transformation using appropriate vectors. Tools for codon optimization for expression in a heterologous host are readily available. Some tools for codon optimization are available based on the GC content of the host organism.

Once the relevant pathway genes are identified and isolated they may be transformed into suitable expression hosts by means well known in the art. Vectors or cassettes useful for the transformation of a variety of host cells are common and commercially available from companies such as EPICENTRE® (Madison, Wis.), Invitrogen Corp. (Carlsbad, Calif.), Stratagene (La Jolla, Calif.), and New England Biolabs, Inc. (Beverly, Mass.). Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. Both control regions may be derived from genes homologous to the transformed host cell, although it is to be understood that such control regions may also be derived from genes that are not native to the specific species chosen as a production host.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, TEF, CYC1, HIS3, GAL1, GAL10, ADH1, PGK, PHO5, GAPDH, ADC1, TRP1, URA3, LEU2, ENO, TPI, CUP1, FBA, GPD, and GPM (useful for expression in *Saccharomyces*); AOX1 (useful for expression in *Pichia*); and lac, ara, tet, trp, $IP_L$, $IP_R$, T7, tac, and trc (useful for expression in *Escherichia coli, Alcaligenes*, and *Pseudomonas*); the amy, apr, npr promoters and various phage promoters useful for expression in *Bacillus subtilis, Bacillus licheniformis*, and *Paenibacillus macerans*; nisA (useful for expression Gram-positive bacteria, Eichenbaum et al. Appl. Environ. Microbiol. 64(8):2763-2769 (1998)); and the synthetic P11 promoter (useful for expression in *Lactobacillus plantarum*, Rud et al., Microbiology 152:1011-1019 (2006)).

Termination control regions may also be derived from various genes native to the preferred hosts. Optionally, a termination site may be unnecessary.

Certain vectors are capable of replicating in a broad range of host bacteria and can be transferred by conjugation. The complete and annotated sequence of pRK404 and three related vectors—pRK437, pRK442, and pRK442(H) are available. These derivatives have proven to be valuable tools for genetic manipulation in Gram-negative bacteria (Scott et al., Plasmid 50(1):74-79 (2003)). Several plasmid derivatives of broad-host-range Inc P4 plasmid RSF1010 are also available with promoters that can function in a range of Gram-negative bacteria. Plasmid pAYC36 and pAYC37, have active promoters along with multiple cloning sites to allow for the heterologous gene expression in Gram-negative bacteria.

Chromosomal gene replacement tools are also widely available. For example, a thermosensitive variant of the broad-host-range replicon pWV101 has been modified to construct a plasmid pVE6002 which can be used to effect gene replacement in a range of Gram-positive bacteria (Maguin et al., J. Bacteriol. 174(17):5633-5638 (1992)). Additionally, in vitro transposomes are available to create random mutations in a variety of genomes from commercial sources such as EPICENTRE®.

Culture Media and Conditions

Culture medium in the present invention contains suitable carbon source. In addition to an appropriate carbon source, culture medium typically contains suitable minerals, salts, cofactors, buffers and other components, known to those skilled in the art, suitable for the growth of the cultures and promotion of the enzymatic pathway necessary for MBO production, as well as the production of other compounds.

Typically cells are grown at a temperature in the range of 25° C. to 40° C. in an appropriate medium. Suitable growth media in the present invention are common commercially prepared media such as Luria Bertani (LB) broth, Sabouraud Dextrose (SD) broth or Yeast medium (YM) broth. Other defined or synthetic growth media may also be used, and the appropriate medium for growth of the particular microorganism will be known by one skilled in the art of microbiology or fermentation science. Suitable pH ranges for the fermentation are between pH 5.0 to pH 9.0. In some embodiments the initial pH is 6.0 to pH 8.0. Microorganism culture may be performed under aerobic, anaerobic, or microaerobic conditions.

Synthesis of Ethers from 2-methyl-1-butanol or 3-methyl-1-butanol

Oxygenated additives can be used to boost the performance of fuels. Ethers have a much lower water absorbance than alcohols and can be used as a cetane enhancer. One method of the preparation of ethers is the intermolecular condensation of an alcohol using an acid catalyst. This method is used industrially. U.S. Pat. No. 6,218,583 (Apr. 17, 2001) describes the production of n-pentyl ether.

In one aspect, the invention provides a method to chemically convert biosynthetically prepared 2-methyl-1-butanol and 3-methyl-1-butanol to their corresponding ethers, 1-(isopentyloxy)-3-methylbutane and 2-methyl-1-(2-methylbutoxy)butane respectively. The structures are shown below.

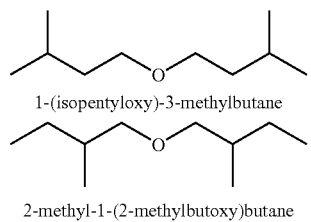

1-(isopentyloxy)-3-methylbutane 2-methyl-1-(2-methylbutoxy)butane

These two ethers are also be referred to as bis-(3-methylbutyl)ether and bis-(2-methylbutyl)ether, respectively. 'Methylbutanol' as used herein, refers to either 2-methylbutanol or 3-methylbutanol. Additional ethers include

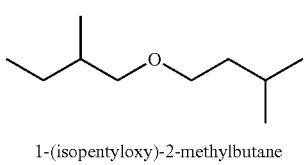

1-(isopentyloxy)-2-methylbutane

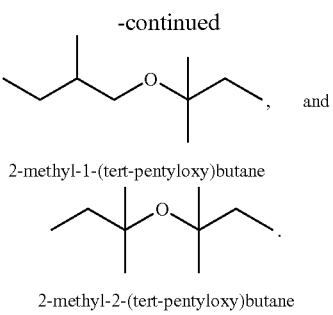

2-methyl-1-(tert-pentyloxy)butane 2-methyl-2-(tert-pentyloxy)butane

In one embodiment, the conversion step of converting methylbutanol to methylbutyl ether comprises treating the methylbutanol with an acid resulting in the formation of methylbutyl ether. Non-limiting examples of acids include hydrochloric acid, hydrobromic acid, sulfuric acid, nitric acid, phosphoric acid, chromic acid, sulfonic acids (methane-, ethane-, benzene-, toluene-, trifluoromethyl-), perfluoroalkane sulfonic acids. In one embodiment, the acid is trifluoromethyl sulfonic acid, $CF_3SO_3H$. In alternative embodiments, the reaction is a heterogeneous mixture and takes place with a solid phase acid catalyst, polymer-bound, or resin-bound acid catalyst. The advantage of this method is that the acid catalyst is easily separated from the reaction mixture.

In certain embodiments, the catalytic amount of acid at the start of the reaction sequence is between 0.001 and 0.20 molar equivalents relative to the alcohol. In other embodiments, the catalytic amount of acid is between 0.001 and 0.05 molar equivalents relative to the alcohol. In other embodiments, the catalytic amount of acid is less than 0.04 molar equivalents relative to the alcohol. In other embodiments, the catalytic amount of acid is less than 0.03 molar equivalents relative to the alcohol. In other embodiments the catalytic amount of acid is between 0.015 and 0.035 molar equivalents relative to the alcohol.

In certain embodiments, the reaction temperature is between 75-400° C. In certain embodiments the reaction temperature is between 75-150° C. In certain embodiments the reaction temperature is between the temperature of the boiling point of the ether and that of the alcohol (2-methyl-1-butanol b.p. 128° C.; 3-methyl-1-butanol b.p. 132° C. In certain embodiments the reaction temperature is the boiling point of the reaction mixture and thus varies depending on the composition of the reaction mixture.

In one embodiment, the conversion step of converting methylbutanol to methylbutyl ether comprises refluxing a solution comprising methylbutanol and a catalytic amount of acid, and removal of water generated from the solution. Removal of the byproduct water generated in the dehydration reaction can be carried out by distillation and shifts the chemical equilibrium in favor of ether formation. Toward the end of the reaction, the mixture may be further neutralized and the ether product isolated. The product may be isolated through any technique known in the art such as extraction, filtration, chromatography, distillation, vacuum distillation or any combination thereof.

Removal of the water generated during the reaction can be carried out with a Dean-Stark or Dean-stark-like apparatus. The Dean-Stark apparatus or Dean-Stark receiver or distilling trap is a piece of laboratory glassware used in synthetic chemistry to collect water (or occasionally other liquid) from a reactor. It is used in combination with a reflux condenser and a batch reactor for continuous removal of the water that is produced during a chemical reaction performed at reflux temperature.

The progress of the reaction may be monitored by sampling the reaction mixture and analyzing the composition. Analysis can be carried out with a number of analytical techniques or instruments such as gas chromatography, high pressure liquid chromatography, nuclear magnetic resonance spectroscopy, and mass spectroscopy. An estimate of reaction progress can also be determined by separating and measuring the amount of water by-product from the reaction mixture.

In one embodiment, the methylbutyl ether product is bis-(3-methylbutyl)ether, bis-(2-methylbutyl)ether, 1-(isopentyloxy)-2-methylbutane, or any combination thereof. Reaction of a single alcohol species produces the corresponding symmetrical ether, such as bis-(3-methylbutyl)ether, bis-(2-methylbutyl)ether. Reaction of alcohols that are composed of mixtures of alcohols, such as 3-methyl-1-butanol and 2-methyl-1-butanol, can result in the formation of both symmetrical and mixed ethers. 1-(isopentyloxy)-2-methylbutane is an example of the mixed ether.

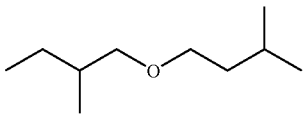

1-(isopentyloxy)-2-methylbutane

Alternatively, ethers can be produced by Williamson ether synthesis. This synthesis consists of a bimolecular nucleophilic substitution reaction between a sodium alkoxide with an alkyl halide, alkyl sulfonate, or alkyl sulfate. For example, the reaction of 1-bromo-3-methyl butane and sodium-2-methylbutan-1-olate yields the mixed ether. Likewise, the reaction of sodium-2-methylbutan-1-olate with 1-bromo-2-methylbutane yields the symmetrical bis-(2-methylbutyl)ether and the reaction of sodium-3-methylbutan-1-olate with 1-bromo-3-methylbutane yields the symmetrical bis-(3-methylbutyl) ether. Reaction conditions can be determined experimentally by a person having ordinary skill in the art.

Carbon Fingerprinting

Compositions that are derived from the biosynthetic methods described herein can be characterized by carbon fingerprinting, and their lack of impurities when compared to petroleum derived fuels. Carbon fingerprinting is valuable in distinguishing MBO and other compounds of interest by the biosynthetic methods described herein from other methods.

Biologically produced compounds of interest described here represent a new source of fuels, such as alcohols, diesel, and gasoline. These new fuels can be distinguished from fuels derived form petrochemical carbon on the basis of dual carbon-isotopic fingerprinting. Additionally, the specific source of biosourced carbon (e.g., glucose vs. glycerol) can be determined by dual carbon-isotopic fingerprinting (see U.S. Pat. No. 7,169,588, which is herein incorporated by reference in its entirety, in particular, see col. 4, line 31, to col. 6, line 8).

The compounds of interest and the associated biofuels, chemicals, and mixtures may be completely distinguished from their petrochemical derived counterparts on the basis of $^{14}C$ ($f_M$) and dual carbon-isotopic fingerprinting.

The compounds of interest described herein have utility in the production of biofuels, chemicals, and biochemicals. For example, MBO and derivatives thereof can be used as a solvent, and in the flavor and fragrance industry. The new products provided by the instant invention additionally may be distinguished on the basis of dual carbon-isotopic fingerprinting from those materials derived solely from petrochemical sources. The ability to distinguish these products is beneficial in tracking these materials in commerce. For example, fuels or chemicals comprising both "new" and "old" carbon isotope profiles may be distinguished from fuels and chemicals made only of "old" materials. Thus, the instant materials may be followed in commerce or identified in commerce as a biofuel on the basis of their unique profile. In addition, other competing materials can be identified as being biologically derived or derived from a petrochemical source.

The compounds of interest described herein have further utility in the production of biodiesels, for example, for transesterification of vegetable oil, animal fats, or wastes thereof. Further uses of the compounds described herein are readily known to one of skill in the art, for example, general chemical uses, and uses as a solvent.

In a non-limiting example, a biofuel composition is made that includes compounds of interest having δ13C of from about −10.9 to about −15.4, wherein the compound or compounds accounts for at least about 85% of biosourced material (i.e., derived from a renewable resource such as cellulosic materials and sugars) in the composition.

The following examples are offered to illustrate but not to limit the invention.

EXAMPLE 1

Increase of Intracellular Threonine

As series of genes encoding enzymes from glucose to threonine were cloned from *Saccharomyces cerevisiae* and *Pichia stipitis*. These genes were tested for functional activity, either by enzyme assay or complementation of deletion mutations in *Saccharomyces cerevisiae* and profiling of intracellular amino acids.

Below are a series of experiments that highlight genes required for elevated threonine production FIGS. 6 through 16 show amino acid production by the overexpression of pathway genes in particular deletion backgrounds.

Amino Acid Analysis of MDH2 (7432), THR1 (7239) and PCK1 (8110) Expressed from p415TEF in Strain 7123

Figure 6:
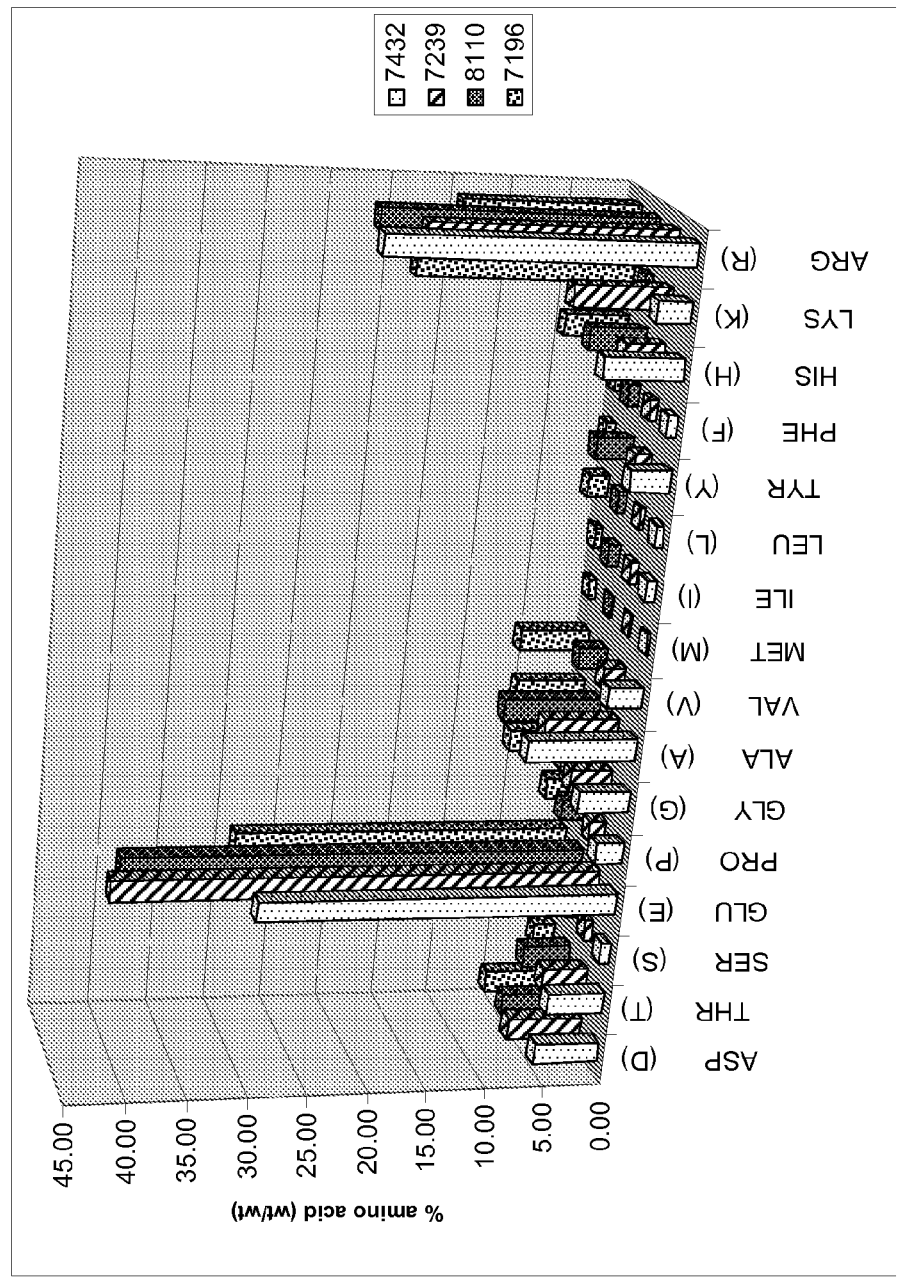
FIG. 6. Amino acid analysis of MDH2 (7432), THR1 (7239) and PCK1 (8110) expressed from p415TEF in strain 7123 (ATCC 200869 (MATα ade2Δ::hisG his3Δ200 leu2Δ0 lys2Δ0 met15Δ0 trp1Δ63 ura3Δ0). Strain 7196 (7123 containing empty p415TEF) was included as a control. Significant differences in L-threonine content were observed in cultures expressing MDH2 and PCK1 only. Amino acid values are expressed as a percentage of individual amino acids in the total amino acid content of the cells.

The impact of various expression vectors encoding different genes of interest on amino acid levels was made. For this analysis, constructs containing the MDH2 (7432), THR1 (7239) and PCK1 (8110) genes on the p415TEF expression vector were introduced into host strain 7123 (ATCC 200869 (MATα ade2Δ::hisG his3Δ200 leu2Δ0 lys2Δ0 met15Δ0 trp1Δ63 ura3Δ0). Strain 7196 (7123 containing empty p415TEF) was included as a control. Cultures were grown overnight in selective medium. Cells were pelleted, washed with sodium phosphate buffer (50 mM, pH 7.0), and extracted by bead beating in warm (50° C.) 80% ethanol. The data is shown in FIG. 6. As depicted, significant differences in L-threonine content were observed in cultures expressing MDH2 and PCK1 only. Amino acid values are expressed as a percentage of individual amino acids in the total amino acid content of the cells.

Amino Acid Analysis of HOM3 (7245) and HOM3-R2 (7242) Expressed from p416TEF in Strain 7123

Figure 7:
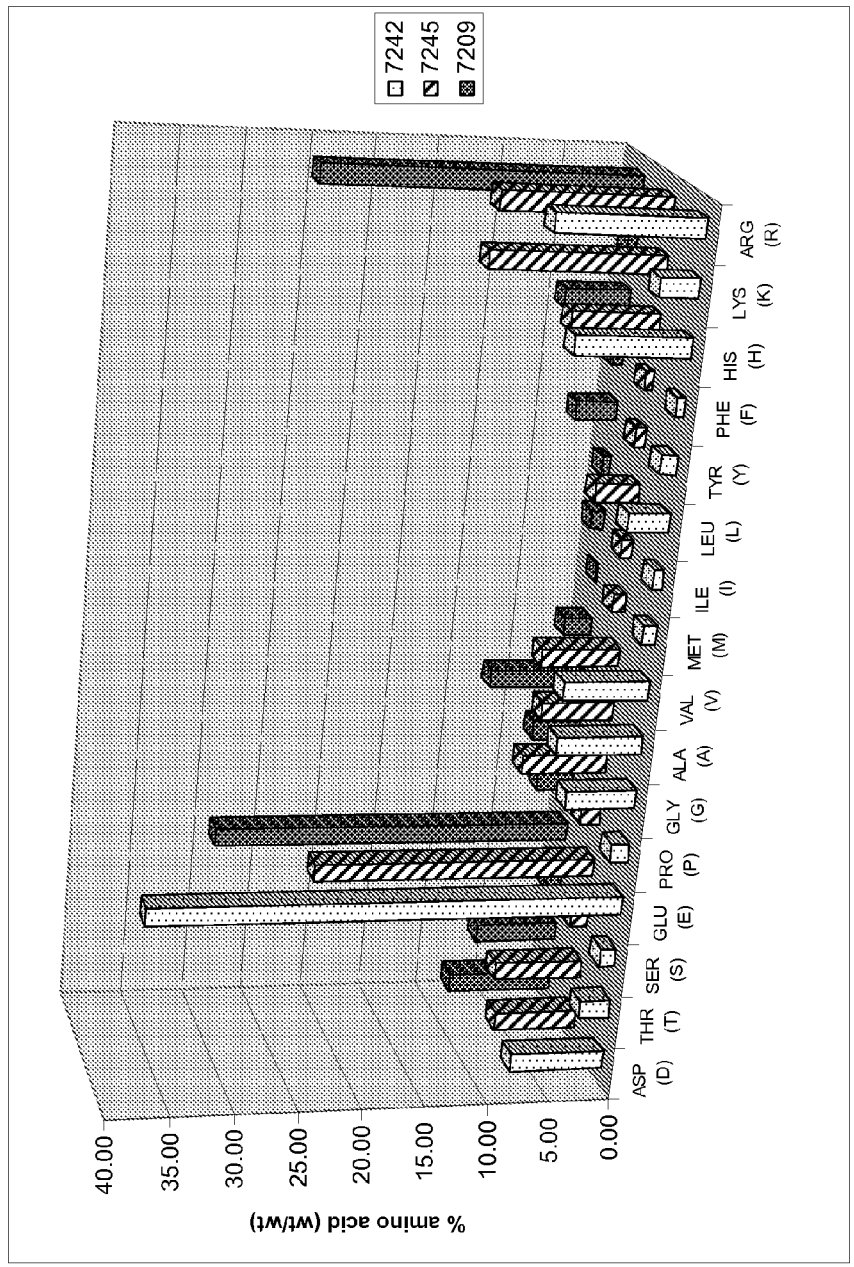
FIG. 7. Shows a bar graph of an amino acid analysis of HOM3 (7245) and HOM3-R2 (7242) expressed from p416TEF in strain 7123. Strain 7123 with empty p416TEF (7209) was included as a control. Significantly lower L-threonine content was observed in cultures expressing HOM3-R2, whereas no significant difference was observed for wild-type HOM3 and the background strain 7209. Amino acid values are expressed as a percentage of individual amino acids in the total amino acid content of the cells.

HOM3 (7245) and HOM3-R2 (7242) expressed from p416TEF in strain 7123 were analyzed. Strain 7123 with an empty expression vector (p416TEF)(7209) was included as a control. Cultures were grown overnight in selective medium and extracted as above. The data is shown in FIG. 7. Significantly lower L-threonine content was observed in cultures expressing HOM3-R2, whereas no significant difference was observed for wild-type HOM3 and the background strain 7209. Amino acid values are expressed as a percentage of individual amino acids in the total amino acid content of the cells.

Amino Acid Analysis of *S. cerevisiae* HOM3 and HOM3-R2 Expressed from p416TEF or p416CYC in Strain 7790 (BY4741 ΔHOM3::KanMX)

Figure 8:
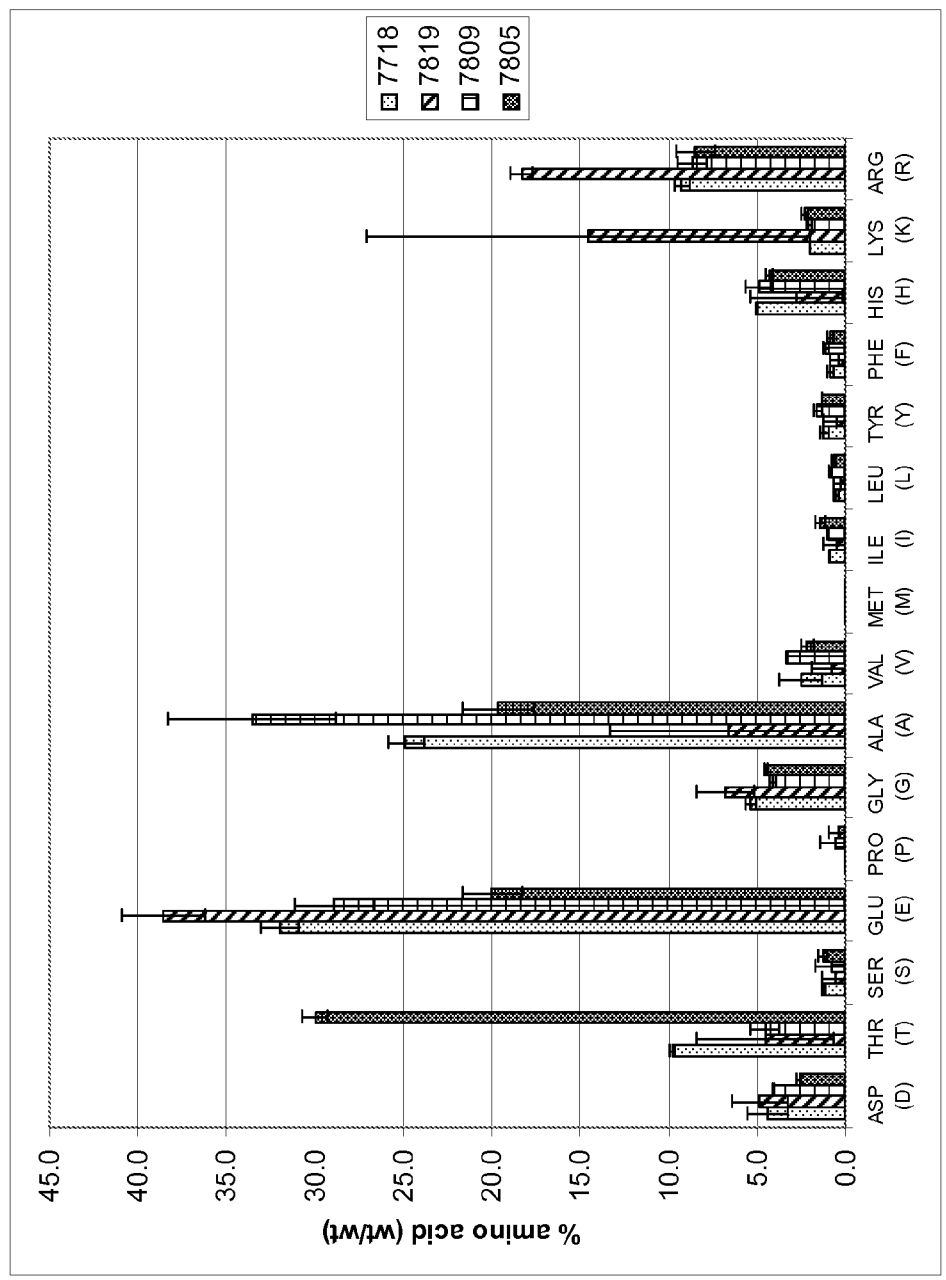
FIG. 8. Shows a bar graph of an amino acid analysis of S. cerevisiae HOM3 and HOM3-R2 expressed from p416TEF or p416CYC in strain 7790 (BY4741 ΔHOM3::KanMX). Strains are p416TEF-HOM3 (7718), p416TEF-HOM3-R2 (7819), p416CYC-HOM3 (7809) and p416CYC-HOM3-R2 (7805). Cultures were grown overnight in a defined medium lacking threonine and isoleucine to select for HOM3 expression. Significantly higher L-threonine content was observed in cultures expressing HOM3-R2 from the CYC promoter as compared to the TEF promoter. A significant increase in L-threonine content was also observed when wild-type HOM3 was expressed from TEF as compared to the CYC promoter. The total L-threonine content of the cells in the CYC expressed HOM3-R2 culture reached 30% (wt/wt). Amino acid values are expressed as a percentage of individual amino acids in the total amino acid content of the cells.

Host organisms containing expression vectors p416TEF-HOM3 (7718), p416TEF-HOM3-R2 (7819), p416CYC-HOM3 (7809), and p416CYC-HOM3-R2 (7805) were prepared. Cultures were grown overnight in a defined medium lacking threonine and isoleucine to select for HOM3 expression. Cells were grown and extracted as before. The results are shown in FIG. 8. Significantly higher L-threonine content was observed in cultures expressing HOM3-R2 from the CYC promoter as compared to the TEF promoter. A significant increase in L-threonine content was also observed when wild-type HOM3 was expressed from TEF as compared to the CYC promoter. The total L-threonine content of the cells in the CYC expressed HOM3-R2 culture reached 30% (wt/wt). Amino acid values are expressed as a percentage of individual amino acids in the total amino acid content of the cells.

Figure 9:
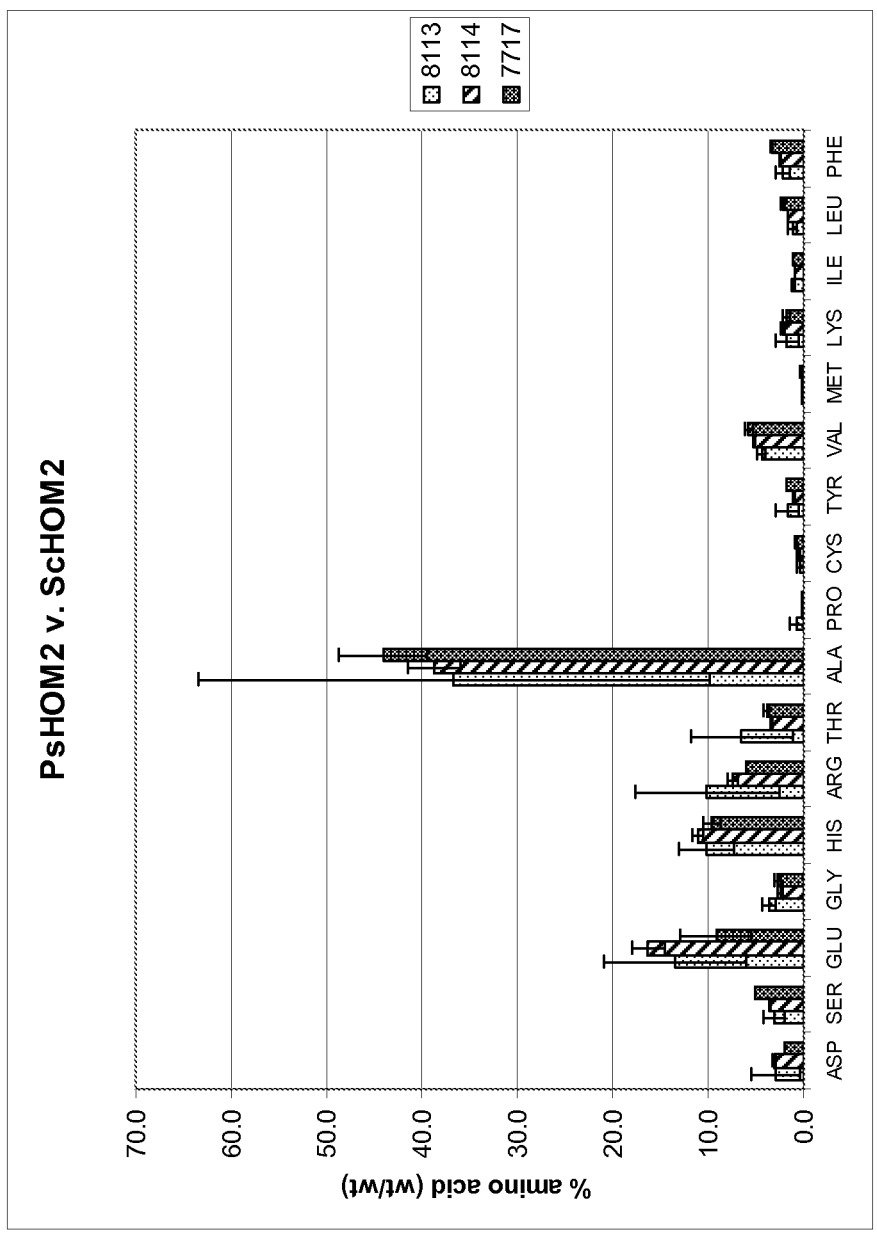
FIG. 9. Shows a bar graph of an amino acid analysis of S. cerevisiae strains; 8113 (ΔHOM2) with p416TEF, 8114 p416TEF-PsHOM2, and 7717 p416TEF-ScHOM2
Figure 10:
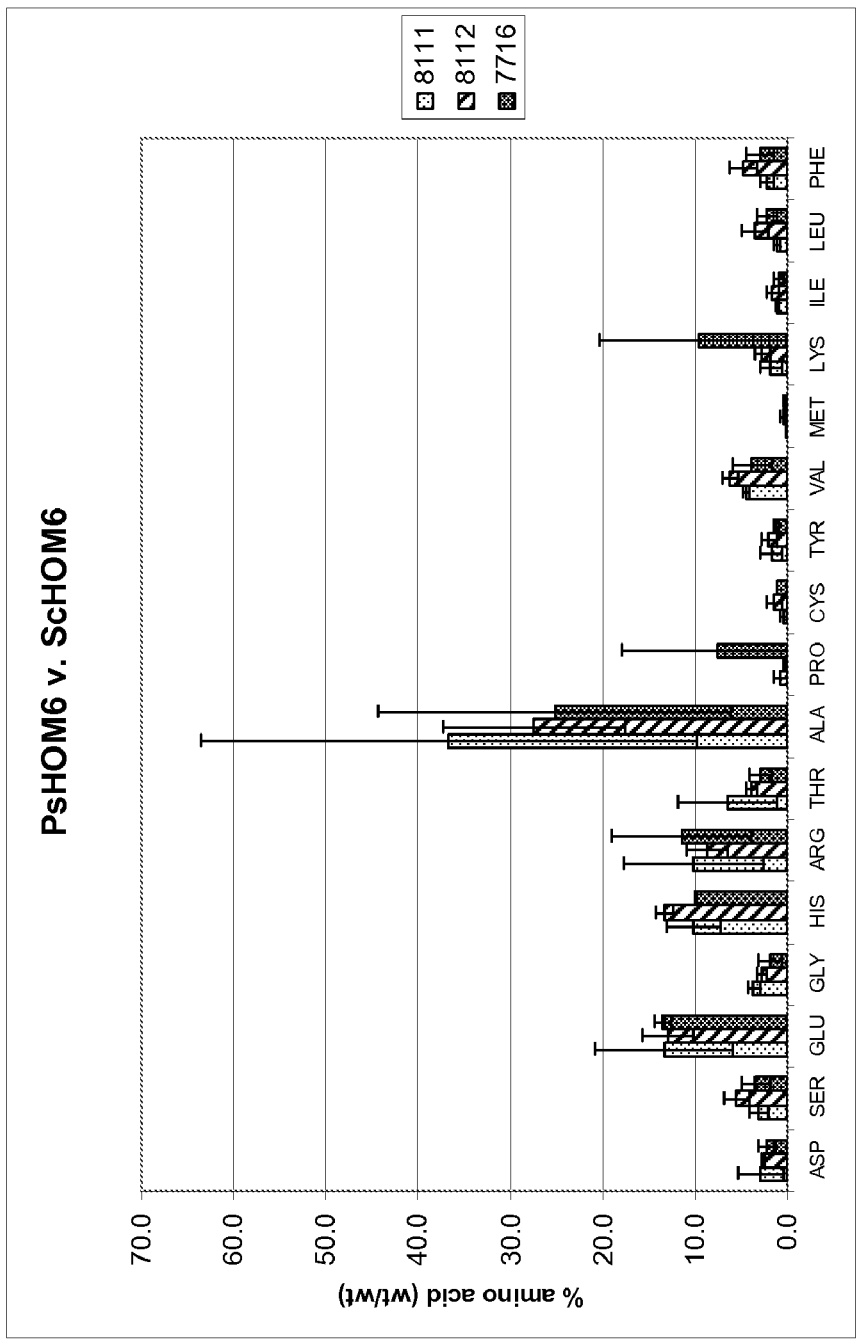
FIG. 10. Shows a bar graph of an amino acid analysis of S. cerevisiae strains 8111 (ΔHOM6) with p415TEF, 8112 p415TEF-PsHOM6, and 7716 p415TEF-ScHOM6
Figure 11:
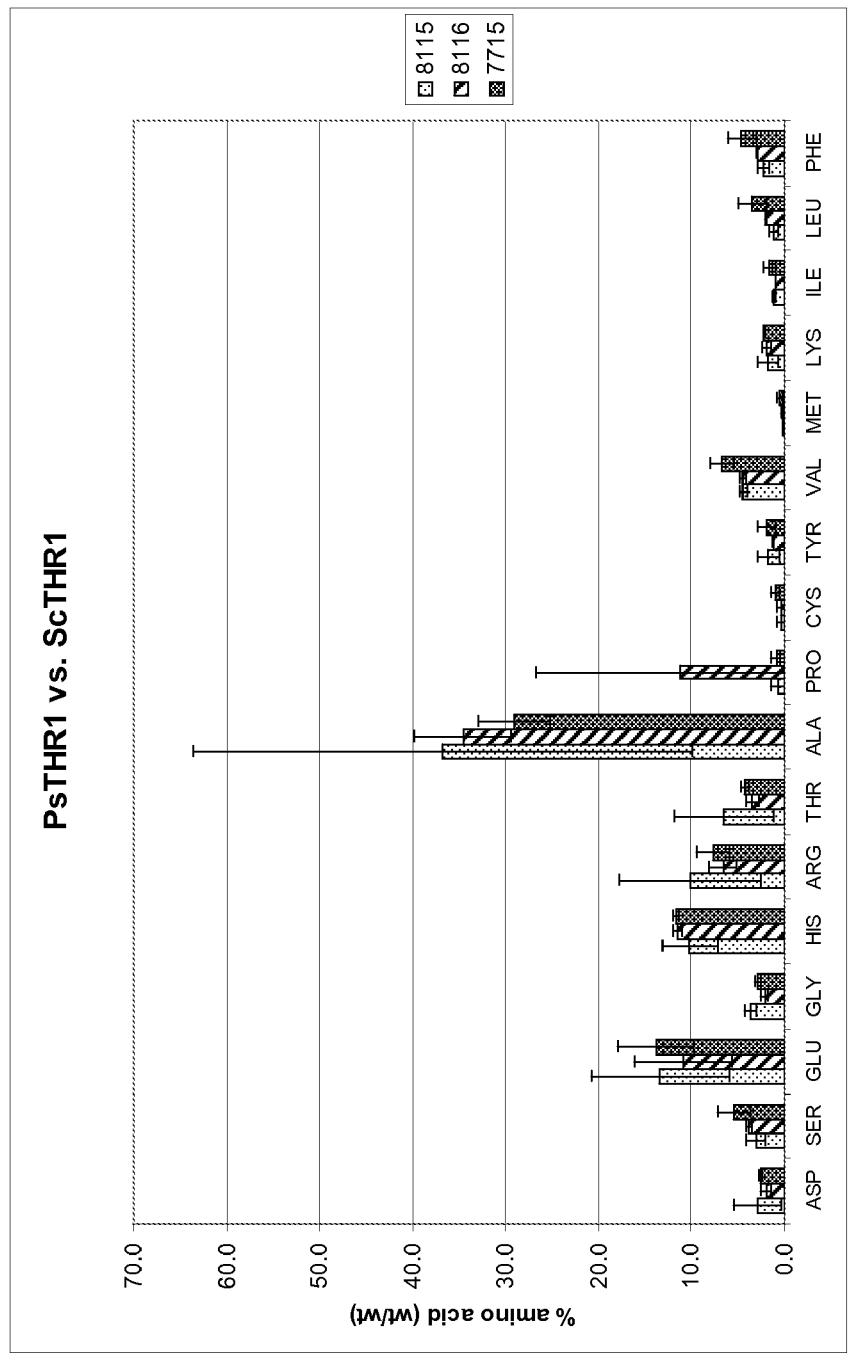
FIG. 11. Shows a bar graph of an amino acid analysis of S. cerevisiae strains 8115 (ΔTHR1) with p415TEF, 8116 p415TEF-PsTHR1, and 7715 p415TEF-ScTHR1
Figure 13:
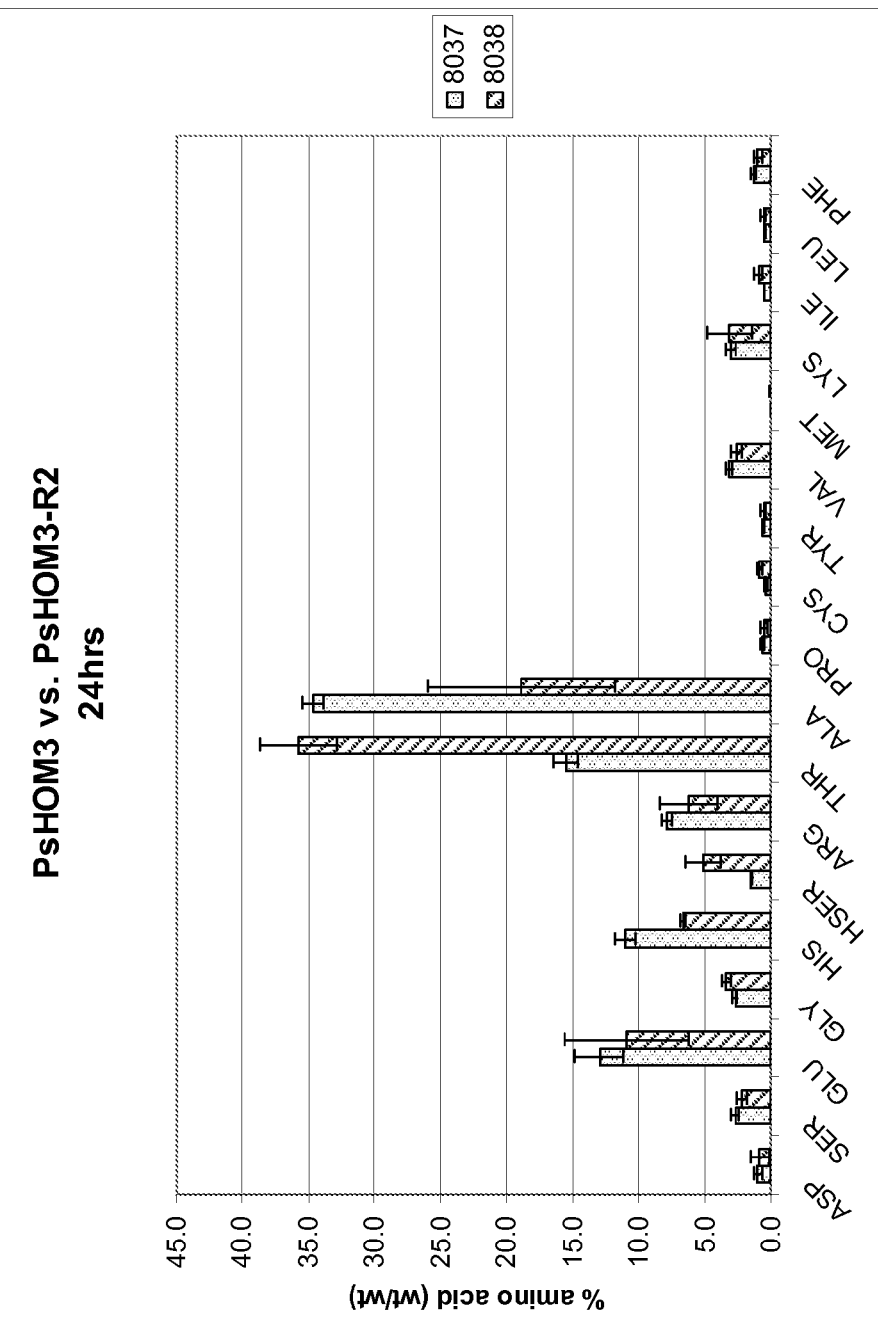
FIG. 13. Shows a bar graph of an amino acid analysis of P. stipitis HOM3 (8037) and HOM3-R2 (8038) expressed from p416TEF in strain 7790 (BY4741 ΔHOM3::KanMX). Cells were grown in defined medium lacking threonine and isoleucine for approximately 24 hrs and extracted as previously stated. Levels of L-threonine were significantly higher in the HOM3-R2 variant, and approached 35% of the total amino acid content of the cells. Although no direct comparison was made, in 7790 the S. cerevisiae HOM3-R2 variant expressed from CYC promoter achieved 30% threonine content compared to 35% for the P. stipitis HOM3-R2 mutant expressed from TEF. The wild-type HOM3 from P. stipitis was also found to produce more threonine than wild-type HOM3 from S. cerevisiae (15% vs. 10%) in strain 7790. Amino acid values are expressed as a percentage of individual amino acids in the total amino acid content of the cells.
Figure 14:
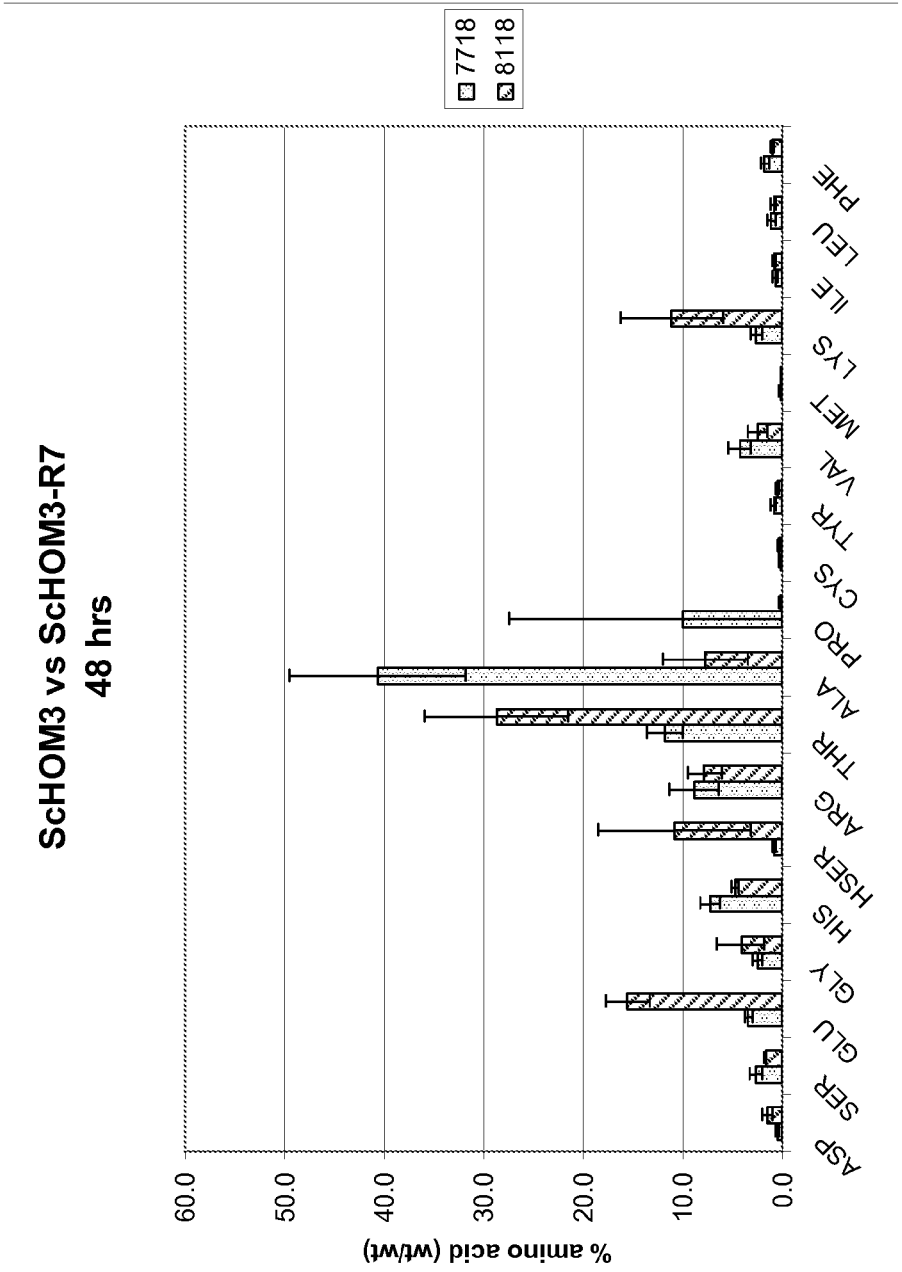
FIG. 14. Shows a bar graph of an amino acid analysis of HOM3 (7718) and HOM3-R7 (8118) expressed from p416TEF in strain 7790 (BY4741 ΔHOM3::KanMX). Cultures were grown for 48 hrs in a defined medium lacking threonine and isoleucine to select for HOM3 complementation. The slow growth of the cells expressing the R7 mutation necessitated the extra 24 hrs of growth compared to cultures expressing the R2 mutation. Significantly higher L-threonine content was observed in cultures expressing HOM3-R7 from the TEF promoter compared to the native HOM3. The total L-threonine content of the cells in the TEF expressed HOM3-R7 culture reached 28% (wt/wt). Amino acid values are expressed as a percentage of individual amino acids in the total amino acid content of the cells.
Figure 15:
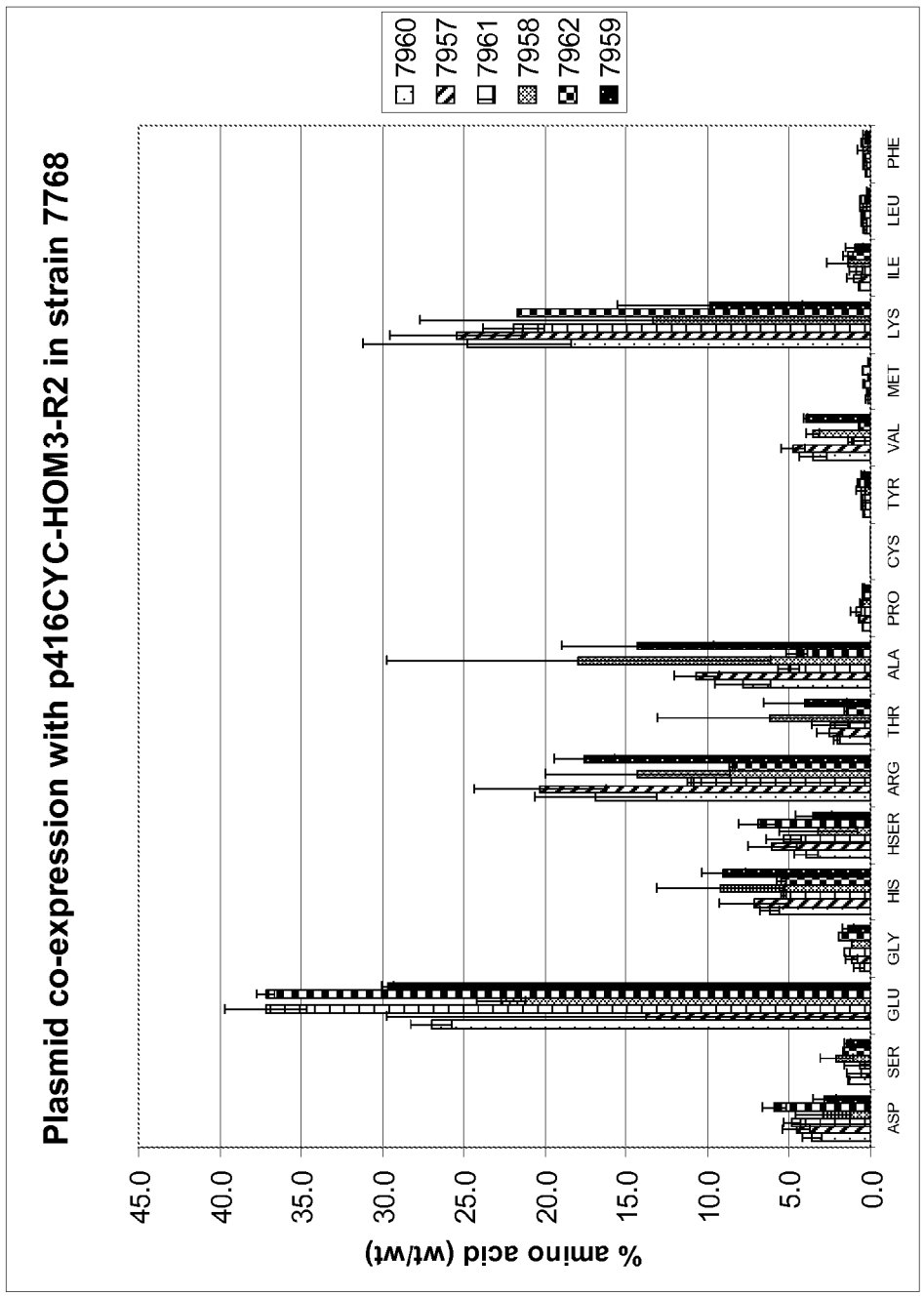
FIG. 15. Shows a bar graph of an amino acid analysis of co-expression of AAT1 (7957), AAT2 (7961), MDH1 (7958), MDH2 (7962) and PCK (7959) together with HOM3-R2. Strain 7960 contained an empty p415TEF plasmid as a control. All enzymes were expressed from p415TEF, with the exception of HOM3-R2, which was expressed from p416CYC. Constructs were made in strain 7768 (BY4741 ILV1::TEF-Ilv1-fbr). Cultures were grown for 24 hrs in a defined medium lacking threonine and isoleucine and cells were prepared for amino acid analysis as described previously. Levels of amino acids were similar, and threonine content was significantly lower than that found in strains containing a wild-type ILV1, indicating that threonine is limiting in 2-MBO production. In cells expressing AAT2 and MDH2, higher levels of homoserine were observed, consistent with what was observed when HOM3-R2 was expressed by itself. Specifically, the 7% homoserine content found in the culture expressing MDH2 with HOM3-R2 was the highest seen in any culture tested, indicating THR1 limitation and potentially higher flux through the Asp/Thr pathway than HOM3-R2 alone. Also of note is the significantly higher alanine content when PCK is expressed with HOM3-R2, potentially indicating an increase in pyruvate concentration, leading to increased alanine. Amino acid values are expressed as a percentage of individual amino acids in the total amino acid content of the cells.

Amino Acid Analysis of *Pichia stipitis* and *Saccharomyces cerevisiae* HOM2, HOM6 and THR1 Expressed from the TEF Promoter in their Respective Deletion Backgrounds The host organisms used in these experiments were: FIG. 9: 8113=7578 (ΔHOM2) with p416TEF, 8114=7578 with p416TEF-PsHOM2, 7717=7578 p416TEF-ScHOM2; FIG. 10: 8111=7582 (ΔHOM6) with p415TEF, 8112=7582 p415TEF-PsHOM6, 7716=7582 p415TEF-ScHOM6; FIG. 11: 8115=7583 (ΔTHR1) with p415TEF, 8116=7583 p415TEF-PsTHR1, 7715=7583 p415TEF-ScTHR1. Cultures were grown overnight in a defined medium lacking threonine and isoleucine to select for complementation of chromosomal deletions. Complementation of the last gene in the threonine pathway, THR4, was not possible due to ΔTHR4 strain growing on media lacking threonine and isoleucine. Cells were grown and extracted as described before. Results are shown in FIGS. 13 to 15. No significant differences in any amino acid were observed when compared to the background BY4741 strain. Amino acid values are expressed as a percentage of individual amino acids in the total amino acid content of the cells.

Figure 12:
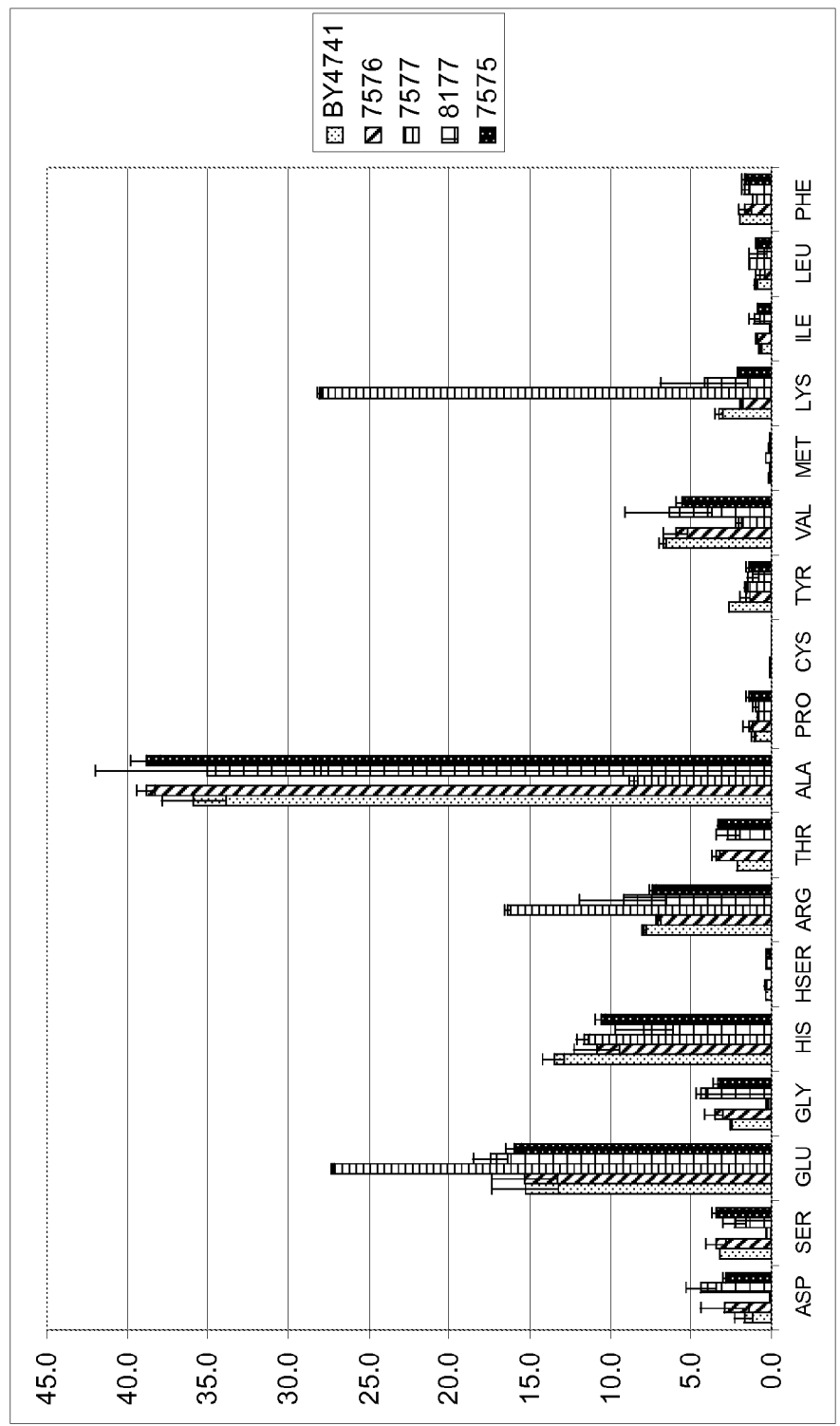
FIG. 12. Shows a bar graph of an amino acid composition in BY4741 parental strain and KanMX deletions of L-threonine pathway enzymes in that background. Strains are as follows: 7576=(ΔAAT1), 7577=(ΔAAT2), 8177=(ΔMDH1) and 7575=(ΔMDH2). Levels of amino acids were not significantly different for any strain other than ΔAAT2, which produced no detectable threonine and significantly higher levels of lysine, glutamate/glutamine and arginine. Amino acid values are expressed as a percentage of individual amino acids in the total amino acid content of the cells.

Amino Acid Composition in BY4741 Parental Strain and KanMX Deletions of L-Threonine Pathway Enzymes in that Background The host organisms used in these experiments were: 7576= (ΔAAT1), 7577 (ΔAAT2), 8177=(ΔMDH1) and 7575= (ΔMDH2). Results are shown in FIG. 12. Levels of amino acids were not significantly different for any strain other than ΔAAT2, which produced no detectable threonine and significantly higher levels of lysine, glutamate/glutamine and arginine. Amino acid values are expressed as a percentage of individual amino acids in the total amino acid content of the cells.

Amino Acid Composition in BY4741 Parental Strain and KanMX Deletions of L-Threonine Pathway Enzymes in that Background Amino acid analysis of *P. stipitis* HOM3 (8037) and HOM3-R2 (8038) expressed from p416TEF in strain 7790 (BY4741 ΔHOM3::KanMX)(FIG. 13). Cells were grown in defined medium lacking threonine and isoleucine for approximately 24 hrs and extracted as previously stated. Levels of L-threonine were significantly higher in the HOM3-R2 variant, and approached 35% of the total amino acid content of the cells. Although no direct comparison was made, in 7790 the *S. cerevisiae* HOM3-R2 variant expressed from CYC promoter achieved 30% threonine content compared to 35% for the P. stipitis HOM3-R2 mutant expressed from TEF. The wild-type HOM3 from P. stipitis was also found to produce more threonine than wild-type HOM3 from S. cerevisiae (15% vs. 10%) in strain 7790. Amino acid values are expressed as a percentage of individual amino acids in the total amino acid content of the cells.

Amino Acid Analysis of HOM3 (7718) and HOM3-R7 (8118) Expressed from p416TEF in Strain 7790 (BY4741 ΔHOM3::KanMX)

Constructs 7718 and 8118 were expressed in strain 7790 (FIG. 14). Cultures were grown for 48 hours in a defined medium lacking threonine and isoleucine to select for HOM3 complementation. The slow growth of the cells expressing the R7 mutation necessitated the extra 24 hours of growth compared to cultures expressing the R2 mutation. Cells were grown and extracted as stated previously. Significantly higher l-threonine content was observed in cultures expressing HOM3-R7 from the TEF promoter compared to the native HOM3. The total l-threonine content of the cells in the TEF expressed HOM3-R7 culture reached 28% (wt/wt). Amino acid values are expressed as a percentage of individual amino acids in the total amino acid content of the cells.

Co-Expression Amino Acid Analysis

Amino acid analysis of co-expression of AAT1 (7957), AAT2 (7961), MDH1 (7958), MDH2 (7962) and PCK (7959) together with HOM3-R2. Strain 7960 contained an empty p415TEF plasmid as a control. (FIG. 15.) All enzymes were expressed from p415TEF, with the exception of HOM3-R2, which was expressed from p416CYC. Constructs were made in strain 7768 (BY4741 ILV1::TEF-Ilv1-fbr). Cultures were grown for 24 hrs in a defined medium lacking threonine and isoleucine and cells were prepared for amino acid analysis as described previously. Levels of amino acids were similar, and threonine content was significantly lower than that found in strains containing a wild-type ILV1, indicating that threonine is limiting in 2-MBO production. In cells expressing AAT2 and MDH2, higher levels of homoserine were observed, consistent with what was observed when HOM3-R2 was expressed by itself. Specifically, the 7% homoserine content found in the culture expressing MDH2 with HOM3-R2 was the highest seen in any culture tested, indicating THR1 limitation and potentially higher flux through the Asp/Thr pathway than HOM3-R2 alone. Also of note is the significantly higher alanine content when PCK is expressed with HOM3-R2, potentially indicating an increase in pyruvate concentration, leading to increased alanine. Amino acid values are expressed as a percentage of individual amino acids in the total amino acid content of the cells.

Amino Acid Analysis of P. stipitis HOM3 and HOM3-R2 Expressed from p416TEF in Strain 7790

Figure 16:
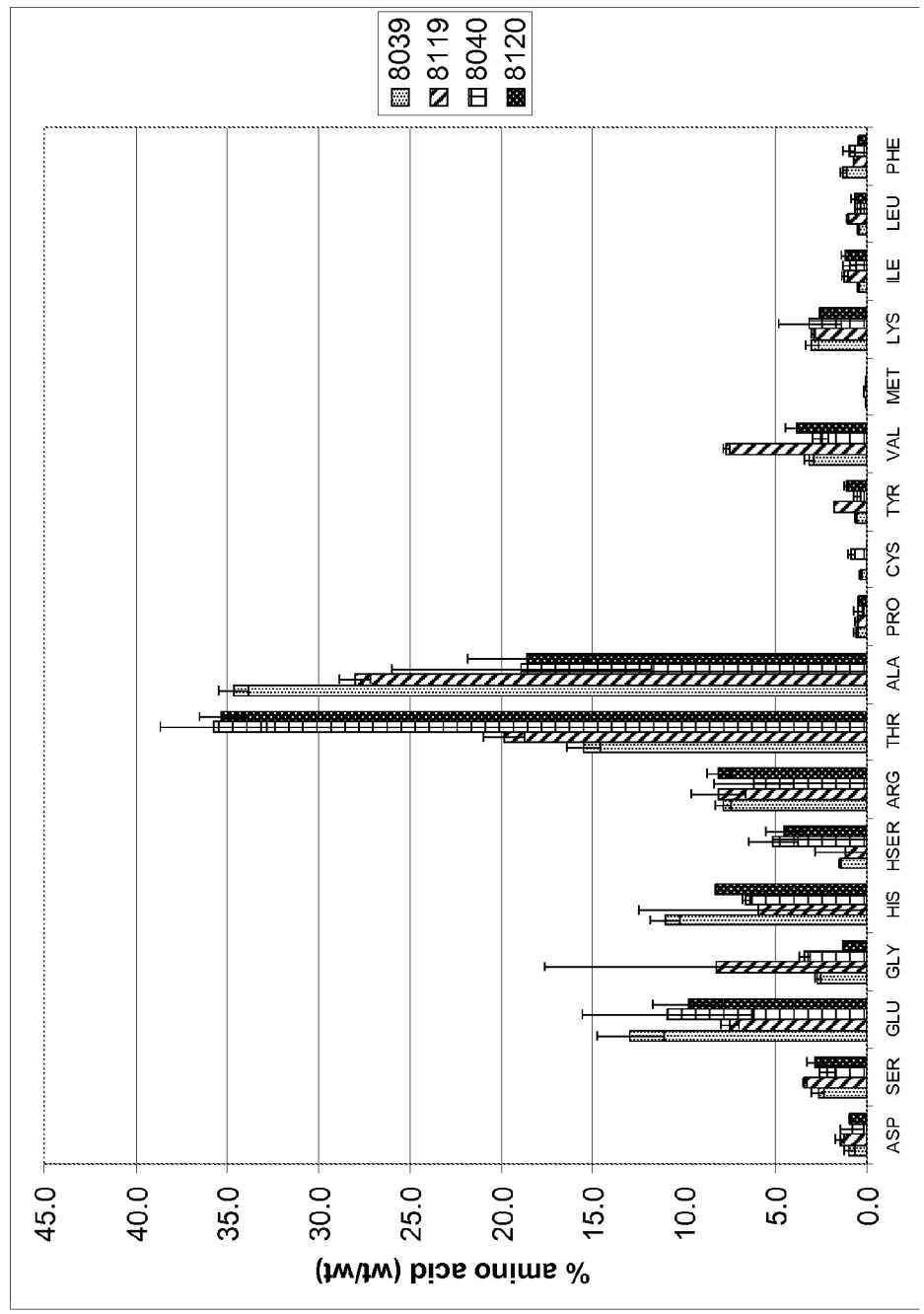
FIG. 16. Shows a bar graph of an amino acid analysis of P. stipitis HOM3 and HOM3-R2 expressed from p416TEF in strain 7790 (HOM3=8039, HOM3-R2=8040) and BY4741 (HOM3=8119, HOM3-R2=8120). Cells were grown in defined medium lacking threonine and isoleucine for approximately 24 hrs and extracted as previously stated. Levels of L-threonine were as observed before in the 7790 strain (35% total amino acid content), and expression of this enzyme in the background of chromosomally encoded S. cerevisiae HOM3 was not significantly different. The threonine level for wild-type P. stipitis HOM3 in 7790 was approximately the same as previously observed (~15%). Surprisingly, this same enzyme expressed in the BY4741 background resulted in a significantly higher threonine level of approximately 5%, suggesting a contribution from the native HOM3. This could be interpreted as showing a theoretical maximal level of threonine achieved by HOM3-R2, since no additional threonine was detected by expression in BY4741. Alternatively, it could indicate a limitation in upstream precursors, specifically oxaloacetate, since aspartate levels appeared constant in the four different experiments. Additionally, alanine levels showed a significant decrease in the HOM3-R2 strains. One possible explanation is increased pyruvate flux into the Asp/Thr pathway via OAA, thereby limiting direct transamination of pyruvate to alanine. Amino acid values are expressed as a percentage of individual amino acids in the total amino acid content of the cells.

An amino acid analysis of P. stipitis HOM3 and HOM3-R2 expressed from p416TEF in strain 7790 (HOM3=8039, HOM3-R2=8040) and BY4741 (HOM3=8119, HOM3-R2=8120) was conducted (FIG. 16). Cells were grown in defined medium lacking threonine and isoleucine for approximately 24 hours and extracted as previously stated. Levels of l-threonine were as observed before in the 7790 strain (35% total amino acid content), and expression of this enzyme in the background of chromosomally encoded S. cerevisiae HOM3 was not significantly different. The threonine level for wild-type P. stipitis HOM3 in 7790 was approximately the same as previously observed (~15%). Surprisingly, this same enzyme expressed in the BY4741 background resulted in a significantly higher threonine level of approximately 5%, suggesting a contribution from the native HOM3. This could be interpreted as showing a theoretical maximal level of threonine achieved by HOM3-R2, since no additional threonine was detected by expression in BY4741. Alternatively, it could indicate a limitation in upstream precursors, specifically oxaloacetate, since aspartate levels appeared constant in the four different experiments. Additionally, alanine levels showed a significant decrease in the HOM3-R2 strains. One possible explanation is increased pyruvate flux into the Asp/Thr pathway via OAA, thereby limiting direct transamination of pyruvate to alanine. Amino acid values are expressed as a percentage of individual amino acids in the total amino acid content of the cells.

EXAMPLE 2

Identification of Genes Relevant for Methylbutanol Production

Figure 17:
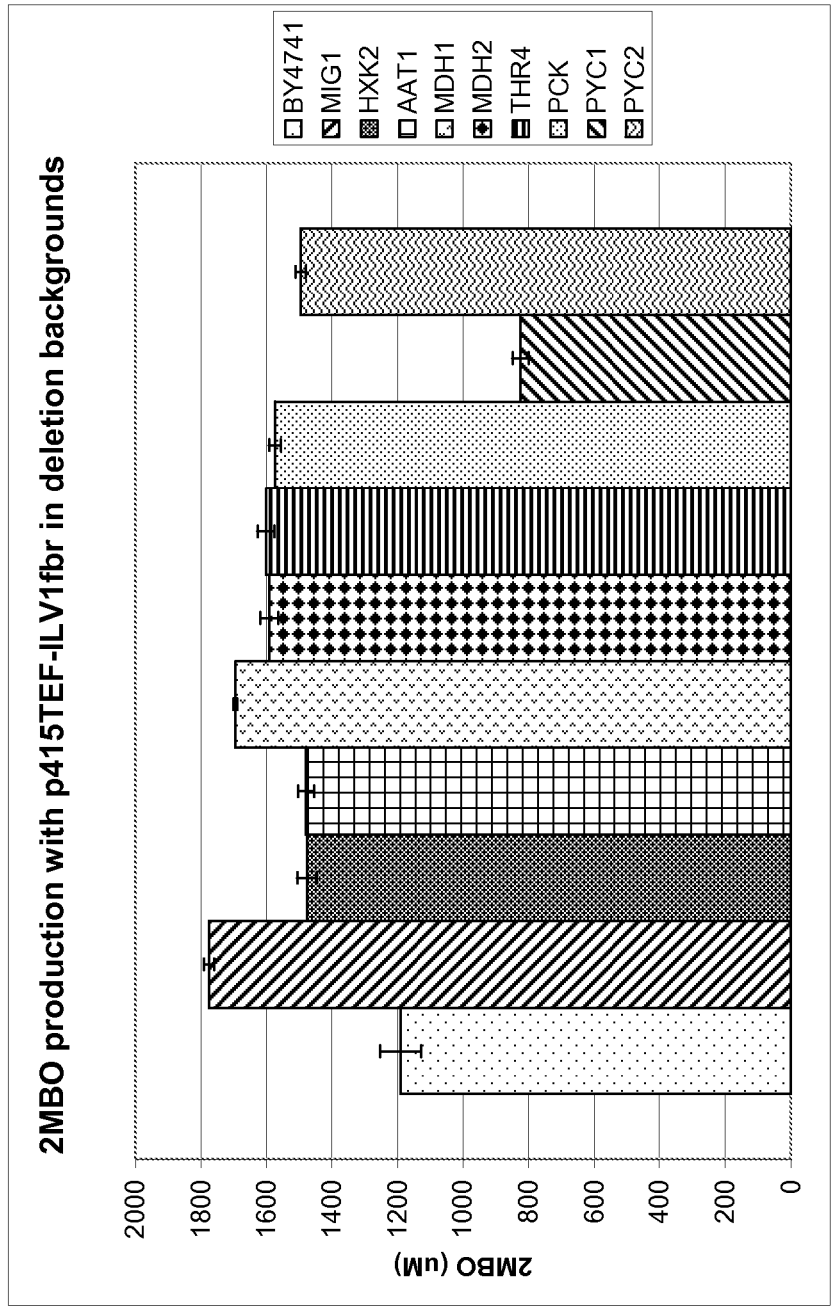
FIG. 17. A bar graph showing production of 2-MBO by BY4741 deletion variants transformed with p415TEF-ILV1FBR.
Figure 18:
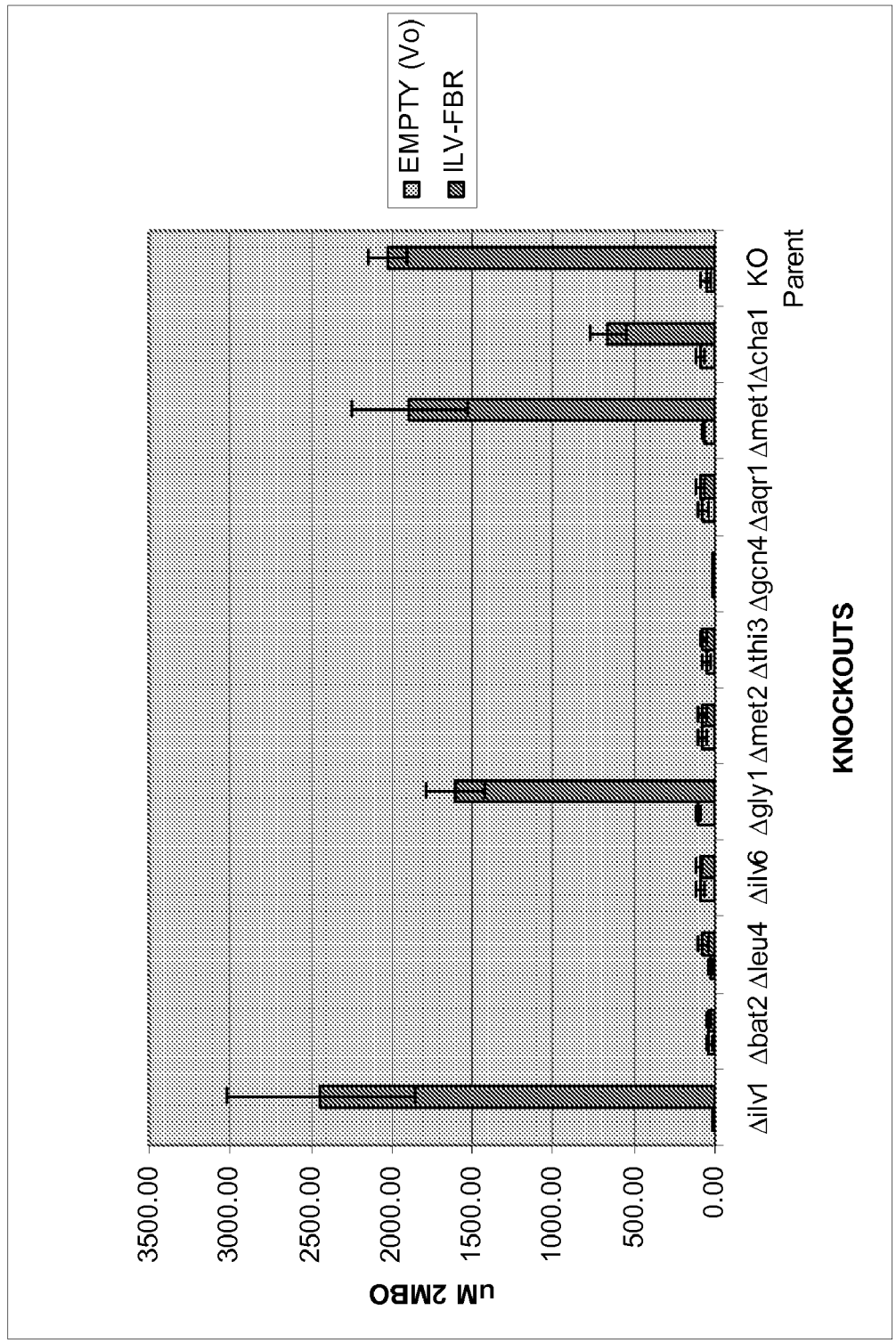
FIG. 18. A bar graph showing production of 2-MBO by BY4741 deletion variants transformed with p415TEF-ILV1FBR and p415TEF (empty vector control).
Figure 19:
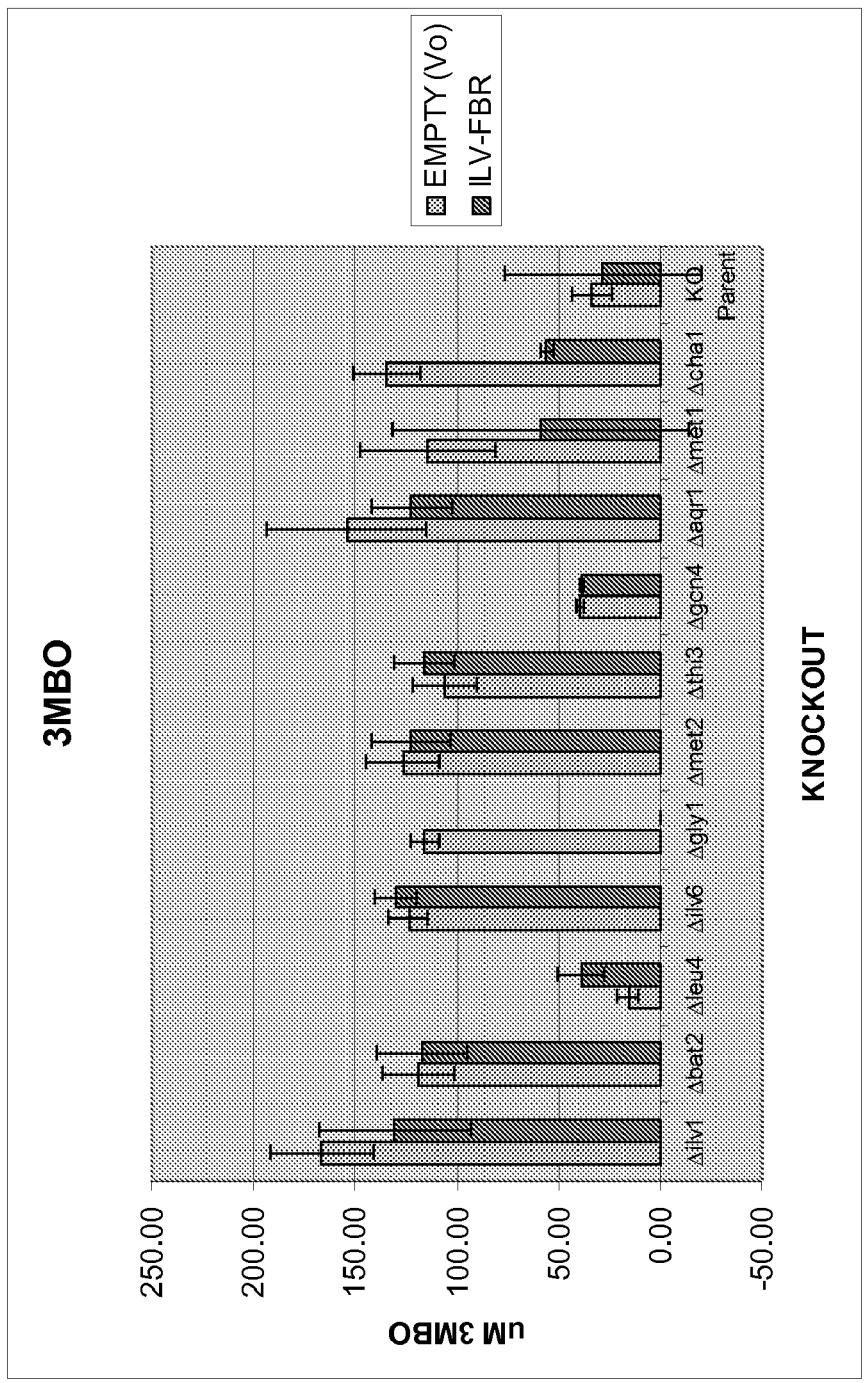
FIG. 19. A bar graph showing production of 2-MBO & 3-MBO by BY4741 deletion variants transformed with p415TEF-ILV1FBR and p415TEF (empty vector control).

The Saccharomyces cerevisiae deletion collection was analyze to ascertain which specific loci are relevant to 2-MBO production. Various strains designated by their gene deletion using nomenclature consistent with the Saccharomyces Genome Database project were transformed with p415TEF-ILV1$^{FBR}$ and the control empty vector p415TEF. FIGS. 17 and 18 show the production of 2-MBO, while FIG. 19 shows the corresponding production of 3-MBO. The table below shows data relating to the production of 2-MBO in HOM3FBR: TEF ILV1$^{FBR}$ host strain with the addition of key genes in the pyruvate to threonine pathway.

| Strain | Genotype | 2-MBO (μM) |
|---|---|---|
| 8102 | TEF HOM3$^{FBR}$: TEF ILV1$^{FBR}$ p413TEF-PCK (Ps) p415TEF-THR1 (Ps) p416TEF-MDH2 (Ps) | 427.49 |
| 8103 | TEF HOM3$^{FBR}$: TEF ILV1$^{FBR}$ p413TEF-PCK (Ps) p415TEF-HOM6 (Ps) p416TEF-PYC (Ps) | 405.55 |
| 8104 | TEF HOM3$^{FBR}$: TEF ILV1$^{FBR}$ p413TEF-PCK (Ps) p415TEF-HOM6 (Ps) p416TEF-MDH2 (Ps) | 1441.41 |
| 8105 | TEF HOM3$^{FBR}$: TEF ILV1$^{FBR}$ 1FBR p413TEF-PCK (Ps) p415TEF-THR1 (Ps) p416TEF-PYC (Ps) | 1122.6 |
| 8050 | TEF HOM3$^{FBR}$: TEF ILV1$^{FBR}$ p415TEF | 2045.39 |
| 8107 | TEF HOM3$^{FBR}$: TEF ILV1$^{FBR}$ p413TEF-PYC (Ps) p415TEF-THR1 (Ps) p416TEF-HOM2 (Ps) | 3339.02 |
| 8108 | TEF HOM3$^{FBR}$: TEF ILV1$^{FBR}$ p413TEF-PYC (Ps) p415TEF-THR1 (Ps) p416TEF-MDH2 (Ps) | 3508.43 |

EXAMPLE 3

Identification and Modification of Genes Relevant for Methylbutanol Production

Figure 20:
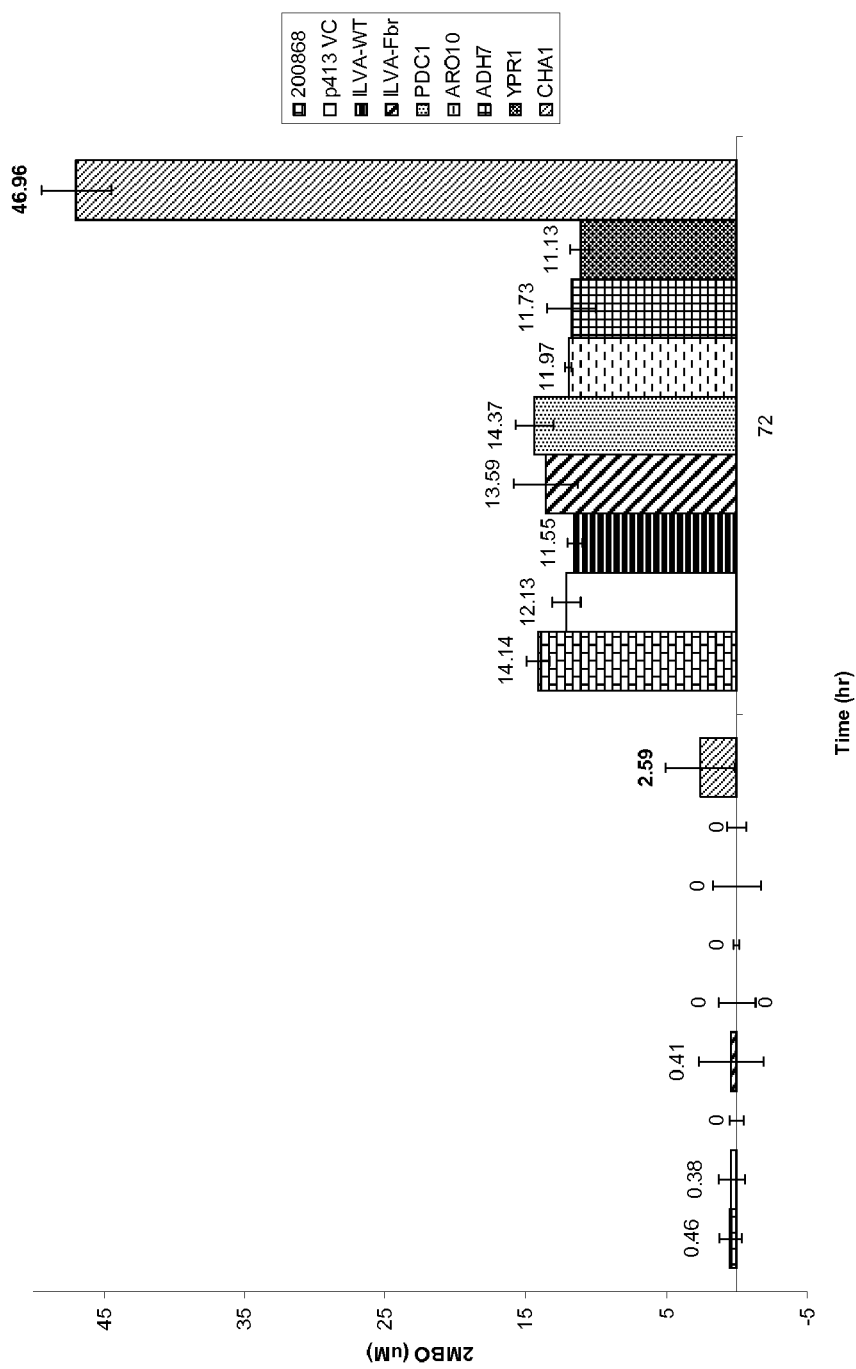
FIG. 20. A bar graph with data demonstrating the overexpression of CHA1 (threonine dehydratase) resulting in an approximately 3 fold increase in 2-MBO production over the wild-type strain.
Figure 21:
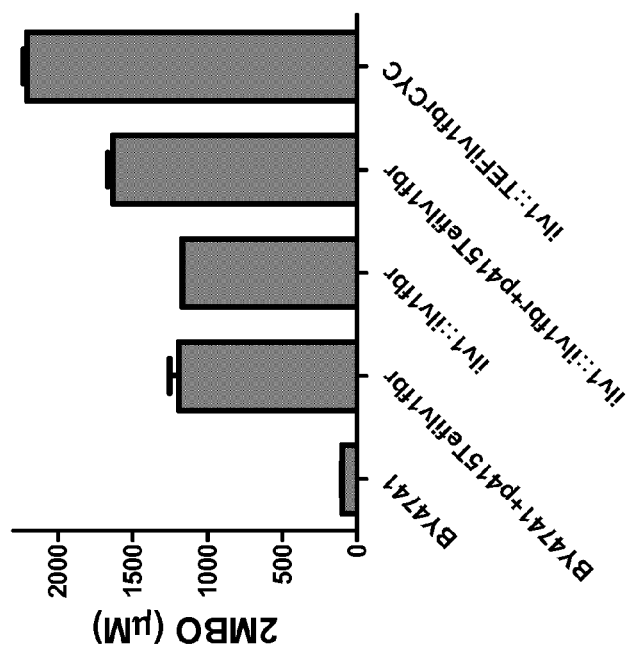
FIG. 21. A bar graph with data demonstrating the overexpression of ILV1 (threonine deaminase) and the feedback resistant (FBR) variant resulting in an approximately 40 fold increase in 2-MBO production over the wild-type strain. Strain information is provided below.

Elevated intracellular pools of threonine accumulate in the cytoplasm of S. cerevisiae. The deamination of threonine is carried out by two enzymes; a catabolic threonine dehydratase (CHA1; FIG. 20) and a mitochondrial threonine deaminase (ILV1; FIG. 21). Experimental evidence has shown that overexpression of either of these enzymes results in increase production of 2-methylbutanol (2-MBO) in the growth medium. The production of 2-MBO can be further elevated by the modification of amino acid sequence ILV1 that are thought to be involved in the binding of isoleucine and create a feedback mechanism to shut down the pathway when intracellular amounts of isoleucine are in excess. The committed steps to isoleucine production and the conversion of threonine take place in the mitochondria. The key enzymes in the pathway (threonine deaminase, acetolactate synthase, acetohydroxyacid reductoisomerase and dihydroxyacid dehydratase are expressed in the nucleus and translocate to the mitochondria). To alleviate potential redox issues and to create a cytoplasmic isoleucine pathway a bioinformatics study was carried out to remove the mitochondrial targeting sequence or express prokaryotic counterparts which have no organelle targeting components (Table 1).

Using the TargetP informatics program, attempts were made to predict the mitochondrial targeting sequence of the isoleucine pathway genes/proteins and to determine which deletions would leave these enzymes residing within the cytoplasm. Table 2 below shows the TargetP results.

TABLE 2

TargetP mitochondrial targeting sequence prediction of *Saccharomyces cerevisiae* isoleucine pathway genes

| Gene (Enzyme) | Length (aa) | mTP | SP | Other | Location | RC | TPlen |
|---|---|---|---|---|---|---|---|
| Ilv1 (threonine deaminase) | 576 | 0.620 | 0.016 | 0.408 | M | 4 | 31 |
| Ilv2 (acetolactate synthase-subunit) | 687 | 0.949 | 0.012 | 0.124 | M | 1 | 37 |
| Ilv6 (acetolactate synthase-subunit) | 309 | 0.962 | 0.028 | 0.057 | M | 1 | 24 |
| Ilv5 (acetohydroxyacid reductoisomerase) | 395 | 0.947 | 0.012 | 0.108 | M | 1 | 22 |
| Ilv3 dihydroxyacid dehydratase | 585 | 0.610 | 0.071 | 0.337 | M | 4 | 20 | mTP = probability that the sequence is mitochondrial targeted
TPlen = length of the predicted N-terminal presequence; for example, cleavage site is predicted to be after 22aa's for ilv5.

A series of experiments were undertaken to evaluate the intracellular location of the wild-type ILV pathway enzymes and their subsequent truncated counterparts. Two sets of deletions were made: one with a 6×His-tag (for localization/identification purposes), and a second set without one (to be used for functionality and complementation experiments). Truncations were created with primers designed to give an N-terminal amino acid deletion and where applicable a C-terminal 6×His-tag.

EXAMPLE 4

Protocols Used for Spheroplast Treatment, Fractionation, and Immunoblot

Spheroplast Treatment

Spheroplast treatment was accomplished by following the manufacturer's instructions. A 500 ml culture of the selected yeast cell line was grown to an $OD_{600}$=1.2-1.8 in SD-Leucine selective liquid media. Cells were harvested by centrifugation at 3000×g for 5 minutes. Two water washes followed with centrifugation steps—3000×g for 5 minutes. The pellet weight was determined. The cell pellet was then resuspended in 1.4 ml/gram wet weight of TE Buffer, pH 8.0. The final volume of the resuspended cells was brought to 3.5 ml/gram wet weight with sterile-filtered Mill-Q water. Next 17.5 µl of β-Mercapto-ethanol per gram wet weight was added to the mixture to remove the mannan layer. The cell mixture was incubated at 30° C. with gentle shaking on an orbital shaker for 15 minutes. Following mannan removal, the cell mixture was centrifuged at 3000×g for 5 minutes at room temperature. The cell pellet was then resuspended in 4.0 ml of S-Buffer (1.0M Sorbitol, 10 mM PIPES, pH 6.5)/gram wet weight and centrifuged again at 3000×g for 5 minutes. Next, the cell pellet was resuspended again in 4.0 ml S-Buffer/gram wet weight, with the addition of 50 U of Zymolyase to remove the cell wall. This cell mixture was incubated for 60 minutes at 30° C. with gentle shaking on an orbital shaker. Post Zymolyase activity, the spheroplasts were harvested by centrifuging at 3000×g for 5 minutes at 4° C. Spheroplasts were then resuspended in 2.0 ml S-Buffer per gram wet weight and centrifuged again at 3000×g for 5 minutes. This step was repeated for two washes, and the final pellet was resuspended in 20 ml S-Buffer ready for fractionation.

Fractionation

Cells were lysed via MICROFLUIDIZER at 1200 psi (Microfluidics Inc.). The cell volume was passed through the microfluidizer 5 times with rest periods on ice for 1 minute between passes. A diluted sample of cells was checked under the microscope to ensure at least 80% lysis. Three 100 µl samples of this mixture were saved at labeled "crude extract." The crude extract was then centrifuged at 1000×g for 5 minutes at 4° C. The supernatant was transferred into a new sterile centrifuge tube and centrifuged again at 13,000×g in a JA-20000 rotor for 10 minutes at 4° C. The pellet from the first (1000×g) spin was resuspended in 1.0 ml of Tris Buffer, pH 7.5, and three 300p aliquots were saved. Once the second (13,000×g) spin finished, the supernatant was transferred to a new sterile tube and the pellet was resuspended in 1.0 ml of Tris Buffer, pH 7.5. Three 1.0 ml aliquots of the supernatant were saved and labeled cytosolic fraction. Three 300 l aliquots of the resuspended pellet were saved and labeled mitochondrial fraction. Protein concentrations of each fraction were determined via BCA assay kit (Thermo Scientific Inc).

Western Blot Analysis

A 4-12% Bis-Tris SDS-PAGE gel (Invitrogen Inc.) was run, with a total protein concentration of 7.0 ug of each fraction. The gel was run in 1×MES buffer for 35 minutes. One gel was saved to Coomassie stain, and the second was transferred to a PVDF membrane via iBlot system (Invitrogen Inc.). Detection of his-tagged protein was accomplished via Western Breeze chemiluminescent kit (Invitrogen Inc.). The primary antibody was an anti-his (C-term)/AP Ab used according to manufacturer's recommendation=1:2000 dilution for 2 hr at room temperature (cat# 46-0284; Invitrogen Inc).

FIG. 22 A-D shows the results of this work.

The functional activity of these putative cytoplasmic variants of the *Saccharomyces* pathway was demonstrated by complementation of deletion strains.

TABLE 3

Complementation of deletion strains for Isoleucine pathway

| Host strain Genotype | Plasmid | Gene source | Complementation on SD-ILe | Complementation on 5FOA | Strain number |
|---|---|---|---|---|---|
| Mata his3Δ1 leu2Δ0 met15Δ0 | p415TefIlv1 | *S. cerevisiae* | +++ | | 7683 |
| | p415TefIlv1-Fbr | *S. cerevisiae* | +++ | | 7748 |
| | p415Tefilv1Δ25 | *S. cerevisiae* | +++ | | 7757 |

TABLE 3-continued

Complementation of deletion strains for Isoleucine pathway

| Host strain Genotype | Plasmid | Gene source | Complementation on SD-ILe | Complementation on 5FOA | Strain number |
|---|---|---|---|---|---|
| ura3Δ0 | p415TefIlv1Δ35 | S. cerevisiae | ++ | | 7684 |
| ilv1::KanMX | p415TefIlv1Δ45 | S. cerevisiae | ++ | | 7685 |
| | p415TefIlv1-FbrΔ45 | S. cerevisiae | ++ | | 7934 |
| | p415TefilvA (c. opt) | C. glutamicum | − | | — |
| | p415TefilvA-Fbr | E. coli | ++ | | 7510 |
| | p415TefilvA | E. coli | ++ | | — |
| | p415TefCimA (Kozak) | L. interrogans | − | | — |
| | p415TefIlv1fbr | P. stipitis | +++ | | — |
| Mata his3Δ1 | p415TefIlv5 full | S. cerevisiae | | ++++ | — |
| leu2Δ0 | p415TefIlv5Δ15 | S. cerevisiae | | ++++ | — |
| met15Δ0 | p415TefIlv5Δ25 | S. cerevisiae | | + | — |
| ura3Δ0 | p415TefIlv5Δ35 | S. cerevisiae | | − | — |
| ilv5::KanMX | p415TefIlv5Δ45 | S. cerevisiae | | − | — |
| p416TefIlv5 | p415TefIlv5Δ35 | P. stipitis | | + | — |

A similar experiment was carried out with analogous genes from *Pichia stipidis* the constructs shown in the below. The results are provided in FIG. 23A-D.

| Strain | Description | Strain number |
|---|---|---|
| S7209 | p416TEF | 7209 |
| B | p415TEF ilvB (Ec) | 7302 |
| B + N | p415TEF ilvB (Ec) p414TEFilvN (Ec) | 8129 |
| G | p413TEF ilvG' (Ec) p415TEF | 7307 |
| G + M | p415TEF ilvG' (Ec) p416TEFilvM (Ec) | 7558 |
| I | p415TEF ilvI (Ec) | 7560 |
| I + H | p415TEF ilvI (Ec) p416TEF ilvH (Ec) | 7559 |
| S ce2 | p414TEF ILV2 p415TEF | 7309 |
| 2 + 6 | p415 TEF ILV6 p414TEF ILV2 | 7313 |
| B (C glu) | p415TEF ilvB (Cg) | 7306 |

EXAMPLE 5

Identification/Evolution of a Keto Acid Decarboxylase for Increased 2-Methylbutanol Production Pyruvate, 2-ketobutyrate and 2-keto-3-methylvalerate are the three critical keto acids whose fate is linked to the amount of 2-MBO production. All these three keto acids can be converted to their respective aldehydes by a decarboxylation reaction performed by a keto acid decarboxylase.

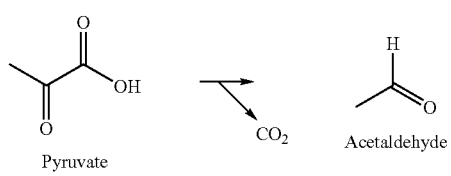

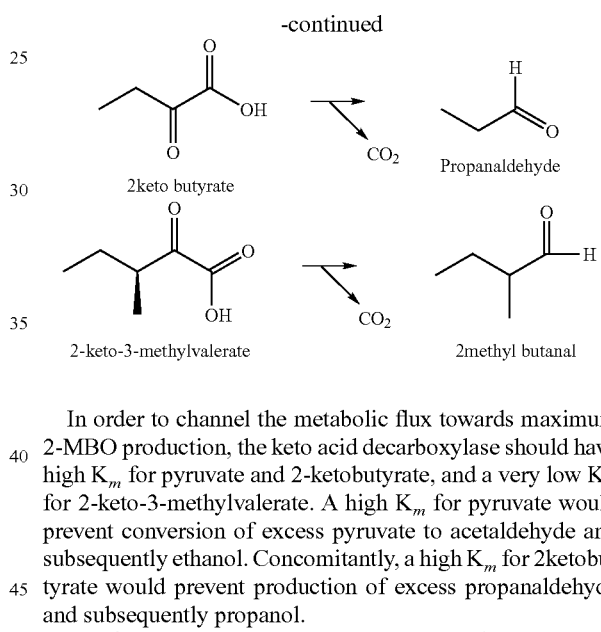

In order to channel the metabolic flux towards maximum 2-MBO production, the keto acid decarboxylase should have high $K_m$ for pyruvate and 2-ketobutyrate, and a very low $K_m$ for 2-keto-3-methylvalerate. A high $K_m$ for pyruvate would prevent conversion of excess pyruvate to acetaldehyde and subsequently ethanol. Concomitantly, a high $K_m$ for 2ketobutyrate would prevent production of excess propanaldehyde and subsequently propanol.

*Saccharomyces cerevisiae* possesses several genes encoding keto acid decarboxylases. These enzymes have been listed as PDC1, PDC5 and PDC6. PDC1 is the major of the three decarboxylase isozymes and is involved in ethanolic fermentation. Transcription of the other isoforms is glucose and ethanol dependent. PDC1 and PDC5 expression may also be controlled by autoregulation.

PDCs from heterologous sources have been reported for high affinity for branched keto acids. KdcA of *Lactococcus lactis* is the most prominent branched chain keto acid decarboxylase (Gocke et al, 2007; Berthold et al, 2007). The activity of this enzyme, when expressed in *S. cerevisiae*, has however not been described earlier. Other unexplored heterologous PDCs include those of the xylose fermenting yeast *Pichia stipitis* (PDC1, PDC2 and PDC3(6).

The *Lactococcus lactis* KdcA and *S. cerevisiae* and *P. stipitis* PDCs were cloned into yeast expression vector p415 under the control of TEF promoter. The host strain was a PDC1 deletion strain. Crude extracts were prepared for enzymatic assays by incubating cell pellet with CelLytic (Sigma), followed by bead beating. The decarboxylase reaction was performed in 100 mM Citrate Phosphate buffer with 1 mM Thiamine diphosphate, 1 mM $MgCl_2$ and 50 μM to 20 mM aldehyde. The assay was coupled to an alcohol dehydrogenase which enabled continuous monitoring of NADH or NADPH oxidation at 340 nm.

The substrate specificity of the crude extract overexpressing different PDC/Kdcs was tested with a broad range of aldehydes. This included acetaldehyde, butyraldehyde and 2-methylbutyraldehyde. The concentration of the aldehydes was varied from 50 μM to 20 mM to determine the $K_m$ and $V_{max}$ values.

EXAMPLE 6

Decarboxylase Activity on 2-keto-3-methylvalerate 2-keto-3-methylvalerate (2K3MV) was tested for decarboxylation and subsequent reduction using PDC/KDC-ADH6 coupled assays. The results are shown in FIG. 24 (a-g). The assays show that P. stipitis PDC3/6 has the lowest $K_m$ (0.84 mM) for 2-keto-3-methylvalerate. This indicates that P. stipitis PDC 3/6 is functional in yeast and an important candidate gene for increased 2-methylbutanol production. The other enzyme with low $K_m$ for 2-keto-3-methylvalerate is KDCA from L. lactis with a $K_m$ of 3.7 mM. However, the $V_{max}$ value of Pichia PDC3-6 is 3.4 fold higher than KdcA indicating that it is the most active enzyme on 2-keto-3-methylvalerate.

Decarboxylase Activity on 2-keto Butyrate

NADH dependent coupled assays with yeast ADH1 were carried out to determine the decarboxylase activity of yeast and heterologous enzymes on the substrate 2 keto butyrate (2KB). 2KB is an intermediate in the production of 2-methylbutanol. A high decarboxylase activity on 2KB can lead to its conversion to propanal and reduce the yield of 2-MBO. Hence, a decarboxylase with a high $K_m$ for 2-ketobutyrate is of high value. Enzyme assays show that L. lactis KDCA, Pichia stipitis PDC3-6 and the Kdc-PDC3/6 fusion protein KPK are equivalent in their affinity for 2-ketobutyrate. (See FIG. 25 a-g.) The enzyme with the lowest $K_m$ for 2-ketobutyrate is yeast PDC1 and therefore the corresponding gene needs to be deleted in the 2-MBO production strain (data not shown). The Vmax value of PDC3/6 is about 3.4 fold higher than KDCA. However, the Kms of the two enzymes are relatively close which suggests equal affinity for 2 keto butyrate.

Decarboxylase Activity on Pyruvate

Pyruvate is the target for multiple enzymes and a decarboxylation of the compound can lead to the production of acetaldehyde and subsequently ethanol. To prevent decarboxylation of pyruvate and increase 2-MBO production, a keto acid decarboxylase with a very high $K_m$ for pyruvate is ideal. Hence, all the enzymes overexpressed in S. cerevisiae were tested for their activity with pyruvate as substrate. The kinetic curves obtained with pyruvate as substrate were sigmoidal. This could be due to the fact that there are multiple enzymes in the crude extract with different $K_m$ for pyruvate. The final curve is therefore the superposition of individual curves. Absolute $K_m$ values could therefore to be calculated. (FIG. 26.)

The Km and Vmax values for different enzymes and substrates are summarized below.

Km (mM)           Vmax (uM/min/mg)

| Strain | 2 keto 3 methyl valerate | 2 keto butyrate | 2 keto 3 methyl valerate | 2 keto butyrate | Pyruvate |
|---|---|---|---|---|---|
| ΔPDC1 | 5.263 | 6.741 | 834.0 | 4924.0 | 8189 |
| L. lactis KDCA | 3.749 | 6.054 | 987.3 | 2053.0 | 10069 |
| P. stipitis PDC 3/6 | 0.8399 | 6.5090 | 3359. | 5389 | 12624 |
| KPK (KDCA-PDC3/6 fusion) | 8.563 | 4.909 | 819. | 1934 | 6880 |

From the above results, it can be concluded that either Lactococcus lactis KdcA or PDC3-6 from Pichia stipitis are the most suitable keto acid decarboxylases for increased 2-MBO production. Pichia stipitis PDC3/6 is however a superior enzyme for decarboxylation of branched keto acids.

EXAMPLE 7

Identification of an Alcohol Dehydrogenase (ADH) with High Affinity for Branched Aldehydes The genome of S. cerevisiae shows the presence of 7 different alcohol dehydrogenases (ADHs). The ideal ADH for 2-MBO production should be able to reduce branched aldehydes. Therefore, the enzymes ADH1, ADH6, and ADH7 were overexpressed in yeast and were tested for their reductase activity on various aldehydes. Yeast ADH1, which is also commercially available was very active on acetaldehyde and butyraldehyde, but was ~5000 fold less active on 2-methyl butaraldehyde than acetaldehyde. (FIG. 27.) This suggested that ADH1 is not an ideal enzyme in the 2-MBO production pathway.

Yeast ADH6 and ADH7 have been reported as broad substrate specificity alcohol dehydrogenases. These enzymes were therefore overexpressed in S. cerevisiae under the control of TEF promoter and enzyme assays were carried out with crude extracts. Both ADH6 and ADH7 were active on 2-methylbutanal and were NADPH dependent reductases.

ADH6 showed higher affinity for branched aldehyde and was subsequently cloned as a histidine tagged protein in the yeast expression vector p415TEF and purified by affinity chromatography.

Enzyme assays for aldehyde reductase activity were carried out in 100 mM citrate phosphate buffer pH6.2, 0.5 mM NADPH and 0.05 to 20 mM substrate (acetaldehyde or 2-methylbutanal). The reaction was monitored for 5 minutes at 340 nm for oxidation of NADPH to NADP+. Results are shown in FIG. 28.

The pure enzyme showed Michaelis Menten kinetics for both the substrates. The $K_m$ and $V_{max}$ values were determined for both acetaldehyde and 2-methyl butyraldehyde and are summarized in FIG. 29.

Figure 30:
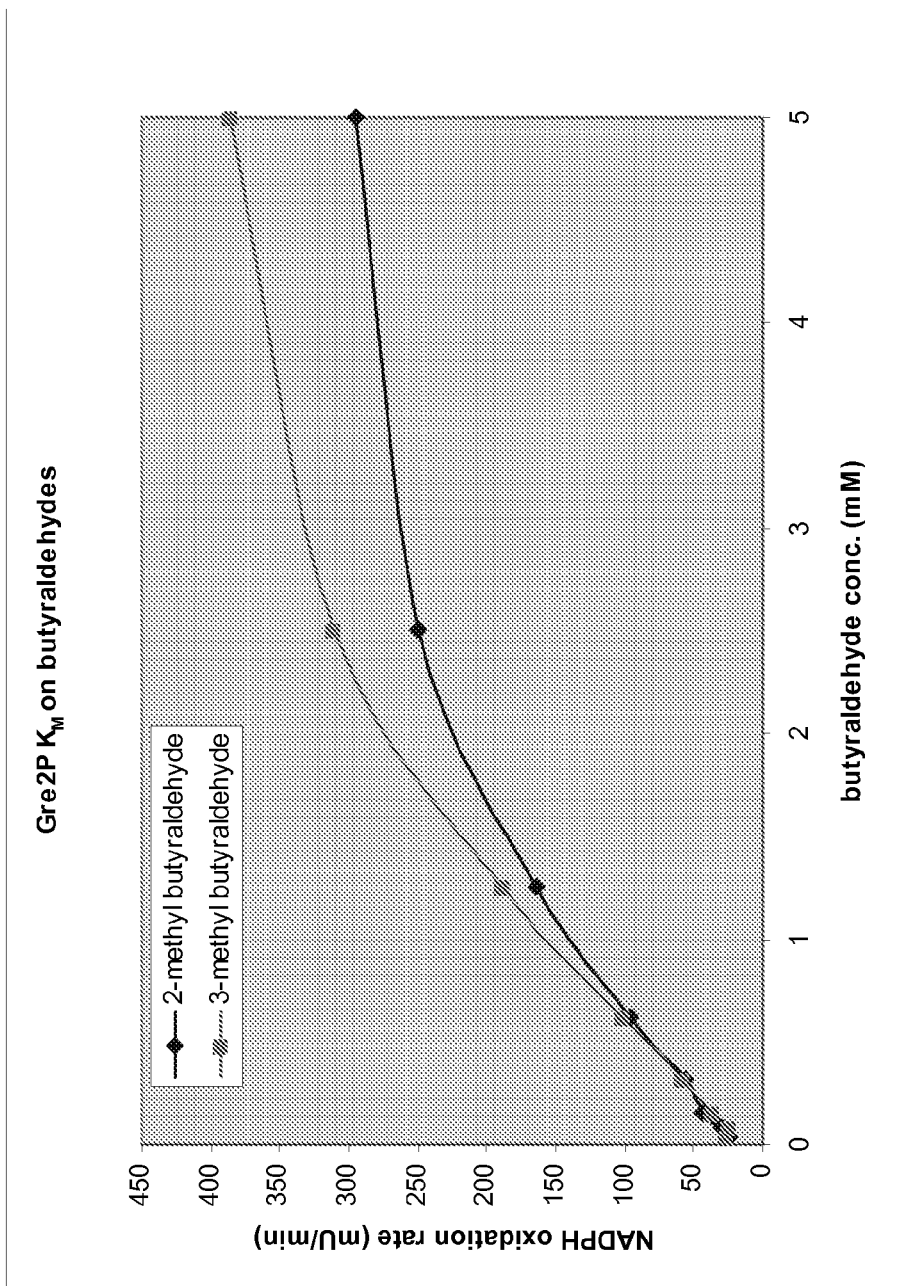

As evident from the above figures, yeast ADH6 shows a lower $K_m$ (0.36 mM) for 2-methyl butyraldehyde than acetaldehyde (0.58m). The $V_{max}$ value (cofactor oxidation rate) for 2-methyl butyraldehyde is also 1.3 fold higher than acetaldehyde. (FIGS. 30 and 31.)

ADH6 was therefore identified as the ideal enzyme for 2-MBO production due to its ability to perform reduction of 2-methyl butyraldehyde to 2-methylbutanol.

EXAMPLE 8

Pyruvate (PDC) and Keto-Acid Decarboxylase (Kdc) Screening

Genes screened for increased production of 2-MBO included: PDC1 (S. cerevisiae), PDC5 (S. cerevisiae), PDC6

(*S. cerevisiae*), THI3 (*S. cerevisiae*), PDC1 (*P. stipitis*), PDC2 (*P. stipitis*), PDC3-6 (*P. stipitis*), KivD (*L. lactis*), KdcA (*L. lactis*), KdcA-S286Y (*L. lactis*), and Kdc (*M. tuberculosis*).

The aim of the characterization of these genes was to distinguish decarboxylases with a low Km for 2-keto-3-methylvalerate and a high Km for pyruvate.

Bioinformatic and structural analysis show structure similarities to pyruvate decarboxylase and keto acid decarboxylases. Amino acid and conserved domain analysis showed the potential for mutation or switching active sites with the possibility of turning a PDC into a Kdc, thereby altering the affinity of *Saccharomyces* PDC for pyruvate and other keto acids and forcing the conversion of 2-keto-3-methylvalerate to the 2 methyl-butyraldehyde.

PDC1 Mutant Library

Pdc1p (*S. cerevisiae*) was aligned with KdcAp (*L. lactis*) to determine if the same sites altered in KdcAp to increase affinity for 2-keto-3-methyl-valerate could be saturated in Pdc1p via degenerate primers to (FIG. 32.) Primers were designed to produce various mutants, as exemplified in FIG. 33. Exemplary exchange sites were selected, as illustrated in FIGS. 34 and 35. Exemplary constructions were generated as shown in FIGS. 36-38.

These mutant libraries were transformed into yeast and tested in high-throughput style for increased levels of 2-MBO when fed threonine at 20 mM.

Fusion Proteins

To attain the strong characteristics of PDC1 and KDCA, high activity in *S. cerevisiae* and high affinity towards 2-keto-3-methyl-valerate, respectively, different protein fusions were created linking the two proteins at different domain locations. Images of the domains were downloaded from NCBI and sites were chosen by visualizing the crystal structure of both Pdc1p and KdcAp.

Additional fusion proteins between *L. lactis* KDCA and *P. stipitis* PDC3-6 were also made as shown in FIG. 39-41.

EXAMPLE 9

Evaluation of Transcripts (mRNA) by Semi-Quantitative PCR

Method for RNA Extraction from Yeast Cells Using Glass Beads 2.0 ml tubes containing 0.25 g acid washed glass beads (0.5 mm diameter) and 250 pt Phenol:$CHCl_3$:isoamyl alcohol (25:24:1) were prepared in advance and placed on ice. Yeast was collected at 5 $OD_{600}$ units (e.g., 10 ml of $OD_{600}$ 0.5). Cells were spun at 4° C. for 5 minutes at 2000 rpm, then resuspended in 2 ml of ice cold DEPC-treated HE (10 mM HEPES, 1 mM EDTA, pH 8) and transferred to microfuge tubes. Cells were then spun a second time at 4° C. for 30 seconds at top speed. Pellets were stored on ice for immediate use. Cells were resuspended a second time in 250 pt HENS buffer (10 mM HEPES-NaOH, pH 7.5 Treat with DEPC, 1 mM EDTA, 300 mM NaCl, and 0.2% SDS) and quickly transferred to 2.0 ml tubes with glass beads. Cells were then vortexed for 10 seconds, doing one tube at a time and placed on ice. All tubes were then vortexed at 4° C. for 30 minutes (25-75% breakage). The tubes were then spun for 30 minutes at 4° C. at top speed. 200 pt of the supernatant was transferred to a 1.5 ml microfuge tube without collecting any of the interface. Extraction was repeated adding an equal volume Phenol:$CHCl_3$: isoamyl alcohol, then vortexed for 15 seconds and spun for 5 minutes at top speed. Three volumes of 100% EtOH was added to the supernatant then mixed thoroughly. Samples were precipitated overnight at −20° C. Samples were then spun at 4° C. for 30 minutes at top speed. Supernatant was carefully removed and pellets were washed with 150 μl of 75% EtOH (DEPC treated). Pellets were spun again for 5 minutes at top speed, supernatant was carefully removed. Samples were dried in Speed-Vac and resuspended in 10 pt DEPC-treated ddH2O per 1 OD600 unit. RNA solution was kept on ice once pellet was dissolved and used immediately with the INVITROGEN SUPERSCRIPT III REVERSE TRANSCRIPTASE KIT. RNA was tested for equal concentration prior to cDNA production via equal loading on an RNA denaturation gel. RNA was stored at −20° C. for a maximum of one week.

TABLE 4

This 2-MBO production in the PDC1Δ background.

| SGI # | Full Name | 3-MBO | 2-MBO |
|---|---|---|---|
| 7658 | ΔPDC1: p415TEF-Kdc (Mt) | 98.69 | 61.42 |
|  |  | 98.37 | 61.79 |
|  |  | 100.10 | 66.77 |
| 7659 | ΔPDC1: p415TEF-KdcA(L1) | 183.94 | 170.07 |
|  |  | 187.04 | 181.92 |
|  |  | 190.16 | 190.95 |
| 7660 | ΔPDC1: p415TEF-PDC1 | 106.13 | 84.49 |
|  |  | 101.55 | 79.94 |
|  |  | 106.81 | 91.68 |

Data shows that KdcAp from *Lactococcus lactis* is better for final MBO production

TABLE 5

Primers used for RNA expression analysis of specific yeast genes.

| Primer # | Gene Amplified | Primer | SEQ ID NO |
|---|---|---|---|
| 283 | KdcA Forward Primer | 5'-atgtatactgtgggggattatttgttggat-3' | SEQ ID NO: 91 |
| 284 | KdcA Reverse Primer | 5'-ttatttgttttgctcagcaaatagtttccc-3' | SEQ ID NO: 92 |
| 370 | ACT1 Forward Primer | 5'-atggattctgaggttgctgctt-3' | SEQ ID NO: 93 |
| 371 | ACT1 Reverse Primer | 5'-ttagaaacacttgtggtgaacgatag-3' | SEQ ID NO: 94 |
| 372 | ADH6 Forward Primer | 5'-atgtcttatcctgagaaatttgaaggta-3' | SEQ ID NO: 95 |
| 373 | ADH6 Reverse Primer | 5'-ctagtctgaaaattctttgtcgtag-3' | SEQ ID NO: 96 |

The synthetic SGI YACv1.0 was created by Isothermal assembly reaction using individual gene cassettes, and also truncated-hybrid cassettes. The individual gene cassette method is first described. The following genes were previously subcloned into p4xx series yeast plasmids. All plasmids contained the TEF promoter and CYC terminator. Promoter-ORF-Terminator cassettes were amplified from plasmids with primers to create 40 base overlaps to either tandem cassettes or pYAC4 EcoRI flanking bases. (See FIG. 42.)

EXAMPLE 10

Individual Gene Cassette Method

Six cassettes were amplified and gel purified, then mixed together with the pYAC4 digested with EcoRI and gel purified in equal molar ratios and assembled by Isothermal Assembly method. The genes included in each cassette are listed below.

| Cassette | Gene | Source Organism |
|---|---|---|
| 1 | ilvA$^{FBR}$ | E. coli |
| 2 | ilvG | E. coli |
| 3 | ilvC | E. coli |
| 4 | ilvD | E. coli |
| 5 | kdcA | L. lactis |
| 6 | ADH6 | S. cerevisiae |

The Isothermal Assembly Reaction was setup in 20 µl reactions. The final concentrations were: FINAL 80 µl mixture; containing 100 mM Tris-Cl pH 7.5), 10 mM MgCl$_2$, 200 µM dGTP, 200 µM dATP, 200 µM dTTP, 200 µM dCTP, 10 mM DTT, 5% PEG-8000, 1 mM NAD, 0.004 U µl$^{-1}$ T5 exonuclease (Epicentre), 0.025 U µl$^{-1}$ Phusion polymerase (NEB), 4 U µl Taq Ligase (NEB), and DNA mixture ~40 ng per kb.

The reaction was left at 50° C. for 1 hr, then phenol chloroform extracted, and NaCl precipitated. It was resuspended in 20 µl H$_2$0, and transformed into S. cerevisiae ATCC 200897 strain (MATα ade2Δ::hisG his3Δ200 leu2Δ0 met15Δ0 trp1Δ63 ura3Δ0) and selected on SD-ura-trp agar plates with 20 mg/L of adenine for red and white colony selection in pYAC4. This is because the Sup-4-o suppressor tRNAgene has the EcoRI site in the middle, and this was where we inserted our cassettes. Colony PCR (RedTaq) was used to screen 96 colonies. Primers were designed to amplify a 1.6 kb band from the middle of ilvC to the middle of ilvD. The hit was then streaked out, and the new circular YAC was purified using the Yeast Plasmid Prep II kit (Zymo Research). This was transformed into STBL4 cells (Invitrogen), and 3 colonies were grown and sent to sequencing. The preps were put through PCR profiling that spanned across the construct from the middle of one gene to the middle of the next tandem gene (data not shown).

Plasmid preps from 3 different STBL4 transformants as well as the empty vector were put into 8 different PCR reactions each. A=1.6 kb amplified from −400 bases upstream of the EcoRI site in pYAC4 to the middle of ilvA. B=2.5 kb amplified from the middle of ilvA to the middle of ilvG. C=2.7 kb amplified from the middle of ilvG to the middle of ilvC. D=1.8 kb amplified from the middle of ilvC to the middle of ilvD. E=2.3 kb amplified from the middle of ilvD to the middle of kdcA. F=2.4 kb amplified from the middle of kdcA to the middle of adh6. G=1.3 kb amplified from the middle of adh6 to +400 bases downstream of the EcoRI site in pYAC4. H=4.1 kb amplified from middle of ilvC to the middle of kdcA. This spans the ilvD, as well as two repeating TEF-CYC elements, thus the prevalent 1.5 kb band is amplified because the template loops large TEF homologies, and the polymerase amplifies the shorter fragment without the ilvD. 4.1 kb band is seen faintly.

EXAMPLE 11

Truncated-Hybrid Method

The same method as the individual cassettes, but truncated hybrid cassettes have repetitive elements tucked in the middle of the cassettes, and partial genes on either side. The truncated hybrid cassettes are created by amplifying the primary cassettes. (FIG. 43). These cassettes are then mixed together in an equal molar ratio, and then PCR amplified again using primers located in the middle of the tandem gene cassette. The product, the truncated-hybrid cassettes have 40 base overlap homology to the next tandem truncated-hybrid cassette. The same was done for the first and last genes using vector as one of the overlapping primary cassettes. Six primary cassettes and vector ends were used to create 7 truncated-hybrid cassettes. These bands were then gel purified and mixed together in equal molar ratios.

Then 3 fragments were stitched together with Isothermal Assembly to create 1 larger fragment of 7 kb (FIG. 44), and the remaining 4 fragments were stitched together to create 1 larger fragment of 8 kb (FIG. 45). The Isothermal conditions were the same as described above, however this time reactions were setup with 400 ng/kb and left at 50 C. for 3 hours. The entire reaction was loaded onto a 0.8% agarose gel and run for 1 hour at 60V, and gel purified using ZymoClean kit. These were mixed with the linearized vector and stitched together with Isothermal Assembly (100 ng/kb, 50 C. 3 hrs), and transformed into S. cerevisiae ATCC 200897 strain. In parallel, the 3 final fragments were also transformed directly into S. cerevisiae to allow for in-vivo recombination of the fragments into a circular molecule. (FIG. 46). Hits were screened the same way as the "Individual Gene Cassette Method" described above and sent to be sequenced. The STBL4 grown plasmids were sequenced by BATJ with 22 primers. The table below represents an entire insert sequenced from the invitro recombination method using the 3 fragments.

EXAMPLE 12

Truncated-Hybrid Method to Create 16 Gene YAC

Used the same method as the truncated-hybrid method to create 6 gene YAC. 16 primary gene cassettes were amplified, then Overlap PCR was used to create the truncated-hybrid cassettes. All genes had TEF promoter, CYC terminator. The genes used were:

| Gene | Source Organism |
|---|---|
| PCK | P. stipitis |
| AAT2 | P. stipitis |
| HOM3$^{FBR}$ | P. stipitis |
| HOM2 | P. stipitis |
| HOM6 | P. stipitis |
| THR1 | P. stipitis |
| THR4 | P. stipitis |

| Gene | Source Organism |
|---|---|
| ilvA$^{FBR}$ | E. coli |
| ilvG | E. coli |
| ilvM | E. coli |
| ilvC | E. coli |
| ilvD | E. coli |
| kdcA | L. lactis |
| ADH6 | S. cerevisiae |

Three 3 sets of 4 fragments with overlap to each other, and 1 set of 3 fragments with overlap to each other, were stitched together with Isothermal Assembly to create larger intermediate fragments, similar to the methods described above, but with 16 genes total and 4 intermediate fragments. The Isothermal conditions were the same as described above, however this time reactions were setup with 400 ng/kb and left at 50 C. for 6 hours. The entire reaction was loaded onto a 0.8% agarose gel and run for 1 hour at 70V, and gel purified using ZymoClean kit. These were mixed with the linearized vector (20 ng/kb each fragment) and transformed into S. cerevisiae ATCC 200897 strain to allow for in-vivo recombination of the fragments into a circular molecule. Colonies were screened using primers to amplify across junctions of recombined intermediate fragments. The presumed insert sequence of the entire insert for 16 gene YAC is provided below (SEQ ID NO:97).

```
atagcttcaaaatgtttctactcctttttactcttccagattttctcgg
actccgcgcatcgccgtaccacttcaaaacacccaagcacagcatactaa
atttcccctctttcttcctctagggtgtcgttaattacccgtactaaagg
tttggaaaagaaaaagagaccgcctcgtttcttttttcttcgtcgaaaaa
ggcaataaaaattttatcacgtttcttttcttgaaaattttttttttg
atttttttctctttcgatgacctcccattgatatttaagttaataaacgg
tcttcaatttctcaagtttcagtttcattttcttgttctattacaactt
tttttacttcttgctcattagaaagaaagcatagcaatctaatctaagtt
ttctagaactagtggatccccatggctgactcgcaacccctgtccggtg
ctccggaaggtgccgaatatttaagagcagtgctgcgcgcgccggtttac
gaggcggcgcaggttacgccgctacaaaaaatggaaaaactgtcgtcgcg
tcttgataacgtcattctggtgaagcgcgaagatcgccagccagtgcaca
gctttaagctgcgcggcgcatacgccatgatggcgggcctgacggaagaa
cagaaagcgcacggcgtgatcactgcttctgcgggtaaccacgcgcaggg
cgtcgcgttttcttctgcgcggttaggcgtgaaggccctgatcgttatgc
caaccgccaccgccgacatcaaagtcgacgcggtgcgcggcttcggcggc
gaagtgctgctccacggcgcgaactttgatgaagcgaaagccaaagcgat
cgaactgtcacagcagcagggggttcacctgggtgccgccgttcgaccatc
cgatggtgattgccgggcaaggcacgctggcgctggaactgctccagcag
gacgccatctcgaccgcgtatttgtgccagtcggcggcggcggtctggc
tgctggcgtggcggtgctgatcaaacaactgatgccgcaaatcaaagtga
tcgccgtagaagcggaagactccgcctgcctgaaagcagcgctggatgcg
ggtcatccggttgatctgccgcgcgtagggctattttgctgaaggcgtagc
ggtaaaacgcatcggtgacgaaaccttccgtttatgccaggagtatctcg
acgacatcatcaccgtcgatagcgatgcgatctgtgcggcgatgaaggat
ttattcgaagatgtgcgcgcggtggcggaaccctctggcgcgctggcgct
ggcgggaatgaaaaatatatcgccctgcacaacattcgcggcgaacggc
tggcgcatattctttccggtgccaacgtgaacttccacggcctgcgctac
gtctcagaacgctgcgaactgggcgaacagcgtgaagcgttgttggcggt
gaccattccggaagaaaaaggcagcttcctcaaattctgccaactgcttg
gcgggcgttcggtcaccgagttcaactaccgttttgccgatgccaaaaac
gcctgcatctttgtcggtgtgcgcctgagccgcggcctcgaagagcgcaa
agaaattttgcagatgctcaacgacggcggctacagcgtggttgatctct
ccgacgacgaaatggcgaagctacacgtgcgctatatggtcggcggacgt
ccatcgcatccgttgcaggaacgcctctacagcttcgaattcccggaatc
accgggcgcgctgctgcgcttcctcaacacgctgggtacgtactggaaca
tttcttgttccactatcacagccatggcaccgactacgggcgcgtactg
gcggcgttcgaacttggcgaccatgaaccggatttcgaaacccggctgaa
tgagctgggctacgattgccacgacgaaaccaataacccggcgttcaggt
tcttttggcgggttagggggctgcaggaattcgatatcaagcttatcga
taccgtcgacctcgagtcatgtaattagttatgtcacgcttacattcacg
ccctcccccacatccgctctaaccgaaaaggaaggagttagacaacctg
aagtctaggtccctatttatttttttatagttatgttagtattaagaacg
ttatttatatttcaaatttttcttttttttctgtacagacgcgtgtacgc
atgtaacattatactgaaaaccttgcttgagaaggttttgggacgctcga
aggctttaatttgcggccggtacccaattcgccctatagtgagtcgtatt
acgcgcgcatagcttcaaaatgtttctactcctttttactcttccagat
tttctcggactccgcgcatcgccgtaccacttcaaaacacccaagcacag
catactaaatttcccctctttcttcctctagggtgtcgttaattacccgt
actaaaggtttggaaaagaaaaagagaccgcctcgtttcttttttcttcg
tcgaaaaaggcaataaaaattttatcacgtttcttttcttgaaaattt
ttttttgattttttctctttcgatgacctcccattgatatttaagtta
ataaacggtcttcaatttctcaagtttcagtttcattttcttgttctat
tacaactttttttacttcttgctcattagaaagaaagcatagcaatctaa
tctaagttttctagaactagtggatccccatgaatggcgcacagtgggt
ggtacatgcgttgcgggcacagggtgtgaacaccgttttcggttatccgg
gtggcgcaattatgccggtttacgatgcattgtatgacggcggcgtggag
cacttgctatgccgacatgagcagggtgcggcaatggcggctatcggtta
tgctcgtgctaccggcaaaactggcgtatgtatcgccacgtctggtccgg
gcgcaaccaacctgataacccgggcttgccggacgcactgttagattccatc
cctgttgttgccatcaccggtcaagtgtccgcaccgtttatcggcactga
cgcatttcaggaagtggatgtcctgggattgtcgttagcctgtaccaagc
acagctttctggtgcagtcgctggaagagttgccgcgcatcatggctgaa
```

-continued

```
gcattcgacgttgcctgctcaggtcgtcctggtccggttctggtcgatat
cccaaaagatatccagttagccagcggtgacctggaaccgtggttcacca
ccgttgaaaacgaagtgactttcccacatgccgaagttgagcaagcgcgc
cagatgctggcaaaagcgcaaaaaccgatgctgtacgttggcggtggcgt
tggtatggcgcaggcagttccggctttgcgtgaatttctcgctgccacaa
aaatgcctgccacctgtacgctgaaagggctgggcgcagtagaagcagat
tatccgtactatctgggcatgctgggaatgcatggcaccaaagcggcgaa
cttcgcggtgcaggagtgcgacttgctgatcgccgtgggtgcacgttttg
atgaccgggtgaccggcaaactgaacaccttcgccaccacgccagtgtt
atccatatggatatcgaccggcagaaatgaacaagctgcgtcaggcaca
tgtggcattacaaggtgatttaaatgctctgttaccagcattacagcagc
cgttaaatatcaatgactggcagctacactgcgcgcagctgcgtgatgaa
catgcctggcgttacgaccatcccggtgacgctatctacgcgccgttgtt
gttaaaacaactgtcagatcgtaaacctgcggattgcgtcgtgaccacag
atgtggggcagcaccagatgtgggctgcgcagcacatcgcccacactcgc
ccggaaaatttcatcacctccagcggcttaggcaccatgggttttggttt
accggcggcggttggcgcgcaagtcgcgcgaccaaacgataccgtcgtct
gtatctccggtgacggctctttcatgatgaatgtgcaagagctgggcacc
gtaaaacgcaagcagttaccgttgaaaatcgtcttactcgataaccaacg
gttagggatggttcgacaatggcagcaactgttttttccaggaacgatata
gcgaaaccacccttaccgataaccccgatttcctcatgttagccagcgcc
ttcggcatccctggccaacacatcacccgtaaagaccaggttgaagcggc
actcgacaccatgctgaacagtgatgggccatacctgcttcatgtctcaa
tcgacgaacttgagaacgtctggccgctggtgccgcctggtgccagtaat
tcagaaatgttggagaaattatcatgatgcaacatcaggtcaatgtatcg
gctctgagggctgcaggaattcgatatcaagcttatcgataccgtcgacc
tcgagtcatgtaattagttatgtcacgcttacattcacgccctcccccca
catccgctctaaccgaaaaggaaggagttagacaacctgaagtctaggtc
cctatttatttttttatagttatgttagtattaagaacgttatttatatt
tcaaattttctttttttttctgtacagacgcgtgtacgcatgtaacatta
tactgaaaaccttgcttgagaaggttttgggacgctcgaaggctttaatt
tgcggcctcactggccgtcgttttacaacgtcgtgactgggaaaaccata
gcttcaaaatgtttctactccttttttactcttccagattttctcggact
ccgcgcatcgccgtaccacttcaaaacacccaagcacagcatactaaatt
tcccctctttcttcctctagggtgtcgttaattaccgtactaaaggtttt
ggaaaagaaaaagagaccgcctcgtttcttttttcttcgtcgaaaaaggc
aataaaaattttttatcacgtttctttttcttgaaaatttttttttttgatt
ttttctctttcgatgactcccattgatatttaagttaataaacggtctt
caatttctcaagttcagtttcattttcttgttctattacaactttttt
tacttcttgctcattagaaagaaagcatagcasatctaatctaagttttc
tagaactagtggatcccccatggctaactacttcaatacactgaatctgc
```

-continued

```
gccaacagctggcacagctgggcaaatgtcgcttatgggccgcgatgaa
ttcgccgatggcgcgagctaccttcagggtaaaaaagtagtcatcgtcgg
ctgtggcgcacagggtctgaaccagggcctgaacatgcgtgattctggtc
tcgatatctcctacgctctgcgtaaagaagcgattgccgagaagcgcgcg
tcctggcgtaaagcgaccgaaaatggttttaaagtgggtacttacgaaga
actgatcccacaggcggatctggtgattaacctgacgccggacaagcagc
actctgatgtagtgcgcaccgtacagccactgatgaaagacggcgcggcg
ctgggctactcgcacggtttcaacatcgtcgaagtgggcgagcagatccg
taaagatatcaccgtagtgatggttgcgccgaaatgcccaggcaccgaag
tgccgtgaagagtacaaacgtgggtcggcgtaccgacgctgattgccctt
cacccggaaaacgatccgaaaggcgaaggcatggcgattgccaaagcctg
ggcggctgcaaccggtggtcaccgtgcgggtgtgctggaatcgtccttcg
ttgcggaagtgaaatctgacctgatgggcgagcaaaccatcctgtgcggt
atgttgcaggctggctctctgctgtgcttcgacaagctggtggaagaagg
taccgatccagcatacgcagaaaaactgattcagttcggttgggaaacca
tcaccgaagcactgaaacagggcggcatcaccctgatgatggaccgtctc
tctaacccggcgaaactgcgtgcttatgcgctttctgaacagctgaaaga
gatcatggcacccctgttccagaaacatatggacgacatcatctccggcg
aattctcttccggtatgatggcggactgggccaacgatgataagaaactg
ctgacctggcgtgaagagaccggcaaaaccgcgtttgaaaccgcgccgca
gtatgaaggcaaaatcggcgagcaggagtacttcgataaaggcgtactga
tgattgcgatggtgaaagcgggcgttgaactggcgttcgaaaccatggtc
gattccggcatcattgaagagtctgcatattatgaatcactgcacgagct
gccgctgattgccaacaccatcgcccgtaagcgtttgtacgaaatgaacg
tggttatctctgataccgctgagtacggtaactatctgttctcttacgct
tgtgtgccgttgctgaaaccgtttatggcagagctgcaaccgggcgacct
gggtaaagctattccggaaggcgcgggtagataacgggcaactgcgtgatg
tgaacgaagcgattcgcagccatgcgattgagcaggtaggtaagaaactg
cgcggctatatgacagatatgaaacgtattgctgttgcgggttaagtggg
ctgcaggaattcgatatcaagcttatcgataccgtcgacctcgagtcatg
taattagttatgtcacgcttacattcacgccctcccccacatccgctct
aaccgaaaaggaaggagttagacaacctgaagtctaggtccctatttatt
ttttatagttatgttagtattaagaacgttatttatatttcaattttt
cttttttttctgtacagacgcgtgtacgcatgtaacattatactgaaaac
cttgcttgagaaggttttgggacgctcgaaggctttaatttgcggccctg
gcgttacccaacttaatcgccttgcagcacatcccccatagcttcaaaat
gtttctactccttttttactcttccagattttctcggactccgcgcatcg
ccgtaccacttcaaaacacccaagcacagcatactaaatttcccctcttt
cttcctctagggtgtcgttaattaccgtactaaaggtttggaaaagaaa
aaagagaccgcctcgtttcttttttcttcgtcgaaaaaggcaataaaaatt
```

-continued tttatcacgtttcttttttcttgaaaatttttttttttgatttttttctctt
tcgatgacctcccattgatatttaagttaataaacggtcttcaatttctc
aagtttcagtttcattttttcttgttctattacaactttttttacttcttg
ctcattagaaagaaagcatagcaatctaatctaagttttctagaactagt
ggatcccccatgcctaagtaccgttccgccaccaccactcatggtcgtaa
tatggcgggtgctcgtgcgctgtggcgcgccaccggaatgaccgacgccg
atttcggtaagccgattatcgcggttgtgaactcgttcacccaatttgta
ccgggtcacgtccatctgcgcgatctcggtaaactggtcgccgaacaaat
tgaagcggctggcggcgttgccaaagagttcaacaccattgcggtggatg
atgggattgccatgggccacgggggatgctttattcactgccatctcgc
gaactgatcgctgattccgttgagtatatggtcaacgccactgcgccga
cgccatggtctgcatctctaactgcgacaaaatcaccccggggatgctga
tggcttccctgcgcctgaatattccggtgatctttgtttccggcggcccg
atggaggccgggaaaaccaaactttccgatcagatcatcaagctcgatct
ggttgatgcgatgatccagggcgcagacccgaaagtatctgactcccaga
gcgatcaggttgaacgttccgcgtgtccgacctgcggttcctgctccggg
atgtttaccgctaactcaatgaactgcctgaccgaagcgctgggcctgtc
gcagccgggcaacggctcgctgctggcaacccacgccgaccgtaagcagc
tgttccttaatgctggtaaacgcattgttgaattgaccaaacgttattac
gagcaaaacgacgaaagtgcactgccgcgtaatatcgccagtaaggcggc
gtttgaaaacgccatgacgctggatatcgcgatgggtggatcgactaaca
ccgtacttcacctgctggcggcggcgcaggaagcggaaatcgacttcacc
atgagtgatatcgataagctttcccgcaaggttccacagctgtgtaaagt
tgcgccgagcacccagaaataccatatggaagatgttcaccgtgctggtg
gtgttatcggtattctcggcgaactggatcgcgcggggttactgaaccgt
gatgtgaaaaacgtacttggcctgacgttgccgcaaacgctggaacaata
cgacgttatgctgacccaggatgacgcggtaaaaaatatgttccgcgcag
gtcctgcaggcattcgtaccacacaggcattctcgcaagattgccgttgg
gatacgctggacgacgatcgcgccaatggctgtatccgctcgctggaaca
cgcctacagcaaagacggcggcctggcggtgctctacggtaactttgcgg
aaaacggctgcatcgtgaaaacggcaggcgtcgatgacagcatcctcaaa
ttcaccggcccggcgaaagtgtacgaaagccaggacgatgcggtagaagc
gattctcggcgtaaagttgtcgccggagatgtggtagtaattcgctatg
aaggcccgaaaggcggtccggggatgcaggaaatgctctacccaaccagc
ttcctgaaatcaatgggtctcggcaaagcctgtgcgctgatcaccgacgg
tcgtttctctggtgcacctctggtctttccatcggccacgtctcaccgg
aagcggcaagcggcggcagcattggcctgattgaagatggtgacctgatc
gctatcgacatcccgaaccgtggcattcagttacaggtaagcgatgccga
actggcggcgcgtcgtgaagcgcaggacgctcgaggtgacaaagcctgga
cgccgaaaaatcgtgaacgtcaggtctcctttgccctgcgtgcttatgcc
agcctggcaaccagcgccgacaaaggcgcggtgcgcgataaatcgaaact -continued gggggggttaagggctgcaggaattcgatatcaagcttatcgataccgtcg
acctcgagtcatgtaattagttatgtcacgcttacattcacgccctcccc
ccacatccgctctaaccgaaaaggaaggagttagacaacctgaagtctag
gtccctatttatttttttatagttatgttagtattaagaacgttatttat
atttcaaattttttcttttttttctgtacagacgcgtgtacgcatgtaaca
ttatactgaaaaccttgcttgagaaggttttgggacgctcgaaggcttta
atttgcggccttttcgccagctggcgtaatagcgaagaggccccgcaccga
tatagcttcaaaatgtttctactccttttttactcttccagattttctcg
gactccgcgcatcgccgtaccacttcaaaacacccaagcacagcatacta
aatttcccctctttcttcctctagggtgtcgttaattacccgtactaaag
gtttggaaaagaaaaaagagaccgcctcgtttcttttttcttcgtcgaaaa
aggcaataaaaattttttatcacgtttcttttttcttgaaaattttttttt
gatttttttctctttcgatgacctcccattgatatttaagttaataaacg
gtcttcaatttctaagtttcagtttacttttttcttgttctattacaactt
ttttttacttcttgctcattagaaagaaagcatagcaatctaatctaagtt
ttctagaactagtggatcccccatgtatactgtgggggattattttgttgg
ataggttgcatgaattaggcatcgaggaaatctttggtgtacctggagat
tacaatttgcaatttctgaccagatcatatcgagagaggatatgaaatg
gattggtaacgccaatgaattaaatgccagctatatggccgatggctatg
ctcgtaccaagaaagctgctgcttttctgacaacttttggtgtcggtgaa
ttgtctgctattaacggactggccggtagttatgctgaaaatttgccagt
agttgaaatagtcggaagcccaacttctaaagtgcaaaacgatggcaaat
tcgtgcatcatactctggcagatggtgattttaagcacttcatgaaaatg
catgaacccgtaacggctgccagaactcttttaacagccgagaatgcgac
atatgaaattgatcgtgtactttctcagcttttaaaggagagaaaacctg
tttacataaacttacctgtcgatgttgctgctgccaaagcagagaagcca
gccctgtctcttgaaaagaaagctccaccaccaacactaccgaacaagt
gatattatctaaaattgaggaatcacttaaaaacgctcagaaaccagtag
tcatagcgggtcatgaagtcataagtttcggtcttgaaaagactgtaaca
caatttgtcagcgaaacaaaattgcctatcactactttgaactttggcaa
aagtgcggtcgacgagtcgttgccatcatttttgggtatctacaatggca
aactatcagaaatctcattgaaaaatttcgtagaaagtgcggatttcatt
ctgatgtgggcgtcaagctgacggattcttctacggggcttcactca
ccatttggatgaaaacaaaatgatttcattgaacatcgatgaagggatca
tctttaataaggtagtggaagatttcgattttagagccgtggttcctcc
ttatcagagttaaaaggtattgagtacgaagggcagtatattgataagca
gtacgaggaatttattccttcttctgctccacttttctcaagatcgtttat
ggcaagcagtcgagtccctgacacaaagcaacgagactatagttgcagag
caggggacctcattctttggtgcctctacaattttttctgaaatccaacag
cagatttataggacaacccctttggggctctattggatatacttttcccg -continued

```
cagcccttggttcacaaatcgcagataaggagtcaagacatctgttattc
ataggtgatggtagtctacaattaacagttcaagaattaggcctatcaat
aagggagaagttaaacccaatctgtttcataattaacaatgacggctaca
ctgttgaaagggagatccacggaccaacacaatcatacaatgatattccc
atgtggaactatagcaaattaccggagactttcggcgcaaccgaggatag
agtagtttcgaagatcgttaggactgagaatgaatttgttagcgttatga
aggaagcccaggctgatgtcaatagaatgtattggattgaattagttttg
gaaaaggaagatgcacctaaattactaaaaaagatggggaaactatttgc
tgagcaaaacaaataagggctgcaggaattcgatatcaagcttatcgata
ccgtcgacctcgagtcatgtaattagttatgtcacgcttacattcacgcc
ctcccccacatccgctctaaccgaaaaggaaggagttagacaacctgaa
gtctaggtccctatttattttttatagttatgttagtattaagaacgtt
atttatatttcaaattttctttttttctgtacagacgcgtgtacgcat
gtaacattatactgaaaaccttgcttgagaaggttttgggacgctcgaag
gctttaatttgcggcccgcccttcccaacagttgcgcagcctgaatggcg
aatggcatagcttcaaaatgtttctactccttttttactcttccagattt
tctcggactccgcgcatcgccgtaccacttcaaaacacccaagcacagca
tactaaatttcccctctttcttcctctagggtgtcgttaattacccgtac
taaaggtttggaaaagaaaaaagagaccgcctcgtttcttttttcttcgtc
gaaaaaggcaataaaaattttttatcacgtttcttttcttgaaaattttttt
ttttgatttttttctcttcgatgacctcccattgatattttaagttaat
aaacggtcttcaatttctcaagtttcagtttcattttttcttgttctatta
caactttttttacttcttgctcattagaaagaaagcatagcaatctaatc
taagttttctagaactagtggatcccccatgtcttatcctgagaaatttg
aaggtatcgctattcaatcacacgaagattggaaaaacccaaagaagaca
aagtatgacccaaaaccattttacgatcatgacattgacattaagatcga
agcatgtggtgtctgcggtagtgatattcattgtgcagctggtcattggg
gcaatatgaagatgccgctagtcgttggtcatgaaatcgttggtaaagtt
gtcaagctagggcccaagtcaaacagtgggttgaaagtcggtcaacgtgt
tggtgtaggtgctcaagtcttttcatgcttggaatgtgaccgttgtaaga
atgataatgaaccatactgcaccaagtttgttaccacatacagtcagcct
tatgaagacggctatgtgtcgcagggtggctatgcaaactacgtcagagt
tcatgaacattttgtggtgcctatcccagagaatattccatcacatttgg
ctgctccactattatgtggtggtttgactgtgtactctccattggttcgt
aacggttgcggtccaggtaaaaaagttggtatagttggtcttggtggtat
cggcagtatgggtacattgattccaaagccatggggcagagacgtatg
ttatttctcgttcttcgagaaaagagaagatgcaatgaagatgggcgcc
gatcactacattgctacattagaagaaggtgattggggtgaaaagtactt
tgacaccttcgacctgattgtagtctgtgcttcctcccttaccgacattg
acttcaacattatgccaaaggctatgaaggttggtggtagaattgtctca
atctctataccagaacaacacgaaatgttatcgctaaagccatatggctt
aaaggctgtctccatttcttacagtgctttaggttccatcaaagaattga
accaactcttgaaattagtctctgaaaaagatatcaaaatttgggtggaa
acattacctgttggtgaagccggcgtccatgaagccttcgaaaggatgga
aaagggtgacgttagatatagatttaccttagtcggctacgacaaagaat
tttcagactagggctgcaggaattcgatatcaagcttatcgataccgtc
gacctcgagtcatgtaattagttatgtcacgcttacattcacgccctccc
cccacatccgctctaaccgaaaaggaaggagttagacaacctgaagtcta
ggtccctatttattttttatagttatgttagtattaagaacgttattta
tatttcaaattttcttttttttctgtacagacgcgtgtacgcatgtaac
attatactgaaaaccttgcttgagaaggttttgggacgctcgaaggcttt
aatttgcggcc
```

Fermentation Data

Threonine Deaminase

The conversion of L-threonine to 2-keto butyrate (2-oxobutanoate) is catalyzed by Threonine Deaminase (TD). Two types of TD have been described. The catabolic TD is expressed during the utilization of threonine as a nitrogen source. This enzyme, encoded by the CHA1 gene, is primarily genetically regulated. The biosynthetic TD, encoded by the ILV1 gene in S. cerevisiae, catalyzes the same reaction. However, this enzyme is subject to allosteric regulation by isoleucine. Deregulation of TD either by expression of the catabolic TD or expression of a biosynthetic TD that is insensitive to isoleucine increased production of 2-MBO (FIG. 47).

Screening in tubes produced a similar result (1500-2000 µM 2-MBO in 24 hours).

EXAMPLE 13

Cytosolic TD

In yeast, the metabolic reactions in isoleucine biosynthesis from threonine are thought to occur predominantly in the mitochondria. Expression of isoleucine-insensitive, cytosolic TD resulted in the accumulation of propanol. Propanol results from the decarboxylation and subsequent reduction of 2-KB. The accumulation of propanol confirms the activity of the recombinant or modified TD.

TABLE 5

Fermentation products during expression of cytosolic TD.

| Strain ID | Description | 3-MBO[1] | 2-MBO | Propanol | Isobutanol |
|---|---|---|---|---|---|
| 8002 | p415TEF ILV1$^{FBR}$ delta45::His | 130 | 102 | 632 | 1121 |
| 7466 | p414TEF ilvA$^{FBR}$ (Gg) p415TEF | 78 | 36 | 522 | 233 |
| 7511 | p416Tef ilvA$^{FBR}$ (Ec) p415TEF | 75 | 52 | 1855 | 373 |
| N/A | Controls | 73 | 125 | 317 | 514 |

[1]All concentrations are in µM.

EXAMPLE 14

Acetolactate Synthase (Acetohydroxy Acid Synthase, ALS)

The first committed step in Valine/Leucine biosynthesis and Isoleucine biosynthesis is catalyzed by ALS. This enzyme catalyzes the formation of either 2-acetolactate from two pyruvate molecules or formation of 2-aceto-2-hydroxybutyrate from 1 molecule pyruvate and 1 molecule of 2-KB. The regulation of this enzymatic step is complex and its biochemistry in S. cerevisiae has not been well characterized.

Expression of various ALS genes alone primarily lead to increased isobutanol production (Valine production) in tube experiments.

The first reaction in Threonine biosynthesis is catalyzed by the allosteric enzyme aspartate kinase (AK), encoded by the HOM3 gene in yeasts. The accumulation of intracellular threonine in strains expressing threonine-insensitive AK suggests that flux through this pathway had been increased. Expression in a strain co-expressing an isoleucine-insensitive TD increased 2-MBO specific productivity (FIG. 48) Fermentation titer was further increased by expression of either THR1 or THR4.

TABLE 6

Fermentation products during ALS expression.

| Strain ID | Name | 2-MBO[1] | 3-MBO | nPrOH | iBuOH |
|---|---|---|---|---|---|
| 7305 | p415TEF ILV6 | 56.05 | 194.37 | 349.65 | 210.21 |
| 7306 | p415TEF ilvB (Cg) | 55.55 | 183.79 | 294.29 | 256.52 |
| 7308 | p415TEF ilvB (Ec) | 54.35 | 153.11 | 297.14 | 348.00 |
| 7309 | p414TEF ilv2 + p415TEF | 53.44 | 187.23 | 309.37 | 506.19 |
| 7558 | p415TEF ilvG' (Ec) p416TEF ilvM(Ec) | 19.59 | 32.39 | 140.09 | 111.81 |
| 7559 | p415TEF ilvI (Ec) p416TEF ilvH(Ec) | 58.24 | 93.93 | 325.29 | 377.38 |
| 7560 | p415TEF ilvI(Ec) | 17.47 | 23.17 | 54.78 | 103.03 |
| 7561 | p415TEF ilvG'(E) | 15.54 | 20.36 | 46.35 | 87.06 |
| 7732 | p415TEF AlsS (Bs) | 48.00 | 67.33 | 217.07 | 360.02 |
| 7733 | p415TEF AlsS* (Bs) | 56.19 | 74.99 | 310.28 | 503.28 |
| 7888 | p415TEF ilv2(Δ45::His) | 87.91 | 106.90 | 350.70 | 992.34 |
| 7890 | p415TEF AlsS (Bs)-AHFGQ | 95.04 | 125.21 | 355.78 | 1039.90 |
| 7891 | p415TEF AlsS (Bs)-VHFNQ | 86.93 | 142.12 | 318.68 | 796.19 |
| 7892 | p415TEF AlsS (Bs)-VHFPQ | 96.46 | 123.53 | 362.70 | 1111.76 |
| 7893 | p415TEF AlsS (Bs)-VHFQQ | 100.83 | 128.40 | 354.80 | 1125.82 |
| 7914 | p415TEF ilv2::His | 86.85 | 128.99 | 342.29 | 1375.85 |
| 7915 | p415TEF ilv2 (Δ25::His) | 95.57 | 111.87 | 327.92 | 941.70 |
| 7916 | p415TEF ilv2: (Δ35::His | 81.87 | 123.46 | 285.78 | 624.58 |

[1]All concentrations are in μM.

EXAMPLE 15

TD and ALS

Co-expression of a cytosolic TD with a cytosolic ALS decreases propanol production, indicating that the ALS is competing with KDC for the 2-KB (Table 7). If the subsequent enzymes in the pathway were expressed in the cytoplasm, increased 2-MBO production would be expected.

TABLE 7

Fermentation products during co-expression of TD and ALS.

| Strain ID | Name | 2-MBO[1] | 3-MBO | nPrOH | iBuOH |
|---|---|---|---|---|---|
| 7511 | p416TEF ilvA$^{FBR}$ (Ec) p415TEF | 51 | 75 | 1854 | 373 |
| 7720 | p415TEF ilvG' (Ec) p413TEF-ilvA$^{FBR}$ (Ec) | 49 | 76 | 896 | 497 |
| 7729 | p415TEFilvI (Ec) p413TEF-ilvA$^{FBR}$ (Ec) | 48 | 74 | 1061 | 580 |

[1]All concentrations are in μM.

Aspartate Kinase and TD

TABLE 8

Fermentation products in TD and AK expression.

| Strain | Genotype | 3-MBO | 2-MBO | Propanol | isobutanol |
|---|---|---|---|---|---|
| 8020 | :TEF ILV$^{FBR}$ p413TEF p415TEF p416CYC HOM3-R2 | 118 | 2170 | 543 | 867 |
| 8021 | :TEF ILV$^{FBR}$ p413TEF p415TEF HOM2 p416CYC HOM3-R2 | 125 | 2429 | 699 | 975 |
| 8022 | :TEF ILV$^{FBR}$ p413TEF HOM6 p415TEF HOM2 p416CYC HOM3-R2 | 124 | 2414 | 499 | 856 |
| 8023 | :TEF ILV$^{FBR}$ p413TEF THR1 p415TEF Hom2 p416CYC HOM3-R2 | 132 | 2748 | 904 | 1068 |
| 8024 | :TEF ILV$^{FBR}$ p413TEF THR4 p415TEF | 140 | 2834 | 581 | 824 |

TABLE 8-continued

Fermentation products in TD and AK expression.

| Strain Genotype | 3-MBO | 2-MBO | Propanol | isobutanol |
|---|---|---|---|---|
| HOM2 p416CYC HOM3-R2) | | | | |

Selection of ADH

Biochemical studies determined that the conversion of 2-MBA to 2-MBO is not effectively performed by the endogenously expressed alcohol dehydrogenases, which is presumed to be ADH1. This was evaluated in vivo by supplementing growth medium with the aldehyde precursor of 2-MBO in cultures expressing various alcohol dehydrogenases.

Cultures of S. cerevisiae expressing various ADH enzymes in an otherwise isogenic background were incubated by standard methods for 12 hours. A bolus of 2-MBA was added to the medium at 12 hours EFT. Aldehydes are not charged and can freely diffuse into the cells. Samples were collected hourly and 2-MBO in the fermentation broth was measured. The specific rate of 2-MBO production (μmol 1-1 OD600-1 h-1) was determined during the period of excess 2-MBA (FIG. 49) Based on these studies, expression of ADH6 from S. cerevisiae is the most effective enzyme for the conversion of 2-MBA to 2-MBO, though Ms-ADH1 and SFA1 were also effective and likely not significantly different than the ADH6.

Maximum Production

Increasing initial glucose concentration or feeding carbon increased the final production of 2-MBO (FIG. 50).

GCN4 ("General Control Nondepressible") encodes a transcriptional activator and was originally characterized as a positive regulator of genes expressed during amino acid starvation. In addition to the derepression of genes involved in 19 out of 20 amino acid biosynthetic pathways, Gcn4p may directly or indirectly regulate the expression of genes involved in purine biosynthesis, organelle biosynthesis, autophagy, glycogen homeostasis, and multiple stress responses Under environmental stresses, such as amino acid starvation, purine limitation, or nitrogen limitation, the translation of GCN4 is induced. Gcn4p is a member of the basic leucine-zipper (bZIP) family and binds DNA as a homodimer. Gcn4p has been shown to bind the consensus sequence TGACTC, located upstream of many genes induced during amino acid starvation.

Constitutive expression of GCN4 from a plasmid in the context of a GCN4+ strain increased 2-MBO productivity. Strains with a chromosomal deletion in GCN4 complemented with GCN4 did not produce this phenotype.

The 2-MBO specific productivity of these genotypes was compared to a TDFBR strain. (FIG. 51.)

EXAMPLE 16

Citramalate Pathway

The heterologous citramalate pathway (FIG. 52) provides a threonine-independent alternative to 2-oxobutanoate, an intermediate in isoleucine biosynthesis and 2-MBO. Currently, published data encompasses characterization of this alternate pathway for isoleucine biosynthesis in *Methanococcus jannaschii* and *Geobacter sulfurreducens*.

Included here are:
1. The heterologous expression and proof of functionality of uncharacterized putative citramalate synthase genes (annotated as isopropylmalate synthase (leuA) from *Synechocystis* and *T. maritima* in *S. cerevisiae*;
2. The heterologous expression of isopropylmalate dehydrogenase (leuB) from *M. jannaschii* and evidence of their functionality in *S. cerevisiae*;
3. The heterologous expression of isopropylmalate isomerase (leuC and leuD) from *M. jannaschii* and evidence of their functionality in *S. cerevisiae*;
4. The heterologous expression of the characterized cimA gene from *G. sulfurreducens*. The gene was codon-optimized and shown to be functional in *S. cerevisiae*;
5. The expression of the entire heterologous citramalate pathway in *S. cerevisiae*. No published data describes the cloning and functionality of all four genes heterologously expressed in a single host organism; and
6. Deletion of carboxy-terminus portions of the leuA protein of *T. maritima* to produce feedback-inhibition resistant gene products. These D316 and L381 truncations remove a possible allosteric domain inhibited by isoleucine.

Citramalate Synthase (cimA/leuA)

The cimA/leuA gene has been cloned from 3 sources (*Synechocystis*, *T. maritima*, and *G. sulfurreducens*) using either high and/or low copy yeast vectors and driven by the TEF1 or GPD constitutive promoters. To date, all three have shown some level of conversion of pyruvate and Ac-CoA to citramalate. The *Synechocystis* gene driven by the TEF1 promoter

TABLE 9

2-MBO production of GCN4 overexpressing strains

| Strain # | Description | 3-MBO | 2-MBO | Propanol | Isobutanol |
|---|---|---|---|---|---|
| 8003 | p415GPD GCN4 | 75 | 1369 | 316 | 409 |
| 8004 | p415CYC GCN4 | 103 | 2340 | 418 | 491 |
| 8031 | ΔGCN4 p415CYC GCN4 | 101 | 79 | 184 | 690 |
| 8032 | ΔGCN4 p415GPD GCN4 | 91 | 73 | 340 | 836 |
| 8033 | ΔGCN4 p415TEF GCN4 | 105 | 83 | 247 | 802 |
| 8034 | ΔGCN4 p415CYC GCN4 p413TEF ILV1$^{FBR}$ | 88 | 1852 | 264 | 514 |
| 8035 | ΔGCN4 p415TEF GCN4 p413TEF ILV1$^{FBR}$ | 91 | 1763 | 323 | 718 | produced up to 25 µM citramalate, and the *G. sulfurreducens* and *T. maritima* cimA/leuA driven by the GPD promoter yielded about a 15-fold to 50-fold increase at 450 µM to 1600 µM, respectively. (FIG. 53.)

A lower level or no citramalate is detected in yeast strains with full-length cimA/leuA when grown in SD medium supplemented with Ile (isoleucine) compared to SD medium with no Ile, suggesting a possible post-translational allosteric inhibition by Ile. There is a regulatory domain on the C-terminus that, when deleted, may allow for feedback inhibition-resistance. This truncated version has been cloned to produce a feedback inhibition-resistant cimA/leuA(cimA$^{FBR}$/leuA$^{FBR}$).

EXAMPLE 17

Isopropylmalate Isomerase and Isopropylmalate Dehydrogenase

Yeast express endogenous isopropylmalate isomerase (LEU1) and isopropylmalate dehydrogenase (LEU2) in the cytoplasm. When cimA/leuA variants are introduced into an ILV1::KanMX (threonine deaminase knock-out; isoleucine auxotroph) yeast background, complementation is demonstrated. This suggests that LEU1 and LEU2 are sufficient for the conversion of citramalate to 2-oxobutanoate. However, the relatively large accumulation of citramalate (up to 1.6 mM, see above) seems to indicate that the native yeast genes are not very efficient in utilizing the novel citramalate and erythro-β-methyl-D-malate substrates.

Therefore, three other genes were cloned and either integrated into the yeast genome or introduced as a plasmid to complete the heterologous citramalate pathway. leuC and leuD subunits form isopropylmalate isomerase, and leuB is isopropylmalate dehydrogenase.

Data (FIG. 54) shows that introduction of the complete heterologous citramalate pathway does increase MBO production, in particular 2-MBO. Strains containing cimA/leuA (strains E, F), leuCD and leuB (strain C), or cimA/leuA plus leuCD and leuB (strains A1, A2, B1, B2) produce MBO at 1:2 or 1:3 3-MBO:2-MBO ratios without significantly increasing 3-MBO over the control. In the negative controls (strains D, G), the ratio is the inverse at 2:1 3-MBO:2-MBO ratio.

TABLE 10

MBO production of CimA/leuA overexpression strains

| Strain ID | Genotype | Media | 3-MBO µM | 2-MBO µM |
|---|---|---|---|---|
| 8081 | p416GPD-leuA (Tm), p413TEF1-leuD (Mj) | SD-His-Ile-Leu-Ura | 176.68 | 149 |
| 8081 | p416GPD-leuA (Tm), p413TEF1-leuD (Mj) | SD-His-Ile-Leu-Ura | 136.71 | 214 |
| 8080 | p416GPD-cimA (Gc), p413TEF1-leuD (Mj) | SD-His-Ile-Leu-Ura | 186.67 | 112 |
| 8080 | p416GPD-cimA (Gc), p413TEF1-leuD (Mj) | SD-His-Ile-Leu-Ura | 147.04 | 313 |
| 8081 | p416GPD-leuA (Tm), p413TEF1-leuD (Mj) | SD-His-Ile-Leu-Ura | 117.3 | 261 |
| 8081 | p416GPD-leuA (Tm), p413TEF1-leuD (Mj) | SD-His-Ile-Leu-Ura | 119.75 | 364 |
| 8080 | p416GPD-leuA (Gc), p413TEF1-leuD (Mj) | SD-His-Ile-Leu-Ura | 131.26 | 232 |
| 8080 | p416GPD-leuA (Gc), p413TEF1-leuD (Mj) | SD-His-Ile-Leu-Ura | 162.98 | 561 |
| 8121 | p416GPD, p413TEF1-leuD (Mj) | SD-His-Ile-Leu-Ura | 146.26 | 192 |
| 8122 | p416GPD, p413TEF1 | SD-His-Ile-Leu-Ura | 131.69 | 86 |
| 8055 | p416GPD-leuA (Tm), p415TEF1 | SD-His-Ile-Leu-Ura | 134.29 | 67 |
| 8059 | p416GPD-cimA (Gs), p415TEF1 | SD-His-Ile-Leu-Ura | 128.21 | 107 |
| 8055 | p416GPD-leuA (Tm), p415TEF1 | SD-Leu-Ura | 94.21 | 209 |
| 8059 | p416GPD-cimA (Gs), p415TEF1 | SD-Leu-Ura | 113.7 | 228 |
| 8123 | p426TEF, p415TEF1 | SD-Leu-Ura | 111.5 | 73 |
| media only | | SD-His-Ile-Leu-Ura | 0 | 0 |
| 8081 | p416GPD-cimA (Tm), p413TEF1-leuD (Mj) | SD-His-Ile-Leu-Ura | 176.68 | 149 |
| 8081 | p416GPD-cimA (Tm), p413TEF1-leuD (Mj) | SD-His-Ile-Leu-Ura | 136.71 | 214 |
| 8080 | p416GPD-cimA (Gc), p413TEF1-leuD (Mj) | SD-His-Ile-Leu-Ura | 186.67 | 112 |
| 8080 | p416GPD-cimA (Gc), p413TEF1-leuD (Mj) | SD-His-Ile-Leu-Ura | 147.04 | 313 |
| 8081 | p416GPD-cimA (Tm), p413TEF1-leuD (Mj) | SD-His-Ile-Leu-Ura | 117.3 | 261 |
| 8081 | p416GPD-cimA (Tm), p413TEF1-leuD (Mj) | SD-His-Ile-Leu-Ura | 119.75 | 364 |
| 8080 | p416GPD-cimA (Gc), p413TEF1-leuD (Mj) | SD-His-Ile-Leu-Ura | 131.26 | 232 |
| 8080 | p416GPD-cimA (Gc), p413TEF1-leuD (Mj) | SD-His-Ile-Leu-Ura | 162.98 | 561 |
| 8121 | p416GPD, p413TEF1-leuD (Mj) | SD-His-Ile-Leu-Ura | 146.26 | 192 |
| 8122 | p416GPD, p413TEF1 | SD-His-Ile-Leu-Ura | 131.69 | 86 |

TABLE 10-continued

MBO production of CimA/leuA overexpression strains

| Strain ID | Genotype | Media | 3-MBO μM | 2-MBO μM |
|---|---|---|---|---|
| 8055 | p416GPD-cimA (Tm), p415TEF1 | SD-His-Ile-Leu-Ura | 134.29 | 67 |
| 8059 | p416GPD-cimA (Gs), p415TEF1 | SD-His-Ile-Leu-Ura | 128.21 | 107 |
| 8055 | p416GPD-cimA (Tm), p415TEF1 | SD-Leu-Ura | 94.21 | 209 |
| 8059 | p416GPD-cimA (Gs), p415TEF1 | SD-Leu-Ura | 113.7 | 228 |
| 8123 | p426TEF, p415TEF1 | SD-Leu-Ura | 111.5 | 73 |
| media only | | SD-His-Ile-Leu-Ura | 0 | 0 |

Data normalized to $OD_{600} = 4._,.$

There is an obvious increase in 2-MBO production when strains are grown in media +Isoleucine compared to −Isoleucine. This observation holds true for both strains containing the complete heterologous pathway, as well as strains containing only cimA/leuA. The addition of cimA/leuA alone from either *T. maritima* or *G. sulfurreducens* increases 2-MBO yield 2-fold, whereas introduction of the entire heterologous pathway increases 2-MBO up to 8-fold.

The native yeast genes BAT1 and BAT2 can work reversibly to convert Ile to 2-keto-3-methyl-valerate and 2-MBO. If this were the sole reason for the increase of 2-MBO in the +Ile medium, we would observe a commensurate increase of 2-MBO across the board for strains A1, A2, B1, B2, C, D, E, and F. However, there is an obvious increase in 2-MBO production specifically in strains containing the complete citramalate pathway. This may be because when media is supplemented with Ile, the cells are under less physiological stress and can divert more of the intermediate citramalate and erythro-β-methyl-D-malate compounds to 2-MBO production rather than to isoleucine biosynthesis.

Interestingly, the introduction of only leuB and leuCD (no cimA/leuA) also increases 2-MBO production about 2-fold. When only leuB and leuC are expressed, however, a functional isopropylmalate isomerase cannot be formed and MBO production is similar to that of the negative control. Although no direct functional assays have been performed on the activity and expression of the leuB and leuCD genes, this change in phenotype implies that these heterologous genes are functional in yeast. (FIG. 55.)

EXAMPLE 18

Other Alternative Pathways to 2-MBO

In addition to the incorporation of the citramalate pathway (cimA) to 2-oxobutanoate synthesis, other alternative pathways for 2-MBO production were evaluated using a stoichiometric model of yeast metabolism that allows assessing the effects of genetic manipulations on the maximum theoretical yields of 2-MBO from glucose. The model accounts for the needs of the yeast cell to balance cofactors such as NAD and NADH in the pathway from glucose to 2-MBO and for the need to provide energy in the form of ATP for the biosynthetic pathways. The model was used to compare various alternative scenarios to wild type 2-MBO production, such as the effect of moving the Isoleucine (Ile) pathway from mitochondrion to the cytoplasm and the utilization of a NADPH dependent glycerol-3-phosphate dehydrogenase (GAPD) instead of the native NADH-dependent form of the enzyme. The effects of these manipulations on the maximum theoretical yields were assessed under both aerobic and anaerobic conditions in order to span the range or realistic production environments.

The maximum theoretical 2-MBO yield from glucose for wild type (wt) yeast using the mitochondrial Ile pathway was calculated to be 0.70 mol mol−1 (0.34 g g−1) aerobically and 0.29 mol mol−1 (0.14 g g−1) anaerobically (FIG. 56). Adding a cytoplasmic Ile pathway was predicted to increase the 2-MBO yield by 8.6% and 44% in aerobic and anaerobic conditions respectively. Based on these results, a cytoplasmic Ile pathway would be highly preferred especially in partially aerated conditions. Adding the CimA pathway together with the with the cytoplasmic Ile pathway would provide an additional 2.6% and 15.4% increase in 2-MBO yield in aerobic and anaerobic conditions respectively. The analysis showed that combining the CimA pathway with the native threonine-dependent 2-MBO pathway allows for more efficient balancing of NADH and thus increases 2-MBO yields at the expense of ethanol fermentation. Expression of a NADPH dependent GAPD enzyme in yeast was predicted to result in 2.6% (aerobic) and 9.6% (anaerobic) increase in 2-MBO yield. Combining the three novel pathways (cytoplasmic Ile, CimA, and NADPH-dependent GAPD) increases the maximum theoretical yield of 2-MBO from glucose by 5.2% (aerobic) and 53.8% (anaerobic). The overall result of the three manipulations is predicted to be to make 2-MBO production entirely independent of the level of aeration and thus provide more flexibility for production process design.

The effect of isoleucine on LeuA activity was also examined. Strains (see table below) were grown is selective media to mid-log phase. Cells were harvested by centrifugation and suspended in TES buffer (100 mM, pH 7.5) and disrupted by bead beating. Cell debris was removed by centrifugation (25, 000×g, 30 min, 4° C.) to make cell extracts. Small molecules were removed by diafiltration (3×, 90% volume, 5000 D cut-off filter). Protein concentration was determined by BCA, and final suspensions were diluted to 1 mg/ml.

| Strain | Genotype |
|---|---|
| 8055 | ΔILV1, p416GPD leuA (Tm)), p415TEF |
| 8076 | ΔILV1, p416GPD leuA (Tm)1-381 p415TEF |
| 8077 | ΔILV1, p416GPD leuA (Tm)1-316 p415TEF |
| Control | ΔILV1, p416TEF p415TEF |

Assay mixture contained the following: sodium pyruvate, 10 mM; acetyl-CoA, tri-lithium salt, 1.0 mM; TES buffer, 100 mM at pH 7.5; DTNB, 5 mM. Reactions were initiated with the addition of dialyzed cell extract. Activity was measured by the total increase in A412 after 30 minutes at 22° C., and total absorbance was subtracted from a mixture with pyruvate excluded. Sensitivity of citramalate synthase to isoleucine, a putitive allosteric inhibitor, was tested by adding isoleucine to 10 mM. (FIG. 57.)

EXAMPLE 19

Synthesis of Synthesis of bis(2-methylbutyl)ether and Use as a Fuel Additive Oxygenated additives can be used to boost the performance of fuels. Ethers have a much lower water absorbance than alcohols and can used as a cetane enhancer. The most common way to synthesize ethers is through the intermolecular condensation of alcohols using an acid catalyst. The alcohols can be 2-methylbutanol, 3-methylbutanol, a mixture of both, or a mixture of a methylbutanol and another alcohol. In the case of 2-methylbutanol, the alcohol can be either the single enantiomer or a racemic mixture. The list of catalysts includes, but is not limited to, sulfuric acid, p-toluenesulfonic acid, methanesulfonic acid, trifluoromethanesulfonic acid, phosphoric acid, phosphomolybic acid, phosphotungstic acid, oxalic acid, boric acid, and hydrofluoric acid. Heterogeneous catalysts such as Nafion, acidic ion exchange catalysts and zeolites can also be used.

A preferred synthesis is:

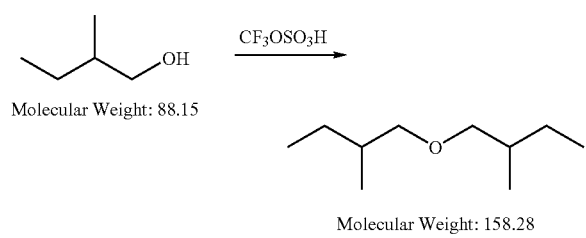

A 5000 ml 3 neck round bottom flask, equipped with magnetic stirring, heating block, and a Dean Stark trap, was charged with 2-methyl-1-butanol (2000.0 g, 22.7 mol) and triflourmethanesulfonic acid (50 ml, 0.57 mol). The solution was heated to reflux (internal temperature≈135° C.) for 68 hours[1]. During this time approximately 230 ml of water had collected in the Dean Stark trap. The reaction had turned a dark yellow. The reaction was washed with water (200 ml) followed by 1 N NaOH (500 ml), and then with brine (200 ml). The liquid was dried over $Na_2SO_4$ (150 g). The crude material (1500 g) was purified by vacuum (30 to 40 mm Hg) distillation through a 150 mm Vigreux column to yield the product as a clear liquid (1077 g, 60% yield; GC purity: 92 area %, 8% other ethers).

[1] Extended reaction times lead to degradation of the product.

This reaction was also conducted on equimolar amounts of 2-methylbutanol and 3-methylbutanol. After distillation a mixture of ethers was isolated in 43% yield. The ratio of bis (3-methylbutyl)ether to bis(2-methylbutyl)ether to the mixed ether was 50:5:45.

EXAMPLE 20

Preparation of 2-methyl-1-(2-methylbutoxy)butane

This example demonstrates the conversion of 2-methylbutyl ether to 2-methyl-1-(2-methylbutoxy)butane, otherwise known as bis-(2-methylbutyl)ether from 2-methylbutanol.

A 1000 mL 3-neck round bottom flask equipped with magnetic stirring, heating mantle, and a Dean-Stark trap was charged with 2-methyl-1-butanol (400.0 g, 4.54 mol) and trifluoromethanesulfonic acid (10 mL, 0.11 mol). The use of triflic acid was found to provide superior results compared to other catalysts. The solution was heated to reflux for 56 to 72 hours. During this time, approximately 43 mL of water had collected in the Dean-Stark trap. The reaction turned either pale yellow or black depending on the reaction time. The reaction was washed with 1 N NaOH (100 mL), then saturated $NaHCO_3$ (50 mL) and finally with brine (25 mL). The liquid was dried over $Na_2SO_4$. The crude material was purified by vacuum distillation (ca. 50 mmHg, b.p. 52 to 72° C.).

A reaction time of 56 hours gave a 70% yield of product. A reaction time of 70 hours gave a 35% yield of product. The purity of the product was analyzed by gas chromatography (GC). In the procedure wherein the reaction time was 56 hours, the GC peak area of a sample of the reaction mixture reflected the following amounts: 74% desired product, 18% alcohol, and 8% other ethers. In the procedure wherein the reaction time was 70 hours, the GC peak area of a sample of the reaction mixture reflected the following amounts: 98% desired product, 2% other ethers.

In addition, the bis-(2-methylbutyl)ether was tested as a diesel fuel additive, and was found to have a calculated cetane number between 126 and 160.

EXAMPLE 21

Use of MBO in the Production of Biodiesels

Biodiesel, an alternative diesel fuel derived from vegetable oil, animal fats, or waste vegetable oils, is obtained by the transesterification of triglycerides with an alcohol in presence of a catalyst to give the corresponding alkyl esters. It provides a market for excess production of vegetables oils and animal fats; it decreases the country's dependence on imported petroleum; it is a renewable fuel and does not contribute to global warming due to its closed carbon cycle; it has lower exhaust emissions than regular diesel fuel; and can be used in diesel engines without extensive engine modifications.

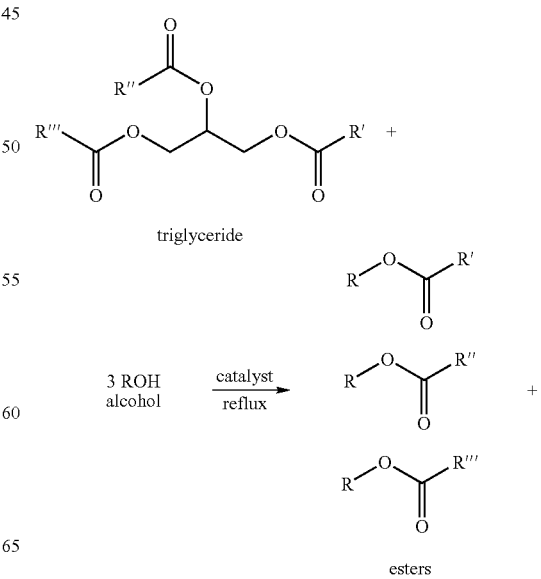

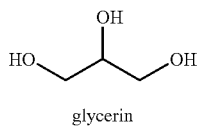

Two major indicators of biodiesel fuel quality are: the cloud point, the temperature at which waxy solids first appear during the cooling of diesel fuel; and the cetane number (CN), the measure of the readiness fuel to autoignite when injected into the engine.

This example shows the synthesis of biodiesel 2-methylbutyl esters and biodiesel methyl esters, compares the cloud points and cetane numbers, and demonstrates that methylbutyl esters are a viable replacement for methyl esters.

Soybean oil 2-methylbutyl esters and canola oil 2-methyl butyl esters were synthesized by transesterifying the triglyceride with 2-methylbutyl alcohol in presence of catalyst. The catalyst could be acidic or basic, aqueous or organic, free or bounded on solid support; it includes but is not limited to: potassium hydroxide, sodium hydroxide, sulfuric acid, p-toluenesulfonic acid, potassium carbonate, sodium hydride, DOWEX Marathon A OH form, magnesium oxide, and calcium oxide.

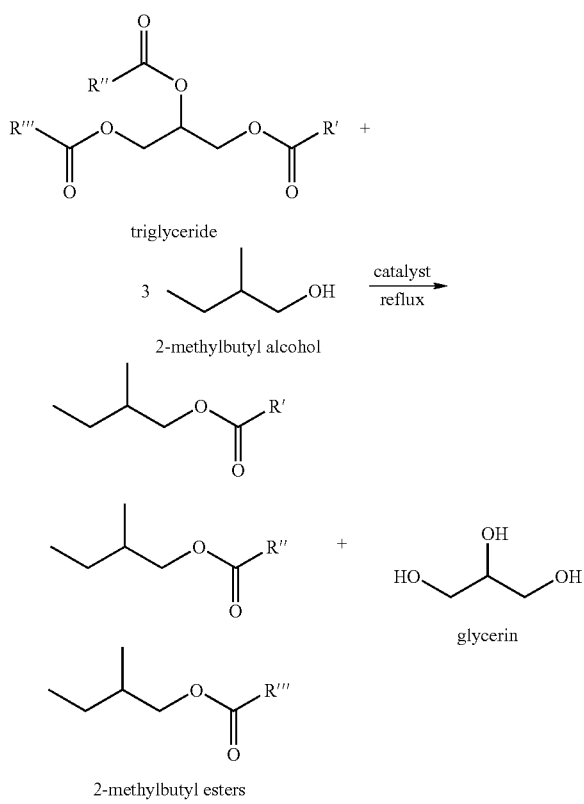

Synthesis of 2-methylbutyl esters. A solution of canola oil (530.00 g) in 2-methylbutanol (370.79 g, 4.206 mol) was stirred at 50° C.; sulfuric acid (0.61 g, 0.006 mol, 0.01 equiv.) was added. The reaction mixture continued stirring at reflux (~125° C.) until diglycerides were not detected by GC-FID (~70 h). The reaction mixture was allowed to cool to ambient temperatures and transferred to a separatory funnel where glycerin was allowed to settle and then removed. The remaining solution was washed with sat'd aq. $NaHCO_3$ (500 mL), sat'd aq. $NHCl_3$ (2×500 mL), brine (500 mL), and dried over $Na_2SO_4$ (100.00 g). The crude product was distilled under vacuum to afford 2-methylbutyl esters as an off-white liquid. Yield 573.76 g.

Soybean oil methyl esters and canola oil methyl esters were synthesized by transesterifying the triglyceride with methanol in presence of catalyst. The catalyst could be acidic or basic, aqueous or organic, free or bounded on solid support; it includes but is not limited to: potassium hydroxide and sodium hydroxide.

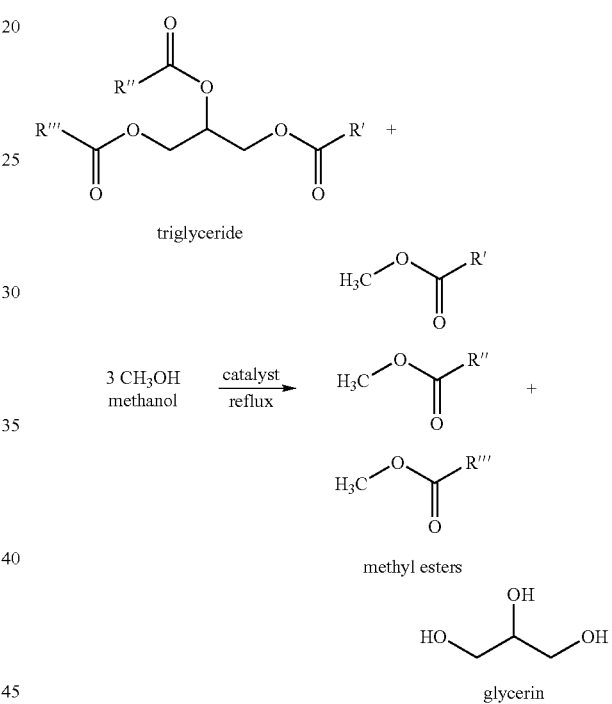

Synthesis of methyl esters. Canola oil (400.20 g) was stirred at 60° C.; potassium hydroxide (1.80 g, 0.028 mol) dissolved in methanol (58.12 g, 1.814 mol) was added. The reaction mixture continued stirring at reflux (~63° C.) until triglycerides were not detected and diglycerides levels were low by GC-FID (~5 h). The reaction mixture was allowed to cool to ambient temperatures and transferred to a separatory funnel where glycerin was allowed to settle and be removed. The remaining solution was washed with sat'd aq. $NHCl_3$ (2×250 mL), brine (2×200 mL), and dried over $Na_2SO_4$ (40.00 g). Crude yield 396.19 g. The crude product was combined with a second lot of canola oil methyl esters and distilled under vacuum to afford methyl esters as an off-white liquid.

| Biodiesel Fuel Properties for Methyl Esters and 2-Methylbutyl Esters | | | | | |
|---|---|---|---|---|---|
| | Test Method | Methyl Esters | | 2-Methylbutyl Esters | |
| Triglyceride | — | Soybean oil | Canola oil | Soybean oil | Canola oil |
| Cloud Point, °C. | ASTM D2500 | −5 | −6 | −7 | −11 |
| Total Glycerin, % mass | ASTM D6584 | 0.169 | 0.172 | 0.139 | 0.142 |
| Free Glycerin, % mass | ASTM D6584 | 0.006 | 0.006 | 0.008 | 0.007 |
| Cetane Number, B20 | ASTM D613 | 43.7 | 41.7 | 41.1 | 43.4 |
| Cetane Number | Extrapolated | 51.7 | 41.7 | 38.7 | 50.2 |
| Notebook Ref. | — | 1053-82-1 | 1053-83-1 | 1077-73E | 1077-74F |

The table above shows the fuel properties of soybean 2-methylbutyl esters, canola 2-methylbutyl esters, soybean methyl esters and canola methyl esters that. The cloud points and the cetane numbers of 2-methylbutyl esters and the methyl ester were comparable.

EXAMPLE 22

Differentiation of Biological MBO and Ethers Thereof

A chirality test is used to determine the source of the MBO. MBO produced biologically using the methods of the present invention will be chiral, but chemically produced MBO will be racemic. 2-MBO enantiomers were successfully separated on the BGB-174 chiral column (FIGS. 58A and 58B). This demonstrated that the samples are authentic and contain only S-2-MBO. Three various derivatives were generated independently for this test: the trimethyl-silyl, the trifluouroacetate, and the benzoate derivatives of 2-MBO.

The R- and S-2 MBO racemic mixture was separated using GCMS under the following experimental conditions:

Column: BGB-174, 30m×250 μm×0.25 μm, BGB-Analytik P/N 27430-025

Carrier gas: helium, 17 psi.

Oven: 60° C. for 5 min, then 0.5° C./min to 70° C. for 0.5 min.

Injector: split 1:40, temp 220° C., 1 μL injection volume.

Detector: MS, SIM ion of 57.1.

Samples prepared in $CH_2Cl_2$ at approximately 1 mM.

S-2-MBO was extracted from the fermentation broth with methylene chloride under conditions similar to those presented above (FIG. 58C).

EXAMPLE 23

Exemplary YAC Constructs

The following gene combinations were used to assemble yeast artificial chromosomes encoding specific enzymes in the pathways of interest for the production of 2-MBO. See FIGS. 59-73 for schematic illustrations of the assemblies.

| GENE | YAC6* | YAC8* | YAC10* | YAC7* | YAC9* | YAC5* | YAC5Δ* | YAC14* | YAC14Δ* |
|---|---|---|---|---|---|---|---|---|---|
| DH2 (Ps) | | X | X | | | | | | |
| PYC1 (Ps) | | X | X | X | X | | | X | X |
| AAT2 (Ps) | | X | X | X | X | | | X | X |
| HOM3$^{FBR}$ (Ps) | | X | X | X* | X* | | | X* | X* |
| HOM2 (Ps) | | X | X | X | X | | | X | X |
| HOM6 (Ps) | | X | X | X | X | | | X | X |
| THR1 (Ps) | | X | X | X | X | | | X | X |
| THR4 (Ps) | | X | X | X | X | | | X | X |
| ILV1 (Ps)$^{FBR}$ | | | | | | X* | | | |
| ILV1 (Ps) Δ15 | | | | | | | X* | X* | X* |
| IlvA (Ec) | X | | | | | | | | |
| ILV2 (Ps) | | | | | | X | | X | |
| ILV2 (Ps)Δ26 | | | | | | | X | | X |
| ILV6 (Ps) | | | | | | X | X | X | X |
| IvG(Ec) | X | | | | | | | | |
| ILV5 (Ps) | | | | | | X | | X | |
| ILV5 (Ps) Δ40 | | | | | | | X | | X |
| IlvC (Ec) | X | | | | | | | | |
| ILV3 (Sc) | | | | | | | | | |

-continued

| GENE | YAC6* | YAC8* | YAC10* | YAC7* | YAC9* | YAC5* | YAC5Δ* | YAC14* | YAC14Δ* |
|---|---|---|---|---|---|---|---|---|---|
| ILV3 (Ps) | | | | | | X | | X | |
| ILV3 (Ps)Δ34 | | | | | | | X | | X |
| IlvD (Ec) | X | | | | | | | | |
| PDC 3-6 (Ps) | | | | | X | | | X | X |
| KdcA(Ll) | X | | X | | | | | | |
| ADH6 (Sc) | X | | X | X | | | | X | X |

X* = X(PTEF & PCUP)
(Ps) = *Pichia stipitis* version
(Ec) = *Escherichia coli* version
(Sc) = *Saccharomyces cerevisiae* version
(Ll) = *Lactococcus lactis* version

EXAMPLE 24

Methods of Recovery of MBO and Other Compounds Produced in Culture Media and Analysis by GC-FID GC-FID was used to monitor a variety of produced compounds including methanol, ethanol, n-propanol, n-butanol, i-butanol, sum of isovaleric acid–2MeBu acid, 2-MBO, 3-MBO, and 2,3-butanediol.

Instrument and analysis conditions:
Agilent 7890A gas chromatography system.
Flow: 1.1 ml/min He (39.5 cm/sec @ 45° C.), constant flow control
Gradient Timetable: 45° C. for 3.2 min, then 25° C./min to 60° C., then 45° C./min to 200° C. Post run time is at 230° C. for 2.2 min.
Column: DB-624 (Agilent), 20m×0.18 mm×1 µm.
Inlet: 230° C., split 40:1 (back) 100:1 (front).
Detector: FID at 230° C., $H_2$ 45 ml/min, air 450 ml/min, Constant column+makeup gas 50 ml/min.
Needle rinse: 1-acetonitrile, 2-water.
Injection type: simultaneous injection into two identical columns of two different samples or two identical standard working solutions.
Injection volume: 1 µl.
Quantification: Internal standard method (IS: 1-pentanol). Calibration is set between 50 mM-25 µM for ethanol, 5 mM-25 µM for n-propanol, i-butanol, and n-butanol, 10 mM-50 µM for methanol, and 1 mM-5 µM for MBO and MBO acid.

Representative chromatograms showing the separation of compounds are provided in FIGS. 74 (*a-c*). Other methods of recovery include gas stripping, fractional distillation, chromatography, pervaporation, adsorption, and solid-liquid extraction.

EXAMPLE 25

GC/MS Analysis of MBO-Related Compounds Extracted in $CH_2Cl_2$

MBO and derivatives found in spent media were extracted in $CH_2Cl_2$ and analyzed by GC/MS. The internal standard method was applied for quantification (IS 1-pentanol). No pH adjustment was needed. Sample preparation: add 900 µl methylene chloride, 200 µl of 1-pentanol in $Na_2SO_4$ aqueous solution, and 500 µl sample or standard in a GC vial. Vortex the vial, allow 5 min for the phases to separate, and analyze the organic phase without removing the aqueous phase. The LOQ is 3 µM (see representative chromatograms in FIG. 75 (*a-c*)).

Instrument and analysis conditions:
Agilent 7890A gas chromatography system connected to a 5975C inert MSD mass spectrometer. The method is called "MBOorg3"
Flow: 0.75 ml/min He, constant flow control
Gradient Timetable: 70° C. for 1.0 min, then 10° C./min to 110° C. for 0.5 min, then 20° C./min to 140° C. for 0.5 min. Post run time is at 200° C. for 2.0 min.
Column: Rtx624 (Restek), 20m×0.18 mm×1 um.
Inlet: 230° C., split 20:1
Detector: MS with interface temperature set to 230° C. The selective ion monitoring is set for ions 55, 57, 58, and 70. The scan analysis was also run simultaneously for the mass range 35-200 m.u.
Masses for SIM analysis (dwell time 3 msec).

| | |
|---|---|
| 2-Me-butyraldehyde | 57.1 |
| Isovaleraldehyde | 58.1 |
| 2-Me-butanol | 55.1 |
| 3-Me-butanol | 57.1 |
| 2-Me-butyl acetate | 70.1 |
| Isopentyl acetate | 70.1 |

Needle rinse: 1-methylene chloride:methanol 1:1, 2-methylene chloride
To avoid carry-over, the syringe is washed three times with solvent 1, then solvent 2, and eight times with the sample.
Injection volume: 1 µl.
Quantification: Internal standard method (IS: 1-pentanol). Calibration is set between 10 mM-3 µM for the alcohols and aldehydes, and 5 mM-1.5 µM for the esters.

EXAMPLE 26

MBO and Ether Fuel Properties

|  | | Alcohol Fuels | | | | |
|---|---|---|---|---|---|---|
| | Property | Ethanol | Butanol | 2-MBO | 3-MBO | Gasoline |
| Chemical Properties | Formula | $C_2H_6O$ | $C_4H_{10}O$ | $C_5H_{12}O$ | $C_5H_{12}O$ | $C_4$-$C_{12}$ |
| | Oxygen (% wt) | 35 | 22 | 18 | 18 | 0 |
| Physical Properties | Flash Point, min (° C.) | 13 | 36 | 43 | 43 | −43 |
| | Boiling Point, max (° C.) | 79 | 118 | 130 | 130 | 27-225 |
| | Freezing Point, max (° C.) | −114 | −90 | −70 | −117 | −40 |
| | Fuel Solubility in Water (wt %)[1] | 100 | 8 | 3 | 2 | Immiscible |
| | Water Solubility in Fuel (wt %)[1] | 100 | 21 | 9 | 9 | Immiscible |
| Fuel Properties - Neat Fuel | Energy Content (BTU/gal) | 84,519 | 107,196 | 113,627 | 112,240 | 109,000-119,000 |
| | Pump Octane (R + M)/2[2] | 130.9 | 105.7 | 102.0 | 101.0 | 80-85 |
| | Reid Vapor Pressure (psi) | 2.3 | 0.7 | 2.3 | 2.3 | 7.8-15 |
| Fuel Properties - 10% Blend in Gasoline[3] | Energy Content (BTU/gal) | 111,052 | 113,320 | 113,963 | 113,824 | NA |
| | Pump Octane (R + M)/2 | 85.9 | 83.3 | 83.0 | 82.0 | |
| | Reid Vapor Pressure (psi) | ~8.2[A] | ~7[B] | ~7[B] | ~7[B] | |
| | Vol % to 2.7 wt % $O_2$[4] | 7.8 | 12.5 | 14.8 | 14.8 | |

Comparison of petroleum gasoline with substitutable alcohol fuels
[1]Based on literature review
[2]Extrapolated from tests on blended fuels (i.e. these are blending octanes)
[3]The testing was performed with an RBOB tested at a Pump Octane of 80.85 and an RVP of 7.37
[4]Oxygen content requirement in US Reformulated Gasoline markets
[A]RVP was measured at 8.8 psi for 5% blend in RBOB; reported value for 10% blend is based on literature review
[B]Value was measured with 9.5% volumetric blend of butanol (or 2MBO) in RBOB There are considerations in determining blend levels for 2-MBO and 3-MBO in gasoline. Clean air regulations in the US have historically required the presence of oxygen in gasoline in amounts between 2% and 2.7% (in weight). Given that 18% of MBO in weight is oxygen (while conventional gasoline contains no oxygen) and making adjustment for the different density of MBO and gasoline, then in order to satisfy the 2-2.7% range, you can add between 9.5-13% of MBO in gasoline (the number for ethanol is only 5-7% because ethanol has higher oxygen weight %). Similar calculations can be made for any similar restrictions in oxygen content.

| | | | | | | | | |
|---|---|---|---|---|---|---|---|---|
| | Fuel Properties: MBO & Other Alcohol Fuels vs. Regular Gasoline | | | | | | | |
| Fuel tested | Description | RON[1] N° | MON[2] N° | Measured Octane N° | Implied Octane N° | Measured RVP[3] psi | Implied RVP psi | Considerations |
| RBOB | Reference for octane & RVP testing of alcohol fuels | 78.9 | 82.8 | 80.9 | — | 7.4 | — | |
| 5% EtOH/ 95% RBOB | ~2% oxygen level | 81.5 | 85.2 | 83.4 | 130.9 | 8.8 | 35.6 | RVP for EtOH blends is not linear |
| 8% 1-Butanol/ 92% RBOB | ~2% oxygen level | 80.8 | 84.9 | 82.9 | 105.9 | 7.1 | 4.4 | |
| 8% isoButanol/ 92% RBOB | ~2% oxygen level | 82.0 | 86.0 | 84.0 | 120.2 | 7.1 | 4.5 | |
| 11% isoButanol/ 89% RBOB | ~2.7% oxygen level | 82.4 | 87.4 | 84.9 | 117.7 | 7.0 | 4.4 | |
| 9.5% 2MBO/ 90.5% RBOB | ~2% oxygen level | 81.0 | 85.0 | 83.0 | 103.5 | 7.0 | 3.7 | |
| 13% 2MBO/ 87% RBOB | ~2.7% oxygen level | 81.4 | 85.7 | 83.6 | 101.6 | 6.9 | 3.7 | |

EXAMPLE 27

| Fuel tested | Solubility in Water ppm | Measured Cetane[3] N° | Implied Cetane[3] N° | Pou °C. | Cloud °C. | CFPP[1] °C. | Flash °F. | Lubricity[4] cp |
|---|---|---|---|---|---|---|---|---|
| Ether Fuel Testing | | | | | | | | |
| ULSD[2] Reference fuel for testing | | 45.7 | — | −18 | −13 | −16 | 176 | 340 |
| ULSD w/ 2% 3MBO-ether | | 46.3 | 75.7 | −18 | −13 | −16 | 173 | |
| ULSD w/ 10% 3MBO-ether | | 48.3 | 71.7 | | | | | |
| ULSD w/ 2% 2MBO-ether | | 48.0 | 160.7 | | | | | |
| ULSD w/ 10% 2MBO-ether | | 53.8 | 126.7 | | | | | |
| ULSD w/ 10% 2MBO-ether | | | | | | | 152 | |
| ULSD w/ 10% 3MBO-ether | | | | | | | 162 | |
| 2MBO-ether | <500 | | | | | | 118 | |
| Hexadecane Reference for lubricity testing | | | | | | | | 534 |
| Hexadecane w/ 2% 3MBO-ether | | | | <−24 | <−21 | <−50 | | 610 |

[1]Cold Filter Plugging Point
[2]Ultra Low Sulfur Diesel
[3]ASTM Requirements for Cetane: >40
[4]ASTM Requirements for Flash Point: >100° F.

REFERENCES

Rieder, S. E., and Emr, S. C. (2000). Overview of subcellular fractionation procedures for yeast *Saccharomyces cerevisiae*. Current Protocols in Cell Biology: 3.7.1-3.7.25

Rieder, S. E., and Emr, S. C. (2000). Isolation of subcellular fractions from yeast *Saccharomyces cerevisiae*. Current Protocols in Cell Biology: 3.8.1-3.8.68

Gocke D, Nguyen C L, Pohl M, Stillger T., Walter L, her M. M. (2007). Branched-Chain Keto Acid Decarboxylase from *Lactococcus lactis* (KdcA), a Valuable Thiamine Diphosphate-Dependent Enzyme for Asymmetric C—C Bond Formation Adv. Synth. Catal. 349: 1425-1435

Berthold C. L., Gocke D., Wood M. D., Leeper F. J., Pohl M., Schneider G. (2007). Structure of the branched-chain keto acid decarboxylase (KdcA) from *Lactococcus lactis* provides insights into the structural basis for the chemoselective and enantioselective carboligation reaction. Acta Crystallographica Section D. 63: 1217-1224

What is claimed is:

1. A method for producing a methylbutyl ether product, comprising
    culturing a recombinant microorganism in a culture medium containing a carbon source,
    wherein said recombinant microorganism comprises at least one exogenous nucleic acid molecule, wherein said at least one exogenous nucleic acid molecule comprises a pyruvate decarboxylase or a pyruvate decarboxylase isoform derived from the genus *Pichia* and an alcohol dehydrogenase derived from the genus *Saccharomyces*;
    further wherein said recombinant microorganism is a member of a genus selected from the group consisting of *Clostridium, Zymomonas, Escherichia, Pseudomonas, Bacillus, Klebsiella, Corynebacterium, Pichia*, and *Saccharomyces*;
    wherein the recombinant microorganism produces spent culture medium from the culture medium by metabolizing the carbon source to 2-methylbutanol;
    recovering said 2-methylbutanol from the spent culture medium; and converting said 2-methylbutanol to a methylbutyl ether product comprising one or more of 1-(isopentyloxy)-3-methylbutane, 2-methyl-1-(2-methylbutoxy)butane, 1-(isopentyloxy)-2-methylbutane, 2-methyl-1-(tert-pentyloxy)butane, and 2-methyl-2-(tert-pentyloxy)butane.

2. The method of claim 1, wherein the pyruvate decarboxylase has at least 90% amino acid sequence identity to a *Pichia stipitis* pyruvate decarboxylase PDC3-6 gene product (SEQ ID NO:53).

3. The method of claim 2, wherein the alcohol dehydrogenase has at least 90% amino acid sequence identity to *Saccharomyces cerevisiae* ADH6 (SEQ ID NO:66) or *Saccharomyces cerevisiae* SFA1 (SEQ ID NO:76).

4. The method of claim 3, wherein the alcohol dehydrogenase is *Saccharomyces cerevisiae* ADH6 (SEQ ID NO:66).

5. The method of claim 1, wherein said recombinant microorganism is *Escherichia coli, Pseudomonas putida, Bacillus subtilis, Corynebacterium glutamicum, Pichia stipitis, Pichia pastoris*, or *Saccharomyces cerevisiae*.

6. The method of claim 5, wherein said recombinant microorganism is *Escherichia coli*.

7. The method of claim 5, wherein said recombinant microorganism is *Corynebacterium glutamicum*.

8. The method of claim 5, wherein said recombinant microorganism is *Saccharomyces cerevisiae*.

9. The method of claim 1, wherein said 2-methylbutanol is removed from said culture by gas stripping, fractional distillation, chromatography, pervaporation, adsorption, liquid-liquid extraction, or solid-liquid extraction.

10. The method of claim 1, wherein the recovering step comprises extracting 2-methylbutanol using liquid-liquid extraction, wherein a solvent is used to continuously extract at least 2-methylbutanol from the spent culture medium.

11. The method of claim 10, wherein the solvent is diisopropyl ether, heptane or isooctane.

12. The method of claim 11, wherein the solvent is diisopropyl ether; and wherein at least 90% of 2-methylbutanol is extracted from the spent culture medium.

13. The method of claim 1, wherein the conversion step of converting 2-methylbutanol to a methyl butyl ether product comprises treating the 2-ethylbutanol with an acid resulting in the formation of methyl butyl ether.

14. The method of claim 13, wherein the acid is hydrochloric acid, hydrobromic acid, sulfuric acid, nitric acid, phosphoric acid, chromic acid, or a sulfonic acid.

15. The method of claim 14, wherein the acid is a methane sulfonic acid, an ethane sulfonic acid, a benzene sulfonic acid, a toluene sulfonic acid, trifluoromethyl sulfonic acid, or perfluoroalkane sulfonic acid.

16. The method of claim 14, wherein the acid is trifluoromethanesulfonic acid.

* * * * *